US010822587B2

(12) United States Patent
Regev et al.

(10) Patent No.: US 10,822,587 B2
(45) Date of Patent: Nov. 3, 2020

(54) T CELL BALANCE GENE EXPRESSION, COMPOSITIONS OF MATTERS AND METHODS OF USE THEREOF

(71) Applicants: The Broad Institute, Inc., Cambridge, MA (US); Massachusetts Institute of Technology, Cambrige, MA (US); President and Fellows of Harvard College, Cambridge, MA (US); The Brigham and Women's Hospital, Inc., Boston, MA (US)

(72) Inventors: Aviv Regev, Cambridge, MA (US); Vijay Kuchroo, Newton, MA (US); Hongkun Park, Lexington, MA (US); Nir Yosef, Richmond, CA (US); Alexander K. Shalek, Cambridge, MA (US); Jellert Gaublomme, Cambridge, MA (US); Nicole C. Joller, Brookline, MA (US); Chuan Wu, Boston, MA (US); Ana Carrizosa Anderson, Brookline, MA (US)

(73) Assignees: The Broad Institute, Inc., Cambridge, MA (US); Massachusetts Institute of Technology, Cambridge, MA (US); President and Fellows of Harvard College, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 254 days.

(21) Appl. No.: 14/837,702

(22) Filed: Aug. 27, 2015

(65) Prior Publication Data
US 2015/0361396 A1 Dec. 17, 2015

Related U.S. Application Data

(63) Continuation-in-part of application No. PCT/US2014/019127, filed on Feb. 27, 2014.
(Continued)

(51) Int. Cl.
| C12N 5/071 | (2010.01) |
| C12N 5/00 | (2006.01) |
| C12N 5/02 | (2006.01) |
| C07H 21/04 | (2006.01) |
| C12N 5/0783 | (2010.01) |
| C12Q 1/6881 | (2018.01) |
| A61K 31/12 | (2006.01) |
| A61K 31/198 | (2006.01) |
| A61K 31/37 | (2006.01) |
| A61K 31/4745 | (2006.01) |
(Continued)

(52) U.S. Cl.
CPC ............ *C12N 5/0636* (2013.01); *A61K 31/12* (2013.01); *A61K 31/198* (2013.01); *A61K 31/37* (2013.01); *A61K 31/4745* (2013.01); *A61K 31/66* (2013.01); *A61K 31/661* (2013.01); *A61K 31/7076* (2013.01); *A61K 31/7088* (2013.01); *A61K 31/739* (2013.01); *A61K 33/00* (2013.01); *A61K 33/06* (2013.01); *A61K 33/24* (2013.01); *A61K 38/1767* (2013.01); *A61K 38/1866* (2013.01); *A61K 38/191* (2013.01); *A61K 38/363* (2013.01); *A61K 38/4866* (2013.01); *C07K 16/28* (2013.01); *C12N 5/0637* (2013.01); *C12N 15/113* (2013.01); *C12Q 1/6881* (2013.01); *G01N 33/56972* (2013.01); *A61K 48/00* (2013.01); *C07K 2317/76* (2013.01); *C12N 2310/14* (2013.01); *C12N 2320/30* (2013.01); *C12N 2501/15* (2013.01); *C12N 2501/2301* (2013.01); *C12N 2501/2306* (2013.01); *C12N 2501/2323* (2013.01); *C12N 2501/25* (2013.01); *C12N 2501/90* (2013.01); *C12Q 2600/112* (2013.01); *C12Q 2600/136* (2013.01); *C12Q 2600/158* (2013.01); *C12Y 304/21069* (2013.01); *G01N 2570/00* (2013.01); *G01N 2800/56* (2013.01)

(58) Field of Classification Search
None
See application file for complete search history.

(56) References Cited

U.S. PATENT DOCUMENTS

2010/0166784 A1 7/2010 Murphy et al.

FOREIGN PATENT DOCUMENTS

| JP | 2010051307 A | 3/2010 |
| WO | 2009023267 A2 | 2/2009 |
(Continued)

OTHER PUBLICATIONS

Whisstock et al., 2003, Quart. Rev. Biophys 36: 307-340.*
(Continued)

*Primary Examiner* — Amy E Juedes
(74) *Attorney, Agent, or Firm* — Johnson, Marcou, Isaacs & Nix, LLC; F. Brent Nix, Esq.; Michael Scher, Esq.

(57) ABSTRACT

This invention relates generally to compositions and methods for identifying the regulatory network that modulates, controls or otherwise influences T cell balance, for example, Th17 cell differentiation, maintenance and/or function, as well compositions and methods for exploiting the regulatory network that modulates, controls or otherwise influences T cell balance in a variety of therapeutic and/or diagnostic indications. This invention also relates generally to identifying and exploiting target genes and/or target gene products that modulate, control or otherwise influence T cell balance in a variety of therapeutic and/or diagnostic indications.

4 Claims, 77 Drawing Sheets
Specification includes a Sequence Listing.

Related U.S. Application Data

(60) Provisional application No. 61/770,036, filed on Feb. 27, 2013.

(51) Int. Cl.

| | | |
|---|---|---|
| A61K 31/66 | (2006.01) | |
| A61K 31/661 | (2006.01) | |
| A61K 31/7076 | (2006.01) | |
| A61K 31/7088 | (2006.01) | |
| A61K 31/739 | (2006.01) | |
| A61K 33/00 | (2006.01) | |
| A61K 33/06 | (2006.01) | |
| A61K 33/24 | (2019.01) | |
| A61K 38/17 | (2006.01) | |
| A61K 38/18 | (2006.01) | |
| A61K 38/19 | (2006.01) | |
| A61K 38/36 | (2006.01) | |
| A61K 38/48 | (2006.01) | |
| C07K 16/28 | (2006.01) | |
| C12N 15/113 | (2010.01) | |
| G01N 33/569 | (2006.01) | |
| A61K 48/00 | (2006.01) | |

(56) References Cited

FOREIGN PATENT DOCUMENTS

| | | |
|---|---|---|
| WO | 2009092087 A2 | 7/2009 |
| WO | 2009117597 A1 | 9/2009 |
| WO | 2013000872 A2 | 1/2013 |
| WO | 2014134351 A2 | 9/2014 |
| WO | 2014134351 A3 | 12/2014 |

OTHER PUBLICATIONS

Wang et al., 2006, BLood. vol. 108: 4071-4077.*
Milner et al., 2015, Blood. vol. 125: 591-599.*
Martinez et al., 2014, vol. 276: 142-149.*
Geary, 2010, Nonpeptide ligands for peptidergic G protein-coupled receptors, pp. 10-26.*
Stockinger et al., 2017, Nat. Rev. Immunol. vol. 17: 535-544.*
Heo et al., 2010, Immunol. Let. vol. 127: 150-156.*
Estelle Bettelli, et al., $T_H$-17 Cells in the Circle of Immunity and Autoimmunity, Nature Immunology (2007) vol. 8, No. 4, p. 345-350.
Talal Chatila, The Regulatory T Cell Transcriptosome: E Pluribus Unum, Immunity (2007) vol. 27, No. 5, p. 693-695.
Maria Ciofani, et al. A Validated Regulatory Network for Th17 Cell Specification, Cell (2012) vol. 151, p. 289-303.
John J. O'Shea, et al., Signal Transduction and Th17 Cell Differentiation, Microbes and Infection (2009) vol. 11, p. 599-611.
Anneli Peters, et al., The Many Faces of Th17 Cells, Current Opinion in Immunology (2011) vol. 23, p. 702-705.
Nir Yosef, et al., Dynamic Regulatory Network Controlling $T_H$-17 Cell Differentiation, Nature (2013) vol. 496, p. 461-468.
Liang Zhou, et al., Transcriptional Regulatory Networks in Th17 Cell Differentiation, Current Opinion in Immunology (2009) vol. 21, p. 146-152.
International Preliminary Report on Patentability and Written Opinion dated Sep. 11, 2015, which issued during prosecution of International Application No. PCT/US2014/019127.
The Broad Institute, Inc. et al., "Communication pursuant to Article 94(3) EPC for EP 14715725.9", Oct. 15, 2019, 12 pages.
Shi, et al., "Unlike Th1, Th17 Cells Mediate Sustained Autoimmune Inflammation and Are Highly Resistant to Restimulation Induced Death", The Journal of Immunology, vol. 183, No. 11, Nov. 4, 2009, pp. 7547-7556.
Zhang, et al., "Th17 Cells Undergo Fas-Mediated Activation-Induced Cell Death Independent of IFN-[gamma]", The Journal of Immunology, vol. 181, No. 1, Jun. 19, 2008, pp. 190-196.
The Broad Institute, Inc., "International Search Report and Written Opinion issued in International Application No. PCT/US2014/019127", dated Nov. 14, 2014, 18 pages.
The Broad Institute, Inc., "Office Action for EP Patent Application No. 14715725.9", dated Jan. 5, 2018, 4 pages.
The Broad Institute, Inc., "Office Action for RU Patent Application No. 2015140941", dated Mar. 6, 2018, 6 pages of Office Action and 3 pages of English Translation.
Abadja, et al., "Significance of T helper 17 immunity in transplantation", Curr Opin Organ Transplant., vol. 17, No. 1, Feb. 2012, 8-14.
Bettelli, et al., "Th-17 cells in the circle of immunity and autoimmunity", Nature Immunology, vol. 8, 2007, 345-350.
Durant, et al., "Diverse Targets of the Transcription Factor STAT3 Contribute to T Cell Pathogenicity and Homeostasis", Immunity, vol. 32, No. 5, May 28, 2010, 605-615.
Feng, et al., "Apoptosis-Inducing Effect for Mouse Mammary Cancer Cells Transfected with IL-23 Gene in Vitro and in vivo", Zhongliu, CAPLUS [online], [retrieved on Jan. 30 2018], CAPLUS Accession No. 2009:1176369, 2008, p. 842-846 (abstract).
Hirota, et al., "Preferential Recruitment of CCR6-Expressing Th17 Cells to Inflamed Joints via CCL20 in Rheumatoid Arthritis and Its Animal Model", The Journal of Experimental medicine, 2007, pp. 2803-2812.
Lee, et al., "Inhibition of TCR-Induced CD8 T cell Death by IL-12: Regulation of Fas Ligand and Cellular FLIP Expression and Caspase Activation of IL-12", The Journal of Immunology, 2003, p. 2456-2460.
Menon, et al., "IL-18, a Product of Choriodecidual Cells, Increases During Premature Rupture of Membranes but Fails to Turn on the Fas-FasL-Mediated Apoptosis Pathway", Journal of Assisted Reproduction and Genetics, 2001, pp. 276-284.
Nakae, et al., "Phenotypic Differences between Th1 and Th17 Cells and Negative Regulation on Th1 Cell Differentiation by IL-17", Journal of Leukocyte Biology, 2007, pp. 1258-1268.
Peters, et al., "The many faces of Th17 cells", Current Opinion in Immunology, vol. 23, No. 6, 2011, pp. 702-706.
Rautajoki, et al., "Interleukin-4 Inhibits Caspase-3 by Regulating Several Proteins in the Fas Pathway during Initial Stages of Human T Helper 2 Cell Differentiation", Molecular & Cellular Proteomics, 2007, pp. 238-251.
Sundrud, et al., "Halofuginone inhibits TH17 cell differentiation by activating the amino acid starvation response", Science, vol. 324, 2009, 1334-1338.
The Brigham and Women'S Hospital, et al., "Examination Report for AU 2014223344", dated Mar. 20, 2019, 5 pages.
The Broad Institute, Inc., "Office Action for EP 14715725.9", dated Dec. 4, 2018, 9 pages.
The Broad Institute. Inc., et al., "Notice of Reasons for Rejection for JP Application No. 2015-560328", with English translation, dated Oct. 5, 2018, 15 pages.
Waldner, et al., "Fas- and FasL-deficient mice are resistant to induction of autoimmune encephalomyelitis", The Journal of Immunology, vol. 159, Issue 7, Oct. 1, 1997, 3100-3103.
Watanabe, et al., "The Role of IL-8 in Fas-expression and apoptosis in T-and-B-lymphocytes During Systemic Inflammation in Mice", Shock, Abstract No. P15, EMBASE [online], [retrieved on Jan. 30 2018], EMBASE Accession No. 0050183681, 2009, Abstract only.
Xiao, et al., "Retinoic acid increases Foxp3+ regulatory T cells and inhibits development of Th17 cells by enhancing TGF-beta-driven Smad3 signaling and inhibiting IL-6 and IL-23 receptor expression", Journal of Immunology, vol. 181, 2008, 2277-2284.
Yang, et al., "Opposing regulation of the locus encoding IL-17 through direct, reciprocal actions of STAT3 and STAT5", Nat. Immunol., vol. 12, No. 3, Mar. 2011, 247-254.
Yu, et al., "Expressions of Fas and Fas-L Proteins in Rat Liver Fibrosis Model and the Role of IFN-gamma", Bengbu Yixueyuan Xuebao, CAPLUS [online], [retrieved on Jan. 30, 2018], CAPLUS Accession No. 2009:34268, 2007, pp. 643-645, C3 (abstract).

(56) References Cited

OTHER PUBLICATIONS

Zielenski, et al., "Pathogen-induced human TH17 cells produce IFN or IL-10 and are regulated by IL", Nature, vol. 484, No. 7395, Apr. 2012, 514-518.
The Broad Institute, Inc., "Communication Pursuant to Article 94(3) EPC for EP 14715725.9", Aug. 26, 2020, 10 pages.
Menschikowski, et al., "Expression and Shedding of Endothelial Protein C Receptor in Prostate Cancer Cells", Cancer Cell International, vol. 11, 2011, 10 pages.

* cited by examiner

Early Network

Intermediate Network

FIGURE 5D
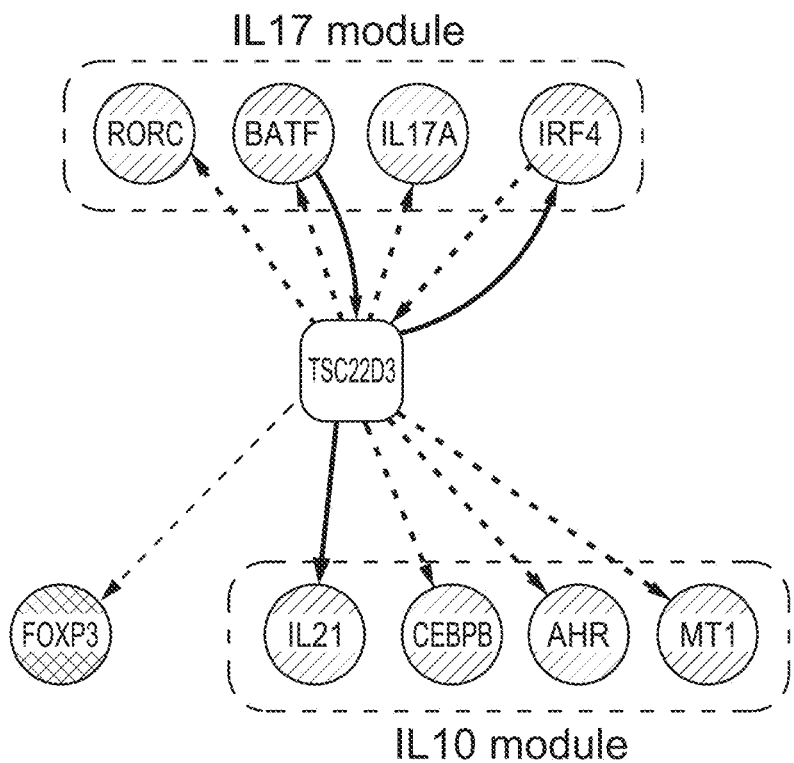
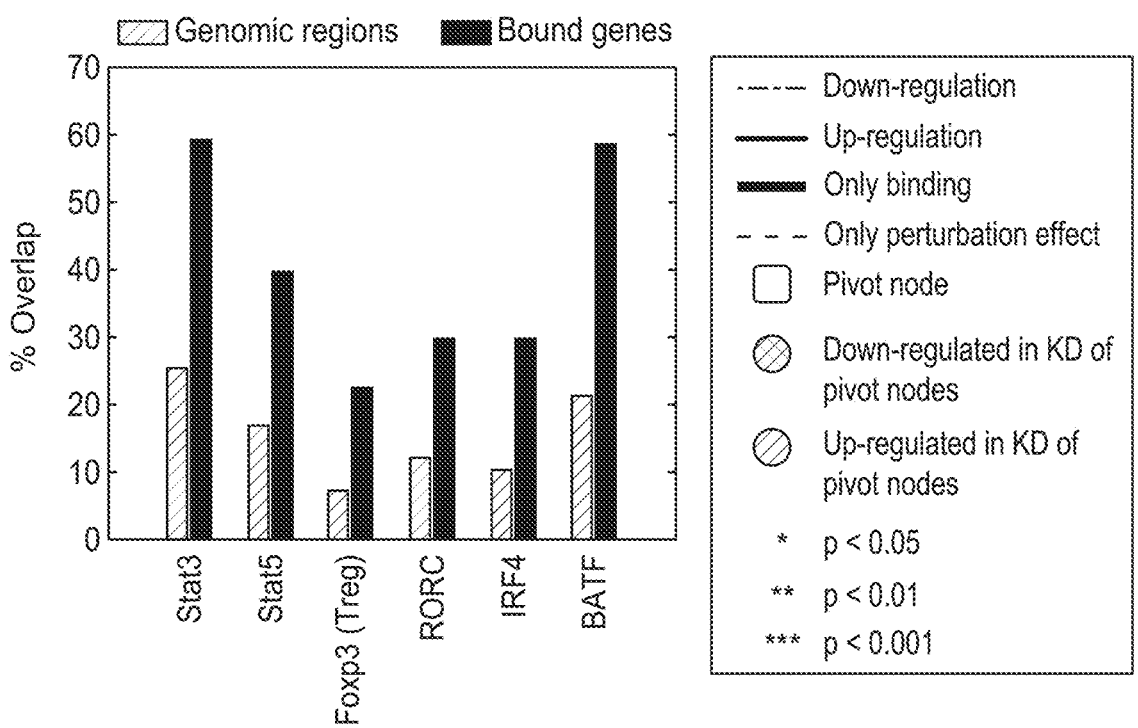

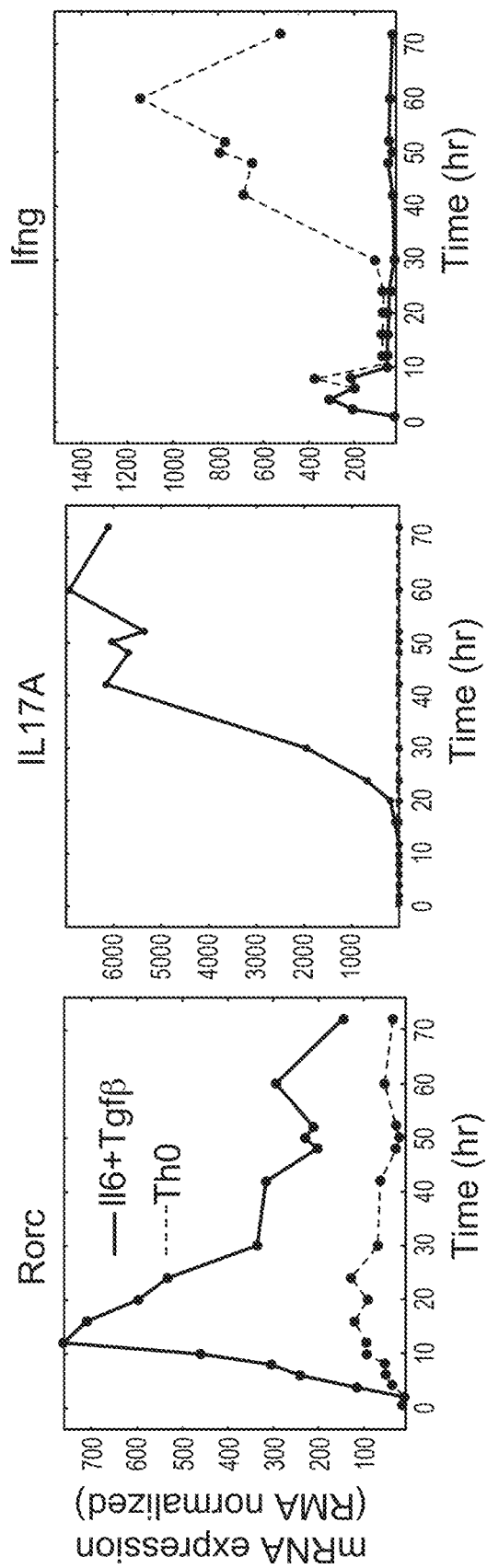

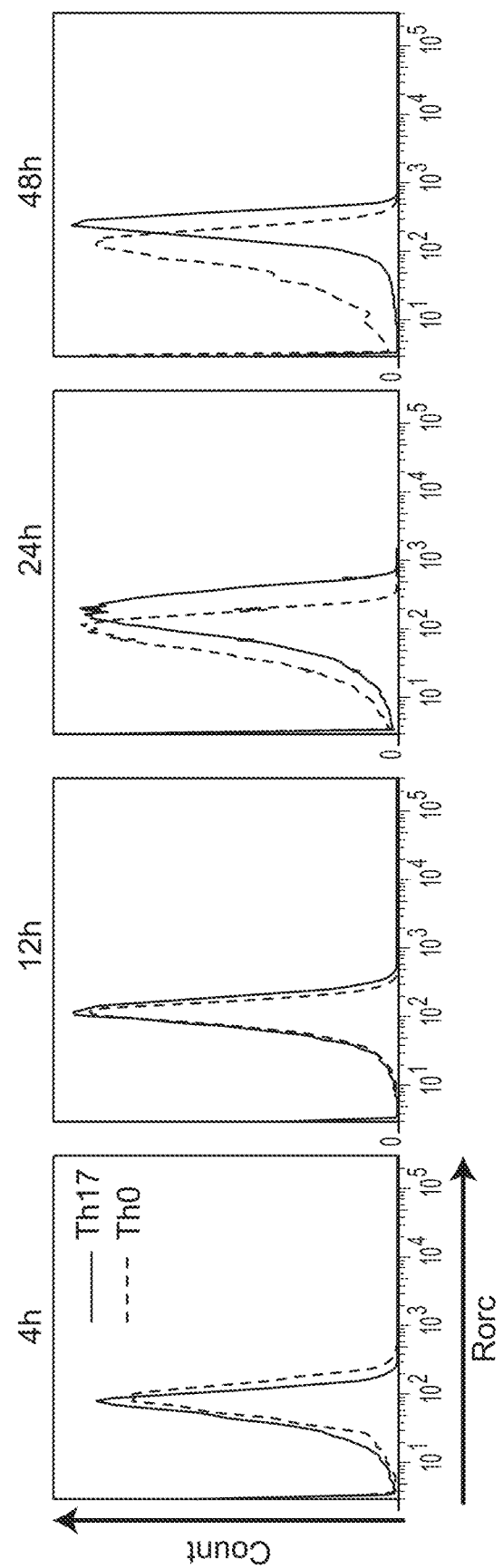

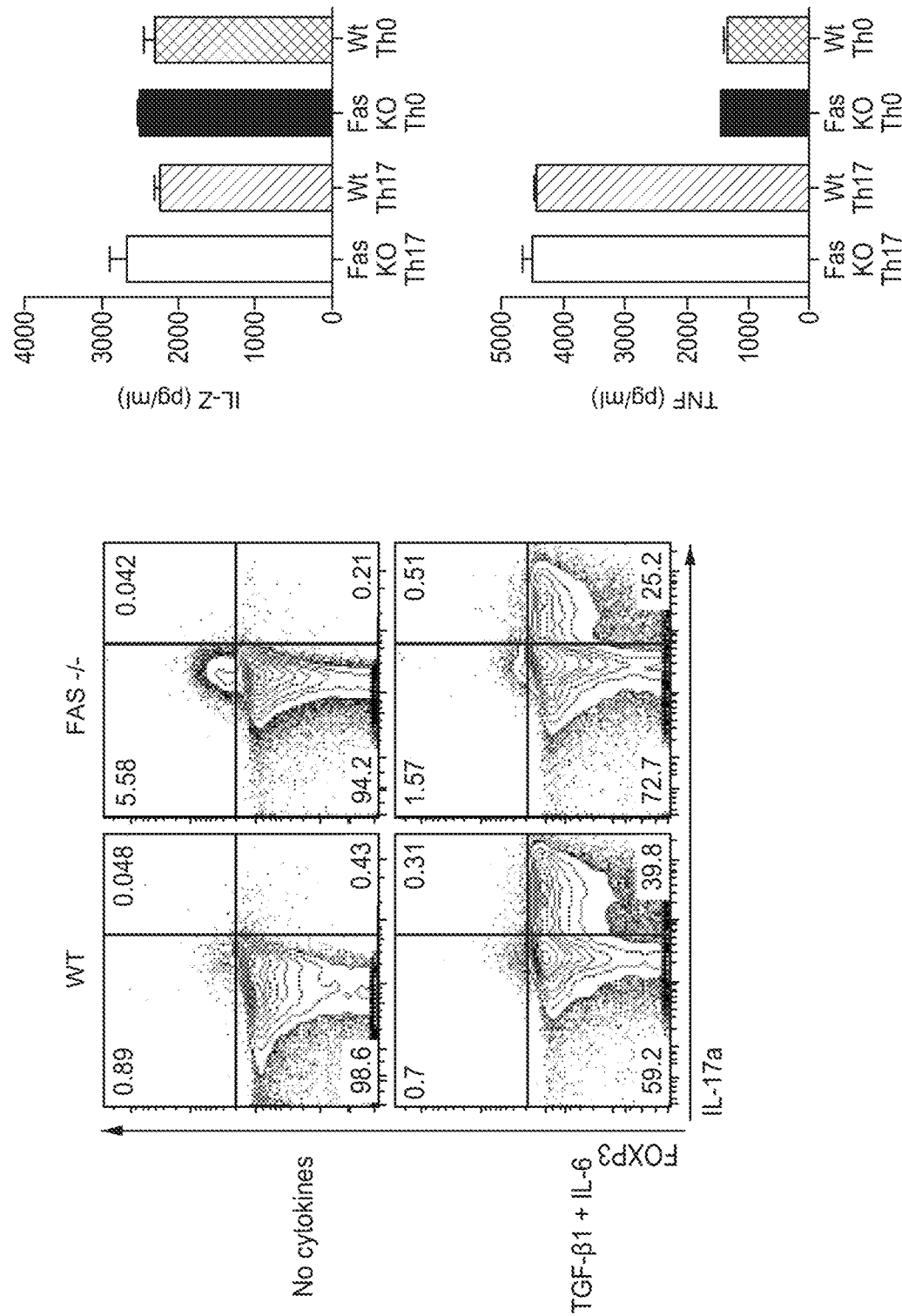

FIGURE 17A
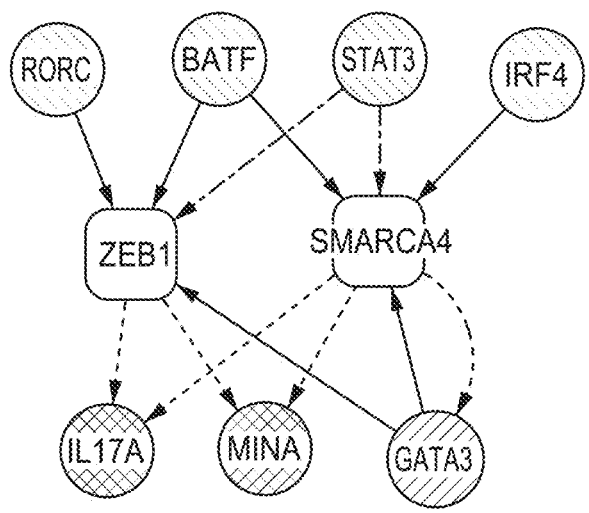
FIGURE 17B
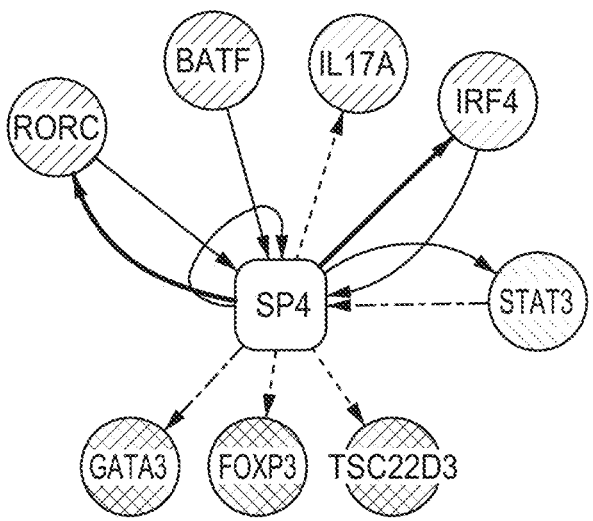
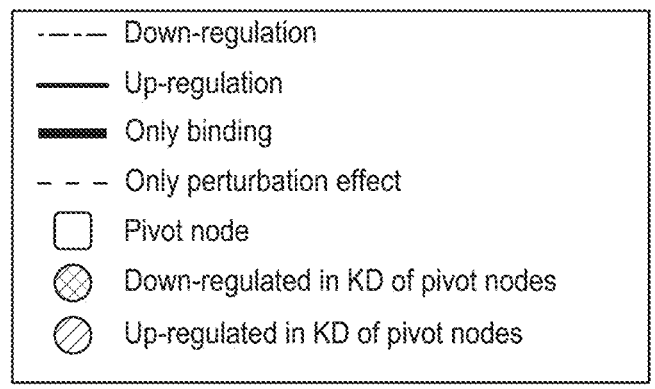

*PROCR*

*PROCR*

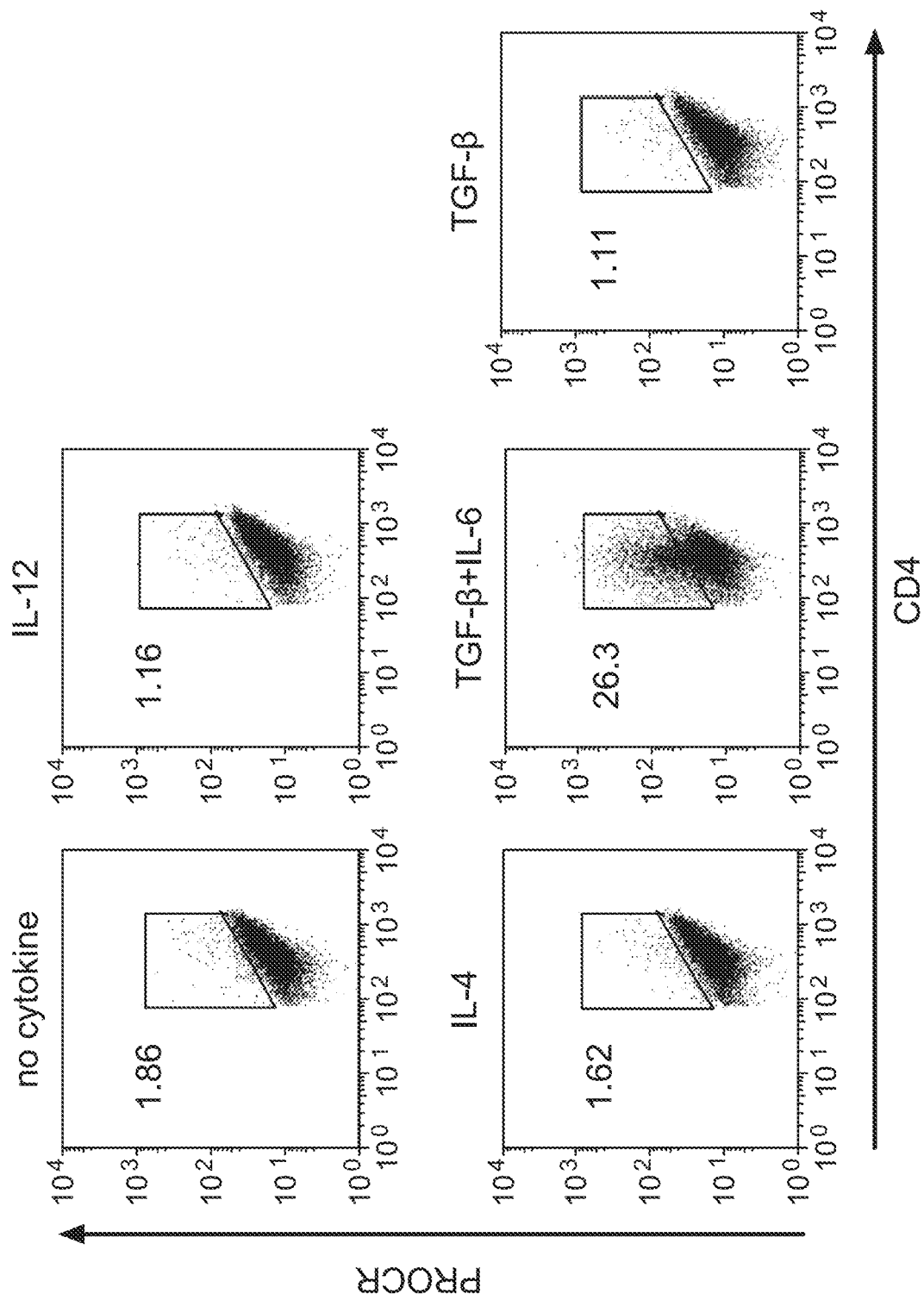

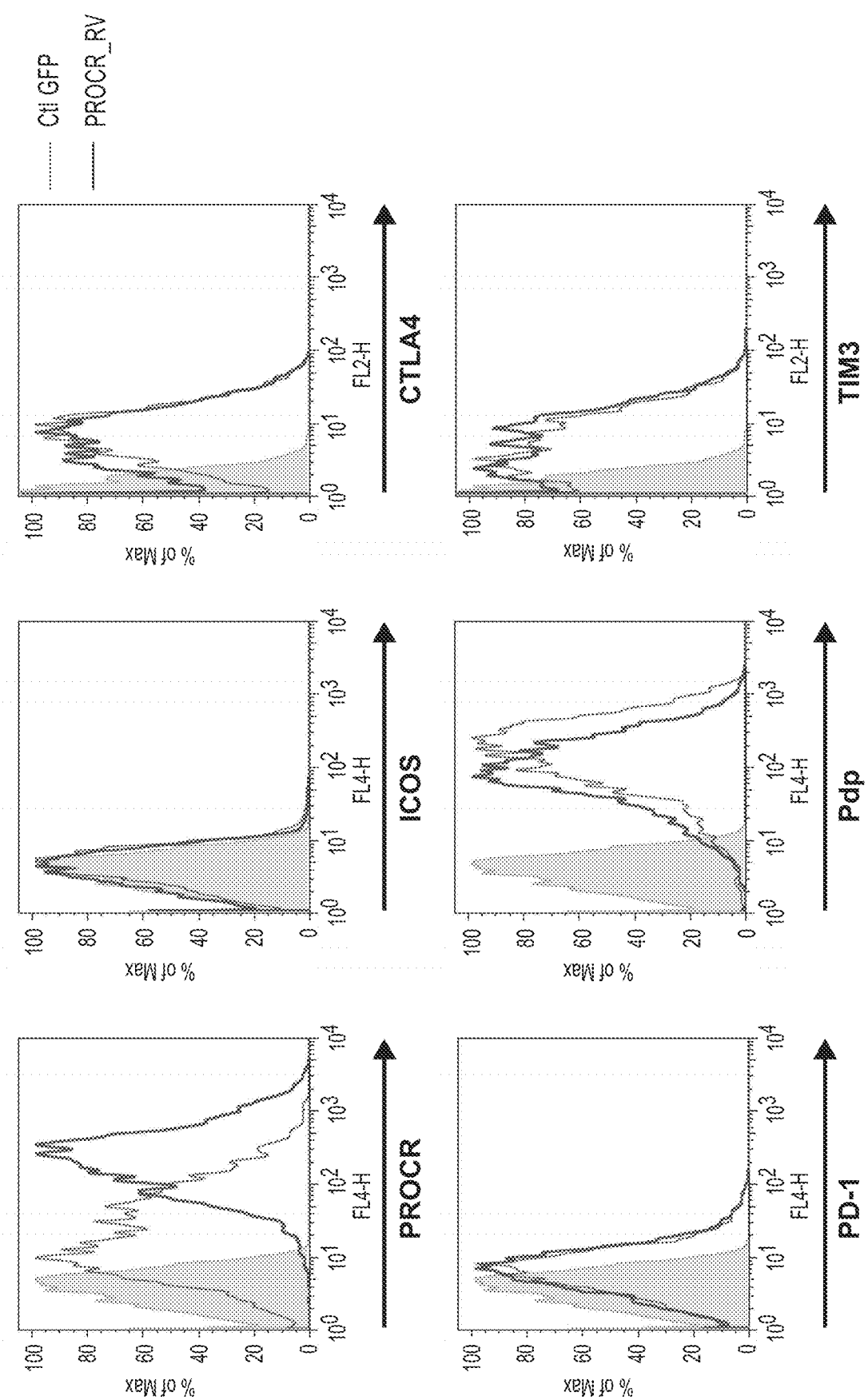

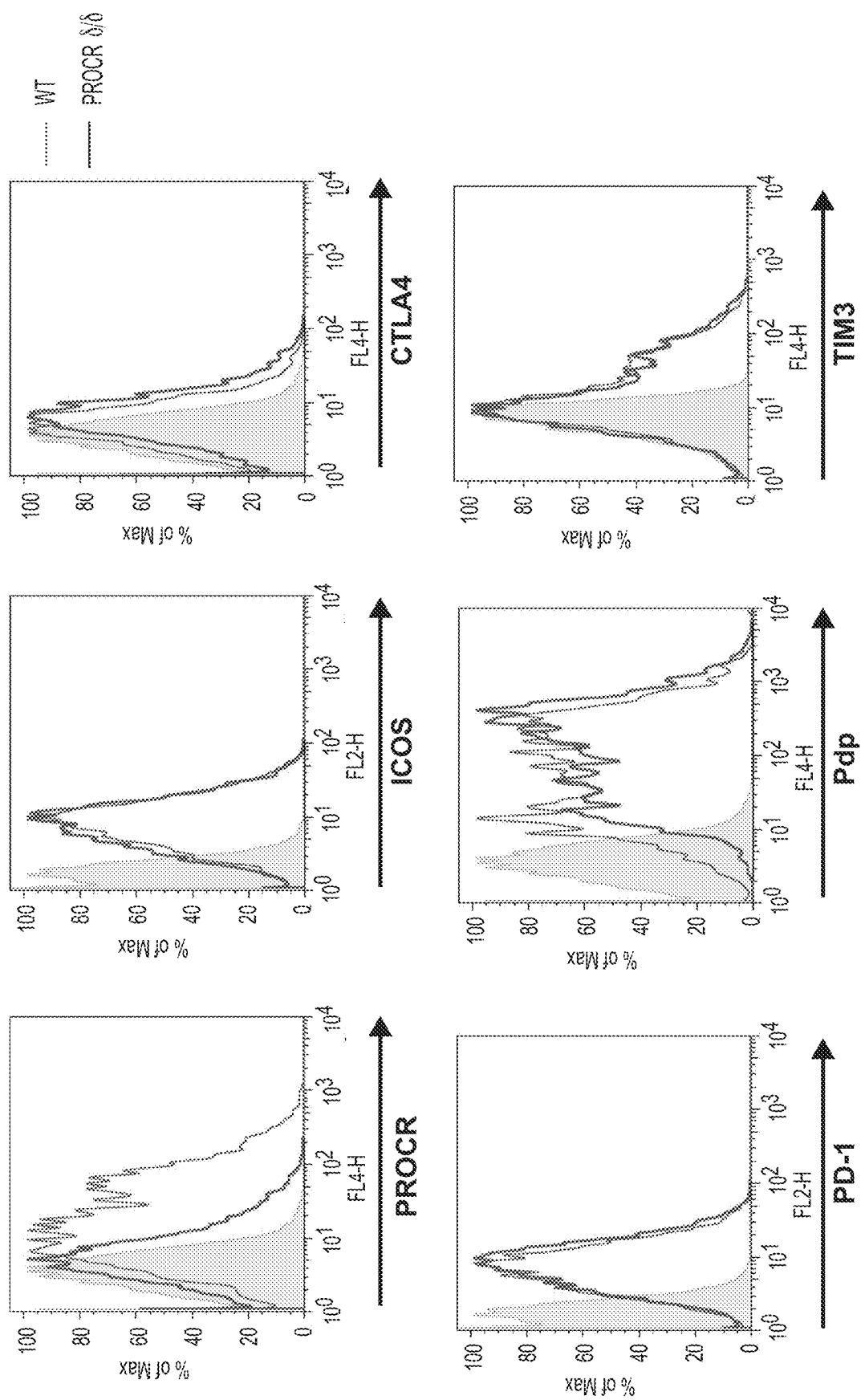

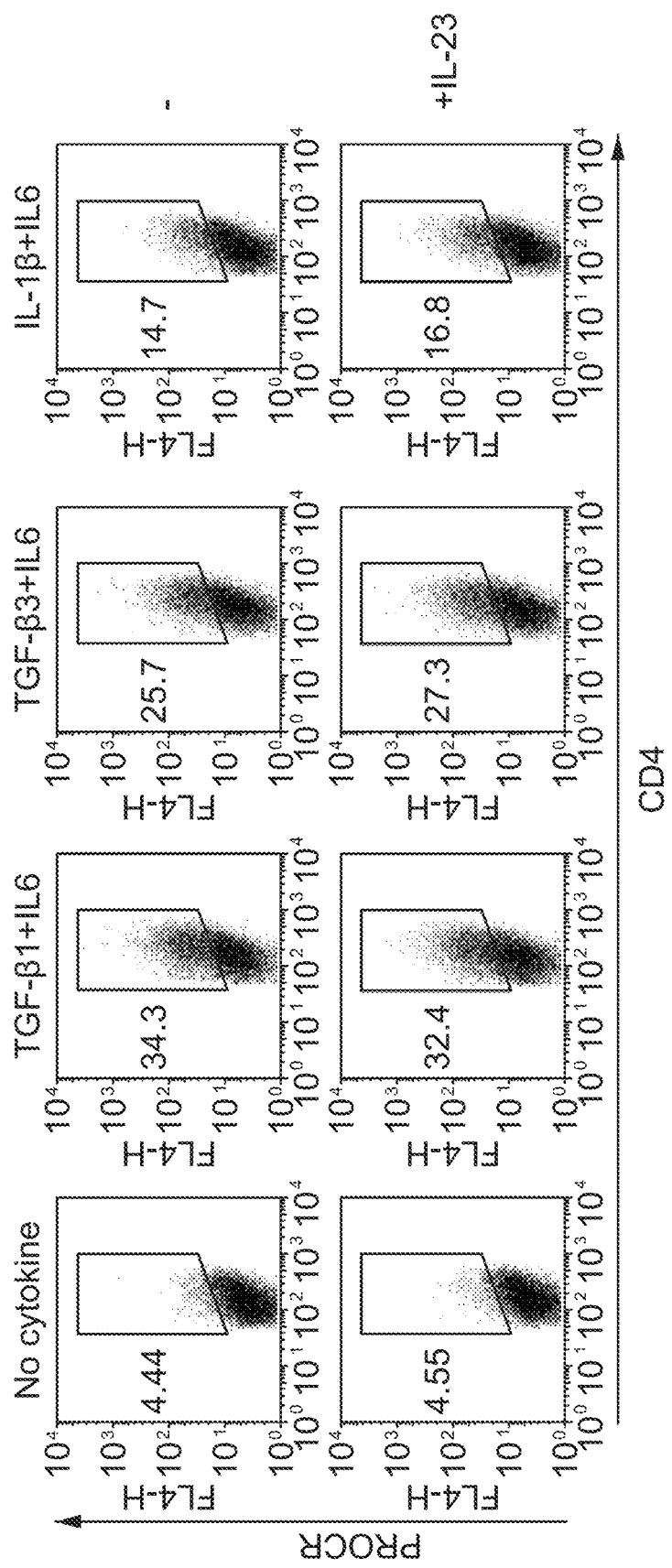

| Group | Group Name | Mice/Group | Mean Macrorun score | Day of Onset | Dead Mice | Disease incidence |
|---|---|---|---|---|---|---|
| 1 | CU RV | 4 | 2.75+/-0.35 | 20 | 0 | 2/4 (50%) |
| 2 | PROCR RV | 4 | 0 | - | 0 | 0/4 (0%) |

FIGURE 27C
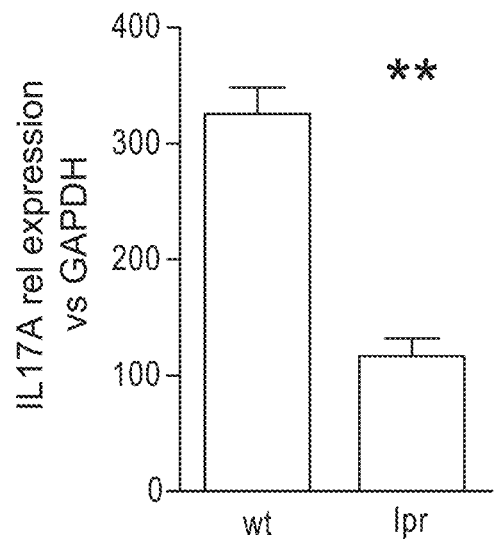
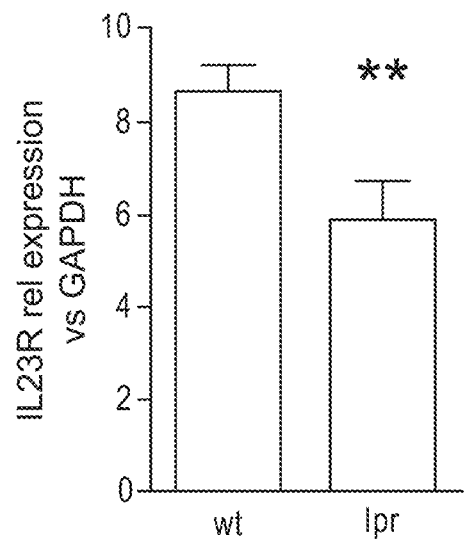
FIGURE 28A
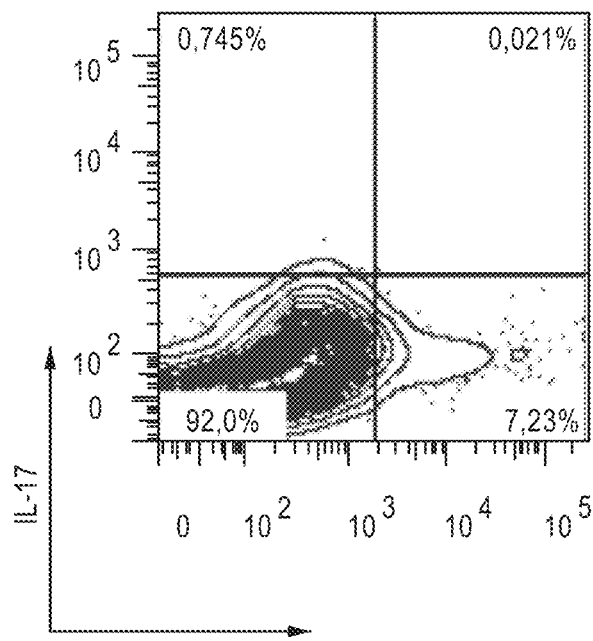
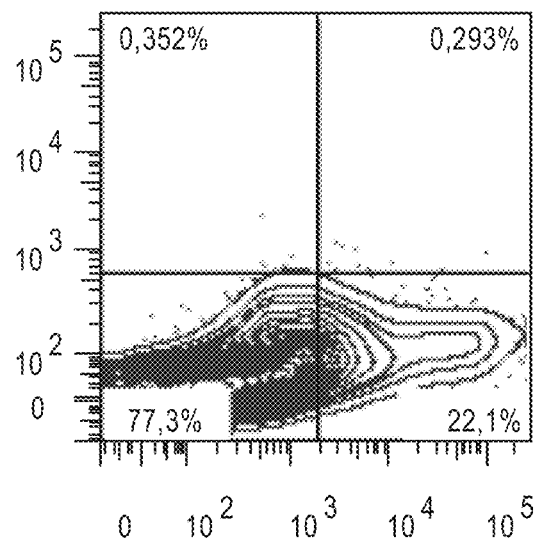

SEQUENCE LISTING

```
<160> NUMBER OF SEQ ID NOS: 1394

<210> SEQ ID NO 1
<211> LENGTH: 18
<212> TYPE: DNA
<213> ORGANISM: Mus sp.

<400> SEQUENCE: 1
ggccagagct tgaccatc                                                 18

<210> SEQ ID NO 2
<211> LENGTH: 18
<212> TYPE: DNA
<213> ORGANISM: Mus sp.

<400> SEQUENCE: 2
agcaagccag ccaaacag                                                 18

<210> SEQ ID NO 3
<211> LENGTH: 18
```

-continued

<212> TYPE: DNA
<213> ORGANISM: Mus sp.

<400> SEQUENCE: 3
agccaatttt gaagggca                                                 18

<210> SEQ ID NO 4
<211> LENGTH: 18
<212> TYPE: DNA
<213> ORGANISM: Mus sp.

<400> SEQUENCE: 4
ggaagccctg catttcct                                                 18

<210> SEQ ID NO 5
<211> LENGTH: 18
<212> TYPE: DNA
<213> ORGANISM: Mus sp.

<400> SEQUENCE: 5
tataacccct gggccctc                                                 18

<210> SEQ ID NO 6
<211> LENGTH: 18
<212> TYPE: DNA
<213> ORGANISM: Mus sp.

<400> SEQUENCE: 6
gttgcagccc tcgttgtc                                                 18

<210> SEQ ID NO 7
<211> LENGTH: 18
<212> TYPE: DNA
<213> ORGANISM: Mus sp.

<400> SEQUENCE: 7
gtcgggacat cttgacgg                                                 18

<210> SEQ ID NO 8
<211> LENGTH: 18
<212> TYPE: DNA
<213> ORGANISM: Mus sp.

<400> SEQUENCE: 8
ggaggatgca aaacccct                                                 18

<210> SEQ ID NO 9
<211> LENGTH: 18
<212> TYPE: DNA
<213> ORGANISM: Mus sp.

<400> SEQUENCE: 9
gcatgggtac tgctggct                                                 18

<210> SEQ ID NO 10
<211> LENGTH: 18
<212> TYPE: DNA
<213> ORGANISM: Mus sp.

<400> SEQUENCE: 10
tgaggaggtt cacagccc                                                 18

<210> SEQ ID NO 11

```
<211> LENGTH: 18
<212> TYPE: DNA
<213> ORGANISM: Mus sp.

<400> SEQUENCE: 11
ggacgcgtga aaggtttg                                                 18

<210> SEQ ID NO 12
<211> LENGTH: 19
<212> TYPE: DNA
<213> ORGANISM: Mus sp.

<400> SEQUENCE: 12
tgcactatgg ccttatcgg                                                19

<210> SEQ ID NO 13
<211> LENGTH: 18
<212> TYPE: DNA
<213> ORGANISM: Mus sp.

<400> SEQUENCE: 13
tgcctaagct ccattggc                                                 18

<210> SEQ ID NO 14
<211> LENGTH: 18
<212> TYPE: DNA
<213> ORGANISM: Mus sp.

<400> SEQUENCE: 14
acggcaaggc agcaatac                                                 18

<210> SEQ ID NO 15
<211> LENGTH: 18
<212> TYPE: DNA
<213> ORGANISM: Mus sp.

<400> SEQUENCE: 15
gggtattggg cgtcactg                                                 18

<210> SEQ ID NO 16
<211> LENGTH: 18
<212> TYPE: DNA
<213> ORGANISM: Mus sp.

<400> SEQUENCE: 16
ccacggcaga ctggttct                                                 18

<210> SEQ ID NO 17
<211> LENGTH: 18
<212> TYPE: DNA
<213> ORGANISM: Mus sp.

<400> SEQUENCE: 17
atgcacactc tgggagcc                                                 18

<210> SEQ ID NO 18
<211> LENGTH: 19
<212> TYPE: DNA
<213> ORGANISM: Mus sp.

<400> SEQUENCE: 18
ccaaggacct gcaaagagg                                                19
```

-continued

```
<210> SEQ ID NO 19
<211> LENGTH: 18
<212> TYPE: DNA
<213> ORGANISM: Mus sp.

<400> SEQUENCE: 19
agctgccata ccactggc                                                 18

<210> SEQ ID NO 20
<211> LENGTH: 18
<212> TYPE: DNA
<213> ORGANISM: Mus sp.

<400> SEQUENCE: 20
aggcacatgg gatctgga                                                 18

<210> SEQ ID NO 21
<211> LENGTH: 18
<212> TYPE: DNA
<213> ORGANISM: Mus sp.

<400> SEQUENCE: 21
cttcactgca ttcgccct                                                 18

<210> SEQ ID NO 22
<211> LENGTH: 18
<212> TYPE: DNA
<213> ORGANISM: Mus sp.

<400> SEQUENCE: 22
cacaggacaa cggaagca                                                 18

<210> SEQ ID NO 23
<211> LENGTH: 18
<212> TYPE: DNA
<213> ORGANISM: Mus sp.

<400> SEQUENCE: 23
caccgccatg ggttagag                                                 18

<210> SEQ ID NO 24
<211> LENGTH: 18
<212> TYPE: DNA
<213> ORGANISM: Mus sp.

<400> SEQUENCE: 24
tgggatccgg attcagtg                                                 18

<210> SEQ ID NO 25
<211> LENGTH: 20
<212> TYPE: DNA
<213> ORGANISM: Mus sp.

<400> SEQUENCE: 25
aaggaaaaat gcgagcaaga                                               20

<210> SEQ ID NO 26
<211> LENGTH: 19
<212> TYPE: DNA
<213> ORGANISM: Mus sp.

<400> SEQUENCE: 26
tctcccgtct catgtcagg                                                19
```

-continued

```
<210> SEQ ID NO 27
<211> LENGTH: 18
<212> TYPE: DNA
<213> ORGANISM: Mus sp.

<400> SEQUENCE: 27
atgggggaca gacgaggt                                                 18

<210> SEQ ID NO 28
<211> LENGTH: 18
<212> TYPE: DNA
<213> ORGANISM: Mus sp.

<400> SEQUENCE: 28
tgcctaagcc cttcatgg                                                 18

<210> SEQ ID NO 29
<211> LENGTH: 18
<212> TYPE: DNA
<213> ORGANISM: Mus sp.

<400> SEQUENCE: 29
gatgatggct tggccagt                                                 18

<210> SEQ ID NO 30
<211> LENGTH: 18
<212> TYPE: DNA
<213> ORGANISM: Mus sp.

<400> SEQUENCE: 30
tggccaattg ggttcact                                                 18

<210> SEQ ID NO 31
<211> LENGTH: 18
<212> TYPE: DNA
<213> ORGANISM: Mus sp.

<400> SEQUENCE: 31
catttgggaa atggctcg                                                 18

<210> SEQ ID NO 32
<211> LENGTH: 18
<212> TYPE: DNA
<213> ORGANISM: Mus sp.

<400> SEQUENCE: 32
atgggcccaa cattctga                                                 18

<210> SEQ ID NO 33
<211> LENGTH: 18
<212> TYPE: DNA
<213> ORGANISM: Mus sp.

<400> SEQUENCE: 33
aagctctgcg tgtctgcc                                                 18

<210> SEQ ID NO 34
<211> LENGTH: 18
<212> TYPE: DNA
<213> ORGANISM: Mus sp.

<400> SEQUENCE: 34
accacagctg gcttggag                                                 18
```

```
<210> SEQ ID NO 35
<211> LENGTH: 18
<212> TYPE: DNA
<213> ORGANISM: Mus sp.

<400> SEQUENCE: 35
cgtggatcca gccacttc                                                   18

<210> SEQ ID NO 36
<211> LENGTH: 18
<212> TYPE: DNA
<213> ORGANISM: Mus sp.

<400> SEQUENCE: 36
atcattcgct gtggcgtt                                                   18

<210> SEQ ID NO 37
<211> LENGTH: 18
<212> TYPE: DNA
<213> ORGANISM: Mus sp.

<400> SEQUENCE: 37
atctgccgtg cccattta                                                   18

<210> SEQ ID NO 38
<211> LENGTH: 18
<212> TYPE: DNA
<213> ORGANISM: Mus sp.

<400> SEQUENCE: 38
acgagcccat gtccttga                                                   18

<210> SEQ ID NO 39
<211> LENGTH: 18
<212> TYPE: DNA
<213> ORGANISM: Mus sp.

<400> SEQUENCE: 39
ggctcaacag caggaagc                                                   18

<210> SEQ ID NO 40
<211> LENGTH: 22
<212> TYPE: DNA
<213> ORGANISM: Mus sp.

<400> SEQUENCE: 40
ttaatttgaa gacatcatgg ca                                              22

<210> SEQ ID NO 41
<211> LENGTH: 18
<212> TYPE: DNA
<213> ORGANISM: Mus sp.

<400> SEQUENCE: 41
cccagaagcc acagagga                                                   18

<210> SEQ ID NO 42
<211> LENGTH: 18
<212> TYPE: DNA
<213> ORGANISM: Mus sp.

<400> SEQUENCE: 42
```
ttccagccct ttccttcc                                                 18

<210> SEQ ID NO 43
<211> LENGTH: 18
<212> TYPE: DNA
<213> ORGANISM: Mus sp.

<400> SEQUENCE: 43
gtgccatttg acacagcg                                                 18

<210> SEQ ID NO 44
<211> LENGTH: 18
<212> TYPE: DNA
<213> ORGANISM: Mus sp.

<400> SEQUENCE: 44
ctggcctacc ctccacct                                                 18

<210> SEQ ID NO 45
<211> LENGTH: 18
<212> TYPE: DNA
<213> ORGANISM: Mus sp.

<400> SEQUENCE: 45
caagccaggc tggaagaa                                                 18

<210> SEQ ID NO 46
<211> LENGTH: 18
<212> TYPE: DNA
<213> ORGANISM: Mus sp.

<400> SEQUENCE: 46
tgggtcgttt ctgctgtg                                                 18

<210> SEQ ID NO 47
<211> LENGTH: 18
<212> TYPE: DNA
<213> ORGANISM: Mus sp.

<400> SEQUENCE: 47
gacacgcttc gggttcac                                                 18

<210> SEQ ID NO 48
<211> LENGTH: 19
<212> TYPE: DNA
<213> ORGANISM: Mus sp.

<400> SEQUENCE: 48
caactgtgat gaggccagc                                                19

<210> SEQ ID NO 49
<211> LENGTH: 18
<212> TYPE: DNA
<213> ORGANISM: Mus sp.

<400> SEQUENCE: 49
cccagcatta aggctcca                                                 18

<210> SEQ ID NO 50
<211> LENGTH: 18
<212> TYPE: DNA
<213> ORGANISM: Mus sp.

<400> SEQUENCE: 50
aggagcaaca ggggacct                                                18

<210> SEQ ID NO 51
<211> LENGTH: 21
<212> TYPE: DNA
<213> ORGANISM: Mus sp.

<400> SEQUENCE: 51
cagctttgaa cacagggtct t                                            21

<210> SEQ ID NO 52
<211> LENGTH: 21
<212> TYPE: DNA
<213> ORGANISM: Mus sp.

<400> SEQUENCE: 52
agctgactga aattcctccc t                                            21

<210> SEQ ID NO 53
<211> LENGTH: 18
<212> TYPE: DNA
<213> ORGANISM: Mus sp.

<400> SEQUENCE: 53
tcacagtgga catcggga                                                18

<210> SEQ ID NO 54
<211> LENGTH: 18
<212> TYPE: DNA
<213> ORGANISM: Mus sp.

<400> SEQUENCE: 54
cactcaccct gggcatct                                                18

<210> SEQ ID NO 55
<211> LENGTH: 18
<212> TYPE: DNA
<213> ORGANISM: Mus sp.

<400> SEQUENCE: 55
ctactgcagg gaggagcg                                                18

<210> SEQ ID NO 56
<211> LENGTH: 18
<212> TYPE: DNA
<213> ORGANISM: Mus sp.

<400> SEQUENCE: 56
gggtccctct ttagggca                                                18

<210> SEQ ID NO 57
<211> LENGTH: 18
<212> TYPE: DNA
<213> ORGANISM: Mus sp.

<400> SEQUENCE: 57
gtccgtgcag tttggctt                                                18

<210> SEQ ID NO 58
<211> LENGTH: 18
<212> TYPE: DNA
<213> ORGANISM: Mus sp.

```
<400> SEQUENCE: 58
ggtttgggga caggcttt                                              18

<210> SEQ ID NO 59
<211> LENGTH: 19
<212> TYPE: DNA
<213> ORGANISM: Mus sp.

<400> SEQUENCE: 59
cctttgcagt gagttggga                                             19

<210> SEQ ID NO 60
<211> LENGTH: 22
<212> TYPE: DNA
<213> ORGANISM: Mus sp.

<400> SEQUENCE: 60
cgttttgaaa atctgcagag aa                                         22

<210> SEQ ID NO 61
<211> LENGTH: 18
<212> TYPE: DNA
<213> ORGANISM: Mus sp.

<400> SEQUENCE: 61
gcgggaaaca ctcaaagc                                              18

<210> SEQ ID NO 62
<211> LENGTH: 18
<212> TYPE: DNA
<213> ORGANISM: Mus sp.

<400> SEQUENCE: 62
tgctgaagat catgccga                                              18

<210> SEQ ID NO 63
<211> LENGTH: 18
<212> TYPE: DNA
<213> ORGANISM: Mus sp.

<400> SEQUENCE: 63
gccactggag ctgaagga                                              18

<210> SEQ ID NO 64
<211> LENGTH: 18
<212> TYPE: DNA
<213> ORGANISM: Mus sp.

<400> SEQUENCE: 64
tgacctctcc tgcccgta                                              18

<210> SEQ ID NO 65
<211> LENGTH: 18
<212> TYPE: DNA
<213> ORGANISM: Mus sp.

<400> SEQUENCE: 65
ccctgctcct gcatctgt                                              18

<210> SEQ ID NO 66
<211> LENGTH: 18
<212> TYPE: DNA
<213> ORGANISM: Mus sp.
```

<400> SEQUENCE: 66
aaatcttccg acccagcc                                                  18

<210> SEQ ID NO 67
<211> LENGTH: 18
<212> TYPE: DNA
<213> ORGANISM: Mus sp.

<400> SEQUENCE: 67
tcctgctttt cccatcca                                                  18

<210> SEQ ID NO 68
<211> LENGTH: 19
<212> TYPE: DNA
<213> ORGANISM: Mus sp.

<400> SEQUENCE: 68
ccagcaacac aagaccagc                                                 19

<210> SEQ ID NO 69
<211> LENGTH: 18
<212> TYPE: DNA
<213> ORGANISM: Mus sp.

<400> SEQUENCE: 69
tccagtctgg gcaagagg                                                  18

<210> SEQ ID NO 70
<211> LENGTH: 18
<212> TYPE: DNA
<213> ORGANISM: Mus sp.

<400> SEQUENCE: 70
ggcagcagag ggtggata                                                  18

<210> SEQ ID NO 71
<211> LENGTH: 18
<212> TYPE: DNA
<213> ORGANISM: Mus sp.

<400> SEQUENCE: 71
atgtcttccc tgcctccc                                                  18

<210> SEQ ID NO 72
<211> LENGTH: 18
<212> TYPE: DNA
<213> ORGANISM: Mus sp.

<400> SEQUENCE: 72
aagcccaaag cacagacg                                                  18

<210> SEQ ID NO 73
<211> LENGTH: 18
<212> TYPE: DNA
<213> ORGANISM: Mus sp.

<400> SEQUENCE: 73
ggaacatcgg ccttcaaa                                                  18

<210> SEQ ID NO 74
<211> LENGTH: 18
<212> TYPE: DNA

```
<213> ORGANISM: Mus sp.

<400> SEQUENCE: 74
cattccagcg gcatcata                                                 18

<210> SEQ ID NO 75
<211> LENGTH: 18
<212> TYPE: DNA
<213> ORGANISM: Mus sp.

<400> SEQUENCE: 75
cggcacagct ggaatctt                                                 18

<210> SEQ ID NO 76
<211> LENGTH: 18
<212> TYPE: DNA
<213> ORGANISM: Mus sp.

<400> SEQUENCE: 76
ggttgacggc atagccag                                                 18

<210> SEQ ID NO 77
<211> LENGTH: 18
<212> TYPE: DNA
<213> ORGANISM: Mus sp.

<400> SEQUENCE: 77
ctacccagag gcccagtg                                                 18

<210> SEQ ID NO 78
<211> LENGTH: 18
<212> TYPE: DNA
<213> ORGANISM: Mus sp.

<400> SEQUENCE: 78
aactatccac cccctgcc                                                 18

<210> SEQ ID NO 79
<211> LENGTH: 18
<212> TYPE: DNA
<213> ORGANISM: Mus sp.

<400> SEQUENCE: 79
tcctgagggc aaagagga                                                 18

<210> SEQ ID NO 80
<211> LENGTH: 17
<212> TYPE: DNA
<213> ORGANISM: Mus sp.

<400> SEQUENCE: 80
gatttggctt gcctggg                                                  17

<210> SEQ ID NO 81
<211> LENGTH: 19
<212> TYPE: DNA
<213> ORGANISM: Mus sp.

<400> SEQUENCE: 81
aactgaatgg ggaggttgg                                                19

<210> SEQ ID NO 82
<211> LENGTH: 18
```

```
<212> TYPE: DNA
<213> ORGANISM: Mus sp.

<400> SEQUENCE: 82
ttacagccgc ctttcagg                                                 18

<210> SEQ ID NO 83
<211> LENGTH: 18
<212> TYPE: DNA
<213> ORGANISM: Mus sp.

<400> SEQUENCE: 83
ccagccctgg atctcctt                                                 18

<210> SEQ ID NO 84
<211> LENGTH: 19
<212> TYPE: DNA
<213> ORGANISM: Mus sp.

<400> SEQUENCE: 84
gccactttca tcaccacca                                                19

<210> SEQ ID NO 85
<211> LENGTH: 16
<212> TYPE: DNA
<213> ORGANISM: Mus sp.

<400> SEQUENCE: 85
tgcaccgagg ggacac                                                   16

<210> SEQ ID NO 86
<211> LENGTH: 18
<212> TYPE: DNA
<213> ORGANISM: Mus sp.

<400> SEQUENCE: 86
aaccccgcag gaacatct                                                 18

<210> SEQ ID NO 87
<211> LENGTH: 18
<212> TYPE: DNA
<213> ORGANISM: Mus sp.

<400> SEQUENCE: 87
tgccgtcatt ttctgcct                                                 18

<210> SEQ ID NO 88
<211> LENGTH: 19
<212> TYPE: DNA
<213> ORGANISM: Mus sp.

<400> SEQUENCE: 88
cgtggcaatg atctcaaca                                                19

<210> SEQ ID NO 89
<211> LENGTH: 18
<212> TYPE: DNA
<213> ORGANISM: Mus sp.

<400> SEQUENCE: 89
aggaccttga tggagccc                                                 18

<210> SEQ ID NO 90
```

```
<211> LENGTH: 18
<212> TYPE: DNA
<213> ORGANISM: Mus sp.

<400> SEQUENCE: 90
ctggcatcca gggtcaac                                                   18

<210> SEQ ID NO 91
<211> LENGTH: 18
<212> TYPE: DNA
<213> ORGANISM: Mus sp.

<400> SEQUENCE: 91
catgagggag gatgctgg                                                   18

<210> SEQ ID NO 92
<211> LENGTH: 22
<212> TYPE: DNA
<213> ORGANISM: Mus sp.

<400> SEQUENCE: 92
aaatccctgc tatcaaaaat cc                                              22

<210> SEQ ID NO 93
<211> LENGTH: 19
<212> TYPE: DNA
<213> ORGANISM: Mus sp.

<400> SEQUENCE: 93
gctctctgtc tccaagggc                                                  19

<210> SEQ ID NO 94
<211> LENGTH: 18
<212> TYPE: DNA
<213> ORGANISM: Mus sp.

<400> SEQUENCE: 94
actcacaacc cagaccgc                                                   18

<210> SEQ ID NO 95
<211> LENGTH: 18
<212> TYPE: DNA
<213> ORGANISM: Mus sp.

<400> SEQUENCE: 95
ggcctgatga cctggaga                                                   18

<210> SEQ ID NO 96
<211> LENGTH: 18
<212> TYPE: DNA
<213> ORGANISM: Mus sp.

<400> SEQUENCE: 96
tccctacttt tgccgcct                                                   18

<210> SEQ ID NO 97
<211> LENGTH: 17
<212> TYPE: DNA
<213> ORGANISM: Mus sp.

<400> SEQUENCE: 97
gagggctggg accattg                                                    17
```

```
<210> SEQ ID NO 98
<211> LENGTH: 18
<212> TYPE: DNA
<213> ORGANISM: Mus sp.

<400> SEQUENCE: 98
gcagctgccc agaatctt                                                 18

<210> SEQ ID NO 99
<211> LENGTH: 20
<212> TYPE: DNA
<213> ORGANISM: Mus sp.

<400> SEQUENCE: 99
gcagcaggct gtttcttacc                                               20

<210> SEQ ID NO 100
<211> LENGTH: 18
<212> TYPE: DNA
<213> ORGANISM: Mus sp.

<400> SEQUENCE: 100
ttcctcccca ctcatcca                                                 18

<210> SEQ ID NO 101
<211> LENGTH: 18
<212> TYPE: DNA
<213> ORGANISM: Mus sp.

<400> SEQUENCE: 101
aaggagggca aggaccag                                                 18

<210> SEQ ID NO 102
<211> LENGTH: 18
<212> TYPE: DNA
<213> ORGANISM: Mus sp.

<400> SEQUENCE: 102
gagcttgggt cgggattt                                                 18

<210> SEQ ID NO 103
<211> LENGTH: 18
<212> TYPE: DNA
<213> ORGANISM: Mus sp.

<400> SEQUENCE: 103
ggagatggct tgccagaa                                                 18

<210> SEQ ID NO 104
<211> LENGTH: 18
<212> TYPE: DNA
<213> ORGANISM: Mus sp.

<400> SEQUENCE: 104
actcgaattc cgttgcca                                                 18

<210> SEQ ID NO 105
<211> LENGTH: 19
<212> TYPE: DNA
<213> ORGANISM: Mus sp.

<400> SEQUENCE: 105
gccagatcca tgactgacg                                                19
```

```
<210> SEQ ID NO 106
<211> LENGTH: 18
<212> TYPE: DNA
<213> ORGANISM: Mus sp.

<400> SEQUENCE: 106
tttggttgcc tggacgat                                                 18

<210> SEQ ID NO 107
<211> LENGTH: 18
<212> TYPE: DNA
<213> ORGANISM: Mus sp.

<400> SEQUENCE: 107
cagggaacat ccaccagc                                                 18

<210> SEQ ID NO 108
<211> LENGTH: 18
<212> TYPE: DNA
<213> ORGANISM: Mus sp.

<400> SEQUENCE: 108
tagcatcacc ctttgggg                                                 18

<210> SEQ ID NO 109
<211> LENGTH: 18
<212> TYPE: DNA
<213> ORGANISM: Mus sp.

<400> SEQUENCE: 109
cattgtcagt gggcgtca                                                 18

<210> SEQ ID NO 110
<211> LENGTH: 17
<212> TYPE: DNA
<213> ORGANISM: Mus sp.

<400> SEQUENCE: 110
gaatcacagg ctcgccc                                                  17

<210> SEQ ID NO 111
<211> LENGTH: 18
<212> TYPE: DNA
<213> ORGANISM: Mus sp.

<400> SEQUENCE: 111
ccagatctac cgcaggga                                                 18

<210> SEQ ID NO 112
<211> LENGTH: 18
<212> TYPE: DNA
<213> ORGANISM: Mus sp.

<400> SEQUENCE: 112
catgaccaga aggggcag                                                 18

<210> SEQ ID NO 113
<211> LENGTH: 18
<212> TYPE: DNA
<213> ORGANISM: Mus sp.

<400> SEQUENCE: 113
gtcaaccagg gatggcag                                                 18
```

```
<210> SEQ ID NO 114
<211> LENGTH: 18
<212> TYPE: DNA
<213> ORGANISM: Mus sp.

<400> SEQUENCE: 114
cagttttccc cagagcga                                                 18

<210> SEQ ID NO 115
<211> LENGTH: 18
<212> TYPE: DNA
<213> ORGANISM: Mus sp.

<400> SEQUENCE: 115
gctgtggatc tgggctgt                                                 18

<210> SEQ ID NO 116
<211> LENGTH: 18
<212> TYPE: DNA
<213> ORGANISM: Mus sp.

<400> SEQUENCE: 116
cccccattca ttttgcag                                                 18

<210> SEQ ID NO 117
<211> LENGTH: 18
<212> TYPE: DNA
<213> ORGANISM: Mus sp.

<400> SEQUENCE: 117
tggaaacacc cagccact                                                 18

<210> SEQ ID NO 118
<211> LENGTH: 18
<212> TYPE: DNA
<213> ORGANISM: Mus sp.

<400> SEQUENCE: 118
ggcaagactc ctggggat                                                 18

<210> SEQ ID NO 119
<211> LENGTH: 18
<212> TYPE: DNA
<213> ORGANISM: Mus sp.

<400> SEQUENCE: 119
tggatggctt cgtctgtg                                                 18

<210> SEQ ID NO 120
<211> LENGTH: 18
<212> TYPE: DNA
<213> ORGANISM: Mus sp.

<400> SEQUENCE: 120
tgcagctgtg ggttgtgt                                                 18

<210> SEQ ID NO 121
<211> LENGTH: 18
<212> TYPE: DNA
<213> ORGANISM: Mus sp.

<400> SEQUENCE: 121
```
gtgccgacat ctatgccc                                                 18

<210> SEQ ID NO 122
<211> LENGTH: 18
<212> TYPE: DNA
<213> ORGANISM: Mus sp.

<400> SEQUENCE: 122
gcactcccgc atcatctt                                                 18

<210> SEQ ID NO 123
<211> LENGTH: 18
<212> TYPE: DNA
<213> ORGANISM: Mus sp.

<400> SEQUENCE: 123
ggcctcgggt ctttcagt                                                 18

<210> SEQ ID NO 124
<211> LENGTH: 18
<212> TYPE: DNA
<213> ORGANISM: Mus sp.

<400> SEQUENCE: 124
ctaggcagct gggctcac                                                 18

<210> SEQ ID NO 125
<211> LENGTH: 17
<212> TYPE: DNA
<213> ORGANISM: Mus sp.

<400> SEQUENCE: 125 ggagggtgg ctttcaa                                                   17

<210> SEQ ID NO 126
<211> LENGTH: 18
<212> TYPE: DNA
<213> ORGANISM: Mus sp.

<400> SEQUENCE: 126
aagattctcg gggtccca                                                 18

<210> SEQ ID NO 127
<211> LENGTH: 18
<212> TYPE: DNA
<213> ORGANISM: Mus sp.

<400> SEQUENCE: 127
ggaacagctg ggcaaaga                                                 18

<210> SEQ ID NO 128
<211> LENGTH: 18
<212> TYPE: DNA
<213> ORGANISM: Mus sp.

<400> SEQUENCE: 128
gcctgggtcc acactgaa                                                 18

<210> SEQ ID NO 129
<211> LENGTH: 18
<212> TYPE: DNA
<213> ORGANISM: Mus sp.

<400> SEQUENCE: 129

```
gtgggtgttt gggactgc                                                    18

<210> SEQ ID NO 130
<211> LENGTH: 18
<212> TYPE: DNA
<213> ORGANISM: Mus sp.

<400> SEQUENCE: 130
atcaagggga tggtggct                                                    18

<210> SEQ ID NO 131
<211> LENGTH: 18
<212> TYPE: DNA
<213> ORGANISM: Mus sp.

<400> SEQUENCE: 131
tgggggtacc acgactgt                                                    18

<210> SEQ ID NO 132
<211> LENGTH: 18
<212> TYPE: DNA
<213> ORGANISM: Mus sp.

<400> SEQUENCE: 132
gggcgtgtag ccttgaga                                                    18

<210> SEQ ID NO 133
<211> LENGTH: 18
<212> TYPE: DNA
<213> ORGANISM: Mus sp.

<400> SEQUENCE: 133
aatcctcctc gactgggg                                                    18

<210> SEQ ID NO 134
<211> LENGTH: 18
<212> TYPE: DNA
<213> ORGANISM: Mus sp.

<400> SEQUENCE: 134
tgacacctgc aatgctgc                                                    18

<210> SEQ ID NO 135
<211> LENGTH: 18
<212> TYPE: DNA
<213> ORGANISM: Mus sp.

<400> SEQUENCE: 135
ccgatagcct gtggatgg                                                    18

<210> SEQ ID NO 136
<211> LENGTH: 18
<212> TYPE: DNA
<213> ORGANISM: Mus sp.

<400> SEQUENCE: 136
gtcgatgctg atccccac                                                    18

<210> SEQ ID NO 137
<211> LENGTH: 18
<212> TYPE: DNA
<213> ORGANISM: Mus sp.
```

<400> SEQUENCE: 137
agccttcgcc atgtcaac                     18

<210> SEQ ID NO 138
<211> LENGTH: 18
<212> TYPE: DNA
<213> ORGANISM: Mus sp.

<400> SEQUENCE: 138
cgccttcagc gagagaga                     18

<210> SEQ ID NO 139
<211> LENGTH: 18
<212> TYPE: DNA
<213> ORGANISM: Mus sp.

<400> SEQUENCE: 139
gcaaatagcc aaccccag                     18

<210> SEQ ID NO 140
<211> LENGTH: 18
<212> TYPE: DNA
<213> ORGANISM: Mus sp.

<400> SEQUENCE: 140
gttgcaagac tgaccccg                     18

<210> SEQ ID NO 141
<211> LENGTH: 18
<212> TYPE: DNA
<213> ORGANISM: Mus sp.

<400> SEQUENCE: 141
ggagtcccag tcccacct                     18

<210> SEQ ID NO 142
<211> LENGTH: 18
<212> TYPE: DNA
<213> ORGANISM: Mus sp.

<400> SEQUENCE: 142
tggaccttct tctccccc                     18

<210> SEQ ID NO 143
<211> LENGTH: 18
<212> TYPE: DNA
<213> ORGANISM: Mus sp.

<400> SEQUENCE: 143
tccaaccagg tggagcac                     18

<210> SEQ ID NO 144
<211> LENGTH: 19
<212> TYPE: DNA
<213> ORGANISM: Mus sp.

<400> SEQUENCE: 144
tcatctcaga gtccagccg                    19

<210> SEQ ID NO 145
<211> LENGTH: 18
<212> TYPE: DNA
<213> ORGANISM: Mus sp.

```
<400> SEQUENCE: 145
atggcaaact tggacccc                                                18

<210> SEQ ID NO 146
<211> LENGTH: 18
<212> TYPE: DNA
<213> ORGANISM: Mus sp.

<400> SEQUENCE: 146
caagatctgt gcagggca                                                18

<210> SEQ ID NO 147
<211> LENGTH: 18
<212> TYPE: DNA
<213> ORGANISM: Mus sp.

<400> SEQUENCE: 147
cggatttgag cgcttctg                                                18

<210> SEQ ID NO 148
<211> LENGTH: 18
<212> TYPE: DNA
<213> ORGANISM: Mus sp.

<400> SEQUENCE: 148
agtcactggt gggtggga                                                18

<210> SEQ ID NO 149
<211> LENGTH: 18
<212> TYPE: DNA
<213> ORGANISM: Mus sp.

<400> SEQUENCE: 149
tggcaagccc tctcactt                                                18

<210> SEQ ID NO 150
<211> LENGTH: 19
<212> TYPE: DNA
<213> ORGANISM: Mus sp.

<400> SEQUENCE: 150
aaacacacac aaccacgca                                               19

<210> SEQ ID NO 151
<211> LENGTH: 20
<212> TYPE: DNA
<213> ORGANISM: Mus sp.

<400> SEQUENCE: 151
tgctcaaaat tcacgaggtg                                              20

<210> SEQ ID NO 152
<211> LENGTH: 18
<212> TYPE: DNA
<213> ORGANISM: Mus sp.

<400> SEQUENCE: 152
cacgggtacg tcatgctg                                                18

<210> SEQ ID NO 153
<211> LENGTH: 18
<212> TYPE: DNA
```

```
<213> ORGANISM: Mus sp.

<400> SEQUENCE: 153
caccctggtc gcagagtt                                              18

<210> SEQ ID NO 154
<211> LENGTH: 18
<212> TYPE: DNA
<213> ORGANISM: Mus sp.

<400> SEQUENCE: 154
ggttgtgttg gggcattc                                              18

<210> SEQ ID NO 155
<211> LENGTH: 17
<212> TYPE: DNA
<213> ORGANISM: Mus sp.

<400> SEQUENCE: 155
ctggctgtgg gcatctg                                               17

<210> SEQ ID NO 156
<211> LENGTH: 18
<212> TYPE: DNA
<213> ORGANISM: Mus sp.

<400> SEQUENCE: 156
ggagttgtgg tcaagggc                                              18

<210> SEQ ID NO 157
<211> LENGTH: 19
<212> TYPE: DNA
<213> ORGANISM: Mus sp.

<400> SEQUENCE: 157
tgctggtgta ggcgtcttt                                             19

<210> SEQ ID NO 158
<211> LENGTH: 20
<212> TYPE: DNA
<213> ORGANISM: Mus sp.

<400> SEQUENCE: 158
tctcagcaat cacagtgcaa                                            20

<210> SEQ ID NO 159
<211> LENGTH: 19
<212> TYPE: DNA
<213> ORGANISM: Mus sp.

<400> SEQUENCE: 159
tggccttaat gtgcctgtc                                             19

<210> SEQ ID NO 160
<211> LENGTH: 18
<212> TYPE: DNA
<213> ORGANISM: Mus sp.

<400> SEQUENCE: 160
tgctggcttg cccttttac                                             18

<210> SEQ ID NO 161
<211> LENGTH: 21
```

```
<212> TYPE: DNA
<213> ORGANISM: Mus sp.

<400> SEQUENCE: 161
tggcttgtta catgagcaaa a                                              21

<210> SEQ ID NO 162
<211> LENGTH: 19
<212> TYPE: DNA
<213> ORGANISM: Mus sp.

<400> SEQUENCE: 162
ccgatgtgtg ctgtgactg                                                 19

<210> SEQ ID NO 163
<211> LENGTH: 20
<212> TYPE: DNA
<213> ORGANISM: Mus sp.

<400> SEQUENCE: 163
ggatacgaat gggactggaa                                                20

<210> SEQ ID NO 164
<211> LENGTH: 18
<212> TYPE: DNA
<213> ORGANISM: Mus sp.

<400> SEQUENCE: 164
ccaacgcttg aactggct                                                  18

<210> SEQ ID NO 165
<211> LENGTH: 21
<212> TYPE: DNA
<213> ORGANISM: Mus sp.

<400> SEQUENCE: 165
ttccctgcaa tagaagtctg g                                              21

<210> SEQ ID NO 166
<211> LENGTH: 21
<212> TYPE: DNA
<213> ORGANISM: Mus sp.

<400> SEQUENCE: 166
tgaagtaatc tgtcctcccg a                                              21

<210> SEQ ID NO 167
<211> LENGTH: 18
<212> TYPE: DNA
<213> ORGANISM: Mus sp.

<400> SEQUENCE: 167
ccggcctact catcctga                                                  18

<210> SEQ ID NO 168
<211> LENGTH: 22
<212> TYPE: DNA
<213> ORGANISM: Mus sp.

<400> SEQUENCE: 168
aactttattg gagcaacaca cg                                             22

<210> SEQ ID NO 169
```

```
<211> LENGTH: 18
<212> TYPE: DNA
<213> ORGANISM: Mus sp.

<400> SEQUENCE: 169
gttgtgatgc caaagggc                                                 18

<210> SEQ ID NO 170
<211> LENGTH: 18
<212> TYPE: DNA
<213> ORGANISM: Mus sp.

<400> SEQUENCE: 170
caagcgtgca ttggactg                                                 18

<210> SEQ ID NO 171
<211> LENGTH: 18
<212> TYPE: DNA
<213> ORGANISM: Mus sp.

<400> SEQUENCE: 171
tccaatcttg ccaccacc                                                 18

<210> SEQ ID NO 172
<211> LENGTH: 18
<212> TYPE: DNA
<213> ORGANISM: Mus sp.

<400> SEQUENCE: 172
ttccagcact ttgggagc                                                 18

<210> SEQ ID NO 173
<211> LENGTH: 18
<212> TYPE: DNA
<213> ORGANISM: Mus sp.

<400> SEQUENCE: 173
ccaggttttg caccaagg                                                 18

<210> SEQ ID NO 174
<211> LENGTH: 18
<212> TYPE: DNA
<213> ORGANISM: Mus sp.

<400> SEQUENCE: 174
cctcccagac ccctctgt                                                 18

<210> SEQ ID NO 175
<211> LENGTH: 18
<212> TYPE: DNA
<213> ORGANISM: Mus sp.

<400> SEQUENCE: 175
cactgatgtg cctgctgc                                                 18

<210> SEQ ID NO 176
<211> LENGTH: 18
<212> TYPE: DNA
<213> ORGANISM: Mus sp.

<400> SEQUENCE: 176
tgaggcgcag ctttctct                                                 18
```

```
<210> SEQ ID NO 177
<211> LENGTH: 18
<212> TYPE: DNA
<213> ORGANISM: Mus sp.

<400> SEQUENCE: 177
taccatccca gggaagca                                                 18

<210> SEQ ID NO 178
<211> LENGTH: 18
<212> TYPE: DNA
<213> ORGANISM: Mus sp.

<400> SEQUENCE: 178
gcaggttggc agcagtct                                                 18

<210> SEQ ID NO 179
<211> LENGTH: 18
<212> TYPE: DNA
<213> ORGANISM: Mus sp.

<400> SEQUENCE: 179
gcttccgaaa tctgccaa                                                 18

<210> SEQ ID NO 180
<211> LENGTH: 18
<212> TYPE: DNA
<213> ORGANISM: Mus sp.

<400> SEQUENCE: 180
cgccatccat ggagttct                                                 18

<210> SEQ ID NO 181
<211> LENGTH: 18
<212> TYPE: DNA
<213> ORGANISM: Mus sp.

<400> SEQUENCE: 181
ggccatcaaa gaagccct                                                 18

<210> SEQ ID NO 182
<211> LENGTH: 18
<212> TYPE: DNA
<213> ORGANISM: Mus sp.

<400> SEQUENCE: 182
gctgtcatgt tcaaggcg                                                 18

<210> SEQ ID NO 183
<211> LENGTH: 18
<212> TYPE: DNA
<213> ORGANISM: Mus sp.

<400> SEQUENCE: 183
gttgaccccg cactgtct                                                 18

<210> SEQ ID NO 184
<211> LENGTH: 18
<212> TYPE: DNA
<213> ORGANISM: Mus sp.

<400> SEQUENCE: 184
attccgagga ggctttgg                                                 18
```

```
<210> SEQ ID NO 185
<211> LENGTH: 18
<212> TYPE: DNA
<213> ORGANISM: Mus sp.

<400> SEQUENCE: 185
cctgtggacc cagatgct                                                       18

<210> SEQ ID NO 186
<211> LENGTH: 18
<212> TYPE: DNA
<213> ORGANISM: Mus sp.

<400> SEQUENCE: 186
gacggagttc agctccca                                                       18

<210> SEQ ID NO 187
<211> LENGTH: 22
<212> TYPE: DNA
<213> ORGANISM: Mus sp.

<400> SEQUENCE: 187
gattctgaga aaggagtacg ca                                                  22

<210> SEQ ID NO 188
<211> LENGTH: 18
<212> TYPE: DNA
<213> ORGANISM: Mus sp.

<400> SEQUENCE: 188
gccagtgttc cagttgcc                                                       18

<210> SEQ ID NO 189
<211> LENGTH: 18
<212> TYPE: DNA
<213> ORGANISM: Mus sp.

<400> SEQUENCE: 189
gcgagagagc gagtgagc                                                       18

<210> SEQ ID NO 190
<211> LENGTH: 18
<212> TYPE: DNA
<213> ORGANISM: Mus sp.

<400> SEQUENCE: 190
ccacggaagc tagcctga                                                       18

<210> SEQ ID NO 191
<211> LENGTH: 18
<212> TYPE: DNA
<213> ORGANISM: Mus sp.

<400> SEQUENCE: 191
atggagcaga cgcaatcc                                                       18

<210> SEQ ID NO 192
<211> LENGTH: 18
<212> TYPE: DNA
<213> ORGANISM: Mus sp.

<400> SEQUENCE: 192
aaaggccgaa gttttggg                                                       18
```

<210> SEQ ID NO 193
<211> LENGTH: 18
<212> TYPE: DNA
<213> ORGANISM: Mus sp.

<400> SEQUENCE: 193
gtgggcatct gtggtggt                                            18

<210> SEQ ID NO 194
<211> LENGTH: 18
<212> TYPE: DNA
<213> ORGANISM: Mus sp.

<400> SEQUENCE: 194
tggagcggga gcatagtc                                            18

<210> SEQ ID NO 195
<211> LENGTH: 18
<212> TYPE: DNA
<213> ORGANISM: Mus sp.

<400> SEQUENCE: 195
cagagtccca ctggaccg                                            18

<210> SEQ ID NO 196
<211> LENGTH: 18
<212> TYPE: DNA
<213> ORGANISM: Mus sp.

<400> SEQUENCE: 196
aggcacaact gtcagggc                                            18

<210> SEQ ID NO 197
<211> LENGTH: 18
<212> TYPE: DNA
<213> ORGANISM: Mus sp.

<400> SEQUENCE: 197
gcagccaact caaaaggc                                            18

<210> SEQ ID NO 198
<211> LENGTH: 18
<212> TYPE: DNA
<213> ORGANISM: Mus sp.

<400> SEQUENCE: 198
gtgatgctcc ctggttgg                                            18

<210> SEQ ID NO 199
<211> LENGTH: 18
<212> TYPE: DNA
<213> ORGANISM: Mus sp.

<400> SEQUENCE: 199
tcagacaggt tccagccc                                            18

<210> SEQ ID NO 200
<211> LENGTH: 18
<212> TYPE: DNA
<213> ORGANISM: Mus sp.

<400> SEQUENCE: 200

```
tcttctcgct cagacgca                                                    18

<210> SEQ ID NO 201
<211> LENGTH: 18
<212> TYPE: DNA
<213> ORGANISM: Mus sp.

<400> SEQUENCE: 201
ccttcagccc cagtggta                                                    18

<210> SEQ ID NO 202
<211> LENGTH: 18
<212> TYPE: DNA
<213> ORGANISM: Mus sp.

<400> SEQUENCE: 202
agctcagcct gggttcct                                                    18

<210> SEQ ID NO 203
<211> LENGTH: 18
<212> TYPE: DNA
<213> ORGANISM: Mus sp.

<400> SEQUENCE: 203
aagggacact tcccggag                                                    18

<210> SEQ ID NO 204
<211> LENGTH: 18
<212> TYPE: DNA
<213> ORGANISM: Mus sp.

<400> SEQUENCE: 204
tttcctgcag ttccccag                                                    18

<210> SEQ ID NO 205
<211> LENGTH: 17
<212> TYPE: DNA
<213> ORGANISM: Mus sp.

<400> SEQUENCE: 205
cggtgcggga actatcc                                                     17

<210> SEQ ID NO 206
<211> LENGTH: 21
<212> TYPE: DNA
<213> ORGANISM: Mus sp.

<400> SEQUENCE: 206
catttggtca agaactccct g                                                21

<210> SEQ ID NO 207
<211> LENGTH: 18
<212> TYPE: DNA
<213> ORGANISM: Mus sp.

<400> SEQUENCE: 207
gaaggagctg tcaggcca                                                    18

<210> SEQ ID NO 208
<211> LENGTH: 18
<212> TYPE: DNA
<213> ORGANISM: Mus sp.

<400> SEQUENCE: 208
```

-continued gcatccaggg atgtggac                                          18

<210> SEQ ID NO 209
<211> LENGTH: 18
<212> TYPE: DNA
<213> ORGANISM: Mus sp.

<400> SEQUENCE: 209
gtccttccaa tgaccccc                                          18

<210> SEQ ID NO 210
<211> LENGTH: 19
<212> TYPE: DNA
<213> ORGANISM: Mus sp.

<400> SEQUENCE: 210
cctccagggc caagaatag                                         19

<210> SEQ ID NO 211
<211> LENGTH: 18
<212> TYPE: DNA
<213> ORGANISM: Mus sp.

<400> SEQUENCE: 211
gtctgccgga gcatcagt                                          18

<210> SEQ ID NO 212
<211> LENGTH: 18
<212> TYPE: DNA
<213> ORGANISM: Mus sp.

<400> SEQUENCE: 212
taatgtggag ggaggccc                                          18

<210> SEQ ID NO 213
<211> LENGTH: 18
<212> TYPE: DNA
<213> ORGANISM: Mus sp.

<400> SEQUENCE: 213
caaggagatg gcgtggat                                          18

<210> SEQ ID NO 214
<211> LENGTH: 18
<212> TYPE: DNA
<213> ORGANISM: Mus sp.

<400> SEQUENCE: 214
tgggatcagc aactgggt                                          18

<210> SEQ ID NO 215
<211> LENGTH: 18
<212> TYPE: DNA
<213> ORGANISM: Mus sp.

<400> SEQUENCE: 215
tggccctctg gtctcaac                                          18

<210> SEQ ID NO 216
<211> LENGTH: 19
<212> TYPE: DNA
<213> ORGANISM: Mus sp.

```
<400> SEQUENCE: 216
tttcatactc agcccgacg                                              19

<210> SEQ ID NO 217
<211> LENGTH: 18
<212> TYPE: DNA
<213> ORGANISM: Mus sp.

<400> SEQUENCE: 217
aagaactttt gggccgct                                               18

<210> SEQ ID NO 218
<211> LENGTH: 18
<212> TYPE: DNA
<213> ORGANISM: Mus sp.

<400> SEQUENCE: 218
gcactgtggc tgggagtt                                               18

<210> SEQ ID NO 219
<211> LENGTH: 20
<212> TYPE: DNA
<213> ORGANISM: Mus sp.

<400> SEQUENCE: 219
gctgaaaacc caaaatacga                                             20

<210> SEQ ID NO 220
<211> LENGTH: 18
<212> TYPE: DNA
<213> ORGANISM: Mus sp.

<400> SEQUENCE: 220
acttcactgc tgtgcccc                                               18

<210> SEQ ID NO 221
<211> LENGTH: 18
<212> TYPE: DNA
<213> ORGANISM: Mus sp.

<400> SEQUENCE: 221
atcaggacgc gcaaacat                                               18

<210> SEQ ID NO 222
<211> LENGTH: 18
<212> TYPE: DNA
<213> ORGANISM: Mus sp.

<400> SEQUENCE: 222
gacgtggaac ggttgagg                                               18

<210> SEQ ID NO 223
<211> LENGTH: 17
<212> TYPE: DNA
<213> ORGANISM: Mus sp.

<400> SEQUENCE: 223
cactgcaagg cagcagg                                                17

<210> SEQ ID NO 224
<211> LENGTH: 22
<212> TYPE: DNA
<213> ORGANISM: Mus sp.
```

<400> SEQUENCE: 224
cgtttggttt gttgttgttt tg                                    22

<210> SEQ ID NO 225
<211> LENGTH: 18
<212> TYPE: DNA
<213> ORGANISM: Mus sp.

<400> SEQUENCE: 225
tcggacggca atttcact                                         18

<210> SEQ ID NO 226
<211> LENGTH: 18
<212> TYPE: DNA
<213> ORGANISM: Mus sp.

<400> SEQUENCE: 226
gttgctggag atgctggg                                         18

<210> SEQ ID NO 227
<211> LENGTH: 18
<212> TYPE: DNA
<213> ORGANISM: Mus sp.

<400> SEQUENCE: 227
actgatcgtc gcgtctcc                                         18

<210> SEQ ID NO 228
<211> LENGTH: 21
<212> TYPE: DNA
<213> ORGANISM: Mus sp.

<400> SEQUENCE: 228
ttggtctgtc ttccaagtgc t                                     21

<210> SEQ ID NO 229
<211> LENGTH: 18
<212> TYPE: DNA
<213> ORGANISM: Mus sp.

<400> SEQUENCE: 229
ctgaccaccc gatgcagt                                         18

<210> SEQ ID NO 230
<211> LENGTH: 18
<212> TYPE: DNA
<213> ORGANISM: Mus sp.

<400> SEQUENCE: 230
tccaggtaac gctgcaca                                         18

<210> SEQ ID NO 231
<211> LENGTH: 18
<212> TYPE: DNA
<213> ORGANISM: Mus sp.

<400> SEQUENCE: 231
ggctgcagct gaacatca                                         18

<210> SEQ ID NO 232
<211> LENGTH: 20
<212> TYPE: DNA

<213> ORGANISM: Mus sp.

<400> SEQUENCE: 232
aagctgagcc attagccaaa                                          20

<210> SEQ ID NO 233
<211> LENGTH: 18
<212> TYPE: DNA
<213> ORGANISM: Mus sp.

<400> SEQUENCE: 233
aggcaggagg atggcttc                                            18

<210> SEQ ID NO 234
<211> LENGTH: 17
<212> TYPE: DNA
<213> ORGANISM: Mus sp.

<400> SEQUENCE: 234 tcatggggt ggaggac                                              17

<210> SEQ ID NO 235
<211> LENGTH: 18
<212> TYPE: DNA
<213> ORGANISM: Mus sp.

<400> SEQUENCE: 235
ggtttgccca tcaactcg                                            18

<210> SEQ ID NO 236
<211> LENGTH: 18
<212> TYPE: DNA
<213> ORGANISM: Mus sp.

<400> SEQUENCE: 236
ggatccattt gggcctttt                                           18

<210> SEQ ID NO 237
<211> LENGTH: 18
<212> TYPE: DNA
<213> ORGANISM: Mus sp.

<400> SEQUENCE: 237
gcaaaggaca ggactggg                                            18

<210> SEQ ID NO 238
<211> LENGTH: 18
<212> TYPE: DNA
<213> ORGANISM: Mus sp.

<400> SEQUENCE: 238
tttgacaccc tccccaaa                                            18

<210> SEQ ID NO 239
<211> LENGTH: 18
<212> TYPE: DNA
<213> ORGANISM: Mus sp.

<400> SEQUENCE: 239
gcaggcaaat gcctcaac                                            18

<210> SEQ ID NO 240
<211> LENGTH: 18

```
<212> TYPE: DNA
<213> ORGANISM: Mus sp.

<400> SEQUENCE: 240
gtggccattg tgcagaca                                                 18

<210> SEQ ID NO 241
<211> LENGTH: 17
<212> TYPE: DNA
<213> ORGANISM: Mus sp.

<400> SEQUENCE: 241
ctcgagcagc tgggacc                                                  17

<210> SEQ ID NO 242
<211> LENGTH: 18
<212> TYPE: DNA
<213> ORGANISM: Mus sp.

<400> SEQUENCE: 242
ccagcaggga ccctcttt                                                 18

<210> SEQ ID NO 243
<211> LENGTH: 18
<212> TYPE: DNA
<213> ORGANISM: Mus sp.

<400> SEQUENCE: 243
tcattcgcta tgcagcca                                                 18

<210> SEQ ID NO 244
<211> LENGTH: 18
<212> TYPE: DNA
<213> ORGANISM: Mus sp.

<400> SEQUENCE: 244
ggcctgttgt gccaattc                                                 18

<210> SEQ ID NO 245
<211> LENGTH: 18
<212> TYPE: DNA
<213> ORGANISM: Mus sp.

<400> SEQUENCE: 245
aagaacccca aagcaggg                                                 18

<210> SEQ ID NO 246
<211> LENGTH: 18
<212> TYPE: DNA
<213> ORGANISM: Mus sp.

<400> SEQUENCE: 246
cagcgatctc tgagggga                                                 18

<210> SEQ ID NO 247
<211> LENGTH: 18
<212> TYPE: DNA
<213> ORGANISM: Mus sp.

<400> SEQUENCE: 247
tctccactct ggccaaca                                                 18

<210> SEQ ID NO 248
```

```
<211> LENGTH: 19
<212> TYPE: DNA
<213> ORGANISM: Mus sp.

<400> SEQUENCE: 248
ctgcatccag gtcaggaga                                                  19

<210> SEQ ID NO 249
<211> LENGTH: 18
<212> TYPE: DNA
<213> ORGANISM: Mus sp.

<400> SEQUENCE: 249
tggcctagtc tccccgat                                                   18

<210> SEQ ID NO 250
<211> LENGTH: 17
<212> TYPE: DNA
<213> ORGANISM: Mus sp.

<400> SEQUENCE: 250
cgagcggttt gcactgt                                                    17

<210> SEQ ID NO 251
<211> LENGTH: 18
<212> TYPE: DNA
<213> ORGANISM: Mus sp.

<400> SEQUENCE: 251
ctgtggaaga tgccaggg                                                   18

<210> SEQ ID NO 252
<211> LENGTH: 18
<212> TYPE: DNA
<213> ORGANISM: Mus sp.

<400> SEQUENCE: 252
gtggttggtg gcagtggt                                                   18

<210> SEQ ID NO 253
<211> LENGTH: 18
<212> TYPE: DNA
<213> ORGANISM: Mus sp.

<400> SEQUENCE: 253
gttcgtggaa ccccagtg                                                   18

<210> SEQ ID NO 254
<211> LENGTH: 18
<212> TYPE: DNA
<213> ORGANISM: Mus sp.

<400> SEQUENCE: 254
tccccttgac tctggctg                                                   18

<210> SEQ ID NO 255
<211> LENGTH: 18
<212> TYPE: DNA
<213> ORGANISM: Mus sp.

<400> SEQUENCE: 255
ggccacagag cttcagga                                                   18
```

```
<210> SEQ ID NO 256
<211> LENGTH: 18
<212> TYPE: DNA
<213> ORGANISM: Mus sp.

<400> SEQUENCE: 256
ccagctcact cttggga                                                  18

<210> SEQ ID NO 257
<211> LENGTH: 18
<212> TYPE: DNA
<213> ORGANISM: Mus sp.

<400> SEQUENCE: 257
tctgactctt gcaggccc                                                 18

<210> SEQ ID NO 258
<211> LENGTH: 18
<212> TYPE: DNA
<213> ORGANISM: Mus sp.

<400> SEQUENCE: 258
tggcacaatc caaagcct                                                 18

<210> SEQ ID NO 259
<211> LENGTH: 18
<212> TYPE: DNA
<213> ORGANISM: Mus sp.

<400> SEQUENCE: 259
actatgcgtg ggctggag                                                 18

<210> SEQ ID NO 260
<211> LENGTH: 18
<212> TYPE: DNA
<213> ORGANISM: Mus sp.

<400> SEQUENCE: 260
gcaggagctg gtgcaagt                                                 18

<210> SEQ ID NO 261
<211> LENGTH: 18
<212> TYPE: DNA
<213> ORGANISM: Mus sp.

<400> SEQUENCE: 261
gcctccagcc catcctat                                                 18

<210> SEQ ID NO 262
<211> LENGTH: 19
<212> TYPE: DNA
<213> ORGANISM: Mus sp.

<400> SEQUENCE: 262
tgagggattt attcgggga                                                19

<210> SEQ ID NO 263
<211> LENGTH: 18
<212> TYPE: DNA
<213> ORGANISM: Mus sp.

<400> SEQUENCE: 263
tacgagtgca cctgccaa                                                 18
```

```
<210> SEQ ID NO 264
<211> LENGTH: 18
<212> TYPE: DNA
<213> ORGANISM: Mus sp.

<400> SEQUENCE: 264
gcagcgtcct ggaatgtc                                                 18

<210> SEQ ID NO 265
<211> LENGTH: 18
<212> TYPE: DNA
<213> ORGANISM: Mus sp.

<400> SEQUENCE: 265
atcacgtgac cacagccc                                                 18

<210> SEQ ID NO 266
<211> LENGTH: 18
<212> TYPE: DNA
<213> ORGANISM: Mus sp.

<400> SEQUENCE: 266
ctctgatacc ctgccgga                                                 18

<210> SEQ ID NO 267
<211> LENGTH: 18
<212> TYPE: DNA
<213> ORGANISM: Mus sp.

<400> SEQUENCE: 267
tctgggcttc tcctcctg                                                 18

<210> SEQ ID NO 268
<211> LENGTH: 19
<212> TYPE: DNA
<213> ORGANISM: Mus sp.

<400> SEQUENCE: 268
tccttttgcc agttcctcc                                                19

<210> SEQ ID NO 269
<211> LENGTH: 18
<212> TYPE: DNA
<213> ORGANISM: Mus sp.

<400> SEQUENCE: 269
ggggctgagc tgcagagt                                                 18

<210> SEQ ID NO 270
<211> LENGTH: 18
<212> TYPE: DNA
<213> ORGANISM: Mus sp.

<400> SEQUENCE: 270
tggtgttcag ctgcagga                                                 18

<210> SEQ ID NO 271
<211> LENGTH: 18
<212> TYPE: DNA
<213> ORGANISM: Mus sp.

<400> SEQUENCE: 271
aaggctggcc tcgaactt                                                 18
```

<210> SEQ ID NO 272
<211> LENGTH: 18
<212> TYPE: DNA
<213> ORGANISM: Mus sp.

<400> SEQUENCE: 272
gggcagggaa ccaaactt                                                 18

<210> SEQ ID NO 273
<211> LENGTH: 20
<212> TYPE: DNA
<213> ORGANISM: Mus sp.

<400> SEQUENCE: 273
tggtgacata catccttgcc                                               20

<210> SEQ ID NO 274
<211> LENGTH: 18
<212> TYPE: DNA
<213> ORGANISM: Mus sp.

<400> SEQUENCE: 274
tgtgtggcat tggtcagc                                                 18

<210> SEQ ID NO 275
<211> LENGTH: 18
<212> TYPE: DNA
<213> ORGANISM: Mus sp.

<400> SEQUENCE: 275
gcttcaccca gaacaccg                                                 18

<210> SEQ ID NO 276
<211> LENGTH: 18
<212> TYPE: DNA
<213> ORGANISM: Mus sp.

<400> SEQUENCE: 276
cccatatgtt ggtgccgt                                                 18

<210> SEQ ID NO 277
<211> LENGTH: 18
<212> TYPE: DNA
<213> ORGANISM: Mus sp.

<400> SEQUENCE: 277
tgccgaatac accaagca                                                 18

<210> SEQ ID NO 278
<211> LENGTH: 18
<212> TYPE: DNA
<213> ORGANISM: Mus sp.

<400> SEQUENCE: 278
tccgccggtt ctttacaa                                                 18

<210> SEQ ID NO 279
<211> LENGTH: 18
<212> TYPE: DNA
<213> ORGANISM: Mus sp.

<400> SEQUENCE: 279

```
ggggcaggta gttgctca                                                    18
```

<210> SEQ ID NO 280
<211> LENGTH: 19
<212> TYPE: DNA
<213> ORGANISM: Mus sp.

<400> SEQUENCE: 280

```
tcgggatcaa ggacacaga                                                   19
```

<210> SEQ ID NO 281
<211> LENGTH: 19
<212> TYPE: DNA
<213> ORGANISM: Mus sp.

<400> SEQUENCE: 281

```
ccatcttgga gtgcgagaa                                                   19
```

<210> SEQ ID NO 282
<211> LENGTH: 18
<212> TYPE: DNA
<213> ORGANISM: Mus sp.

<400> SEQUENCE: 282

```
gctcagtcag gcccttca                                                    18
```

<210> SEQ ID NO 283
<211> LENGTH: 18
<212> TYPE: DNA
<213> ORGANISM: Mus sp.

<400> SEQUENCE: 283

```
tgtgctggcc atatccct                                                    18
```

<210> SEQ ID NO 284
<211> LENGTH: 18
<212> TYPE: DNA
<213> ORGANISM: Mus sp.

<400> SEQUENCE: 284

```
aggcacagga gcagttgg                                                    18
```

<210> SEQ ID NO 285
<211> LENGTH: 18
<212> TYPE: DNA
<213> ORGANISM: Mus sp.

<400> SEQUENCE: 285

```
agctccacgg ctacatgg                                                    18
```

<210> SEQ ID NO 286
<211> LENGTH: 18
<212> TYPE: DNA
<213> ORGANISM: Mus sp.

<400> SEQUENCE: 286

```
cgtttcggag cttcagga                                                    18
```

<210> SEQ ID NO 287
<211> LENGTH: 18
<212> TYPE: DNA
<213> ORGANISM: Mus sp.

<400> SEQUENCE: 287
caagtgattg ccgcagtg                                                18

<210> SEQ ID NO 288
<211> LENGTH: 20
<212> TYPE: DNA
<213> ORGANISM: Mus sp.

<400> SEQUENCE: 288
cattggtcat acatgcaggg                                              20

<210> SEQ ID NO 289
<211> LENGTH: 18
<212> TYPE: DNA
<213> ORGANISM: Mus sp.

<400> SEQUENCE: 289
cggccgatca taggatgt                                                18

<210> SEQ ID NO 290
<211> LENGTH: 18
<212> TYPE: DNA
<213> ORGANISM: Mus sp.

<400> SEQUENCE: 290
ttccctggga gctgtctg                                                18

<210> SEQ ID NO 291
<211> LENGTH: 19
<212> TYPE: DNA
<213> ORGANISM: Mus sp.

<400> SEQUENCE: 291
cgaaacaaca gcaaatgcc                                               19

<210> SEQ ID NO 292
<211> LENGTH: 18
<212> TYPE: DNA
<213> ORGANISM: Mus sp.

<400> SEQUENCE: 292
cggtgaaccg tccttgtc                                                18

<210> SEQ ID NO 293
<211> LENGTH: 18
<212> TYPE: DNA
<213> ORGANISM: Mus sp.

<400> SEQUENCE: 293
acccgaggtc cagtggta                                                18

<210> SEQ ID NO 294
<211> LENGTH: 18
<212> TYPE: DNA
<213> ORGANISM: Mus sp.

<400> SEQUENCE: 294
tctcattccg agggctca                                                18

<210> SEQ ID NO 295
<211> LENGTH: 18
<212> TYPE: DNA
<213> ORGANISM: Mus sp.

```
<400> SEQUENCE: 295
tgcaagagag gtttccga                                          18

<210> SEQ ID NO 296
<211> LENGTH: 18
<212> TYPE: DNA
<213> ORGANISM: Mus sp.

<400> SEQUENCE: 296
gttcccaagg aggtggct                                          18

<210> SEQ ID NO 297
<211> LENGTH: 18
<212> TYPE: DNA
<213> ORGANISM: Mus sp.

<400> SEQUENCE: 297
agcagaagca cccacagg                                          18

<210> SEQ ID NO 298
<211> LENGTH: 18
<212> TYPE: DNA
<213> ORGANISM: Mus sp.

<400> SEQUENCE: 298
tcctggcact gctcacaa                                          18

<210> SEQ ID NO 299
<211> LENGTH: 20
<212> TYPE: DNA
<213> ORGANISM: Mus sp.

<400> SEQUENCE: 299
tggaaaattc tgcgagtgtg                                        20

<210> SEQ ID NO 300
<211> LENGTH: 18
<212> TYPE: DNA
<213> ORGANISM: Mus sp.

<400> SEQUENCE: 300
ttggcccttg aaacttgg                                          18

<210> SEQ ID NO 301
<211> LENGTH: 18
<212> TYPE: DNA
<213> ORGANISM: Mus sp.

<400> SEQUENCE: 301
ccctccaaaa gggcctaa                                          18

<210> SEQ ID NO 302
<211> LENGTH: 19
<212> TYPE: DNA
<213> ORGANISM: Mus sp.

<400> SEQUENCE: 302
ggcaaaaaca aagtcccca                                         19

<210> SEQ ID NO 303
<211> LENGTH: 18
<212> TYPE: DNA
<213> ORGANISM: Mus sp.
```

```
<400> SEQUENCE: 303
agtgcacaga agggctgc                                                   18

<210> SEQ ID NO 304
<211> LENGTH: 19
<212> TYPE: DNA
<213> ORGANISM: Mus sp.

<400> SEQUENCE: 304
ccagcaaatg gagaaatgg                                                  19

<210> SEQ ID NO 305
<211> LENGTH: 18
<212> TYPE: DNA
<213> ORGANISM: Mus sp.

<400> SEQUENCE: 305
aggacgcctg ctctacca                                                   18

<210> SEQ ID NO 306
<211> LENGTH: 18
<212> TYPE: DNA
<213> ORGANISM: Mus sp.

<400> SEQUENCE: 306
gctgcaaatc tgtcccca                                                   18

<210> SEQ ID NO 307
<211> LENGTH: 18
<212> TYPE: DNA
<213> ORGANISM: Mus sp.

<400> SEQUENCE: 307
cggagaagca gaagcacc                                                   18

<210> SEQ ID NO 308
<211> LENGTH: 18
<212> TYPE: DNA
<213> ORGANISM: Mus sp.

<400> SEQUENCE: 308
actttgggcc cactctga                                                   18

<210> SEQ ID NO 309
<211> LENGTH: 18
<212> TYPE: DNA
<213> ORGANISM: Mus sp.

<400> SEQUENCE: 309
gccgcttaga ggctcatc                                                   18

<210> SEQ ID NO 310
<211> LENGTH: 18
<212> TYPE: DNA
<213> ORGANISM: Mus sp.

<400> SEQUENCE: 310
tgctccagct cgacaatg                                                   18

<210> SEQ ID NO 311
<211> LENGTH: 18
<212> TYPE: DNA
```

```
<213> ORGANISM: Mus sp.

<400> SEQUENCE: 311
tggggtgcca tccagtat                                                 18

<210> SEQ ID NO 312
<211> LENGTH: 18
<212> TYPE: DNA
<213> ORGANISM: Mus sp.

<400> SEQUENCE: 312
attccacatg gctttggc                                                 18

<210> SEQ ID NO 313
<211> LENGTH: 19
<212> TYPE: DNA
<213> ORGANISM: Mus sp.

<400> SEQUENCE: 313
tcagccattt caccaggag                                                19

<210> SEQ ID NO 314
<211> LENGTH: 18
<212> TYPE: DNA
<213> ORGANISM: Mus sp.

<400> SEQUENCE: 314
taacgttttc gctcccca                                                 18

<210> SEQ ID NO 315
<211> LENGTH: 18
<212> TYPE: DNA
<213> ORGANISM: Mus sp.

<400> SEQUENCE: 315
ggggtctagc ccaattcc                                                 18

<210> SEQ ID NO 316
<211> LENGTH: 18
<212> TYPE: DNA
<213> ORGANISM: Mus sp.

<400> SEQUENCE: 316
gccggggaga gaggttag                                                 18

<210> SEQ ID NO 317
<211> LENGTH: 21
<212> TYPE: DNA
<213> ORGANISM: Mus sp.

<400> SEQUENCE: 317
tggtaagctt tccttctttc c                                             21

<210> SEQ ID NO 318
<211> LENGTH: 19
<212> TYPE: DNA
<213> ORGANISM: Mus sp.

<400> SEQUENCE: 318
tcatcacatc aggaagggc                                                19

<210> SEQ ID NO 319
<211> LENGTH: 18
```

```
<212> TYPE: DNA
<213> ORGANISM: Mus sp.

<400> SEQUENCE: 319
gcaccccatc ctcagcta                                               18

<210> SEQ ID NO 320
<211> LENGTH: 18
<212> TYPE: DNA
<213> ORGANISM: Mus sp.

<400> SEQUENCE: 320
caagtccagc tcggtggt                                               18

<210> SEQ ID NO 321
<211> LENGTH: 18
<212> TYPE: DNA
<213> ORGANISM: Mus sp.

<400> SEQUENCE: 321
taagcacggc tgggacat                                               18

<210> SEQ ID NO 322
<211> LENGTH: 18
<212> TYPE: DNA
<213> ORGANISM: Mus sp.

<400> SEQUENCE: 322
cagcagagct gcccttgt                                               18

<210> SEQ ID NO 323
<211> LENGTH: 18
<212> TYPE: DNA
<213> ORGANISM: Mus sp.

<400> SEQUENCE: 323
ctccccagcg attgtcat                                               18

<210> SEQ ID NO 324
<211> LENGTH: 18
<212> TYPE: DNA
<213> ORGANISM: Mus sp.

<400> SEQUENCE: 324
cagcccaaac cagtcagg                                               18

<210> SEQ ID NO 325
<211> LENGTH: 18
<212> TYPE: DNA
<213> ORGANISM: Mus sp.

<400> SEQUENCE: 325
gagcgggaac tcaggacc                                               18

<210> SEQ ID NO 326
<211> LENGTH: 18
<212> TYPE: DNA
<213> ORGANISM: Mus sp.

<400> SEQUENCE: 326
gggaaaatga ccactgcg                                               18

<210> SEQ ID NO 327
```

```
<211> LENGTH: 18
<212> TYPE: DNA
<213> ORGANISM: Mus sp.

<400> SEQUENCE: 327
tgccctaggg gacaaaaa                                                 18

<210> SEQ ID NO 328
<211> LENGTH: 18
<212> TYPE: DNA
<213> ORGANISM: Mus sp.

<400> SEQUENCE: 328
caagcgggtc tcatgctt                                                 18

<210> SEQ ID NO 329
<211> LENGTH: 19
<212> TYPE: DNA
<213> ORGANISM: Mus sp.

<400> SEQUENCE: 329
tggagcatga atccacacc                                                19

<210> SEQ ID NO 330
<211> LENGTH: 18
<212> TYPE: DNA
<213> ORGANISM: Mus sp.

<400> SEQUENCE: 330
tgagggtccc atgagtgg                                                 18

<210> SEQ ID NO 331
<211> LENGTH: 18
<212> TYPE: DNA
<213> ORGANISM: Mus sp.

<400> SEQUENCE: 331
ctcaggagat ggagcgga                                                 18

<210> SEQ ID NO 332
<211> LENGTH: 18
<212> TYPE: DNA
<213> ORGANISM: Mus sp.

<400> SEQUENCE: 332
cctcgtcact cccgacac                                                 18

<210> SEQ ID NO 333
<211> LENGTH: 18
<212> TYPE: DNA
<213> ORGANISM: Mus sp.

<400> SEQUENCE: 333
cacggtggtg aaggttcc                                                 18

<210> SEQ ID NO 334
<211> LENGTH: 18
<212> TYPE: DNA
<213> ORGANISM: Mus sp.

<400> SEQUENCE: 334
gaaaggaggg agggagga                                                 18
```

-continued

```
<210> SEQ ID NO 335
<211> LENGTH: 18
<212> TYPE: DNA
<213> ORGANISM: Mus sp.

<400> SEQUENCE: 335
tgcctgtgct tgctctga                                                 18

<210> SEQ ID NO 336
<211> LENGTH: 18
<212> TYPE: DNA
<213> ORGANISM: Mus sp.

<400> SEQUENCE: 336
gaagaagggc cagaaggg                                                 18

<210> SEQ ID NO 337
<211> LENGTH: 18
<212> TYPE: DNA
<213> ORGANISM: Mus sp.

<400> SEQUENCE: 337
ccgaggagcc tcttagcc                                                 18

<210> SEQ ID NO 338
<211> LENGTH: 18
<212> TYPE: DNA
<213> ORGANISM: Mus sp.

<400> SEQUENCE: 338
gtctggatcg ggagatgc                                                 18

<210> SEQ ID NO 339
<211> LENGTH: 18
<212> TYPE: DNA
<213> ORGANISM: Mus sp.

<400> SEQUENCE: 339
actgccttca gccaggtg                                                 18

<210> SEQ ID NO 340
<211> LENGTH: 18
<212> TYPE: DNA
<213> ORGANISM: Mus sp.

<400> SEQUENCE: 340
cagcttctca cccaggga                                                 18

<210> SEQ ID NO 341
<211> LENGTH: 19
<212> TYPE: DNA
<213> ORGANISM: Mus sp.

<400> SEQUENCE: 341
cctggagtgg tatcatcgc                                                19

<210> SEQ ID NO 342
<211> LENGTH: 19
<212> TYPE: DNA
<213> ORGANISM: Mus sp.

<400> SEQUENCE: 342
tgcgttggtt ctgattgtg                                                19
```

```
<210> SEQ ID NO 343
<211> LENGTH: 18
<212> TYPE: DNA
<213> ORGANISM: Mus sp.

<400> SEQUENCE: 343
cacaccatgc tgctcctg                                                 18

<210> SEQ ID NO 344
<211> LENGTH: 18
<212> TYPE: DNA
<213> ORGANISM: Mus sp.

<400> SEQUENCE: 344
ctccttggct ttccacga                                                 18

<210> SEQ ID NO 345
<211> LENGTH: 19
<212> TYPE: DNA
<213> ORGANISM: Mus sp.

<400> SEQUENCE: 345
cagagaaacg cattcctgg                                                19

<210> SEQ ID NO 346
<211> LENGTH: 19
<212> TYPE: DNA
<213> ORGANISM: Mus sp.

<400> SEQUENCE: 346
agtccaccag ctggctttt                                                19

<210> SEQ ID NO 347
<211> LENGTH: 18
<212> TYPE: DNA
<213> ORGANISM: Mus sp.

<400> SEQUENCE: 347
tattggccgg cagacttt                                                 18

<210> SEQ ID NO 348
<211> LENGTH: 18
<212> TYPE: DNA
<213> ORGANISM: Mus sp.

<400> SEQUENCE: 348
gcctggcact tacaagcc                                                 18

<210> SEQ ID NO 349
<211> LENGTH: 18
<212> TYPE: DNA
<213> ORGANISM: Mus sp.

<400> SEQUENCE: 349
agggaaggaa gacgccac                                                 18

<210> SEQ ID NO 350
<211> LENGTH: 19
<212> TYPE: DNA
<213> ORGANISM: Mus sp.

<400> SEQUENCE: 350
tggccatgta aaagccaaa                                                19
```

```
<210> SEQ ID NO 351
<211> LENGTH: 18
<212> TYPE: DNA
<213> ORGANISM: Mus sp.

<400> SEQUENCE: 351
gtctccaacg cccagcta                                                18

<210> SEQ ID NO 352
<211> LENGTH: 18
<212> TYPE: DNA
<213> ORGANISM: Mus sp.

<400> SEQUENCE: 352
atctcttccc tttgccgc                                                18

<210> SEQ ID NO 353
<211> LENGTH: 18
<212> TYPE: DNA
<213> ORGANISM: Mus sp.

<400> SEQUENCE: 353
actgctaggg gtcctggg                                                18

<210> SEQ ID NO 354
<211> LENGTH: 18
<212> TYPE: DNA
<213> ORGANISM: Mus sp.

<400> SEQUENCE: 354
tgagccatag gtctgggc                                                18

<210> SEQ ID NO 355
<211> LENGTH: 18
<212> TYPE: DNA
<213> ORGANISM: Mus sp.

<400> SEQUENCE: 355
gaagctgttt ggcttcgc                                                18

<210> SEQ ID NO 356
<211> LENGTH: 18
<212> TYPE: DNA
<213> ORGANISM: Mus sp.

<400> SEQUENCE: 356
tcattcctcc cccagaca                                                18

<210> SEQ ID NO 357
<211> LENGTH: 18
<212> TYPE: DNA
<213> ORGANISM: Mus sp.

<400> SEQUENCE: 357
tcgaggcgct cacataca                                                18

<210> SEQ ID NO 358
<211> LENGTH: 18
<212> TYPE: DNA
<213> ORGANISM: Mus sp.

<400> SEQUENCE: 358
```
cggacaacat ctggctga                                               18

<210> SEQ ID NO 359
<211> LENGTH: 18
<212> TYPE: DNA
<213> ORGANISM: Mus sp.

<400> SEQUENCE: 359
ctcaactgag cgggcaat                                               18

<210> SEQ ID NO 360
<211> LENGTH: 18
<212> TYPE: DNA
<213> ORGANISM: Mus sp.

<400> SEQUENCE: 360
agggttgagg cacatgga                                               18

<210> SEQ ID NO 361
<211> LENGTH: 18
<212> TYPE: DNA
<213> ORGANISM: Mus sp.

<400> SEQUENCE: 361
ccttctccag ctccctcc                                               18

<210> SEQ ID NO 362
<211> LENGTH: 18
<212> TYPE: DNA
<213> ORGANISM: Mus sp.

<400> SEQUENCE: 362
cctcttggca atgttggg                                               18

<210> SEQ ID NO 363
<211> LENGTH: 18
<212> TYPE: DNA
<213> ORGANISM: Mus sp.

<400> SEQUENCE: 363
gtaaaggccg gctccagt                                               18

<210> SEQ ID NO 364
<211> LENGTH: 19
<212> TYPE: DNA
<213> ORGANISM: Mus sp.

<400> SEQUENCE: 364
tttccagtgg aggatgtgc                                              19

<210> SEQ ID NO 365
<211> LENGTH: 18
<212> TYPE: DNA
<213> ORGANISM: Mus sp.

<400> SEQUENCE: 365
aggtctggcc acaacacc                                               18

<210> SEQ ID NO 366
<211> LENGTH: 18
<212> TYPE: DNA
<213> ORGANISM: Mus sp.

<400> SEQUENCE: 366

| | |
|---|---|
| ggccacagtc acgttcaa | 18 |

<210> SEQ ID NO 367
<211> LENGTH: 18
<212> TYPE: DNA
<213> ORGANISM: Mus sp.

<400> SEQUENCE: 367

| | |
|---|---|
| agggcttcca aggtgctt | 18 |

<210> SEQ ID NO 368
<211> LENGTH: 20
<212> TYPE: DNA
<213> ORGANISM: Mus sp.

<400> SEQUENCE: 368

| | |
|---|---|
| tgctctttag gctttccagg | 20 |

<210> SEQ ID NO 369
<211> LENGTH: 18
<212> TYPE: DNA
<213> ORGANISM: Mus sp.

<400> SEQUENCE: 369

| | |
|---|---|
| gaggctgagg ctgctgag | 18 |

<210> SEQ ID NO 370
<211> LENGTH: 18
<212> TYPE: DNA
<213> ORGANISM: Mus sp.

<400> SEQUENCE: 370

| | |
|---|---|
| atcctgggga cacaccct | 18 |

<210> SEQ ID NO 371
<211> LENGTH: 20
<212> TYPE: DNA
<213> ORGANISM: Mus sp.

<400> SEQUENCE: 371

| | |
|---|---|
| ggtgctttga gcagttctga | 20 |

<210> SEQ ID NO 372
<211> LENGTH: 18
<212> TYPE: DNA
<213> ORGANISM: Mus sp.

<400> SEQUENCE: 372

| | |
|---|---|
| gccctgcaca agcaaagt | 18 |

<210> SEQ ID NO 373
<211> LENGTH: 18
<212> TYPE: DNA
<213> ORGANISM: Mus sp.

<400> SEQUENCE: 373

| | |
|---|---|
| gcctggctat gggaggat | 18 |

<210> SEQ ID NO 374
<211> LENGTH: 18
<212> TYPE: DNA
<213> ORGANISM: Mus sp.

```
<400> SEQUENCE: 374
ccgtggacct tccttgtc                                                  18

<210> SEQ ID NO 375
<211> LENGTH: 18
<212> TYPE: DNA
<213> ORGANISM: Mus sp.

<400> SEQUENCE: 375
cctgagccct accaccaa                                                  18

<210> SEQ ID NO 376
<211> LENGTH: 18
<212> TYPE: DNA
<213> ORGANISM: Mus sp.

<400> SEQUENCE: 376
gggcagctct atggaggg                                                  18

<210> SEQ ID NO 377
<211> LENGTH: 18
<212> TYPE: DNA
<213> ORGANISM: Mus sp.

<400> SEQUENCE: 377
cgcgcagtag tctggctc                                                  18

<210> SEQ ID NO 378
<211> LENGTH: 18
<212> TYPE: DNA
<213> ORGANISM: Mus sp.

<400> SEQUENCE: 378
aagatgaggg ccttgggt                                                  18

<210> SEQ ID NO 379
<211> LENGTH: 18
<212> TYPE: DNA
<213> ORGANISM: Mus sp.

<400> SEQUENCE: 379
caacaaaggg cagcaagc                                                  18

<210> SEQ ID NO 380
<211> LENGTH: 19
<212> TYPE: DNA
<213> ORGANISM: Mus sp.

<400> SEQUENCE: 380
ttcaacacaa gggcagagg                                                 19

<210> SEQ ID NO 381
<211> LENGTH: 18
<212> TYPE: DNA
<213> ORGANISM: Mus sp.

<400> SEQUENCE: 381
ttagctggat gagcccca                                                  18

<210> SEQ ID NO 382
<211> LENGTH: 18
<212> TYPE: DNA
<213> ORGANISM: Mus sp.
```

-continued

```
<400> SEQUENCE: 382
atgttgctgc tgtggtgg                                                 18

<210> SEQ ID NO 383
<211> LENGTH: 18
<212> TYPE: DNA
<213> ORGANISM: Mus sp.

<400> SEQUENCE: 383
gccagacggt agtggtgg                                                 18

<210> SEQ ID NO 384
<211> LENGTH: 18
<212> TYPE: DNA
<213> ORGANISM: Mus sp.

<400> SEQUENCE: 384
cgtgctgtgt atggctcg                                                 18

<210> SEQ ID NO 385
<211> LENGTH: 18
<212> TYPE: DNA
<213> ORGANISM: Mus sp.

<400> SEQUENCE: 385
gatgacggag ggcaaaga                                                 18

<210> SEQ ID NO 386
<211> LENGTH: 18
<212> TYPE: DNA
<213> ORGANISM: Mus sp.

<400> SEQUENCE: 386
ggggttgagg ctggatct                                                 18

<210> SEQ ID NO 387
<211> LENGTH: 18
<212> TYPE: DNA
<213> ORGANISM: Mus sp.

<400> SEQUENCE: 387
accctggcta tgcacctg                                                 18

<210> SEQ ID NO 388
<211> LENGTH: 18
<212> TYPE: DNA
<213> ORGANISM: Mus sp.

<400> SEQUENCE: 388
gggaagctgg attgagca                                                 18

<210> SEQ ID NO 389
<211> LENGTH: 18
<212> TYPE: DNA
<213> ORGANISM: Mus sp.

<400> SEQUENCE: 389
gagagcgagg accgagtg                                                 18

<210> SEQ ID NO 390
<211> LENGTH: 18
<212> TYPE: DNA
```

<213> ORGANISM: Mus sp.

<400> SEQUENCE: 390
ccttccacat cacagccc											18

<210> SEQ ID NO 391
<211> LENGTH: 18
<212> TYPE: DNA
<213> ORGANISM: Mus sp.

<400> SEQUENCE: 391
tgcgacaagg tgcagaaa											18

<210> SEQ ID NO 392
<211> LENGTH: 18
<212> TYPE: DNA
<213> ORGANISM: Mus sp.

<400> SEQUENCE: 392
gagctcgcga tcagaagg											18

<210> SEQ ID NO 393
<211> LENGTH: 18
<212> TYPE: DNA
<213> ORGANISM: Mus sp.

<400> SEQUENCE: 393
gccccttccc accattta											18

<210> SEQ ID NO 394
<211> LENGTH: 18
<212> TYPE: DNA
<213> ORGANISM: Mus sp.

<400> SEQUENCE: 394
ctccccctgc tgctacaa											18

<210> SEQ ID NO 395
<211> LENGTH: 18
<212> TYPE: DNA
<213> ORGANISM: Mus sp.

<400> SEQUENCE: 395
ggctaggcac aaggcaga											18

<210> SEQ ID NO 396
<211> LENGTH: 18
<212> TYPE: DNA
<213> ORGANISM: Mus sp.

<400> SEQUENCE: 396
agcgctccct ctggagat											18

<210> SEQ ID NO 397
<211> LENGTH: 18
<212> TYPE: DNA
<213> ORGANISM: Mus sp.

<400> SEQUENCE: 397
acagcctcgt gtggtggt											18

<210> SEQ ID NO 398
<211> LENGTH: 18

-continued

```
<212> TYPE: DNA
<213> ORGANISM: Mus sp.

<400> SEQUENCE: 398
ggccattggc ttctgcta                                                 18

<210> SEQ ID NO 399
<211> LENGTH: 18
<212> TYPE: DNA
<213> ORGANISM: Mus sp.

<400> SEQUENCE: 399
gcctctatgg cctcacca                                                 18

<210> SEQ ID NO 400
<211> LENGTH: 18
<212> TYPE: DNA
<213> ORGANISM: Mus sp.

<400> SEQUENCE: 400
acttccagga gttggccc                                                 18

<210> SEQ ID NO 401
<211> LENGTH: 18
<212> TYPE: DNA
<213> ORGANISM: Mus sp.

<400> SEQUENCE: 401
tgggaagctg agagtcgc                                                 18

<210> SEQ ID NO 402
<211> LENGTH: 18
<212> TYPE: DNA
<213> ORGANISM: Mus sp.

<400> SEQUENCE: 402
gccttctgcc tttccaca                                                 18

<210> SEQ ID NO 403
<211> LENGTH: 18
<212> TYPE: DNA
<213> ORGANISM: Mus sp.

<400> SEQUENCE: 403
tggttagcgt agggcagg                                                 18

<210> SEQ ID NO 404
<211> LENGTH: 18
<212> TYPE: DNA
<213> ORGANISM: Mus sp.

<400> SEQUENCE: 404
cccatgggga tatgcact                                                 18

<210> SEQ ID NO 405
<211> LENGTH: 18
<212> TYPE: DNA
<213> ORGANISM: Mus sp.

<400> SEQUENCE: 405
atctgtgggc gctctgac                                                 18

<210> SEQ ID NO 406
```

```
<211> LENGTH: 18
<212> TYPE: DNA
<213> ORGANISM: Mus sp.

<400> SEQUENCE: 406
ggactgtcaa gatggggc                                                 18

<210> SEQ ID NO 407
<211> LENGTH: 18
<212> TYPE: DNA
<213> ORGANISM: Mus sp.

<400> SEQUENCE: 407
ttctggcagg gacgaaac                                                 18

<210> SEQ ID NO 408
<211> LENGTH: 20
<212> TYPE: DNA
<213> ORGANISM: Mus sp.

<400> SEQUENCE: 408
tttggtcctg tgccttacaa                                               20

<210> SEQ ID NO 409
<211> LENGTH: 18
<212> TYPE: DNA
<213> ORGANISM: Mus sp.

<400> SEQUENCE: 409
tgctccccaa aattccaa                                                 18

<210> SEQ ID NO 410
<211> LENGTH: 18
<212> TYPE: DNA
<213> ORGANISM: Mus sp.

<400> SEQUENCE: 410
aggaatgccg tatcgggt                                                 18

<210> SEQ ID NO 411
<211> LENGTH: 18
<212> TYPE: DNA
<213> ORGANISM: Mus sp.

<400> SEQUENCE: 411
accaaccagg actgctgc                                                 18

<210> SEQ ID NO 412
<211> LENGTH: 18
<212> TYPE: DNA
<213> ORGANISM: Mus sp.

<400> SEQUENCE: 412
ccctgtggac aggagcac                                                 18

<210> SEQ ID NO 413
<211> LENGTH: 18
<212> TYPE: DNA
<213> ORGANISM: Mus sp.

<400> SEQUENCE: 413
tcacctggag caatgcaa                                                 18
```

```
<210> SEQ ID NO 414
<211> LENGTH: 18
<212> TYPE: DNA
<213> ORGANISM: Mus sp.

<400> SEQUENCE: 414
tggtaccatt ggcatccg                                                 18

<210> SEQ ID NO 415
<211> LENGTH: 18
<212> TYPE: DNA
<213> ORGANISM: Mus sp.

<400> SEQUENCE: 415
tttccctctt ggtggcct                                                 18

<210> SEQ ID NO 416
<211> LENGTH: 18
<212> TYPE: DNA
<213> ORGANISM: Mus sp.

<400> SEQUENCE: 416
tccctcccca caccacta                                                 18

<210> SEQ ID NO 417
<211> LENGTH: 18
<212> TYPE: DNA
<213> ORGANISM: Mus sp.

<400> SEQUENCE: 417
ttgttgggcg acttttgc                                                 18

<210> SEQ ID NO 418
<211> LENGTH: 19
<212> TYPE: DNA
<213> ORGANISM: Mus sp.

<400> SEQUENCE: 418
tggagagttg agggacgaa                                                19

<210> SEQ ID NO 419
<211> LENGTH: 18
<212> TYPE: DNA
<213> ORGANISM: Mus sp.

<400> SEQUENCE: 419
tgggtgaaca ttcctgcc                                                 18

<210> SEQ ID NO 420
<211> LENGTH: 18
<212> TYPE: DNA
<213> ORGANISM: Mus sp.

<400> SEQUENCE: 420
aaacagcaac cctcaccg                                                 18

<210> SEQ ID NO 421
<211> LENGTH: 18
<212> TYPE: DNA
<213> ORGANISM: Mus sp.

<400> SEQUENCE: 421
tgcaggagag cggattct                                                 18
```

```
<210> SEQ ID NO 422
<211> LENGTH: 18
<212> TYPE: DNA
<213> ORGANISM: Mus sp.

<400> SEQUENCE: 422
gaactggctg cgtgcttc                                                 18

<210> SEQ ID NO 423
<211> LENGTH: 18
<212> TYPE: DNA
<213> ORGANISM: Mus sp.

<400> SEQUENCE: 423
cctccgctag aagctccc                                                 18

<210> SEQ ID NO 424
<211> LENGTH: 19
<212> TYPE: DNA
<213> ORGANISM: Mus sp.

<400> SEQUENCE: 424
gctcttacac gagaggccc                                                19

<210> SEQ ID NO 425
<211> LENGTH: 18
<212> TYPE: DNA
<213> ORGANISM: Mus sp.

<400> SEQUENCE: 425
cgcctgagtg gctgtctt                                                 18

<210> SEQ ID NO 426
<211> LENGTH: 18
<212> TYPE: DNA
<213> ORGANISM: Mus sp.

<400> SEQUENCE: 426
atgtcatgga tggtgccc                                                 18

<210> SEQ ID NO 427
<211> LENGTH: 21
<212> TYPE: DNA
<213> ORGANISM: Mus sp.

<400> SEQUENCE: 427
ctgcttgaat atggatcagc a                                             21

<210> SEQ ID NO 428
<211> LENGTH: 18
<212> TYPE: DNA
<213> ORGANISM: Mus sp.

<400> SEQUENCE: 428
ccaactagtg cacccccgt                                                18

<210> SEQ ID NO 429
<211> LENGTH: 19
<212> TYPE: DNA
<213> ORGANISM: Mus sp.

<400> SEQUENCE: 429
caatggatgc caacgtttc                                                19
```

<210> SEQ ID NO 430
<211> LENGTH: 18
<212> TYPE: DNA
<213> ORGANISM: Mus sp.

<400> SEQUENCE: 430
ccttgccagt ccctgtgt                                          18

<210> SEQ ID NO 431
<211> LENGTH: 18
<212> TYPE: DNA
<213> ORGANISM: Mus sp.

<400> SEQUENCE: 431
ggcccccgtg gactatac                                          18

<210> SEQ ID NO 432
<211> LENGTH: 18
<212> TYPE: DNA
<213> ORGANISM: Mus sp.

<400> SEQUENCE: 432
cacacacaca cgcacacg                                          18

<210> SEQ ID NO 433
<211> LENGTH: 20
<212> TYPE: DNA
<213> ORGANISM: Mus sp.

<400> SEQUENCE: 433
ttgagactgt atcccccagc                                        20

<210> SEQ ID NO 434
<211> LENGTH: 20
<212> TYPE: DNA
<213> ORGANISM: Mus sp.

<400> SEQUENCE: 434
gcagggtctt caaaggtcag                                        20

<210> SEQ ID NO 435
<211> LENGTH: 19
<212> TYPE: DNA
<213> ORGANISM: Mus sp.

<400> SEQUENCE: 435
tgggtttcca gttgcagtt                                         19

<210> SEQ ID NO 436
<211> LENGTH: 22
<212> TYPE: DNA
<213> ORGANISM: Mus sp.

<400> SEQUENCE: 436
gcctttatta aacacctccc tg                                     22

<210> SEQ ID NO 437
<211> LENGTH: 18
<212> TYPE: DNA
<213> ORGANISM: Mus sp.

<400> SEQUENCE: 437
ccctgggtgt gtgcagtc                                                    18

<210> SEQ ID NO 438
<211> LENGTH: 18
<212> TYPE: DNA
<213> ORGANISM: Mus sp.

<400> SEQUENCE: 438
aaggggttga aagggtg                                                     18

<210> SEQ ID NO 439
<211> LENGTH: 18
<212> TYPE: DNA
<213> ORGANISM: Mus sp.

<400> SEQUENCE: 439
cccaaaagac tgcatcgg                                                    18

<210> SEQ ID NO 440
<211> LENGTH: 19
<212> TYPE: DNA
<213> ORGANISM: Mus sp.

<400> SEQUENCE: 440
tccacagggt aaggctgaa                                                   19

<210> SEQ ID NO 441
<211> LENGTH: 18
<212> TYPE: DNA
<213> ORGANISM: Mus sp.

<400> SEQUENCE: 441 cgaccccaa tgtaagga                                                     18

<210> SEQ ID NO 442
<211> LENGTH: 18
<212> TYPE: DNA
<213> ORGANISM: Mus sp.

<400> SEQUENCE: 442
tagcccaccc tgatggaa                                                    18

<210> SEQ ID NO 443
<211> LENGTH: 18
<212> TYPE: DNA
<213> ORGANISM: Mus sp.

<400> SEQUENCE: 443 ggtccctgc agtgtctg                                                     18

<210> SEQ ID NO 444
<211> LENGTH: 18
<212> TYPE: DNA
<213> ORGANISM: Mus sp.

<400> SEQUENCE: 444
cttccgtttt cgtggctg                                                    18

<210> SEQ ID NO 445
<211> LENGTH: 18
<212> TYPE: DNA
<213> ORGANISM: Mus sp.

<400> SEQUENCE: 445
ccatgaccac atggacga 18

<210> SEQ ID NO 446
<211> LENGTH: 18
<212> TYPE: DNA
<213> ORGANISM: Mus sp.

<400> SEQUENCE: 446
ccaagctatc acctcggc 18

<210> SEQ ID NO 447
<211> LENGTH: 18
<212> TYPE: DNA
<213> ORGANISM: Mus sp.

<400> SEQUENCE: 447
actcagcgcc cacttcag 18

<210> SEQ ID NO 448
<211> LENGTH: 18
<212> TYPE: DNA
<213> ORGANISM: Mus sp.

<400> SEQUENCE: 448
gctctgcaaa ggcgttgt 18

<210> SEQ ID NO 449
<211> LENGTH: 18
<212> TYPE: DNA
<213> ORGANISM: Mus sp.

<400> SEQUENCE: 449
gccaaagtcc cctggaat 18

<210> SEQ ID NO 450
<211> LENGTH: 18
<212> TYPE: DNA
<213> ORGANISM: Mus sp.

<400> SEQUENCE: 450
aaggaaggca ggaggagg 18

<210> SEQ ID NO 451
<211> LENGTH: 18
<212> TYPE: DNA
<213> ORGANISM: Mus sp.

<400> SEQUENCE: 451
gggagccttc caaggtgt 18

<210> SEQ ID NO 452
<211> LENGTH: 18
<212> TYPE: DNA
<213> ORGANISM: Mus sp.

<400> SEQUENCE: 452
ggcattatag cccctccg 18

<210> SEQ ID NO 453
<211> LENGTH: 15
<212> TYPE: DNA
<213> ORGANISM: Mus sp.

<400> SEQUENCE: 453
cggtggtcct tcgcc                                              15

<210> SEQ ID NO 454
<211> LENGTH: 19
<212> TYPE: DNA
<213> ORGANISM: Mus sp.

<400> SEQUENCE: 454
tgcagagcca ttcaacaca                                          19

<210> SEQ ID NO 455
<211> LENGTH: 18
<212> TYPE: DNA
<213> ORGANISM: Mus sp.

<400> SEQUENCE: 455
ggacctcatc agccaagc                                           18

<210> SEQ ID NO 456
<211> LENGTH: 18
<212> TYPE: DNA
<213> ORGANISM: Mus sp.

<400> SEQUENCE: 456
gcaggtttga gatgccca                                           18

<210> SEQ ID NO 457
<211> LENGTH: 21
<212> TYPE: DNA
<213> ORGANISM: Mus sp.

<400> SEQUENCE: 457
cggcaatatt gttatccaga a                                       21

<210> SEQ ID NO 458
<211> LENGTH: 18
<212> TYPE: DNA
<213> ORGANISM: Mus sp.

<400> SEQUENCE: 458
gggcgtcttc ccactttt                                           18

<210> SEQ ID NO 459
<211> LENGTH: 18
<212> TYPE: DNA
<213> ORGANISM: Mus sp.

<400> SEQUENCE: 459
tgctgtccca gggatgat                                           18

<210> SEQ ID NO 460
<211> LENGTH: 20
<212> TYPE: DNA
<213> ORGANISM: Mus sp.

<400> SEQUENCE: 460
caaatagccc aggataccca                                         20

<210> SEQ ID NO 461
<211> LENGTH: 17
<212> TYPE: DNA
<213> ORGANISM: Mus sp.

```
<400> SEQUENCE: 461
gctggcttgg catcctt                                                  17

<210> SEQ ID NO 462
<211> LENGTH: 18
<212> TYPE: DNA
<213> ORGANISM: Mus sp.

<400> SEQUENCE: 462
ttgatcttct cgccctcg                                                 18

<210> SEQ ID NO 463
<211> LENGTH: 18
<212> TYPE: DNA
<213> ORGANISM: Mus sp.

<400> SEQUENCE: 463
gatgtggcag ctgtgtgc                                                 18

<210> SEQ ID NO 464
<211> LENGTH: 18
<212> TYPE: DNA
<213> ORGANISM: Mus sp.

<400> SEQUENCE: 464
ttgaagacat cggggctc                                                 18

<210> SEQ ID NO 465
<211> LENGTH: 18
<212> TYPE: DNA
<213> ORGANISM: Mus sp.

<400> SEQUENCE: 465
ttcttgggca gtgaaccc                                                 18

<210> SEQ ID NO 466
<211> LENGTH: 18
<212> TYPE: DNA
<213> ORGANISM: Mus sp.

<400> SEQUENCE: 466
tcgcgggatc atcaactt                                                 18

<210> SEQ ID NO 467
<211> LENGTH: 19
<212> TYPE: DNA
<213> ORGANISM: Mus sp.

<400> SEQUENCE: 467
ctccatgaag ctcagccaa                                                19

<210> SEQ ID NO 468
<211> LENGTH: 18
<212> TYPE: DNA
<213> ORGANISM: Mus sp.

<400> SEQUENCE: 468
ttgattacgc aggtgcca                                                 18

<210> SEQ ID NO 469
<211> LENGTH: 18
<212> TYPE: DNA
```

<213> ORGANISM: Mus sp.

<400> SEQUENCE: 469
aggacttccc ttcacgcc                                              18

<210> SEQ ID NO 470
<211> LENGTH: 21
<212> TYPE: DNA
<213> ORGANISM: Mus sp.

<400> SEQUENCE: 470
agccaggatt caactttgtg a                                          21

<210> SEQ ID NO 471
<211> LENGTH: 19
<212> TYPE: DNA
<213> ORGANISM: Mus sp.

<400> SEQUENCE: 471
tgcttttgcc agtgtgacc                                             19

<210> SEQ ID NO 472
<211> LENGTH: 18
<212> TYPE: DNA
<213> ORGANISM: Mus sp.

<400> SEQUENCE: 472
acgcccaggg agtttaca                                              18

<210> SEQ ID NO 473
<211> LENGTH: 18
<212> TYPE: DNA
<213> ORGANISM: Mus sp.

<400> SEQUENCE: 473
tgatgtcagc tctgggca                                              18

<210> SEQ ID NO 474
<211> LENGTH: 18
<212> TYPE: DNA
<213> ORGANISM: Mus sp.

<400> SEQUENCE: 474
tctgcagcga gaaccaaa                                              18

<210> SEQ ID NO 475
<211> LENGTH: 18
<212> TYPE: DNA
<213> ORGANISM: Mus sp.

<400> SEQUENCE: 475
ggaaggcacc agggatct                                              18

<210> SEQ ID NO 476
<211> LENGTH: 18
<212> TYPE: DNA
<213> ORGANISM: Mus sp.

<400> SEQUENCE: 476
ctcgtcgcaa gcctctgt                                              18

<210> SEQ ID NO 477
<211> LENGTH: 18

```
<212> TYPE: DNA
<213> ORGANISM: Mus sp.

<400> SEQUENCE: 477
tctgccttgt gcctgaca                                                 18

<210> SEQ ID NO 478
<211> LENGTH: 18
<212> TYPE: DNA
<213> ORGANISM: Mus sp.

<400> SEQUENCE: 478
acgggtgcat cagcctaa                                                 18

<210> SEQ ID NO 479
<211> LENGTH: 18
<212> TYPE: DNA
<213> ORGANISM: Mus sp.

<400> SEQUENCE: 479
aggggacctg gactctgg                                                 18

<210> SEQ ID NO 480
<211> LENGTH: 18
<212> TYPE: DNA
<213> ORGANISM: Mus sp.

<400> SEQUENCE: 480
gacaagttgg ggccaatg                                                 18

<210> SEQ ID NO 481
<211> LENGTH: 17
<212> TYPE: DNA
<213> ORGANISM: Mus sp.

<400> SEQUENCE: 481
gtgaccgctt gatgggg                                                  17

<210> SEQ ID NO 482
<211> LENGTH: 18
<212> TYPE: DNA
<213> ORGANISM: Mus sp.

<400> SEQUENCE: 482
gctgtgtcgg ctgatgaa                                                 18

<210> SEQ ID NO 483
<211> LENGTH: 18
<212> TYPE: DNA
<213> ORGANISM: Mus sp.

<400> SEQUENCE: 483
cctggcctct cagttcca                                                 18

<210> SEQ ID NO 484
<211> LENGTH: 18
<212> TYPE: DNA
<213> ORGANISM: Mus sp.

<400> SEQUENCE: 484
agaggccttt cagcaggc                                                 18

<210> SEQ ID NO 485
```

```
<211> LENGTH: 18
<212> TYPE: DNA
<213> ORGANISM: Mus sp.

<400> SEQUENCE: 485
agcagccaag tgcggtag                                            18

<210> SEQ ID NO 486
<211> LENGTH: 18
<212> TYPE: DNA
<213> ORGANISM: Mus sp.

<400> SEQUENCE: 486
tgccacaagg agaggtcc                                            18

<210> SEQ ID NO 487
<211> LENGTH: 18
<212> TYPE: DNA
<213> ORGANISM: Mus sp.

<400> SEQUENCE: 487
cctctgaccc gtctccct                                            18

<210> SEQ ID NO 488
<211> LENGTH: 18
<212> TYPE: DNA
<213> ORGANISM: Mus sp.

<400> SEQUENCE: 488
gcttccagaa gccagggt                                            18

<210> SEQ ID NO 489
<211> LENGTH: 18
<212> TYPE: DNA
<213> ORGANISM: Mus sp.

<400> SEQUENCE: 489
atgaaaggct atgccccc                                            18

<210> SEQ ID NO 490
<211> LENGTH: 18
<212> TYPE: DNA
<213> ORGANISM: Mus sp.

<400> SEQUENCE: 490
gtgcacaatg gtggcctt                                            18

<210> SEQ ID NO 491
<211> LENGTH: 18
<212> TYPE: DNA
<213> ORGANISM: Mus sp.

<400> SEQUENCE: 491
gaccctgcac ctcattgg                                            18

<210> SEQ ID NO 492
<211> LENGTH: 18
<212> TYPE: DNA
<213> ORGANISM: Mus sp.

<400> SEQUENCE: 492
gaagccagcc acagcaat                                            18
```

```
<210> SEQ ID NO 493
<211> LENGTH: 18
<212> TYPE: DNA
<213> ORGANISM: Mus sp.

<400> SEQUENCE: 493
aggacccagg agagtcgg                                                 18

<210> SEQ ID NO 494
<211> LENGTH: 18
<212> TYPE: DNA
<213> ORGANISM: Mus sp.

<400> SEQUENCE: 494
atctccacag cctgcacc                                                 18

<210> SEQ ID NO 495
<211> LENGTH: 18
<212> TYPE: DNA
<213> ORGANISM: Mus sp.

<400> SEQUENCE: 495
atggggagtc cttctgcc                                                 18

<210> SEQ ID NO 496
<211> LENGTH: 18
<212> TYPE: DNA
<213> ORGANISM: Mus sp.

<400> SEQUENCE: 496
taggccctgc atcagctc                                                 18

<210> SEQ ID NO 497
<211> LENGTH: 18
<212> TYPE: DNA
<213> ORGANISM: Mus sp.

<400> SEQUENCE: 497
tctgggattt gccatcca                                                 18

<210> SEQ ID NO 498
<211> LENGTH: 18
<212> TYPE: DNA
<213> ORGANISM: Mus sp.

<400> SEQUENCE: 498
gtgcaggaag agcaggga                                                 18

<210> SEQ ID NO 499
<211> LENGTH: 18
<212> TYPE: DNA
<213> ORGANISM: Mus sp.

<400> SEQUENCE: 499
cgagccatgt gggaaaag                                                 18

<210> SEQ ID NO 500
<211> LENGTH: 18
<212> TYPE: DNA
<213> ORGANISM: Mus sp.

<400> SEQUENCE: 500
gaggctgaga gatgggca                                                 18
```

<210> SEQ ID NO 501
<211> LENGTH: 21
<212> TYPE: DNA
<213> ORGANISM: Mus sp.

<400> SEQUENCE: 501
ttgtaacgca ctttgagatc c                                              21

<210> SEQ ID NO 502
<211> LENGTH: 18
<212> TYPE: DNA
<213> ORGANISM: Mus sp.

<400> SEQUENCE: 502
cgtgcctttt tggtagcc                                                  18

<210> SEQ ID NO 503
<211> LENGTH: 18
<212> TYPE: DNA
<213> ORGANISM: Mus sp.

<400> SEQUENCE: 503
aagcgctgtg tccctttg                                                  18

<210> SEQ ID NO 504
<211> LENGTH: 18
<212> TYPE: DNA
<213> ORGANISM: Mus sp.

<400> SEQUENCE: 504
gtgagatgcc ccagtgct                                                  18

<210> SEQ ID NO 505
<211> LENGTH: 18
<212> TYPE: DNA
<213> ORGANISM: Mus sp.

<400> SEQUENCE: 505
aatttgggtc ctctcggc                                                  18

<210> SEQ ID NO 506
<211> LENGTH: 18
<212> TYPE: DNA
<213> ORGANISM: Mus sp.

<400> SEQUENCE: 506
gctcgagatg ccagtgct                                                  18

<210> SEQ ID NO 507
<211> LENGTH: 18
<212> TYPE: DNA
<213> ORGANISM: Mus sp.

<400> SEQUENCE: 507
cctcccacct gggatagc                                                  18

<210> SEQ ID NO 508
<211> LENGTH: 18
<212> TYPE: DNA
<213> ORGANISM: Mus sp.

<400> SEQUENCE: 508
ccgtcacagg aggaccaa                                                  18

<210> SEQ ID NO 509
<211> LENGTH: 20
<212> TYPE: DNA
<213> ORGANISM: Mus sp.

<400> SEQUENCE: 509
caagcatgca aagtctgagc                                              20

<210> SEQ ID NO 510
<211> LENGTH: 18
<212> TYPE: DNA
<213> ORGANISM: Mus sp.

<400> SEQUENCE: 510
cgttatgagc ggggtttg                                                18

<210> SEQ ID NO 511
<211> LENGTH: 18
<212> TYPE: DNA
<213> ORGANISM: Mus sp.

<400> SEQUENCE: 511
gcagcagtgg tctggtca                                                18

<210> SEQ ID NO 512
<211> LENGTH: 18
<212> TYPE: DNA
<213> ORGANISM: Mus sp.

<400> SEQUENCE: 512
tgtcaccaac aggggctt                                                18

<210> SEQ ID NO 513
<211> LENGTH: 18
<212> TYPE: DNA
<213> ORGANISM: Mus sp.

<400> SEQUENCE: 513
caaggtgctg gagatgcc                                                18

<210> SEQ ID NO 514
<211> LENGTH: 18
<212> TYPE: DNA
<213> ORGANISM: Mus sp.

<400> SEQUENCE: 514
gcggcccagg ttagagtt                                                18

<210> SEQ ID NO 515
<211> LENGTH: 18
<212> TYPE: DNA
<213> ORGANISM: Mus sp.

<400> SEQUENCE: 515
ggtgcgttcc tcataccg                                                18

<210> SEQ ID NO 516
<211> LENGTH: 18
<212> TYPE: DNA
<213> ORGANISM: Mus sp.

<400> SEQUENCE: 516
aggccaggat gacgatgt                                              18

<210> SEQ ID NO 517
<211> LENGTH: 18
<212> TYPE: DNA
<213> ORGANISM: Mus sp.

<400> SEQUENCE: 517
gaggtagagg cctgggga                                              18

<210> SEQ ID NO 518
<211> LENGTH: 18
<212> TYPE: DNA
<213> ORGANISM: Mus sp.

<400> SEQUENCE: 518
tttaagctct gccgcctc                                              18

<210> SEQ ID NO 519
<211> LENGTH: 18
<212> TYPE: DNA
<213> ORGANISM: Mus sp.

<400> SEQUENCE: 519
cgatgtcgtg gtctccct                                              18

<210> SEQ ID NO 520
<211> LENGTH: 18
<212> TYPE: DNA
<213> ORGANISM: Mus sp.

<400> SEQUENCE: 520
gtcctgctgc agctcctc                                              18

<210> SEQ ID NO 521
<211> LENGTH: 18
<212> TYPE: DNA
<213> ORGANISM: Mus sp.

<400> SEQUENCE: 521
ggacccagtc caaaccct                                              18

<210> SEQ ID NO 522
<211> LENGTH: 18
<212> TYPE: DNA
<213> ORGANISM: Mus sp.

<400> SEQUENCE: 522
cggcaatcag gaccgtat                                              18

<210> SEQ ID NO 523
<211> LENGTH: 18
<212> TYPE: DNA
<213> ORGANISM: Mus sp.

<400> SEQUENCE: 523
aacaagcctt tcaggggg                                              18

<210> SEQ ID NO 524
<211> LENGTH: 18
<212> TYPE: DNA
<213> ORGANISM: Mus sp.

<400> SEQUENCE: 524
agagatcttg gcccagcc                                                    18

<210> SEQ ID NO 525
<211> LENGTH: 18
<212> TYPE: DNA
<213> ORGANISM: Mus sp.

<400> SEQUENCE: 525
tgccagtgtg ctccagaa                                                    18

<210> SEQ ID NO 526
<211> LENGTH: 18
<212> TYPE: DNA
<213> ORGANISM: Mus sp.

<400> SEQUENCE: 526
ctgtgcacaa agccatgc                                                    18

<210> SEQ ID NO 527
<211> LENGTH: 17
<212> TYPE: DNA
<213> ORGANISM: Mus sp.

<400> SEQUENCE: 527
cgccaagatt tccgtga                                                     17

<210> SEQ ID NO 528
<211> LENGTH: 18
<212> TYPE: DNA
<213> ORGANISM: Mus sp.

<400> SEQUENCE: 528
tccccgattt cttccaca                                                    18

<210> SEQ ID NO 529
<211> LENGTH: 18
<212> TYPE: DNA
<213> ORGANISM: Mus sp.

<400> SEQUENCE: 529
gcccactggc cttcattt                                                    18

<210> SEQ ID NO 530
<211> LENGTH: 22
<212> TYPE: DNA
<213> ORGANISM: Mus sp.

<400> SEQUENCE: 530
tgggatatca aagaaactgt ca                                               22

<210> SEQ ID NO 531
<211> LENGTH: 18
<212> TYPE: DNA
<213> ORGANISM: Mus sp.

<400> SEQUENCE: 531
gccaaaacgt caccatcc                                                    18

<210> SEQ ID NO 532
<211> LENGTH: 18
<212> TYPE: DNA
<213> ORGANISM: Mus sp.

```
<400> SEQUENCE: 532
acggccacat cgaagaag                                                  18

<210> SEQ ID NO 533
<211> LENGTH: 19
<212> TYPE: DNA
<213> ORGANISM: Mus sp.

<400> SEQUENCE: 533
tcccttaaaa caggagcca                                                 19

<210> SEQ ID NO 534
<211> LENGTH: 18
<212> TYPE: DNA
<213> ORGANISM: Mus sp.

<400> SEQUENCE: 534
cttccccttg acaagcca                                                  18

<210> SEQ ID NO 535
<211> LENGTH: 19
<212> TYPE: DNA
<213> ORGANISM: Mus sp.

<400> SEQUENCE: 535
gcctgagaaa acggtaggg                                                 19

<210> SEQ ID NO 536
<211> LENGTH: 20
<212> TYPE: DNA
<213> ORGANISM: Mus sp.

<400> SEQUENCE: 536
catgtgcctg atggattttt                                                20

<210> SEQ ID NO 537
<211> LENGTH: 18
<212> TYPE: DNA
<213> ORGANISM: Mus sp.

<400> SEQUENCE: 537
tgagccatca aaggcaaa                                                  18

<210> SEQ ID NO 538
<211> LENGTH: 17
<212> TYPE: DNA
<213> ORGANISM: Mus sp.

<400> SEQUENCE: 538
gcttgttcac ctggccc                                                   17

<210> SEQ ID NO 539
<211> LENGTH: 18
<212> TYPE: DNA
<213> ORGANISM: Mus sp.

<400> SEQUENCE: 539
acgtgcccct gtctgaag                                                  18

<210> SEQ ID NO 540
<211> LENGTH: 17
<212> TYPE: DNA
<213> ORGANISM: Mus sp.
```

-continued

```
<400> SEQUENCE: 540
gagtggtggg acagggc                                                  17

<210> SEQ ID NO 541
<211> LENGTH: 18
<212> TYPE: DNA
<213> ORGANISM: Mus sp.

<400> SEQUENCE: 541
gcaaccagga acgcagac                                                 18

<210> SEQ ID NO 542
<211> LENGTH: 18
<212> TYPE: DNA
<213> ORGANISM: Mus sp.

<400> SEQUENCE: 542
tcttcggcaa gaacctgg                                                 18

<210> SEQ ID NO 543
<211> LENGTH: 18
<212> TYPE: DNA
<213> ORGANISM: Mus sp.

<400> SEQUENCE: 543
ggtggaggca gcagagtg                                                 18

<210> SEQ ID NO 544
<211> LENGTH: 18
<212> TYPE: DNA
<213> ORGANISM: Mus sp.

<400> SEQUENCE: 544
catcctcatc tggcaggc                                                 18

<210> SEQ ID NO 545
<211> LENGTH: 18
<212> TYPE: DNA
<213> ORGANISM: Mus sp.

<400> SEQUENCE: 545
cagtctcagt gcgagcca                                                 18

<210> SEQ ID NO 546
<211> LENGTH: 18
<212> TYPE: DNA
<213> ORGANISM: Mus sp.

<400> SEQUENCE: 546
atgtcctccc ggtcatca                                                 18

<210> SEQ ID NO 547
<211> LENGTH: 18
<212> TYPE: DNA
<213> ORGANISM: Mus sp.

<400> SEQUENCE: 547
acgcccccag agaagagt                                                 18

<210> SEQ ID NO 548
<211> LENGTH: 18
<212> TYPE: DNA
```

-continued

<213> ORGANISM: Mus sp.

<400> SEQUENCE: 548
ctgggtcagg ggaaggag                                                 18

<210> SEQ ID NO 549
<211> LENGTH: 22
<212> TYPE: DNA
<213> ORGANISM: Mus sp.

<400> SEQUENCE: 549
tcgcatgtac agtgaaagaa ga                                            22

<210> SEQ ID NO 550
<211> LENGTH: 18
<212> TYPE: DNA
<213> ORGANISM: Mus sp.

<400> SEQUENCE: 550
ctttggaaac gcctccct                                                 18

<210> SEQ ID NO 551
<211> LENGTH: 18
<212> TYPE: DNA
<213> ORGANISM: Mus sp.

<400> SEQUENCE: 551
gccttgattg acatgggg                                                 18

<210> SEQ ID NO 552
<211> LENGTH: 22
<212> TYPE: DNA
<213> ORGANISM: Mus sp.

<400> SEQUENCE: 552
aagaaaaagg gaaaacaac ca                                             22

<210> SEQ ID NO 553
<211> LENGTH: 18
<212> TYPE: DNA
<213> ORGANISM: Mus sp.

<400> SEQUENCE: 553
tcccaaccct gtgctcat                                                 18

<210> SEQ ID NO 554
<211> LENGTH: 18
<212> TYPE: DNA
<213> ORGANISM: Mus sp.

<400> SEQUENCE: 554
cagtgtgggc agaactgg                                                 18

<210> SEQ ID NO 555
<211> LENGTH: 18
<212> TYPE: DNA
<213> ORGANISM: Mus sp.

<400> SEQUENCE: 555
tggttatgtg gacgcagc                                                 18

<210> SEQ ID NO 556
<211> LENGTH: 18

-continued

```
<212> TYPE: DNA
<213> ORGANISM: Mus sp.

<400> SEQUENCE: 556
ggaagggact tctgggga                                                 18

<210> SEQ ID NO 557
<211> LENGTH: 18
<212> TYPE: DNA
<213> ORGANISM: Mus sp.

<400> SEQUENCE: 557
gcccctctgg gatcaact                                                 18

<210> SEQ ID NO 558
<211> LENGTH: 18
<212> TYPE: DNA
<213> ORGANISM: Mus sp.

<400> SEQUENCE: 558
ggggtgagtc actggtgg                                                 18

<210> SEQ ID NO 559
<211> LENGTH: 18
<212> TYPE: DNA
<213> ORGANISM: Mus sp.

<400> SEQUENCE: 559
aaatcctccc caagtggc                                                 18

<210> SEQ ID NO 560
<211> LENGTH: 18
<212> TYPE: DNA
<213> ORGANISM: Mus sp.

<400> SEQUENCE: 560
tgcagagttc agggaggg                                                 18

<210> SEQ ID NO 561
<211> LENGTH: 18
<212> TYPE: DNA
<213> ORGANISM: Mus sp.

<400> SEQUENCE: 561
ctgggtgcct tggacttg                                                 18

<210> SEQ ID NO 562
<211> LENGTH: 18
<212> TYPE: DNA
<213> ORGANISM: Mus sp.

<400> SEQUENCE: 562
cgcctcatcc aactctgg                                                 18

<210> SEQ ID NO 563
<211> LENGTH: 18
<212> TYPE: DNA
<213> ORGANISM: Mus sp.

<400> SEQUENCE: 563
taccgtgcct cagggaaa                                                 18

<210> SEQ ID NO 564
```

```
<211> LENGTH: 18
<212> TYPE: DNA
<213> ORGANISM: Mus sp.

<400> SEQUENCE: 564
ccccggtctt ctgctttt                                                 18

<210> SEQ ID NO 565
<211> LENGTH: 18
<212> TYPE: DNA
<213> ORGANISM: Mus sp.

<400> SEQUENCE: 565
ttcagcgaga gcagcaaa                                                 18

<210> SEQ ID NO 566
<211> LENGTH: 18
<212> TYPE: DNA
<213> ORGANISM: Mus sp.

<400> SEQUENCE: 566
aaatgcctcc tccttggg                                                 18

<210> SEQ ID NO 567
<211> LENGTH: 18
<212> TYPE: DNA
<213> ORGANISM: Mus sp.

<400> SEQUENCE: 567
tctctcttgc cttggga                                                  18

<210> SEQ ID NO 568
<211> LENGTH: 18
<212> TYPE: DNA
<213> ORGANISM: Mus sp.

<400> SEQUENCE: 568
ggcccgaaac acctctct                                                 18

<210> SEQ ID NO 569
<211> LENGTH: 18
<212> TYPE: DNA
<213> ORGANISM: Mus sp.

<400> SEQUENCE: 569
gctggacgtt ggaggaaa                                                 18

<210> SEQ ID NO 570
<211> LENGTH: 18
<212> TYPE: DNA
<213> ORGANISM: Mus sp.

<400> SEQUENCE: 570
ctcatccggg gaggagat                                                 18

<210> SEQ ID NO 571
<211> LENGTH: 18
<212> TYPE: DNA
<213> ORGANISM: Mus sp.

<400> SEQUENCE: 571
gtttcccaca ttggctgc                                                 18
```

```
<210> SEQ ID NO 572
<211> LENGTH: 18
<212> TYPE: DNA
<213> ORGANISM: Mus sp.

<400> SEQUENCE: 572
agcccgggac tgtctacc                                                 18

<210> SEQ ID NO 573
<211> LENGTH: 18
<212> TYPE: DNA
<213> ORGANISM: Mus sp.

<400> SEQUENCE: 573
tacagagcgc ttgtcccc                                                 18

<210> SEQ ID NO 574
<211> LENGTH: 18
<212> TYPE: DNA
<213> ORGANISM: Mus sp.

<400> SEQUENCE: 574
gccaccatgc catgtttt                                                 18

<210> SEQ ID NO 575
<211> LENGTH: 19
<212> TYPE: DNA
<213> ORGANISM: Mus sp.

<400> SEQUENCE: 575
ccagacgtag ttgggcaga                                                19

<210> SEQ ID NO 576
<211> LENGTH: 18
<212> TYPE: DNA
<213> ORGANISM: Mus sp.

<400> SEQUENCE: 576
tgctgctggc agttggta                                                 18

<210> SEQ ID NO 577
<211> LENGTH: 18
<212> TYPE: DNA
<213> ORGANISM: Mus sp.

<400> SEQUENCE: 577
ctgaaagagc ctcacggc                                                 18

<210> SEQ ID NO 578
<211> LENGTH: 18
<212> TYPE: DNA
<213> ORGANISM: Mus sp.

<400> SEQUENCE: 578
ccatcatgca ctctggga                                                 18

<210> SEQ ID NO 579
<211> LENGTH: 21
<212> TYPE: DNA
<213> ORGANISM: Mus sp.

<400> SEQUENCE: 579
ttctggtgct tgtctcactg a                                             21
```

```
<210> SEQ ID NO 580
<211> LENGTH: 22
<212> TYPE: DNA
<213> ORGANISM: Mus sp.

<400> SEQUENCE: 580
cagtatgttc ggcttcccat tc                                              22

<210> SEQ ID NO 581
<211> LENGTH: 22
<212> TYPE: DNA
<213> ORGANISM: Mus sp.

<400> SEQUENCE: 581
gacgactcct ttcagaccaa gt                                              22

<210> SEQ ID NO 582
<211> LENGTH: 24
<212> TYPE: DNA
<213> ORGANISM: Mus sp.

<400> SEQUENCE: 582
aaattttctc catcataagc aacc                                            24

<210> SEQ ID NO 583
<211> LENGTH: 20
<212> TYPE: DNA
<213> ORGANISM: Mus sp.

<400> SEQUENCE: 583
gcatcgcggt caatagtagg                                                 20

<210> SEQ ID NO 584
<211> LENGTH: 19
<212> TYPE: DNA
<213> ORGANISM: Mus sp.

<400> SEQUENCE: 584
caccgttgat caccagctt                                                  19

<210> SEQ ID NO 585
<211> LENGTH: 20
<212> TYPE: DNA
<213> ORGANISM: Mus sp.

<400> SEQUENCE: 585
tcctgtcacg aaacaacagc                                                 20

<210> SEQ ID NO 586
<211> LENGTH: 20
<212> TYPE: DNA
<213> ORGANISM: Mus sp.

<400> SEQUENCE: 586
acggaatcag gatgacttgc                                                 20

<210> SEQ ID NO 587
<211> LENGTH: 20
<212> TYPE: DNA
<213> ORGANISM: Mus sp.

<400> SEQUENCE: 587
tcccatgggc aggaatatag                                                 20
```

<210> SEQ ID NO 588
<211> LENGTH: 20
<212> TYPE: DNA
<213> ORGANISM: Mus sp.

<400> SEQUENCE: 588
ccattggctt cagaaagagg                                               20

<210> SEQ ID NO 589
<211> LENGTH: 21
<212> TYPE: DNA
<213> ORGANISM: Mus sp.

<400> SEQUENCE: 589
aagtgtaacc actgcgacag g                                             21

<210> SEQ ID NO 590
<211> LENGTH: 20
<212> TYPE: DNA
<213> ORGANISM: Mus sp.

<400> SEQUENCE: 590
tcttcatatg gagcgcaaga                                               20

<210> SEQ ID NO 591
<211> LENGTH: 18
<212> TYPE: DNA
<213> ORGANISM: Mus sp.

<400> SEQUENCE: 591
catggacccc aactgctc                                                 18

<210> SEQ ID NO 592
<211> LENGTH: 18
<212> TYPE: DNA
<213> ORGANISM: Mus sp.

<400> SEQUENCE: 592
agcaggagca gcagcttt                                                 18

<210> SEQ ID NO 593
<211> LENGTH: 22
<212> TYPE: DNA
<213> ORGANISM: Mus sp.

<400> SEQUENCE: 593
ctgctgtgag ggaagtgtat ga                                            22

<210> SEQ ID NO 594
<211> LENGTH: 20
<212> TYPE: DNA
<213> ORGANISM: Mus sp.

<400> SEQUENCE: 594
cgagcagtct gcctagcttt                                               20

<210> SEQ ID NO 595
<211> LENGTH: 20
<212> TYPE: DNA
<213> ORGANISM: Mus sp.

<400> SEQUENCE: 595
agccctcctg tggtgtgata                                              20

<210> SEQ ID NO 596
<211> LENGTH: 20
<212> TYPE: DNA
<213> ORGANISM: Mus sp.

<400> SEQUENCE: 596
tggtcttggg acttccatgt                                              20

<210> SEQ ID NO 597
<211> LENGTH: 18
<212> TYPE: DNA
<213> ORGANISM: Mus sp.

<400> SEQUENCE: 597
gcttcgggac tggtagcc                                                18

<210> SEQ ID NO 598
<211> LENGTH: 20
<212> TYPE: DNA
<213> ORGANISM: Mus sp.

<400> SEQUENCE: 598
gcggcttgat atcctcagtg                                              20

<210> SEQ ID NO 599
<211> LENGTH: 20
<212> TYPE: DNA
<213> ORGANISM: Mus sp.

<400> SEQUENCE: 599
ccagtgcagg acctcatttt                                              20

<210> SEQ ID NO 600
<211> LENGTH: 20
<212> TYPE: DNA
<213> ORGANISM: Mus sp.

<400> SEQUENCE: 600
ggtctccaac atgcctctct                                              20

<210> SEQ ID NO 601
<211> LENGTH: 20
<212> TYPE: DNA
<213> ORGANISM: Mus sp.

<400> SEQUENCE: 601
tggagcaaca tgtggaactc                                              20

<210> SEQ ID NO 602
<211> LENGTH: 18
<212> TYPE: DNA
<213> ORGANISM: Mus sp.

<400> SEQUENCE: 602
cagcagccgg ttaccaag                                                18

<210> SEQ ID NO 603
<211> LENGTH: 20
<212> TYPE: DNA
<213> ORGANISM: Mus sp.

<400> SEQUENCE: 603
ggcaaattca acggcacagt    20

<210> SEQ ID NO 604
<211> LENGTH: 19
<212> TYPE: DNA
<213> ORGANISM: Mus sp.

<400> SEQUENCE: 604
agatggtgat gggcttccc    19

<210> SEQ ID NO 605
<211> LENGTH: 18
<212> TYPE: DNA
<213> ORGANISM: Mus sp.

<400> SEQUENCE: 605
atgatggctt ggccagtg    18

<210> SEQ ID NO 606
<211> LENGTH: 22
<212> TYPE: DNA
<213> ORGANISM: Mus sp.

<400> SEQUENCE: 606 ccatttctc caacatccaa tc    22

<210> SEQ ID NO 607
<211> LENGTH: 24
<212> TYPE: DNA
<213> ORGANISM: Mus sp.

<400> SEQUENCE: 607
gatactggaa aagtcaagtc atcg    24

<210> SEQ ID NO 608
<211> LENGTH: 21
<212> TYPE: DNA
<213> ORGANISM: Mus sp.

<400> SEQUENCE: 608
aatgggtgga gacaaaaatg a    21

<210> SEQ ID NO 609
<211> LENGTH: 20
<212> TYPE: DNA
<213> ORGANISM: Mus sp.

<400> SEQUENCE: 609
cagagccaca tgctcctaga    20

<210> SEQ ID NO 610
<211> LENGTH: 20
<212> TYPE: DNA
<213> ORGANISM: Mus sp.

<400> SEQUENCE: 610
gtccagctgg tcctttgttt    20

<210> SEQ ID NO 611
<211> LENGTH: 20
<212> TYPE: DNA
<213> ORGANISM: Mus sp.

```
<400> SEQUENCE: 611
cgaaactcca gaacccaaga                                              20

<210> SEQ ID NO 612
<211> LENGTH: 21
<212> TYPE: DNA
<213> ORGANISM: Mus sp.

<400> SEQUENCE: 612
aatggtgaca cttggcaaga c                                            21

<210> SEQ ID NO 613
<211> LENGTH: 21
<212> TYPE: DNA
<213> ORGANISM: Mus sp.

<400> SEQUENCE: 613
tgcagaatgg gagatgaatt t                                            21

<210> SEQ ID NO 614
<211> LENGTH: 19
<212> TYPE: DNA
<213> ORGANISM: Mus sp.

<400> SEQUENCE: 614
ggcactattc cggtcatcc                                               19

<210> SEQ ID NO 615
<211> LENGTH: 20
<212> TYPE: DNA
<213> ORGANISM: Mus sp.

<400> SEQUENCE: 615
cctagtgctg catgaggaga                                              20

<210> SEQ ID NO 616
<211> LENGTH: 23
<212> TYPE: DNA
<213> ORGANISM: Mus sp.

<400> SEQUENCE: 616
tcttcctcat cttcttgctc ttc                                          23

<210> SEQ ID NO 617
<211> LENGTH: 21
<212> TYPE: DNA
<213> ORGANISM: Mus sp.

<400> SEQUENCE: 617
cagcattagc ctggctcagt a                                            21

<210> SEQ ID NO 618
<211> LENGTH: 20
<212> TYPE: DNA
<213> ORGANISM: Mus sp.

<400> SEQUENCE: 618
atggatgggt ctgctctgtt                                              20

<210> SEQ ID NO 619
<211> LENGTH: 20
<212> TYPE: DNA
<213> ORGANISM: Mus sp.
```

<400> SEQUENCE: 619
gttcatccat gtggctcaga    20

<210> SEQ ID NO 620
<211> LENGTH: 18
<212> TYPE: DNA
<213> ORGANISM: Mus sp.

<400> SEQUENCE: 620
tcacagccat cagcgtgt    18

<210> SEQ ID NO 621
<211> LENGTH: 20
<212> TYPE: DNA
<213> ORGANISM: Mus sp.

<400> SEQUENCE: 621
atggcgttgc tgtctctagg    20

<210> SEQ ID NO 622
<211> LENGTH: 19
<212> TYPE: DNA
<213> ORGANISM: Mus sp.

<400> SEQUENCE: 622
cttcccaacc tggatgagc    19

<210> SEQ ID NO 623
<211> LENGTH: 20
<212> TYPE: DNA
<213> ORGANISM: Mus sp.

<400> SEQUENCE: 623
gcagcacaac atacggaaaa    20

<210> SEQ ID NO 624
<211> LENGTH: 21
<212> TYPE: DNA
<213> ORGANISM: Mus sp.

<400> SEQUENCE: 624
tctgtacggg atcttcttgg a    21

<210> SEQ ID NO 625
<211> LENGTH: 22
<212> TYPE: DNA
<213> ORGANISM: Mus sp.

<400> SEQUENCE: 625
ctcagagcaa gagaaagcac tg    22

<210> SEQ ID NO 626
<211> LENGTH: 23
<212> TYPE: DNA
<213> ORGANISM: Mus sp.

<400> SEQUENCE: 626
cgttgatgaa ccagttacag acc    23

<210> SEQ ID NO 627
<211> LENGTH: 20
<212> TYPE: DNA

```
<213> ORGANISM: Mus sp.

<400> SEQUENCE: 627
tccctgaagg atgtgcctac                                              20

<210> SEQ ID NO 628
<211> LENGTH: 18
<212> TYPE: DNA
<213> ORGANISM: Mus sp.

<400> SEQUENCE: 628
aagggttttc ccgtttgc                                                18

<210> SEQ ID NO 629
<211> LENGTH: 20
<212> TYPE: DNA
<213> ORGANISM: Mus sp.

<400> SEQUENCE: 629
gccatcaatg gattccctaa                                              20

<210> SEQ ID NO 630
<211> LENGTH: 24
<212> TYPE: DNA
<213> ORGANISM: Mus sp.

<400> SEQUENCE: 630
catttggacg tgatatagac atgc                                         24

<210> SEQ ID NO 631
<211> LENGTH: 20
<212> TYPE: DNA
<213> ORGANISM: Mus sp.

<400> SEQUENCE: 631
cttcaaggat aagggcgaca                                              20

<210> SEQ ID NO 632
<211> LENGTH: 20
<212> TYPE: DNA
<213> ORGANISM: Mus sp.

<400> SEQUENCE: 632
gacagattgt ggcgaattga                                              20

<210> SEQ ID NO 633
<211> LENGTH: 21
<212> TYPE: DNA
<213> ORGANISM: Mus sp.

<400> SEQUENCE: 633
ccacagaagg agagtcaagg a                                            21

<210> SEQ ID NO 634
<211> LENGTH: 19
<212> TYPE: DNA
<213> ORGANISM: Mus sp.

<400> SEQUENCE: 634
gtgttttcct ggggatgct                                               19

<210> SEQ ID NO 635
<211> LENGTH: 18
```

```
<212> TYPE: DNA
<213> ORGANISM: Mus sp.

<400> SEQUENCE: 635
gagctgggcc attcacac                                              18

<210> SEQ ID NO 636
<211> LENGTH: 19
<212> TYPE: DNA
<213> ORGANISM: Mus sp.

<400> SEQUENCE: 636
tccatgtctt gggatctgg                                             19

<210> SEQ ID NO 637
<211> LENGTH: 22
<212> TYPE: DNA
<213> ORGANISM: Mus sp.

<400> SEQUENCE: 637
gggaagttta ttcgcttgaa ga                                         22

<210> SEQ ID NO 638
<211> LENGTH: 18
<212> TYPE: DNA
<213> ORGANISM: Mus sp.

<400> SEQUENCE: 638
atctcccagc ctcccatt                                              18

<210> SEQ ID NO 639
<211> LENGTH: 19
<212> TYPE: DNA
<213> ORGANISM: Mus sp.

<400> SEQUENCE: 639
tggccttgtt agaccgtga                                             19

<210> SEQ ID NO 640
<211> LENGTH: 23
<212> TYPE: DNA
<213> ORGANISM: Mus sp.

<400> SEQUENCE: 640
aagtatttct ggcagtcctc ctc                                        23

<210> SEQ ID NO 641
<211> LENGTH: 19
<212> TYPE: DNA
<213> ORGANISM: Mus sp.

<400> SEQUENCE: 641
gctctttgtt ccccagcat                                             19

<210> SEQ ID NO 642
<211> LENGTH: 21
<212> TYPE: DNA
<213> ORGANISM: Mus sp.

<400> SEQUENCE: 642
ctaccacgat gaccacgatt t                                          21

<210> SEQ ID NO 643
```

```
<211> LENGTH: 23
<212> TYPE: DNA
<213> ORGANISM: Mus sp.

<400> SEQUENCE: 643
agtcttacgg aaatgaaaaa cga                                            23

<210> SEQ ID NO 644
<211> LENGTH: 20
<212> TYPE: DNA
<213> ORGANISM: Mus sp.

<400> SEQUENCE: 644
ccaaccactg cccataagat                                                20

<210> SEQ ID NO 645
<211> LENGTH: 20
<212> TYPE: DNA
<213> ORGANISM: Mus sp.

<400> SEQUENCE: 645
gaccctggta acaccacagg                                                20

<210> SEQ ID NO 646
<211> LENGTH: 18
<212> TYPE: DNA
<213> ORGANISM: Mus sp.

<400> SEQUENCE: 646
tcacgacgtc atgccaag                                                  18

<210> SEQ ID NO 647
<211> LENGTH: 21
<212> TYPE: DNA
<213> ORGANISM: Mus sp.

<400> SEQUENCE: 647
ggaaataacg gtgaaggtgc t                                              21

<210> SEQ ID NO 648
<211> LENGTH: 20
<212> TYPE: DNA
<213> ORGANISM: Mus sp.

<400> SEQUENCE: 648
catgtcaaac gtgagcgact                                                20

<210> SEQ ID NO 649
<211> LENGTH: 20
<212> TYPE: DNA
<213> ORGANISM: Mus sp.

<400> SEQUENCE: 649
cgttttgcaa tgcagacgta                                                20

<210> SEQ ID NO 650
<211> LENGTH: 19
<212> TYPE: DNA
<213> ORGANISM: Mus sp.

<400> SEQUENCE: 650
ggaatccacc tccttctcg                                                 19
```

```
<210> SEQ ID NO 651
<211> LENGTH: 19
<212> TYPE: DNA
<213> ORGANISM: Mus sp.

<400> SEQUENCE: 651
tcctcctcag accgctttt                                                    19

<210> SEQ ID NO 652
<211> LENGTH: 21
<212> TYPE: DNA
<213> ORGANISM: Mus sp.

<400> SEQUENCE: 652
cctggttcat catcgctaat c                                                 21

<210> SEQ ID NO 653
<211> LENGTH: 18
<212> TYPE: DNA
<213> ORGANISM: Mus sp.

<400> SEQUENCE: 653
gaacttccgc cagcttcc                                                     18

<210> SEQ ID NO 654
<211> LENGTH: 22
<212> TYPE: DNA
<213> ORGANISM: Mus sp.

<400> SEQUENCE: 654
ctggtaaggc gtccagtaat ct                                                22

<210> SEQ ID NO 655
<211> LENGTH: 20
<212> TYPE: DNA
<213> ORGANISM: Mus sp.

<400> SEQUENCE: 655
ctgcacacct ctcaatgcag                                                   20

<210> SEQ ID NO 656
<211> LENGTH: 22
<212> TYPE: DNA
<213> ORGANISM: Mus sp.

<400> SEQUENCE: 656
ggaagcggta gtgtacagag gt                                                22

<210> SEQ ID NO 657
<211> LENGTH: 19
<212> TYPE: DNA
<213> ORGANISM: Mus sp.

<400> SEQUENCE: 657
tgggatctgt catcgtgct                                                    19

<210> SEQ ID NO 658
<211> LENGTH: 22
<212> TYPE: DNA
<213> ORGANISM: Mus sp.

<400> SEQUENCE: 658
atcaccatgt ttctcttgat cg                                                22
```

```
<210> SEQ ID NO 659
<211> LENGTH: 21
<212> TYPE: DNA
<213> ORGANISM: Mus sp.

<400> SEQUENCE: 659
acagcacctt atggctctct g                                              21

<210> SEQ ID NO 660
<211> LENGTH: 20
<212> TYPE: DNA
<213> ORGANISM: Mus sp.

<400> SEQUENCE: 660
atggggtggc atcatgtagt                                                20

<210> SEQ ID NO 661
<211> LENGTH: 20
<212> TYPE: DNA
<213> ORGANISM: Mus sp.

<400> SEQUENCE: 661
ccagcaagac attgatgacc                                                20

<210> SEQ ID NO 662
<211> LENGTH: 20
<212> TYPE: DNA
<213> ORGANISM: Mus sp.

<400> SEQUENCE: 662
gatcttgcct tctccagtgc                                                20

<210> SEQ ID NO 663
<211> LENGTH: 22
<212> TYPE: DNA
<213> ORGANISM: Mus sp.

<400> SEQUENCE: 663
cctgttccag gctattctgt tc                                             22

<210> SEQ ID NO 664
<211> LENGTH: 19
<212> TYPE: DNA
<213> ORGANISM: Mus sp.

<400> SEQUENCE: 664
tcatggtctt tcccccaag                                                 19

<210> SEQ ID NO 665
<211> LENGTH: 21
<212> TYPE: DNA
<213> ORGANISM: Mus sp.

<400> SEQUENCE: 665
aggaaccctc cgaagactat g                                              21

<210> SEQ ID NO 666
<211> LENGTH: 20
<212> TYPE: DNA
<213> ORGANISM: Mus sp.

<400> SEQUENCE: 666
ttcctcctgt atggcttgct                                                20
```

<210> SEQ ID NO 667
<211> LENGTH: 24
<212> TYPE: DNA
<213> ORGANISM: Mus sp.

<400> SEQUENCE: 667
ttgcagagat ggatactatg aagc                     24

<210> SEQ ID NO 668
<211> LENGTH: 22
<212> TYPE: DNA
<213> ORGANISM: Mus sp.

<400> SEQUENCE: 668
caccgaatac ccaaattttg aa                       22

<210> SEQ ID NO 669
<211> LENGTH: 20
<212> TYPE: DNA
<213> ORGANISM: Mus sp.

<400> SEQUENCE: 669
ggagagacct tccatgtgct                          20

<210> SEQ ID NO 670
<211> LENGTH: 22
<212> TYPE: DNA
<213> ORGANISM: Mus sp.

<400> SEQUENCE: 670
aagacaaagc tatggtcctg gt                       22

<210> SEQ ID NO 671
<211> LENGTH: 20
<212> TYPE: DNA
<213> ORGANISM: Mus sp.

<400> SEQUENCE: 671
aagatcaagc tggggcacta                          20

<210> SEQ ID NO 672
<211> LENGTH: 19
<212> TYPE: DNA
<213> ORGANISM: Mus sp.

<400> SEQUENCE: 672
catgggacag cggtcatac                           19

<210> SEQ ID NO 673
<211> LENGTH: 21
<212> TYPE: DNA
<213> ORGANISM: Mus sp.

<400> SEQUENCE: 673
ccctacgacc ctaagtcaag c                        21

<210> SEQ ID NO 674
<211> LENGTH: 20
<212> TYPE: DNA
<213> ORGANISM: Mus sp.

<400> SEQUENCE: 674

-continued tgtggctgtg catgatagtg  20

<210> SEQ ID NO 675
<211> LENGTH: 18
<212> TYPE: DNA
<213> ORGANISM: Mus sp.

<400> SEQUENCE: 675
tacctgctgg ctggatgg  18

<210> SEQ ID NO 676
<211> LENGTH: 20
<212> TYPE: DNA
<213> ORGANISM: Mus sp.

<400> SEQUENCE: 676
cacagcctcg gcatatttct  20

<210> SEQ ID NO 677
<211> LENGTH: 22
<212> TYPE: DNA
<213> ORGANISM: Mus sp.

<400> SEQUENCE: 677
tgaaatgctt taacgacctc ag  22

<210> SEQ ID NO 678
<211> LENGTH: 20
<212> TYPE: DNA
<213> ORGANISM: Mus sp.

<400> SEQUENCE: 678
gtggcttgaa gtcgacacct  20

<210> SEQ ID NO 679
<211> LENGTH: 24
<212> TYPE: DNA
<213> ORGANISM: Mus sp.

<400> SEQUENCE: 679
gcactagaca aagttcacct gaga  24

<210> SEQ ID NO 680
<211> LENGTH: 20
<212> TYPE: DNA
<213> ORGANISM: Mus sp.

<400> SEQUENCE: 680
cgctatccac atcaaagcaa  20

<210> SEQ ID NO 681
<211> LENGTH: 19
<212> TYPE: DNA
<213> ORGANISM: Mus sp.

<400> SEQUENCE: 681
ggagtgaccc cgtcatctt  19

<210> SEQ ID NO 682
<211> LENGTH: 19
<212> TYPE: DNA
<213> ORGANISM: Mus sp.

<400> SEQUENCE: 682
aggagcagca gcatgtgag                                                19

<210> SEQ ID NO 683
<211> LENGTH: 20
<212> TYPE: DNA
<213> ORGANISM: Mus sp.

<400> SEQUENCE: 683
gagccagatc ctccctgact                                               20

<210> SEQ ID NO 684
<211> LENGTH: 19
<212> TYPE: DNA
<213> ORGANISM: Mus sp.

<400> SEQUENCE: 684
ggcatatccg gtcaccagt                                                19

<210> SEQ ID NO 685
<211> LENGTH: 20
<212> TYPE: DNA
<213> ORGANISM: Mus sp.

<400> SEQUENCE: 685
caaagcgaga gaccagagga                                               20

<210> SEQ ID NO 686
<211> LENGTH: 20
<212> TYPE: DNA
<213> ORGANISM: Mus sp.

<400> SEQUENCE: 686
aagtggactt tggcttggtg                                               20

<210> SEQ ID NO 687
<211> LENGTH: 20
<212> TYPE: DNA
<213> ORGANISM: Mus sp.

<400> SEQUENCE: 687
gatcgtaggc aacaccaagg                                               20

<210> SEQ ID NO 688
<211> LENGTH: 18
<212> TYPE: DNA
<213> ORGANISM: Mus sp.

<400> SEQUENCE: 688
cttcaggatg cctgcaca                                                 18

<210> SEQ ID NO 689
<211> LENGTH: 19
<212> TYPE: DNA
<213> ORGANISM: Mus sp.

<400> SEQUENCE: 689
catgctctgg caaaaatcc                                                19

<210> SEQ ID NO 690
<211> LENGTH: 20
<212> TYPE: DNA
<213> ORGANISM: Mus sp.

```
<400> SEQUENCE: 690
actcgaacac cctggtatgg                                              20

<210> SEQ ID NO 691
<211> LENGTH: 19
<212> TYPE: DNA
<213> ORGANISM: Mus sp.

<400> SEQUENCE: 691
cccagaccgc agtatccat                                               19

<210> SEQ ID NO 692
<211> LENGTH: 19
<212> TYPE: DNA
<213> ORGANISM: Mus sp.

<400> SEQUENCE: 692
gctccaggtc tcgcttctt                                               19

<210> SEQ ID NO 693
<211> LENGTH: 20
<212> TYPE: DNA
<213> ORGANISM: Mus sp.

<400> SEQUENCE: 693
gtgctcccga caaacgtatc                                              20

<210> SEQ ID NO 694
<211> LENGTH: 20
<212> TYPE: DNA
<213> ORGANISM: Mus sp.

<400> SEQUENCE: 694
cccattcctc agcatctttg                                              20

<210> SEQ ID NO 695
<211> LENGTH: 20
<212> TYPE: DNA
<213> ORGANISM: Mus sp.

<400> SEQUENCE: 695
cgagctggtc tttcaagtca                                              20

<210> SEQ ID NO 696
<211> LENGTH: 18
<212> TYPE: DNA
<213> ORGANISM: Mus sp.

<400> SEQUENCE: 696
ctggctgccg tgaacaat                                                18

<210> SEQ ID NO 697
<211> LENGTH: 19
<212> TYPE: DNA
<213> ORGANISM: Mus sp.

<400> SEQUENCE: 697
tgacgaggtt ccagaggtg                                               19

<210> SEQ ID NO 698
<211> LENGTH: 21
<212> TYPE: DNA
<213> ORGANISM: Mus sp.
```

```
<400> SEQUENCE: 698
tgcagaggtg cacatagtct g                                          21

<210> SEQ ID NO 699
<211> LENGTH: 18
<212> TYPE: DNA
<213> ORGANISM: Mus sp.

<400> SEQUENCE: 699
acgccactgt cgcttttc                                              18

<210> SEQ ID NO 700
<211> LENGTH: 20
<212> TYPE: DNA
<213> ORGANISM: Mus sp.

<400> SEQUENCE: 700
gcaaacagct cgaaggagac                                            20

<210> SEQ ID NO 701
<211> LENGTH: 20
<212> TYPE: DNA
<213> ORGANISM: Mus sp.

<400> SEQUENCE: 701
tgggatgact aggctggaga                                            20

<210> SEQ ID NO 702
<211> LENGTH: 20
<212> TYPE: DNA
<213> ORGANISM: Mus sp.

<400> SEQUENCE: 702
agtggatcat gggctttgag                                            20

<210> SEQ ID NO 703
<211> LENGTH: 19
<212> TYPE: DNA
<213> ORGANISM: Mus sp.

<400> SEQUENCE: 703
cggcagtcaa cacaaacaa                                             19

<210> SEQ ID NO 704
<211> LENGTH: 20
<212> TYPE: DNA
<213> ORGANISM: Mus sp.

<400> SEQUENCE: 704 tcagggaac tagtccatgc                                             20

<210> SEQ ID NO 705
<211> LENGTH: 20
<212> TYPE: DNA
<213> ORGANISM: Mus sp.

<400> SEQUENCE: 705
agaaccagcc accttcacac                                            20

<210> SEQ ID NO 706
<211> LENGTH: 20
<212> TYPE: DNA
```

```
<213> ORGANISM: Mus sp.

<400> SEQUENCE: 706
gtgttgaaga aagggccagt                                                   20

<210> SEQ ID NO 707
<211> LENGTH: 19
<212> TYPE: DNA
<213> ORGANISM: Mus sp.

<400> SEQUENCE: 707
ctcgacccgt ccttcactc                                                    19

<210> SEQ ID NO 708
<211> LENGTH: 24
<212> TYPE: DNA
<213> ORGANISM: Mus sp.

<400> SEQUENCE: 708
ttgactctcc cttctgaatc ttct                                              24

<210> SEQ ID NO 709
<211> LENGTH: 20
<212> TYPE: DNA
<213> ORGANISM: Mus sp.

<400> SEQUENCE: 709
tccctcagaa gcacttgacc                                                   20

<210> SEQ ID NO 710
<211> LENGTH: 20
<212> TYPE: DNA
<213> ORGANISM: Mus sp.

<400> SEQUENCE: 710
gagttctgct tgctggggta                                                   20

<210> SEQ ID NO 711
<211> LENGTH: 18
<212> TYPE: DNA
<213> ORGANISM: Mus sp.

<400> SEQUENCE: 711
ggggcagtga aagcctct                                                     18

<210> SEQ ID NO 712
<211> LENGTH: 22
<212> TYPE: DNA
<213> ORGANISM: Mus sp.

<400> SEQUENCE: 712
gcttttcact atagcccagg ag                                                22

<210> SEQ ID NO 713
<211> LENGTH: 23
<212> TYPE: DNA
<213> ORGANISM: Mus sp.

<400> SEQUENCE: 713
aatatcaata acgactggcg tgt                                               23

<210> SEQ ID NO 714
<211> LENGTH: 19
```

```
<212> TYPE: DNA
<213> ORGANISM: Mus sp.

<400> SEQUENCE: 714
catgtttgcc tctggccta                                              19

<210> SEQ ID NO 715
<211> LENGTH: 20
<212> TYPE: DNA
<213> ORGANISM: Mus sp.

<400> SEQUENCE: 715
ttacgtgtga aggctgcaag                                             20

<210> SEQ ID NO 716
<211> LENGTH: 20
<212> TYPE: DNA
<213> ORGANISM: Mus sp.

<400> SEQUENCE: 716
ggagtaggtg gcattgctct                                             20

<210> SEQ ID NO 717
<211> LENGTH: 20
<212> TYPE: DNA
<213> ORGANISM: Mus sp.

<400> SEQUENCE: 717
gagaaagaga cgtccccaca                                             20

<210> SEQ ID NO 718
<211> LENGTH: 25
<212> TYPE: DNA
<213> ORGANISM: Mus sp.

<400> SEQUENCE: 718
tcaaagctct tgtaggagta gaagc                                       25

<210> SEQ ID NO 719
<211> LENGTH: 20
<212> TYPE: DNA
<213> ORGANISM: Mus sp.

<400> SEQUENCE: 719
tctccacgag cttcacattg                                             20

<210> SEQ ID NO 720
<211> LENGTH: 19
<212> TYPE: DNA
<213> ORGANISM: Mus sp.

<400> SEQUENCE: 720
gaccaccaag ggcagagac                                              19

<210> SEQ ID NO 721
<211> LENGTH: 22
<212> TYPE: DNA
<213> ORGANISM: Mus sp.

<400> SEQUENCE: 721
gaagatcaca tcagcatctc ca                                          22

<210> SEQ ID NO 722
```

```
<211> LENGTH: 21
<212> TYPE: DNA
<213> ORGANISM: Mus sp.

<400> SEQUENCE: 722
caggattcac acttccaacc t                                               21

<210> SEQ ID NO 723
<211> LENGTH: 20
<212> TYPE: DNA
<213> ORGANISM: Mus sp.

<400> SEQUENCE: 723
atccctccac cctatgacaa                                                 20

<210> SEQ ID NO 724
<211> LENGTH: 19
<212> TYPE: DNA
<213> ORGANISM: Mus sp.

<400> SEQUENCE: 724
gccccaggta agcaaactt                                                  19

<210> SEQ ID NO 725
<211> LENGTH: 18
<212> TYPE: DNA
<213> ORGANISM: Mus sp.

<400> SEQUENCE: 725
ctggggttgc tgcttctg                                                   18

<210> SEQ ID NO 726
<211> LENGTH: 24
<212> TYPE: DNA
<213> ORGANISM: Mus sp.

<400> SEQUENCE: 726
agatgtttgg ttgcagtaaa tctg                                            24

<210> SEQ ID NO 727
<211> LENGTH: 18
<212> TYPE: DNA
<213> ORGANISM: Mus sp.

<400> SEQUENCE: 727
gacagaacca ggcgtcca                                                   18

<210> SEQ ID NO 728
<211> LENGTH: 22
<212> TYPE: DNA
<213> ORGANISM: Mus sp.

<400> SEQUENCE: 728
agctcagaag ggaattcaga tg                                              22

<210> SEQ ID NO 729
<211> LENGTH: 23
<212> TYPE: DNA
<213> ORGANISM: Mus sp.

<400> SEQUENCE: 729
tgtgctcaca atggagtata agg                                             23
```

```
<210> SEQ ID NO 730
<211> LENGTH: 20
<212> TYPE: DNA
<213> ORGANISM: Mus sp.

<400> SEQUENCE: 730
ctcaggagga ggatgctgat                                               20

<210> SEQ ID NO 731
<211> LENGTH: 20
<212> TYPE: DNA
<213> ORGANISM: Mus sp.

<400> SEQUENCE: 731
agccaaccat gctcaacttc                                               20

<210> SEQ ID NO 732
<211> LENGTH: 24
<212> TYPE: DNA
<213> ORGANISM: Mus sp.

<400> SEQUENCE: 732
ggcttttcag aaattagttc catt                                          24

<210> SEQ ID NO 733
<211> LENGTH: 20
<212> TYPE: DNA
<213> ORGANISM: Mus sp.

<400> SEQUENCE: 733
ttcctctccc gaatttttca                                               20

<210> SEQ ID NO 734
<211> LENGTH: 20
<212> TYPE: DNA
<213> ORGANISM: Mus sp.

<400> SEQUENCE: 734
ccacggagca tttaacaagg                                               20

<210> SEQ ID NO 735
<211> LENGTH: 20
<212> TYPE: DNA
<213> ORGANISM: Mus sp.

<400> SEQUENCE: 735
catgatggac ttggagttgc                                               20

<210> SEQ ID NO 736
<211> LENGTH: 21
<212> TYPE: DNA
<213> ORGANISM: Mus sp.

<400> SEQUENCE: 736
cctccaaagg atgtcaatca a                                             21

<210> SEQ ID NO 737
<211> LENGTH: 23
<212> TYPE: DNA
<213> ORGANISM: Mus sp.

<400> SEQUENCE: 737
acagacttca acttcctcat ggt                                           23
```

```
<210> SEQ ID NO 738
<211> LENGTH: 20
<212> TYPE: DNA
<213> ORGANISM: Mus sp.

<400> SEQUENCE: 738
ctgtcagcaa gcatcacctt                                          20

<210> SEQ ID NO 739
<211> LENGTH: 20
<212> TYPE: DNA
<213> ORGANISM: Mus sp.

<400> SEQUENCE: 739
ctccgtgcta cccactcact                                          20

<210> SEQ ID NO 740
<211> LENGTH: 19
<212> TYPE: DNA
<213> ORGANISM: Mus sp.

<400> SEQUENCE: 740
atgacggtga ccagagtgc                                           19

<210> SEQ ID NO 741
<211> LENGTH: 18
<212> TYPE: DNA
<213> ORGANISM: Mus sp.

<400> SEQUENCE: 741
atggatccca gcagcaag                                            18

<210> SEQ ID NO 742
<211> LENGTH: 21
<212> TYPE: DNA
<213> ORGANISM: Mus sp.

<400> SEQUENCE: 742
ccagtgttat agccgaactg c                                        21

<210> SEQ ID NO 743
<211> LENGTH: 26
<212> TYPE: DNA
<213> ORGANISM: Mus sp.

<400> SEQUENCE: 743
tgttggagga cttagaagat ctaacc                                   26

<210> SEQ ID NO 744
<211> LENGTH: 20
<212> TYPE: DNA
<213> ORGANISM: Mus sp.

<400> SEQUENCE: 744
aggccagctg tactctttgg                                          20

<210> SEQ ID NO 745
<211> LENGTH: 20
<212> TYPE: DNA
<213> ORGANISM: Mus sp.

<400> SEQUENCE: 745
gccagcagtc atgatgaaaa                                          20
```

```
<210> SEQ ID NO 746
<211> LENGTH: 20
<212> TYPE: DNA
<213> ORGANISM: Mus sp.

<400> SEQUENCE: 746
tatcacaata cgggcaggtg                                              20

<210> SEQ ID NO 747
<211> LENGTH: 21
<212> TYPE: DNA
<213> ORGANISM: Mus sp.

<400> SEQUENCE: 747
aacagctttc gatgaagcca t                                            21

<210> SEQ ID NO 748
<211> LENGTH: 21
<212> TYPE: DNA
<213> ORGANISM: Mus sp.

<400> SEQUENCE: 748
tgggtatccg atgtccacaa t                                            21

<210> SEQ ID NO 749
<211> LENGTH: 20
<212> TYPE: DNA
<213> ORGANISM: Mus sp.

<400> SEQUENCE: 749
acacacctgt gcaagaagca                                              20

<210> SEQ ID NO 750
<211> LENGTH: 20
<212> TYPE: DNA
<213> ORGANISM: Mus sp.

<400> SEQUENCE: 750
gctcttgttg gttgggaatc                                              20

<210> SEQ ID NO 751
<211> LENGTH: 20
<212> TYPE: DNA
<213> ORGANISM: Mus sp.

<400> SEQUENCE: 751
tgagagccat gtctgtgacc                                              20

<210> SEQ ID NO 752
<211> LENGTH: 19
<212> TYPE: DNA
<213> ORGANISM: Mus sp.

<400> SEQUENCE: 752
ctcctgcagc ctcatcttg                                               19

<210> SEQ ID NO 753
<211> LENGTH: 21
<212> TYPE: DNA
<213> ORGANISM: Mus sp.

<400> SEQUENCE: 753
```
gagtggagtc ctagcatcac g                                          21

<210> SEQ ID NO 754
<211> LENGTH: 19
<212> TYPE: DNA
<213> ORGANISM: Mus sp.

<400> SEQUENCE: 754
cagtggaagg cgctgtatc                                             19

<210> SEQ ID NO 755
<211> LENGTH: 20
<212> TYPE: DNA
<213> ORGANISM: Mus sp.

<400> SEQUENCE: 755
tcccacttga aagcacatca                                            20

<210> SEQ ID NO 756
<211> LENGTH: 20
<212> TYPE: DNA
<213> ORGANISM: Mus sp.

<400> SEQUENCE: 756
acttcttgca aaacgccact                                            20

<210> SEQ ID NO 757
<211> LENGTH: 19
<212> TYPE: DNA
<213> ORGANISM: Mus sp.

<400> SEQUENCE: 757
gaatctgagg accggatcg                                             19

<210> SEQ ID NO 758
<211> LENGTH: 23
<212> TYPE: DNA
<213> ORGANISM: Mus sp.

<400> SEQUENCE: 758
tgggaaagta caacaaatct cca                                        23

<210> SEQ ID NO 759
<211> LENGTH: 18
<212> TYPE: DNA
<213> ORGANISM: Mus sp.

<400> SEQUENCE: 759
ctggacccca tggacatc                                              18

<210> SEQ ID NO 760
<211> LENGTH: 20
<212> TYPE: DNA
<213> ORGANISM: Mus sp.

<400> SEQUENCE: 760
aggatgactg cacacattgc                                            20

<210> SEQ ID NO 761
<211> LENGTH: 21
<212> TYPE: DNA
<213> ORGANISM: Mus sp.

<400> SEQUENCE: 761

-continued tggctaccag tatctccgtg t                                    21

<210> SEQ ID NO 762
<211> LENGTH: 20
<212> TYPE: DNA
<213> ORGANISM: Mus sp.

<400> SEQUENCE: 762
tggtaaacgc tgctgatgtc                                      20

<210> SEQ ID NO 763
<211> LENGTH: 20
<212> TYPE: DNA
<213> ORGANISM: Mus sp.

<400> SEQUENCE: 763
ttcaacgacc ttcgattcgt                                      20

<210> SEQ ID NO 764
<211> LENGTH: 20
<212> TYPE: DNA
<213> ORGANISM: Mus sp.

<400> SEQUENCE: 764
ttggtgaaca cggtgattgt                                      20

<210> SEQ ID NO 765
<211> LENGTH: 20
<212> TYPE: DNA
<213> ORGANISM: Mus sp.

<400> SEQUENCE: 765
agagaagcag tggctcaagg                                      20

<210> SEQ ID NO 766
<211> LENGTH: 19
<212> TYPE: DNA
<213> ORGANISM: Mus sp.

<400> SEQUENCE: 766
atttcttctg ccggacctc                                       19

<210> SEQ ID NO 767
<211> LENGTH: 20
<212> TYPE: DNA
<213> ORGANISM: Mus sp.

<400> SEQUENCE: 767
ttccctcagg gctatgacac                                      20

<210> SEQ ID NO 768
<211> LENGTH: 19
<212> TYPE: DNA
<213> ORGANISM: Mus sp.

<400> SEQUENCE: 768
ctgtcgctga cctcctgac                                       19

<210> SEQ ID NO 769
<211> LENGTH: 20
<212> TYPE: DNA
<213> ORGANISM: Mus sp.

<400> SEQUENCE: 769
ttcacgacac accagatcct                                           20

<210> SEQ ID NO 770
<211> LENGTH: 21
<212> TYPE: DNA
<213> ORGANISM: Mus sp.

<400> SEQUENCE: 770
tgagcatctt gttacccttg c                                         21

<210> SEQ ID NO 771
<211> LENGTH: 21
<212> TYPE: DNA
<213> ORGANISM: Mus sp.

<400> SEQUENCE: 771
ttctggtgct tgtctcactg a                                         21

<210> SEQ ID NO 772
<211> LENGTH: 22
<212> TYPE: DNA
<213> ORGANISM: Mus sp.

<400> SEQUENCE: 772
cagtatgttc ggcttcccat tc                                        22

<210> SEQ ID NO 773
<211> LENGTH: 21
<212> TYPE: DNA
<213> ORGANISM: Mus sp.

<400> SEQUENCE: 773
ccagagcttg accatcatca g                                         21

<210> SEQ ID NO 774
<211> LENGTH: 25
<212> TYPE: DNA
<213> ORGANISM: Mus sp.

<400> SEQUENCE: 774
tcctttacaa atcatacagg actgg                                     25

<210> SEQ ID NO 775
<211> LENGTH: 18
<212> TYPE: DNA
<213> ORGANISM: Mus sp.

<400> SEQUENCE: 775
cccttcaccc tggtcctt                                             18

<210> SEQ ID NO 776
<211> LENGTH: 20
<212> TYPE: DNA
<213> ORGANISM: Mus sp.

<400> SEQUENCE: 776
cttcctcgaa ttaggccaga                                           20

<210> SEQ ID NO 777
<211> LENGTH: 23
<212> TYPE: DNA
<213> ORGANISM: Mus sp.

```
<400> SEQUENCE: 777
ctcaggatca ctttcagaag agc                                       23

<210> SEQ ID NO 778
<211> LENGTH: 20
<212> TYPE: DNA
<213> ORGANISM: Mus sp.

<400> SEQUENCE: 778
ggcattcatc tttggaatcg                                           20

<210> SEQ ID NO 779
<211> LENGTH: 18
<212> TYPE: DNA
<213> ORGANISM: Mus sp.

<400> SEQUENCE: 779
tgatgcaatc cggatcaa                                             18

<210> SEQ ID NO 780
<211> LENGTH: 19
<212> TYPE: DNA
<213> ORGANISM: Mus sp.

<400> SEQUENCE: 780
cacgtgtgtt gcgtcagtc                                            19

<210> SEQ ID NO 781
<211> LENGTH: 20
<212> TYPE: DNA
<213> ORGANISM: Mus sp.

<400> SEQUENCE: 781
aagagaggac cagaccagca                                           20

<210> SEQ ID NO 782
<211> LENGTH: 27
<212> TYPE: DNA
<213> ORGANISM: Mus sp.

<400> SEQUENCE: 782 cttttttggtg acttctgagt agagaat                                  27

<210> SEQ ID NO 783
<211> LENGTH: 19
<212> TYPE: DNA
<213> ORGANISM: Mus sp.

<400> SEQUENCE: 783
cagccgaagg gtgctctac                                            19

<210> SEQ ID NO 784
<211> LENGTH: 21
<212> TYPE: DNA
<213> ORGANISM: Mus sp.

<400> SEQUENCE: 784
aaatctggca gaagatgatg g                                         21

<210> SEQ ID NO 785
<211> LENGTH: 19
<212> TYPE: DNA
```

```
<213> ORGANISM: Mus sp.

<400> SEQUENCE: 785 aggggagac cagagttcc                                                    19

<210> SEQ ID NO 786
<211> LENGTH: 18
<212> TYPE: DNA
<213> ORGANISM: Mus sp.

<400> SEQUENCE: 786
gccattggag caggtcaa                                                    18

<210> SEQ ID NO 787
<211> LENGTH: 20
<212> TYPE: DNA
<213> ORGANISM: Mus sp.

<400> SEQUENCE: 787
agtctcagcg gcaatacgag                                                  20

<210> SEQ ID NO 788
<211> LENGTH: 20
<212> TYPE: DNA
<213> ORGANISM: Mus sp.

<400> SEQUENCE: 788
gcaaactgga actgcaggat                                                  20

<210> SEQ ID NO 789
<211> LENGTH: 20
<212> TYPE: DNA
<213> ORGANISM: Mus sp.

<400> SEQUENCE: 789
cagctgggga agtcattttt                                                  20

<210> SEQ ID NO 790
<211> LENGTH: 21
<212> TYPE: DNA
<213> ORGANISM: Mus sp.

<400> SEQUENCE: 790
ggcaacagca atatggagaa a                                                21

<210> SEQ ID NO 791
<211> LENGTH: 23
<212> TYPE: DNA
<213> ORGANISM: Mus sp.

<400> SEQUENCE: 791
ccaatgagac cttgaacaaa act                                              23

<210> SEQ ID NO 792
<211> LENGTH: 20
<212> TYPE: DNA
<213> ORGANISM: Mus sp.

<400> SEQUENCE: 792
gtaggaggca gtgccatttg                                                  20

<210> SEQ ID NO 793
<211> LENGTH: 19
```

```
<212> TYPE: DNA
<213> ORGANISM: Mus sp.

<400> SEQUENCE: 793
cggcatctgc tagctcagt                                                  19

<210> SEQ ID NO 794
<211> LENGTH: 24
<212> TYPE: DNA
<213> ORGANISM: Mus sp.

<400> SEQUENCE: 794
tgccatagtt tcattgttag aagc                                            24

<210> SEQ ID NO 795
<211> LENGTH: 20
<212> TYPE: DNA
<213> ORGANISM: Mus sp.

<400> SEQUENCE: 795
ggcaaattca acggcacagt                                                 20

<210> SEQ ID NO 796
<211> LENGTH: 19
<212> TYPE: DNA
<213> ORGANISM: Mus sp.

<400> SEQUENCE: 796
agatggtgat gggcttccc                                                  19

<210> SEQ ID NO 797
<211> LENGTH: 18
<212> TYPE: DNA
<213> ORGANISM: Mus sp.

<400> SEQUENCE: 797
agagggtggg gaccaaac                                                   18

<210> SEQ ID NO 798
<211> LENGTH: 21
<212> TYPE: DNA
<213> ORGANISM: Mus sp.

<400> SEQUENCE: 798
tgcttcatgt tgattgtctc g                                               21

<210> SEQ ID NO 799
<211> LENGTH: 18
<212> TYPE: DNA
<213> ORGANISM: Mus sp.

<400> SEQUENCE: 799
gccccaccga cctactct                                                   18

<210> SEQ ID NO 800
<211> LENGTH: 23
<212> TYPE: DNA
<213> ORGANISM: Mus sp.

<400> SEQUENCE: 800
tgtctgtgtc catactttct tgg                                             23

<210> SEQ ID NO 801
```

-continued

```
<211> LENGTH: 20
<212> TYPE: DNA
<213> ORGANISM: Mus sp.

<400> SEQUENCE: 801
agaagaaagg ctcgctcaga                                                  20

<210> SEQ ID NO 802
<211> LENGTH: 20
<212> TYPE: DNA
<213> ORGANISM: Mus sp.

<400> SEQUENCE: 802
ggctccatcg tgtaatccat                                                  20

<210> SEQ ID NO 803
<211> LENGTH: 19
<212> TYPE: DNA
<213> ORGANISM: Mus sp.

<400> SEQUENCE: 803
gaggacgaag acccaggtg                                                   19

<210> SEQ ID NO 804
<211> LENGTH: 22
<212> TYPE: DNA
<213> ORGANISM: Mus sp.

<400> SEQUENCE: 804
cagtgtatcg cttcctcttc ac                                               22

<210> SEQ ID NO 805
<211> LENGTH: 20
<212> TYPE: DNA
<213> ORGANISM: Mus sp.

<400> SEQUENCE: 805
tgcagacatg ctgtggatct                                                  20

<210> SEQ ID NO 806
<211> LENGTH: 21
<212> TYPE: DNA
<213> ORGANISM: Mus sp.

<400> SEQUENCE: 806
cttaactgtg agccagcaag c                                                21

<210> SEQ ID NO 807
<211> LENGTH: 25
<212> TYPE: DNA
<213> ORGANISM: Mus sp.

<400> SEQUENCE: 807
cccaggaaga catacttaga agaaa                                            25

<210> SEQ ID NO 808
<211> LENGTH: 23
<212> TYPE: DNA
<213> ORGANISM: Mus sp.

<400> SEQUENCE: 808
caacagtagc aaagacttga cca                                              23
```

```
<210> SEQ ID NO 809
<211> LENGTH: 20
<212> TYPE: DNA
<213> ORGANISM: Mus sp.

<400> SEQUENCE: 809
tggcaacaat gaagctatcg                                               20

<210> SEQ ID NO 810
<211> LENGTH: 20
<212> TYPE: DNA
<213> ORGANISM: Mus sp.

<400> SEQUENCE: 810
atgtcgggac cagtaggaca                                               20

<210> SEQ ID NO 811
<211> LENGTH: 22
<212> TYPE: DNA
<213> ORGANISM: Mus sp.

<400> SEQUENCE: 811
caagaaatta ggcacctgaa gc                                            22

<210> SEQ ID NO 812
<211> LENGTH: 20
<212> TYPE: DNA
<213> ORGANISM: Mus sp.

<400> SEQUENCE: 812
acacaggaaa cccagggata                                               20

<210> SEQ ID NO 813
<211> LENGTH: 22
<212> TYPE: DNA
<213> ORGANISM: Mus sp.

<400> SEQUENCE: 813
tgcctgtttg acaactttga gt                                            22

<210> SEQ ID NO 814
<211> LENGTH: 23
<212> TYPE: DNA
<213> ORGANISM: Mus sp.

<400> SEQUENCE: 814
gtggtctgca cagtatttgt cat                                           23

<210> SEQ ID NO 815
<211> LENGTH: 19
<212> TYPE: DNA
<213> ORGANISM: Mus sp.

<400> SEQUENCE: 815 acctctttc acgggagga                                                 19

<210> SEQ ID NO 816
<211> LENGTH: 19
<212> TYPE: DNA
<213> ORGANISM: Mus sp.

<400> SEQUENCE: 816
tcccacatct cccacattg                                                19
```

```
<210> SEQ ID NO 817
<211> LENGTH: 19
<212> TYPE: DNA
<213> ORGANISM: Mus sp.

<400> SEQUENCE: 817
cagctcctca tcgtgttgg                                                19

<210> SEQ ID NO 818
<211> LENGTH: 20
<212> TYPE: DNA
<213> ORGANISM: Mus sp.

<400> SEQUENCE: 818
cagaggtggc agaaacactg                                               20

<210> SEQ ID NO 819
<211> LENGTH: 20
<212> TYPE: DNA
<213> ORGANISM: Mus sp.

<400> SEQUENCE: 819
tccctgaagg atgtgcctac                                               20

<210> SEQ ID NO 820
<211> LENGTH: 18
<212> TYPE: DNA
<213> ORGANISM: Mus sp.

<400> SEQUENCE: 820
aagggttttc ccgtttgc                                                 18

<210> SEQ ID NO 821
<211> LENGTH: 19
<212> TYPE: DNA
<213> ORGANISM: Mus sp.

<400> SEQUENCE: 821
tgcaagcgca gtatcacag                                                19

<210> SEQ ID NO 822
<211> LENGTH: 20
<212> TYPE: DNA
<213> ORGANISM: Mus sp.

<400> SEQUENCE: 822
tgacgtaatg cctctgcatc                                               20

<210> SEQ ID NO 823
<211> LENGTH: 19
<212> TYPE: DNA
<213> ORGANISM: Mus sp.

<400> SEQUENCE: 823
agaaagccga caccct tca                                               19

<210> SEQ ID NO 824
<211> LENGTH: 18
<212> TYPE: DNA
<213> ORGANISM: Mus sp.

<400> SEQUENCE: 824
cggagagctg cgttctgt                                                 18
```

<210> SEQ ID NO 825
<211> LENGTH: 19
<212> TYPE: DNA
<213> ORGANISM: Mus sp.

<400> SEQUENCE: 825
ccagagatgg gaggcaaac                                                    19

<210> SEQ ID NO 826
<211> LENGTH: 21
<212> TYPE: DNA
<213> ORGANISM: Mus sp.

<400> SEQUENCE: 826
agtgcattgt atacgccttc c                                                 21

<210> SEQ ID NO 827
<211> LENGTH: 20
<212> TYPE: DNA
<213> ORGANISM: Mus sp.

<400> SEQUENCE: 827
tatgacctca cccgctacct                                                   20

<210> SEQ ID NO 828
<211> LENGTH: 18
<212> TYPE: DNA
<213> ORGANISM: Mus sp.

<400> SEQUENCE: 828
gggccccagg tagttcag                                                     18

<210> SEQ ID NO 829
<211> LENGTH: 20
<212> TYPE: DNA
<213> ORGANISM: Mus sp.

<400> SEQUENCE: 829
cgtttcccta tggcaatgtc                                                   20

<210> SEQ ID NO 830
<211> LENGTH: 18
<212> TYPE: DNA
<213> ORGANISM: Mus sp.

<400> SEQUENCE: 830
cccactgctt ggtggtgt                                                     18

<210> SEQ ID NO 831
<211> LENGTH: 23
<212> TYPE: DNA
<213> ORGANISM: Mus sp.

<400> SEQUENCE: 831
ttgacatagt gctttggtac agg                                               23

<210> SEQ ID NO 832
<211> LENGTH: 23
<212> TYPE: DNA
<213> ORGANISM: Mus sp.

<400> SEQUENCE: 832
tcgtatgtct ttccatctga agc              23

<210> SEQ ID NO 833
<211> LENGTH: 21
<212> TYPE: DNA
<213> ORGANISM: Mus sp.

<400> SEQUENCE: 833
ccagaagatg gtgtggtgtt t                21

<210> SEQ ID NO 834
<211> LENGTH: 18
<212> TYPE: DNA
<213> ORGANISM: Mus sp.

<400> SEQUENCE: 834
ctgaccctct ccccttgc                    18

<210> SEQ ID NO 835
<211> LENGTH: 19
<212> TYPE: DNA
<213> ORGANISM: Mus sp.

<400> SEQUENCE: 835
gccaagagtt tgccatgtg                   19

<210> SEQ ID NO 836
<211> LENGTH: 20
<212> TYPE: DNA
<213> ORGANISM: Mus sp.

<400> SEQUENCE: 836
cttgcagttc tcacgagtgc                  20

<210> SEQ ID NO 837
<211> LENGTH: 22
<212> TYPE: DNA
<213> ORGANISM: Mus sp.

<400> SEQUENCE: 837
tgacgtgtgg aagctgtaaa gt               22

<210> SEQ ID NO 838
<211> LENGTH: 21
<212> TYPE: DNA
<213> ORGANISM: Mus sp.

<400> SEQUENCE: 838
catttcttcc agcacaaagg t                21

<210> SEQ ID NO 839
<211> LENGTH: 19
<212> TYPE: DNA
<213> ORGANISM: Mus sp.

<400> SEQUENCE: 839
ggaacgcggt tattccagt                   19

<210> SEQ ID NO 840
<211> LENGTH: 21
<212> TYPE: DNA
<213> ORGANISM: Mus sp.

<400> SEQUENCE: 840
catcttccaa catggacacc t                                             21

<210> SEQ ID NO 841
<211> LENGTH: 20
<212> TYPE: DNA
<213> ORGANISM: Mus sp.

<400> SEQUENCE: 841
tagcgaaggt tgcggtagac                                               20

<210> SEQ ID NO 842
<211> LENGTH: 24
<212> TYPE: DNA
<213> ORGANISM: Mus sp.

<400> SEQUENCE: 842
ggtttatgac tttccatctt ggac                                          24

<210> SEQ ID NO 843
<211> LENGTH: 19
<212> TYPE: DNA
<213> ORGANISM: Mus sp.

<400> SEQUENCE: 843
tcctcctcag accgctttt                                                19

<210> SEQ ID NO 844
<211> LENGTH: 21
<212> TYPE: DNA
<213> ORGANISM: Mus sp.

<400> SEQUENCE: 844
cctggttcat catcgctaat c                                             21

<210> SEQ ID NO 845
<211> LENGTH: 18
<212> TYPE: DNA
<213> ORGANISM: Mus sp.

<400> SEQUENCE: 845
tgcacaagga gtggacga                                                 18

<210> SEQ ID NO 846
<211> LENGTH: 20
<212> TYPE: DNA
<213> ORGANISM: Mus sp.

<400> SEQUENCE: 846
aggaagctgg tctgggtat                                                20

<210> SEQ ID NO 847
<211> LENGTH: 21
<212> TYPE: DNA
<213> ORGANISM: Mus sp.

<400> SEQUENCE: 847
cacattcaag gcttcctgtt t                                             21

<210> SEQ ID NO 848
<211> LENGTH: 23
<212> TYPE: DNA
<213> ORGANISM: Mus sp.

<400> SEQUENCE: 848
gtattggatt ggtacagggt gag                                          23

<210> SEQ ID NO 849
<211> LENGTH: 21
<212> TYPE: DNA
<213> ORGANISM: Mus sp.

<400> SEQUENCE: 849
ccatcctgtt gttcctcatt g                                            21

<210> SEQ ID NO 850
<211> LENGTH: 23
<212> TYPE: DNA
<213> ORGANISM: Mus sp.

<400> SEQUENCE: 850
tccacatcta gcattctcac ttg                                          23

<210> SEQ ID NO 851
<211> LENGTH: 20
<212> TYPE: DNA
<213> ORGANISM: Mus sp.

<400> SEQUENCE: 851
tcgcctccat agtgatagcc                                              20

<210> SEQ ID NO 852
<211> LENGTH: 19
<212> TYPE: DNA
<213> ORGANISM: Mus sp.

<400> SEQUENCE: 852
ctcgctaggc agaggaagc                                               19

<210> SEQ ID NO 853
<211> LENGTH: 20
<212> TYPE: DNA
<213> ORGANISM: Mus sp.

<400> SEQUENCE: 853
gcaagtgcac agtcacaggt                                              20

<210> SEQ ID NO 854
<211> LENGTH: 19
<212> TYPE: DNA
<213> ORGANISM: Mus sp.

<400> SEQUENCE: 854
ttgcctgctg cttttgtgt                                               19

<210> SEQ ID NO 855
<211> LENGTH: 21
<212> TYPE: DNA
<213> ORGANISM: Mus sp.

<400> SEQUENCE: 855
gctgttgatg gacctacagg a                                            21

<210> SEQ ID NO 856
<211> LENGTH: 20
<212> TYPE: DNA
<213> ORGANISM: Mus sp.

```
<400> SEQUENCE: 856
ttcaattctg tggcctgctt                                                   20

<210> SEQ ID NO 857
<211> LENGTH: 21
<212> TYPE: DNA
<213> ORGANISM: Mus sp.

<400> SEQUENCE: 857
ctacagcagt tccctcaaac g                                                 21

<210> SEQ ID NO 858
<211> LENGTH: 19
<212> TYPE: DNA
<213> ORGANISM: Mus sp.

<400> SEQUENCE: 858
tgtctttcct ggggctcat                                                    19

<210> SEQ ID NO 859
<211> LENGTH: 24
<212> TYPE: DNA
<213> ORGANISM: Mus sp.

<400> SEQUENCE: 859
ctttgtcgtg tatcattggg tatt                                              24

<210> SEQ ID NO 860
<211> LENGTH: 20
<212> TYPE: DNA
<213> ORGANISM: Mus sp.

<400> SEQUENCE: 860
ttggtagctg gagtttgcag                                                   20

<210> SEQ ID NO 861
<211> LENGTH: 21
<212> TYPE: DNA
<213> ORGANISM: Mus sp.

<400> SEQUENCE: 861
aacggtgctg tgttactgag g                                                 21

<210> SEQ ID NO 862
<211> LENGTH: 20
<212> TYPE: DNA
<213> ORGANISM: Mus sp.

<400> SEQUENCE: 862
cagctgggcc atttactacc                                                   20

<210> SEQ ID NO 863
<211> LENGTH: 18
<212> TYPE: DNA
<213> ORGANISM: Mus sp.

<400> SEQUENCE: 863
cggtgcagtg tcagcttc                                                     18

<210> SEQ ID NO 864
<211> LENGTH: 20
<212> TYPE: DNA
```

```
<213> ORGANISM: Mus sp.

<400> SEQUENCE: 864
ctcccgcaaa caacagagtt                                        20

<210> SEQ ID NO 865
<211> LENGTH: 18
<212> TYPE: DNA
<213> ORGANISM: Mus sp.

<400> SEQUENCE: 865
ccgccggaga gaaaagtt                                          18

<210> SEQ ID NO 866
<211> LENGTH: 19
<212> TYPE: DNA
<213> ORGANISM: Mus sp.

<400> SEQUENCE: 866
ctggatcagt gccacacct                                         19

<210> SEQ ID NO 867
<211> LENGTH: 18
<212> TYPE: DNA
<213> ORGANISM: Mus sp.

<400> SEQUENCE: 867
tacctgctgg ctggatgg                                          18

<210> SEQ ID NO 868
<211> LENGTH: 20
<212> TYPE: DNA
<213> ORGANISM: Mus sp.

<400> SEQUENCE: 868
cacagcctcg gcatatttct                                        20

<210> SEQ ID NO 869
<211> LENGTH: 20
<212> TYPE: DNA
<213> ORGANISM: Mus sp.

<400> SEQUENCE: 869
caactgcaga gtttggagga                                        20

<210> SEQ ID NO 870
<211> LENGTH: 20
<212> TYPE: DNA
<213> ORGANISM: Mus sp.

<400> SEQUENCE: 870
tgtgtctgcc tgtcctgact                                        20

<210> SEQ ID NO 871
<211> LENGTH: 20
<212> TYPE: DNA
<213> ORGANISM: Mus sp.

<400> SEQUENCE: 871
tcccagaggg aactcatcac                                        20

<210> SEQ ID NO 872
<211> LENGTH: 19
```

<212> TYPE: DNA
<213> ORGANISM: Mus sp.

<400> SEQUENCE: 872
ccagaccctc gtcttcctc                                                     19

<210> SEQ ID NO 873
<211> LENGTH: 20
<212> TYPE: DNA
<213> ORGANISM: Mus sp.

<400> SEQUENCE: 873
ctggccctca tcagaacaat                                                    20

<210> SEQ ID NO 874
<211> LENGTH: 21
<212> TYPE: DNA
<213> ORGANISM: Mus sp.

<400> SEQUENCE: 874
ggcgactgct ttaccaaaat c                                                  21

<210> SEQ ID NO 875
<211> LENGTH: 20
<212> TYPE: DNA
<213> ORGANISM: Mus sp.

<400> SEQUENCE: 875
gcctcctctg tcagttgctc                                                    20

<210> SEQ ID NO 876
<211> LENGTH: 20
<212> TYPE: DNA
<213> ORGANISM: Mus sp.

<400> SEQUENCE: 876
aagcagagga tgagcaggaa                                                    20

<210> SEQ ID NO 877
<211> LENGTH: 19
<212> TYPE: DNA
<213> ORGANISM: Mus sp.

<400> SEQUENCE: 877
tcaggagccc accagtaca                                                     19

<210> SEQ ID NO 878
<211> LENGTH: 21
<212> TYPE: DNA
<213> ORGANISM: Mus sp.

<400> SEQUENCE: 878
tctgaaggca gagtcaggag a                                                  21

<210> SEQ ID NO 879
<211> LENGTH: 22
<212> TYPE: DNA
<213> ORGANISM: Mus sp.

<400> SEQUENCE: 879
gacattcatc attgacctcg tg                                                 22

<210> SEQ ID NO 880

```
<211> LENGTH: 20
<212> TYPE: DNA
<213> ORGANISM: Mus sp.

<400> SEQUENCE: 880
tcacaggaag ggcatttagc                                              20

<210> SEQ ID NO 881
<211> LENGTH: 19
<212> TYPE: DNA
<213> ORGANISM: Mus sp.

<400> SEQUENCE: 881
aaacggcctg catctaagg                                               19

<210> SEQ ID NO 882
<211> LENGTH: 20
<212> TYPE: DNA
<213> ORGANISM: Mus sp.

<400> SEQUENCE: 882
agcagcagta agggcacaat                                              20

<210> SEQ ID NO 883
<211> LENGTH: 18
<212> TYPE: DNA
<213> ORGANISM: Mus sp.

<400> SEQUENCE: 883
gcaacaaagg gcagcaag                                                18

<210> SEQ ID NO 884
<211> LENGTH: 24
<212> TYPE: DNA
<213> ORGANISM: Mus sp.

<400> SEQUENCE: 884
agacatcttt aggaaaccaa gacc                                         24

<210> SEQ ID NO 885
<211> LENGTH: 20
<212> TYPE: DNA
<213> ORGANISM: Mus sp.

<400> SEQUENCE: 885
tacaccttgc gagagaccag                                              20

<210> SEQ ID NO 886
<211> LENGTH: 20
<212> TYPE: DNA
<213> ORGANISM: Mus sp.

<400> SEQUENCE: 886
ggacgttggt ctcactttcc                                              20

<210> SEQ ID NO 887
<211> LENGTH: 20
<212> TYPE: DNA
<213> ORGANISM: Mus sp.

<400> SEQUENCE: 887
gattgccagc aacacctatg                                              20
```

```
<210> SEQ ID NO 888
<211> LENGTH: 22
<212> TYPE: DNA
<213> ORGANISM: Mus sp.

<400> SEQUENCE: 888
ttgatttgtt gagagggact tg                                          22

<210> SEQ ID NO 889
<211> LENGTH: 19
<212> TYPE: DNA
<213> ORGANISM: Mus sp.

<400> SEQUENCE: 889
ccctggctta tcccagact                                              19

<210> SEQ ID NO 890
<211> LENGTH: 20
<212> TYPE: DNA
<213> ORGANISM: Mus sp.

<400> SEQUENCE: 890
agatgccaga ggagttccaa                                             20

<210> SEQ ID NO 891
<211> LENGTH: 18
<212> TYPE: DNA
<213> ORGANISM: Mus sp.

<400> SEQUENCE: 891
acgccactgt cgcttttc                                               18

<210> SEQ ID NO 892
<211> LENGTH: 20
<212> TYPE: DNA
<213> ORGANISM: Mus sp.

<400> SEQUENCE: 892
gcaaacagct cgaaggagac                                             20

<210> SEQ ID NO 893
<211> LENGTH: 18
<212> TYPE: DNA
<213> ORGANISM: Mus sp.

<400> SEQUENCE: 893
ctggggaccc tcatcctt                                               18

<210> SEQ ID NO 894
<211> LENGTH: 18
<212> TYPE: DNA
<213> ORGANISM: Mus sp.

<400> SEQUENCE: 894
tggtgaggaa gccaccat                                               18

<210> SEQ ID NO 895
<211> LENGTH: 20
<212> TYPE: DNA
<213> ORGANISM: Mus sp.

<400> SEQUENCE: 895
gaacaacagc ctgaacatgg                                             20
```

```
<210> SEQ ID NO 896
<211> LENGTH: 18
<212> TYPE: DNA
<213> ORGANISM: Mus sp.

<400> SEQUENCE: 896
tctgagcgtt cacgttgg                                                 18

<210> SEQ ID NO 897
<211> LENGTH: 20
<212> TYPE: DNA
<213> ORGANISM: Mus sp.

<400> SEQUENCE: 897
gccctagaga gccagaaagg                                               20

<210> SEQ ID NO 898
<211> LENGTH: 22
<212> TYPE: DNA
<213> ORGANISM: Mus sp.

<400> SEQUENCE: 898
tggtacagga agtaagcagt gg                                            22

<210> SEQ ID NO 899
<211> LENGTH: 20
<212> TYPE: DNA
<213> ORGANISM: Mus sp.

<400> SEQUENCE: 899
ggttcaaccg gagttactgg                                               20

<210> SEQ ID NO 900
<211> LENGTH: 19
<212> TYPE: DNA
<213> ORGANISM: Mus sp.

<400> SEQUENCE: 900
tgggcaaaga tgctcagac                                                19

<210> SEQ ID NO 901
<211> LENGTH: 19
<212> TYPE: DNA
<213> ORGANISM: Mus sp.

<400> SEQUENCE: 901
gacagcatgg acagcgact                                                19

<210> SEQ ID NO 902
<211> LENGTH: 20
<212> TYPE: DNA
<213> ORGANISM: Mus sp.

<400> SEQUENCE: 902
acgaccaggg tacgctcata                                               20

<210> SEQ ID NO 903
<211> LENGTH: 20
<212> TYPE: DNA
<213> ORGANISM: Mus sp.

<400> SEQUENCE: 903
agttccggta caaggaatgc                                               20
```

<210> SEQ ID NO 904
<211> LENGTH: 20
<212> TYPE: DNA
<213> ORGANISM: Mus sp.

<400> SEQUENCE: 904
acaggagtca gcccatctgt                                               20

<210> SEQ ID NO 905
<211> LENGTH: 20
<212> TYPE: DNA
<213> ORGANISM: Mus sp.

<400> SEQUENCE: 905
tcctgtggca gtctgtgtct                                               20

<210> SEQ ID NO 906
<211> LENGTH: 20
<212> TYPE: DNA
<213> ORGANISM: Mus sp.

<400> SEQUENCE: 906
ctacgcagaa cgggatgaag                                               20

<210> SEQ ID NO 907
<211> LENGTH: 20
<212> TYPE: DNA
<213> ORGANISM: Mus sp.

<400> SEQUENCE: 907
ggacaccttc attcgccata                                               20

<210> SEQ ID NO 908
<211> LENGTH: 21
<212> TYPE: DNA
<213> ORGANISM: Mus sp.

<400> SEQUENCE: 908
ctgccactta accaggaaca t                                             21

<210> SEQ ID NO 909
<211> LENGTH: 19
<212> TYPE: DNA
<213> ORGANISM: Mus sp.

<400> SEQUENCE: 909
gtcggcgact aggaggact                                                19

<210> SEQ ID NO 910
<211> LENGTH: 23
<212> TYPE: DNA
<213> ORGANISM: Mus sp.

<400> SEQUENCE: 910
tccaccatct tttgctaata acc                                           23

<210> SEQ ID NO 911
<211> LENGTH: 19
<212> TYPE: DNA
<213> ORGANISM: Mus sp.

<400> SEQUENCE: 911
tcaagaagac ggggcagtt                                                    19

<210> SEQ ID NO 912
<211> LENGTH: 18
<212> TYPE: DNA
<213> ORGANISM: Mus sp.

<400> SEQUENCE: 912
ccgaccatcc agtgacct                                                     18

<210> SEQ ID NO 913
<211> LENGTH: 24
<212> TYPE: DNA
<213> ORGANISM: Mus sp.

<400> SEQUENCE: 913
gaggatctct tctgtaccct gaaa                                              24

<210> SEQ ID NO 914
<211> LENGTH: 23
<212> TYPE: DNA
<213> ORGANISM: Mus sp.

<400> SEQUENCE: 914
ttgttgagat gctttgacac ttg                                               23

<210> SEQ ID NO 915
<211> LENGTH: 20
<212> TYPE: DNA
<213> ORGANISM: Mus sp.

<400> SEQUENCE: 915
atccctccac cctatgacaa                                                   20

<210> SEQ ID NO 916
<211> LENGTH: 19
<212> TYPE: DNA
<213> ORGANISM: Mus sp.

<400> SEQUENCE: 916
gccccaggta agcaaactt                                                    19

<210> SEQ ID NO 917
<211> LENGTH: 18
<212> TYPE: DNA
<213> ORGANISM: Mus sp.

<400> SEQUENCE: 917
gttggtccca tcctcgtg                                                     18

<210> SEQ ID NO 918
<211> LENGTH: 20
<212> TYPE: DNA
<213> ORGANISM: Mus sp.

<400> SEQUENCE: 918
gattgctgca gtagctgtcg                                                   20

<210> SEQ ID NO 919
<211> LENGTH: 20
<212> TYPE: DNA
<213> ORGANISM: Mus sp.

<400> SEQUENCE: 919
ctgcagatgg agcatgttgt                                               20

<210> SEQ ID NO 920
<211> LENGTH: 19
<212> TYPE: DNA
<213> ORGANISM: Mus sp.

<400> SEQUENCE: 920
gccatttctg cttcactgg                                                19

<210> SEQ ID NO 921
<211> LENGTH: 19
<212> TYPE: DNA
<213> ORGANISM: Mus sp.

<400> SEQUENCE: 921
gaagccgaat cagcctagc                                                19

<210> SEQ ID NO 922
<211> LENGTH: 20
<212> TYPE: DNA
<213> ORGANISM: Mus sp.

<400> SEQUENCE: 922
cagcgttact atcccgctct                                               20

<210> SEQ ID NO 923
<211> LENGTH: 20
<212> TYPE: DNA
<213> ORGANISM: Mus sp.

<400> SEQUENCE: 923
tggaaccgat cagtgtgagt                                               20

<210> SEQ ID NO 924
<211> LENGTH: 20
<212> TYPE: DNA
<213> ORGANISM: Mus sp.

<400> SEQUENCE: 924
gggcaggaag atcctattga                                               20

<210> SEQ ID NO 925
<211> LENGTH: 22
<212> TYPE: DNA
<213> ORGANISM: Mus sp.

<400> SEQUENCE: 925
tgccctaatg gagcaaattt ta                                            22

<210> SEQ ID NO 926
<211> LENGTH: 21
<212> TYPE: DNA
<213> ORGANISM: Mus sp.

<400> SEQUENCE: 926
ttatatggcc acgttgggta a                                             21

<210> SEQ ID NO 927
<211> LENGTH: 18
<212> TYPE: DNA
<213> ORGANISM: Mus sp.

```
<400> SEQUENCE: 927
agcatggggg agaccttc                                                 18

<210> SEQ ID NO 928
<211> LENGTH: 19
<212> TYPE: DNA
<213> ORGANISM: Mus sp.

<400> SEQUENCE: 928
ggggctgaag aaggacaag                                                19

<210> SEQ ID NO 929
<211> LENGTH: 20
<212> TYPE: DNA
<213> ORGANISM: Mus sp.

<400> SEQUENCE: 929
tcttgtggcc ctactgtgtg                                               20

<210> SEQ ID NO 930
<211> LENGTH: 20
<212> TYPE: DNA
<213> ORGANISM: Mus sp.

<400> SEQUENCE: 930
gcaatgcaga atccatcaga                                               20

<210> SEQ ID NO 931
<211> LENGTH: 20
<212> TYPE: DNA
<213> ORGANISM: Mus sp.

<400> SEQUENCE: 931
tggcatgaac atgaggtcag                                               20

<210> SEQ ID NO 932
<211> LENGTH: 20
<212> TYPE: DNA
<213> ORGANISM: Mus sp.

<400> SEQUENCE: 932
gccaacatct gagcattcaa                                               20

<210> SEQ ID NO 933
<211> LENGTH: 25
<212> TYPE: DNA
<213> ORGANISM: Mus sp.

<400> SEQUENCE: 933
tggaaacttt tcctagagtt tgaga                                         25

<210> SEQ ID NO 934
<211> LENGTH: 19
<212> TYPE: DNA
<213> ORGANISM: Mus sp.

<400> SEQUENCE: 934
tttccccctc ggtttgtaa                                                19

<210> SEQ ID NO 935
<211> LENGTH: 21
<212> TYPE: DNA
<213> ORGANISM: Mus sp.
```

<400> SEQUENCE: 935
gatgcttcga cagttcacag g                                               21

<210> SEQ ID NO 936
<211> LENGTH: 18
<212> TYPE: DNA
<213> ORGANISM: Mus sp.

<400> SEQUENCE: 936
ggaaccccgg aagtatgg                                                   18

<210> SEQ ID NO 937
<211> LENGTH: 23
<212> TYPE: DNA
<213> ORGANISM: Mus sp.

<400> SEQUENCE: 937
gtctggctcc tttctctaca cag                                             23

<210> SEQ ID NO 938
<211> LENGTH: 21
<212> TYPE: DNA
<213> ORGANISM: Mus sp.

<400> SEQUENCE: 938
agtgatgagg atgacgaggt c                                               21

<210> SEQ ID NO 939
<211> LENGTH: 21
<212> TYPE: DNA
<213> ORGANISM: Mus sp.

<400> SEQUENCE: 939
aacagctttc gatgaagcca t                                               21

<210> SEQ ID NO 940
<211> LENGTH: 21
<212> TYPE: DNA
<213> ORGANISM: Mus sp.

<400> SEQUENCE: 940
tgggtatccg atgtccacaa t                                               21

<210> SEQ ID NO 941
<211> LENGTH: 18
<212> TYPE: DNA
<213> ORGANISM: Mus sp.

<400> SEQUENCE: 941
cagagcagga gccagagc                                                   18

<210> SEQ ID NO 942
<211> LENGTH: 22
<212> TYPE: DNA
<213> ORGANISM: Mus sp.

<400> SEQUENCE: 942
gccaagttca tcatacacgt tc                                              22

<210> SEQ ID NO 943
<211> LENGTH: 22
<212> TYPE: DNA

-continued

```
<213> ORGANISM: Mus sp.

<400> SEQUENCE: 943
gaggctgact tcctgtatgc tt                                              22

<210> SEQ ID NO 944
<211> LENGTH: 18
<212> TYPE: DNA
<213> ORGANISM: Mus sp.

<400> SEQUENCE: 944
aaccacgacc cgtcctttt                                                  18

<210> SEQ ID NO 945
<211> LENGTH: 22
<212> TYPE: DNA
<213> ORGANISM: Mus sp.

<400> SEQUENCE: 945
gatattcgcc attgagatag cc                                              22

<210> SEQ ID NO 946
<211> LENGTH: 24
<212> TYPE: DNA
<213> ORGANISM: Mus sp.

<400> SEQUENCE: 946
tggtaggtgt ccttgtaaaa ctcc                                            24

<210> SEQ ID NO 947
<211> LENGTH: 19
<212> TYPE: DNA
<213> ORGANISM: Mus sp.

<400> SEQUENCE: 947
gaggggcttt gagagtgct                                                  19

<210> SEQ ID NO 948
<211> LENGTH: 20
<212> TYPE: DNA
<213> ORGANISM: Mus sp.

<400> SEQUENCE: 948
tgtcctgtgt gcctgtcttg                                                 20

<210> SEQ ID NO 949
<211> LENGTH: 20
<212> TYPE: DNA
<213> ORGANISM: Mus sp.

<400> SEQUENCE: 949
acagaaagtg gcagatgcag                                                 20

<210> SEQ ID NO 950
<211> LENGTH: 20
<212> TYPE: DNA
<213> ORGANISM: Mus sp.

<400> SEQUENCE: 950
tctcgctgga acaatgtcag                                                 20

<210> SEQ ID NO 951
<211> LENGTH: 20
```

```
<212> TYPE: DNA
<213> ORGANISM: Mus sp.

<400> SEQUENCE: 951
tgaggccacc attagagagg                                               20

<210> SEQ ID NO 952
<211> LENGTH: 20
<212> TYPE: DNA
<213> ORGANISM: Mus sp.

<400> SEQUENCE: 952
agcagcagcg agtagtctga                                               20

<210> SEQ ID NO 953
<211> LENGTH: 18
<212> TYPE: DNA
<213> ORGANISM: Mus sp.

<400> SEQUENCE: 953
ggaccaggga gcagaacc                                                 18

<210> SEQ ID NO 954
<211> LENGTH: 19
<212> TYPE: DNA
<213> ORGANISM: Mus sp.

<400> SEQUENCE: 954
gtccggcaca gggtaaatc                                                19

<210> SEQ ID NO 955
<211> LENGTH: 20
<212> TYPE: DNA
<213> ORGANISM: Mus sp.

<400> SEQUENCE: 955
cctggacctc caactgaaga                                               20

<210> SEQ ID NO 956
<211> LENGTH: 19
<212> TYPE: DNA
<213> ORGANISM: Mus sp.

<400> SEQUENCE: 956
tcctctgcaa tgtggcaat                                                19

<210> SEQ ID NO 957
<211> LENGTH: 21
<212> TYPE: DNA
<213> ORGANISM: Mus sp.

<400> SEQUENCE: 957
tccaatttag gagagccaag c                                             21

<210> SEQ ID NO 958
<211> LENGTH: 20
<212> TYPE: DNA
<213> ORGANISM: Mus sp.

<400> SEQUENCE: 958
gccgacatca gtccacatag                                               20

<210> SEQ ID NO 959
```

-continued

```
<211> LENGTH: 20
<212> TYPE: DNA
<213> ORGANISM: Mus sp.

<400> SEQUENCE: 959
ggaacagctg gaacagtggt                                                     20

<210> SEQ ID NO 960
<211> LENGTH: 18
<212> TYPE: DNA
<213> ORGANISM: Mus sp.

<400> SEQUENCE: 960
gtagctgccg aaggtgga                                                       18

<210> SEQ ID NO 961
<211> LENGTH: 20
<212> TYPE: DNA
<213> ORGANISM: Mus sp.

<400> SEQUENCE: 961
ggagtgagga agttcggaaa                                                     20

<210> SEQ ID NO 962
<211> LENGTH: 19
<212> TYPE: DNA
<213> ORGANISM: Mus sp.

<400> SEQUENCE: 962
tggattcggg agtctccat                                                      19

<210> SEQ ID NO 963
<211> LENGTH: 21
<212> TYPE: DNA
<213> ORGANISM: Mus sp.

<400> SEQUENCE: 963
ttctggtgct tgtctcactg a                                                   21

<210> SEQ ID NO 964
<211> LENGTH: 22
<212> TYPE: DNA
<213> ORGANISM: Mus sp.

<400> SEQUENCE: 964
cagtatgttc ggcttcccat tc                                                  22

<210> SEQ ID NO 965
<211> LENGTH: 21
<212> TYPE: DNA
<213> ORGANISM: Mus sp.

<400> SEQUENCE: 965
gccttggagt actttgcatc a                                                   21

<210> SEQ ID NO 966
<211> LENGTH: 20
<212> TYPE: DNA
<213> ORGANISM: Mus sp.

<400> SEQUENCE: 966
aaatccgcag ggttgttgta                                                     20
```

```
<210> SEQ ID NO 967
<211> LENGTH: 20
<212> TYPE: DNA
<213> ORGANISM: Mus sp.

<400> SEQUENCE: 967
gagacatccg ttccccctac                                               20

<210> SEQ ID NO 968
<211> LENGTH: 20
<212> TYPE: DNA
<213> ORGANISM: Mus sp.

<400> SEQUENCE: 968
gtcggaactg acccttgaaa                                               20

<210> SEQ ID NO 969
<211> LENGTH: 18
<212> TYPE: DNA
<213> ORGANISM: Mus sp.

<400> SEQUENCE: 969
aggcagcacg agacctga                                                 18

<210> SEQ ID NO 970
<211> LENGTH: 21
<212> TYPE: DNA
<213> ORGANISM: Mus sp.

<400> SEQUENCE: 970
ggcatctagc acttgacgtt c                                             21

<210> SEQ ID NO 971
<211> LENGTH: 20
<212> TYPE: DNA
<213> ORGANISM: Mus sp.

<400> SEQUENCE: 971
agaccatggg caagaacact                                               20

<210> SEQ ID NO 972
<211> LENGTH: 19
<212> TYPE: DNA
<213> ORGANISM: Mus sp.

<400> SEQUENCE: 972
gccccaggat ctgataagg                                                19

<210> SEQ ID NO 973
<211> LENGTH: 21
<212> TYPE: DNA
<213> ORGANISM: Mus sp.

<400> SEQUENCE: 973
gctgctcact gtgaaggaag t                                             21

<210> SEQ ID NO 974
<211> LENGTH: 20
<212> TYPE: DNA
<213> ORGANISM: Mus sp.

<400> SEQUENCE: 974
tggggaatgc attttaccat                                               20
```

-continued

```
<210> SEQ ID NO 975
<211> LENGTH: 18
<212> TYPE: DNA
<213> ORGANISM: Mus sp.

<400> SEQUENCE: 975
gctcccattc ctcgtcac                                                 18

<210> SEQ ID NO 976
<211> LENGTH: 19
<212> TYPE: DNA
<213> ORGANISM: Mus sp.

<400> SEQUENCE: 976
aagggcttgg cagttctgt                                                19

<210> SEQ ID NO 977
<211> LENGTH: 21
<212> TYPE: DNA
<213> ORGANISM: Mus sp.

<400> SEQUENCE: 977
tacatctgcg aatgactctg c                                             21

<210> SEQ ID NO 978
<211> LENGTH: 21
<212> TYPE: DNA
<213> ORGANISM: Mus sp.

<400> SEQUENCE: 978
ggctgaggtg gtctagaggt t                                             21

<210> SEQ ID NO 979
<211> LENGTH: 25
<212> TYPE: DNA
<213> ORGANISM: Mus sp.

<400> SEQUENCE: 979
ggattggaat gcattatagt gaaaa                                         25

<210> SEQ ID NO 980
<211> LENGTH: 21
<212> TYPE: DNA
<213> ORGANISM: Mus sp.

<400> SEQUENCE: 980
tgctctggcc tgataactga g                                             21

<210> SEQ ID NO 981
<211> LENGTH: 20
<212> TYPE: DNA
<213> ORGANISM: Mus sp.

<400> SEQUENCE: 981
cagaccagcc tgtgtgattg                                               20

<210> SEQ ID NO 982
<211> LENGTH: 23
<212> TYPE: DNA
<213> ORGANISM: Mus sp.

<400> SEQUENCE: 982
ccaagacaag tgaaacaaaa ggt                                           23
```

<210> SEQ ID NO 983
<211> LENGTH: 20
<212> TYPE: DNA
<213> ORGANISM: Mus sp.

<400> SEQUENCE: 983
tccctcttcg ttctgattgg                                          20

<210> SEQ ID NO 984
<211> LENGTH: 19
<212> TYPE: DNA
<213> ORGANISM: Mus sp.

<400> SEQUENCE: 984
gcttgcgctt cagaccttt                                           19

<210> SEQ ID NO 985
<211> LENGTH: 20
<212> TYPE: DNA
<213> ORGANISM: Mus sp.

<400> SEQUENCE: 985
cgccaagcta ctggctaaaa                                          20

<210> SEQ ID NO 986
<211> LENGTH: 24
<212> TYPE: DNA
<213> ORGANISM: Mus sp.

<400> SEQUENCE: 986
cgtacctcag accttgagat aggt                                     24

<210> SEQ ID NO 987
<211> LENGTH: 20
<212> TYPE: DNA
<213> ORGANISM: Mus sp.

<400> SEQUENCE: 987
ggcaaattca acggcacagt                                          20

<210> SEQ ID NO 988
<211> LENGTH: 19
<212> TYPE: DNA
<213> ORGANISM: Mus sp.

<400> SEQUENCE: 988
agatggtgat gggcttccc                                           19

<210> SEQ ID NO 989
<211> LENGTH: 24
<212> TYPE: DNA
<213> ORGANISM: Mus sp.

<400> SEQUENCE: 989
ccctcctgta cttgttccta ctca                                     24

<210> SEQ ID NO 990
<211> LENGTH: 20
<212> TYPE: DNA
<213> ORGANISM: Mus sp.

<400> SEQUENCE: 990
gcaatggctt caaccctagt    20

<210> SEQ ID NO 991
<211> LENGTH: 23
<212> TYPE: DNA
<213> ORGANISM: Mus sp.

<400> SEQUENCE: 991
ttcgccactc taatcagtag gac    23

<210> SEQ ID NO 992
<211> LENGTH: 22
<212> TYPE: DNA
<213> ORGANISM: Mus sp.

<400> SEQUENCE: 992
tctggtgtag aaagggaagt gg    22

<210> SEQ ID NO 993
<211> LENGTH: 21
<212> TYPE: DNA
<213> ORGANISM: Mus sp.

<400> SEQUENCE: 993
gaatgacgac agaggttcct g    21

<210> SEQ ID NO 994
<211> LENGTH: 19
<212> TYPE: DNA
<213> ORGANISM: Mus sp.

<400> SEQUENCE: 994
gcccaggttg gcttcttat    19

<210> SEQ ID NO 995
<211> LENGTH: 21
<212> TYPE: DNA
<213> ORGANISM: Mus sp.

<400> SEQUENCE: 995
actttaagca cattgccaag c    21

<210> SEQ ID NO 996
<211> LENGTH: 21
<212> TYPE: DNA
<213> ORGANISM: Mus sp.

<400> SEQUENCE: 996
ggagagaaag gttgtgacga a    21

<210> SEQ ID NO 997
<211> LENGTH: 19
<212> TYPE: DNA
<213> ORGANISM: Mus sp.

<400> SEQUENCE: 997
agtgagcaag ctggacgac    19

<210> SEQ ID NO 998
<211> LENGTH: 20
<212> TYPE: DNA
<213> ORGANISM: Mus sp.

<400> SEQUENCE: 998
gaagccaggt actgggtgtg                                          20

<210> SEQ ID NO 999
<211> LENGTH: 21
<212> TYPE: DNA
<213> ORGANISM: Mus sp.

<400> SEQUENCE: 999
cgcagccgag taatgtacaa g                                        21

<210> SEQ ID NO 1000
<211> LENGTH: 19
<212> TYPE: DNA
<213> ORGANISM: Mus sp.

<400> SEQUENCE: 1000
aacgggaaat ctgcacctc                                           19

<210> SEQ ID NO 1001
<211> LENGTH: 22
<212> TYPE: DNA
<213> ORGANISM: Mus sp.

<400> SEQUENCE: 1001
gcctctgttt tgctcttcag tt                                       22

<210> SEQ ID NO 1002
<211> LENGTH: 19
<212> TYPE: DNA
<213> ORGANISM: Mus sp.

<400> SEQUENCE: 1002
gcattttgac ggtggatca                                           19

<210> SEQ ID NO 1003
<211> LENGTH: 20
<212> TYPE: DNA
<213> ORGANISM: Mus sp.

<400> SEQUENCE: 1003
taggtcagat cgggtcatcc                                          20

<210> SEQ ID NO 1004
<211> LENGTH: 19
<212> TYPE: DNA
<213> ORGANISM: Mus sp.

<400> SEQUENCE: 1004
gtggggtcct ctttcaagg                                           19

<210> SEQ ID NO 1005
<211> LENGTH: 18
<212> TYPE: DNA
<213> ORGANISM: Mus sp.

<400> SEQUENCE: 1005
tgcggagagg ctccacta                                            18

<210> SEQ ID NO 1006
<211> LENGTH: 18
<212> TYPE: DNA
<213> ORGANISM: Mus sp.

<400> SEQUENCE: 1006
tgggttgctt tccgtttg					18

<210> SEQ ID NO 1007
<211> LENGTH: 19
<212> TYPE: DNA
<213> ORGANISM: Mus sp.

<400> SEQUENCE: 1007
atttcgcttc gggactagc					19

<210> SEQ ID NO 1008
<211> LENGTH: 20
<212> TYPE: DNA
<213> ORGANISM: Mus sp.

<400> SEQUENCE: 1008
aacttgctgt gggtgaccat					20

<210> SEQ ID NO 1009
<211> LENGTH: 19
<212> TYPE: DNA
<213> ORGANISM: Mus sp.

<400> SEQUENCE: 1009
atccagcagc cttccatct					19

<210> SEQ ID NO 1010
<211> LENGTH: 20
<212> TYPE: DNA
<213> ORGANISM: Mus sp.

<400> SEQUENCE: 1010
ggcttagggc tgtgattctg					20

<210> SEQ ID NO 1011
<211> LENGTH: 20
<212> TYPE: DNA
<213> ORGANISM: Mus sp.

<400> SEQUENCE: 1011
tccctgaagg atgtgcctac					20

<210> SEQ ID NO 1012
<211> LENGTH: 18
<212> TYPE: DNA
<213> ORGANISM: Mus sp.

<400> SEQUENCE: 1012
aagggttttc ccgtttgc					18

<210> SEQ ID NO 1013
<211> LENGTH: 22
<212> TYPE: DNA
<213> ORGANISM: Mus sp.

<400> SEQUENCE: 1013
tgatgctctt atgaagcagg ac				22

<210> SEQ ID NO 1014
<211> LENGTH: 19
<212> TYPE: DNA
<213> ORGANISM: Mus sp.

```
<400> SEQUENCE: 1014
cgtctgtccc ccatctctt                                              19

<210> SEQ ID NO 1015
<211> LENGTH: 21
<212> TYPE: DNA
<213> ORGANISM: Mus sp.

<400> SEQUENCE: 1015
gaggacacat ggatggaatg t                                           21

<210> SEQ ID NO 1016
<211> LENGTH: 20
<212> TYPE: DNA
<213> ORGANISM: Mus sp.

<400> SEQUENCE: 1016
acccttgtgt agcacctcca                                             20

<210> SEQ ID NO 1017
<211> LENGTH: 18
<212> TYPE: DNA
<213> ORGANISM: Mus sp.

<400> SEQUENCE: 1017
caggccactg gtctctcc                                               18

<210> SEQ ID NO 1018
<211> LENGTH: 22
<212> TYPE: DNA
<213> ORGANISM: Mus sp.

<400> SEQUENCE: 1018
tccgtcttac acagttcaag ga                                          22

<210> SEQ ID NO 1019
<211> LENGTH: 19
<212> TYPE: DNA
<213> ORGANISM: Mus sp.

<400> SEQUENCE: 1019
cggagactgc agaaagcag                                              19

<210> SEQ ID NO 1020
<211> LENGTH: 20
<212> TYPE: DNA
<213> ORGANISM: Mus sp.

<400> SEQUENCE: 1020
ggtttggctt cgtctacagc                                             20

<210> SEQ ID NO 1021
<211> LENGTH: 20
<212> TYPE: DNA
<213> ORGANISM: Mus sp.

<400> SEQUENCE: 1021
gaggagcttt tgccactgac                                             20

<210> SEQ ID NO 1022
<211> LENGTH: 18
<212> TYPE: DNA
```

```
<213> ORGANISM: Mus sp.

<400> SEQUENCE: 1022
gctcatccat gccctcag                                                 18

<210> SEQ ID NO 1023
<211> LENGTH: 20
<212> TYPE: DNA
<213> ORGANISM: Mus sp.

<400> SEQUENCE: 1023
tgtggggtgg agatctcagt                                               20

<210> SEQ ID NO 1024
<211> LENGTH: 20
<212> TYPE: DNA
<213> ORGANISM: Mus sp.

<400> SEQUENCE: 1024
tctccttcct ggacacatga                                               20

<210> SEQ ID NO 1025
<211> LENGTH: 20
<212> TYPE: DNA
<213> ORGANISM: Mus sp.

<400> SEQUENCE: 1025
atcatcacct ttgccgagtc                                               20

<210> SEQ ID NO 1026
<211> LENGTH: 20
<212> TYPE: DNA
<213> ORGANISM: Mus sp.

<400> SEQUENCE: 1026
tcactgcctt ccttggaaat                                               20

<210> SEQ ID NO 1027
<211> LENGTH: 18
<212> TYPE: DNA
<213> ORGANISM: Mus sp.

<400> SEQUENCE: 1027
gacaagcacg cactgagc                                                 18

<210> SEQ ID NO 1028
<211> LENGTH: 21
<212> TYPE: DNA
<213> ORGANISM: Mus sp.

<400> SEQUENCE: 1028
cattttcgca gaagatgacc t                                             21

<210> SEQ ID NO 1029
<211> LENGTH: 20
<212> TYPE: DNA
<213> ORGANISM: Mus sp.

<400> SEQUENCE: 1029
atggattctt tggcgttgtc                                               20

<210> SEQ ID NO 1030
<211> LENGTH: 18
```

-continued

```
<212> TYPE: DNA
<213> ORGANISM: Mus sp.

<400> SEQUENCE: 1030
tgacggtctt ggcttgct                                                 18

<210> SEQ ID NO 1031
<211> LENGTH: 18
<212> TYPE: DNA
<213> ORGANISM: Mus sp.

<400> SEQUENCE: 1031
ggaggaaacc agccaagg                                                 18

<210> SEQ ID NO 1032
<211> LENGTH: 22
<212> TYPE: DNA
<213> ORGANISM: Mus sp.

<400> SEQUENCE: 1032
tgccagaatc agtcactttc ac                                            22

<210> SEQ ID NO 1033
<211> LENGTH: 22
<212> TYPE: DNA
<213> ORGANISM: Mus sp.

<400> SEQUENCE: 1033
actctgcaaa caacagaaga cg                                            22

<210> SEQ ID NO 1034
<211> LENGTH: 22
<212> TYPE: DNA
<213> ORGANISM: Mus sp.

<400> SEQUENCE: 1034 tcttttccg gaccatatct gt                                             22

<210> SEQ ID NO 1035
<211> LENGTH: 19
<212> TYPE: DNA
<213> ORGANISM: Mus sp.

<400> SEQUENCE: 1035
tcctcctcag accgctttt                                                19

<210> SEQ ID NO 1036
<211> LENGTH: 21
<212> TYPE: DNA
<213> ORGANISM: Mus sp.

<400> SEQUENCE: 1036
cctggttcat catcgctaat c                                             21

<210> SEQ ID NO 1037
<211> LENGTH: 22
<212> TYPE: DNA
<213> ORGANISM: Mus sp.

<400> SEQUENCE: 1037
ggagacgagt tcaacgaaac tt                                            22

<210> SEQ ID NO 1038
```

```
<211> LENGTH: 26
<212> TYPE: DNA
<213> ORGANISM: Mus sp.

<400> SEQUENCE: 1038
aacagttgta agataaccat ttgagg                                          26

<210> SEQ ID NO 1039
<211> LENGTH: 23
<212> TYPE: DNA
<213> ORGANISM: Mus sp.

<400> SEQUENCE: 1039
tcgtctttca caagtgtctt cag                                             23

<210> SEQ ID NO 1040
<211> LENGTH: 21
<212> TYPE: DNA
<213> ORGANISM: Mus sp.

<400> SEQUENCE: 1040
ttgccagtag attcggtctt c                                               21

<210> SEQ ID NO 1041
<211> LENGTH: 20
<212> TYPE: DNA
<213> ORGANISM: Mus sp.

<400> SEQUENCE: 1041
gagcagcagc tcttgcataa                                                 20

<210> SEQ ID NO 1042
<211> LENGTH: 22
<212> TYPE: DNA
<213> ORGANISM: Mus sp.

<400> SEQUENCE: 1042
gatgtcgcag tacaaaagca ac                                              22

<210> SEQ ID NO 1043
<211> LENGTH: 19
<212> TYPE: DNA
<213> ORGANISM: Mus sp.

<400> SEQUENCE: 1043
ttatcaagcc caagcgaag                                                  19

<210> SEQ ID NO 1044
<211> LENGTH: 20
<212> TYPE: DNA
<213> ORGANISM: Mus sp.

<400> SEQUENCE: 1044
tggtggtggt ctgacagttc                                                 20

<210> SEQ ID NO 1045
<211> LENGTH: 25
<212> TYPE: DNA
<213> ORGANISM: Mus sp.

<400> SEQUENCE: 1045
ctattaaccg tgttcaaaac atgaa                                           25
```

```
<210> SEQ ID NO 1046
<211> LENGTH: 22
<212> TYPE: DNA
<213> ORGANISM: Mus sp.

<400> SEQUENCE: 1046
cacctgcaat tccaaaatct ta                                          22

<210> SEQ ID NO 1047
<211> LENGTH: 21
<212> TYPE: DNA
<213> ORGANISM: Mus sp.

<400> SEQUENCE: 1047
ccagtgccaa cagtagtgac a                                           21

<210> SEQ ID NO 1048
<211> LENGTH: 20
<212> TYPE: DNA
<213> ORGANISM: Mus sp.

<400> SEQUENCE: 1048
ttgggagaga aagcttctgg                                             20

<210> SEQ ID NO 1049
<211> LENGTH: 21
<212> TYPE: DNA
<213> ORGANISM: Mus sp.

<400> SEQUENCE: 1049
cttcagcact ttcttccgag a                                           21

<210> SEQ ID NO 1050
<211> LENGTH: 20
<212> TYPE: DNA
<213> ORGANISM: Mus sp.

<400> SEQUENCE: 1050
tgtagtgtgg tgacccttgc                                             20

<210> SEQ ID NO 1051
<211> LENGTH: 18
<212> TYPE: DNA
<213> ORGANISM: Mus sp.

<400> SEQUENCE: 1051
tcggaacaag tcggaggt                                               18

<210> SEQ ID NO 1052
<211> LENGTH: 20
<212> TYPE: DNA
<213> ORGANISM: Mus sp.

<400> SEQUENCE: 1052
tcagcagctg tatgccaaag                                             20

<210> SEQ ID NO 1053
<211> LENGTH: 18
<212> TYPE: DNA
<213> ORGANISM: Mus sp.

<400> SEQUENCE: 1053
agcgcaagga gaacgtgt                                               18
```

```
<210> SEQ ID NO 1054
<211> LENGTH: 18
<212> TYPE: DNA
<213> ORGANISM: Mus sp.

<400> SEQUENCE: 1054
gggttcagag ccctcctc                                                 18

<210> SEQ ID NO 1055
<211> LENGTH: 20
<212> TYPE: DNA
<213> ORGANISM: Mus sp.

<400> SEQUENCE: 1055
gagctgcgtc atcacctacc                                               20

<210> SEQ ID NO 1056
<211> LENGTH: 21
<212> TYPE: DNA
<213> ORGANISM: Mus sp.

<400> SEQUENCE: 1056
tgcaggcctt gtacatcttc t                                             21

<210> SEQ ID NO 1057
<211> LENGTH: 20
<212> TYPE: DNA
<213> ORGANISM: Mus sp.

<400> SEQUENCE: 1057
ggtggcccta gacaacaaga                                               20

<210> SEQ ID NO 1058
<211> LENGTH: 20
<212> TYPE: DNA
<213> ORGANISM: Mus sp.

<400> SEQUENCE: 1058
tcaagcagct cacgaatctg                                               20

<210> SEQ ID NO 1059
<211> LENGTH: 18
<212> TYPE: DNA
<213> ORGANISM: Mus sp.

<400> SEQUENCE: 1059
tacctgctgg ctggatgg                                                 18

<210> SEQ ID NO 1060
<211> LENGTH: 20
<212> TYPE: DNA
<213> ORGANISM: Mus sp.

<400> SEQUENCE: 1060
cacagcctcg gcatatttct                                               20

<210> SEQ ID NO 1061
<211> LENGTH: 20
<212> TYPE: DNA
<213> ORGANISM: Mus sp.

<400> SEQUENCE: 1061
cccactgctg atagggtgac                                               20
```

<210> SEQ ID NO 1062
<211> LENGTH: 26
<212> TYPE: DNA
<213> ORGANISM: Mus sp.

<400> SEQUENCE: 1062
gcataggtac ataagaatga actgga                                          26

<210> SEQ ID NO 1063
<211> LENGTH: 20
<212> TYPE: DNA
<213> ORGANISM: Mus sp.

<400> SEQUENCE: 1063
tggttctgaa ggtgacagga                                                 20

<210> SEQ ID NO 1064
<211> LENGTH: 22
<212> TYPE: DNA
<213> ORGANISM: Mus sp.

<400> SEQUENCE: 1064
caaccagaga gaagagcaac ac                                              22

<210> SEQ ID NO 1065
<211> LENGTH: 25
<212> TYPE: DNA
<213> ORGANISM: Mus sp.

<400> SEQUENCE: 1065
cggtatcatt tagtaaagag gcaaa                                           25

<210> SEQ ID NO 1066
<211> LENGTH: 22
<212> TYPE: DNA
<213> ORGANISM: Mus sp.

<400> SEQUENCE: 1066
gtagagtgta gaggggcaga cc                                              22

<210> SEQ ID NO 1067
<211> LENGTH: 20
<212> TYPE: DNA
<213> ORGANISM: Mus sp.

<400> SEQUENCE: 1067
tccgagttcg aggacttttg                                                 20

<210> SEQ ID NO 1068
<211> LENGTH: 19
<212> TYPE: DNA
<213> ORGANISM: Mus sp.

<400> SEQUENCE: 1068
gagcggcaca gtgacttct                                                  19

<210> SEQ ID NO 1069
<211> LENGTH: 19
<212> TYPE: DNA
<213> ORGANISM: Mus sp.

<400> SEQUENCE: 1069
tctaaacagg gccttgcag                                              19

<210> SEQ ID NO 1070
<211> LENGTH: 22
<212> TYPE: DNA
<213> ORGANISM: Mus sp.

<400> SEQUENCE: 1070
gcagagccct ttttgataat gt                                          22

<210> SEQ ID NO 1071
<211> LENGTH: 21
<212> TYPE: DNA
<213> ORGANISM: Mus sp.

<400> SEQUENCE: 1071
cagggagagc ttcatctgtg t                                           21

<210> SEQ ID NO 1072
<211> LENGTH: 20
<212> TYPE: DNA
<213> ORGANISM: Mus sp.

<400> SEQUENCE: 1072
gctgagcttt gagggatgat                                             20

<210> SEQ ID NO 1073
<211> LENGTH: 20
<212> TYPE: DNA
<213> ORGANISM: Mus sp.

<400> SEQUENCE: 1073
ttggtgaagc caggctagag                                             20

<210> SEQ ID NO 1074
<211> LENGTH: 20
<212> TYPE: DNA
<213> ORGANISM: Mus sp.

<400> SEQUENCE: 1074
cttcagggca ttgaagtcgt                                             20

<210> SEQ ID NO 1075
<211> LENGTH: 20
<212> TYPE: DNA
<213> ORGANISM: Mus sp.

<400> SEQUENCE: 1075
caccagatct cggaatggac                                             20

<210> SEQ ID NO 1076
<211> LENGTH: 20
<212> TYPE: DNA
<213> ORGANISM: Mus sp.

<400> SEQUENCE: 1076
aggagcagca gctcttcttg                                             20

<210> SEQ ID NO 1077
<211> LENGTH: 18
<212> TYPE: DNA
<213> ORGANISM: Mus sp.

<400> SEQUENCE: 1077

-continued cgctctgctg agatgctg                                    18

<210> SEQ ID NO 1078
<211> LENGTH: 19
<212> TYPE: DNA
<213> ORGANISM: Mus sp.

<400> SEQUENCE: 1078
ctccactgcc atgatggtt                                   19

<210> SEQ ID NO 1079
<211> LENGTH: 25
<212> TYPE: DNA
<213> ORGANISM: Mus sp.

<400> SEQUENCE: 1079
acttcctgtt tatcacctat gagga                            25

<210> SEQ ID NO 1080
<211> LENGTH: 20
<212> TYPE: DNA
<213> ORGANISM: Mus sp.

<400> SEQUENCE: 1080
aactcacaga tgcgttgcac                                  20

<210> SEQ ID NO 1081
<211> LENGTH: 23
<212> TYPE: DNA
<213> ORGANISM: Mus sp.

<400> SEQUENCE: 1081
ttacacgaag atgagtgcaa atg                              23

<210> SEQ ID NO 1082
<211> LENGTH: 26
<212> TYPE: DNA
<213> ORGANISM: Mus sp.

<400> SEQUENCE: 1082
caacactgga taggacttta ttcatc                           26

<210> SEQ ID NO 1083
<211> LENGTH: 18
<212> TYPE: DNA
<213> ORGANISM: Mus sp.

<400> SEQUENCE: 1083
acgccactgt cgcttttc                                    18

<210> SEQ ID NO 1084
<211> LENGTH: 20
<212> TYPE: DNA
<213> ORGANISM: Mus sp.

<400> SEQUENCE: 1084
gcaaacagct cgaaggagac                                  20

<210> SEQ ID NO 1085
<211> LENGTH: 22
<212> TYPE: DNA
<213> ORGANISM: Mus sp.

<400> SEQUENCE: 1085
tccagacatt cttcagtgtg ga        22

<210> SEQ ID NO 1086
<211> LENGTH: 20
<212> TYPE: DNA
<213> ORGANISM: Mus sp.

<400> SEQUENCE: 1086
tctggttcct ccatttccag        20

<210> SEQ ID NO 1087
<211> LENGTH: 18
<212> TYPE: DNA
<213> ORGANISM: Mus sp.

<400> SEQUENCE: 1087
ccagccagca tcctctgt        18

<210> SEQ ID NO 1088
<211> LENGTH: 20
<212> TYPE: DNA
<213> ORGANISM: Mus sp.

<400> SEQUENCE: 1088
agcaggttcc tggatctcac        20

<210> SEQ ID NO 1089
<211> LENGTH: 19
<212> TYPE: DNA
<213> ORGANISM: Mus sp.

<400> SEQUENCE: 1089
ctacccggtg gaagacctc        19

<210> SEQ ID NO 1090
<211> LENGTH: 21
<212> TYPE: DNA
<213> ORGANISM: Mus sp.

<400> SEQUENCE: 1090
aatgttgatc atgccatctc c        21

<210> SEQ ID NO 1091
<211> LENGTH: 20
<212> TYPE: DNA
<213> ORGANISM: Mus sp.

<400> SEQUENCE: 1091
tcctttgact tcagcctcca        20

<210> SEQ ID NO 1092
<211> LENGTH: 18
<212> TYPE: DNA
<213> ORGANISM: Mus sp.

<400> SEQUENCE: 1092
ccatgtctgg gcacctct        18

<210> SEQ ID NO 1093
<211> LENGTH: 20
<212> TYPE: DNA
<213> ORGANISM: Mus sp.

```
<400> SEQUENCE: 1093
tggtctggtc cctgttcaat                                              20

<210> SEQ ID NO 1094
<211> LENGTH: 18
<212> TYPE: DNA
<213> ORGANISM: Mus sp.

<400> SEQUENCE: 1094
ctgggctcca accacatc                                                18

<210> SEQ ID NO 1095
<211> LENGTH: 20
<212> TYPE: DNA
<213> ORGANISM: Mus sp.

<400> SEQUENCE: 1095
tgtgccaagt ctggagatga                                              20

<210> SEQ ID NO 1096
<211> LENGTH: 24
<212> TYPE: DNA
<213> ORGANISM: Mus sp.

<400> SEQUENCE: 1096
ttctttgttc ttgctcagat cagt                                         24

<210> SEQ ID NO 1097
<211> LENGTH: 18
<212> TYPE: DNA
<213> ORGANISM: Mus sp.

<400> SEQUENCE: 1097
tggaagaccc ggatagca                                                18

<210> SEQ ID NO 1098
<211> LENGTH: 18
<212> TYPE: DNA
<213> ORGANISM: Mus sp.

<400> SEQUENCE: 1098
gtctagcgct gggtccac                                                18

<210> SEQ ID NO 1099
<211> LENGTH: 20
<212> TYPE: DNA
<213> ORGANISM: Mus sp.

<400> SEQUENCE: 1099
caaagccaaa gcacacatca                                              20

<210> SEQ ID NO 1100
<211> LENGTH: 20
<212> TYPE: DNA
<213> ORGANISM: Mus sp.

<400> SEQUENCE: 1100
agtcgccgct ttaaaaacct                                              20

<210> SEQ ID NO 1101
<211> LENGTH: 19
<212> TYPE: DNA
```

<213> ORGANISM: Mus sp.

<400> SEQUENCE: 1101
aaagcaagag gcccaagtg                                            19

<210> SEQ ID NO 1102
<211> LENGTH: 20
<212> TYPE: DNA
<213> ORGANISM: Mus sp.

<400> SEQUENCE: 1102
tgcattgctg ctagagttcc                                           20

<210> SEQ ID NO 1103
<211> LENGTH: 20
<212> TYPE: DNA
<213> ORGANISM: Mus sp.

<400> SEQUENCE: 1103
tcaaccagca ccagacagag                                           20

<210> SEQ ID NO 1104
<211> LENGTH: 22
<212> TYPE: DNA
<213> ORGANISM: Mus sp.

<400> SEQUENCE: 1104
aaacatcctg taatggcttg tg                                        22

<210> SEQ ID NO 1105
<211> LENGTH: 23
<212> TYPE: DNA
<213> ORGANISM: Mus sp.

<400> SEQUENCE: 1105
gagacttctc ctcctgactt tcc                                       23

<210> SEQ ID NO 1106
<211> LENGTH: 19
<212> TYPE: DNA
<213> ORGANISM: Mus sp.

<400> SEQUENCE: 1106
ggacttcagt ccccacacc                                            19

<210> SEQ ID NO 1107
<211> LENGTH: 20
<212> TYPE: DNA
<213> ORGANISM: Mus sp.

<400> SEQUENCE: 1107
atccctccac cctatgacaa                                           20

<210> SEQ ID NO 1108
<211> LENGTH: 19
<212> TYPE: DNA
<213> ORGANISM: Mus sp.

<400> SEQUENCE: 1108
gccccaggta agcaaactt                                            19

<210> SEQ ID NO 1109
<211> LENGTH: 20

-continued

```
<212> TYPE: DNA
<213> ORGANISM: Mus sp.

<400> SEQUENCE: 1109
aactgggtga aaagggctgt                                           20

<210> SEQ ID NO 1110
<211> LENGTH: 20
<212> TYPE: DNA
<213> ORGANISM: Mus sp.

<400> SEQUENCE: 1110
gtccaattcc atcccaaaaa                                           20

<210> SEQ ID NO 1111
<211> LENGTH: 21
<212> TYPE: DNA
<213> ORGANISM: Mus sp.

<400> SEQUENCE: 1111
gcatgtagag gccatcaaag a                                         21

<210> SEQ ID NO 1112
<211> LENGTH: 19
<212> TYPE: DNA
<213> ORGANISM: Mus sp.

<400> SEQUENCE: 1112
cgggtctgca cacatgtta                                            19

<210> SEQ ID NO 1113
<211> LENGTH: 21
<212> TYPE: DNA
<213> ORGANISM: Mus sp.

<400> SEQUENCE: 1113
tgctcaggag cacctaacaa c                                         21

<210> SEQ ID NO 1114
<211> LENGTH: 20
<212> TYPE: DNA
<213> ORGANISM: Mus sp.

<400> SEQUENCE: 1114
tggagatgga ccacactctg                                           20

<210> SEQ ID NO 1115
<211> LENGTH: 20
<212> TYPE: DNA
<213> ORGANISM: Mus sp.

<400> SEQUENCE: 1115
tggagtcctg gtgtcattcc                                           20

<210> SEQ ID NO 1116
<211> LENGTH: 23
<212> TYPE: DNA
<213> ORGANISM: Mus sp.

<400> SEQUENCE: 1116
tgtgtgttct tcacagaagc att                                       23

<210> SEQ ID NO 1117
```

-continued

```
<211> LENGTH: 20
<212> TYPE: DNA
<213> ORGANISM: Mus sp.

<400> SEQUENCE: 1117
atctggagga actggcaaaa                                              20

<210> SEQ ID NO 1118
<211> LENGTH: 26
<212> TYPE: DNA
<213> ORGANISM: Mus sp.

<400> SEQUENCE: 1118
ttcaagactt caaagagtct gaggta                                       26

<210> SEQ ID NO 1119
<211> LENGTH: 20
<212> TYPE: DNA
<213> ORGANISM: Mus sp.

<400> SEQUENCE: 1119
tttcctgacc aaactcagca                                              20

<210> SEQ ID NO 1120
<211> LENGTH: 20
<212> TYPE: DNA
<213> ORGANISM: Mus sp.

<400> SEQUENCE: 1120
tctggatgtt ctggtcgtca                                              20

<210> SEQ ID NO 1121
<211> LENGTH: 20
<212> TYPE: DNA
<213> ORGANISM: Mus sp.

<400> SEQUENCE: 1121
ggagaaactc ggcgtgtact                                              20

<210> SEQ ID NO 1122
<211> LENGTH: 20
<212> TYPE: DNA
<213> ORGANISM: Mus sp.

<400> SEQUENCE: 1122
cagccattgc atttacagga                                              20

<210> SEQ ID NO 1123
<211> LENGTH: 21
<212> TYPE: DNA
<213> ORGANISM: Mus sp.

<400> SEQUENCE: 1123
tctacctagg ctgggtctcc t                                            21

<210> SEQ ID NO 1124
<211> LENGTH: 20
<212> TYPE: DNA
<213> ORGANISM: Mus sp.

<400> SEQUENCE: 1124
ccgacgggtt ctacagtgag                                              20
```

```
<210> SEQ ID NO 1125
<211> LENGTH: 20
<212> TYPE: DNA
<213> ORGANISM: Mus sp.

<400> SEQUENCE: 1125
ggattttctg catgcctctg                                               20

<210> SEQ ID NO 1126
<211> LENGTH: 22
<212> TYPE: DNA
<213> ORGANISM: Mus sp.

<400> SEQUENCE: 1126
gacaacagtt ctgggatttt cc                                            22

<210> SEQ ID NO 1127
<211> LENGTH: 18
<212> TYPE: DNA
<213> ORGANISM: Mus sp.

<400> SEQUENCE: 1127
ctcacgttcg gtgctgtg                                                 18

<210> SEQ ID NO 1128
<211> LENGTH: 19
<212> TYPE: DNA
<213> ORGANISM: Mus sp.

<400> SEQUENCE: 1128
tccctcctcc acattgtca                                                19

<210> SEQ ID NO 1129
<211> LENGTH: 24
<212> TYPE: DNA
<213> ORGANISM: Mus sp.

<400> SEQUENCE: 1129
tgcatctgtc tctcttagtc tgct                                          24

<210> SEQ ID NO 1130
<211> LENGTH: 24
<212> TYPE: DNA
<213> ORGANISM: Mus sp.

<400> SEQUENCE: 1130
tctggaaact ccatactgtc ttca                                          24

<210> SEQ ID NO 1131
<211> LENGTH: 21
<212> TYPE: DNA
<213> ORGANISM: Mus sp.

<400> SEQUENCE: 1131
aacagctttc gatgaagcca t                                             21

<210> SEQ ID NO 1132
<211> LENGTH: 21
<212> TYPE: DNA
<213> ORGANISM: Mus sp.

<400> SEQUENCE: 1132
tgggtatccg atgtccacaa t                                             21
```

<210> SEQ ID NO 1133
<211> LENGTH: 20
<212> TYPE: DNA
<213> ORGANISM: Mus sp.

<400> SEQUENCE: 1133
gccctctctc tcctcttgct                                            20

<210> SEQ ID NO 1134
<211> LENGTH: 18
<212> TYPE: DNA
<213> ORGANISM: Mus sp.

<400> SEQUENCE: 1134
gagggtcaga gcccattg                                              18

<210> SEQ ID NO 1135
<211> LENGTH: 18
<212> TYPE: DNA
<213> ORGANISM: Mus sp.

<400> SEQUENCE: 1135
gctgccgtca ttttctgc                                              18

<210> SEQ ID NO 1136
<211> LENGTH: 18
<212> TYPE: DNA
<213> ORGANISM: Mus sp.

<400> SEQUENCE: 1136
tctcactggc ccgtcatc                                              18

<210> SEQ ID NO 1137
<211> LENGTH: 20
<212> TYPE: DNA
<213> ORGANISM: Mus sp.

<400> SEQUENCE: 1137
tccctttcgc tgtgagacat                                            20

<210> SEQ ID NO 1138
<211> LENGTH: 20
<212> TYPE: DNA
<213> ORGANISM: Mus sp.

<400> SEQUENCE: 1138
gggcgtgtat gaaattcgtt                                            20

<210> SEQ ID NO 1139
<211> LENGTH: 21
<212> TYPE: DNA
<213> ORGANISM: Mus sp.

<400> SEQUENCE: 1139
tggctaatgg aaattgaggt g                                          21

<210> SEQ ID NO 1140
<211> LENGTH: 20
<212> TYPE: DNA
<213> ORGANISM: Mus sp.

<400> SEQUENCE: 1140
catcaggacc cacatggtct                                            20

```
<210> SEQ ID NO 1141
<211> LENGTH: 19
<212> TYPE: DNA
<213> ORGANISM: Mus sp.

<400> SEQUENCE: 1141
gcagacatgc acacaccac                                              19

<210> SEQ ID NO 1142
<211> LENGTH: 20
<212> TYPE: DNA
<213> ORGANISM: Mus sp.

<400> SEQUENCE: 1142
tgagagctcc ctctccagat                                             20

<210> SEQ ID NO 1143
<211> LENGTH: 24
<212> TYPE: DNA
<213> ORGANISM: Mus sp.

<400> SEQUENCE: 1143
ccaagtatat tgtgcatgtg aaga                                        24

<210> SEQ ID NO 1144
<211> LENGTH: 23
<212> TYPE: DNA
<213> ORGANISM: Mus sp.

<400> SEQUENCE: 1144
agcttgaggc aagatattgt tgt                                         23

<210> SEQ ID NO 1145
<211> LENGTH: 20
<212> TYPE: DNA
<213> ORGANISM: Mus sp.

<400> SEQUENCE: 1145
ctccgaaaag aggcacaagt                                             20

<210> SEQ ID NO 1146
<211> LENGTH: 22
<212> TYPE: DNA
<213> ORGANISM: Mus sp.

<400> SEQUENCE: 1146
gcgagaactt tttaaggcag tc                                          22

<210> SEQ ID NO 1147
<211> LENGTH: 18
<212> TYPE: DNA
<213> ORGANISM: Mus sp.

<400> SEQUENCE: 1147
cgcaccagcc tcttcact                                               18

<210> SEQ ID NO 1148
<211> LENGTH: 21
<212> TYPE: DNA
<213> ORGANISM: Mus sp.

<400> SEQUENCE: 1148
```
ttccgaagtc ctcaaaacct t                                              21

<210> SEQ ID NO 1149
<211> LENGTH: 21
<212> TYPE: DNA
<213> ORGANISM: Mus sp.

<400> SEQUENCE: 1149
ttgggtcaaa aatgagacca g                                              21

<210> SEQ ID NO 1150
<211> LENGTH: 24
<212> TYPE: DNA
<213> ORGANISM: Mus sp.

<400> SEQUENCE: 1150
ccttgaaata cactgcatta acga                                           24

<210> SEQ ID NO 1151
<211> LENGTH: 18
<212> TYPE: DNA
<213> ORGANISM: Mus sp.

<400> SEQUENCE: 1151
gagctcggga gaccacag                                                  18

<210> SEQ ID NO 1152
<211> LENGTH: 21
<212> TYPE: DNA
<213> ORGANISM: Mus sp.

<400> SEQUENCE: 1152
tggtcgctac ttagcctcaa t                                              21

<210> SEQ ID NO 1153
<211> LENGTH: 20
<212> TYPE: DNA
<213> ORGANISM: Mus sp.

<400> SEQUENCE: 1153
ggagaggacg gcgttatttt                                                20

<210> SEQ ID NO 1154
<211> LENGTH: 19
<212> TYPE: DNA
<213> ORGANISM: Mus sp.

<400> SEQUENCE: 1154
ttttcatacc ccggaggag                                                 19

<210> SEQ ID NO 1155
<211> LENGTH: 19
<212> TYPE: RNA
<213> ORGANISM: Mus sp.

<400> SEQUENCE: 1155
caaagaaucu agucuauga                                                 19

<210> SEQ ID NO 1156
<211> LENGTH: 19
<212> TYPE: RNA
<213> ORGANISM: Mus sp.

<400> SEQUENCE: 1156

-continued

| | |
|---|---|
| ugacaggacu gauuguaua | 19 |

<210> SEQ ID NO 1157
<211> LENGTH: 19
<212> TYPE: RNA
<213> ORGANISM: Mus sp.

<400> SEQUENCE: 1157

| | |
|---|---|
| gcagaaacau gcaggaaug | 19 |

<210> SEQ ID NO 1158
<211> LENGTH: 19
<212> TYPE: RNA
<213> ORGANISM: Mus sp.

<400> SEQUENCE: 1158

| | |
|---|---|
| ggcaauaugu guaaugaaa | 19 |

<210> SEQ ID NO 1159
<211> LENGTH: 19
<212> TYPE: RNA
<213> ORGANISM: Mus sp.

<400> SEQUENCE: 1159

| | |
|---|---|
| ccaaugcacg cuugauuua | 19 |

<210> SEQ ID NO 1160
<211> LENGTH: 19
<212> TYPE: RNA
<213> ORGANISM: Mus sp.

<400> SEQUENCE: 1160

| | |
|---|---|
| gaaggagagu ucuuguuac | 19 |

<210> SEQ ID NO 1161
<211> LENGTH: 19
<212> TYPE: RNA
<213> ORGANISM: Mus sp.

<400> SEQUENCE: 1161

| | |
|---|---|
| ccgcaagaug uuauuaaua | 19 |

<210> SEQ ID NO 1162
<211> LENGTH: 19
<212> TYPE: RNA
<213> ORGANISM: Mus sp.

<400> SEQUENCE: 1162

| | |
|---|---|
| ccaguucucu uaugagugc | 19 |

<210> SEQ ID NO 1163
<211> LENGTH: 19
<212> TYPE: RNA
<213> ORGANISM: Mus sp.

<400> SEQUENCE: 1163

| | |
|---|---|
| ggaagaacgu guaugauga | 19 |

<210> SEQ ID NO 1164
<211> LENGTH: 19
<212> TYPE: RNA
<213> ORGANISM: Mus sp.

<400> SEQUENCE: 1164
gaagagggau ucgcucaug                                                19

<210> SEQ ID NO 1165
<211> LENGTH: 19
<212> TYPE: RNA
<213> ORGANISM: Mus sp.

<400> SEQUENCE: 1165
ccucuaaacu ucaccggua                                                19

<210> SEQ ID NO 1166
<211> LENGTH: 19
<212> TYPE: RNA
<213> ORGANISM: Mus sp.

<400> SEQUENCE: 1166
ggucaucccu gcuuuccca                                                19

<210> SEQ ID NO 1167
<211> LENGTH: 19
<212> TYPE: RNA
<213> ORGANISM: Mus sp.

<400> SEQUENCE: 1167
gcaucgauau gauagauaa                                                19

<210> SEQ ID NO 1168
<211> LENGTH: 19
<212> TYPE: RNA
<213> ORGANISM: Mus sp.

<400> SEQUENCE: 1168
caguaaaggu ggaagauaa                                                19

<210> SEQ ID NO 1169
<211> LENGTH: 19
<212> TYPE: RNA
<213> ORGANISM: Mus sp.

<400> SEQUENCE: 1169
gaaauacggg ugaaaucua                                                19

<210> SEQ ID NO 1170
<211> LENGTH: 19
<212> TYPE: RNA
<213> ORGANISM: Mus sp.

<400> SEQUENCE: 1170
ugucguagga ugugaccga                                                19

<210> SEQ ID NO 1171
<211> LENGTH: 19
<212> TYPE: RNA
<213> ORGANISM: Mus sp.

<400> SEQUENCE: 1171
gaacgcagcu cuccgcaaa                                                19

<210> SEQ ID NO 1172
<211> LENGTH: 19
<212> TYPE: RNA
<213> ORGANISM: Mus sp.

```
<400> SEQUENCE: 1172
ucaaacagcu caccgagga                                      19

<210> SEQ ID NO 1173
<211> LENGTH: 19
<212> TYPE: RNA
<213> ORGANISM: Mus sp.

<400> SEQUENCE: 1173
gaggaaaguu cagaggaga                                      19

<210> SEQ ID NO 1174
<211> LENGTH: 19
<212> TYPE: RNA
<213> ORGANISM: Mus sp.

<400> SEQUENCE: 1174
ucaaguacuu cacaucagu                                      19

<210> SEQ ID NO 1175
<211> LENGTH: 19
<212> TYPE: RNA
<213> ORGANISM: Mus sp.

<400> SEQUENCE: 1175
ggaguuaucu cucaguguu                                      19

<210> SEQ ID NO 1176
<211> LENGTH: 19
<212> TYPE: RNA
<213> ORGANISM: Mus sp.

<400> SEQUENCE: 1176
ugaaguuucu acugguuua                                      19

<210> SEQ ID NO 1177
<211> LENGTH: 19
<212> TYPE: RNA
<213> ORGANISM: Mus sp.

<400> SEQUENCE: 1177
gcuaugacau cgauuaugg                                      19

<210> SEQ ID NO 1178
<211> LENGTH: 19
<212> TYPE: RNA
<213> ORGANISM: Mus sp.

<400> SEQUENCE: 1178
ugaaacaaau ugcggcuca                                      19

<210> SEQ ID NO 1179
<211> LENGTH: 19
<212> TYPE: RNA
<213> ORGANISM: Mus sp.

<400> SEQUENCE: 1179
gcacauaugc ggucaacuu                                      19

<210> SEQ ID NO 1180
<211> LENGTH: 19
<212> TYPE: RNA
```

```
<213> ORGANISM: Mus sp.

<400> SEQUENCE: 1180
ccaauugccu acuccuuaa                                                19

<210> SEQ ID NO 1181
<211> LENGTH: 19
<212> TYPE: RNA
<213> ORGANISM: Mus sp.

<400> SEQUENCE: 1181
gaacggauga uuaugacaa                                                19

<210> SEQ ID NO 1182
<211> LENGTH: 19
<212> TYPE: RNA
<213> ORGANISM: Mus sp.

<400> SEQUENCE: 1182
uguaugagaa ggaagaaua                                                19

<210> SEQ ID NO 1183
<211> LENGTH: 19
<212> TYPE: RNA
<213> ORGANISM: Mus sp.

<400> SEQUENCE: 1183
cgacagcagu cccaucuac                                                19

<210> SEQ ID NO 1184
<211> LENGTH: 19
<212> TYPE: RNA
<213> ORGANISM: Mus sp.

<400> SEQUENCE: 1184
ugacaucgcu cugaauaau                                                19

<210> SEQ ID NO 1185
<211> LENGTH: 19
<212> TYPE: RNA
<213> ORGANISM: Mus sp.

<400> SEQUENCE: 1185
acuccacuau ccacuauua                                                19

<210> SEQ ID NO 1186
<211> LENGTH: 19
<212> TYPE: RNA
<213> ORGANISM: Mus sp.

<400> SEQUENCE: 1186
augcguaacu ucagucgua                                                19

<210> SEQ ID NO 1187
<211> LENGTH: 19
<212> TYPE: RNA
<213> ORGANISM: Mus sp.

<400> SEQUENCE: 1187
gaagguauca ucaauauug                                                19

<210> SEQ ID NO 1188
<211> LENGTH: 19
```

```
<212> TYPE: RNA
<213> ORGANISM: Mus sp.

<400> SEQUENCE: 1188
gaucucccgu auccgagua                                                19

<210> SEQ ID NO 1189
<211> LENGTH: 19
<212> TYPE: RNA
<213> ORGANISM: Mus sp.

<400> SEQUENCE: 1189
ucucuaccau ccguaauuu                                                19

<210> SEQ ID NO 1190
<211> LENGTH: 19
<212> TYPE: RNA
<213> ORGANISM: Mus sp.

<400> SEQUENCE: 1190
ugacaugacu ggagagaag                                                19

<210> SEQ ID NO 1191
<211> LENGTH: 19
<212> TYPE: RNA
<213> ORGANISM: Mus sp.

<400> SEQUENCE: 1191
guagagauca gccgggaga                                                19

<210> SEQ ID NO 1192
<211> LENGTH: 19
<212> TYPE: RNA
<213> ORGANISM: Mus sp.

<400> SEQUENCE: 1192
gaucagguuu gugaccaau                                                19

<210> SEQ ID NO 1193
<211> LENGTH: 19
<212> TYPE: RNA
<213> ORGANISM: Mus sp.

<400> SEQUENCE: 1193
ucuuuaaugu ugccaaaug                                                19

<210> SEQ ID NO 1194
<211> LENGTH: 19
<212> TYPE: RNA
<213> ORGANISM: Mus sp.

<400> SEQUENCE: 1194
ugagauacua uuacgacaa                                                19

<210> SEQ ID NO 1195
<211> LENGTH: 19
<212> TYPE: RNA
<213> ORGANISM: Mus sp.

<400> SEQUENCE: 1195
gcuuagagau guagcgaug                                                19

<210> SEQ ID NO 1196
```

```
<210> SEQ ID NO 1196
<211> LENGTH: 19
<212> TYPE: RNA
<213> ORGANISM: Mus sp.

<400> SEQUENCE: 1196
ccuguuacac cucggauua                                                19

<210> SEQ ID NO 1197
<211> LENGTH: 19
<212> TYPE: RNA
<213> ORGANISM: Mus sp.

<400> SEQUENCE: 1197
cagcuacggu aucgagcau                                                19

<210> SEQ ID NO 1198
<211> LENGTH: 19
<212> TYPE: RNA
<213> ORGANISM: Mus sp.

<400> SEQUENCE: 1198
ucaaguauga gaacgacua                                                19

<210> SEQ ID NO 1199
<211> LENGTH: 19
<212> TYPE: RNA
<213> ORGANISM: Mus sp.

<400> SEQUENCE: 1199
gaucaacagc aauacauua                                                19

<210> SEQ ID NO 1200
<211> LENGTH: 19
<212> TYPE: RNA
<213> ORGANISM: Mus sp.

<400> SEQUENCE: 1200
ugaauuugcu caacaacaa                                                19

<210> SEQ ID NO 1201
<211> LENGTH: 19
<212> TYPE: RNA
<213> ORGANISM: Mus sp.

<400> SEQUENCE: 1201
uagagcagau gaucaaaga                                                19

<210> SEQ ID NO 1202
<211> LENGTH: 19
<212> TYPE: RNA
<213> ORGANISM: Mus sp.

<400> SEQUENCE: 1202
gaaugacuuu ggaaucaag                                                19

<210> SEQ ID NO 1203
<211> LENGTH: 19
<212> TYPE: RNA
<213> ORGANISM: Mus sp.

<400> SEQUENCE: 1203
gaacaaacau gaccuauga                                                19
```

```
<210> SEQ ID NO 1204
<211> LENGTH: 19
<212> TYPE: RNA
<213> ORGANISM: Mus sp.

<400> SEQUENCE: 1204
caaagaggau uccgcuac                                                   19

<210> SEQ ID NO 1205
<211> LENGTH: 19
<212> TYPE: RNA
<213> ORGANISM: Mus sp.

<400> SEQUENCE: 1205
gcauuaagca ggaacgaau                                                  19

<210> SEQ ID NO 1206
<211> LENGTH: 19
<212> TYPE: RNA
<213> ORGANISM: Mus sp.

<400> SEQUENCE: 1206
cgccacuacu acaaacuaa                                                  19

<210> SEQ ID NO 1207
<211> LENGTH: 19
<212> TYPE: RNA
<213> ORGANISM: Mus sp.

<400> SEQUENCE: 1207
gaguaaauac aucccgaga                                                  19

<210> SEQ ID NO 1208
<211> LENGTH: 19
<212> TYPE: RNA
<213> ORGANISM: Mus sp.

<400> SEQUENCE: 1208
ggaggcgggu ucaugaaac                                                  19

<210> SEQ ID NO 1209
<211> LENGTH: 19
<212> TYPE: RNA
<213> ORGANISM: Mus sp.

<400> SEQUENCE: 1209
cgcagaaccu uagauaaau                                                  19

<210> SEQ ID NO 1210
<211> LENGTH: 19
<212> TYPE: RNA
<213> ORGANISM: Mus sp.

<400> SEQUENCE: 1210
guaccaaucu caugggaag                                                  19

<210> SEQ ID NO 1211
<211> LENGTH: 19
<212> TYPE: RNA
<213> ORGANISM: Mus sp.

<400> SEQUENCE: 1211
gaagacaccu uuacaagug                                                  19
```

```
<210> SEQ ID NO 1212
<211> LENGTH: 19
<212> TYPE: RNA
<213> ORGANISM: Mus sp.

<400> SEQUENCE: 1212
ggacaacaac aguaaauuu                                                    19

<210> SEQ ID NO 1213
<211> LENGTH: 19
<212> TYPE: RNA
<213> ORGANISM: Mus sp.

<400> SEQUENCE: 1213
ggagauaccu uggauuuua                                                    19

<210> SEQ ID NO 1214
<211> LENGTH: 19
<212> TYPE: RNA
<213> ORGANISM: Mus sp.

<400> SEQUENCE: 1214
gaaaucagca auccagaaa                                                    19

<210> SEQ ID NO 1215
<211> LENGTH: 19
<212> TYPE: RNA
<213> ORGANISM: Mus sp.

<400> SEQUENCE: 1215
gaagaugucu agcaaaucg                                                    19

<210> SEQ ID NO 1216
<211> LENGTH: 19
<212> TYPE: RNA
<213> ORGANISM: Mus sp.

<400> SEQUENCE: 1216
cggaagaugu cuagcaaau                                                    19

<210> SEQ ID NO 1217
<211> LENGTH: 19
<212> TYPE: RNA
<213> ORGANISM: Mus sp.

<400> SEQUENCE: 1217
guacauggaa gcucaguau                                                    19

<210> SEQ ID NO 1218
<211> LENGTH: 19
<212> TYPE: RNA
<213> ORGANISM: Mus sp.

<400> SEQUENCE: 1218
agaaagagug ccucaagua                                                    19

<210> SEQ ID NO 1219
<211> LENGTH: 19
<212> TYPE: RNA
<213> ORGANISM: Mus sp.

<400> SEQUENCE: 1219
caucugaauu cccuucuga                                                    19
```

```
<210> SEQ ID NO 1220
<211> LENGTH: 19
<212> TYPE: RNA
<213> ORGANISM: Mus sp.

<400> SEQUENCE: 1220
gaacacggac aucagcauc                                               19

<210> SEQ ID NO 1221
<211> LENGTH: 19
<212> TYPE: RNA
<213> ORGANISM: Mus sp.

<400> SEQUENCE: 1221
gucgaaugau agcaaagua                                               19

<210> SEQ ID NO 1222
<211> LENGTH: 19
<212> TYPE: RNA
<213> ORGANISM: Mus sp.

<400> SEQUENCE: 1222
cggugagguc cguuaggaa                                               19

<210> SEQ ID NO 1223
<211> LENGTH: 19
<212> TYPE: RNA
<213> ORGANISM: Mus sp.

<400> SEQUENCE: 1223
gauggugccu gacucaaug                                               19

<210> SEQ ID NO 1224
<211> LENGTH: 19
<212> TYPE: RNA
<213> ORGANISM: Mus sp.

<400> SEQUENCE: 1224
cgacugaacg gccaacuuu                                               19

<210> SEQ ID NO 1225
<211> LENGTH: 19
<212> TYPE: RNA
<213> ORGANISM: Mus sp.

<400> SEQUENCE: 1225
gugaaggccu uuaagugug                                               19

<210> SEQ ID NO 1226
<211> LENGTH: 19
<212> TYPE: RNA
<213> ORGANISM: Mus sp.

<400> SEQUENCE: 1226
gaacucacac cugucauca                                               19

<210> SEQ ID NO 1227
<211> LENGTH: 19
<212> TYPE: RNA
<213> ORGANISM: Mus sp.

<400> SEQUENCE: 1227
```
ggacagauuu gaggagguu                                                    19

<210> SEQ ID NO 1228
<211> LENGTH: 19
<212> TYPE: RNA
<213> ORGANISM: Mus sp.

<400> SEQUENCE: 1228
gaauaguacu ugucuggau                                                    19

<210> SEQ ID NO 1229
<211> LENGTH: 19
<212> TYPE: RNA
<213> ORGANISM: Mus sp.

<400> SEQUENCE: 1229
ucugggagcu cgagaagaa                                                    19

<210> SEQ ID NO 1230
<211> LENGTH: 19
<212> TYPE: RNA
<213> ORGANISM: Mus sp.

<400> SEQUENCE: 1230
gagagcaacu ccaaaauca                                                    19

<210> SEQ ID NO 1231
<211> LENGTH: 19
<212> TYPE: RNA
<213> ORGANISM: Mus sp.

<400> SEQUENCE: 1231
guccagagau uucacauuu                                                    19

<210> SEQ ID NO 1232
<211> LENGTH: 19
<212> TYPE: RNA
<213> ORGANISM: Mus sp.

<400> SEQUENCE: 1232
agacuuaccu ugaaacaaa                                                    19

<210> SEQ ID NO 1233
<211> LENGTH: 19
<212> TYPE: RNA
<213> ORGANISM: Mus sp.

<400> SEQUENCE: 1233
gaacuucacu gccauuugu                                                    19

<210> SEQ ID NO 1234
<211> LENGTH: 19
<212> TYPE: RNA
<213> ORGANISM: Mus sp.

<400> SEQUENCE: 1234
gcacagagcu gaccgugaa                                                    19

<210> SEQ ID NO 1235
<211> LENGTH: 19
<212> TYPE: RNA
<213> ORGANISM: Mus sp.

<400> SEQUENCE: 1235

```
ggauuaaacc ugucguaug                                              19

<210> SEQ ID NO 1236
<211> LENGTH: 19
<212> TYPE: RNA
<213> ORGANISM: Mus sp.

<400> SEQUENCE: 1236
uaagaugccu ggcuagaaa                                              19

<210> SEQ ID NO 1237
<211> LENGTH: 19
<212> TYPE: RNA
<213> ORGANISM: Mus sp.

<400> SEQUENCE: 1237
gcaaaccgcu cgccugaga                                              19

<210> SEQ ID NO 1238
<211> LENGTH: 19
<212> TYPE: RNA
<213> ORGANISM: Mus sp.

<400> SEQUENCE: 1238
gaaagucguu uaucgcaaa                                              19

<210> SEQ ID NO 1239
<211> LENGTH: 19
<212> TYPE: RNA
<213> ORGANISM: Mus sp.

<400> SEQUENCE: 1239
ccauaucaau guccuguga                                              19

<210> SEQ ID NO 1240
<211> LENGTH: 19
<212> TYPE: RNA
<213> ORGANISM: Mus sp.

<400> SEQUENCE: 1240
cgaguuaccu gaacacguu                                              19

<210> SEQ ID NO 1241
<211> LENGTH: 19
<212> TYPE: RNA
<213> ORGANISM: Mus sp.

<400> SEQUENCE: 1241
uaucagagcu gcaaguguu                                              19

<210> SEQ ID NO 1242
<211> LENGTH: 19
<212> TYPE: RNA
<213> ORGANISM: Mus sp.

<400> SEQUENCE: 1242
ggacacaccu augauguua                                              19

<210> SEQ ID NO 1243
<211> LENGTH: 19
<212> TYPE: RNA
<213> ORGANISM: Mus sp.
```

<400> SEQUENCE: 1243
ggacauuucu gagccauau							19

<210> SEQ ID NO 1244
<211> LENGTH: 19
<212> TYPE: RNA
<213> ORGANISM: Mus sp.

<400> SEQUENCE: 1244
gagcgaaguu ccugagaug							19

<210> SEQ ID NO 1245
<211> LENGTH: 19
<212> TYPE: RNA
<213> ORGANISM: Mus sp.

<400> SEQUENCE: 1245
gcaagggcgu guucgugaa							19

<210> SEQ ID NO 1246
<211> LENGTH: 19
<212> TYPE: RNA
<213> ORGANISM: Mus sp.

<400> SEQUENCE: 1246
gcaacgcggu ggugugcaa							19

<210> SEQ ID NO 1247
<211> LENGTH: 19
<212> TYPE: RNA
<213> ORGANISM: Mus sp.

<400> SEQUENCE: 1247
gcgaugacug gcagacaua							19

<210> SEQ ID NO 1248
<211> LENGTH: 19
<212> TYPE: RNA
<213> ORGANISM: Mus sp.

<400> SEQUENCE: 1248
gaguggcccu augaaguua							19

<210> SEQ ID NO 1249
<211> LENGTH: 19
<212> TYPE: RNA
<213> ORGANISM: Mus sp.

<400> SEQUENCE: 1249
ggacaauguu cgcgauaaa							19

<210> SEQ ID NO 1250
<211> LENGTH: 19
<212> TYPE: RNA
<213> ORGANISM: Mus sp.

<400> SEQUENCE: 1250
ccagacaccu ccaacauua							19

<210> SEQ ID NO 1251
<211> LENGTH: 19
<212> TYPE: RNA
<213> ORGANISM: Mus sp.

-continued

```
<400> SEQUENCE: 1251
gaacaggugg cacagcuua                                                      19

<210> SEQ ID NO 1252
<211> LENGTH: 19
<212> TYPE: RNA
<213> ORGANISM: Mus sp.

<400> SEQUENCE: 1252
gaaacgaccu ucuacgacg                                                      19

<210> SEQ ID NO 1253
<211> LENGTH: 19
<212> TYPE: RNA
<213> ORGANISM: Mus sp.

<400> SEQUENCE: 1253
ccaagaacgu gaccgacga                                                      19

<210> SEQ ID NO 1254
<211> LENGTH: 19
<212> TYPE: RNA
<213> ORGANISM: Mus sp.

<400> SEQUENCE: 1254
gccaagaacu cggaccuuc                                                      19

<210> SEQ ID NO 1255
<211> LENGTH: 19
<212> TYPE: RNA
<213> ORGANISM: Mus sp.

<400> SEQUENCE: 1255
caaccuggcg gaucccuau                                                      19

<210> SEQ ID NO 1256
<211> LENGTH: 19
<212> TYPE: RNA
<213> ORGANISM: Mus sp.

<400> SEQUENCE: 1256
caacagcaac ggcgugauc                                                      19

<210> SEQ ID NO 1257
<211> LENGTH: 19
<212> TYPE: RNA
<213> ORGANISM: Mus sp.

<400> SEQUENCE: 1257
uggaacagcc uuucuauca                                                      19

<210> SEQ ID NO 1258
<211> LENGTH: 19
<212> TYPE: RNA
<213> ORGANISM: Mus sp.

<400> SEQUENCE: 1258
acaccaaccu cagcaguua                                                      19

<210> SEQ ID NO 1259
<211> LENGTH: 19
<212> TYPE: RNA
```

<213> ORGANISM: Mus sp.

<400> SEQUENCE: 1259
gcaguaaccu caaaugaac                                            19

<210> SEQ ID NO 1260
<211> LENGTH: 19
<212> TYPE: RNA
<213> ORGANISM: Mus sp.

<400> SEQUENCE: 1260
ucacauaugc agaugagua                                            19

<210> SEQ ID NO 1261
<211> LENGTH: 19
<212> TYPE: RNA
<213> ORGANISM: Mus sp.

<400> SEQUENCE: 1261
gaagaaccau ccaaaugcu                                            19

<210> SEQ ID NO 1262
<211> LENGTH: 19
<212> TYPE: RNA
<213> ORGANISM: Mus sp.

<400> SEQUENCE: 1262
aaacaagccc agauucgaa                                            19

<210> SEQ ID NO 1263
<211> LENGTH: 19
<212> TYPE: RNA
<213> ORGANISM: Mus sp.

<400> SEQUENCE: 1263
gaagggcucc cguaacaug                                            19

<210> SEQ ID NO 1264
<211> LENGTH: 19
<212> TYPE: RNA
<213> ORGANISM: Mus sp.

<400> SEQUENCE: 1264
aaagaggccc ugcggcaaa                                            19

<210> SEQ ID NO 1265
<211> LENGTH: 19
<212> TYPE: RNA
<213> ORGANISM: Mus sp.

<400> SEQUENCE: 1265
gcucgagaga uccggauga                                            19

<210> SEQ ID NO 1266
<211> LENGTH: 19
<212> TYPE: RNA
<213> ORGANISM: Mus sp.

<400> SEQUENCE: 1266
agacacagua aaugacguu                                            19

<210> SEQ ID NO 1267
<211> LENGTH: 19

```
<212> TYPE: RNA
<213> ORGANISM: Mus sp.

<400> SEQUENCE: 1267
guaaacaguu gccaagguu                                                    19

<210> SEQ ID NO 1268
<211> LENGTH: 19
<212> TYPE: RNA
<213> ORGANISM: Mus sp.

<400> SEQUENCE: 1268
gcaccuacca gaacaauuc                                                    19

<210> SEQ ID NO 1269
<211> LENGTH: 19
<212> TYPE: RNA
<213> ORGANISM: Mus sp.

<400> SEQUENCE: 1269
gaaauggaac ggagacgau                                                    19

<210> SEQ ID NO 1270
<211> LENGTH: 19
<212> TYPE: RNA
<213> ORGANISM: Mus sp.

<400> SEQUENCE: 1270
ggucaccaau ucguguuaa                                                    19

<210> SEQ ID NO 1271
<211> LENGTH: 19
<212> TYPE: RNA
<213> ORGANISM: Mus sp.

<400> SEQUENCE: 1271
gacgagaccu ucaucaaga                                                    19

<210> SEQ ID NO 1272
<211> LENGTH: 19
<212> TYPE: RNA
<213> ORGANISM: Mus sp.

<400> SEQUENCE: 1272
gacagcagcu cgcccaaau                                                    19

<210> SEQ ID NO 1273
<211> LENGTH: 19
<212> TYPE: RNA
<213> ORGANISM: Mus sp.

<400> SEQUENCE: 1273
gaauuucuau caccagcaa                                                    19

<210> SEQ ID NO 1274
<211> LENGTH: 19
<212> TYPE: RNA
<213> ORGANISM: Mus sp.

<400> SEQUENCE: 1274
guacagcccu auucaucu                                                     19

<210> SEQ ID NO 1275
```

-continued

```
<211> LENGTH: 19
<212> TYPE: RNA
<213> ORGANISM: Mus sp.

<400> SEQUENCE: 1275
gaugauccgg caacuagaa                                                    19

<210> SEQ ID NO 1276
<211> LENGTH: 19
<212> TYPE: RNA
<213> ORGANISM: Mus sp.

<400> SEQUENCE: 1276
guuagaccgu gaggauaua                                                    19

<210> SEQ ID NO 1277
<211> LENGTH: 19
<212> TYPE: RNA
<213> ORGANISM: Mus sp.

<400> SEQUENCE: 1277
cgacugauuc cuauuaaau                                                    19

<210> SEQ ID NO 1278
<211> LENGTH: 19
<212> TYPE: RNA
<213> ORGANISM: Mus sp.

<400> SEQUENCE: 1278
gccuaucgcu guucuugaa                                                    19

<210> SEQ ID NO 1279
<211> LENGTH: 19
<212> TYPE: RNA
<213> ORGANISM: Mus sp.

<400> SEQUENCE: 1279
gaacaugaau ccaaugaug                                                    19

<210> SEQ ID NO 1280
<211> LENGTH: 19
<212> TYPE: RNA
<213> ORGANISM: Mus sp.

<400> SEQUENCE: 1280
gaacauggga ggacaguuu                                                    19

<210> SEQ ID NO 1281
<211> LENGTH: 19
<212> TYPE: RNA
<213> ORGANISM: Mus sp.

<400> SEQUENCE: 1281
ucaagaaucu gcuaccaaa                                                    19

<210> SEQ ID NO 1282
<211> LENGTH: 19
<212> TYPE: RNA
<213> ORGANISM: Mus sp.

<400> SEQUENCE: 1282
ccaagaagau ggugaagau                                                    19
```

```
<210> SEQ ID NO 1283
<211> LENGTH: 19
<212> TYPE: RNA
<213> ORGANISM: Mus sp.

<400> SEQUENCE: 1283
gacaugggau uucaggaua                                                        19

<210> SEQ ID NO 1284
<211> LENGTH: 19
<212> TYPE: RNA
<213> ORGANISM: Mus sp.

<400> SEQUENCE: 1284
ggauuucgau uccgcuaug                                                        19

<210> SEQ ID NO 1285
<211> LENGTH: 19
<212> TYPE: RNA
<213> ORGANISM: Mus sp.

<400> SEQUENCE: 1285
cuacggaacu gggcaaaug                                                        19

<210> SEQ ID NO 1286
<211> LENGTH: 19
<212> TYPE: RNA
<213> ORGANISM: Mus sp.

<400> SEQUENCE: 1286
ggaaacgcca gaagcuuau                                                        19

<210> SEQ ID NO 1287
<211> LENGTH: 19
<212> TYPE: RNA
<213> ORGANISM: Mus sp.

<400> SEQUENCE: 1287
gaacaacucc uuccacuuu                                                        19

<210> SEQ ID NO 1288
<211> LENGTH: 19
<212> TYPE: RNA
<213> ORGANISM: Mus sp.

<400> SEQUENCE: 1288
ggaaacaacu gcaagaaug                                                        19

<210> SEQ ID NO 1289
<211> LENGTH: 19
<212> TYPE: RNA
<213> ORGANISM: Mus sp.

<400> SEQUENCE: 1289
gaaccaggcu acacaggaa                                                        19

<210> SEQ ID NO 1290
<211> LENGTH: 19
<212> TYPE: RNA
<213> ORGANISM: Mus sp.

<400> SEQUENCE: 1290
gaagguguau acugugaaa                                                        19
```

<210> SEQ ID NO 1291
<211> LENGTH: 19
<212> TYPE: RNA
<213> ORGANISM: Mus sp.

<400> SEQUENCE: 1291
gaucgagccu gagguguua								19

<210> SEQ ID NO 1292
<211> LENGTH: 19
<212> TYPE: RNA
<213> ORGANISM: Mus sp.

<400> SEQUENCE: 1292
uuacaaagau ugcagguau								19

<210> SEQ ID NO 1293
<211> LENGTH: 19
<212> TYPE: RNA
<213> ORGANISM: Mus sp.

<400> SEQUENCE: 1293
gccaagaguu auuugauga								19

<210> SEQ ID NO 1294
<211> LENGTH: 19
<212> TYPE: RNA
<213> ORGANISM: Mus sp.

<400> SEQUENCE: 1294
gcauguauga ccauguaa								19

<210> SEQ ID NO 1295
<211> LENGTH: 19
<212> TYPE: RNA
<213> ORGANISM: Mus sp.

<400> SEQUENCE: 1295
gcgcaagucc aauaucuuc								19

<210> SEQ ID NO 1296
<211> LENGTH: 19
<212> TYPE: RNA
<213> ORGANISM: Mus sp.

<400> SEQUENCE: 1296
agugguaccu caagcauga								19

<210> SEQ ID NO 1297
<211> LENGTH: 19
<212> TYPE: RNA
<213> ORGANISM: Mus sp.

<400> SEQUENCE: 1297
gcgcagacau ugagaagca								19

<210> SEQ ID NO 1298
<211> LENGTH: 19
<212> TYPE: RNA
<213> ORGANISM: Mus sp.

<400> SEQUENCE: 1298
cagcauaucu acuccuuua								19

<210> SEQ ID NO 1299
<211> LENGTH: 19
<212> TYPE: RNA
<213> ORGANISM: Mus sp.

<400> SEQUENCE: 1299
gaagaaagcg uggccauac                                                19

<210> SEQ ID NO 1300
<211> LENGTH: 19
<212> TYPE: RNA
<213> ORGANISM: Mus sp.

<400> SEQUENCE: 1300
cggaguaugu gucccauga                                                19

<210> SEQ ID NO 1301
<211> LENGTH: 19
<212> TYPE: RNA
<213> ORGANISM: Mus sp.

<400> SEQUENCE: 1301
ucacuaaugu cacgccaag                                                19

<210> SEQ ID NO 1302
<211> LENGTH: 19
<212> TYPE: RNA
<213> ORGANISM: Mus sp.

<400> SEQUENCE: 1302
gcaacacgua cgagcucaa                                                19

<210> SEQ ID NO 1303
<211> LENGTH: 19
<212> TYPE: RNA
<213> ORGANISM: Mus sp.

<400> SEQUENCE: 1303
ggagagaccc accuacaua                                                19

<210> SEQ ID NO 1304
<211> LENGTH: 19
<212> TYPE: RNA
<213> ORGANISM: Mus sp.

<400> SEQUENCE: 1304
gcaauacagu agugagaaa                                                19

<210> SEQ ID NO 1305
<211> LENGTH: 19
<212> TYPE: RNA
<213> ORGANISM: Mus sp.

<400> SEQUENCE: 1305
ggaaggacau cuaccguuc                                                19

<210> SEQ ID NO 1306
<211> LENGTH: 19
<212> TYPE: RNA
<213> ORGANISM: Mus sp.

<400> SEQUENCE: 1306
guacauacau agugaacga                                          19

<210> SEQ ID NO 1307
<211> LENGTH: 19
<212> TYPE: RNA
<213> ORGANISM: Mus sp.

<400> SEQUENCE: 1307
uaucugaccc aguucgaaa                                          19

<210> SEQ ID NO 1308
<211> LENGTH: 19
<212> TYPE: RNA
<213> ORGANISM: Mus sp.

<400> SEQUENCE: 1308
uaacuccgau ggcucccaa                                          19

<210> SEQ ID NO 1309
<211> LENGTH: 19
<212> TYPE: RNA
<213> ORGANISM: Mus sp.

<400> SEQUENCE: 1309
guaaguuucc ggccaaaga                                          19

<210> SEQ ID NO 1310
<211> LENGTH: 19
<212> TYPE: RNA
<213> ORGANISM: Mus sp.

<400> SEQUENCE: 1310
ccaaacaggu cgcucuuac                                          19

<210> SEQ ID NO 1311
<211> LENGTH: 19
<212> TYPE: RNA
<213> ORGANISM: Mus sp.

<400> SEQUENCE: 1311
ccaaacgacu cacuaggga                                          19

<210> SEQ ID NO 1312
<211> LENGTH: 19
<212> TYPE: RNA
<213> ORGANISM: Mus sp.

<400> SEQUENCE: 1312
ucucaacccu gugcguuua                                          19

<210> SEQ ID NO 1313
<211> LENGTH: 19
<212> TYPE: RNA
<213> ORGANISM: Mus sp.

<400> SEQUENCE: 1313
gcagacggca uuacuggau                                          19

<210> SEQ ID NO 1314
<211> LENGTH: 19
<212> TYPE: RNA
<213> ORGANISM: Mus sp.

<400> SEQUENCE: 1314

-continued

| | |
|---|---|
| guagaagccg aaacaaugu | 19 |

<210> SEQ ID NO 1315
<211> LENGTH: 19
<212> TYPE: RNA
<213> ORGANISM: Mus sp.

<400> SEQUENCE: 1315

| | |
|---|---|
| ggaguacccu gaagcuaua | 19 |

<210> SEQ ID NO 1316
<211> LENGTH: 19
<212> TYPE: RNA
<213> ORGANISM: Mus sp.

<400> SEQUENCE: 1316

| | |
|---|---|
| gaagaagagu ccuucaau | 19 |

<210> SEQ ID NO 1317
<211> LENGTH: 19
<212> TYPE: RNA
<213> ORGANISM: Mus sp.

<400> SEQUENCE: 1317

| | |
|---|---|
| uaugagaccu ucaagagua | 19 |

<210> SEQ ID NO 1318
<211> LENGTH: 19
<212> TYPE: RNA
<213> ORGANISM: Mus sp.

<400> SEQUENCE: 1318

| | |
|---|---|
| gaauccagac caacaauaa | 19 |

<210> SEQ ID NO 1319
<211> LENGTH: 19
<212> TYPE: RNA
<213> ORGANISM: Mus sp.

<400> SEQUENCE: 1319

| | |
|---|---|
| ugaguauagu ccagaacga | 19 |

<210> SEQ ID NO 1320
<211> LENGTH: 19
<212> TYPE: RNA
<213> ORGANISM: Mus sp.

<400> SEQUENCE: 1320

| | |
|---|---|
| caauggaagu cguccuagu | 19 |

<210> SEQ ID NO 1321
<211> LENGTH: 19
<212> TYPE: RNA
<213> ORGANISM: Mus sp.

<400> SEQUENCE: 1321

| | |
|---|---|
| gaguggaaca ucugcaaua | 19 |

<210> SEQ ID NO 1322
<211> LENGTH: 19
<212> TYPE: RNA
<213> ORGANISM: Mus sp.

```
<400> SEQUENCE: 1322
gcucaucagc uccauauuu                                                    19

<210> SEQ ID NO 1323
<211> LENGTH: 19
<212> TYPE: RNA
<213> ORGANISM: Mus sp.

<400> SEQUENCE: 1323
ugaccacccu ggcgagcua                                                    19

<210> SEQ ID NO 1324
<211> LENGTH: 19
<212> TYPE: RNA
<213> ORGANISM: Mus sp.

<400> SEQUENCE: 1324
gcaacucgcc caccaacau                                                    19

<210> SEQ ID NO 1325
<211> LENGTH: 19
<212> TYPE: RNA
<213> ORGANISM: Mus sp.

<400> SEQUENCE: 1325
gagcuucacu cugaccauc                                                    19

<210> SEQ ID NO 1326
<211> LENGTH: 19
<212> TYPE: RNA
<213> ORGANISM: Mus sp.

<400> SEQUENCE: 1326
acaaauccgc cacaaguug                                                    19

<210> SEQ ID NO 1327
<211> LENGTH: 19
<212> TYPE: RNA
<213> ORGANISM: Mus sp.

<400> SEQUENCE: 1327
caaaggauau gauggvuga                                                    19

<210> SEQ ID NO 1328
<211> LENGTH: 19
<212> TYPE: RNA
<213> ORGANISM: Mus sp.

<400> SEQUENCE: 1328
gaaacgagcc ggaaucuca                                                    19

<210> SEQ ID NO 1329
<211> LENGTH: 19
<212> TYPE: RNA
<213> ORGANISM: Mus sp.

<400> SEQUENCE: 1329
gaagggagca cagacguua                                                    19

<210> SEQ ID NO 1330
<211> LENGTH: 19
<212> TYPE: RNA
<213> ORGANISM: Mus sp.
```

-continued

```
<400> SEQUENCE: 1330
gcacgcggaa uuuguauug                                                    19

<210> SEQ ID NO 1331
<211> LENGTH: 19
<212> TYPE: RNA
<213> ORGANISM: Mus sp.

<400> SEQUENCE: 1331
gaccaucucu uguuucgug                                                    19

<210> SEQ ID NO 1332
<211> LENGTH: 19
<212> TYPE: RNA
<213> ORGANISM: Mus sp.

<400> SEQUENCE: 1332
ggaaagagau ugagcggcu                                                    19

<210> SEQ ID NO 1333
<211> LENGTH: 19
<212> TYPE: RNA
<213> ORGANISM: Mus sp.

<400> SEQUENCE: 1333
gcugguuccu ccaauaaga                                                    19

<210> SEQ ID NO 1334
<211> LENGTH: 19
<212> TYPE: RNA
<213> ORGANISM: Mus sp.

<400> SEQUENCE: 1334
ugaaggagaa guucgacua                                                    19

<210> SEQ ID NO 1335
<211> LENGTH: 19
<212> TYPE: RNA
<213> ORGANISM: Mus sp.

<400> SEQUENCE: 1335
gaaggacugu ugcagauag                                                    19

<210> SEQ ID NO 1336
<211> LENGTH: 19
<212> TYPE: RNA
<213> ORGANISM: Mus sp.

<400> SEQUENCE: 1336
gcaaaggagu gcaguugga                                                    19

<210> SEQ ID NO 1337
<211> LENGTH: 19
<212> TYPE: RNA
<213> ORGANISM: Mus sp.

<400> SEQUENCE: 1337
gaaguaggac ugcaccaua                                                    19

<210> SEQ ID NO 1338
<211> LENGTH: 19
<212> TYPE: RNA
```

```
<213> ORGANISM: Mus sp.

<400> SEQUENCE: 1338
aaagagcaau ugagaguuu                                              19

<210> SEQ ID NO 1339
<211> LENGTH: 19
<212> TYPE: RNA
<213> ORGANISM: Mus sp.

<400> SEQUENCE: 1339
ggucaacggu guccucaaa                                              19

<210> SEQ ID NO 1340
<211> LENGTH: 19
<212> TYPE: RNA
<213> ORGANISM: Mus sp.

<400> SEQUENCE: 1340
gauaauggcc uacaagaug                                              19

<210> SEQ ID NO 1341
<211> LENGTH: 19
<212> TYPE: RNA
<213> ORGANISM: Mus sp.

<400> SEQUENCE: 1341
gagcgaaugc ggaggcuua                                              19

<210> SEQ ID NO 1342
<211> LENGTH: 19
<212> TYPE: RNA
<213> ORGANISM: Mus sp.

<400> SEQUENCE: 1342
caacgggccu uuccucauc                                              19

<210> SEQ ID NO 1343
<211> LENGTH: 19
<212> TYPE: RNA
<213> ORGANISM: Mus sp.

<400> SEQUENCE: 1343
gcacagagau gcuucgaca                                              19

<210> SEQ ID NO 1344
<211> LENGTH: 19
<212> TYPE: RNA
<213> ORGANISM: Mus sp.

<400> SEQUENCE: 1344
ccacgggaau ccuaucuau                                              19

<210> SEQ ID NO 1345
<211> LENGTH: 19
<212> TYPE: RNA
<213> ORGANISM: Mus sp.

<400> SEQUENCE: 1345
agaauggcgu ggccugcua                                              19

<210> SEQ ID NO 1346
<211> LENGTH: 19
```

```
<212> TYPE: RNA
<213> ORGANISM: Mus sp.

<400> SEQUENCE: 1346
ugaggaauuc agcgauuua                                              19

<210> SEQ ID NO 1347
<211> LENGTH: 19
<212> TYPE: RNA
<213> ORGANISM: Mus sp.

<400> SEQUENCE: 1347
ggacaacagc agauuauua                                              19

<210> SEQ ID NO 1348
<211> LENGTH: 19
<212> TYPE: RNA
<213> ORGANISM: Mus sp.

<400> SEQUENCE: 1348
gacaauaggu gcuguuagu                                              19

<210> SEQ ID NO 1349
<211> LENGTH: 19
<212> TYPE: RNA
<213> ORGANISM: Mus sp.

<400> SEQUENCE: 1349
aauuagaccu ggcguuuca                                              19

<210> SEQ ID NO 1350
<211> LENGTH: 19
<212> TYPE: RNA
<213> ORGANISM: Mus sp.

<400> SEQUENCE: 1350
ggaguuccag uaacaauca                                              19

<210> SEQ ID NO 1351
<211> LENGTH: 19
<212> TYPE: RNA
<213> ORGANISM: Mus sp.

<400> SEQUENCE: 1351
gcaaauagca cccagcaac                                              19

<210> SEQ ID NO 1352
<211> LENGTH: 19
<212> TYPE: RNA
<213> ORGANISM: Mus sp.

<400> SEQUENCE: 1352
caaacgagcg gcagagaug                                              19

<210> SEQ ID NO 1353
<211> LENGTH: 19
<212> TYPE: RNA
<213> ORGANISM: Mus sp.

<400> SEQUENCE: 1353
ucagugaucu gccauacca                                              19

<210> SEQ ID NO 1354
```

```
<211> LENGTH: 19
<212> TYPE: RNA
<213> ORGANISM: Mus sp.

<400> SEQUENCE: 1354
gccaagauuu cagaagcua                                                 19

<210> SEQ ID NO 1355
<211> LENGTH: 19
<212> TYPE: RNA
<213> ORGANISM: Mus sp.

<400> SEQUENCE: 1355
aaacugaccu gucgagacu                                                 19

<210> SEQ ID NO 1356
<211> LENGTH: 19
<212> TYPE: RNA
<213> ORGANISM: Mus sp.

<400> SEQUENCE: 1356
ccaauacguu caccuagug                                                 19

<210> SEQ ID NO 1357
<211> LENGTH: 19
<212> TYPE: RNA
<213> ORGANISM: Mus sp.

<400> SEQUENCE: 1357
gaucagccua gcucaguua                                                 19

<210> SEQ ID NO 1358
<211> LENGTH: 19
<212> TYPE: RNA
<213> ORGANISM: Mus sp.

<400> SEQUENCE: 1358
gcaagcggcu gauuacaua                                                 19

<210> SEQ ID NO 1359
<211> LENGTH: 19
<212> TYPE: RNA
<213> ORGANISM: Mus sp.

<400> SEQUENCE: 1359 gcaauggcg gauauguau                                                  19

<210> SEQ ID NO 1360
<211> LENGTH: 19
<212> TYPE: RNA
<213> ORGANISM: Mus sp.

<400> SEQUENCE: 1360
gcgagcagau uauuagaag                                                 19

<210> SEQ ID NO 1361
<211> LENGTH: 19
<212> TYPE: RNA
<213> ORGANISM: Mus sp.

<400> SEQUENCE: 1361
cuacgguucu ggaguaaau                                                 19
```

-continued

```
<210> SEQ ID NO 1362
<211> LENGTH: 19
<212> TYPE: RNA
<213> ORGANISM: Mus sp.

<400> SEQUENCE: 1362
gaaguucgag agucaaaca                                                  19

<210> SEQ ID NO 1363
<211> LENGTH: 19
<212> TYPE: RNA
<213> ORGANISM: Mus sp.

<400> SEQUENCE: 1363
gugagcugcu ugagaagaa                                                  19

<210> SEQ ID NO 1364
<211> LENGTH: 19
<212> TYPE: RNA
<213> ORGANISM: Mus sp.

<400> SEQUENCE: 1364
cuguacgacu ccaggauuu                                                  19

<210> SEQ ID NO 1365
<211> LENGTH: 19
<212> TYPE: RNA
<213> ORGANISM: Mus sp.

<400> SEQUENCE: 1365
cuauauagcc auaaugcgu                                                  19

<210> SEQ ID NO 1366
<211> LENGTH: 19
<212> TYPE: RNA
<213> ORGANISM: Mus sp.

<400> SEQUENCE: 1366
cagugagccu gucguguca                                                  19

<210> SEQ ID NO 1367
<211> LENGTH: 19
<212> TYPE: RNA
<213> ORGANISM: Mus sp.

<400> SEQUENCE: 1367
cagaaucgau ggaguccca                                                  19

<210> SEQ ID NO 1368
<211> LENGTH: 19
<212> TYPE: RNA
<213> ORGANISM: Mus sp.

<400> SEQUENCE: 1368
gaugguagca uauguuuag                                                  19

<210> SEQ ID NO 1369
<211> LENGTH: 19
<212> TYPE: RNA
<213> ORGANISM: Mus sp.

<400> SEQUENCE: 1369
ggaaugcagu uauauuugg                                                  19
```

```
<210> SEQ ID NO 1370
<211> LENGTH: 19
<212> TYPE: RNA
<213> ORGANISM: Mus sp.

<400> SEQUENCE: 1370
gaagagaguu ucggccauu                                                    19

<210> SEQ ID NO 1371
<211> LENGTH: 19
<212> TYPE: RNA
<213> ORGANISM: Mus sp.

<400> SEQUENCE: 1371
ggacuugccu gcuggcuac                                                    19

<210> SEQ ID NO 1372
<211> LENGTH: 19
<212> TYPE: RNA
<213> ORGANISM: Mus sp.

<400> SEQUENCE: 1372
ugacacaggu agcgcgagu                                                    19

<210> SEQ ID NO 1373
<211> LENGTH: 19
<212> TYPE: RNA
<213> ORGANISM: Mus sp.

<400> SEQUENCE: 1373
cuacagcaga cuagaacaa                                                    19

<210> SEQ ID NO 1374
<211> LENGTH: 19
<212> TYPE: RNA
<213> ORGANISM: Mus sp.

<400> SEQUENCE: 1374
gcacugaguu ggcccgaca                                                    19

<210> SEQ ID NO 1375
<211> LENGTH: 19
<212> TYPE: RNA
<213> ORGANISM: Mus sp.

<400> SEQUENCE: 1375
ucucaaaccu gcuuucauc                                                    19

<210> SEQ ID NO 1376
<211> LENGTH: 19
<212> TYPE: RNA
<213> ORGANISM: Mus sp.

<400> SEQUENCE: 1376
gagucaaacu aacguggua                                                    19

<210> SEQ ID NO 1377
<211> LENGTH: 19
<212> TYPE: RNA
<213> ORGANISM: Mus sp.

<400> SEQUENCE: 1377
ggaucacccu gaauucauu                                                    19
```

<210> SEQ ID NO 1378
<211> LENGTH: 19
<212> TYPE: RNA
<213> ORGANISM: Mus sp.

<400> SEQUENCE: 1378
ugacaugucu ucuccacuu                                            19

<210> SEQ ID NO 1379
<211> LENGTH: 19
<212> TYPE: RNA
<213> ORGANISM: Mus sp.

<400> SEQUENCE: 1379
gaacccagcu ugaacguca                                            19

<210> SEQ ID NO 1380
<211> LENGTH: 19
<212> TYPE: RNA
<213> ORGANISM: Mus sp.

<400> SEQUENCE: 1380
gaaagagcac uuacggauu                                            19

<210> SEQ ID NO 1381
<211> LENGTH: 19
<212> TYPE: RNA
<213> ORGANISM: Mus sp.

<400> SEQUENCE: 1381
gguuugguau cucccauaa                                            19

<210> SEQ ID NO 1382
<211> LENGTH: 19
<212> TYPE: RNA
<213> ORGANISM: Mus sp.

<400> SEQUENCE: 1382
gaaguguauu agcuugaug                                            19

<210> SEQ ID NO 1383
<211> LENGTH: 19
<212> TYPE: RNA
<213> ORGANISM: Mus sp.

<400> SEQUENCE: 1383
ccuccgcucu gacauauuu                                            19

<210> SEQ ID NO 1384
<211> LENGTH: 19
<212> TYPE: RNA
<213> ORGANISM: Mus sp.

<400> SEQUENCE: 1384
gauucucggu auccgguuu                                            19

<210> SEQ ID NO 1385
<211> LENGTH: 19
<212> TYPE: RNA
<213> ORGANISM: Mus sp.

<400> SEQUENCE: 1385
ccgccaagau uuccgugaa 19

<210> SEQ ID NO 1386
<211> LENGTH: 19
<212> TYPE: RNA
<213> ORGANISM: Mus sp.

<400> SEQUENCE: 1386
aaagaccauu ugcguguca 19

<210> SEQ ID NO 1387
<211> LENGTH: 19
<212> TYPE: RNA
<213> ORGANISM: Mus sp.

<400> SEQUENCE: 1387
gcaccaccgc gauguauua 19

<210> SEQ ID NO 1388
<211> LENGTH: 19
<212> TYPE: RNA
<213> ORGANISM: Mus sp.

<400> SEQUENCE: 1388
gaacaacgua ccagauuga 19

<210> SEQ ID NO 1389
<211> LENGTH: 19
<212> TYPE: RNA
<213> ORGANISM: Mus sp.

<400> SEQUENCE: 1389
aagcaaggcc cgauaagua 19

<210> SEQ ID NO 1390
<211> LENGTH: 19
<212> TYPE: RNA
<213> ORGANISM: Mus sp.

<400> SEQUENCE: 1390
gaucaguacu cuggcaaau 19

<210> SEQ ID NO 1391
<211> LENGTH: 19
<212> TYPE: RNA
<213> ORGANISM: Mus sp.

<400> SEQUENCE: 1391
ucaagacgcc ugcccauuu 19

<210> SEQ ID NO 1392
<211> LENGTH: 19
<212> TYPE: RNA
<213> ORGANISM: Mus sp.

<400> SEQUENCE: 1392
ucagcagccu uaaggguga 19

<210> SEQ ID NO 1393
<211> LENGTH: 19
<212> TYPE: RNA
<213> ORGANISM: Mus sp.

<400> SEQUENCE: 1393

```
ggagcuggcg agccucuuu                                                    19

<210> SEQ ID NO 1394
<211> LENGTH: 19
<212> TYPE: RNA
<213> ORGANISM: Mus sp.

<400> SEQUENCE: 1394
cgaauccccu cacauguuu                                                    19
```

T CELL BALANCE GENE EXPRESSION, COMPOSITIONS OF MATTERS AND METHODS OF USE THEREOF

RELATED APPLICATIONS AND INCORPORATION BY REFERENCE

This application is a continuation-in-part application of international patent application Serial No. PCT/US2014/019127 filed Feb. 27, 2014, which published as PCT Publication No. WO 2014/134351 on Sep. 4, 2014, which claims benefit of and priority to U.S. Provisional Application No. 61/770,036, filed Feb. 27, 2013.

The foregoing applications, and all documents cited therein or during their prosecution ("appin cited documents") and all documents cited or referenced in the appin cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FEDERAL FUNDING LEGEND

This invention was made with government support under Grant Nos. OD003958, HG006193, NS030843, NS045937, AI073748, AI045757, AI056299, OD003893 and HG005062 awarded by the National Institutes of Health. The government has certain rights in the invention.

FIELD OF THE INVENTION

This invention relates generally to compositions and methods for identifying the regulatory network that modulates, controls or otherwise influences T cell balance, for example, Th17 cell differentiation, maintenance and/or function, as well compositions and methods for exploiting the regulatory network that modulates, controls or otherwise influences T cell balance in a variety of therapeutic and/or diagnostic indications. This invention also relates generally to identifying and exploiting target genes and/or target gene products that modulate, control or otherwise influence T cell balance in a variety of therapeutic and/or diagnostic indications.

BACKGROUND OF THE INVENTION

Despite their importance, the molecular circuits that control the balance of T cells, including the differentiation of naïve T cells, remain largely unknown. Recent studies that reconstructed regulatory networks in mammalian cells have focused on short-term responses and relied on perturbation-based approaches that cannot be readily applied to primary T cells. Accordingly, there exists a need for a better understanding of the dynamic regulatory network that modulates, controls, or otherwise influences T cell balance, including Th17 cell differentiation, maintenance and function, and means for exploiting this network in a variety of therapeutic and diagnostic methods.

Citation or identification of any document in this application is not an admission that such document is available as prior art to the present invention.

SUMMARY OF THE INVENTION

The invention provides compositions and methods for modulating T cell balance. As used herein, the term "modulating" includes up-regulation of, or otherwise increasing, the expression of one or more genes, down-regulation of, or otherwise decreasing, the expression of one or more genes, inhibiting or otherwise decreasing the expression, activity and/or function of one or more gene products, and/or enhancing or otherwise increasing the expression, activity and/or function of one or more gene products.

As used herein, the term "modulating T cell balance" includes the modulation of any of a variety of T cell-related functions and/or activities, including by way of non-limiting example, controlling or otherwise influencing the networks that regulate T cell differentiation; controlling or otherwise influencing the networks that regulate T cell maintenance, for example, over the lifespan of a T cell; controlling or otherwise influencing the networks that regulate T cell function; controlling or otherwise influencing the networks that regulate helper T cell (Th cell) differentiation; controlling or otherwise influencing the networks that regulate Th cell maintenance, for example, over the lifespan of a Th cell; controlling or otherwise influencing the networks that regulate Th cell function; controlling or otherwise influencing the networks that regulate Th17 cell differentiation; controlling or otherwise influencing the networks that regulate Th17 cell maintenance, for example, over the lifespan of a Th17 cell; controlling or otherwise influencing the networks that regulate Th17 cell function; controlling or otherwise influencing the networks that regulate regulatory T cell (Treg) differentiation; controlling or otherwise influencing the networks that regulate Treg cell maintenance, for example, over the lifespan of a Treg cell; controlling or otherwise influencing the networks that regulate Treg cell function; controlling or otherwise influencing the networks that regulate other CD4+ T cell differentiation; controlling or otherwise influencing the networks that regulate other CD4+ T cell maintenance; controlling or otherwise influencing the networks that regulate other CD4+ T cell function; manipulating or otherwise influencing the ratio of T cells such as, for example, manipulating or otherwise influencing the ratio of Th17 cells to other T cell types such as Tregs or other CD4+ T cells; manipulating or otherwise influencing the ratio of different types of Th17 cells such as, for example, pathogenic Th17 cells and non-pathogenic Th17 cells; manipulating or otherwise influencing at least one function or biological activity of a T cell; manipulating or otherwise influencing at least one function or biological activity of Th cell; manipulating or otherwise influencing at least one function or biological activity of a Treg cell; manipulating or otherwise influencing at least one function or biological activity of a Th17 cell; and/or manipulating or otherwise influencing at least one function or biological activity of another CD4+ T cell.

The invention provides T cell modulating agents that modulate T cell balance. For example, in some embodiments, the invention provides T cell modulating agents and methods of using these T cell modulating agents to regulate, influence or otherwise impact the level(s) of and/or balance between T cell types, e.g., between Th17 and other T cell types, for example, regulatory T cells (Tregs), and/or Th17 activity and inflammatory potential. As used herein, terms such as "Th17 cell" and/or "Th17 phenotype" and all grammatical variations thereof refer to a differentiated T helper cell that expresses one or more cytokines selected from the group the consisting of interleukin 17A (IL-17A), interleukin 17F (IL-17F), and interleukin 17A/F heterodimer (IL17-AF). As used herein, terms such as "Th1 cell" and/or "Th1 phenotype" and all grammatical variations thereof refer to a differentiated T helper cell that expresses interferon gamma (IFNγ). As used herein, terms such as "Th2 cell" and/or "Th2 phenotype" and all grammatical variations thereof refer to a differentiated T helper cell that expresses one or more cytokines selected from the group the consisting of interleukin 4 (IL-4), interleukin 5 (IL-5) and interleukin 13 (IL-13). As used herein, terms such as "Treg cell" and/or "Treg phenotype" and all grammatical variations thereof refer to a differentiated T cell that expresses Foxp3.

For example, in some embodiments, the invention provides T cell modulating agents and methods of using these T cell modulating agents to regulate, influence or otherwise impact the level of and/or balance between Th17 phenotypes, and/or Th17 activity and inflammatory potential. Suitable T cell modulating agents include an antibody, a soluble polypeptide, a polypeptide agent, a peptide agent, a nucleic acid agent, a nucleic acid ligand, or a small molecule agent.

For example, in some embodiments, the invention provides T cell modulating agents and methods of using these T cell modulating agents to regulate, influence or otherwise impact the level of and/or balance between Th17 cell types, e.g., between pathogenic and non-pathogenic Th17 cells. For example, in some embodiments, the invention provides T cell modulating agents and methods of using these T cell modulating agents to regulate, influence or otherwise impact the level of and/or balance between pathogenic and non-pathogenic Th17 activity.

For example, in some embodiments, the invention provides T cell modulating agents and methods of using these T cell modulating agents to influence or otherwise impact the differentiation of a population of T cells, for example toward Th17 cells, with or without a specific pathogenic distinction, or away from Th17 cells, with or without a specific pathogenic distinction.

For example, in some embodiments, the invention provides T cell modulating agents and methods of using these T cell modulating agents to influence or otherwise impact the differentiation of a population of T cells, for example toward a non-Th17 T cell subset or away from a non-Th17 cell subset. For example, in some embodiments, the invention provides T cell modulating agents and methods of using these T cell modulating agents to induce T-cell plasticity, i.e., converting Th17 cells into a different subtype, or into a new state.

For example, in some embodiments, the invention provides T cell modulating agents and methods of using these T cell modulating agents to induce T cell plasticity, e.g., converting Th17 cells into a different subtype, or into a new state.

For example, in some embodiments, the invention provides T cell modulating agents and methods of using these T cell modulating agents to achieve any combination of the above.

In some embodiments, the T cells are naïve T cells. In some embodiments, the T cells are differentiated T cells. In some embodiments, the T cells are partially differentiated T cells. In some embodiments, the T cells are a mixture of naïve T cells and differentiated T cells. In some embodiments, the T cells are mixture of naïve T cells and partially differentiated T cells. In some embodiments, the T cells are mixture of partially differentiated T cells and differentiated T cells. In some embodiments, the T cells are mixture of naïve T cells, partially differentiated T cells, and differentiated T cells.

The T cell modulating agents are used to modulate the expression of one or more target genes or one or more products of one or more target genes that have been identified as genes responsive to Th17-related perturbations. These target genes are identified, for example, by contacting a T cell, e.g., naïve T cells, partially differentiated T cells, differentiated T cells and/or combinations thereof, with a T cell modulating agent and monitoring the effect, if any, on the expression of one or more signature genes or one or more products of one or more signature genes. In some embodiments, the one or more signature genes are selected from those listed in Table 1 or Table 2 of the specification.

In some embodiments, the target gene is one or more Th17-associated cytokine(s) or receptor molecule(s) selected from those listed in Table 3 of the specification. In some embodiments, the target gene is one or more Th17-associated transcription regulator(s) selected from those shown in Table 4 of the specification.

In some embodiments, the target gene is one or more Th17-associated transcription regulator(s) selected from those shown in Table 5 of the specification. In some embodiments, the target gene is one or more Th17-associated receptor molecule(s) selected from those listed in Table 6 of the specification. In some embodiments, the target gene is one or more Th17-associated kinase(s) selected from those listed in Table 7 of the specification. In some embodiments, the target gene is one or more Th17-associated signaling molecule(s) selected from those listed in Table 8 of the specification. In some embodiments, the target gene is one or more Th17-associated receptor molecule(s) selected from those listed in Table 9 of the specification.

In some embodiments, the target gene is one or more target genes involved in induction of Th17 differentiation such as, for example, IRF1, IRF8, IRF9, STAT2, STAT3, IRF7, STAT1, ZFP281, IFI35, REL, TBX21, FLI1, BATF, IRF4, one or more of the target genes listed in Table 5 as being associated with the early stage of Th17 differentiation, maintenance and/or function, e.g., AES, AHR, ARID5A, BATF, BCL11B, BCL3, CBFB, CBX4, CHD7, CITED2, CREB1, E2F4, EGR1, EGR2, ELL2, ETS1, ETS2, ETV6, EZH1, FLI1, FOXO1, GATA3, GATAD2B, HIF1A, ID2, IFI35, IKZF4, IRF1, IRF2, IRF3, IRF4, IRF7, IRF9, JMJD1C, JUN, LEF1, LRRFIP1, MAX, NCOA3, NFE2L2, NFIL3, NFKB1, NMI, NOTCH1, NR3C1, PHF21A, PML, PRDM1, REL, RELA, RUNX1, SAP18, SATB1, SMAD2, SMARCA4, SP100, SP4, STAT1, STAT2, STAT3, STAT4, STAT5B, STAT6, TFEB, TP53, TRIM24, and/or ZFP161, or any combination thereof.

In some embodiments, the target gene is one or more target genes involved in onset of Th17 phenotype and amplification of Th17 T cells such as, for example, IRF8, STAT2, STAT3, IRF7, JUN, STAT5B, ZPF2981, CHD7, TBX21, FLI1, SATB1, RUNX1, BATF, RORC, SP4, one or more of the target genes listed in Table 5 as being associated with the intermediate stage of Th17 differentiation, maintenance and/or function, e.g., AES, AHR, ARID3A, ARID5A, ARNTL, ASXL1, BATF, BCL11B, BCL3, BCL6, CBFB, CBX4, CDC5L, CEBPB, CHD7, CREB1, CREB3L2, CREM, E2F4, E2F8, EGR1, EGR2, ELK3, ELL2, ETS1, ETS2, ETV6, EZH1, FLI1, FOSL2, FOXJ2, FOXO1, FUS, HIF1A, HMGB2, ID1, ID2, IFI35, IKZF4, IRF3, IRF4, IRF7, IRF8, IRF9, JUN, JUNB, KAT2B, KLF10, KLF6, KLF9, LEF1, LRRFIP1, MAFF, MAX, MAZ, MINA, MTA3, MYC, MYST4, NCOA1, NCOA3, NFE2L2, NFIL3, NFKB1, NMI, NOTCH1, NR3C1, PHF21A, PML, POU2AF1, POU2F2, PRDM1, RARA, RBPJ, RELA, RORA, RUNX1, SAP18, SATB1, SKI, SKIL, SMAD2, SMAD7, SMARCA4, SMOX, SP1, SP4, SS18, STAT1, STAT2, STAT3, STAT5A, STATSB, STAT6, SUZ12, TBX21, TFEB, TLE1, TP53, TRIM24, TRIM28, TRPS1, VAV1, ZEB1, ZEB2, ZFP161, ZFP62, ZNF238, ZNF281, and/or ZNF703, or any combination thereof.

In some embodiments, the target gene is one or more target genes involved in stabilization of Th17 cells and/or modulating Th17-associated interleukin 23 (IL-23) signaling such as, for example, STAT2, STAT3, JUN, STATSB, CHD7, SATB1, RUNX1, BATF, RORC, SP4 IRF4, one or more of the target genes listed in Table 5 as being associated with the late stage of Th17 differentiation, maintenance and/or function, e.g., AES, AHR, ARID3A, ARID5A, ARNTL, ASXL1, ATF3, ATF4, BATF, BATF3, BCL11B, BCL3, BCL6, C210RF66, CBFB, CBX4, CDC5L, CDYL, CEBPB, CHD7, CHMP1B, CIC, CITED2, CREB1, CREB3L2, CREM, CSDA, DDIT3, E2F1, E2F4, E2F8, EGR1, EGR2, ELK3, ELL2, ETS1, ETS2, EZH1, FLI1, FOSL2, FOXJ2, FOXO1, FUS, GATA3, GATAD2B, HCLS1, HIF1A, ID1, ID2, IFI35, IKZF4, IRF3, IRF4, IRF7, IRF8, IRF9, JARID2, JMJD1C, JUN, JUNB, KAT2B, KLF10, KLF6, KLF7, KLF9, LASS4, LEF1, LRRFIP1, MAFF, MAX, MEN1, MINA, MTA3, MXI1, MYC, MYST4, NCOA1, NCOA3, NFE2L2, NFIL3, NFKB1, NMI, NOTCH1, NR3C1, PHF13, PHF21A, PML, POU2AF1, POU2F2, PRDM1, RARA, RBPJ, REL, RELA, RNF11, RORA, RORC, RUNX1, RUNX2, SAP18, SAP30, SATB1, SERTAD1, SIRT2, SKI, SKIL, SMAD2, SMAD4, SMAD7, SMARCA4, SMOX, SP1, SP100, SP4, SS18, STAT1, STAT3, STAT4, STAT5A, STATSB, STAT6, SUZ12, TBX21, TFEB, TGIF1, TLE1, TP53, TRIM24, TRPS1, TSC22D3, UBE2B, VAV1, VAX2, XBP1, ZEB1, ZEB2, ZFP161, ZFP36L1, ZFP36L2, ZNF238, ZNF281, ZNF703, ZNRF1, and/or ZNRF2, or any combination thereof.

In some embodiments, the target gene is one or more of the target genes listed in Table 6 as being associated with the early stage of Th17 differentiation, maintenance and/or function, e.g., FAS, CCR5, IL6ST, IL17RA, IL2RA, MYD88, CXCR5, PVR, IL15RA, IL12RB1, or any combination thereof.

In some embodiments, the target gene is one or more of the target genes listed in Table 6 as being associated with the intermediate stage of Th17 differentiation, maintenance and/or function, e.g., IL7R, ITGA3, IL1R1, CCR5, CCR6, ACVR2A, IL6ST, IL17RA, CCR5, DDR1, PROCR, IL2RA, IL12RB2, MYD88, PTPRJ, TNFRSF13B, CXCR3, IL1RN, CXCR5, CCR4, IL4R, IL2RB, TNFRSF12A, CXCR4, KLRD1, IRAK1BP1, PVR, IL12RB1, IL18R1, TRAF3, or any combination thereof.

In some embodiments, the target gene is one or more of the target genes listed in Table 6 as being associated with the late stage of Th17 differentiation, maintenance and/or function, e.g., IL7R, ITGA3, IL1R1, FAS, CCR5, CCR6, ACVR2A, IL6ST, IL17RA, DDR1, PROCR, IL2RA, IL12RB2, MYD88, BMPR1A, PTPRJ, TNFRSF13B, CXCR3, IL1RN, CXCR5, CCR4, IL4R, IL2RB, TNFRSF12A, CXCR4, KLRD1, IRAK1BP1, PVR, IL15RA, TLR1, ACVR1B, IL12RB1, IL18R1, TRAF3, IFNGR1, PLAUR, IL21R, IL23R, or any combination thereof.

In some embodiments, the target gene is one or more of the target genes listed in Table 7 as being associated with the early stage of Th17 differentiation, maintenance and/or function, e.g., EIF2AK2, DUSP22, HK2, RIPK1, RNASEL, TEC, MAP3K8, SGK1, PRKCQ, DUSP16, BMP2K, PIM2, or any combination thereof.

In some embodiments, the target gene is one or more of the target genes listed in Table 7 as being associated with the intermediate stage of Th17 differentiation, maintenance and/or function, e.g., PSTPIP1, PTPN1, ACP5, TXK, RIPK3, PTPRF, NEK4, PPME1, PHACTR2, HK2, GMFG, DAPP1, TEC, GMFB, PIM1, NEK6, ACVR2A, FES, CDK6, ZAK, DUSP14, SGK1, JAK3, ULK2, PTPRJ, SPHK1, TNK2, PCTK1, MAP4K3, TGFBR1, HK1, DDR1, BMP2K, DUSP10, ALPK2, or any combination thereof.

In some embodiments, the target gene is one or more of the target genes listed in Table 7 as being associated with the late stage of Th17 differentiation, maintenance and/or function, e.g., PTPLA, PSTPIP1, TK1, PTEN, BPGM, DCK, PTPRS, PTPN18, MKNK2, PTPN1, PTPRE, SH2D1A, PLK2, DUSP6, CDC25B, SLK, MAP3K5, BMPR1A, ACP5, TXK, RIPK3, PPP3CA, PTPRF, PACSIN1, NEK4, PIP4K2A, PPME1, SRPK2, DUSP2, PHACTR2, DCLK1, PPP2R5A, RIPK1, GK, RNASEL, GMFG, STK4, HINT3, DAPP1, TEC, GMFB, PTPN6, RIPK2, PIM1, NEK6, ACVR2A, AURKB, FES, ACVR1B, CDK6, ZAK, VRK2, MAP3K8, DUSP14, SGK1, PRKCQ, JAK3, ULK2, HIPK2, PTPRJ, INPP1, TNK2, PCTK1, DUSP1, NUDT4, TGFBR1, PTP4A1, HK1, DUSP16, ANP32A, DDR1, ITK, WNK1, NAGK, STK38, BMP2K, BUB1, AAK1, SIK1, DUSP10, PRKCA, PIM2, STK17B, TK2, STK39, ALPK2, MST4, PHLPP1, or any combination thereof.

In some embodiments, the target gene is one or more of the target genes listed in Table 8 as being associated with the early stage of Th17 differentiation, maintenance and/or function, e.g., HK2, CDKN1A, DUT, DUSP1, NADK, LIMK2, DUSP11, TAOK3, PRPS1, PPP2R4, MKNK2, SGK1, BPGM, TEC, MAPK6, PTP4A2, PRPF4B, ACP1, CCRN4L, or any combination thereof.

In some embodiments, the target gene is one or more of the target genes listed in Table 8 as being associated with the intermediate stage of Th17 differentiation, maintenance and/or function, e.g., HK2, ZAP70, NEK6, DUSP14, SH2D1A, ITK, DUT, PPP1R11, DUSP1, PMVK, TK1, TAOK3, GMFG, PRPS1, SGK1, TXK, WNK1, DUSP19, TEC, RPS6KA1, PKM2, PRPF4B, ADRBK1, CKB, ULK2, PLK1, PPP2R5A, PLK2, or any combination thereof.

In some embodiments, the target gene is one or more of the target genes listed in Table 8 as being associated with the late stage of Th17 differentiation, maintenance and/or function, e.g., ZAP70, PFKP, NEK6, DUSP14, SH2D1A, INPP5B, ITK, PFKL, PGK1, CDKN1A, DUT, PPP1R11, DUSP1, PMVK, PTPN22, PSPH, TK1, PGAM1, LIMK2, CLK1, DUSP11, TAOK3, RIOK2, GMFG, UCKL1, PRPS1, PPP2R4, MKNK2, DGKA, SGK1, TXK, WNK1, DUSP19, CHP, BPGM, PIP5K1A, TEC, MAP2K1, MAPK6, RPS6KA1, PTP4A2, PKM2, PRPF4B, ADRBK1, CKB, ACP1, ULK2, CCRN4L, PRKCH, PLK1, PPP2R5A, PLK2, or any combination thereof.

In some embodiments, the target gene is one or more of the target genes listed in Table 9 as being associated with the early stage of Th17 differentiation, maintenance and/or function, e.g., CD200, CD40LG, CD24, CCND2, ADAM17, BSG, ITGAL, FAS, GPR65, SIGMAR1, CAP1, PLAUR, SRPRB, TRPV2, IL2RA, KDELR2, TNFRSF9, or any combination thereof.

In some embodiments, the target gene is one or more of the target genes listed in Table 9 as being associated with the intermediate stage of Th17 differentiation, maintenance and/or function, e.g., CTLA4, CD200, CD24, CD6L, CD9, IL2RB, CD53, CD74, CAST, CCR6, IL2RG, ITGAV, FAS, IL4R, PROCR, GPR65, TNFRSF18, RORA, IL1RN, RORC, CYSLTR1, PNRC2, LOC390243, ADAM10, TNFSF9, CD96, CD82, SLAMF7, CD27, PGRMC1, TRPV2, ADRBK1, TRAF6, IL2RA, THY1, IL12RB2, TNFRSF9, or any combination thereof.

In some embodiments, the target gene is one or more of the target genes listed in Table 9 as being associated with the late stage of Th17 differentiation, maintenance and/or function, e.g., CTLA4, TNFRSF4, CD44, PDCD1, CD200, CD247, CD24, CD6L, CCND2, CD9, IL2RB, CD53, CD74, ADAM17, BSG, CAST, CCR6, IL2RG, CD81, CD6, CD48, ITGAV, TFRC, ICAM2, ATP1B3, FAS, IL4R, CCR7, CD52, PROCR, GPR65, TNFRSF18, FCRL1, RORA, IL1RN, RORC, P2RX4, SSR2, PTPN22, SIGMAR1, CYSLTR1, LOC390243, ADAM10, TNFSF9, CD96, CAP1, CD82, SLAMF7, PLAUR, CD27, SIVA1, PGRMC1, SRPRB, TRPV2, NR1H2, ADRBK1, GABARAPL1, TRAF6, IL2RA, THY1, KDELR2, IL12RB2, TNFRSF9, SCARB1, IFNGR1, or any combination thereof.

The desired gene or combination of target genes is selected, and after determining whether the selected target gene(s) is overexpressed or under-expressed during Th17 differentiation and/or Th17 maintenance, a suitable antagonist or agonist is used depending on the desired differentiation, maintenance and/or function outcome. For example, for target genes that are identified as positive regulators of Th17 differentiation, use of an antagonist that interacts with those target genes will shift differentiation away from the Th17 phenotype, while use of an agonist that interacts with those target genes will shift differentiation toward the Th17 phenotype. For target genes that are identified as negative regulators of Th17 differentiation, use of an antagonist that interacts with those target genes will shift differentiation toward from the Th17 phenotype, while use of an agonist that interacts with those target genes will shift differentiation away the Th17 phenotype. For example, for target genes that are identified as positive regulators of Th17 maintenance, use of an antagonist that interacts with those target genes will reduce the number of cells with the Th17 phenotype, while use of an agonist that interacts with those target genes will increase the number of cells with the Th17 phenotype. For target genes that are identified as negative regulators of Th17 differentiation, use of an antagonist that interacts with those target genes will increase the number of cells with the Th17 phenotype, while use of an agonist that interacts with those target genes will reduce the number of cells with the Th17 phenotype. Suitable T cell modulating agents include an antibody, a soluble polypeptide, a polypeptide agent, a peptide agent, a nucleic acid agent, a nucleic acid ligand, or a small molecule agent.

In some embodiments, the positive regulator of Th17 differentiation is a target gene selected from MINA, TRPS1, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, ITGA3, and combinations thereof. In some embodiments, the positive regulator of Th17 differentiation is a target gene selected from MINA, PML, POU2AF1, PROCR, SMARCA4, ZEB1, EGR2, CCR6, FAS and combinations thereof.

In some embodiments, the negative regulator of Th17 differentiation is a target gene selected from SP4, ETS2, IKZF4, TSC22D3, IRF1 and combinations thereof. In some embodiments, the negative regulator of Th17 differentiation is a target gene selected from SP4, IKZF4, TSC22D3 and combinations thereof.

In some embodiments, the T cell modulating agent is a soluble Fas polypeptide or a polypeptide derived from FAS. In some embodiments, the T cell modulating agent is an agent that enhances or otherwise increases the expression, activity, and/or function of FAS in Th17 cells. As shown herein, expression of FAS in T cell populations induced or otherwise influenced differentiation toward Th17 cells. In some embodiments, these T cell modulating agents are useful in the treatment of an immune response, for example, an autoimmune response or an inflammatory response. In some embodiments, these T cell modulating agents are useful in the treatment of an infectious disease or other pathogen-based disorders. In some embodiments, the T cell modulating agent is an antibody, a soluble polypeptide, a polypeptide agonist, a peptide agonist, a nucleic acid agonist, a nucleic acid ligand, or a small molecule agonist. In some embodiments, the T cells are naïve T cells. In some embodiments, the T cells are differentiated T cells. In some embodiments, the T cells are partially differentiated T cells. In some embodiments, the T cells are a mixture of naïve T cells and differentiated T cells. In some embodiments, the T cells are mixture of naïve T cells and partially differentiated T cells. In some embodiments, the T cells are mixture of partially differentiated T cells and differentiated T cells. In some embodiments, the T cells are mixture of naïve T cells, partially differentiated T cells, and differentiated T cells.

In some embodiments, the T cell modulating agent is an agent that inhibits the expression, activity and/or function of FAS. Inhibition of FAS expression, activity and/or function in T cell populations repressed or otherwise influenced differentiation away from Th17 cells and/or induced or otherwise influenced differentiation toward regulatory T cells (Tregs) and towards Th1 cells. In some embodiments, these T cell modulating agents are useful in the treatment of an immune response, for example, an autoimmune response or an inflammatory response. In some embodiments, these T cell modulating agents are useful in the treatment of autoimmune diseases such as psoriasis, inflammatory bowel disease (IBD), ankylosing spondylitis, multiple sclerosis, Sjögren's syndrome, uveitis, and rheumatoid arthritis, asthma, systemic lupus erythematosus, transplant rejection including allograft rejection, and combinations thereof. In addition, enhancement of Th17 cells is also useful for clearing fungal infections and extracellular pathogens. In some embodiments, the T cell modulating agent is an antibody, a soluble polypeptide, a polypeptide antagonist, a peptide antagonist, a nucleic acid antagonist, a nucleic acid ligand, or a small molecule antagonist. In some embodiments, the T cells are naïve T cells. In some embodiments, the T cells are differentiated T cells. In some embodiments, the T cells are partially differentiated T cells that express additional cytokines. In some embodiments, the T cells are a mixture of naïve T cells and differentiated T cells. In some embodiments, the T cells are mixture of naïve T cells and partially differentiated T cells. In some embodiments, the T cells are mixture of partially differentiated T cells and differentiated T cells. In some embodiments, the T cells are mixture of naïve T cells, partially differentiated T cells, and differentiated T cells.

In some embodiments, the T cell modulating agent is an agent that inhibits the expression, activity and/or function of CCR5. Inhibition of CCR5 expression, activity and/or function in T cell populations repressed or otherwise influenced differentiation away from Th17 cells and/or induced or otherwise influenced differentiation toward regulatory T cells (Tregs) and towards Th1 cells. In some embodiments, these T cell modulating agents are useful in the treatment of an immune response, for example, an autoimmune response or an inflammatory response. In some embodiments, the T cell modulating agent is an inhibitor or neutralizing agent. In some embodiments, the T cell modulating agent is an antibody, a soluble polypeptide, a polypeptide antagonist, a peptide antagonist, a nucleic acid antagonist, a nucleic acid ligand, or a small molecule antagonist. In some embodiments, the T cells are naïve T cells. In some embodiments, the T cells are differentiated T cells. In some embodiments, the T cells are partially differentiated T cells. In some embodiments, the T cells are a mixture of naïve T cells and differentiated T cells. In some embodiments, the T cells are mixture of naïve T cells and partially differentiated T cells. In some embodiments, the T cells are mixture of partially differentiated T cells and differentiated T cells. In some embodiments, the T cells are mixture of naïve T cells, partially differentiated T cells, and differentiated T cells.

In some embodiments, the T cell modulating agent is an agent that inhibits the expression, activity and/or function of CCR6. Inhibition of CCR6 expression, activity and/or function in T cell populations repressed or otherwise influenced differentiation away from Th17 cells and/or induced or otherwise influenced differentiation toward regulatory T cells (Tregs) and towards Th1 cells. In some embodiments, these T cell modulating agents are useful in the treatment of an immune response, for example, an autoimmune response or an inflammatory response. In some embodiments, the T cell modulating agent is an antibody, a soluble polypeptide, a polypeptide antagonist, a peptide antagonist, a nucleic acid antagonist, a nucleic acid ligand, or a small molecule antagonist. In some embodiments, the T cells are naïve T cells. In some embodiments, the T cells are differentiated T cells. In some embodiments, the T cells are partially differentiated T cells. In some embodiments, the T cells are a mixture of naïve T cells and differentiated T cells. In some embodiments, the T cells are mixture of naïve T cells and partially differentiated T cells. In some embodiments, the T cells are mixture of partially differentiated T cells and differentiated T cells. In some embodiments, the T cells are mixture of naïve T cells, partially differentiated T cells, and differentiated T cells.

In some embodiments, the T cell modulating agent is an agent that inhibits the expression, activity and/or function of EGR1. Inhibition of EGR1 expression, activity and/or function in T cell populations repressed or otherwise influenced differentiation away from Th17 cells and/or induced or otherwise influenced differentiation toward regulatory T cells (Tregs) and towards Th1 cells. In some embodiments, these T cell modulating agents are useful in the treatment of an immune response, for example, an autoimmune response or an inflammatory response. In some embodiments, the T cell modulating agent is an antibody, a soluble polypeptide, a polypeptide antagonist, a peptide antagonist, a nucleic acid antagonist, a nucleic acid ligand, or a small molecule antagonist. In some embodiments, the T cells are naïve T cells. In some embodiments, the T cells are differentiated T cells. In some embodiments, the T cells are partially differentiated T cells. In some embodiments, the T cells are a mixture of naïve T cells and differentiated T cells. In some embodiments, the T cells are mixture of naïve T cells and partially differentiated T cells. In some embodiments, the T cells are mixture of partially differentiated T cells and differentiated T cells. In some embodiments, the T cells are mixture of naïve T cells, partially differentiated T cells, and differentiated T cells.

In some embodiments, the T cell modulating agent is an agent that inhibits the expression, activity and/or function of EGR2. Inhibition of EGR2 expression, activity and/or function in T cell populations repressed or otherwise influenced differentiation away from Th17 cells and/or induced or otherwise influenced differentiation toward regulatory T cells (Tregs) and towards Th1 cells. In some embodiments, these T cell modulating agents are useful in the treatment of an immune response, for example, an autoimmune response or an inflammatory response. In some embodiments, the T cell modulating agent is an antibody, a soluble polypeptide, a polypeptide antagonist, a peptide antagonist, a nucleic acid antagonist, a nucleic acid ligand, or a small molecule antagonist. In some embodiments, the T cells are naïve T cells. In some embodiments, the T cells are differentiated T cells. In some embodiments, the T cells are partially differentiated T cells. In some embodiments, the T cells are a mixture of naïve T cells and differentiated T cells. In some embodiments, the T cells are mixture of naïve T cells and partially differentiated T cells. In some embodiments, the T cells are mixture of partially differentiated T cells and differentiated T cells. In some embodiments, the T cells are mixture of naïve T cells, partially differentiated T cells, and differentiated T cells.

For example, in some embodiments, the invention provides T cell modulating agents and methods of using these T cell modulating agents to regulate, influence or otherwise impact the phenotype of a Th17 cell or population of cells, for example, by influencing a naïve T cell or population of cells to differentiate to a pathogenic or non-pathogenic Th17 cell or population of cells, by causing a pathogenic Th17 cell or population of cells to switch to a non-pathogenic Th17 cell or population of T cells (e.g., populations of naïve T cells, partially differentiated T cells, differentiated T cells and combinations thereof), or by causing a non-pathogenic Th17 cell or population of T cells (e.g., populations of naïve T cells, partially differentiated T cells, differentiated T cells and combinations thereof) to switch to a pathogenic Th17 cell or population of cells.

The terms "pathogenic" or "non-pathogenic" as used herein are not to be construed as implying that one Th17 cell phenotype is more desirable than the other. As described herein, there are instances in which inhibiting the induction of pathogenic Th17 cells or modulating the Th17 phenotype towards the non-pathogenic Th17 phenotype is desirable. Likewise, there are instances where inhibiting the induction of non-pathogenic Th17 cells or modulating the Th17 phenotype towards the pathogenic Th17 phenotype is desirable.

As used herein, terms such as "pathogenic Th17 cell" and/or "pathogenic Th17 phenotype" and all grammatical variations thereof refer to Th17 cells that, when induced in the presence of TGF-β3, express an elevated level of one or more genes selected from Cxcl3, IL22, IL3, Ccl4, Gzmb, Lrmp, Ccl5, Casp1, Csf2, Ccl3, Tbx21, Icos, IL17r, Stat4, Lgals3 and Lag, as compared to the level of expression in a TGF-β3-induced Th17 cells. As used herein, terms such as "non-pathogenic Th17 cell" and/or "non-pathogenic Th17 phenotype" and all grammatical variations thereof refer to Th17 cells that, when induced in the presence of TGF-β3, express a decreased level of one or more genes selected from IL6st, IL1rn, Ikzf3, Maf, Ahr, IL9 and IL10, as compared to the level of expression in a TGF-β3-induced Th17 cells.

In some embodiments, the T cell modulating agent is an agent that enhances or otherwise increases the expression, activity and/or function of Protein C Receptor (PROCR, also called EPCR or CD201) in Th17 cells. As shown herein, expression of PROCR in Th17 cells reduced the pathogenicity of the Th17 cells, for example, by switching Th17 cells from a pathogenic to non-pathogenic signature. Thus, PROCR and/or these agonists of PROCR are useful in the treatment of a variety of indications, particularly in the treatment of aberrant immune response, for example in autoimmune diseases and/or inflammatory disorders. In some embodiments, the T cell modulating agent is an antibody, a soluble polypeptide, a polypeptide agonist, a peptide agonist, a nucleic acid agonist, a nucleic acid ligand, or a small molecule agonist.

In some embodiments, the T cell modulating agent is an agent that inhibits the expression, activity and/or function of the Protein C Receptor (PROCR, also called EPCR or CD201). Inhibition of PROCR expression, activity and/or function in Th17 cells switches non-pathogenic Th17 cells to pathogenic Th17 cells. Thus, these PROCR antagonists are useful in the treatment of a variety of indications, for example, infectious disease and/or other pathogen-based disorders. In some embodiments, the T cell modulating agent is an antibody, a soluble polypeptide, a polypeptide antagonist, a peptide antagonist, a nucleic acid antagonist, a nucleic acid ligand, or a small molecule antagonist. In some embodiments, the T cell modulating agent is a soluble Protein C Receptor (PROCR, also called EPCR or CD201) polypeptide or a polypeptide derived from PROCR.

In some embodiments, the invention provides a method of inhibiting Th17 differentiation, maintenance and/or function in a cell population and/or increasing expression, activity and/or function of one or more non-Th17-associated cytokines, one or more non-Th17 associated receptor molecules, or non-Th17-associated transcription regulators selected from FOXP3, interferon gamma (IFN-γ), GATA3, STAT4 and TBX21, which may comprise contacting a T cell with an agent that inhibits expression, activity and/or function of MINA, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, ITGA3 or combinations thereof. In some embodiments, the agent inhibits expression, activity and/or function of at least one of MINA, PML, POU2AF1, PROCR, SMARCA4, ZEB1, EGR2, CCR6, FAS or combinations thereof. In some embodiments, the agent is an antibody, a soluble polypeptide, a polypeptide antagonist, a peptide antagonist, a nucleic acid antagonist, a nucleic acid ligand, or a small molecule antagonist. In some embodiments, the antibody is a monoclonal antibody. In some embodiments, the antibody is a chimeric, humanized or fully human monoclonal antibody. In some embodiments, the T cell is a naïve T cell, and wherein the agent is administered in an amount that is sufficient to modulate the phenotype of the T cell to become and/or produce a desired non-Th17 T cell phenotype, for example, a regulatory T cell (Treg) phenotype or another CD4+ T cell phenotype. In some embodiments, the T cell is a partially differentiated T cell, and wherein the agent is administered in an amount that is sufficient to modulate the phenotype of the partially differentiated T cell to become and/or produce a desired non-Th17 T cell phenotype, for example, a regulatory T cell (Treg) phenotype or another CD4+ T cell phenotype. In some embodiments, the T cell is a Th17 T cell, and wherein the agent is administered in an amount that is sufficient to modulate the phenotype of the Th17 T cell to become and/or produce a CD4+ T cell phenotype other than a Th17 T cell phenotype. In some embodiments, the T cell is a Th17 T cell, and wherein the agent is administered in an amount that is sufficient to modulate the phenotype of the Th17 T cell to become and/or produce a shift in the Th17 T cell phenotype, e.g., between pathogenic or non-pathogenic Th17 cell phenotype.

In some embodiments, the invention provides a method of inhibiting Th17 differentiation in a cell population and/or increasing expression, activity and/or function of one or more non-Th17-associated cytokines, one or more non-Th17-associated receptor molecules, or non-Th17-associated transcription factor selected from FOXP3, interferon gamma (IFN-γ), GATA3, STAT4 and TBX21, which may comprise contacting a T cell with an agent that enhances expression, activity and/or function of SP4, ETS2, IKZF4, TSC22D3, IRF1 or combinations thereof. In some embodiments, the agent enhances expression, activity and/or function of at least one of SP4, IKZF4, TSC22D3 or combinations thereof. In some embodiments, the agent is an antibody, a soluble polypeptide, a polypeptide agonist, a peptide agonist, a nucleic acid agonist, a nucleic acid ligand, or a small molecule agonist. In some embodiments, the antibody is a monoclonal antibody. In some embodiments, the T cell is a naïve T cell, and wherein the agent is administered in an amount that is sufficient to modulate the phenotype of the T cell to become and/or produce a desired non-Th17 T cell phenotype, for example, a regulatory T cell (Treg) phenotype or another CD4+ T cell phenotype. In some embodiments, the T cell is a partially differentiated T cell, and wherein the agent is administered in an amount that is sufficient to modulate the phenotype of the partially differentiated T cell to become and/or produce a desired non-Th17 T cell phenotype, for example, a regulatory T cell (Treg) phenotype or another CD4+ T cell phenotype. In some embodiments, the T cell is a Th17 T cell, and wherein the agent is administered in an amount that is sufficient to modulate the phenotype of the Th17 T cell to become and/or produce a CD4+ T cell phenotype other than a Th17 T cell phenotype. In some embodiments, the T cell is a Th17 T cell, and wherein the agent is administered in an amount that is sufficient to modulate the phenotype of the Th17 T cell to become and/or produce a shift in the Th17 T cell phenotype, e.g., between pathogenic or non-pathogenic Th17 cell phenotype.

In some embodiments, the invention provides a method of enhancing Th17 differentiation in a cell population increasing expression, activity and/or function of one or more Th17-associated cytokines, one or more Th17-associated receptor molecules, or one or more Th17-associated transcription regulators selected from interleukin 17F (IL-17F), interleukin 17A (IL-17A), STAT3, interleukin 21 (IL-21) and RAR-related orphan receptor C (RORC), and/or decreasing expression, activity and/or function of one or more non-Th17-associated cytokines, one or more Th17-associated receptor molecules, or one or more non-Th17-associated transcription regulators selected from FOXP3, interferon gamma (IFN-γ), GATA3, STAT4 and TBX21, which may comprise contacting a T cell with an agent that inhibits expression, activity and/or function of SP4, ETS2, IKZF4, TSC22D3, IRF1 or combinations thereof. In some embodiments, the agent inhibits expression, activity and/or function of at least one of SP4, IKZF4, TSC22D3 or combinations thereof. In some embodiments, the agent is an antibody, a soluble polypeptide, a polypeptide antagonist, a peptide antagonist, a nucleic acid antagonist, a nucleic acid ligand, or a small molecule antagonist. In some embodiments, the antibody is a monoclonal antibody. In some embodiments, the antibody is a chimeric, humanized or fully human monoclonal antibody. In some embodiments, the T cell is a naïve T cell, and wherein the agent is administered in an amount that is sufficient to modulate the phenotype of the T cell to become and/or produce a desired Th17 T cell phenotype. In some embodiments, the T cell is a partially differentiated T cell, and wherein the agent is administered in an amount that is sufficient to modulate the phenotype of the partially differentiated T cell to become and/or produce a desired Th17 T cell phenotype. In some embodiments, the T cell is a CD4+ T cell other than a Th17 T cell, and wherein the agent is administered in an amount that is sufficient to modulate the phenotype of the non-Th17 T cell to become and/or produce a Th17 T cell phenotype. In some embodiments, the T cell is a Th17 T cell, and wherein the agent is administered in an amount that is sufficient to modulate the phenotype of the Th17 T cell to become and/or produce a shift in the Th17 T cell phenotype, e.g., between pathogenic or non-pathogenic Th17 cell phenotype.

In some embodiments, the invention provides a method of enhancing Th17 differentiation in a cell population, increasing expression, activity and/or function of one or more Th17-associated cytokines, one or more Th17-associated receptor molecules, and/or one or more Th17-associated transcription regulators selected from interleukin 17F (IL-17F), interleukin 17A (IL-17A), STAT3, interleukin 21 (IL-21) and RAR-related orphan receptor C (RORC), and/or decreasing expression, activity and/or function of one or more non-Th17-associated cytokines, one or more Th17-associated receptor molecules, or one or more non-Th17-associated transcription regulators selected from FOXP3, interferon gamma (IFN-γ), GATA3, STAT4 and TBX21, which may comprise contacting a T cell with an agent that enhances expression, activity and/or function of MINA, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, ITGA3 or combinations thereof. In some embodiments, the agent enhances expression, activity and/or function of at least one of MINA, PML, POU2AF1, PROCR, SMARCA4, ZEB1, EGR2, CCR6, FAS or combinations thereof. In some embodiments, the agent is an antibody, a soluble polypeptide, a polypeptide agonist, a peptide agonist, a nucleic acid agonist, a nucleic acid ligand, or a small molecule agonist. In some embodiments, the antibody is a monoclonal antibody. In some embodiments, the antibody is a chimeric, humanized or fully human monoclonal antibody. In some embodiments, the agent is administered in an amount sufficient to inhibit Foxp3, IFN-γ, GATA3, STAT4 and/or TBX21 expression, activity and/or function. In some embodiments, the T cell is a naïve T cell, and wherein the agent is administered in an amount that is sufficient to modulate the phenotype of the T cell to become and/or produce a desired Th17 T cell phenotype. In some embodiments, the T cell is a partially differentiated T cell, and wherein the agent is administered in an amount that is sufficient to modulate the phenotype of the partially differentiated T cell to become and/or produce a desired Th17 T cell phenotype. In some embodiments, the T cell is a CD4+ T cell other than a Th17 T cell, and wherein the agent is administered in an amount that is sufficient to modulate the phenotype of the non-Th17 T cell to become and/or produce a Th17 T cell phenotype. In some embodiments, the T cell is a Th17 T cell, and wherein the agent is administered in an amount that is sufficient to modulate the phenotype of the Th17 T cell to become and/or produce a shift in the Th17 T cell phenotype, e.g., between pathogenic or non-pathogenic Th17 cell phenotype.

In some embodiments, the invention provides a method of identifying genes or genetic elements associated with Th17 differentiation which may comprise: a) contacting a T cell with an inhibitor of Th17 differentiation or an agent that enhances Th17 differentiation; and b) identifying a gene or genetic element whose expression is modulated by step (a). In some embodiments, the method also may comprise c) perturbing expression of the gene or genetic element identified in step b) in a T cell that has been in contact with an inhibitor of Th17 differentiation or an agent that enhances Th17 differentiation; and d) identifying a gene whose expression is modulated by step c). In some embodiments, the inhibitor of Th17 differentiation is an agent that inhibits the expression, activity and/or function of MINA, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, ITGA3 or combinations thereof. In some embodiments, the agent inhibits expression, activity and/or function of at least one of MINA, PML, POU2AF1, PROCR, SMARCA4, ZEB1, EGR2, CCR6, FAS or combinations thereof. In some embodiments, the inhibitor of Th17 differentiation is an agent that enhances expression, activity and/or function of SP4, ETS2, IKZF4, TSC22D3, IRF1 or combinations thereof. In some embodiments, the agent enhances expression, activity and/or function of at least one of SP4, IKZF4 or TSC22D3. In some embodiments, the agent that enhances Th17 differentiation is an agent that inhibits expression, activity and/or function of SP4, ETS2, IKZF4, TSC22D3, IRF1 or combinations thereof. In some embodiments, wherein the agent that enhances Th17 differentiation is an agent that enhances expression, activity and/or function of MINA, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, ITGA3 or combinations thereof. In some embodiments, the agent is an antibody, a soluble polypeptide, a polypeptide antagonist, a peptide antagonist, a nucleic acid antagonist, a nucleic acid ligand, or a small molecule antagonist.

In some embodiments, the invention provides a method of modulating induction of Th17 differentiation which may comprise contacting a T cell with an agent that modulates expression, activity and/or function of one or more target genes or one or more products of one or more target genes selected from IRF1, IRF8, IRF9, STAT2, STAT3, IRF7, STAT1, ZFP281, IFI35, REL, TBX21, FLI1, BATF, IRF4, one or more of the target genes listed in Table 5 as being associated with the early stage of Th17 differentiation, maintenance and/or function, e.g., AES, AHR, ARID5A, BATF, BCL11B, BCL3, CBFB, CBX4, CHD7, CITED2, CREB1, E2F4, EGR1, EGR2, ELL2, ETS1, ETS2, ETV6, EZH1, FLI1, FOXO1, GATA3, GATAD2B, HIF1A, ID2, IFI35, IKZF4, IRF1, IRF2, IRF3, IRF4, IRF7, IRF9, JMJD1C, JUN, LEF1, LRRFIP1, MAX, NCOA3, NFE2L2, NFIL3, NFKB1, NMI, NOTCH1, NR3C1, PHF21A, PML, PRDM1, REL, RELA, RUNX1, SAP18, SATB1, SMAD2, SMARCA4, SP100, SP4, STAT1, STAT2, STAT3, STAT4, STATSB, STAT6, TFEB, TP53, TRIM24, and/or ZFP161, or any combination thereof.

In some embodiments, the invention provides a method of modulating onset of Th17 phenotype and amplification of Th17 T cells which may comprise contacting a T cell with an agent that modulates expression, activity and/or function of one or more target genes or one or more products of one or more target genes selected from IRF8, STAT2, STAT3, IRF7, JUN, STATSB, ZPF2981, CHD7, TBX21, FLI1, SATB1, RUNX1, BATF, RORC, SP4, one or more of the target genes listed in Table 5 as being associated with the intermediate stage of Th17 differentiation, maintenance and/or function, e.g., AES, AHR, ARID3A, ARID5A, ARNTL, ASXL1, BATF, BCL11B, BCL3, BCL6, CBFB, CBX4, CDC5L, CEBPB, CHD7, CREB1, CREB3L2, CREM, E2F4, E2F8, EGR1, EGR2, ELK3, ELL2, ETS1, ETS2, ETV6, EZH1, FLI1, FOSL2, FOXJ2, FOXO1, FUS, HIF1A, HMGB2, ID1, ID2, IFI35, IKZF4, IRF3, IRF4, IRF7, IRF8, IRF9, JUN, JUNB, KAT2B, KLF10, KLF6, KLF9, LEF1, LRRFIP1, MAFF, MAX, MAZ, MINA, MTA3, MYC, MYST4, NCOA1, NCOA3, NFE2L2, NFIL3, NFKB1, NMI, NOTCH1, NR3C1, PHF21A, PML, POU2AF1, POU2F2, PRDM1, RARA, RBPJ, RELA, RORA, RUNX1, SAP18, SATB1, SKI, SKIL, SMAD2, SMAD7, SMARCA4, SMOX, SP1, SP4, SS18, STAT1, STAT2, STAT3, STAT5A, STATSB, STAT6, SUZ12, TBX21, TFEB, TLE1, TP53, TRIM24, TRIM28, TRPS1, VAV1, ZEB1, ZEB2, ZFP161, ZFP62, ZNF238, ZNF281, and/or ZNF703, or any combination thereof.

In some embodiments, the invention provides a method of modulating stabilization of Th17 cells and/or modulating Th17-associated interleukin 23 (IL-23) signaling which may comprise contacting a T cell with an agent that modulates expression, activity and/or function of one or more target genes or one or more products of one or more target genes selected from STAT2, STAT3, JUN, STATSB, CHD7, SATB1, RUNX1, BATF, RORC, SP4 IRF4, one or more of the target genes listed in Table 5 as being associated with the late stage of Th17 differentiation, maintenance and/or function, e.g., AES, AHR, ARID3A, ARID5A, ARNTL, ASXL1, ATF3, ATF4, BATF, BATF3, BCL11B, BCL3, BCL6, C21ORF66, CBFB, CBX4, CDC5L, CDYL, CEBPB, CHD7, CHMP1B, CIC, CITED2, CREB1, CREB3L2, CREM, CSDA, DDIT3, E2F1, E2F4, E2F8, EGR1, EGR2, ELK3, ELL2, ETS1, ETS2, EZH1, FLI1, FOSL2, FOXJ2, FOXO1, FUS, GATA3, GATAD2B, HCLS1, HIF1A, ID1, ID2, IFI35, IKZF4, IRF3, IRF4, IRF7, IRF8, IRF9, JARID2, JMJD1C, JUN, JUNB, KAT2B, KLF10, KLF6, KLF7, KLF9, LASS4, LEF1, LRRFIP1, MAFF, MAX, MEN1, MINA, MTA3, MXI1, MYC, MYST4, NCOA1, NCOA3, NFE2L2, NFIL3, NFKB1, NMI, NOTCH1, NR3C1, PHF13, PHF21A, PML, POU2AF1, POU2F2, PRDM1, RARA, RBPJ, REL, RELA, RNF11, RORA, RORC, RUNX1, RUNX2, SAP18, SAP30, SATB1, SERTAD1, SIRT2, SKI, SKIL, SMAD2, SMAD4, SMAD7, SMARCA4, SMOX, SP1, SP100, SP4, SS18, STAT1, STAT3, STAT4, STAT5A, STATSB, STAT6, SUZ12, TBX21, TFEB, TGIF1, TLE1, TP53, TRIM24, TRPS1, TSC22D3, UBE2B, VAV1, VAX2, XBP1, ZEB1, ZEB2, ZFP161, ZFP36L1, ZFP36L2, ZNF238, ZNF281, ZNF703, ZNRF1, and/or ZNRF2, or any combination thereof.

In some embodiments, the invention provides a method of modulating one or more of the target genes listed in Table 6 as being associated with the early stage of Th17 differentiation, maintenance and/or function, e.g., FAS, CCR5, IL6ST, IL17RA, IL2RA, MYD88, CXCR5, PVR, IL15RA, IL12RB1, or any combination thereof.

In some embodiments, the invention provides a method of modulating one or more of the target genes listed in Table 6 as being associated with the intermediate stage of Th17 differentiation, maintenance and/or function, e.g., IL7R, ITGA3, IL1R1, CCR5, CCR6, ACVR2A, IL6ST, IL17RA, CCR5, DDR1, PROCR, IL2RA, IL12RB2, MYD88, PTPRJ, TNFRSF13B, CXCR3, IL1RN, CXCR5, CCR4, IL4R, IL2RB, TNFRSF12A, CXCR4, KLRD1, IRAK1BP1, PVR, IL12RB1, IL18R1, TRAF3, or any combination thereof.

In some embodiments, the invention provides a method of modulating one or more of the target genes listed in Table 6 as being associated with the late stage of Th17 differentiation, maintenance and/or function, e.g., IL7R, ITGA3, IL1R1, FAS, CCR5, CCR6, ACVR2A, IL6ST, IL17RA, DDR1, PROCR, IL2RA, IL12RB2, MYD88, BMPR1A, PTPRJ, TNFRSF13B, CXCR3, IL1RN, CXCR5, CCR4, IL4R, IL2RB, TNFRSF12A, CXCR4, KLRD1, IRAK1BP1, PVR, IL15RA, TLR1, ACVR1B, IL12RB1, IL18R1, TRAF3, IFNGR1, PLAUR, IL21R, IL23R, or any combination thereof.

In some embodiments, the invention provides a method of modulating one or more of the target genes listed in Table 7 as being associated with the early stage of Th17 differentiation, maintenance and/or function, e.g., EIF2AK2, DUSP22, HK2, RIPK1, RNASEL, TEC, MAP3K8, SGK1, PRKCQ, DUSP16, BMP2K, PIM2, or any combination thereof.

In some embodiments, the invention provides a method of modulating one or more of the target genes listed in Table 7 as being associated with the intermediate stage of Th17 differentiation, maintenance and/or function, e.g., PSTPIP1, PTPN1, ACP5, TXK, RIPK3, PTPRF, NEK4, PPME1, PHACTR2, HK2, GMFG, DAPP1, TEC, GMFB, PIM1, NEK6, ACVR2A, FES, CDK6, ZAK, DUSP14, SGK1, JAK3, ULK2, PTPRJ, SPHK1, TNK2, PCTK1, MAP4K3, TGFBR1, HK1, DDR1, BMP2K, DUSP10, ALPK2, or any combination thereof.

In some embodiments, the invention provides a method of modulating one or more of the target genes listed in Table 7 as being associated with the late stage of Th17 differentiation, maintenance and/or function, e.g., PTPLA, PSTPIP1, TK1, PTEN, BPGM, DCK, PTPRS, PTPN18, MKNK2, PTPN1, PTPRE, SH2D1A, PLK2, DUSP6, CDC25B, SLK, MAP3K5, BMPR1A, ACP5, TXK, RIPK3, PPP3CA, PTPRF, PACSIN1, NEK4, PIP4K2A, PPME1, SRPK2, DUSP2, PHACTR2, DCLK1, PPP2R5A, RIPK1, GK, RNASEL, GMFG, STK4, HINT3, DAPP1, TEC, GMFB, PTPN6, RIPK2, PIM1, NEK6, ACVR2A, AURKB, FES, ACVR1B, CDK6, ZAK, VRK2, MAP3K8, DUSP14, SGK1, PRKCQ, JAK3, ULK2, HIPK2, PTPRJ, INPP1, TNK2, PCTK1, DUSP1, NUDT4, TGFBR1, PTP4A1, HK1, DUSP16, ANP32A, DDR1, ITK, WNK1, NAGK, STK38, BMP2K, BUB1, AAK1, SIK1, DUSP10, PRKCA, PIM2, STK17B, TK2, STK39, ALPK2, MST4, PHLPP1, or any combination thereof.

In some embodiments, the invention provides a method of modulating is one or more of the target genes listed in Table 8 as being associated with the early stage of Th17 differentiation, maintenance and/or function, e.g., HK2, CDKN1A, DUT, DUSP1, NADK, LIMK2, DUSP11, TAOK3, PRPS1, PPP2R4, MKNK2, SGK1, BPGM, TEC, MAPK6, PTP4A2, PRPF4B, ACP1, CCRN4L, or any combination thereof.

In some embodiments, the invention provides a method of modulating one or more of the target genes listed in Table 8 as being associated with the intermediate stage of Th17 differentiation, maintenance and/or function, e.g., HK2, ZAP70, NEK6, DUSP14, SH2D1A, ITK, DUT, PPP1R11, DUSP1, PMVK, TK1, TAOK3, GMFG, PRPS1, SGK1, TXK, WNK1, DUSP19, TEC, RPS6KA1, PKM2, PRPF4B, ADRBK1, CKB, ULK2, PLK1, PPP2R5A, PLK2, or any combination thereof.

In some embodiments, the invention provides a method of modulating one or more of the target genes listed in Table 8 as being associated with the late stage of Th17 differentiation, maintenance and/or function, e.g., ZAP70, PFKP, NEK6, DUSP14, SH2D1A, INPP5B, ITK, PFKL, PGK1, CDKN1A, DUT, PPP1R11, DUSP1, PMVK, PTPN22, PSPH, TK1, PGAM1, LIMK2, CLK1, DUSP11, TAOK3, RIOK2, GMFG, UCKL1, PRPS1, PPP2R4, MKNK2, DGKA, SGK1, TXK, WNK1, DUSP19, CHP, BPGM, PIP5K1A, TEC, MAP2K1, MAPK6, RPS6KA1, PTP4A2, PKM2, PRPF4B, ADRBK1, CKB, ACP1, ULK2, CCRN4L, PRKCH, PLK1, PPP2R5A, PLK2, or any combination thereof.

In some embodiments, the invention provides a method of modulating one or more of the target genes listed in Table 9 as being associated with the early stage of Th17 differentiation, maintenance and/or function, e.g., CD200, CD40LG, CD24, CCND2, ADAM17, BSG, ITGAL, FAS, GPR65, SIGMAR1, CAP1, PLAUR, SRPRB, TRPV2, IL2RA, KDELR2, TNFRSF9, or any combination thereof.

In some embodiments, the invention provides a method of modulating one or more of the target genes listed in Table 9 as being associated with the intermediate stage of Th17 differentiation, maintenance and/or function, e.g., CTLA4, CD200, CD24, CD6L, CD9, IL2RB, CD53, CD74, CAST, CCR6, IL2RG, ITGAV, FAS, IL4R, PROCR, GPR65, TNFRSF18, RORA, IL1RN, RORC, CYSLTR1, PNRC2, LOC390243, ADAM10, TNFSF9, CD96, CD82, SLAMF7, CD27, PGRMC1, TRPV2, ADRBK1, TRAF6, IL2RA, THY1, IL12RB2, TNFRSF9, or any combination thereof.

In some embodiments, the invention provides a method of modulating one or more of the target genes listed in Table 9 as being associated with the late stage of Th17 differentiation, maintenance and/or function, e.g., CTLA4, TNFRSF4, CD44, PDCD1, CD200, CD247, CD24, CD6L, CCND2, CD9, IL2RB, CD53, CD74, ADAM17, BSG, CAST, CCR6, IL2RG, CD81, CD6, CD48, ITGAV, TFRC, ICAM2, ATP1B3, FAS, IL4R, CCR7, CD52, PROCR, GPR65, TNFRSF18, FCRL1, RORA, IL1RN, RORC, P2RX4, SSR2, PTPN22, SIGMAR1, CYSLTR1, LOC390243, ADAM10, TNFSF9, CD96, CAP1, CD82, SLAMF7, PLAUR, CD27, SIVA1, PGRMC1, SRPRB, TRPV2, NR1H2, ADRBK1, GABARAPL1, TRAF6, IL2RA, THY1, KDELR2, IL12RB2, TNFRSF9, SCARB1, IFNGR1, or any combination thereof.

In some embodiments, the invention provides a method of inhibiting tumor growth in a subject in need thereof by administering to the subject a therapeutically effective amount of an inhibitor of Protein C Receptor (PROCR). In some embodiments, the inhibitor of PROCR is an antibody, a soluble polypeptide, a polypeptide agent, a peptide agent, a nucleic acid agent, a nucleic acid ligand, or a small molecule agent. In some embodiments, the inhibitor of PROCR is one or more agents selected from the group consisting of lipopolysaccharide; cisplatin; fibrinogen; 1, 10-phenanthroline; 5-N-ethylcarboxamido adenosine; cystathionine; hirudin; phospholipid; Drotrecogin alfa; VEGF; Phosphatidylethanolamine; serine; gamma-carboxyglutamic acid; calcium; warfarin; endotoxin; curcumin; lipid; and nitric oxide.

In some embodiments, the invention provides a method of diagnosing an immune response in a subject, which may comprise detecting a level of expression, activity and/or function of one or more signature genes or one or more products of one or more signature genes selected from those listed in Table 1 or Table 2 and comparing the detected level to a control of level of signature gene or gene product expression, activity and/or function, wherein a difference between the detected level and the control level indicates that the presence of an immune response in the subject. In some embodiments, the immune response is an autoimmune response. In some embodiments, the immune response is an inflammatory response, including inflammatory response(s) associated with an autoimmune response and/or inflammatory response(s) associated with an infectious disease or other pathogen-based disorder.

In some embodiments, the invention provides a method of monitoring an immune response in a subject, which may comprise detecting a level of expression, activity and/or function of one or more signature genes or one or more products of one or more signature genes, e.g., one or more signature genes selected from those listed in Table 1 or Table 2 at a first time point, detecting a level of expression, activity and/or function of one or more signature genes or one or more products of one or more signature genes, e.g., one or more signature genes selected from those listed in Table 1 or Table 2 at a second time point, and comparing the first detected level of expression, activity and/or function with the second detected level of expression, activity and/or function, wherein a change between the first and second detected levels indicates a change in the immune response in the subject. In some embodiments, the immune response is an autoimmune response. In some embodiments, the immune response is an inflammatory response.

In some embodiments, the invention provides a method of monitoring an immune response in a subject, which may comprise isolating a population of T cells from the subject at a first time point, determining a first ratio of T cell subtypes within the T cell population at a first time point, isolating a population of T cells from the subject at a second time point, determining a second ratio of T cell subtypes within the T cell population at a second time point, and comparing the first and second ratio of T cell subtypes, wherein a change in the first and second detected ratios indicates a change in the immune response in the subject. In some embodiments, the immune response is an autoimmune response. In some embodiments, the immune response is an inflammatory response.

In some embodiments, the invention provides a method of activating therapeutic immunity by exploiting the blockade of immune checkpoints. The progression of a productive immune response requires that a number of immunological checkpoints be passed. Immunity response is regulated by the counterbalancing of stimulatory and inhibitory signal. The immunoglobulin superfamily occupies a central importance in this coordination of immune responses, and the CD28/cytotoxic T-lymphocyte antigen-4 (CTLA-4):B7.1/B7.2 receptor/ligand grouping represents the archetypal example of these immune regulators (see e.g., Korman A J, Peggs K S, Allison J P, "Checkpoint blockade in cancer immunotherapy." Adv Immunol. 2006; 90:297-339). In part the role of these checkpoints is to guard against the possibility of unwanted and harmful self-directed activities. While this is a necessary function, aiding in the prevention of autoimmunity, it may act as a barrier to successful immunotherapies aimed at targeting malignant self-cells that largely display the same array of surface molecules as the cells from which they derive. The expression of immune-checkpoint proteins can be dysregulated in a disease or disorder and can be an important immune resistance mechanism. Therapies aimed at overcoming these mechanisms of peripheral tolerance, in particular by blocking the inhibitory checkpoints, offer the potential to generate therapeutic activity, either as monotherapies or in synergism with other therapies.

Thus, the present invention relates to a method of engineering T-cells, especially for immunotherapy, which may comprise modulating T cell balance to inactivate or otherwise inhibit at least one gene or gene product involved in the immune check-point.

Suitable T cell modulating agent(s) for use in any of the compositions and methods provided herein include an antibody, a soluble polypeptide, a polypeptide agent, a peptide agent, a nucleic acid agent, a nucleic acid ligand, or a small molecule agent. By way of non-limiting example, suitable T cell modulating agents or agents for use in combination with one or more T cell modulating agents are shown in Table 10 of the specification.

One skilled in the art will appreciate that the T cell modulating agents have a variety of uses. For example, the T cell modulating agents are used as therapeutic agents as described herein. The T cell modulating agents can be used as reagents in screening assays, diagnostic kits or as diagnostic tools, or these T cell modulating agents can be used in competition assays to generate therapeutic reagents.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 1A depicts an overview of approach. FIGS. 1B-1 and 1B-2 depict gene expression profiles during Th17 differentiation. Shown are the differential expression levels for genes (rows) at 18 time points (columns) in Th17 polarizing conditions (TGF-β1 and IL-6; left panel, Z-normalized per row) or Th17 polarizing conditions relative to control activated Th0 cells (right panel, log 2(ratio)). The genes are partitioned into 20 clusters (C1-C20, color bars, right). Right: mean expression (Y axis) and standard deviation (error bar) at each time point (X axis) for genes in representative clusters. Cluster size ("n"), enriched functional annotations ("F"), and representative genes ("M") are denoted. FIG. 1C depicts three major transcriptional phases. Shown is a correlation matrix (red (right side of correlation scale): high; blue (left side of correlation scale): low) between every pair of time points. FIG. 1D depicts transcriptional profiles of key cytokines and receptor molecules. Shown are the differential expression levels (log 2(ratio)) for each gene (column) at each of 18 time points (rows) in Th17 polarizing conditions (TGF-β1 and IL-6; left panel, Z-normalized per row) vs. control activated Th0 cells.

FIGS. 2A, 2B, 2C, 2D, 2E-1, 2E-2 and 2E-3 are a series of graphs and illustrations depicting a model of the dynamic regulatory network of Th17 differentiation. FIG. 2A depicts an overview of computational analysis. FIG. 2B depicts a schematic of temporal network 'snapshots'. Shown are three consecutive cartoon networks (top and matrix columns), with three possible interactions from regulator (A) to targets (B, C & D), shown as edges (top) and matrix rows (A→B—top row; A→C—middle row; A→D—bottom row). FIG. 1C depicts 18 network 'snapshots'. Left: each row corresponds to a TF-target interaction that occurs in at least one network; columns correspond to the network at each time point. A purple entry: interaction is active in that network. The networks are clustered by similarity of active interactions (dendrogram, top), forming three temporally consecutive clusters (early, intermediate, late, bottom). Right: a heatmap denoting edges for selected regulators. FIG. 1D depicts dynamic regulator activity. Shown is, for each regulator (rows), the number of target genes (normalized by its maximum number of targets) in each of the 18 networks (columns, left), and in each of the three canonical networks (middle) obtained by collapsing (arrows). Right: regulators chosen for perturbation (pink), known Th17 regulators (grey), and the maximal number of target genes across the three canonical networks (green, ranging from 0 to 250 targets). FIGS. 1E-1, 1E-2, and 1E-3 depict that at the heart of each network is its 'transcriptional circuit', connecting active TFs to target genes that themselves encode TFs. The transcription factor circuits shown (in each of the 3 canonical networks) are the portions of each of the inferred networks associating transcription regulators to targets that themselves encode transcription regulators. Yellow nodes denote transcription factor genes that are over-expressed (compared to Th0) during the respective time segment. Edge color reflects the data type supporting the regulatory interaction (legend).

FIG. 3A depicts unbiased ranking of perturbation candidates. Shown are the genes ordered from left to right based on their ranking for perturbation (columns, top ranking is leftmost). Two top matrices: criteria for ranking by 'Network Information' (topmost) and 'Gene Expression Information'. Purple entry: gene has the feature (intensity proportional to feature strength; top five features are binary). Bar chart: ranking score. 'Perturbed' row: dark grey: genes successfully perturbed by knockdown followed by high quality mRNA quantification; light grey: genes where an attempt to knockdown was made, but could not achieve or maintain sufficient knockdown or did not obtain enough replicates; Black: genes perturbed by knockout or for which knockout data was already available. Known row: orange entry: a gene was previously associated with Th17 function (this information was not used to rank the genes; FIG. 3B depicts scanning electron micrograph of primary T cells (false colored purple) cultured on vertical silicon nanowires. FIG. 3C depicts delivery by silicon nanowire neither activates nor induces differentiation of naïve T cells and does not affect their response to conventional TCR stimulation with anti-CD3/CD28. FIG. 3D depicts effective knockdown by siRNA delivered on nanowires. Shown is the % of mRNA remaining after knockdown (by qPCR, Y axis: mean±standard error relative to non-targeting siRNA control, n=12, black bar on left) at 48 hrs after introduction of polarizing cytokines. In FIG. 3A and FIG. 2D, the candidate regulators shown are those listed in Table 5. In FIG. 3A, the candidate regulators are listed on the x axis and are, in order from left to right, RORC, SATB1, TRPS1, SMOX, RORA, ARID5A, ETV6, ARNTL, ETS1, UBE2B, BATF, STAT3, STAT1, STAT5A, NR3C1, STAT6, TRIM24, HIF1A, IRF4, IRF8, ETS2, JUN, RUNX1, FLI1, REL, SP4, EGR2, NFKB1, ZFP281, STAT4, RELA, TBX21, STATSB, IRF7, STAT2, IRF3, XBP1, FOXO1, PRDM1, ATF4, IRF1, GATA3, EGR1, MYC, CREB1, IRF9, IRF2, FOXJ2, SMARCA4, TRP53, SUZ12, POU2AF1, CEBPB, ID2, CREM, MYST4, MXI1, RBPJ, CHD7, CREB3L2, VAX2, KLF10, SKI, ELK3, ZEB1, PML, SERTAD1, NOTCH1, LRRFIP1, AHR, 1810007M14RIK, SAP30, ID1, ZFP238, VAV1, MINA, BATF3, CDYL, IKZF4, NCOA1, BCL3, JUNB, SS18, PHF13, MTA3, ASXL1, LASS4, SKIL, DDIT3, FOSL2, RUNX2, TLE1, ATF3, ELL2, AES, BCL11B, JARID2, KLF9, KAT2B, KLF6, E2F8, BCL6, ZNRF2, TSC22D3, KLF7, HMGB2, FUS, SIRT2, MAFF, CHMP1B, GATAD2B, SMAD7, ZFP703, ZNRF1, JMJD1C, ZFP36L2, TSC22D4, NFE2L2, RNF11, ARID3A, MEN1, RARA, CBX4, ZFP62, CIC, HCLS1, ZFP36L1, TGIF1.

FIG. 4A depicts the impact of perturbed genes on a 275-gene signature. Shown are changes in the expression of 275 signature genes (rows) following knockdown or knockout (KO) of 39 factors (columns) at 48 hr (as well as IL-21r and IL-17ra KO at 60 hours). Blue (left side of Fold change (log 2) scale): decreased expression of target following perturbation of a regulator (compared to a non-targeting control); red (right side of Fold change (log 2) scale): increased expression; Grey: not significant; all color (i.e., non-grey) entries are significant (see Methods in Example 1). 'Perturbed' (left): signature genes that are also perturbed as regulators (black entries). Key signature genes are denoted on right. FIG. 4B depicts two coupled and opposing modules. Shown is the perturbation network associating the 'positive regulators' (blue nodes, left side of x-axis) of Th17 signature genes, the 'negative regulators' (red nodes, right side of x-axis), Th17 signature genes (grey nodes, bottom) and signature genes of other CD4+ T cells (grey nodes, top). A blue edge from node A to B indicates that knockdown of A downregulates B; a red edge indicates that knockdown of A upregulates B. Light grey halos: regulators not previously associated with Th17 differentiation. FIG. 4C depicts how knockdown effects validate edges in network model. Venn diagram: compare the set of targets for a factor in the original model of FIG. 2A (pink circle) to the set of genes that respond to that factor's knockdown in an RNA-Seq experiment (yellow circle). Bar chart on bottom: Shown is the −log 10(Pvalue) (Y axis, hypergeometric test) for the significance of this overlap for four factors (X axis). Similar results were obtained with a non-parametric rank-sum test (Mann-Whitney U test, see Methods in Example 1). Red dashed line: P=0.01. FIG. 4D depicts how global knockdown effects are consistent across clusters. Venn diagram: compare the set of genes that respond to a factor's knockdown in an RNA-Seq experiment (yellow circle) to each of the 20 clusters of FIG. 1B (purple circle). The knockdown of a 'Th17 positive' regulator was expected to repress genes in induced clusters, and induce genes in repressed clusters (and vice versa for 'Th17 negative' regulators). Heat map: For each regulator knockdown (rows) and each cluster (columns) shown are the significant overlaps (non grey entries) by the test above. Red (right side of Fold enrichment scale): fold enrichment for up-regulation upon knockdown; Blue (left side of Fold enrichment scale): fold enrichment for down regulation upon knockdown. Orange entries in the top row indicate induced clusters.

FIGS. 5A, 5B, 5C, and 5D are a series of graphs and illustrations depicting that Mina, Fas, Pou2af1, and Tsc22d3 are key novel regulators affecting the Th17 differentiation programs. A color version of these figures can be found in Yosef et al., "Dynamic regulatory network controlling Th17 cell differentiation, Nature, vol. 496: 461-468 (2013)/doi: 10.1038/nature11981. FIGS. 5A-5D, left: Shown are regulatory network models centered on different pivotal regulators (square nodes): (FIG. 5A) Mina, (FIG. 5B) Fas, (FIG. 5C) Pou2af1, and (FIG. 5D) Tsc22d3. In each network, shown are the targets and regulators (round nodes) connected to the pivotal nodes based on perturbation (red and blue dashed edges), TF binding (black solid edges), or both (red and blue solid edges). Genes affected by perturbing the pivotal nodes are colored (blue: target is down-regulated by knockdown of pivotal node; red: target is up-regulated). (FIGS. 5A-5C, middle and right) Intracellular staining and cytokine assays by ELISA or Cytometric Bead Assays (CBA) on culture supernatants at 72 h of in vitro differentiated cells from respective KO mice activated in vitro with anti-CD3+anti-CD28 with or without Th17 polarizing cytokines (TGF-β+IL-6). (FIG. 5D, middle) ChIP-Seq of Tsc22d3. Shown is the proportion of overlap in bound genes (dark grey) or bound regions (light grey) between Tsc22d3 and a host of Th17 canonical factors (X axis). All results are statistically significant (P<$10^{-6}$; see Methods in Example 1).

FIGS. 6A, 6B, 6C, and 6D are a series of graphs and illustrations depicting treatment of Naïve CD4+ T-cells with TGF-β1 and IL-6 for three days induces the differentiation of Th17 cells. A color version of these figures can be found in Yosef et al., "Dynamic regulatory network controlling Th17 cell differentiation, Nature, vol. 496: 461-468 (2013)/ doi: 10.1038/nature11981. FIG. 6A depicts an overview of the time course experiments. Naïve T cells were isolated from WT mice, and treated with IL-6 and TGF-β1. Microarrays were then used to measure global mRNA levels at 18 different time points (0.5 hr-72 hr, see Methods in Example 1). As a control, the same WT naïve T cells under Th0 conditions harvested at the same 18 time points were used. For the last four time points (48 hr-72 hr), cells treated with IL-6, TGF-β1, and IL-23 were also profiled. FIG. 6B depicts generation of Th17 cells by IL-6 and TGF-β1 polarizing conditions. FACS analysis of naïve T cells differentiated with TGF-β1 and IL-6 (right) shows enrichment for IL-17 producing Th17 T cells; these cells are not observed in the Th0 controls. FIG. 6C depicts comparison of the obtained microarray profiles to published data from naïve T-cells and differentiated Th17 cells (Wei et. al, 2009; Langmead, B., Trapnell, C., Pop, M. & Salzberg, S. L. in Genome Biol Vol. 10 R25 (2009)). Shown is the Pearson correlation coefficient (Y axis) between each of the 18 profiles (ordered by time point, X axis) and either the naïve T cell profiles (blue) or the differentiated Th17 profiles (green). The expression profiles gradually transition from a naïve-like state (at t=0.5 hr, r2>0.8, p<$10^{-10}$) to a Th17 differentiated state (at t=72 hr, r2>0.65, p<$10^{-10}$). FIG. 6D depicts expression of key cytokines. Shown are the mRNA levels (Y axis) as measured at each of the 18 time points (X axis) in the Th17 polarizing (blue) and Th0 control (red) conditions for the key Th17 genes RORc (left) and IL-17a (middle), both induced, and for the cytokine IFN-γ, unchanged in the time course.

FIG. 8A depicts transcriptional profiles of key genes. A color version of these figures can be found in Yosef et al., "Dynamic regulatory network controlling Th17 cell differentiation, Nature, vol. 496: 461-468 (2013)/doi: 10.1038/nature11981. Shown are the expression levels (Y axis) of three key genes (IL-22, RORc, IL-4) at each time point (X axis) in Th17 polarizing conditions (blue), Th0 controls (red), and following the addition of IL-23 (beginning at 48 hr post differentiation) to the Th17 polarizing conditions (green). FIG. 8B depicts IL-23-dependent transcriptional clusters. Shown are clusters of differentially expressed genes in the IL-23r$^{-/-}$ time course data (blue) compared to WT cells, both treated with Th17 polarizing cytokines and IL23 (red). For each cluster, shown are the average expression levels (Y axis, ±standard deviation, error bars) at each time point (X axis) in the knockout (blue) and wildtype (red) cells. The cluster size ("n"), enriched functional annotations ("F"), and representative member genes ("M") are denoted on top.

FIGS. 9A and 9B are a series of graphs depicting predicted and validated protein levels of ROR-γt during Th17 differentiation. A color version of these figures can be found in Yosef et al., "Dynamic regulatory network controlling Th17 cell differentiation, Nature, vol. 496: 461-468 (2013)/doi: 10.1038/nature11981. FIG. 9A shows RORγt mRNA levels along the original time course under Th17 polarizing conditions, as measured with microarrays (blue). A sigmoidal fit for the mRNA levels (green) is used as an input for a model (based on Schwanhäusser, B. et al. Global quantification of mammalian gene expression control. Nature 473, 337-342, doi:10.1038/nature10098 (2011)) that predicts the level of RORγt protein at each time point (red). FIG. 9B depicts distribution of measured ROR-γt protein levels (x axis) as determined by FACS analysis in Th17 polarizing conditions (blue) and Th0 conditions (red) at 4, 12, 24, and 48 hr post stimulation.

FIGS. 10A and 10B are a series of graphs depicting predictive features for ranking candidates for knockdown. Shown is the fold enrichment (Y axis, in all cases, p<$10^{-3}$, hypergeometric test) in a curated list of known Th17 factors for different (FIG. 10A) network-based features and (FIG. 10B) expression-base features (as used in FIG. 3A).

FIG. 11A depicts how Nanowires do not activate T cells and do not interfere with physiological stimuli. Shown are the levels of mRNA (mean±standard error, n=3) for key genes, measured 48 hr after activation by qPCR (Y axis, mean and standard error of the mean), in T cells grown in petri dishes (left) or on silicon nanowires (right) without polarizing cytokines ('no cytokines') or in the presence of Th17 polarizing cytokines ('TGF-β1+IL6'). FIG. 11B depicts effective knockdown by siRNA delivered on nanowires. Shown is the % of mRNA remaining after knockdown (by qPCR, Y axis: mean±standard error relative to non-targeting siRNA control, n=12, black bar on left) at 10 hours after introduction of polarizing cytokines. The genes presented are a superset of the 39 genes selected for transcriptional profiling. FIG. 11C. Consistency of NW-based knockdowns and resulting phenotypes. Shown are average target transcript reductions and phenotypic changes (as measured by IL-17f and IL-17a expression) for three different experiments of NW-based knockdown (from at least 2 different cultures) of 9 genes at 48 hours post stimulation. Light blue bars: knockdown level (% remaining relative to siRNA controls); dark grey and light green bars: mRNAs of IL-17f and IL-17a, respectively, relative to siRNA controls.

FIG. 12A depicts a comparison of expression levels measured by Fluidigm (Y axis) and Nanostring (X axis) for the same gene under the same perturbation. Expression values were normalized to control genes as described in Example 1. FIG. 12B depicts how analysis of Fluidigm data recapitulates the partitioning of targeted factors into two modules of positive and negative Th17 regulators. Shown are the changes in transcription of the 82 genes out of the 85 gene signature (rows) that significantly responded to at least one factor knockdown (columns).

FIG. 15A depicts a correlation matrix of knockdown profiles. Shown is the Spearman rank correlation coefficient between the RNA-Seq profiles (fold change relative to NT siRNA controls) of regulators perturbed by knockdowns. Genes that were not significantly differentially expressed in any of the samples were excluded from the profiles. FIG. 15B depicts knockdown effects on known marker genes of different CD4+ T cell lineages. Shown are the expression levels for canonical genes (rows) of different T cell lineages (labeled on right) following knockdown of each of 12 regulators (columns). Red/Blue: increase/decrease in gene expression in knockdown compared to non-targeting control (see Methods in Example 1). Shown are only genes that are significantly differentially expressed in at least one knockdown condition. The experiments are hierarchically clustered, forming distinct clusters for Th17-positive regulators (left) and Th17-negative regulators (right). FIG. 15C depicts knockdown effects on two sub-clusters of the T-regulatory cell signature, as defined by Hill et al., Foxp3 transcription-factor-dependent and -independent regulation of the regulatory T cell transcriptional signature. Immunity 27, 786-800, doi:S1074-7613(07)00492-X [pii] 10.1016/j.immuni.2007.09.010 (2007). Each cluster (annotated in Hill et al as Clusters 1 and 5) includes genes that are over expressed in Tregs cells compared to conventional T cells. However, genes in Cluster 1 are more correlated to Foxp3 and responsive to Foxp3 transduction. Conversely, genes in cluster 1 are more directly responsive to TCR and IL-2 and less responsive to Foxp3 in Treg cells. Knockdown of Th17-positive regulators strongly induces the expression of genes in the 'Foxp3' Cluster 1. The knockdown profiles are hierarchically clustered, forming distinct clusters for Th17-positive regulators (left) and Th17-negative regulators (right). Red/Blue: increase/decrease in gene expression in knockdown compared to non-targeting control (see Methods in Example 1). Shown are only genes that are significantly differentially expressed in at least one knockdown condition.

FIGS. 16A, 16B, 16C, and 16D are a series of graphs depicting quantification of cytokine production in knockout cells at 72 h of in-vitro differentiation using Flow cytometry and Enzyme-linked immunosorbent assay (ELISA). All flow cytometry figures shown, except for Oct1, are representative of at least 3 repeats, and all ELISA data has at least 3 replicates. For Oct1, only a limited amount of cells were available from reconstituted mice, allowing for only 2 repeats of the Oct1 deficient mouse for flow cytometry and ELISA. (FIG. 16A, left) Mina$^{-/-}$ T cells activated under Th0 controls are controls for the graphs shown in FIG. 5A. (FIG. 16A, right) TNF secretion by Mina$^{-/-}$ and WT cells, as measured by cytometric bead assay showing that Mina$^{-/-}$ T cells produce more TNF when compared to control. FIG. 15B depicts intracellular cytokine staining of Pou2af1$^{-/-}$ and WT cells for IFN-γ and IL-17a as measured by flow cytometry. (FIG. 15C, left) Flow cytometric analysis of Fas$^{-/-}$ and WT cells for Foxp3 and 11-17 expression. (FIG. 15C, right) IL-2 and Tnf secretion by Fas$^{-/-}$ and WT cells, as measured by a cytokine bead assay ELISA. (FIG. 15D, left). Flow cytometry on Oct1$^{-/-}$ and WT cells for IFN-γ and IL-17a, showing an increase in IFN-γ positive cells in the Th0 condition for the Oct1 deficient mouse. (FIG. 15D, right) Il-17a, IFN-γ, IL-2 and TNF production by Oct1$^{-/-}$ and WT cells, as measured by cytokine ELISA and cytometric bead assay. Statistical significance in the ELISA figures is denoted by: *p<0.05, p<0.01, and *p<0.001.

FIGS. 17A and 17B are a series of illustrations depicting that Zeb1, Smarca4, and Sp4 are key novel regulators affecting the Th17 differentiation programs. A color version of these figures can be found in Yosef et al., "Dynamic regulatory network controlling Th17 cell differentiation, Nature, vol. 496: 461-468 (2013)/doi: 10.1038/nature11981. Shown are regulatory network models centered on different pivotal regulators (square nodes): (FIG. 17A) Zeb1 and Smarca4, and (FIG. 17B) Sp4. In each network, shown are the targets and regulators (round nodes) connected to the pivotal nodes based on perturbation (red and blue dashed edges), TF binding (black solid edges), or both (red and blue solid edges). Genes affected by perturbing the pivotal nodes are colored (red: target is up-regulated by knockdown of pivotal node; blue: target is down-regulated).

FIGS. 19A, 19B, 19C, and 19D are a series of graphs depicting that PROCR is specifically induced in Th17 cells induced by TGF-β1 with IL-6. FIG. 19A depicts how PROCR expression level was assessed by the microarray analysis under Th0 and Th17 conditions at 18 different time points. FIG. 19B depicts how kinetic expression of PROCR mRNA was measured by quantitative RT-PCR analysis in Th17 cells differentiated with TGF-β1 and IL-6. FIG. 19C depicts how PROCR mRNA expression was measured by quantitative RT-PCR analysis in different T cell subsets 72 hr after stimulation by each cytokine. FIG. 19D depicts how PROCR protein expression was examined by flow cytometry in different T cell subsets 72 hr after stimulation with each cytokine.

FIG. 20A depicts how naïve CD4+ T cells were differentiated into Th17 cells by anti-CD3/anti-CD28 stimulation in the presence of activated protein C (aPC, 300 nM), the ligand of PROCR. On day 3, cells were stimulated with PMA and Ionomycin for 4 hr, stained intracellularly for IFN-γ and IL-17 and analyzed by flow cytometry. FIG. 20B depicts IL-17 production from Th17 cells (TGF-β+IL-6) differentiated with or without activated protein C (aPC and Ctl, respectively) was assessed by ELISA on Day 3 and 5. FIG. 20C depicts how naïve CD4+ T cells were polarized under Th17 conditions (TGF-β+IL-6), transduced with either GFP control retrovirus (Ctl RV) or PROCR-expressing retrovirus (PROCR RV). Intracellular expression of IFN-γ and IL-17 in GFP+ cells were assessed by flow cytometry. FIG. 20D depicts how naïve CD4+ T cells from EPCR δ/δmice and control mice were polarized under Th17 conditions with TGF-β1 and IL-6. Intracellular expression of IFN-γ and IL-17 were assessed by flow cytometry.

FIGS. 21A and 21B are a series of graphs depicting that PROCR expression only induces minor changes in the expression of co-stimulatory molecules on Th17 cells. FIG. 21A depicts how naïve CD4+ T cells were polarized under Th17 conditions (TGF-β+IL-6), transduced with either GFP control retrovirus (Ctl GFP) or PROCR-expressing retrovirus (PROCR RV) and expression of ICOS, CTLA-4, PD-1, Pdp and Tim-3 was analyzed by flow cytometry. FIG. 21B depicts how naïve wild type (WT) or EPCR δ/δ CD4+ T cells were differentiated into Th17 cells by anti-CD3/anti-CD28 stimulation in the presence of TGF-β1 and IL-6. Expression of ICOS, CTLA-4, PD-1, Pdp and Tim-3 was assessed by flow cytometry.

FIGS. 22A, 22B, and 22C are a series of graphs depicting that PROCR is expressed in non-pathogenic Th17 cells. FIG. 22A depicts genes for Th17 cells differentiated with TGF-β3+IL-6 (pathogenic) or TGF-β1+IL-6 (non-pathogenic) and comparison of their expression levels in these two subsets. FIGS. 22B and 22C depict how naïve CD4+ T cells were differentiated with TGF-β1 and IL-6, TGF-β3 and IL-6 or IL-1β and IL-6 and PROCR expression was assessed by (FIG. 22B) quantitative RT-PCR analysis (FIG. 22C) and protein expression was determined by flow cytometry.

FIG. 23A depicts quantitative RT-PCR analysis of mRNA expression of several pathogenic signature genes in Th17 cells differentiated with TGFβ1 and IL-6 in the presence of activated protein C (aPC) for 3 days in vitro. FIG. 23B depicts quantitative RT-PCR analysis of mRNA expression of several pathogenic signature genes in naïve CD4+ T cells polarized under Th17 conditions, transduced with either GFP control retrovirus (Control RV) or PROCR-expressing retrovirus (PROCR RV) for 3 days. FIG. 23C depicts quantitative RT-PCR analysis of mRNA expression of several pathogenic signature genes in Th17 cells from EPCR δ/δmice and control mice differentiated with TGFβ1 and IL-6 for 3 days in vitro.

FIG. 24A depicts ChIP-Seq of Rorγt. The PROCR genomic region is depicted. FIG. 24B depicts how the binding of Rorγt to the Procr promoter in Th17 cells was assessed by chromatin immunoprecipitation (ChIP). ChIP was performed using digested chromatin from Th17 cells and anti-Rorγt antibody. DNA was analyzed by quantitative RT-PCR analysis.

FIG. 24C depicts how naïve CD4+ T cells from Rorγt−/− mice and control mice were polarized under Th17 conditions with TGF-β1 and IL-6 and under Th0 conditions (no cytokines) and PROCR expression was analyzed on day 3 by flow cytometry. FIG. 24D depicts how naïve CD4+ T cells polarized under Th17 conditions were transduced with either GFP control retrovirus (Ctl RV) or Rorγt-expressing retrovirus (Rorγt RV) for 3 days. PROCR mRNA expression was measured by quantitative RT-PCR analysis and PROCR protein expression was assessed by flow cytometry.

FIG. 25A depicts how binding of IRF4 or STAT3 to the Procr promoter was assessed by chromatin immunoprecipitation (ChIP)-PCR. ChIP was performed using digested chromatin from Th17 cells and anti-IRF4 or anti-STAT3 antibody. DNA was analyzed by quantitative RT-PCR analysis. FIG. 25B depicts how naïve CD4+ T cells from Cd4$^{Cre}$STAT3$^{fl/fl}$ mice (STAT3 KO) and control mice (WT) were polarized under Th17 conditions with TGF-β1 and IL-6 and under Th0 condition with no cytokines. On day 3, PROCR expression was determined by quantitative PCR. FIG. 25C depicts how naïve CD4+ T cells from Cd4$^{Cre}$IRF4$^{fl/fl}$ mice and control mice were polarized under Th17 conditions with TGF-β1 and IL-6 and under Th0 condition with no cytokines. On day 3, PROCR expression was determined by flow cytometry.

FIG. 26A depicts frequency of CD4+ T cells expressing IL-17 and PROCR isolated from EAE mice 21d after immunization with MOG$_{35-55}$. FIG. 26B depicts how EAE was induced by adoptive transfer of MOG$_{35-55}$-specific 2D2 cells transduced with a control retrovirus (Ctl_GFP) or a PROCR-expression retrovirus (PROCR_RV) and differentiated into Th17 cells. Mean clinical scores and summaries for each group are shown. Results are representative of one of two experiments. FIG. 26C depicts how Rag1−/− mice were reconstituted with either PROCR-deficient (EPCR δ/δRag1−/−) or WT T cells (WT Rag1−/−) and immunized with MOG$_{35-55}$ to induce EAE. The mean clinical score of each group is shown. Results are representative of one of two experiments. FIG. 26D depicts a schematic representation of PROCR regulation. Rorγt, IRF4, and STAT3 induce PROCR expression. PROCR ligation by activated protein C induces a downregulation of the pathogenic signature genes IL-3, CXCL3, CCL4 and Pdp and reduced pathogenicity in EAE.

FIGS. 27A, 27B, and 27C are a series of graphs depicting that FAS promotes Th17 differentiation. Naïve CD4+ T cells from wild type (WT) or FAS-deficient (LPR) mice were differentiated into Th17 cells by anti-CD3/anti-CD28 stimulation in the presence of IL-1β, IL-6 and IL-23. On day 4, cells were (FIG. 27A) stimulated with PMA and Ionomycin for 4 hr, stained intracellularly for IFN-γ and IL-17 and analyzed by flow cytometry and (FIG. 27B) IL-17 production was assessed by ELISA. FIG. 27C depicts how RNA was extracted and expression of IL17a and Il23r mRNA was determined by quantitative PCR.

FIGS. 28A, 28B, and 28C are a series of graphs depicting that FAS inhibits Th1 differentiation. Naïve CD4+ T cells from wild type (WT) or FAS-deficient (LPR) mice were differentiated into Th1 cells by anti-CD3/anti-CD28 stimulation in the presence of IL-12 and anti-IL-4. On day 4, cells were (FIG. 28A) stimulated with PMA and Ionomycin for 4 hr, stained intracellularly for IFN-γ and IL-17 and analyzed by flow cytometry and (FIG. 28B) IFN-γ production was assessed by ELISA. FIG. 28C depicts how RNA was extracted and expression of Ifng mRNA was determined by quantitative PCR.

FIG. 30A depicts mean clinical score±s.e.m. of each group as shown. FIG. 30B depicts how on day 14 CNS infiltrating lymphocytes were isolated, re-stimulated with PMA and Ionomycin for 4 hours and stained intracellularly for IL-17, IFN-γ, and Foxp3. Cells were analyzed by flow cytometry.

FIG. 31A depicts a schematic representation of PROCR, its ligand activated protein C and the signaling adapter PAR1. FIG. 31B depicts how naïve CD4+ T cells were differentiated under polarizing conditions for the indicated T helper cell lineages. Expression of PROCR was determined by quantitative PCR on day 3. FIG. 31C depicts how mice were immunized for EAE, cells were isolated at peak of disease, and cytokine production (IL-17) and PROCR expression were analyzed by flow cytometry. FIG. 31D depicts how naïve and memory cells were isolated from WT and PROCRd/d mice and stimulated with anti-CD3/CD28. Naïve cells were cultured under Th17 polarizing conditions as indicated; memory cells were cultured in the presence or absence of IL-23. After 3 days IL-17A levels in supernatants were analyzed by ELISA.

FIG. 32A depicts signature genes of pathogenic and non-pathogenic Th17 cells. Naïve CD4+ T cells were differentiated into non-pathogenic (TGFβ+IL-6) or pathogenic (TGFβ3+IL-6 or IL-β+IL-6) Th17 cells and PROCR expression was determined by quantitative PCR. FIG. 32B depicts how naïve WT or PROCRd/d CD4+ T cells were stimulated under Th17 polarizing conditions (TGFβ+IL-6) in the presence or absence of aPC. Quantitative expression of three pathogenic signature genes was determined on day 3. FIG. 32C depicts how naïve 2D2 T cells were transduced with a retrovirus encoding for PROCR or a control (GFP), differentiated into Th17 cells in vitro, and transferred into naïve recipients. Mice were monitored for EAE. FIG. 32D depicts how naïve 2D2 T cells were differentiated into Th17 cells in vitro with TGFβ1+IL-6+IL-23 and transferred into WT or PD-L1−/− recipients. Mice were monitored for EAE.

FIG. 33A depicts how C57BL/6 or BalbC mice were implanted with B16 melanoma or CT26 colon cancer cells respectively. Tumor Infiltrating Lymphocytes were isolated 3 weeks after tumor implantation, sorted based on PD-1 and Tim3 expression and analyzed for PROCR expression using real time PCR. Effector memory (CD44hiCD62Llo) CD8 T cells were sorted from naïve mice. FIG. 33B depicts how PROCR, PD-1 and Tim3 expression on antigen-specific CD8 T cells were measured by FACS from acute (Armstrong) and chronic (Clone 13) LCMV infection at different times points as indicated.

DETAILED DESCRIPTION OF THE INVENTION

Figure 1A:
FIGS. 1A, 1B-1, 1B-2, 1C and 1D are a series of graphs and illustrations depicting genome wide temporal expression profiles of Th17 differentiation.

This invention relates generally to compositions and methods for identifying the regulatory networks that control T cell balance, T cell differentiation, T cell maintenance and/or T cell function, as well compositions and methods for exploiting the regulatory networks that control T cell balance, T cell differentiation, T cell maintenance and/or T cell function in a variety of therapeutic and/or diagnostic indications.

The invention provides compositions and methods for modulating T cell balance. The invention provides T cell modulating agents that modulate T cell balance. For example, in some embodiments, the invention provides T cell modulating agents and methods of using these T cell modulating agents to regulate, influence or otherwise impact the level of and/or balance between T cell types, e.g., between Th17 and other T cell types, for example, regulatory T cells (Tregs). For example, in some embodiments, the invention provides T cell modulating agents and methods of using these T cell modulating agents to regulate, influence or otherwise impact the level of and/or balance between Th17 activity and inflammatory potential. As used herein, terms such as "Th17 cell" and/or "Th17 phenotype" and all grammatical variations thereof refer to a differentiated T helper cell that expresses one or more cytokines selected from the group the consisting of interleukin 17A (IL-17A), interleukin 17F (IL-17F), and interleukin 17A/F heterodimer (IL17-AF). As used herein, terms such as "Th1 cell" and/or "Th1 phenotype" and all grammatical variations thereof refer to a differentiated T helper cell that expresses interferon gamma (IFNγ). As used herein, terms such as "Th2 cell" and/or "Th2 phenotype" and all grammatical variations thereof refer to a differentiated T helper cell that expresses one or more cytokines selected from the group the consisting of interleukin 4 (IL-4), interleukin 5 (IL-5) and interleukin 13 (IL-13). As used herein, terms such as "Treg cell" and/or "Treg phenotype" and all grammatical variations thereof refer to a differentiated T cell that expresses Foxp3.

These compositions and methods use T cell modulating agents to regulate, influence or otherwise impact the level and/or balance between T cell types, e.g., between Th17 and other T cell types, for example, regulatory T cells (Tregs).

The invention provides methods and compositions for modulating T cell differentiation, for example, helper T cell (Th cell) differentiation. The invention provides methods and compositions for modulating T cell maintenance, for example, helper T cell (Th cell) maintenance. The invention provides methods and compositions for modulating T cell function, for example, helper T cell (Th cell) function. These compositions and methods use T cell modulating agents to regulate, influence or otherwise impact the level and/or balance between Th17 cell types, e.g., between pathogenic and non-pathogenic Th17 cells. These compositions and methods use T cell modulating agents to influence or otherwise impact the differentiation of a population of T cells, for example toward the Th17 cell phenotype, with or without a specific pathogenic distinction, or away from the Th17 cell phenotype, with or without a specific pathogenic distinction. These compositions and methods use T cell modulating agents to influence or otherwise impact the maintenance of a population of T cells, for example toward the Th17 cell phenotype, with or without a specific pathogenic distinction, or away from the Th17 cell phenotype, with or without a specific pathogenic distinction. These compositions and methods use T cell modulating agents to influence or otherwise impact the differentiation of a population of Th17 cells, for example toward the pathogenic Th17 cell phenotype or away from the pathogenic Th17 cell phenotype, or toward the non-pathogenic Th17 cell phenotype or away from the non-pathogenic Th17 cell phenotype. These compositions and methods use T cell modulating agents to influence or otherwise impact the maintenance of a population of Th17 cells, for example toward the pathogenic Th17 cell phenotype or away from the pathogenic Th17 cell phenotype, or toward the non-pathogenic Th17 cell phenotype or away from the non-pathogenic Th17 cell phenotype. These compositions and methods use T cell modulating agents to influence or otherwise impact the differentiation of a population of T cells, for example toward a non-Th17 T cell subset or away from a non-Th17 cell subset. These compositions and methods use T cell modulating agents to influence or otherwise impact the maintenance of a population of T cells, for example toward a non-Th17 T cell subset or away from a non-Th17 cell subset.

As used herein, terms such as "pathogenic Th17 cell" and/or "pathogenic Th17 phenotype" and all grammatical variations thereof refer to Th17 cells that, when induced in the presence of TGF-β3, express an elevated level of one or more genes selected from Cxcl3, IL22, IL3, Ccl4, Gzmb, Lrmp, Ccl5, Casp1, Csf2, Ccl3, Tbx21, Icos, IL17r, Stat4, Lgals3 and Lag, as compared to the level of expression in a TGF-β3-induced Th17 cells. As used herein, terms such as "non-pathogenic Th17 cell" and/or "non-pathogenic Th17 phenotype" and all grammatical variations thereof refer to Th17 cells that, when induced in the presence of TGF-β3, express a decreased level of one or more genes selected from IL6st, IL1rn, Ikzf3, Maf, Ahr, IL9 and IL10, as compared to the level of expression in a TGF-β3-induced Th17 cells.

These compositions and methods use T cell modulating agents to influence or otherwise impact the function and/or biological activity of a T cell or T cell population. These compositions and methods use T cell modulating agents to influence or otherwise impact the function and/or biological activity of a helper T cell or helper T cell population. These compositions and methods use T cell modulating agents to influence or otherwise impact the function and/or biological activity of a Th17 cell or Th17 cell population. These compositions and methods use T cell modulating agents to influence or otherwise impact the function and/or biological activity of a non-Th17 T cell or non-Th17 T cell population, such as, for example, a Treg cell or Treg cell population, or another CD4+ T cell or CD4+ T cell population. These compositions and methods use T cell modulating agents to influence or otherwise impact the plasticity of a T cell or T cell population, e.g., by converting Th17 cells into a different subtype, or into a new state.

The methods provided herein combine transcriptional profiling at high temporal resolution, novel computational algorithms, and innovative nanowire-based tools for performing perturbations in primary T cells to systematically derive and experimentally validate a model of the dynamic regulatory network that controls Th17 differentiation. See e.g., Yosef et al., "Dynamic regulatory network controlling Th17 cell differentiation, Nature, vol. 496: 461-468 (2013)/ doi: 10.1038/nature11981, the contents of which are hereby incorporated by reference in their entirety. The network consists of two self-reinforcing, but mutually antagonistic, modules, with novel regulators, whose coupled action may be essential for maintaining the level and/or balance between Th17 and other CD4+ T cell subsets. Overall, 9,159 interactions between 71 regulators and 1,266 genes were active in at least one network; 46 of the 71 are novel. The examples provided herein identify and validate 39 regulatory factors, embedding them within a comprehensive temporal network and reveals its organizational principles, and highlights novel drug targets for controlling Th17 differentiation.

A "Th17-negative" module includes regulators such as SP4, ETS2, IKZF4, TSC22D3 and/or, IRF1. It was found that the transcription factor Tsc22d3, which acts as a negative regulator of a defined subtype of Th17 cells, co-localizes on the genome with key Th17 regulators. The "Th17 positive" module includes regulators such as MINA, PML, POU2AF1, PROCR, SMARCA4, ZEB1, EGR2, CCR6, and/or FAS. Perturbation of the chromatin regulator Mina was found to up-regulate Foxp3 expression, perturbation of the co-activator Pou2af1 was found to up-regulate IFN-γ production in stimulated naïve cells, and perturbation of the TNF receptor Fas was found to up-regulate IL-2 production in stimulated naïve cells. All three factors also control IL-17 production in Th17 cells.

Effective coordination of the immune system requires careful balancing of distinct pro-inflammatory and regulatory CD4+ helper T cell populations. Among those, pro-inflammatory IL-17 producing Th17 cells play a key role in the defense against extracellular pathogens and have also been implicated in the induction of several autoimmune diseases (see e.g., Bettelli, E., Oukka, M. & Kuchroo, V. K. T(H)-17 cells in the circle of immunity and autoimmunity. Nat Immunol 8, 345-350, doi:10.1038/ni0407-345 (2007)), including for example, psoriasis, ankylosing spondylitis, multiple sclerosis and inflammatory bowel disease. Th17 differentiation from naïve T-cells can be triggered in vitro by the cytokines TGF-β1 and IL-6. While TGF-β1 alone induces Foxp3+ regulatory T cells (iTreg) (see e.g., Zhou, L. et al. TGF-beta-induced Foxp3 inhibits T(H)17 cell differentiation by antagonizing RORgammat function. Nature 453, 236-240, doi:nature06878 [pii]10.1038/nature06878 (2008)), the presence of IL-6 inhibits iTreg and induces Th17 differentiation (Bettelli et al., Nat Immunol 2007).

While TGF-β1 is required for the induction of Foxp3+ induced Tregs (iTregs), the presence of IL-6 inhibits the generation of iTregs and initiates the Th17 differentiation program. This led to the hypothesis that a reciprocal relationship between pathogenic Th17 cells and Treg cells exists (Bettelli et al., Nat Immunol 2007), which may depend on the balance between the mutually antagonistic master transcription factors (TFs) ROR-γt (in Th17 cells) and Foxp3 (in Treg cells) (Zhou et al., Nature 2008). Other cytokine combinations have also been shown to induce ROR-γt and differentiation into Th17 cells, in particular TGF-β1 and IL-21 or IL-1β, TGF-β3+IL-6, IL-6, and IL-23 (Ghoreschi, K. et al. Generation of pathogenic T(H)17 cells in the absence of TGF-beta signaling. Nature 467, 967-971, doi: 10.1038/nature09447 (2010)). Finally, although a number of cytokine combinations can induce Th17 cells, exposure to IL-23 is critical for both stabilizing the Th17 phenotype and the induction of pathogenic effector functions in Th17 cells.

Much remains unknown about the regulatory network that controls Th17 cells (O'Shea, J. et al. Signal transduction and Th17 cell differentiation. Microbes Infect 11, 599-611 (2009); Zhou, L. & Littman, D. Transcriptional regulatory networks in Th17 cell differentiation. Curr Opin Immunol 21, 146-152 (2009)). Developmentally, as TGF-β is required for both Th17 and iTreg differentiation, it is not understood how balance is achieved between them or how IL-6 biases toward Th17 differentiation (Bettelli et al., Nat Immunol 2007). Functionally, it is unclear how the pro-inflammatory status of Th17 cells is held in check by the immunosuppressive cytokine IL-10 (O'Shea et al., Microbes Infect 2009; Zhou & Littman, Curr Opin Immunol 2009). Finally, many of the key regulators and interactions that drive development of Th17 remain unknown (Korn, T., Bettelli, E., Oukka, M. & Kuchroo, V. K. IL-17 and Th17 Cells. Annu Rev Immunol 27, 485-517, doi:10.1146/annurev.immunol.021908. 13271010.1146/annurev.immunol.021908. 132710 [pii] (2009)).

Recent studies have demonstrated the power of coupling systematic profiling with perturbation for deciphering mammalian regulatory circuits (Amit, I. et al. Unbiased reconstruction of a mammalian transcriptional network mediating pathogen responses. Science 326, 257-263, doi:10.1126/science.1179050 (2009); Novershtern, N. et al. Densely interconnected transcriptional circuits control cell states in human hematopoiesis. Cell 144, 296-309, doi:10.1016/j.cell.2011.01.004 (2011); Litvak, V. et al. Function of C/EBPdelta in a regulatory circuit that discriminates between transient and persistent TLR4-induced signals. Nat. Immunol. 10, 437-443, doi:10.1038/ni.1721 (2009); Suzuki, H. et al. The transcriptional network that controls growth arrest and differentiation in a human myeloid leukemia cell line. Nat Genet 41, 553-562 (2009); Amit, I., Regev, A. & Hacohen, N. Strategies to discover regulatory circuits of the mammalian immune system. Nature reviews. Immunology 11, 873-880, doi:10.1038/nri3109 (2011); Chevrier, N. et al. Systematic discovery of TLR signaling components delineates viral-sensing circuits. Cell 147, 853-867, doi:10.1016/j.cell.2011.10.022 (2011); Garber, M. et al. A High-Throughput Chromatin Immunoprecipitation Approach Reveals Principles of Dynamic Gene Regulation in Mammals. Molecular cell, doi:10.1016/j.molcel.2012.07.030 (2012)). Most of these studies have relied upon computational circuit-reconstruction algorithms that assume one 'fixed' network. Th17 differentiation, however, spans several days, during which the components and wiring of the regulatory network likely change. Furthermore, naïve T cells and Th17 cells cannot be transfected effectively in vitro by traditional methods without changing their phenotype or function, thus limiting the effectiveness of perturbation strategies for inhibiting gene expression.

These limitations are addressed in the studies presented herein by combining transcriptional profiling, novel computational methods, and nanowire-based siRNA delivery (Shalek, A. K. et al. Vertical silicon nanowires as a universal platform for delivering biomolecules into living cells. Proc. Natl. Acad. Sci. U.S.A. 107, 1870-1875, doi:10.1073/pnas.0909350107 (2010) (FIG. 1A) to construct and validate the transcriptional network of Th17 differentiation. Using genome-wide profiles of mRNA expression levels during differentiation, a model of the dynamic regulatory circuit that controls Th17 differentiation, automatically identifying 25 known regulators and nominating 46 novel regulators that control this system, was built. Silicon nanowires were used to deliver siRNA into naïve T cells (Shalek et al., Proc. Natl. Acad. Sci. U.S.A. 2010) to then perturb and measure the transcriptional effect of 29 candidate transcriptional regulators and 10 candidate receptors on a representative gene signature at two time points during differentiation. Combining this data, a comprehensive validated model of the network was constructed. In particular, the circuit includes 12 novel validated regulators that either suppress or promote Th17 development. The reconstructed model is organized into two coupled, antagonistic, and densely intra-connected modules, one promoting and the other suppressing the Th17 program. The model highlights 12 novel regulators, whose function was further characterized by their effects on global gene expression, DNA binding profiles, or Th17 differentiation in knockout mice. The studies provided herein demonstrate an unbiased systematic and functional approach to understanding the development of the Th17 T cell subset.

The methods provided herein combine a high-resolution transcriptional time course, novel methods to reconstruct regulatory networks, and innovative nanotechnology to perturb T cells, to construct and validate a network model for Th17 differentiation. The model consists of three consecutive, densely intra-connected networks, implicates 71 regulators (46 novel), and suggests substantial rewiring in 3 phases. The 71 regulators significantly overlap with genes genetically associated with inflammatory bowel disease (Jostins, L. et al. Host-microbe interactions have shaped the genetic architecture of inflammatory bowel disease. Nature 491, 119-124, doi:10.1038/nature11582 (2012)) (11 of 71, $p<10^{-9}$). Building on this model, 127 putative regulators (80 novel) were systematically ranked, and top ranking ones were tested experimentally.

It was found that the Th17 regulators are organized into two tightly coupled, self-reinforcing but mutually antagonistic modules, whose coordinated action may explain how the balance between Th17, Treg, and other effector T cell subsets is maintained, and how progressive directional differentiation of Th17 cells is achieved. Within the two modules are 12 novel factors (FIGS. 4 and 5), which were further characterized, highlighting four of the factors (others are in FIGS. 17A, 17B).

This validated model highlights at least 12 novel regulators that either positively or negatively impact the Th17 program (FIGS. 4 and 5). Remarkably, these and known regulators are organized in two tightly coupled, self-reinforcing and mutually antagonistic modules, whose coordinated action may explain how the balance between Th17, Treg, and other effector T cells is maintained, and how progressive directional differentiation of Th17 cells is achieved while repressing differentiation of other T cell subsets. The function of four of the 12 regulators—Mina, Fas, Pou2af1, and Tsc22d3—was further validated and characterized by undertaking Th17 differentiation of T cells from corresponding knockout mice or with ChIP-Seq binding profiles.

The T cell modulating agents are used to modulate the expression of one or more target genes or one or more products of one or more target genes that have been identified as genes responsive to Th17-related perturbations. These target genes are identified, for example, by contacting a T cell, e.g., naïve T cells, partially differentiated T cells, differentiated T cells and/or combinations thereof, with a T cell modulating agent and monitoring the effect, if any, on the expression of one or more signature genes or one or more products of one or more signature genes. In some embodiments, the one or more signature genes are selected from those listed in Table 1 or Table 2 shown below.

TABLE 1

Signature Genes

| | | | |
|---|---|---|---|
| IL17A | IL21R | CCL1 | PSTPIP1 |
| IL7R | BCL3 | CD247 | IER3 |
| IRF4 | DPP4 | PROCR | FZD7 |
| CXCL10 | TGFBR1 | RELA | GLIPR1 |
| IL12RB1 | CD83 | HIF1A | AIM1 |
| TBX21 | RBPJ | PRNP | CD4 |
| ZNF281 | CXCR3 | IL17RA | LMNB1 |
| IL10RA | NOTCH2 | STAT1 | MGLL |
| CXCR4 | CCL4 | LRRFIP1 | LSP1 |
| TNFRSF13B | TAL2 | KLRD1 | GJA1 |
| ACVR1B | IL9 | RUNX1 | LGALS3BP |
| TGIF1 | FAS | ID2 | ARHGEF3 |
| ABCG2 | SPRY1 | STAT5A | BCL2L11 |
| REL | PRF1 | TNFRSF25 | TGM2 |
| ID3 | FASLG | BATF | UBIAD1 |
| ZEB1 | MT2A | KAT2B | MAP3K5 |
| MYD88 | POU2AF1 | NFATC2 | RAB33A |
| EGR2 | IFNG | CD70 | CASP1 |

TABLE 1-continued

Signature Genes

| | | | |
|---|---|---|---|
| AES | PLAC8 | LITAF | FOXP1 |
| PML | IL17F | IL27RA | MTA3 |
| TGFBR3 | DDR1 | IL22 | IFIH1 |
| CCR8 | IL4 | MINA | RASGRP1 |
| ZFP161 | CD28 | XBP1 | XRCC5 |
| IRF1 | TNFSF9 | PRDM1 | NCF1C |
| CCR6 | SMARCA4 | AHR | NUDT4 |
| SMOX | YAX2 | SLAMF7 | PDCD1LG2 |
| ITGB1 | IL21 | IL1RN | PYCR1 |
| CASP6 | SAP30 | MBNL3 | AQP3 |
| NFKBIE | CD9 | ARID5A | SEMA7A |
| LAMP2 | IL24 | TRIM24 | PRC1 |
| GATA3 | STAT5B | CSF2 | IFIT1 |
| RORA | SKI | NFE2L2 | DNTT |
| SGK1 | BCL6 | IL23R | PMEPA1 |
| IL2RA | ELK3 | KLF6 | GAP43 |
| MT1A | CD74 | ACVR2A | PRICKLE1 |
| JAK3 | STAT6 | NR3C1 | OAS2 |
| IL4R | TNFSF8 | CCR4 | ERRFI1 |
| NAMPT | IL3 | CXCR5 | LAD1 |
| ITGA3 | TGFB1 | SKAP2 | TMEM126A |
| TGFB3 | ETV6 | PLEKHF2 | LILRB1, LILRB2, LILRB3, LILRB4, LILRB5 |
| INHBA | CASP4 | STAT2 | KATNA1 |
| KLF7 | CEBPB | IRF7 | B4GALT1 |
| RUNX3 | TRAF3 | FLI1 | ANXA4 |
| NFKBIZ | TRPS1 | IRF9 | SULT2B1 |
| SERPINE2 | JUN | GFI1 | PHLDA1 |
| RXRA | STAT4 | MXI1 | PRKD3 |
| SERTAD1 | CMTM6 | IFI35 | TAP1 |
| MAF | SOCS3 | MAX | TRIM5 |
| IL10 | TSC22D3 | ZNF238 | FLNA |
| BMPR1A | LIF | CHD7 | GUSB |
| PTPRJ | DAXX | FOXM1 | C14ORF83 |
| STAT3 | KLF9 | BCL11B | VAV3 |
| CCR5 | IL6ST | RUNX2 | ARL5A |
| CCL20 | CLCF1 | EMP1 | GRN |
| SPP1 | NFIL3 | PELI2 | PRKCA |
| CD80 | IKZF4 | SEMA4D | PECI |
| RORC | ISG20 | STARD10 | ARMCX2 |
| SERPINB1 | CD86 | TIMP2 | SLC2A1 |
| IL12RB2 | IL2B | KLF10 | RPP14 |
| IFNGR2 | NCOA1 | CTSW | PSMB9 |
| SMAD3 | NOTCH1 | GEM | CASP3 |
| FOXP3 | TNFRSF12A | TRIM25 | TRAT1 |
| CD24 | CD274 | HLA-A | PLAGL1 |
| CD5L | MAFF | MYST4 | RAD51AP1 |
| CD2 | ATF4 | FRMD4B | NKG7 |
| TNFSF11 | ARNTL | RFK | IFITM2 |
| ICOS | IL1R1 | CD44 | HIP1R |
| IRF8 | FOXO1 | ERCC5 | |

TABLE 2

Subset of Signature Genes

| | | | |
|---|---|---|---|
| AHR | HIF1A | IRF4 | REL |
| ARID5A | ICOS | IRF8 | RORA |
| BATF | ID2 | ITGA3 | RORC |
| CASP4 | ID3 | KLF6 | SERPINB1 |
| CASP6 | IFNG | KLRD1 | SGK1 |
| CCL20 | IL10 | LIF | SKAP2 |
| CCL4 | IL10RA | LTA | SKI |
| CCR5 | IL17A | MAF | SMOX |
| CCR6 | IL17F | MAFF | SOCS3 |
| CD24 | IL17RA | MINA | STAT1 |
| CD5L | IL2 | MYC | STAT3 |
| CD80 | IL21 | NFATC2 | STAT4 |
| CEBPB | IL21R | NFE2L2 | TBX21 |
| CLCF1 | IL22 | NFIL3 | TGFBR1 |
| CSF2 | IL23R | NOTCH1 | TGIF1 |
| CXCR3 | IL24 | NUDT4 | TNFRSF25 |

TABLE 2-continued

Subset of Signature Genes

| | | | |
|---|---|---|---|
| EGR2 | IL2RA | PML | TNFSF8 |
| ELK3 | IL7R | POU2AF1 | TRIM24 |
| ETV6 | IL9 | PROCR | TRPS1 |
| FAS | INHBA | PSMB9 | TSC22D3 |
| FOXP3 | IRF1 | RBPJ | ZFP36L1 |
| GATA3 | | | |

In some embodiments, the target gene is one or more Th17-associated cytokine(s) or receptor molecule(s) selected from those listed in Table 3. In some embodiments, the target gene is one or more Th17-associated transcription regulator(s) selected from those shown in Table 4.

TABLE 3

Th17-Associated Receptor Molecules

| | | | |
|---|---|---|---|
| ACVR1B | CXCR4 | IL6ST | PROCR |
| ACVR2A | CXCR5 | IL7R | PTPRJ |
| BMPR1A | DDR1 | IRAK1BP1 | PVR |
| CCR4 | FAS | ITGA3 | TLR1 |
| CCR5 | IL15RA | KLRD1 | TNFRSF12A |
| CCR6 | IL18R1 | MYD88 | TNFRSF13B |
| CCR8 | IL1RN | PLAUR | TRAF3 |
| CXCR3 | | | |

TABLE 4

Th17-Associated Transcription Regulators

| | | | |
|---|---|---|---|
| TRPS1 | SMARCA4 | CDYL | SIRT2 |
| SMOX | ZFP161 | IKZF4 | MAFF |
| ARNTL | TP53 | NCOA1 | CHMP1B |
| UBE2B | SUZ12 | SS18 | GATAD2B |
| NR3C1 | POU2AF1 | PHF13 | ZNF703 |
| TRIM24 | MYST4 | MTA3 | ZNRF1 |
| FLI1 | MXI1 | ASXL1 | JMJD1C |
| SP4 | CHD7 | LASS4 | ZFP36L2 |
| EGR2 | CREB3L2 | SKIL | TSC22D4 |
| ZNF281 | VAX2 | FOSL2 | NFE2L2 |
| RELA | KLF10 | RUNX2 | RNF11 |
| IRF7 | SKI | TLE1 | ARID3A |
| STAT2 | ELK3 | ELL2 | MEN1 |
| IRF3 | ZEB1 | BCL11B | CBX4 |
| XBP1 | LRRFIP1 | KAT2B | ZFP62 |
| PRDM1 | PAXBP1 | KLF6 | CIC |
| ATF4 | ID1 | E2F8 | HCLS1 |
| CREB1 | ZNF238 | ZNRF2 | ZFP36L1 |
| IRF9 | VAV1 | TSC22D3 | TGIF1 |
| IRF2 | MINA | HMGB2 | |
| FOXJ2 | BATF3 | FUS | |

In some embodiments, the target gene is one or more Th17-associated transcription regulator(s) selected from those shown in Table 5. In some embodiments, the target gene is one or more Th17-associated receptor molecule(s) selected from those listed in Table 6. In some embodiments, the target gene is one or more Th17-associated kinase(s) selected from those listed in Table 7. In some embodiments, the target gene is one or more Th17-associated signaling molecule(s) selected from those listed in Table 8. In some embodiments, the target gene is one or more Th17-associated receptor molecule(s) selected from those listed in Table 9.

TABLE 5

Candidate Regulators

| | % Interactions OR differential expression (compared to Th0) | | | IL23R knockout |
|---|---|---|---|---|
| Symbol | Early | Intermediate | Late | (late) |
| IRF4 | 0.892473118 | 0.841397849 | 1 | UNDER-EXPR |
| IFI35 | 1 | 0.952380952 | 0.904761905 | UNDER-EXPR |
| ETS1 | 1 | 0.636363636 | 0.636363636 | UNDER-EXPR |
| NMI | 1 | 0.857142857 | 0 | UNDER-EXPR |
| SAP18 | 0.785714286 | 0.928571429 | 1 | OVER-EXPR |
| FLI1 | 1 | 0.971590909 | 0.869318182 | |
| SP4 | 1 | 0.710900474 | 0.63507109 | UNDER-EXPR |
| SP100 | 1 | 0 | 0 | UNDER-EXPR |
| TBX21 | 0 | 1 | 0 | OVER-EXPR |
| POU2F2 | 0 | 1 | 0 | OVER-EXPR |
| ZNF281 | 0 | 1 | 0 | UNDER-EXPR |
| NFIL3 | 0.611111111 | 0.611111111 | 1 | |
| SMARCA4 | 0.805825243 | 0.757281553 | 1 | OVER-EXPR |
| CSDA | 0 | 0 | 1 | OVER-EXPR |
| STAT3 | 0.855392157 | 0.970588235 | 1 | UNDER-EXPR |
| FOXO1 | 0.875 | 1 | 0.875 | |
| NCOA3 | 0.875 | 1 | 0.9375 | |
| LEF1 | 0.380952381 | 0.904761905 | 1 | UNDER-EXPR |
| SUZ12 | 0 | 1 | 0 | OVER-EXPR |
| CDC5L | 0 | 1 | 0 | UNDER-EXPR |
| CHD7 | 1 | 0.860465116 | 0.686046512 | UNDER-EXPR |
| HIF1A | 0.733333333 | 0.666666667 | 1 | UNDER-EXPR |
| RELA | 0.928571429 | 1 | 0.880952381 | UNDER-EXPR |
| STAT2 | 1 | 0.821428571 | 0 | |
| STAT5B | 1 | 0.848484848 | 0.515151515 | UNDER-EXPR |
| RORC | 0 | 0 | 1 | UNDER-EXPR |
| STAT1 | 1 | 0.635658915 | 0 | UNDER-EXPR |
| MAZ | 0 | 1 | 0 | |
| LRRFIP1 | 0.9 | 0.8 | 1 | |
| REL | 1 | 0 | 0 | OVER-EXPR |
| CITED2 | 1 | 0 | 0 | UNDER-EXPR |
| RUNX1 | 0.925149701 | 0.925149701 | 1 | UNDER-EXPR |
| ID2 | 0.736842105 | 0.789473684 | 1 | |
| SATB1 | 0.452380952 | 0.5 | 1 | UNDER-EXPR |
| TRIM28 | 0 | 1 | 0 | |
| STAT6 | 0.54 | 0.64 | 1 | OVER-EXPR |
| STAT5A | 0 | 0.642241379 | 1 | UNDER-EXPR |
| BATF | 0.811732606 | 0.761255116 | 1 | UNDER-EXPR |
| EGR1 | 0.857142857 | 1 | 0 | OVER-EXPR |
| EGR2 | 0.896428571 | 0.839285714 | 1 | OVER-EXPR |
| AES | 0.888888889 | 1 | 0.777777778 | |
| IRF8 | 0 | 1 | 0.824786325 | OVER-EXPR |
| SMAD2 | 0.806060606 | 0.781818182 | 1 | |
| NFKB1 | 0.266666667 | 0.706666667 | 1 | UNDER-EXPR |
| PHF21A | 1 | 0.533333333 | 0.933333333 | UNDER-EXPR |
| CBFB | 0.35 | 0.9 | 1 | |
| ZFP161 | 0.818181818 | 0.714876033 | 1 | OVER-EXPR |
| ZEB2 | 0 | 0.411764706 | 1 | |
| SP1 | 0 | 0.740740741 | 1 | |
| FOXJ2 | 0 | 1 | 1 | |
| IRF1 | 1 | 0 | 0 | |
| MYC | 0 | 0.595505618 | 1 | UNDER-EXPR |
| IRF2 | 1 | 0 | 0 | |
| EZH1 | 1 | 0.8 | 0.44 | UNDER-EXPR |
| RUNX2 | 0 | 0 | 1 | |
| JUN | 0.647058824 | 0.647058824 | 1 | OVER-EXPR |
| STAT4 | 1 | 0 | 0 | UNDER-EXPR |
| MAX | 0.947368421 | 0.789473684 | 1 | |
| TP53 | 0.292307692 | 0.615384615 | 1 | UNDER-EXPR |
| IRF3 | 1 | 0.485294118 | 0.235294118 | UNDER-EXPR |
| BCL11B | 0.666666667 | 0.611111111 | 1 | |
| E2F1 | 0 | 0 | 1 | OVER-EXPR |
| IRF9 | 1 | 0.440433213 | 0 | UNDER-EXPR |
| GATA3 | 1 | 0 | 0 | OVER-EXPR |
| TRIM24 | 0.965517241 | 1 | 0.965517241 | UNDER-EXPR |
| E2F4 | 0.083333333 | 0.5 | 1 | |
| NR3C1 | 1 | 1 | 0 | UNDER-EXPR |
| ETS2 | 1 | 0.925925926 | 0.864197531 | OVER-EXPR |
| CREB1 | 0.802197802 | 0.706959707 | 1 | |
| IRF7 | 1 | 0.777777778 | 0 | OVER-EXPR |
| TFEB | 0.8 | 0.6 | 1 | |
| TRPS1 | | OVER-EXPR | | UNDER-EXPR |
| SMOX | | OVER-EXPR | OVER-EXPR | UNDER-EXPR |
| RORA | | OVER-EXPR | OVER-EXPR | UNDER-EXPR |

TABLE 5-continued

Candidate Regulators

| Symbol | % Interactions OR differential expression (compared to Th0) | | | IL23R knockout (late) |
|---|---|---|---|---|
| | Early | Intermediate | Late | |
| ARID5A | OVER-EXPR | OVER-EXPR | OVER-EXPR | OVER-EXPR |
| ETV6 | OVER-EXPR | OVER-EXPR | | |
| ARNTL | | OVER-EXPR | | UNDER-EXPR |
| UBE2B | | | OVER-EXPR | UNDER-EXPR |
| XBP1 | | | OVER-EXPR | |
| PRDM1 | OVER-EXPR | OVER-EXPR | | UNDER-EXPR |
| ATF4 | | | OVER-EXPR | OVER-EXPR |
| POU2AF1 | | OVER-EXPR | | UNDER-EXPR |
| CE6PB | | OVER-EXPR | OVER-EXPR | UNDER-EXPR |
| CREM | | OVER-EXPR | OVER-EXPR | UNDER-EXPR |
| MYST4 | | OVER-EXPR | OVER-EXPR | UNDER-EXPR |
| MXI1 | | | OVER-EXPR | UNDER-EXPR |
| RBPJ | | OVER-EXPR | OVER-EXPR | OVER-EXPR |
| CREB3L2 | | OVER-EXPR | OVER-EXPR | UNDER-EXPR |
| VAX2 | | | OVER-EXPR | OVER-EXPR |
| KLF10 | | OVER-EXPR | OVER-EXPR | |
| SKI | | OVER-EXPR | OVER-EXPR | UNDER-EXPR |
| ELK3 | | OVER-EXPR | | OVER-EXPR |
| ZEB1 | | OVER-EXPR | OVER-EXPR | OVER-EXPR |
| PML | OVER-EXPR | OVER-EXPR | | UNDER-EXPR |
| SERTAD1 | | | OVER-EXPR | UNDER-EXPR |
| NOTCH1 | OVER-EXPR | OVER-EXPR | | OVER-EXPR |
| AHR | OVER-EXPR | OVER-EXPR | OVER-EXPR | UNDER-EXPR |
| C21ORF66 | | | OVER-EXPR | UNDER-EXPR |
| SAP30 | | | OVER-EXPR | OVER-EXPR |
| ID1 | | OVER-EXPR | OVER-EXPR | OVER-EXPR |
| ZNF238 | | OVER-EXPR | OVER-EXPR | |
| VAV1 | | OVER-EXPR | | UNDER-EXPR |
| MINA | | OVER-EXPR | OVER-EXPR | UNDER-EXPR |
| BATF3 | | | OVER-EXPR | OVER-EXPR |
| CDYL | | | | UNDER-EXPR |
| IKZF4 | OVER-EXPR | OVER-EXPR | OVER-EXPR | OVER-EXPR |
| NCOA1 | | OVER-EXPR | | OVER-EXPR |
| BCL3 | OVER-EXPR | OVER-EXPR | OVER-EXPR | UNDER-EXPR |
| JUNB | | OVER-EXPR | | UNDER-EXPR |
| SS18 | | OVER-EXPR | | OVER-EXPR |
| PHF13 | | | | OVER-EXPR |
| MTA3 | | OVER-EXPR | | UNDER-EXPR |
| ASXL1 | | OVER-EXPR | | OVER-EXPR |
| LASS4 | | | OVER-EXPR | UNDER-EXPR |
| SKIL | | OVER-EXPR | OVER-EXPR | OVER-EXPR |
| DDIT3 | | | OVER-EXPR | OVER-EXPR |
| FOSL2 | | OVER-EXPR | OVER-EXPR | |
| TLE1 | | OVER-EXPR | OVER-EXPR | |
| ATF3 | | | | OVER-EXPR |
| ELL2 | OVER-EXPR | OVER-EXPR | | OVER-EXPR |
| JARID2 | | | OVER-EXPR | OVER-EXPR |
| KLF9 | | OVER-EXPR | OVER-EXPR | OVER-EXPR |
| KAT2B | | OVER-EXPR | | UNDER-EXPR |
| KLF6 | | OVER-EXPR | OVER-EXPR | UNDER-EXPR |
| E2F8 | | OVER-EXPR | OVER-EXPR | OVER-EXPR |
| BCL6 | | OVER-EXPR | | UNDER-EXPR |
| ZNRF2 | | | | UNDER-EXPR |
| TSC22D3 | | | OVER-EXPR | UNDER-EXPR |
| KLF7 | | | OVER-EXPR | |
| HMGB2 | | OVER-EXPR | | |
| FUS | | OVER-EXPR | | OVER-EXPR |
| SIRT2 | | | OVER-EXPR | |
| MAFF | | OVER-EXPR | OVER-EXPR | OVER-EXPR |
| CHMP1B | | | OVER-EXPR | UNDER-EXPR |
| GATAD2B | OVER-EXPR | | | OVER-EXPR |
| SMAD7 | | OVER-EXPR | | OVER-EXPR |
| ZNF703 | | OVER-EXPR | | OVER-EXPR |
| ZNRF1 | | | OVER-EXPR | OVER-EXPR |
| JMJD1C | OVER-EXPR | | | UNDER-EXPR |
| ZFP36L2 | | | OVER-EXPR | UNDER-EXPR |
| TSC22D4 | | | | |
| NFE2L2 | OVER-EXPR | OVER-EXPR | OVER-EXPR | UNDER-EXPR |
| RNF11 | | | | OVER-EXPR |
| ARID3A | | OVER-EXPR | OVER-EXPR | UNDER-EXPR |
| MEN1 | | | OVER-EXPR | OVER-EXPR |
| RARA | | OVER-EXPR | OVER-EXPR | UNDER-EXPR |
| CBX4 | OVER-EXPR | OVER-EXPR | | OVER-EXPR |
| ZFP62 | | OVER-EXPR | | |

TABLE 5-continued

Candidate Regulators

| Symbol | % Interactions OR differential expression (compared to Th0) | | | IL23R knockout |
|---|---|---|---|---|
| | Early | Intermediate | Late | (late) |
| CIC | | | OVER-EXPR | |
| HCLS1 | | | | UNDER-EXPR |
| ZFP36L1 | | | | UNDER-EXPR |
| TGIF1 | | | | UNDER-EXPR |
| SMAD4 | | | | OVER-EXPR |
| IL7R | | OVER EXPR | OVER EXPR | UNDER EXPR |
| ITGA3 | | OVER EXPR | OVER EXPR | |
| IL1R1 | | OVER EXPR | OVER EXPR | UNDER EXPR |
| FAS | OVER EXPR | | | UNDER EXPR |
| CCR5 | OVER EXPR | OVER EXPR | OVER EXPR | UNDER EXPR |
| CCR6 | | OVER EXPR | OVER EXPR | |
| ACVR2A | | OVER EXPR | OVER EXPR | UNDER EXPR |
| IL6ST | OVER EXPR | OVER EXPR | | UNDER EXPR |
| IL17RA | OVER EXPR | OVER EXPR | | UNDER EXPR |
| CCR8 | | OVER EXPR | | |
| DDR1 | | OVER EXPR | OVER EXPR | UNDER EXPR |
| PROCR | | OVER EXPR | OVER EXPR | OVER EXPR |
| IL2RA | OVER EXPR | OVER EXPR | OVER EXPR | OVER EXPR |
| IL12RB2 | | OVER EXPR | OVER EXPR | UNDER EXPR |
| MYD88 | OVER EXPR | OVER EXPR | | UNDER EXPR |
| BMPR1A | | | OVER EXPR | UNDER EXPR |
| PTPRJ | | OVER EXPR | OVER EXPR | OVER EXPR |
| TNFRSF13B | | OVER EXPR | OVER EXPR | UNDER EXPR |
| CXCR3 | | OVER EXPR | | UNDER EXPR |
| IL1RN | | OVER EXPR | OVER EXPR | UNDER EXPR |
| CXCR5 | OVER EXPR | OVER EXPR | OVER EXPR | UNDER EXPR |
| CCR4 | | OVER EXPR | OVER EXPR | UNDER EXPR |
| IL4R | | OVER EXPR | OVER EXPR | UNDER EXPR |
| IL2RB | | OVER EXPR | OVER EXPR | |
| TNFRSF12A | | OVER EXPR | OVER EXPR | OVER EXPR |
| CXCR4 | | OVER EXPR | OVER EXPR | UNDER EXPR |
| KLRD1 | | OVER EXPR | OVER EXPR | |
| IRAK1BP1 | | OVER EXPR | | OVER EXPR |
| PVR | OVER EXPR | OVER EXPR | OVER EXPR | UNDER EXPR |
| IL15RA | OVER EXPR | | | OVER EXPR |
| TLR1 | | | | OVER EXPR |
| ACVR1B | | | OVER EXPR | OVER EXPR |
| IL12RB1 | OVER EXPR | OVER EXPR | | OVER EXPR |
| IL18R1 | | OVER EXPR | | OVER EXPR |
| TRAF3 | | OVER EXPR | | OVER EXPR |
| IFNGR1 | | | OVER EXPR | UNDER EXPR |
| PLAUR | | | OVER EXPR | OVER EXPR |
| IL21R | | | | UNDER EXPR |
| IL23R | | | OVER EXPR | UNDER EXPR |

TABLE 6

Candidate Receptor Molecules

| Symbol | % Differential expression (compared to Th0) | | | IL23R knockout |
|---|---|---|---|---|
| | Early | Intermediate | Late | (late) |
| PTPLA | | | | UNDER EXPR |
| PSTPIP1 | | OVER EXPR | OVER EXPR | UNDER EXPR |
| TK1 | | | | UNDER EXPR |
| EIF2AK2 | OVER EXPR | | | |
| PTEN | | | | UNDER EXPR |
| BPGM | | | | UNDER EXPR |
| DCK | | | | OVER EXPR |
| PTPRS | | | | OVER EXPR |
| PTPN18 | | | | OVER EXPR |
| MKNK2 | | | | OVER EXPR |
| PTPN1 | | OVER EXPR | | UNDER EXPR |
| PTPRE | | | | UNDER EXPR |
| SH2D1A | | | | OVER EXPR |
| DUSP22 | OVER EXPR | | | |
| PLK2 | | | | OVER EXPR |
| DUSP6 | | | | UNDER EXPR |
| CDC25B | | | | UNDER EXPR |
| SLK | | | OVER EXPR | UNDER EXPR |

TABLE 6-continued

Candidate Receptor Molecules

| | % Differential expression (compared to Th0) | | | IL23R knockout |
|---|---|---|---|---|
| Symbol | Early | Intermediate | Late | (late) |
| MAP3K5 | | | | UNDER EXPR |
| BMPR1A | | | OVER EXPR | UNDER EXPR |
| ACP5 | | OVER EXPR | OVER EXPR | UNDER EXPR |
| TXK | | OVER EXPR | OVER EXPR | UNDER EXPR |
| RIPK3 | | OVER EXPR | OVER EXPR | UNDER EXPR |
| PPP3CA | | | | OVER EXPR |
| PTPRF | | OVER EXPR | OVER EXPR | OVER EXPR |
| PACSIN1 | | | | OVER EXPR |
| NEK4 | | OVER EXPR | | UNDER EXPR |
| PIP4K2A | | | | UNDER EXPR |
| PPME1 | | OVER EXPR | OVER EXPR | UNDER EXPR |
| SRPK2 | | | | UNDER EXPR |
| DUSP2 | | | | OVER EXPR |
| PHACTR2 | | OVER EXPR | | OVER EXPR |
| HK2 | OVER EXPR | OVER EXPR | | |
| DCLK1 | | | | OVER EXPR |
| PPP2R5A | | | | UNDER EXPR |
| RIPK1 | OVER EXPR | | | UNDER EXPR |
| GK | | | | OVER EXPR |
| RNASEL | OVER EXPR | | | OVER EXPR |
| GMFG | | OVER EXPR | OVER EXPR | OVER EXPR |
| STK4 | | | | UNDER EXPR |
| HINT3 | | | | OVER EXPR |
| DAPP1 | | OVER EXPR | | UNDER EXPR |
| TEC | OVER EXPR | OVER EXPR | OVER EXPR | UNDER EXPR |
| GMFB | | OVER EXPR | | OVER EXPR |
| PTPN6 | | | | UNDER EXPR |
| RIPK2 | | | | UNDER EXPR |
| PIM1 | | OVER EXPR | OVER EXPR | OVER EXPR |
| NEK6 | | OVER EXPR | OVER EXPR | UNDER EXPR |
| ACVR2A | | OVER EXPR | OVER EXPR | UNDER EXPR |
| AURKB | | | | UNDER EXPR |
| FES | | OVER EXPR | OVER EXPR | |
| ACVR1B | | | OVER EXPR | OVER EXPR |
| CDK6 | | OVER EXPR | OVER EXPR | UNDER EXPR |
| ZAK | | OVER EXPR | OVER EXPR | UNDER EXPR |
| VRK2 | | | | UNDER EXPR |
| MAP3K8 | OVER EXPR | | | UNDER EXPR |
| DUSP14 | | OVER EXPR | | UNDER EXPR |
| SGK1 | OVER EXPR | OVER EXPR | OVER EXPR | UNDER EXPR |
| PRKCQ | OVER EXPR | | | UNDER EXPR |
| JAK3 | | OVER EXPR | | UNDER EXPR |
| ULK2 | | OVER EXPR | | UNDER EXPR |
| HIPK2 | | | OVER EXPR | OVER EXPR |
| PTPRJ | | OVER EXPR | OVER EXPR | OVER EXPR |
| SPHK1 | | OVER EXPR | | |
| INPP1 | | | | UNDER EXPR |
| TNK2 | | OVER EXPR | OVER EXPR | OVER EXPR |
| PCTK1 | | OVER EXPR | OVER EXPR | OVER EXPR |
| DUSP1 | | | | OVER EXPR |
| NUDT4 | | | | UNDER EXPR |
| MAP4K3 | | OVER EXPR | | |
| TGFBR1 | | OVER EXPR | OVER EXPR | OVER EXPR |
| PTP4A1 | | | | OVER EXPR |
| HK1 | | OVER EXPR | | OVER EXPR |
| DUSP16 | OVER EXPR | | | UNDER EXPR |
| AMP32A | | | | OVER EXPR |
| DDR1 | | OVER EXPR | OVER EXPR | UNDER EXPR |
| ITK | | | | UNDER EXPR |
| WNK1 | | | | UNDER EXPR |
| NAGK | | | OVER EXPR | UNDER EXPR |
| STK38 | | | OVER EXPR | |
| BMP2K | OVER EXPR | OVER EXPR | OVER EXPR | OVER EXPR |
| BUB1 | | | | UNDER EXPR |
| AAK1 | | | | OVER EXPR |
| SIK1 | | | | OVER EXPR |
| DUSP10 | | OVER EXPR | | UNDER EXPR |
| PRKCA | | | | OVER EXPR |
| PIM2 | OVER EXPR | | | UNDER EXPR |
| STK17B | | | OVER EXPR | UNDER EXPR |
| TK2 | | | | UNDER EXPR |
| STK39 | | | | OVER EXPR |
| ALPK2 | | OVER EXPR | OVER EXPR | UNDER EXPR |

TABLE 6-continued

Candidate Receptor Molecules

| Symbol | % Differential expression (compared to Th0) | | | IL23R knockout (late) |
|---|---|---|---|---|
| | Early | Intermediate | Late | |
| MST4 | | | | OVER EXPR |
| PHLPP1 | | | | UNDER EXPR |

TABLE 7

Candidate Kinases

| Symbol | % Differential expression (compared to Th) | | | IL23R knockout (late) |
|---|---|---|---|---|
| | Early | Intermediate | Late | |
| SGK1 | OVER EXPR | OVER EXPR | OVER EXPR | UNDER EXPR |
| HK2 | OVER EXPR | OVER EXPR | OVER EXPR | |
| PRPS1 | | | | UNDER EXPR |
| CAMK4 | | | | |
| ZAP70 | | | | |
| TXK | OVER EXPR | OVER EXPR | OVER EXPR | UNDER EXPR |
| NEK6 | | OVER EXPR | OVER EXPR | |
| MAPKAPK2 | | | OVER EXPR | |
| MFHAS1 | UNDER EXPR | | | OVER EXPR |
| PDXK | | | | |
| PRKCH | | | OVER EXPR | UNDER EXPR |
| CDK6 | | OVER EXPR | OVER EXPR | |
| ZAK | | OVER EXPR | OVER EXPR | UNDER EXPR |
| PKM2 | | OVER EXPR | | |
| JAK2 | | OVER EXPR | UNDER EXPR | UNDER EXPR |
| STK38 | UNDER EXPR | UNDER EXPR | OVER EXPR | |
| ADRBK1 | | | | |
| PTK2B | UNDER EXPR | | | |
| DGUOK | | UNDER EXPR | UNDER EXPR | |
| DGKA | | | | UNDER EXPR |
| RIPK3 | | OVER EXPR | OVER EXPR | UNDER EXPR |
| PIM1 | | OVER EXPR | OVER EXPR | OVER EXPR |
| CDK5 | | | | |
| STK17B | | | OVER EXPR | |
| CLK3 | | | | |
| CLK1 | | | | |
| ITK | | UNDER EXPR | | |
| AKT1 | | | | UNDER EXPR |
| PGK1 | | | | |
| TWF1 | | | | |
| LIMK2 | | | | |
| RFK | | | | UNDER EXPR |
| WNK1 | | UNDER EXPR | OVER EXPR | |
| HIPK1 | | | | |
| AXL | | OVER EXPR | UNDER EXPR | UNDER EXPR |
| RPS6KB1 | | | | |
| CDC42BPA | | | | |
| STK38L | | | | |
| PRKCD | | | | |
| PDK3 | | | | |
| PI4KA | | | | |
| PNKP | | | | |
| CDKN3 | | | | |
| STK19 | | | | |
| PRPF4B | | | | UNDER EXPR |
| MAP4K2 | | | | |
| PDPK1 | | | | |
| VRK1 | | | | |
| TRRAP | | | | |

TABLE 8

Candidate Signaling Molecules From Single Cell Analysis

| | % Differential expression (compared to Th) | | | IL23R knockout |
|---|---|---|---|---|
| Symbol | Early | Intermediate | Late | (late) |
| CTLA4 | | OVER EXPR | OVER EXPR | UNDER EXPR |
| CD9 | | UNDER EXPR | UNDER EXPR | UNDER EXPR |
| IL2RA | OVER EXPR | OVER EXPR | OVER EXPR | OVER EXPR |
| CD5L | | OVER EXPR | OVER EXPR | OVER EXPR |
| CD24 | | OVER EXPR | OVER EXPR | UNDER EXPR |
| CD200 | OVER EXPR | UNDER EXPR | UNDER EXPR | OVER EXPR |
| CD53 | | UNDER EXPR | OVER EXPR | UNDER EXPR |
| TNFRSF9 | UNDER EXPR | UNDER EXPR | | OVER EXPR |
| CD44 | | | UNDER EXPR | |
| CD96 | | UNDER EXPR | UNDER EXPR | |
| CD83 | | UNDER EXPR | UNDER EXPR | |
| IL27RA | | | | |
| CXCR3 | | OVER EXPR | OVER EXPR | |
| TNFRSF4 | | | UNDER EXPR | |
| IL4R | | OVER EXPR | OVER EXPR | |
| PROCR | | OVER EXPR | OVER EXPR | OVER EXPR |
| LAMP2 | OVER EXPR | OVER EXPR | | UNDER EXPR |
| CD74 | | UNDER EXPR | UNDER EXPR | OVER EXPR |
| TNFRSF13B | | OVER EXPR | OVER EXPR | UNDER EXPR |
| PDCD1 | | | UNDER EXPR | |
| TNFRSF1B | | | | |
| IL21R | | UNDER EXPR | UNDER EXPR | |
| IFNGR1 | | | OVER EXPR | UNDER EXPR |
| ICOS | | | UNDER EXPR | OVER EXPR |
| PTPRC | | | | |
| ADAM17 | | | | |
| FCGR2B | | | | |
| TNFSF9 | | UNDER EXPR | UNDER EXPR | UNDER EXPR |
| MS4A6A | | UNDER EXPR | UNDER EXPR | UNDER EXPR |
| CCR4 | | OVER EXPR | OVER EXPR | |
| CD226 | | | | |
| CD3G | | UNDER EXPR | UNDER EXPR | |
| ENTPD1 | | | | |
| ADAM10 | | UNDER EXPR | UNDER EXPR | UNDER EXPR |
| CD27 | UNDER EXPR | UNDER EXPR | UNDER EXPR | UNDER EXPR |
| CD84 | | UNDER EXPR | UNDER EXPR | |
| ITGAL | UNDER EXPR | | | |
| CCND2 | | | | UNDER EXPR |
| BSG | | | | UNDER EXPR |
| CD40LG | | | | |
| PTPRCAP | UNDER EXPR | | UNDER EXPR | UNDER EXPR |
| CD68 | | | | |
| CD63 | | | | |
| SLC3A2 | | | | |
| HLA-DQA1 | | OVER EXPR | | |
| CTSD | | | | |
| CSF1R | | | | |
| CD3D | | UNDER EXPR | | |
| CD247 | | | UNDER EXPR | UNDER EXPR |
| CD14 | | | | |
| ITGAV | | | | |
| FCER1G | | | | |
| IL2RG | | OVER EXPR | | UNDER EXPR |

TABLE 9

Candidate Receptor Molecules From Single Cell Analysis

| | % Differential expression (compared to Th) | | | IL23R knockout |
|---|---|---|---|---|
| Symbol | Early | Intermediate | Late | (late) |
| PLEK | | OVER EXPR | | |
| BHLH40 | OVER EXPR | OVER EXPR | | |
| ARID5A | OVER EXPR | OVER EXPR | OVER EXPR | OVER EXPR |
| ETS1 | | OVER EXPR | OVER EXPR | UNDER EXPR |
| IRF4 | OVER EXPR | OVER EXPR | OVER EXPR | |
| IKZF3 | | | | |
| RORC | | OVER EXPR | OVER EXPR | UNDER EXPR |
| STAT4 | | UNDER EXPR | UNDER EXPR | UNDER EXPR |

TABLE 9-continued

Candidate Receptor Molecules From Single Cell Analysis

| Symbol | % Differential expression (compared to Th) | | | IL23R knockout |
|---|---|---|---|---|
| | Early | Intermediate | Late | (late) |
| RORA | | OVER EXPR | OVER EXPR | UNDER EXPR |
| PHF6 | | | | |
| ID3 | UNDER EXPR | UNDER EXPR | UNDER EXPR | OVER EXPR |
| ZBTB32 | | UNDER EXPR | | OVER EXPR |
| IFI35 | OVER EXPR | | | |
| ID2 | OVER EXPR | OVER EXPR | OVER EXPR | UNDER EXPR |
| MDM4 | | | | |
| CHMP2A | | | | |
| ANKHD1 | | | | |
| CHD7 | | OVER EXPR | OVER EXPR | UNDER EXPR |
| STAT5B | | OVER EXPR | OVER EXPR | |
| MAML2 | | | | |
| ID1 | | OVER EXPR | OVER EXPR | OVER EXPR |
| SS18 | | OVER EXPR | | |
| MAF | | | | |
| ETV6 | OVER EXPR | OVER EXPR | | |
| CCRN4L | | OVER EXPR | OVER EXPR | |
| NASP | | | | |
| BLOC1S1 | | | | OVER EXPR |
| XAB2 | | | | |
| STAT5A | | OVER EXPR | | UNDER EXPR |
| IKZF1 | UNDER EXPR | | | |
| JUNB | | OVER EXPR | OVER EXPR | |
| THRAP3 | | | | OVER EXPR |
| SP100 | OVER EXPR | | | |
| PYCR1 | | OVER EXPR | OVER EXPR | OVER EXPR |
| HMGA1 | | | | |
| TAF1B | | | | UNDER EXPR |
| CNOT2 | | | | |
| NOC4L | OVER EXPR | | | |
| SKI | UNDER EXPR | OVER EXPR | OVER EXPR | |
| VAV1 | | OVER EXPR | OVER EXPR | |
| NR4A2 | | UNDER EXPR | UNDER EXPR | OVER EXPR |
| LGTN | | | | |
| NFKBIA | | | | UNDER EXPR |
| KDM6B | | | | |
| MAZ | | | | |
| CDC5L | | | | UNDER EXPR |
| HCLS1 | UNDER EXPR | | OVER EXPR | |
| BAZ2B | OVER EXPR | | | |
| MXD3 | | | | |
| BATF | OVER EXPR | OVER EXPR | | |
| E2F4 | | | | |
| NFKBIB | | | | |
| RBPJ | | OVER EXPR | OVER EXPR | OVER EXPR |
| TOX4 | | | | |
| CENPT | | | | |
| CASP8AP2 | | | | |
| ECE2 | | | | |
| MIER1 | | | | |
| AHR | OVER EXPR | OVER EXPR | OVER EXPR | |
| SPOP | | | | UNDER EXPR |
| BTG1 | | | | |
| MATR3 | | | | UNDER EXPR |
| JMJD1C | OVER EXPR | OVER EXPR | | |
| HMGB2 | | OVER EXPR | | |
| CREG1 | | | | OVER EXPR |
| NFATC1 | | | | |
| NFE2L2 | OVER EXPR | OVER EXPR | OVER EXPR | |
| WHSC1L1 | | | | |
| TBPL1 | | | | |
| TRIP12 | | | | |
| BTG2 | | | | |
| HMGN1 | | | | UNDER EXPR |
| ATF2 | | | | |
| NR4A3 | | | | |
| C16ORF80 | | | | |
| MBNL1 | | UNDER EXPR | UNDER EXPR | |
| WDHD1 | | | | |
| LASS6 | | | | |
| CREM | | OVER EXPR | OVER EXPR | |
| CARM1 | | | | |

TABLE 9-continued

Candidate Receptor Molecules From Single Cell Analysis

| Symbol | % Differential expression (compared to Th) | | | IL23R knockout |
|---|---|---|---|---|
| | Early | Intermediate | Late | (late) |
| RNF5 | | | | UNDER EXPR |
| SMARCA4 | | | | OVER EXPR |
| GATAD1 | | | | |
| TCERG1 | | | | UNDER EXPR |
| CHRAC1 | | | | |
| NFYC | | | | |
| ATF3 | | | OVER EXPR | OVER EXPR |
| ZNF326 | OVER EXPR | | | |
| KLF13 | | | | |
| TFDP1 | | | | |
| LRRFIP1 | | OVER EXPR | OVER EXPR | |
| MORF4L2 | | | | |
| FOXN3 | | | | |
| HDAC8 | | | | |
| MORF4L1 | | | | |
| DNAJC2 | | | | OVER EXPR |
| MAFG | | | | |
| YBX1 | | | | |

Among the novel 'Th17 positive' factors is the zinc finger E-box binding homeobox 1 Zeb1, which is early-induced and sustained in the Th17 time course (FIG. 17A), analogous to the expression of many known key Th17 factors. Zeb1 knockdown decreases the expression of Th17 signature cytokines (including IL-17A, IL-17F, and IL-21) and TFs (including Rbpj, Maff, and Mina) and of late induced cytokine and receptor molecule genes (p<$10^{-4}$, cluster C19). It is bound in Th17 cells by ROR-γt, Batf and Stat3, and is down-regulated in cells from Stat3 knockout mice (FIG. 17A). Interestingly, Zeb1 is known to interact with the chromatin factor Smarca4/Brg1 to repress the E-cadherin promoter in epithelial cells and induce an epithelial-mesenchymal transition (Sánchez-Tilló, E. et al. ZEB1 represses E-cadherin and induces an EMT by recruiting the SWI/SNF chromatin-remodeling protein BRG1. Oncogene 29, 3490-3500, doi:10.1038/onc.2010.102 (2010)). Smarca4 is a regulator in all three network models (FIGS. 2d,e) and a member of the 'positive module' (FIG. 4B). Although it is not differentially expressed in the Th17 time course, it is bound by Batf, Irf4 and Stat3 (positive regulators of Th17), but also by Gata3 and Stat5 (positive regulators of other lineages, FIG. 17A). Chromatin remodeling complexes that contain Smarca4 are known to displace nucleosomes and remodel chromatin at the IFN-γ promoter and promote its expression in Th1 cells (Zhang, F. & Boothby, M. T helper type 1-specific Brg1 recruitment and remodeling of nucleosomes positioned at the IFN-gamma promoter are Stat4 dependent. J. Exp. Med. 203, 1493-1505, doi:10.1084/jem.20060066 (2006)). There are also potential Smarca4 binding DNA sequences within the vicinity of the IL-17a promoter (Matys, V. et al. TRANSFAC: transcriptional regulation, from patterns to profiles. Nucleic Acids Res. 31, 374-378 (2003)). Taken together, this suggests a model where chromatin remodeling by Smarca4, possibly in interaction with Zeb1, positively regulates Th17 cells and is essential for IL-17 expression.

Conversely, among the novel 'Th17 negative' factors is Sp4, an early-induced gene, predicted in the model as a regulator of ROR-γt and as a target of ROR-γt, Batf, Irf4, Stat3 and Smarca4 (FIG. 17B). Sp4 knockdown results in an increase in ROR-γt expression at 48 h, and an overall stronger and "cleaner" Th17 differentiation as reflected by an increase in the expression of Th17 signature genes, including IL-17, IL-21 and Irf4, and decrease in the expression of signature genes of other CD4+ cells, including Gata3, Foxp3 and Stat4.

These novel and known regulatory factors act coordinately to orchestrate intra- and intermodules interactions and to promote progressive differentiation of Th17 cells, while limiting modules that inhibit directional differentiation of this subset and promote differentiation of T cells into other T cell subsets. For instance, knockdown of Smarca4 and Zeb1 leads to decrease in Mina (due to all-positive interactions between Th17 'positive regulators'), while knockdown of Smarca4 or Mina leads to increase in Tsc22d3 31 expression, due to negative cross-module interactions. As shown using RNAseq, these effects extend beyond the expression of regulatory factors in the network and globally affect the Th17 transcriptional program: e.g. knock-down of Mina has substantial effects on the progression of the Th17 differentiation network from the intermediate to the late phase, as some of its affected down-regulated genes significantly overlap the respective temporal clusters (p<$10^{-5}$, e.g., clusters C9, C19). An opposite trend is observed for the negative regulators Tsc22d3 and Sp4. For example, the transcriptional regulator Sp4 represses differentiating Th17 cells from entering into the late phase of differentiation by inhibiting the cytokine signaling (C19; p<$10^{-7}$) and haematopoiesis (C20; p<$10^{-3}$) clusters, which include Ahr, Batf, ROR-γt, etc. These findings emphasize the power of large-scale functional perturbation studies in understanding the action of complex molecular circuits that govern Th17 differentiation.

Figure 18:
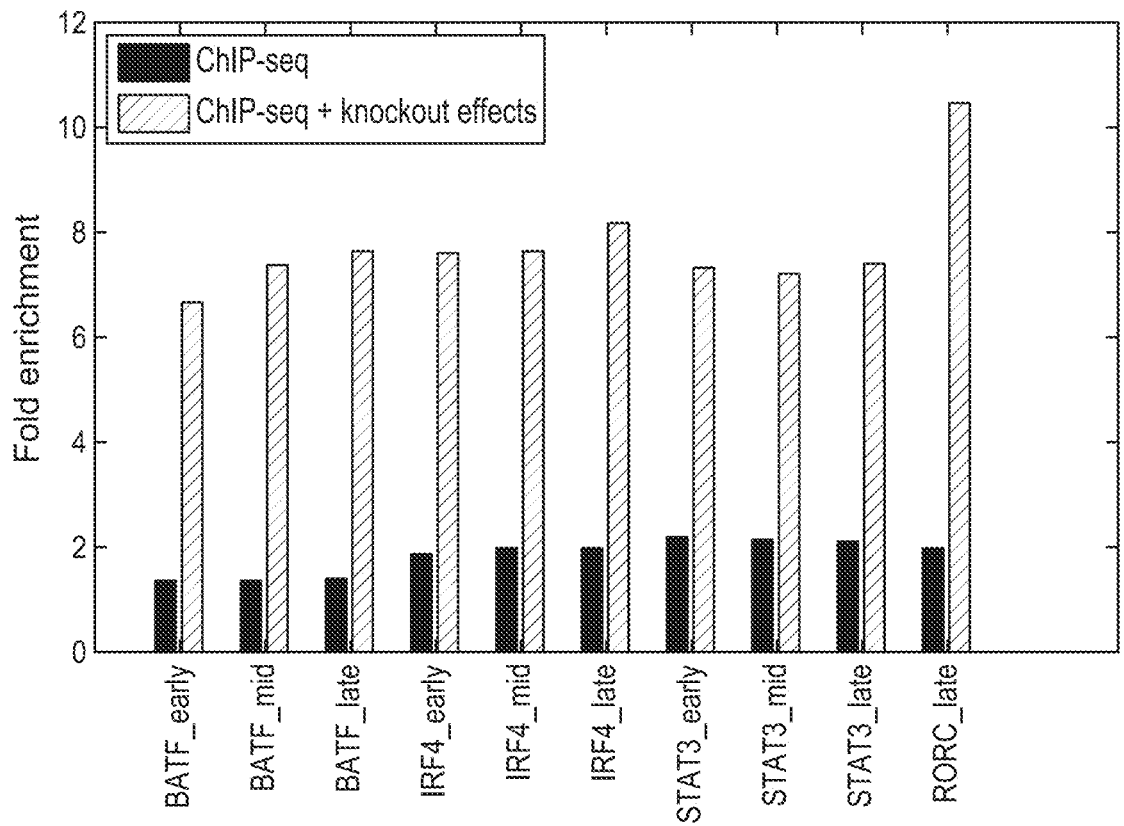
FIG. 18 is a graph depicting the overlap with ChIP-seq and RNA-seq data from Ciofani et al (Cell, 2012). Fold enrichment is shown for the four TF that were studied by Ciofani et al using ChIP-seq and RNA-seq and are predicted as regulators in the three network models (early, intermediate (denoted as "mid"), and late). The results are compared to the ChIP-seq based network of Ciofani et al. (blue) and to their combined ChIP-seq/RNA-seq network (taking a score cutoff of 1.5, as described by the authors; red). In all cases the p-value of the overlap (with ChIP-seq only or with the combined ChIP-seq/RNA-seq network) is below $10^{-1\circ}$ (using Fisher exact test), but the fold enrichment is particularly high in genes that are both bound by a factor and affected by its knockout, the most functional edges.
Figure 19A:
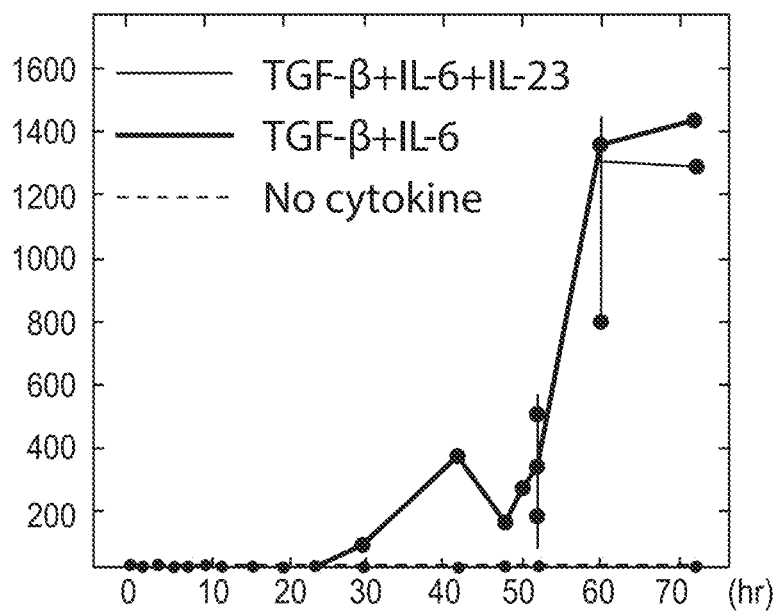
Figure 19B:
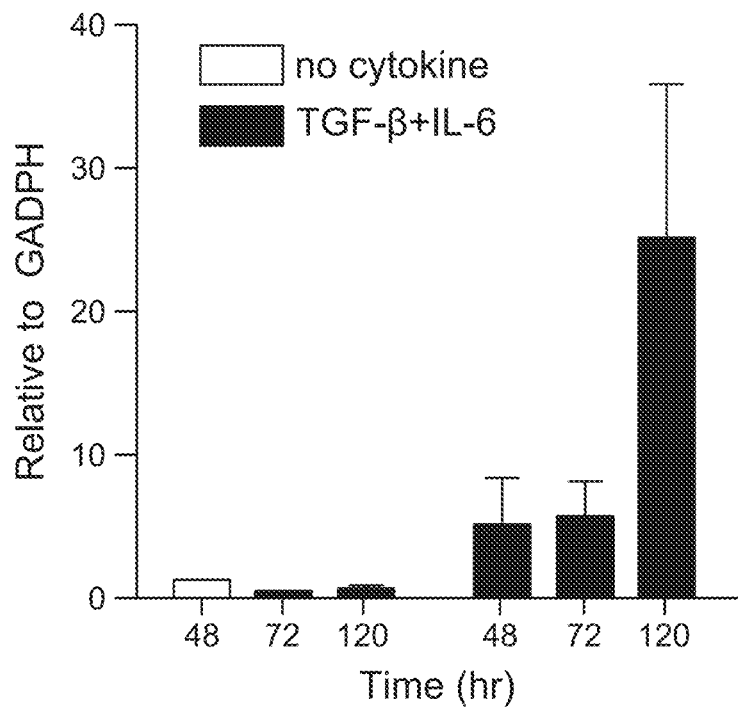
Figure 19C:
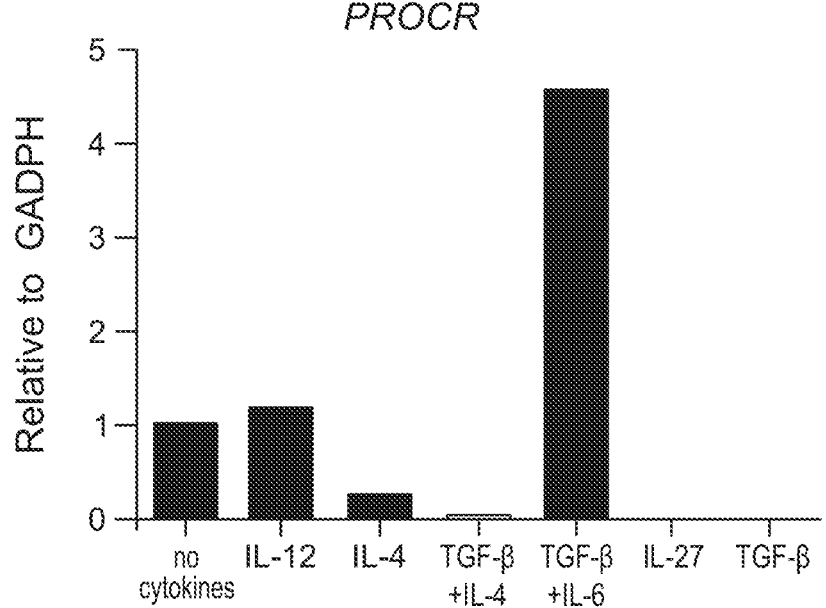
Figure 20A:
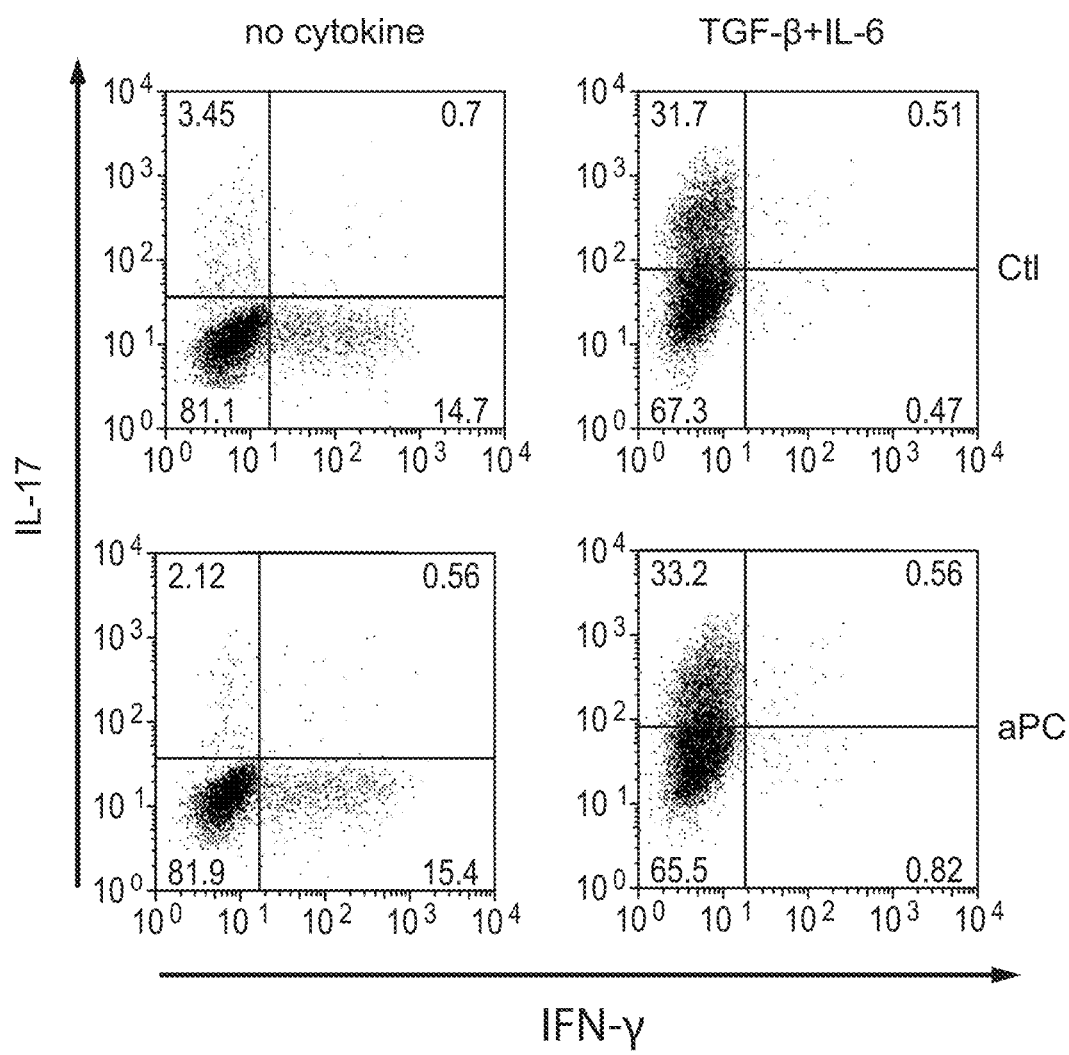
FIGS. 20A, 20B, 20C, and 20D are a series of graphs depicting that PROCR stimulation and expression is not essential for cytokine production from Th17 cells.
Figure 20B:
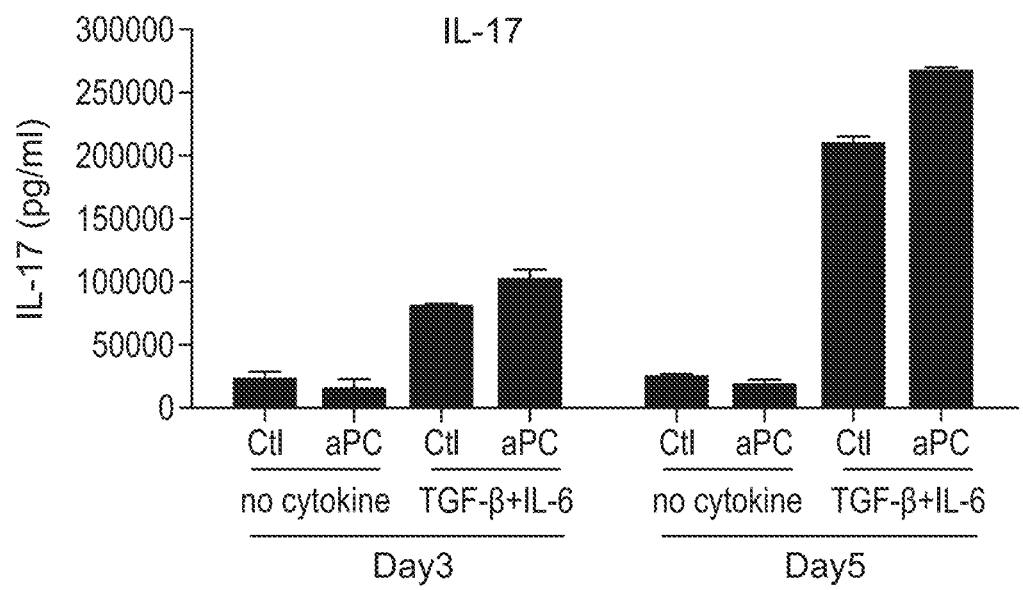
Figure 20C:
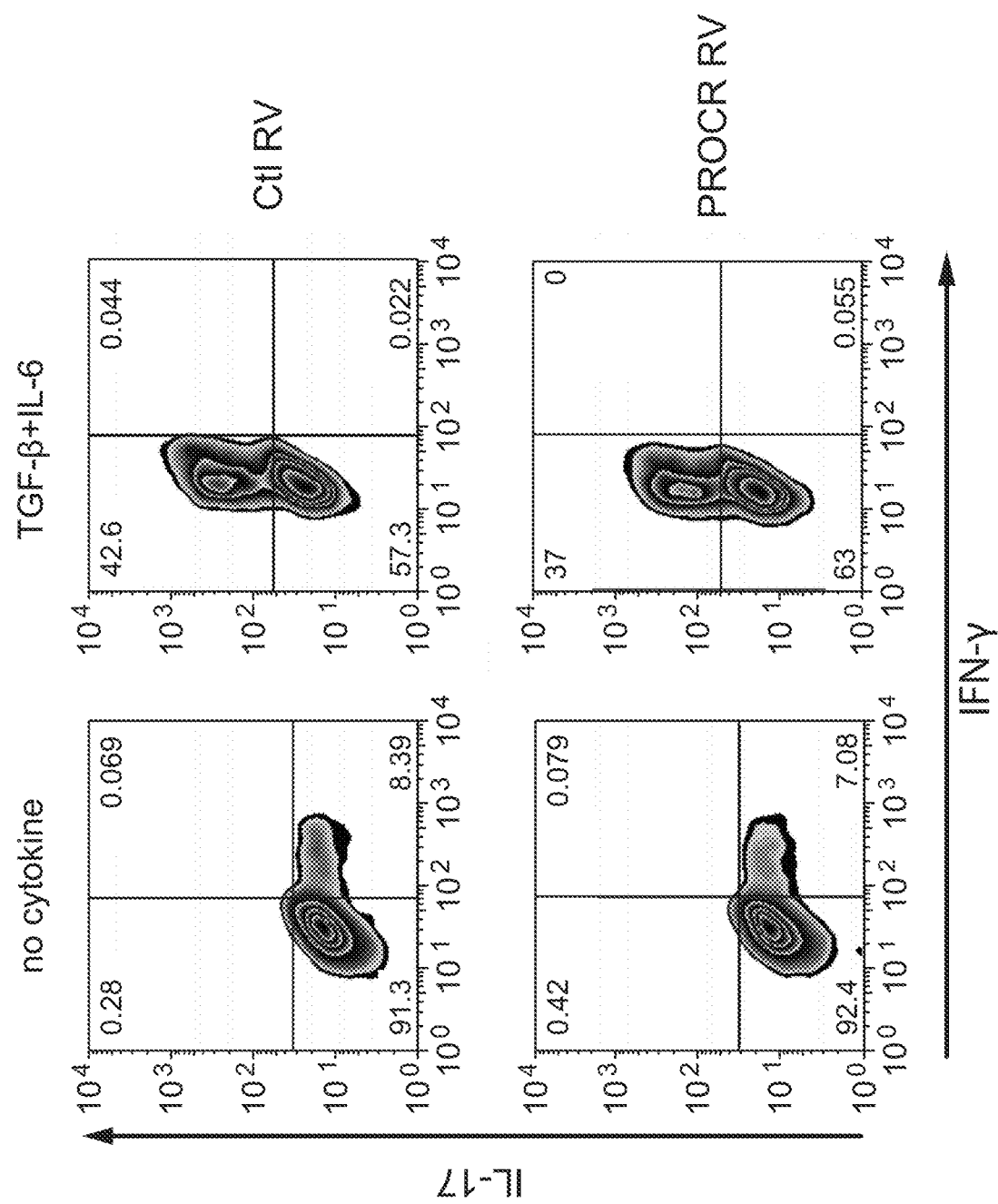
Figure 20D:
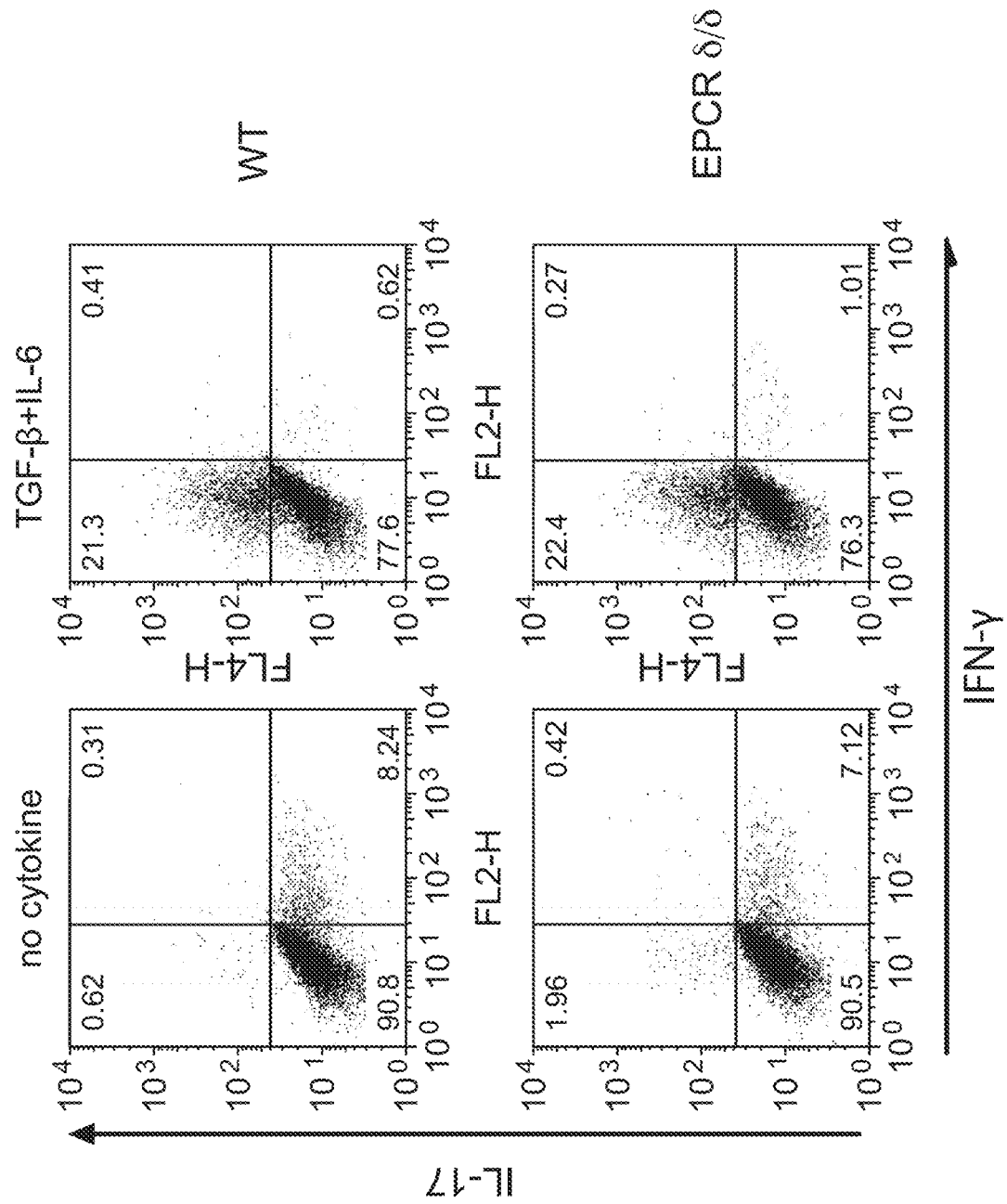
Figure 22A:
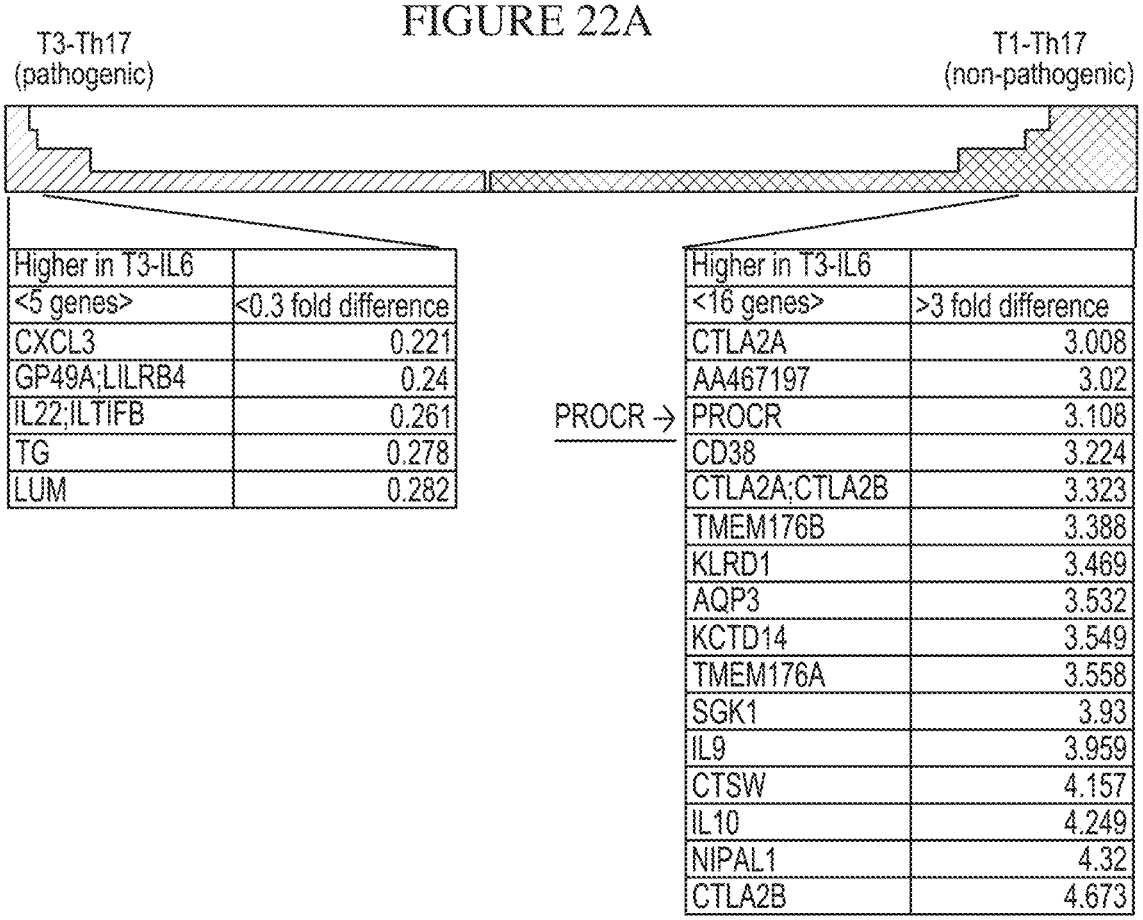
Figure 22B:
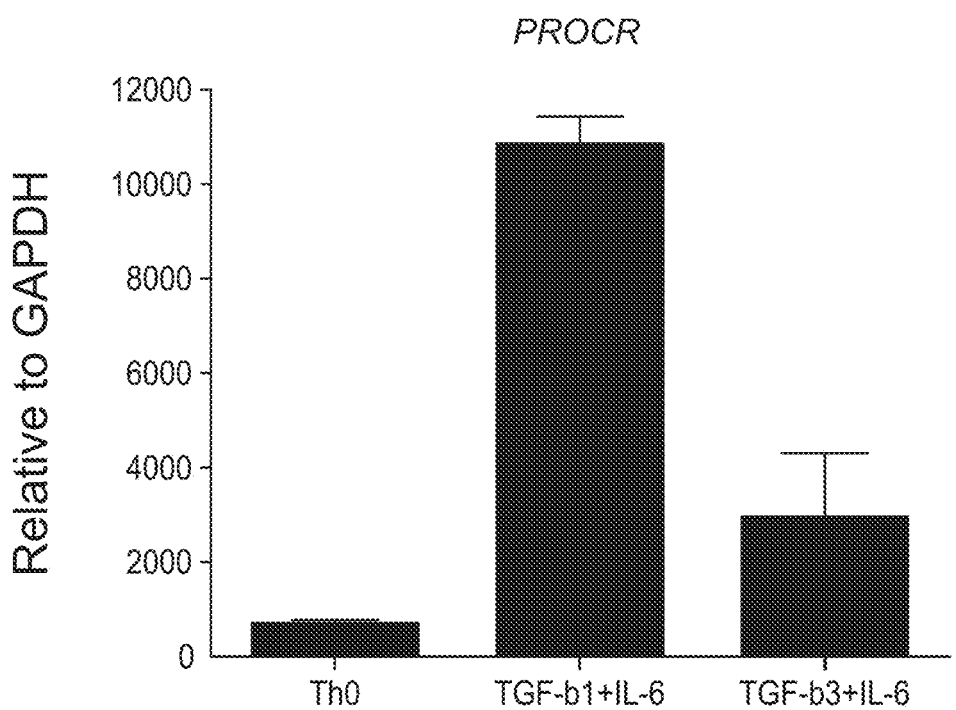
Figure 23A:
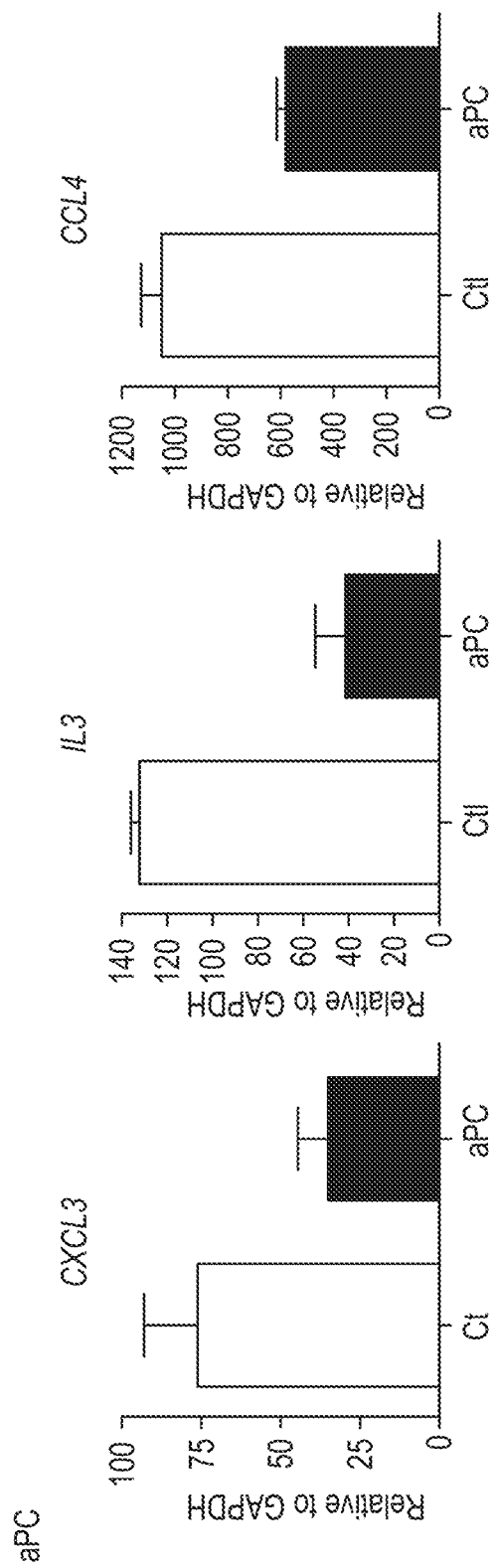
FIGS. 23A, 23B, and 23C are a series of graphs depicting that PROCR stimulation or expression impairs some pathogenic signature genes in Th17 cells.
Figure 23B:
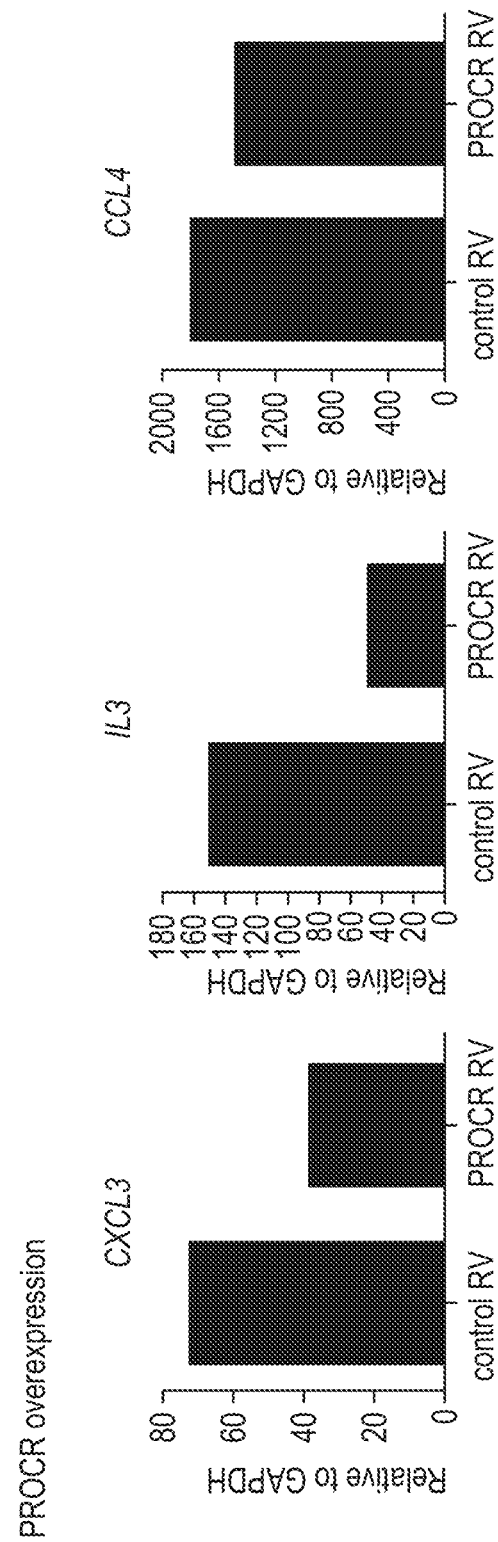
Figure 23C:
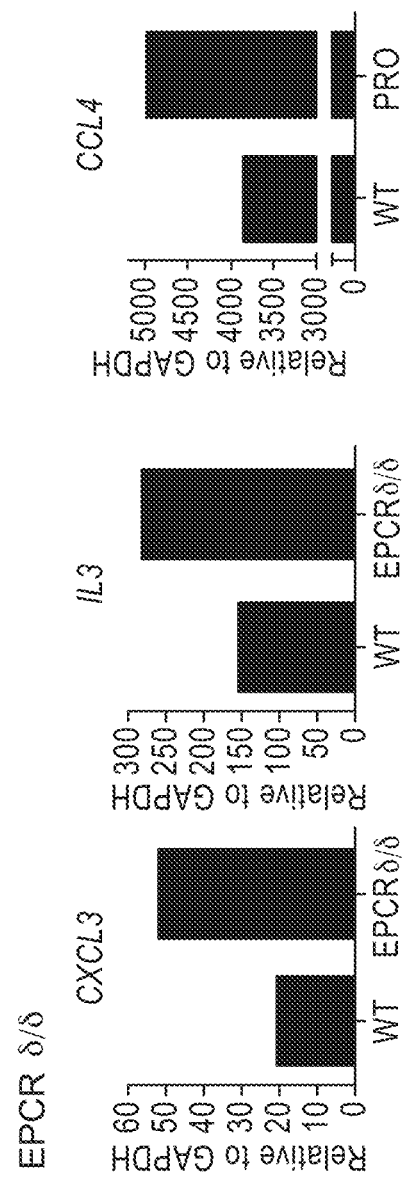
Figure 24A:
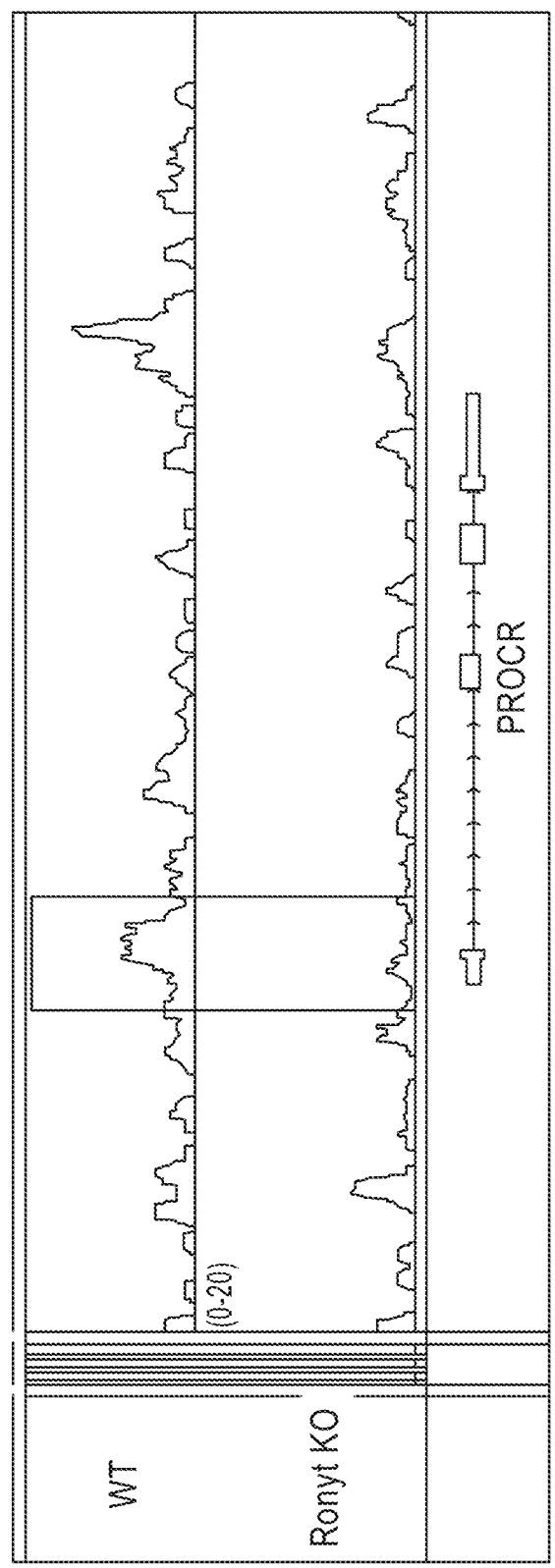
FIGS. 24A, 24B, 24C, and 24D are a series of graphs depicting that Rorγt induces PROCR expression under Th17 conditions polarized with TGF-β1 and IL-6.
Figure 24B:
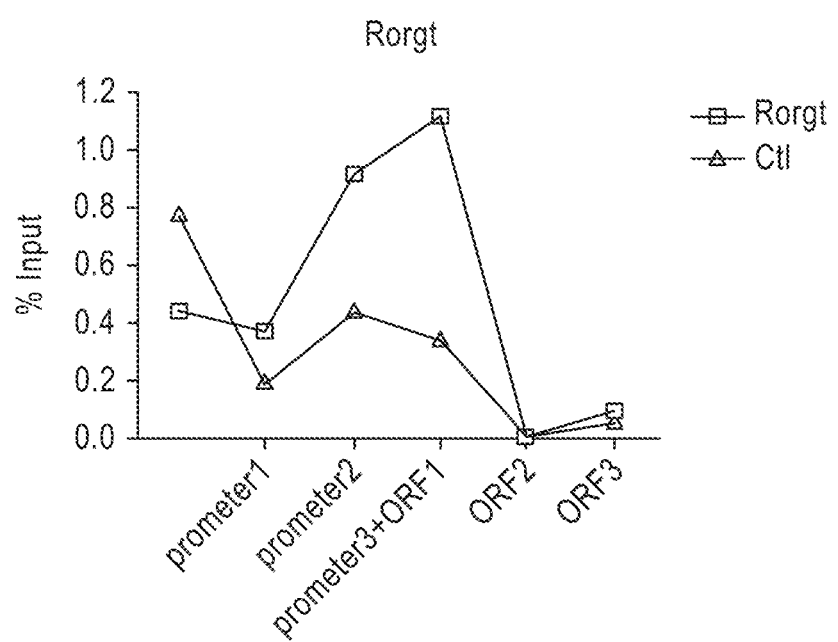
Figure 24C:
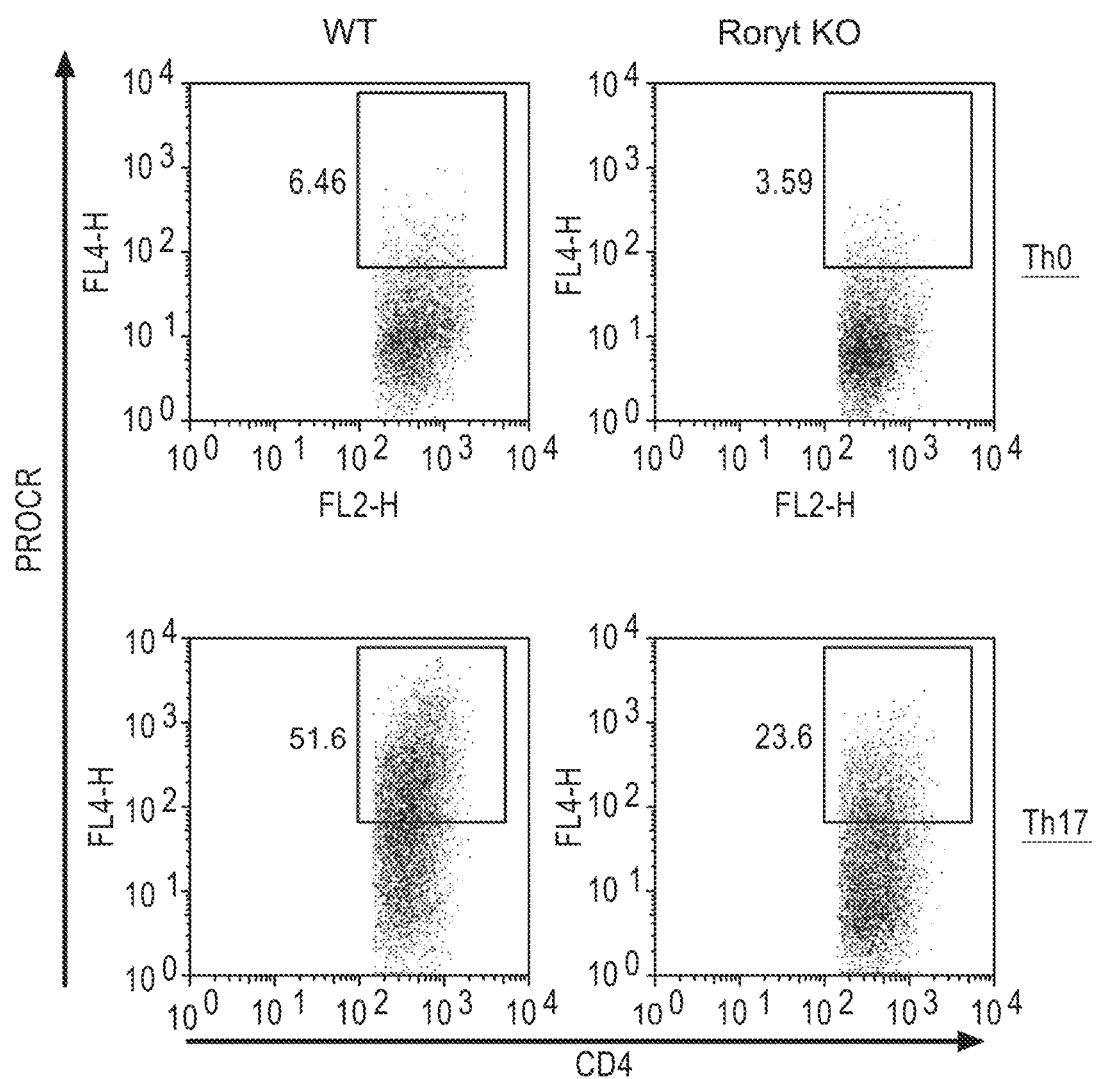
Figure 24D:
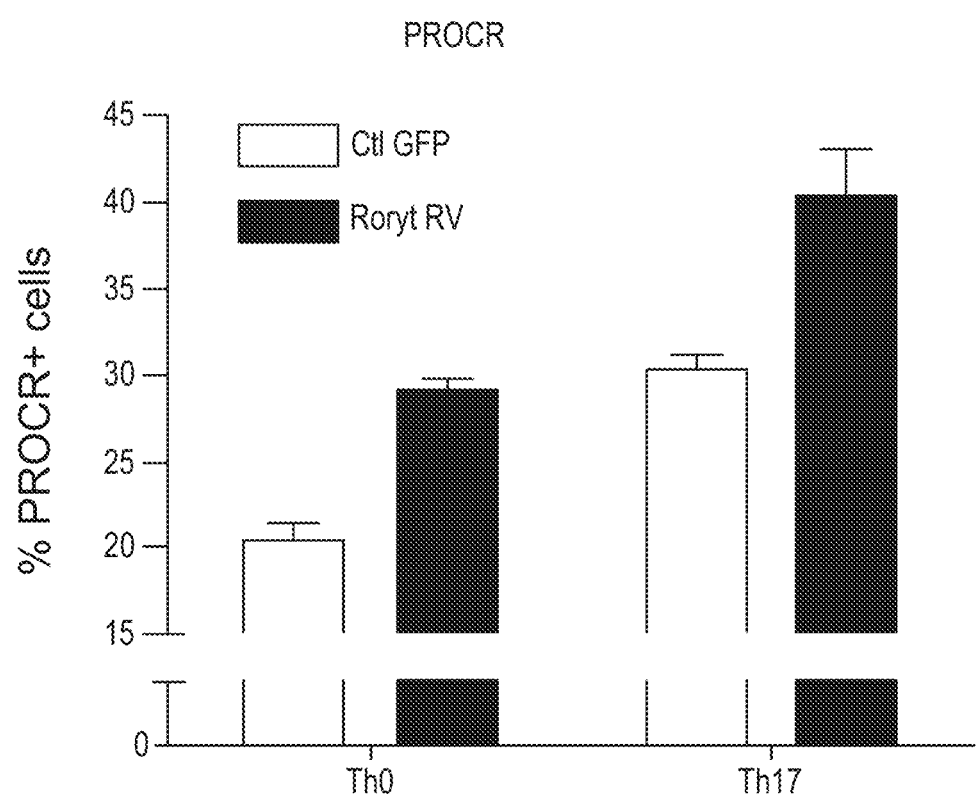
Figure 25A:
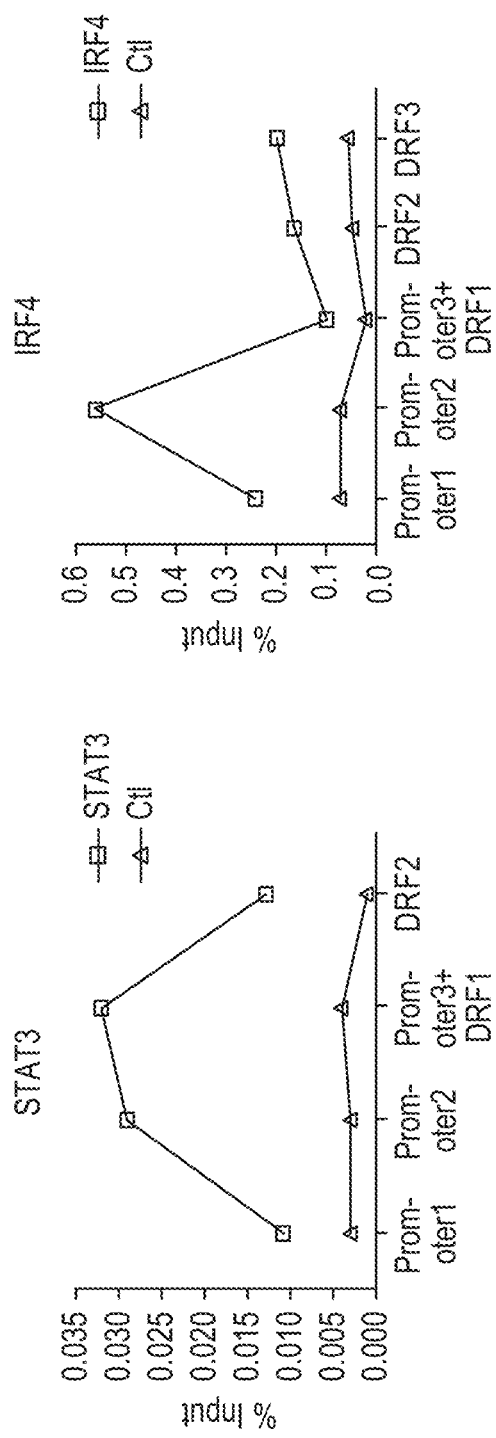
FIGS. 25A, 25B, and 25C are a series of graphs depicting that IRF4 and STAT3 bind to the Procr promoter and induce PROCR expression.
Figure 25B:
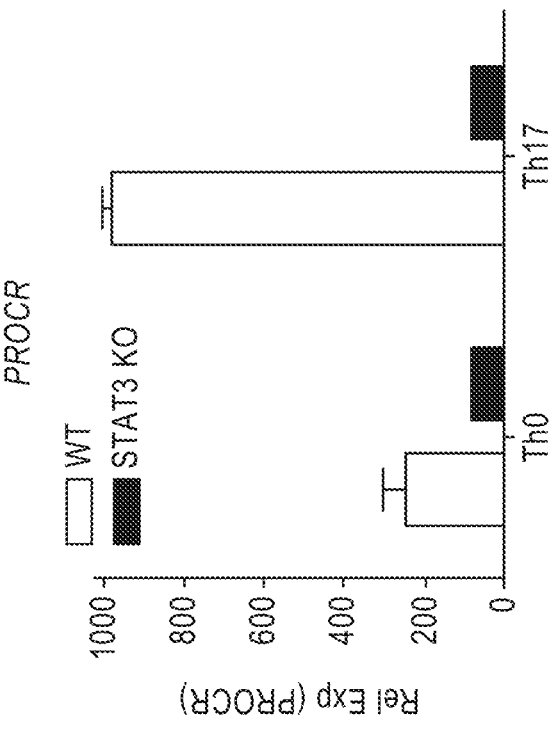
Figure 25C:
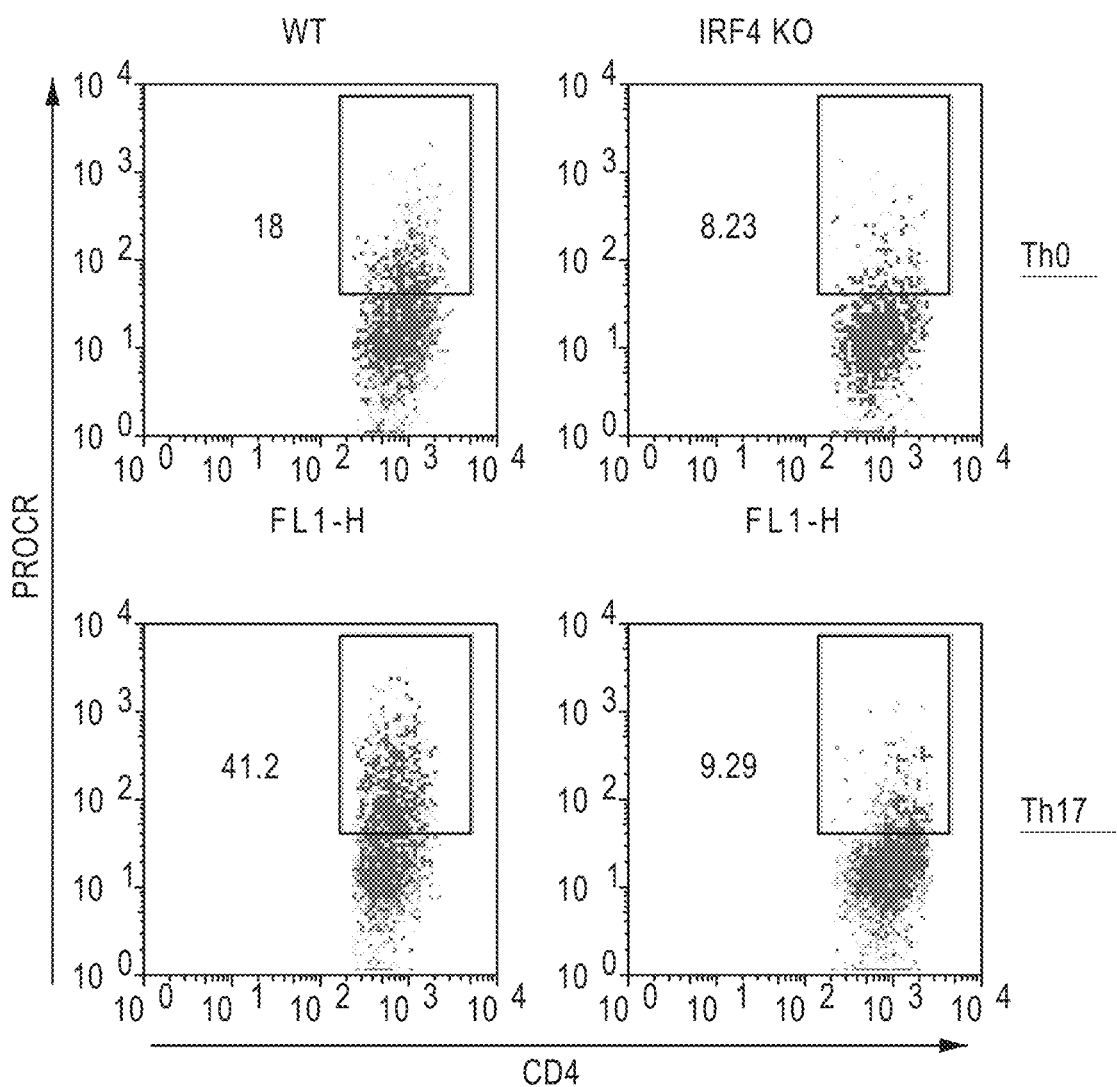

In a recent work, Ciofani et al. (Ciofani, M. et al. A Validated Regulatory Network for Th17 Cell Specification. Cell, doi:10.1016/j.cell.2012.09.016 (2012)) systematically ranked Th17 regulators based on ChIPSeq data for known key factors and transcriptional profiles in wild type and knockout cells. While their network centered on known core Th17 TFs, the complementary approach presented herein perturbed many genes in a physiologically meaningful setting. Reassuringly, their core Th17 network significantly overlaps with the computationally inferred model (FIG. 18).

The wiring of the positive and negative modules (FIGS. 4 and 5) uncovers some of the functional logic of the Th17 program, but likely involve both direct and indirect interactions. The functional model provides an excellent starting point for deciphering the underlying physical interactions with DNA binding profiles (Glasmacher, E. et al. A Genomic Regulatory Element That Directs Assembly and Function of Immune-Specific AP-1-IRF Complexes. Science, doi: 10.1126/science.1228309 (2012)) or protein-protein interactions (Wu, C., Yosef, N. & Thalhamer, T. SGK1 kinase regulates Th17 cells maintenance through IL-23 signaling pathway. (Submitted)). The regulators identified are compelling new targets for regulating the Th17/Tregs balance and for switching pathogenic Th17 into non-pathogenic ones.

Automated Procedure for Selection of Signature Genes

The invention also provides methods of determining gene signatures that are useful in various therapeutic and/or diagnostic indications. The goal of these methods is to select a small signature of genes that will be informative with respect to a process of interest. The basic concept is that different types of information can entail different partitions of the "space" of the entire genome (>20k genes) into subsets of associated genes. This strategy is designed to have the best coverage of these partitions, given the constraint on the signature size. For instance, in some embodiments of this strategy, there are two types of information: (i) temporal expression profiles; and (ii) functional annotations. The first information source partitions the genes into sets of co-expressed genes. The information source partitions the genes into sets of co-functional genes. A small set of genes is then selected such that there are a desired number of representatives from each set, for example, at least 10 representatives from each co-expression set and at least 10 representatives from each co-functional set. The problem of working with multiple sources of information (and thus aiming to "cover" multiple partitions) is known in the theory of computer science as Set-Cover. While this problem cannot be solved to optimality (due to its NP-hardness) it can be approximated to within a small factor. In some embodiments, the desired number of representatives from each set is one or more, at least 2, 5 or more, 10 or more, 15 or more, 20 or more, 25 or more, 30 or more, 35 or more, 40 or more, 50 or more, 60 or more, 70 or more, 80 or more, 90 or more, or 100 or more.

An important feature of this approach is that it can be given either the size of the signature (and then find the best coverage it can under this constraint); or the desired level of coverage (and then select the minimal signature size that can satisfy the coverage demand).

An exemplary embodiment of this procedure is the selection of the 275-gene signature (Table 1), which combined several criteria to reflect as many aspect of the differentiation program as was possible. The following requirements were defined: (1) the signature must include all of the TFs that belong to a Th17 microarray signature (comparing to other CD4+ T cells, see e.g., Wei et al., in Immunity vol. 30 155-167 (2009)), see Methods described herein); that are included as regulators in the network and are at least slightly differentially expressed; or that are strongly differentially expressed; (2) it must include at least 10 representatives from each cluster of genes that have similar expression profiles; (3) it must contain at least 5 representatives from the predicted targets of each TF in the different networks; (4) it must include a minimal number of representatives from each enriched Gene Ontology (GO) category (computed over differentially expressed genes); and, (5) it must include a manually assembled list of ~100 genes that are related to the differentiation process, including the differentially expressed cytokines, receptor molecules and other cell surface molecules. Since these different criteria might generate substantial overlaps, a set-cover algorithm was used to find the smallest subset of genes that satisfies all of five conditions. 18 genes whose expression showed no change (in time or between treatments) in the microarray data were added to this list.

Use of Signature Genes

The invention provides T cell related gene signatures for use in a variety of diagnostic and/or therapeutic indications. For example, the invention provides Th17 related signatures that are useful in a variety of diagnostic and/or therapeutic indications. "Signatures" in the context of the present invention encompasses, without limitation nucleic acids, together with their polymorphisms, mutations, variants, modifications, subunits, fragments, and other analytes or sample-derived measures.

Exemplary signatures are shown in Tables 1 and 2 and are collectively referred to herein as, inter alia, "Th17-associated genes," "Th17-associated nucleic acids," "signature genes," or "signature nucleic acids."

These signatures are useful in methods of diagnosing, prognosing and/or staging an immune response in a subject by detecting a first level of expression, activity and/or function of one or more signature genes or one or more products of one or more signature genes selected from those listed in Table 1 or Table 2 and comparing the detected level to a control of level of signature gene or gene product expression, activity and/or function, wherein a difference in the detected level and the control level indicates that the presence of an immune response in the subject.

These signatures are useful in methods of monitoring an immune response in a subject by detecting a level of expression, activity and/or function of one or more signature genes or one or more products of one or more signature genes selected from those listed in Table 1 or Table 2 at a first time point, detecting a level of expression, activity and/or function of one or more signature genes or one or more products of one or more signature genes selected from those listed in Table 1 or Table 2 at a second time point, and comparing the first detected level of expression, activity and/or function with the second detected level of expression, activity and/or function, wherein a change in the first and second detected levels indicates a change in the immune response in the subject.

These signatures are useful in methods of identifying patient populations at risk or suffering from an immune response based on a detected level of expression, activity and/or function of one or more signature genes or one or more products of one or more signature genes selected from those listed in Table 1 or Table 2. These signatures are also useful in monitoring subjects undergoing treatments and therapies for aberrant immune response(s) to determine efficaciousness of the treatment or therapy. These signatures are also useful in monitoring subjects undergoing treatments and therapies for aberrant immune response(s) to determine whether the patient is responsive to the treatment or therapy. These signatures are also useful for selecting or modifying therapies and treatments that would be efficacious in treating, delaying the progression of or otherwise ameliorating a symptom of an aberrant immune response. The signatures provided herein are useful for selecting a group of patients at a specific state of a disease with accuracy that facilitates selection of treatments.

The present invention also may comprise a kit with a detection reagent that binds to one or more signature nucleic acids. Also provided by the invention is an array of detection reagents, e.g., oligonucleotides that can bind to one or more signature nucleic acids. Suitable detection reagents include nucleic acids that specifically identify one or more signature nucleic acids by having homologous nucleic acid sequences, such as oligonucleotide sequences, complementary to a portion of the signature nucleic acids packaged together in the form of a kit. The oligonucleotides can be fragments of the signature genes. For example the oligonucleotides can be 200, 150, 100, 50, 25, 10 or fewer nucleotides in length. The kit may contain in separate container or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. Instructions (e.g., written, tape, VCR, CD-ROM, etc.) for carrying out the assay may be included in the kit. The assay may for example be in the form of a Northern hybridization or DNA chips or a sandwich ELISA or any other method as known in the art. Alternatively, the kit contains a nucleic acid substrate array which may comprise one or more nucleic acid sequences.

Use of T Cell Modulating Agents

Suitable T cell modulating agent(s) for use in any of the compositions and methods provided herein include an antibody, a soluble polypeptide, a polypeptide agent, a peptide agent, a nucleic acid agent, a nucleic acid ligand, or a small molecule agent. By way of non-limiting example, suitable T cell modulating agents or agents for use in combination with one or more T cell modulating agents are shown below in Table 10.

TABLE 10

| Target | Agent |
|---|---|
| CCR6 | prostaglandin E2, lipopolysaccharide, mip-3alpha, vegf, rantes, calcium, bortezomib, ccl4, larc, tarc, lipid, *E. coli* B5 lipopolysaccharide |
| CCR5 | cholesterol, cyclosporin a, glutamine, methionine, guanine, simvastatin, threonine, indinavir, lipoxin A4, cysteine, prostaglandin E2, zinc, dapta, 17-alpha-ethinylestradiol, polyacrylamide, progesterone, zidovudine, rapamycin, rantes, glutamate, alanine, valine, ccl4, quinine, NSC 651016, methadone, pyrrolidine dithiocarbamate, palmitate, nor-binaltorphimine, interferon beta-1a, vitamin-e, tak779, lipopolysaccharide, cisplatin, albuterol, fluvoxamine, vicriviroc, bevirimat, carbon tetrachloride, galactosylceramide, ATP-gamma-S, cytochalasin d, hemozoin, CP 96345, tyrosine, etravirine, vitamin d, mip 1alpha, ammonium, tyrosine sulfate, isoleucine, isopentenyl diphosphate, il 10, serine, N-acetyl-L-cysteine, histamine, cocaine, ritonavir, tipranavir, aspartate, atazanavir, tretinoin, ATP, ribavirin, butyrate, N-nitro-L-arginine methyl ester, larc, buthionine sulfoximine, DAPTA, aminooxypentane-rantes, triamcinolone acetonide, shikonin, actinomycin d, bucladesine, aplaviroc, nevirapine, N-formyl-Met-Leu-Phe, cyclosporin A, lipoarabinomannan, nucleoside, sirolimus, morphine, mannose, calcium, heparin, c-d4i, pge2, beta-estradiol, mdms, dextran sulfate, dexamethasone, arginine, ivig, mcp 2, cyclic amp, U 50488H, N-methyl-D-aspartate, hydrogen peroxide, 8-carboxamidocyclazocine, latex, groalpha, xanthine, ccl3, retinoic acid, Maraviroc, sdf 1, opiate, efavirenz, estrogen, bicyclam, enfuvirtide, filipin, bleomycin, polysaccharide, tarc, pentoxifylline, *E. coli* B5 lipopolysaccharide, methylcellulose, maraviroc |
| ITGA3 | SP600125, paclitaxel, decitabine, e7820, retinoid, U0126, serine, retinoic acid, tyrosine, forskolin, Ca2+ |
| IRF4 | prostaglandin E2, phorbol myristate acetate, lipopolysaccharide, A23187, tacrolimus, trichostatin A, stallimycin, imatinib, cyclosporin A, tretinoin, bromodeoxyuridine, ATP-gamma-S, ionomycin |
| BATF | Cyclic AMP, serine, tacrolimus, beta-estradiol, cyclosporin A, leucine |
| RBPJ | zinc, tretinoin |
| PROCR | lipopolysaccharide, cisplatin, fibrinogen, 1,10-phenanthroline, 5-N-ethylcarboxamido adenosine, cystathionine, hirudin, phospholipid, Drotrecogin alfa, vegf, Phosphatidylethanolamine, serine, gamma-carboxyglutamic acid, calcium, warfarin, endotoxin, curcumin, lipid, nitric oxide |
| ZEB1 | resveratrol, zinc, sulforafan, sorafenib, progesterone, PD-0332991, dihydrotestosterone, silibinin, LY294002, 4-hydroxytamoxifen, valproic acid, beta-estradiol, forskolin, losartan potassium, fulvestrant, vitamin d |
| POU2AF1 | terbutaline, phorbol myristate acetate, bucladesine, tyrosine, ionomycin, KT5720, H89 |
| EGR1 | ghrelin, ly294002, silicone, sodium, propofol, 1,25 dihydroxy vitamin d3, tetrodotoxin, threonine, cyclopiazonic acid, urea, quercetin, ionomycin, 12-o-tetradecanoylphorbol 13-acetate, fulvestrant, phenylephrine, formaldehyde, cysteine, leukotriene C4, prazosin, LY379196, vegf, rapamycin, leupeptin, pd 98,059, ruboxistaurin, pCPT-cAMP, methamphetamine, nitroprusside, H-7, Ro31-8220, phosphoinositide, lysophosphatidylcholine, bufalin, calcitriol, leuprolide, isobutylmethylxanthine, potassium chloride, acetic acid, cyclothiazide, quinolinic acid, tyrosine, adenylate, resveratrol, topotecan, genistein, thymidine, D-glucose, mifepristone, lysophosphatidic acid, leukotriene D4, carbon monoxide, poly rI:rC-RNA, sp 600125, agar, cocaine, 4-nitroquinoline-1-oxide, tamoxifen, lead, fibrinogen, tretinoin, atropine, mithramycin, K+, epigallocatechin-gallate, ethylenediaminetetraacetic acid, h2o2, carbachol, sphingosine-1-phosphate, iron, 5-hydroxytryptamine, amphetamine, SP600125, actinomycin d, SB203580, |

TABLE 10-continued

T cell Modulating Agents

| Target | Agent |
|---|---|
| | cyclosporin A, norepinephrine, okadaic acid, ornithine, LY294002, pge2, beta-estradiol, glucose, erlotinib, arginine, 1-alpha,25-dihydroxy vitamin D3, dexamethasone, pranlukast, phorbol myristate acetate, nimodipine, desipramine, cyclic amp, N-methyl-D-aspartate, atipamezole, acadesine, losartan, salvin, methylnitronitrosoguanidine, EGTA, gf 109203x, nitroarginine, 5-N-ethylcarboxamido adenosine, 15-deoxy-delta-12,14-PGJ 2, dbc-amp, manganese superoxide, di(2-ethylhexyl) phthalate, egcg, mitomycin C, 6,7-dinitroquinoxaline-2,3-dione, GnRH-A, estrogen, ribonucleic acid, imipramine, bapta, L-triiodothyronine, prostaglandin, forskolin, nogalamycin, losartan potassium, lipid, vincristine, 2-amino-3-phosphonopropionic acid, prostacyclin, methylnitrosourea, cyclosporin a, vitamin K3, thyroid hormone, diethylstilbestrol, D-tubocurarine, tunicamycin, caffeine, phorbol, guanine, bisindolylmaleimide, apomorphine, arachidonic acid, SU6656, prostaglandin E2, zinc, ptx1, progesterone, cyclosporin H, phosphatidylinositol, U0126, hydroxyapatite, epoprostenol, glutamate, 5fluorouracil, indomethacin, 5-fluorouracil, RP 73401, Ca2+, superoxide, trifluoperazine, nitric oxide, lipopolysaccharide, cisplatin, diazoxide, tgf beta1, calmidazolium, anisomycin, paclitaxel, sulindac sulfide, ganciclovir, gemcitabine, testosterone, ag 1478, glutamyl-Se-methylselenocysteine, doxorubicin, tolbutamide, cytochalasin d, PD98059, leucine, SR 144528, cyclic AMP, matrigel, haloperidol, serine, sb 203580, triiodothyronine, reverse, N-acetyl-L-cysteine, ethanol, s-nitroso-n-acetylpenicillamine, curcumin, l-nmma, H89, tpck, calyculin a, chloramphenicol, A23187, dopamine, platelet activating factor, arsenite, selenomethylselenocysteine, ropinirole, saralasin, methylphenidate, gentamicin, reserpine, triamcinolone acetonide, methyl methanesulfonate, wortmannin, thapsigargin, deferoxamine, calyculin A, peptidoglycan, dihydrotestosterone, calcium, phorbol-12-myristate, ceramide, nmda, 6-cyano-7-nitroquinoxaline-2,3-dione, hydrogen peroxide, carrageenan, sch 23390, linsidomine, oxygen, clonidine, fluoxetine, retinoid, troglitazone, retinoic acid, epinephrine, n acetylcysteine, KN-62, carbamylcholine, 2-amino-5-phosphonovaleric acid, oligonucleotide, gnrh, rasagiline, 8-bromo-cAMP, muscarine, tacrolimus, kainic acid, chelerythrine, inositol 1,4,5 trisphosphate, yohimbine, acetylcholine, atp, 15-deoxy-delta-12,14-prostaglandin j2, ryanodine, CpG oligonucleotide, cycloheximide, BAPTA-AM, phenylalanine |
| ETV6 | lipopolysaccharide, retinoic acid, prednisolone, valproic acid, tyrosine, cerivastatin, vegf, agar, imatinib, tretinoin |
| IL17RA | rantes, lipopolysaccharide, 17-alpha-ethinylestradiol, camptothecin, *E. coli* B5 lipopolysaccharide |
| EGR2 | phorbol myristate acetate, lipopolysaccharide, platelet activating factor, carrageenan, edratide, 5-N-ethylcarboxamido adenosine, potassium chloride, dbc-amp, tyrosine, PD98059, camptothecin, formaldehyde, prostaglandin E2, leukotriene C4, zinc, cyclic AMP, GnRH-A, bucladesine, thapsigargin, kainic acid, cyclosporin A, mifepristone, leukotriene D4, LY294002, L-triiodothyronine, calcium, beta-estradiol, H89, dexamethasone, cocaine |
| SP4 | betulinic acid, zinc, phorbol myristate acetate, LY294002, methyl 2-cyano-3,12-dioxoolean-1,9-dien-28-oate, beta-estradiol, Ca2+ |
| IRF8 | oligonucleotide, chloramphenicol, lipopolysaccharide, estrogen, wortmannin, pirinixic acid, carbon monoxide, retinoic acid, tyrosine |
| NFKB1 | Bay 11-7085, Luteolin, Triflusal, Bay 11-7821, Thalidomide, Caffeic acid phenethyl ester, Pranlukast |
| TSC22D3 | phorbol myristate acetate, prednisolone, sodium, dsip, tretinoin, 3-deazaneplanocin, gaba, PD98059, leucine, triamcinolone acetonide, prostaglandin E2, steroid, norepinephrine, U0126, acth, calcium, ethanol, beta-estradiol, lipid, chloropromazine, arginine, dexamethasone |
| PML | lipopolysaccharide, glutamine, thyroid hormone, cadmium, lysine, tretinoin, bromodeoxyuridine, etoposide, retinoid, pic 1, arsenite, arsenic trioxide, butyrate, retinoic acid, alpha-retinoic acid, h2o2, camptothecin, cysteine, leucine, zinc, actinomycin d, proline, stallimycin, U0126 |
| IL12RB1 | prostaglandin E2, phorbol myristate acetate, lipopolysaccharide, bucladesine, 8-bromo-cAMP, gp 130, AGN194204, galactosylceramide-alpha, tyrosine, ionomycin, dexamethasone, il-12 |
| IL21R | azathioprine, lipopolysaccharide, okadaic acid, *E. coli* B5 lipopolysaccharide, calyculin A |
| NOTCH1 | interferon beta-1a, lipopolysaccharide, cisplatin, tretinoin, oxygen, vitamin B12, epigallocatechin-gallate, isobutylmethylxanthine, threonine, apomorphine, matrigel, trichostatin A, vegf, 2-acetylaminofluorene, rapamycin, dihydrotestosterone, poly rI:rC-RNA, hesperetin, valproic acid, asparagine, lipid, curcumin, dexamethasone, glycogen, CpG oligonucleotide, nitric oxide |

TABLE 10-continued

T cell Modulating Agents

| Target | Agent |
|---|---|
| ETS2 | oligonucleotide |
| MINA | phorbol myristate acetate, 4-hydroxytamoxifen |
| SMARCA4 | cyclic amp, cadmium, lysine, tretinoin, latex, androstane, testosterone, sucrose, tyrosine, cysteine, zinc, oligonucleotide, estrogen, steroid, trichostatin A, tpmp, progesterone, histidine, atp, trypsinogen, glucose, agar, lipid, arginine, vancomycin, dihydrofolate |
| FAS | hoechst 33342, ly294002, 2-chlorodeoxyadenosine, glutamine, cd 437, tetrodotoxin, cyclopiazonic acid, arsenic trioxide, phosphatidylserine, niflumic acid, gliadin, ionomycin, safrole oxide, methotrexate, rubitecan, cysteine, propentofylline, vegf, boswellic acids, rapamycin, pd 98,059, captopril, methamphetamine, vesnarinone, tetrapeptide, oridonin, raltitrexed, pirinixic acid, nitroprusside, H-7, beta-boswellic acid, adriamycin, concanamycin a, etoposide, trastuzumab, cyclophosphamide, ifn-alpha, tyrosine, rituximab, selenodiglutathione, chitosan, omega-N-methylarginine, creatinine, resveratrol, topotecan, genistein, trichostatin A, decitabine, thymidine, D-glucose, mifepristone, tetracycline, Sn50 peptide, poly rI:rC-RNA, actinomycin D, sp 600125, doxifluridine, agar, ascorbic acid, acetaminophen, aspirin, tamoxifen, okt3, edelfosine, sulforafan, aspartate, antide, n, n-dimethylsphingosine, epigallocatechin-gallate, N-nitro-L-arginine methyl ester, h2o2, cerulenin, sphingosine-1-phosphate, SP600125, sodium nitroprusside, glycochenodeoxycholic acid, ceramides, actinomycin d, SB203580, cyclosporin A, morphine, LY294002, n(g)-nitro-l-arginine methyl ester, 4-hydroxynonenal, piceatannol, valproic acid, beta-estradiol, 1-alpha,25-dihydroxy vitamin D3, arginine, dexamethasone, sulfadoxine, phorbol myristate acetate, beta-lapachone, nitrofurantoin, chlorambucil, methylnitronitrosoguanidine, CD 437, opiate, egcg, mitomycin C, estrogen, ribonucleic acid, fontolizumab, tanshinone iia, recombinant human endostatin, fluoride, L-triiodothyronine, bleomycin, forskolin, nonylphenol, zymosan A, vincristine, daunorubicin, prednisolone, cyclosporin a, vitamin K3, diethylstilbestrol, deoxyribonucleotide, suberoylanilide hydroxamic acid, orlistat, 3-(4,5-dimethylthiazol-2-yl)-2, 5-diphenyltetrazolium bromide, rottlerin, arachidonic acid, ibuprofen, prostaglandin E2, toremifene, depsipeptide, ochratoxin A, (glc)4, phosphatidylinositol, mitomycin c, rantes, sphingosine, indomethacin, 5fluorouracil, phosphatidylcholine, 5-fluorouracil, mg 132, thymidylate, trans-cinnamaldehyde, sterol, polyadenosine diphosphate ribose, nitric oxide, vitamin e succinate, lipopolysaccharide, cisplatin, herbimycin a, 5-aza-2'deoxycytidine, proteasome inhibitor PSI, 2,5-hexanedione, epothilone B, caffeic acid phenethyl ester, glycerol 3-phosphate, tgf beta1, anisomycin, paclitaxel, gemcitabine, medroxyprogesterone acetate, hymecromone, testosterone, ag 1478, doxombicin, S-nitroso-N-acetylpenicillamine, adpribose, sulforaphane, vitamin d, annexin-v, lactate, reactive oxygen species, sb 203580, serine, N-acetyl-L-cysteine, dutp, infliximab, ethanol, curcumin, cytarabine, tpck, calyculin a, dopamine, gp 130, bromocriptine, apicidin, fatty acid, citrate, glucocorticoid, arsenite, butyrate, peplomycin, oxaliplatin, camptothecin, benzyloxycarbonyl-Leu-Leu-Leu aldehyde, clofibrate, carbon, wortmannin, fludarabine, N-(3-(aminomethyl)benzyl)acetamidine, sirolimus, peptidoglycan, c2ceramide, dihydrotestosterone, 7-aminoactinomycin d, carmustine, heparin, ceramide, paraffin, mitoxantrone, docosahexaenoic acid, vitamin a, ivig, hydrogen peroxide, 7-ethyl-10-hydroxy-camptomecin, oxygen, pydrin, bortezomib, retinoic acid, 1,4-phenylenebis(methylene)selenocyanate, teriflunomide, epinephrine, n acetylcysteine, noxa, irinotecan, oligonucleotide, d-api, rasagiline, 8-bromo-cAMP, atpo, agarose, fansidar, clobetasol propionate, teniposide, aurintricarboxylic acid, polysaccharide, CpG oligonucleotide, cycloheximide |
| IRF1 | tamoxifen, chloramphenicol, polyinosinic-polycytidylic acid, inosine monophosphate, suberoylanilide hydroxamic acid, butyrate, iron, gliadin, zinc, actinomycin d, deferoxamine, phosphatidylinositol, adenine, ornthine, rantes, calcium, 2',5'-oligoadenylate, pge2, poly(i-c), indoleamine, arginine, estradiol, nitric oxide, etoposide, adriamycin, oxygen, retinoid, guanylate, troglitazone, ifn-alpha, retinoic acid, tyrosine, adenylate, am 580, guanosine, oligonucleotide, estrogen, thymidine, tetracycline, serine, sb 203580, pdtc, lipid, cycloheximide |
| MYC | cd 437, 1,25 dihydroxy vitamin d3, phenethyl isothiocyanate, threonine, arsenic trioxide, salicylic acid, quercetin, prostaglandin E1, ionomycin, 12-o-tetradecanoylphorbol 13-acetate, fulvestrant, phenylephrine, fisetin, 4-coumaric acid, dihydroartemisinin, 3-deazaadenosine, nitroprusside, pregna-4,17-diene-3,16-dione, adriamycin, bromodeoxyuridine, AGN 194204, STA-9090, isobutylmethylxanthine, potassium chloride, docetaxel, quinolinic acid, 5,6,7,8-tetrahydrobiopterin, propranolol, delta 7-pga1, topotecan, AVI-4126, trichostatin A, decitabine, thymidine, D-glucose, mifepristone, poly rI:rC-RNA, letrozole, L-threonine, 5-hydroxytryptamine, bucladesine, SB203580, 1'-acetoxychavicol acetate, |

TABLE 10-continued

T cell Modulating Agents

| Target | Agent |
|---|---|
| | cyclosporin A, okadaic acid, dfmo, LY294002, hmba, piceatannol, 2',5'-oligoadenylate, 4-hydroxytamoxifen, butylbenzyl phthalate, dexamethasone, ec 109, phosphatidic acid, grape seed extract, phorbol myristate acetate, coumermycin, tosylphenylalanyl chloromethyl ketone, CD 437, di(2-ethylhexyl) phthalate, butyrine, cytidine, sodium arsenite, tanshinone iia, L-triiodothyronine, niacinamide, glycogen, daunorubicin, vincristine, carvedilol, bizelesin, 3-deazaneplanocin, phorbol, neplanocin a, panobinostat, [alcl], phosphatidylinositol, U0126, dichlororibofuranosylbenzimidazole, flavopiridol, 5-fluorouracil, verapamil, cyclopamine, nitric oxide, cisplatin, hrgbeta1,5,6-dichloro-1-beta-d-ribofuranosylbenzimidazole, amsacrine, gemcitabine, aristeromycin, medroxyprogesterone acetate, gambogic acid, leucine, alpha-naphthyl acetate, cyclic AMP, reactive oxygen species, PD 180970, curcumin, chloramphenicol, A23187, crocidolite asbestos, 6-hydroxydopamine, cb 33, arsenite, gentamicin, benzyloxycarbonyl-Leu-Leu-Leu aldehyde, clofibrate, wortmannin, sirolimus, ceramide, melphalan, 3M-001, linsidomine, CP-55940, hyaluronic acid, ethionine, clonidine, retinoid, bortezomib, oligonucleotide, methyl 2-cyano-3,12-dioxoolean-1,9-dien-28-oate, tacrolimus, embelin, methyl-beta-cyclodextrin, 3M-011, folate, ly294002, PP1, hydroxyurea, aclarubicin, phenylbutyrate, PL) 0325901, methotrexate, Cd2+, prazosin, vegf, rapamycin, alanine, phenobarbital, pd 98,059, trapoxin, 4-hydroperoxycyclophosphamide, methamphetamine, s-(1,2-dichlorovinyl)-l-cysteine, aphidicolin, vesnarinone, ADI PEG20, pirinixic acid, wp631, H-7, carbon tetrachloride, bufalin, 2,2-dimethylbutyric acid, etoposide, calcitriol, trastuzumab, cyclophosphamide, harringtonine, tyrosine, N(6)-(3-iodobenzyl)-5'-N-methylcarboxamidoadenosine, resveratrol, thioguanine, genistein, S-nitroso-N-acetyl-DL-penicillamine, zearalenone, lysophosphatidic acid, Sn50 peptide, roscovitine, actinomycin D, propanil, agar, tamoxifen, acetaminophen, imatinib, tretinoin, mithramycin, ATP, epigallocatechin-gallate, ferric ammonium citrate, acyclic retinoid, L-cysteine, nitroblue tetrazolium, actinomycin d, sodium nitroprusside, 1,2-dimethylhydrazine, dibutyl phthalate, ornithine, 4-hydroxynonenal, beta-estradiol, 1-alpha,25-dihydroxy vitamin D3, cyproterone acetate, nimodipine, nitrofurantoin, temsirolimus, 15-deoxy-delta-12, 14-PGJ 2, estrogen, ribonucleic acid, ciprofibrate, alpha-amanitin, SB 216763, bleomycin, forskolin, prednisolone, cyclosporin a, thyroid hormone, tunicamycin, phosphorothioate, suberoylanilide hydroxamic acid, pga2,3-(4,5-dimethylthiazol-2-yl)-2, 5-diphenyltetrazolium bromide, benzamide riboside, bisindolylmaleimide, SU6656, prostaglandin E2, depsipeptide, zidovudine, cerivastatin, progesterone, sethoxydim, indomethacin, mg 132, mezerein, pyrrolidine dithiocarbamate, vitamin e succinate, herbimycin a, 5-aza-2'deoxycytidine, lipopolysaccharide, diazoxide, anisomycin, paclitaxel, sodium dodecylsulfate, nilotinib, oxysterol, doxombicin, lipofectamine, PD98059, steroid, delta-12-pgj2, serine, H-8, N-acetyl-L-cysteine, ethanol, n-(4-hydroxyphenyl)retinamide, tiazofurin, cytarabine, H89, 10-hydroxycamptothecin, everolimus, lactacystin, n(1), n(12)-bis(ethyl)spermine, silibinin, glucocorticoid, butyrate, camptothecin, triamcinolone acetonide, tocotrienol, n-ethylmaleimide, phorbol 12,13-didecanoate, thapsigargin, deferoxamine, R59949, bryostatin 1, paraffin, romidepsin, vitamin a, docosahexaenoic acid, hydrogen peroxide, droloxifene, saikosaponin, fluoxetine, retinoic acid, n acetylcysteine, dithiothreitol, cordycepin, agarose, 8-bromo-cAMP, D-galactosamine, tachyplesin i, theophylline, metoprolol, SU6657, 15-deoxy-delta-12,14-prostaglandin j2, dmso, 2-amino-5-azotoluene, cycloheximide |

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the invention, which include a T cell modulating agent, are used to treat or alleviate a symptom associated with an immune-related disorder or an aberrant immune response. The present invention also provides methods of treating or alleviating a symptom associated with an immune-related disorder or an aberrant immune response. A therapeutic regimen is carried out by identifying a subject, e.g., a human patient suffering from (or at risk of developing) an immune-related disorder or aberrant immune response, using standard methods. For example, T cell modulating agents are useful therapeutic tools in the treatment of autoimmune diseases and/or inflammatory disorders. In certain embodiments, the use of T cell modulating agents that modulate, e.g., inhibit, neutralize, or interfere with, Th17 T cell differentiation is contemplated for treating autoimmune diseases and/or inflammatory disorders. In certain embodiments, the use of T cell modulating agents that modulate, e.g., enhance or promote, Th17 T cell differentiation is contemplated for augmenting Th17 responses, for example, against certain pathogens and other infectious diseases. The T cell modulating agents are also useful therapeutic tools in various transplant indications, for example, to prevent, delay or otherwise mitigate transplant rejection and/or prolong survival of a transplant, as it has also been shown that in some cases of transplant rejection, Th17 cells might also play an important role. (See e.g., Abadja F, Sarraj B, Ansari M J., "Significance of T helper 17 immunity in transplantation." Curr Opin Organ Transplant. 2012 February; 17(1):8-14. doi: 10.1097/MOT.0b013e32834ef4e4). The T cell modulating agents are also useful therapeutic tools in cancers and/or anti-tumor immunity, as Th17/Treg balance has also been implicated in these indications. For example, some studies have suggested that IL-23 and Th17 cells play a role in some cancers, such as, by way of non-limiting example, colorectal cancers. (See e.g., Ye J, Livergood R S, Peng G. "The role and regulation of human Th17 cells in tumor immunity." Am J Pathol. 2013 January; 182(1):10-20. doi: 10.1016/j.ajpath.2012.08.041. Epub 2012 Nov. 14). The T cell modulating agents are also useful in patients who have genetic defects that exhibit aberrant Th17 cell production, for example, patients that do not produce Th17 cells naturally.

The T cell modulating agents are also useful in vaccines and/or as vaccine adjuvants against autoimmune disorders, inflammatory diseases, etc. The combination of adjuvants for treatment of these types of disorders are suitable for use in combination with a wide variety of antigens from targeted self-antigens, i.e., autoantigens, involved in autoimmunity, e.g., myelin basic protein; inflammatory self-antigens, e.g., amyloid peptide protein, or transplant antigens, e.g., alloantigens. The antigen may comprise peptides or polypeptides derived from proteins, as well as fragments of any of the following: saccharides, proteins, polynucleotides or oligonucleotides, autoantigens, amyloid peptide protein, transplant antigens, allergens, or other macromolecular components. In some instances, more than one antigen is included in the antigenic composition.

Autoimmune diseases include, for example, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis herpetiformis; chronic fatigue immune dysfunction syndrome (CFIDS), chronic inflammatory demyelinating polyneuropathy (CIDP), cicatricial pemphigoid, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barré syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Ménière's disease, mixed connective tissue disease, multiple sclerosis, myasthenia gravis, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjögren's syndrome, stiff-man syndrome, systemic lupus erythematosus, Takayasu arteritis, temporal arteritis/giant cell arteritis, ulcerative colitis, uveitis, vitiligo and Wegener's granulomatosis.

In some embodiments, T cell modulating agents are useful in treating, delaying the progression of, or otherwise ameliorating a symptom of an autoimmune disease having an inflammatory component such as an aberrant inflammatory response in a subject. In some embodiments, T cell modulating agents are useful in treating an autoimmune disease that is known to be associated with an aberrant Th17 response, e.g., aberrant IL-17 production, such as, for example, multiple sclerosis (MS), psoriasis, inflammatory bowel disease, ulcerative colitis, Crohn's disease, uveitis, lupus, ankylosing spondylitis, and rheumatoid arthritis.

Inflammatory disorders include, for example, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

Symptoms associated with these immune-related disorders include, for example, inflammation, fever, general malaise, fever, pain, often localized to the inflamed area, rapid pulse rate, joint pain or aches (arthralgia), rapid breathing or other abnormal breathing patterns, chills, confusion, disorientation, agitation, dizziness, cough, dyspnea, pulmonary infections, cardiac failure, respiratory failure, edema, weight gain, mucopurulent relapses, cachexia, wheezing, headache, and abdominal symptoms such as, for example, abdominal pain, diarrhea or constipation.

Efficaciousness of treatment is determined in association with any known method for diagnosing or treating the particular immune-related disorder. Alleviation of one or more symptoms of the immune-related disorder indicates that the T cell modulating agent confers a clinical benefit.

Administration of a T cell modulating agent to a patient suffering from an immune-related disorder or aberrant immune response is considered successful if any of a variety of laboratory or clinical objectives is achieved. For example, administration of a T cell modulating agent to a patient is considered successful if one or more of the symptoms associated with the immune-related disorder or aberrant immune response is alleviated, reduced, inhibited or does not progress to a further, i.e., worse, state. Administration of T cell modulating agent to a patient is considered successful if the immune-related disorder or aberrant immune response enters remission or does not progress to a further, i.e., worse, state.

A therapeutically effective amount of a T cell modulating agent relates generally to the amount needed to achieve a therapeutic objective. The amount required to be administered will furthermore depend on the specificity of the T cell modulating agent for its specific target, and will also depend on the rate at which an administered T cell modulating agent is depleted from the free volume other subject to which it is administered.

T cell modulating agents can be administered for the treatment of a variety of diseases and disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where polypeptide-based T cell modulating agents are used, the smallest fragment that specifically binds to the target and retains therapeutic function is preferred. Such fragments can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Materials and Methods

Briefly, gene expression profiles were measured at 18 time points (0.5 hr to 72 days) under Th17 conditions (IL-6, TGF-β1) or control (Th0) using Affymetrix microarrays HT_MG-430A. Differentially expressed genes were detected using a consensus over four inference methods, and cluster the genes using k-means, with an automatically derived k. Temporal regulatory interactions were inferred by looking for significant ($p<5*10^{-5}$ and fold enrichment>1.5) overlaps between the regulator's putative targets (e.g., based on ChIPseq) and the target gene's cluster (using four clustering schemes). Candidates for perturbation were ordered lexicographically using network-based and expression-based features. Perturbations were done using SiNW for siRNA delivery. These methods are described in more detail below.

Mice:

C57BL/6 wild-type (wt), $Mt^{-/-}$, $Irf1^{-/-}$, $Fas^{-/-}$, $Irf4^{-/-}$, and $Cd4^{Cre}$ mice were obtained from Jackson Laboratory (Bar Harbor, Me.). $Stat1^{-/-}$ and 129/Sv control mice were purchased from Taconic (Hudson, N.Y.). $IL-12r\beta^{-/-}$ mice were provided by Dr. Pahan Kalipada from Rush University Medical Center. $IL-17Ra^{-/-}$ mice were provided by Dr. Jay Kolls from Louisiana State University/University of Pittsburgh. $Irf8^{fl/fl}$ mice were provided by Dr. Keiko Ozato from the National Institute of Health. Both $Irf4^{fl/fl}$ and $Irf8^{fl/fl}$ mice were crossed to $Cd4^{Cre}$ mice to generate $Cd4^{Cre}xIrf4^{fl/fl}$ and $Cd4^{Cre}xIrf8^{fl/fl}$ mice. All animals were housed and maintained in a conventional pathogen-free facility at the Harvard Institute of Medicine in Boston, Mass. (IACUC protocols: 0311-031-14 (VKK) and 0609-058015 (AR)). All experiments were performed in accordance to the guidelines outlined by the Harvard Medical Area Standing Committee on Animals at the Harvard Medical School (Boston, Mass.). In addition, spleens from $Mina^{-/-}$ mice were provided by Dr. Mark Bix from St. Jude Children's Research Hospital (IACUC Protocol: 453). $Pou2af1^{-/-}$ mice were obtained from the laboratory of Dr. Robert Roeder (Kim, U. et al. The B-cell-specific transcription coactivator OCA-B/OBF-1/Bob-1 is essential for normal production of immunoglobulin isotypes. Nature 383, 542-547, doi:10.1038/383542a0 (1996)). Wild-type and $Oct1^{-/-}$ fetal livers were obtained at day E12.5 and transplanted into sub-lethally irradiated $Rag1^{-/-}$ mice as previously described (Wang, V. E., Tantin, D., Chen, J. & Sharp, P. A. B cell development and immunoglobulin transcription in Oct-1-deficient mice. Proc. Natl. Acad. Sci. U.S.A. 101, 2005-2010, doi:10.1073/pnas.0307304101 (2004)) (IACUC Protocol: 11-09003).

Cell Sorting and In Vitro T-Cell Differentiation in Petri Dishes:

Cd4+ T cells were purified from spleen and lymph nodes using anti-CD4 microbeads (Miltenyi Biotec) then stained in PBS with 1% FCS for 20 min at room temperature with anti-Cd4-PerCP, anti-Cd621-APC, and anti-Cd44-PE antibodies (all Biolegend, Calif.).

Naïve $Cd4^+$ $Cd621^{high}$ $Cd44^{low}$ T cells were sorted using the BD FACSAria cell sorter. Sorted cells were activated with plate bound anti-Cd3 (2 µg/ml) and anti-Cd28 (2 µg/ml) in the presence of cytokines. For Th17 differentiation: 2 ng/mL rhTGF-β1 (Miltenyi Biotec), 25 ng/mL mill-6 (Miltenyi Biotec), 20 ng/ml mill-23 (Miltenyi Biotec), and 20 ng/ml rmIL-β1 (Miltenyi Biotec). Cells were cultured for 0.5-72 hours and harvested for RNA, intracellular cytokine staining, and flow cytometry.

Flow Cytometry and Intracellular Cytokine Staining (ICC):

Sorted naïve T cells were stimulated with phorbol 12-myristate 13-acetate (PMA) (50 ng/ml, Sigma-aldrich, MO), ionomycin (1 µg/ml, Sigma-aldrich, MO) and a protein transport inhibitor containing monensin (Golgistop) (BD Biosciences) for four hours prior to detection by staining with antibodies. Surface markers were stained in PBS with 1% FCS for 20 min at room temperature, then subsequently the cells were fixed in Cytoperm/Cytofix (BD Biosciences), permeabilized with Perm/Wash Buffer (BD Biosciences) and stained with Biolegend conjugated antibodies, i.e. Brilliant Violet 650™ anti-mouse IFN-γ (XMG1.2) and allophycocyanin-anti-IL-17A (TC11-18H10.1), diluted in Perm/Wash buffer as described (Bettelli, E. et al. Reciprocal developmental pathways for the generation of pathogenic effector TH17 and regulatory T cells. Nature 441, 235-238 (2006)) (FIG. 5, FIG. 16). To measure the time-course of RORγt protein expression, a phycoerythrin-conjugated anti-Retinoid-Related Orphan Receptor gamma was used (B2D), also from eBioscience (FIG. 16). FOXP3 staining for cells from knockout mice was performed with the FOXP3 staining kit by eBioscience (00-5523-00) in accordance with their "Onestep protocol for intracellular (nuclear) proteins". Data was collected using either a FACS Calibur or LSR II (Both BD Biosciences), then analyzed using Flow Jo software (Treestar) (Awasthi, A. et al. A dominant function for interleukin 27 in generating interleukin 10-producing anti-inflammatory T cells. Nature immunology 8, 1380-1389, doi:10.1038/ni1541 (2007); Awasthi, A. et al. Cutting edge: IL-23 receptor gfp reporter mice reveal distinct populations of IL-17-producing cells. J Immunol 182, 5904-5908, doi:10.4049/jimmunol.0900732 (2009)).

Quantification of Cytokine Secretion Using Enzyme-Linked Immunosorbent Assay (ELISA):

Naïve T cells from knockout mice and their wild type controls were cultured as described above, their supernatants were collected after 72 h, and cytokine concentrations were determined by ELISA (antibodies for IL-17 and IL-10 from BD Bioscience) or by cytometric bead array for the indicated cytokines (BD Bioscience), according to the manufacturers' instructions (FIG. 5, FIG. 16).

Figures 1, 1B:
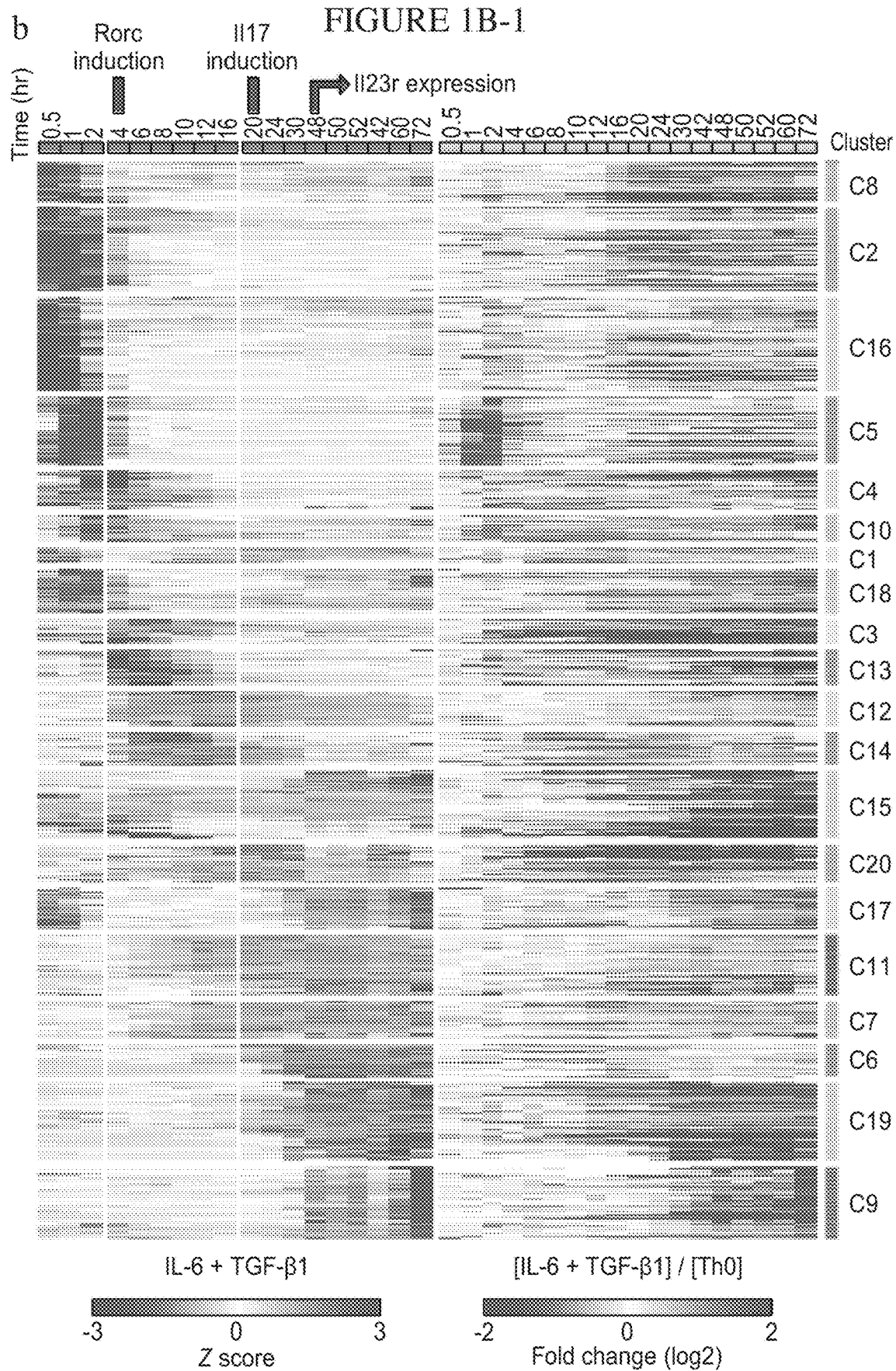
Figure 6A:
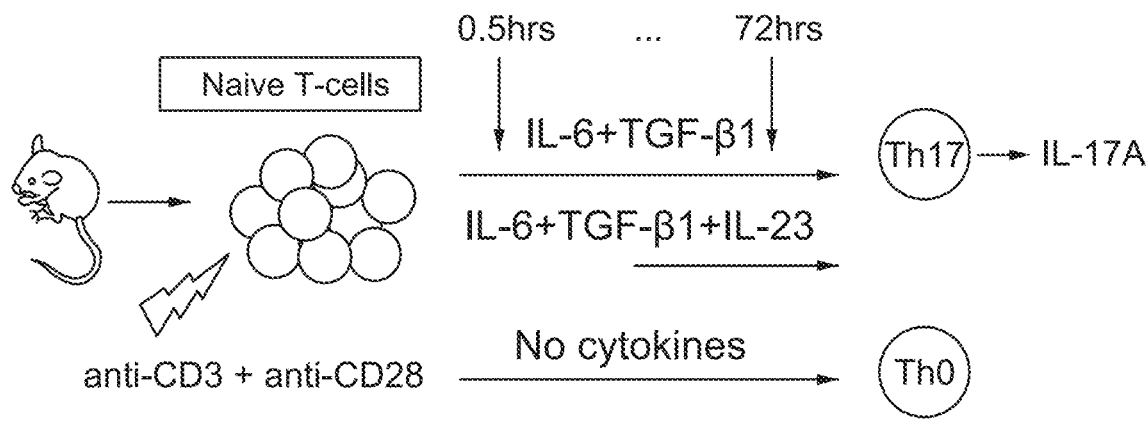
Figure 6B:
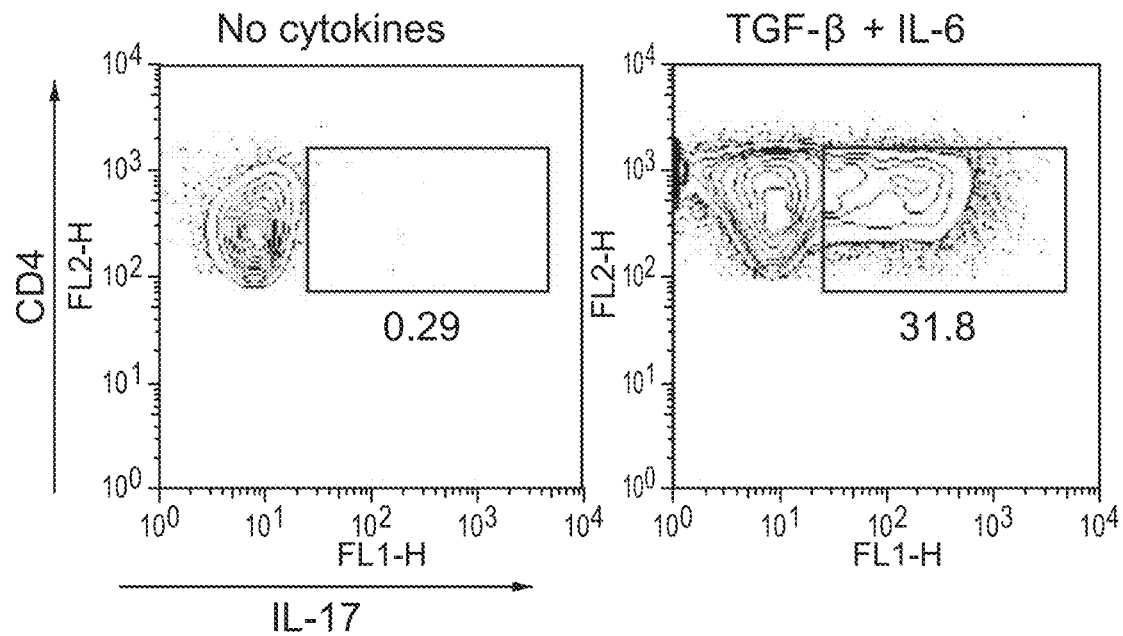
Figure 6C:
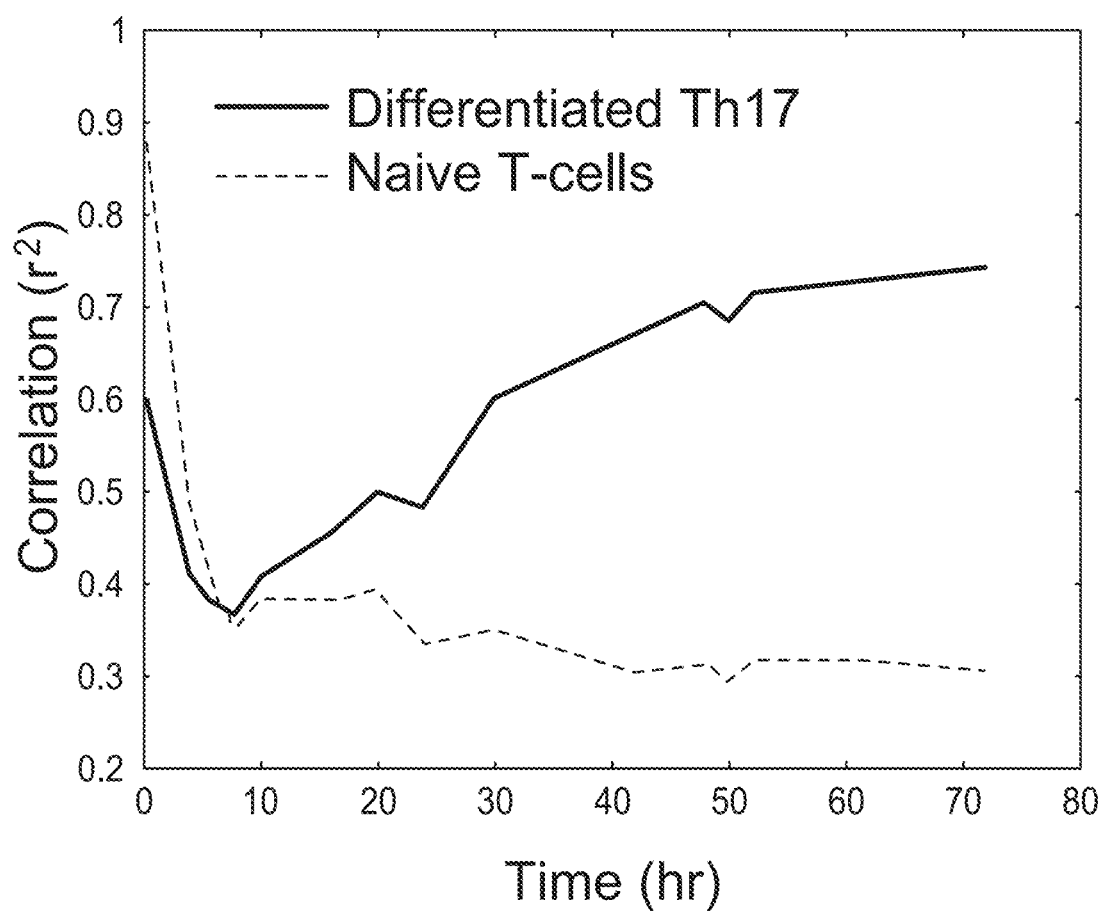

Microarray Data:

Naïve T cells were isolated from WT mice, and treated with IL-6 and TGF-β1. Affymetrix microarrays HT_MG-430A were used to measure the resulting mRNA levels at 18 different time points (0.5-72 h; FIG. 1b). In addition, cells treated initially with IL-6, TGF-β1 and with addition of IL-23 after 48 hr were profiled at five time points (50-72 h). As control, time- and culture-matched WT naïve T cells stimulated under Th0 conditions were used. Biological replicates were measured in eight of the eighteen time points (1 hr, 2 hr, 10 hr, 20 hr, 30 hr, 42 hr, 52 hr, 60 hr) with high reproducibility ($r^2 > 0.98$). For further validation, the differentiation time course was compared to published microarray data of Th17 cells and naïve T cells (Wei, G. et al. in Immunity Vol. 30 155-167 (2009)) (FIG. 6c). In an additional dataset naïve T cells were isolated from WT and Il23r$^{-/-}$ mice, and treated with IL-6, TGF-β1 and IL-23 and profiled at four different time points (49 hr, 54 hr, 65 hr, 72 hr). Expression data was preprocessed using the RMA algorithm followed by quantile normalization (Reich, M. et al. GenePattern 2.0. Nature genetics 38, 500-501, doi: 10.1038/ng0506-500 (2006)).

Detecting Differentially Expressed Genes:

Differentially expressed genes (comparing to the Th0 control) were found using four methods: (1) Fold change. Requiring a 2-fold change (up or down) during at least two time points. (2) Polynomial fit. The EDGE software (Storey, J., Xiao, W., Leek, J., Tompkins, R. & Davis, R. in Proc. Natl. Acad. Sci. U.S.A. vol. 102 12837 (2005); Leek, J. T., Monsen, E., Dabney, A. R. & Storey, J. D. EDGE: extraction and analysis of differential gene expression. Bioinformatics 22, 507-508, doi:10.1093/bioinformatics/btk005 (2006)), designed to identify differential expression in time course data, was used with a threshold of q-value≤0.01. (3) Sigmoidal fit. An algorithm similar to EDGE while replacing the polynomials with a sigmoid function, which is often more adequate for modeling time course gene expression data (Chechik, G. & Koller, D. Timing of gene expression responses to environmental changes. J Comput Biol 16, 279-290, doi:10.1089/cmb.2008.13TT10.1089/cmb.2008.13TT [pii] (2009)), was used. A threshold of q-value≤0.01. (4) ANOVA was used. Gene expression is modeled by: time (using only time points for which there was more than one replicate) and treatment ("TGF-β1+IL-6" or "Th0"). The model takes into account each variable independently, as well as their interaction. Cases in which the p-value assigned with the treatment parameter or the interaction parameter passed an FDR threshold of 0.01 were reported.

Overall, substantial overlap between the methods (average of 82% between any pair of methods) observed. The differential expression score of a gene was defined as the number of tests that detected it. As differentially expressed genes, cases with differential expression score>3 were reported.

For the Il23r$^{-/-}$ time course (compared to the WT T cells) methods 1.3 (above) were used. Here, a fold change cutoff of 1.5 was used, and genes detected by at least two tests were reported.

Clustering:

several ways for grouping the differentially expressed genes were considered, based on their time course expression data: (1) For each time point, two groups were defined: (a) all the genes that are over-expressed and (b) all the genes that are under-expressed relative to Th0 cells (see below); (2) For each time point, two groups were defined: (a) all the genes that are induced and (b) all the genes that are repressed, comparing to the previous time point; (3) K-means clustering using only the Th17 polarizing conditions. The minimal k was used, such that the within-cluster similarity (average Pearson correlation with the cluster's centroid) was higher than 0.75 for all clusters; and, (4) K-means clustering using a concatenation of the Th0 and Th17 profiles.

For methods (1, 2), to decide whether to include a gene, its original mRNA expression profiles (Th0, Th17), and their approximations as sigmoidal functions (Chechik, G. & Koller, D. Timing of gene expression responses to environmental changes. J Comput Biol 16, 279-290, doi:10.1089/cmb.2008.13TT10.1089/cmb.2008.13TT [pii] (2009)) (thus filtering transient fluctuations) were considered. The fold change levels (compared to Th0 (method 1) or to the previous time point (method 2)) were required to pass a cutoff defined as the minimum of the following three values: (1) 1.7; (2) mean+std of the histogram of fold changes across all time points; or (3) the maximum fold change across all time points. The clusters presented in FIG. 1b were obtained with method 4.

Regulatory Network Inference:

potential regulators of Th17 differentiation were identified by computing overlaps between their putative targets and sets of differentially expressed genes grouped according to methods 1-4 above. regulator-target associations from several sources were assembled: (1) in vivo DNA binding profiles (typically measured in other cells) of 298 transcriptional regulators (Linhart, C., Halperin, Y. & Shamir, R. Transcription factor and microRNA motif discovery: the Amadeus platform and a compendium of metazoan target sets. Genome research 18, 1180-1189, doi:10.1101/gr.076117.108 (2008); Zheng, G. et al. ITFP: an integrated platform of mammalian transcription factors. Bioinformatics 24, 2416-2417, doi:10.1093/bioinformatics/btn439 (2008); Wilson, N. K. et al. Combinatorial transcriptional control in blood stem/progenitor cells: genome-wide analysis of ten major transcriptional regulators. Cell Stem Cell 7, 532-544, doi:S1934-5909(10)00440-6 [pii]10.1016/j.stem.2010.07.016 (2010); Lachmann, A. et al. in Bioinformatics Vol. 26 2438-2444 (2010); Liberzon, A. et al. Molecular signatures database (MSigDB) 3.0. Bioinformatics 27, 1739-1740, doi:10.1093/bioinformatics/btr260 (2011); Jiang, C., Xuan, Z., Zhao, F. & Zhang, M. TRED: a transcriptional regulatory element database, new entries and other development. Nucleic Acids Res 35, D137-140 (2007)); (2) transcriptional responses to the knockout of 11 regulatory proteins (Awasthi et al., J. Immunol 2009; Schraml, B. U. et al. The AP-1 transcription factor Batf controls T(H)17 differentiation. Nature 460, 405-409, doi:nature08114 [pii]10.1038/nature08114 (2009); Shi, L. Z. et al. HIF1alpha-dependent glycolytic pathway orchestrates a metabolic checkpoint for the differentiation of TH17 and Treg cells. The Journal of experimental medicine 208, 1367-1376, doi:10.1084/jem.20110278 (2011); Yang, X. P. et al. Opposing regulation of the locus encoding IL-17 through direct, reciprocal actions of STAT3 and STAT5. Nature immunology 12, 247-254, doi:10.1038/ni.1995 (2011); Durant, L. et al. Diverse Targets of the Transcription Factor STAT3 Contribute to T Cell Pathogenicity and Homeostasis. Immunity 32, 605-615, doi:10.1016/j.immuni.2010.05.003 (2010); Jux, B., Kadow, S. & Esser, C. Langerhans cell maturation and contact hypersensitivity are impaired in aryl hydrocarbon receptor-null mice. Journal of immunology (Baltimore, Md.: 1950) 182, 6709-6717, doi:10.4049/jimmunol.0713344 (2009); Amit, I. et al. Unbiased reconstruction of a mammalian transcriptional network mediating pathogen responses. Science 326, 257-263, doi:10.1126/science.1179050 (2009); Xiao, S. et al. Retinoic acid increases Foxp3+ regulatory T cells and inhibits development of Th17 cells by enhancing TGF-beta-driven Smad3 signaling and inhibiting IL-6 and IL-23 receptor expression. J Immunol 181, 2277-2284, doi:181/4/2277 [pii] (2008)); (3) additional potential interactions obtained by applying the Ontogenet algorithm (Jojic et al., under review; regulatory model available at: to data from the mouse ImmGen consortium (January 2010 release (Heng, T. S. & Painter, M. W. The Immunological Genome Project: networks of gene expression in immune cells. Nature immunology 9, 1091-1094, doi:10.1038/ni1008-1091 (2008)), which includes 484 microarray samples from 159 cell subsets from the innate and adaptive immune system of mice; (4) a statistical analysis of cis-regulatory element enrichment in promoter regions (Elkon, R., Linhart, C., Sharan, R., Shamir, R. & Shiloh, Y. in Genome Research Vol. 13 773-780 (2003); Odabasioglu, A., Celik, M. & Pileggi, L. T. in Proceedings of the 1997 IEEE/ACM international conference on Computer-aided design 58-65 (IEEE Computer Society, San Jose, Calif., United States, 1997)); and, (5) the TF enrichment module of the IPA software. For every TF in the database, the statistical significance of the overlap between its putative targets and each of the groups defined above using a Fisher's exact test was computed. Cases where $p<5*10^{-5}$ and the fold enrichment>1.5 were included.

Each edge in the regulatory network was assigned a time stamp based on the expression profiles of its respective regulator and target nodes. For the target node, the time points at which a gene was either differentially expressed or significantly induced or repressed with respect to the previous time point (similarly to grouping methods 1 and 2 above) were considered. A regulator node was defined as 'absent' at a given time point if: (i) it was under expressed compared to Th0; or (ii) the expression is low (<20% of the maximum value in time) and the gene was not over-expressed compared to Th0; or, (iii) up to this point in time the gene was not expressed above a minimal expression value of 100. As an additional constraint, protein expression levels were estimated using the model from Schwanhäusser, B. et al. (Global quantification of mammalian gene expression control. Nature 473, 337-342, doi:10.1038/nature10098 (2011)) and using a sigmoidal fit (Chechik & Koller, J Comput Biol 2009) for a continuous representation of the temporal expression profiles, and the ProtParam software (Wilkins, M. R. et al. Protein identification and analysis tools in the ExPASy server. Methods Mol. Biol. 112, 531-552 (1999)) for estimating protein half-lives. It was required that, in a given time point, the predicted protein level be no less than 1.7 fold below the maximum value attained during the time course, and not be less than 1.7 fold below the Th0 levels. The timing assigned to edges inferred based on a time-point specific grouping (grouping methods 1 and 2 above) was limited to that specific time point. For instance, if an edge was inferred based on enrichment in the set of genes induced at 1 hr (grouping method #2), it will be assigned a "1 hr" time stamp. This same edge could then only have additional time stamps if it was revealed by additional tests.

Selection of Nanostring Signature Genes:

The selection of the 275-gene signature (Table 1) combined several criteria to reflect as many aspect of the differentiation program as was possible. The following requirements were defined: (1) the signature must include all of the TFs that belong to a Th17 microarray signature (comparing to other CD4+ T cells (Wei et al., in Immunity vol. 30 155-167 (2009)), see Methods described herein); that are included as regulators in the network and have a differential expression score>1; or that are strongly differentially expressed (differential expression score=4); (2) it must include at least 10 representatives from each cluster of genes that have similar expression profiles (using clustering method (4) above); (3) it must contain at least 5 representatives from the predicted targets of each TF in the different networks; (4) it must include a minimal number of representatives from each enriched Gene Ontology (GO) category (computed across all differentially expressed genes); and, (5) it must include a manually assembled list of ~100 genes that are related to the differentiation process, including the differentially expressed cytokines, receptor molecules and other cell surface molecules. Since these different criteria might generate substantial overlaps, a set-cover algorithm was used to find the smallest subset of genes that satisfies all of five conditions. To this list 18 genes whose expression showed no change (in time or between treatments) in the microarray data were added.

The 85-gene signature (used for the Fluidigm BioMark qPCR assay) is a subset of the 275-gene signature, selected to include all the key regulators and cytokines discussed. To this list 10 control genes (2900064A13RIK, API5, CAND1, CSNK1A1, EIF3E, EIF3H, FIP1L1, GOLGA3, HSBP1, KHDRBS1, MED24, MKLN1, PCBP2, SLC6A6, SUFU, TMED7, UBE3A, ZFP410) were added.

Selection of Perturbation Targets:

an unbiased approach was used to rank candidate regulators—transcription factor or chromatin modifier genes—of Th17 differentiation. The ranking was based on the following features: (a) whether the gene encoding the regulator belonged to the Th17 microarray signature (comparing to other CD4+ T cells (Wei et al., in Immunity vol. 30 155-167 (2009)), see Methods described herein); (b) whether the regulator was predicted to target key Th17 molecules (IL-17, IL-21, IL23r, and ROR-γt); (c) whether the regulator was detected based on both perturbation and physical binding data from the IPA software; (d) whether the regulator was included in the network using a cutoff of at least 10 target genes; (e) whether the gene encoding for the regulator was significantly induced in the Th17 time course. Only cases where the induction happened after 4 hours were considered to exclude non-specific hits; (f) whether the gene encoding the regulator was differentially expressed in response to Th17-related perturbations in previous studies. For this criterion, a database of transcriptional effects in perturbed Th17 cells was assembled, including: knockouts of Batf (Schraml et al., Nature 2009), ROR-γt (Xiao et al., unpublished), Hif1a (Shi et al., J. Exp. Med. (2011)), Stat3 and Stat5 (Yang et al., Nature Immunol (2011); Durant, L. et al. in Immunity Vol. 32 605-615 (2010), Tbx21 (Awasthi et al., unpublished), IL23r (this study), and Ahr (Jux et al., J. Immunol 2009)). Data from the Th17 response to Digoxin (Huh, J. R. et al. Digoxin and its derivatives suppress TH17 cell differentiation by antagonizing RORgammat activity. Nature 472, 486-490, doi:10.1038/nature09978 (2011)) and Halofuginone (Sundrud, M. S. et al. Halofuginone inhibits TH17 cell differentiation by activating the amino acid starvation response. Science (New York, N.Y.) 324, 1334-1338, doi:10.1126/science.1172638 (2009)), as well as information on direct binding by ROR-γt as inferred from ChIP-seq data (Xiao et al., unpublished) was also included. The analysis of the published expression data sets is described in the Methods described herein. For each regulator, the number of conditions in which it came up as a significant hit (up/down-regulated or bound) was counted; for regulators with 2 to 3 hits (quantiles 3 to 7 out of 10 bins), a score of 1 was then assign; for regulators with more than 3 hits (quantiles 8-10), a score of 2 (a score of 0 is assigned otherwise) was assigned; and, (g) the differential expression score of the gene in the Th17 time course.

The regulators were ordered lexicographically by the above features according to the order: a, b, c, d, (sum of e and f), g—that is, first sort according to a then break ties according to b, and so on. Genes that are not over-expressed during at least one time point were excluded. As an exception, predicted regulators (feature d) that had additional external validation (feature f) were retained. To validate this ranking, a supervised test was used: 74 regulators that were previously associated with Th17 differentiation were manually annotated. All of the features are highly specific for these regulators ($p<10^{-3}$). Moreover, using a supervised learning method (Naïve Bayes), the features provided good predictive ability for the annotated regulators (accuracy of 71%, using 5-fold cross validation), and the resulting ranking was highly correlated with the unsupervised lexicographic ordering (Spearman correlation>0.86).

This strategy was adapted for ranking protein receptors. To this end, feature c was excluded and the remaining "protein-level" features (b and d) were replaced with the following definitions: (b) whether the respective ligand is induced during the Th17 time course; and, (d) whether the receptor was included as a target in the network using a cutoff of at least 5 targeting transcriptional regulators.

Figure 11A:
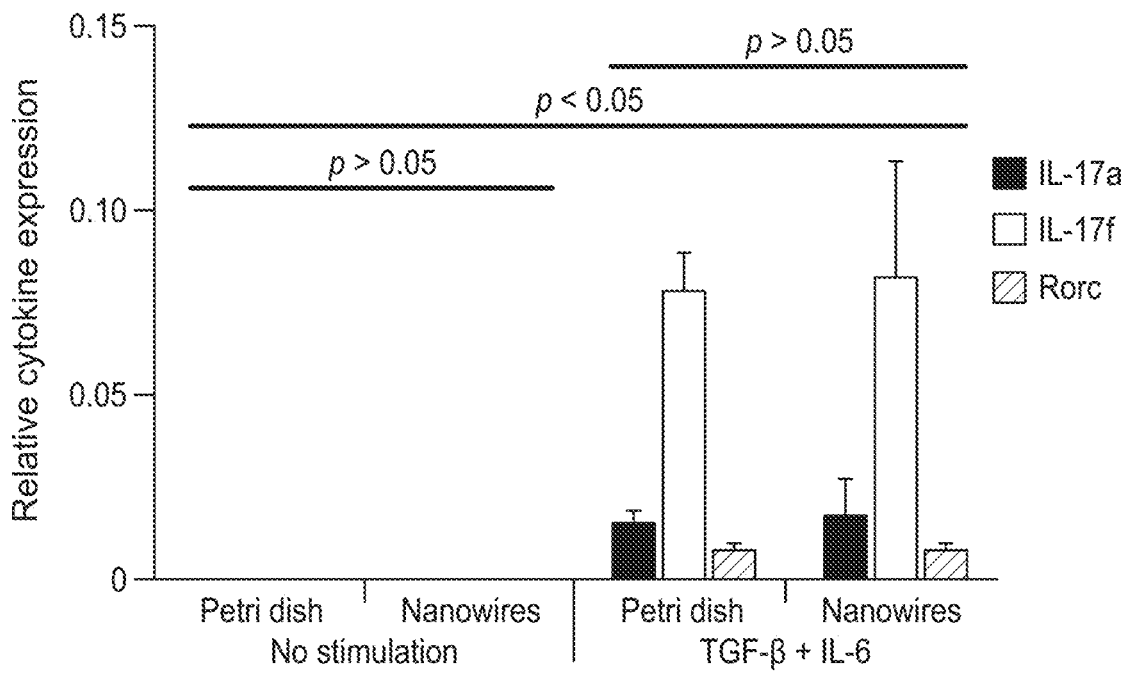
FIGS. 11A, 11B, and 11C are a series of graphs depicting Nanowire activation on T-cells, knockdown at 10 h, and consistency of NW-based knockdowns and resulting phenotypes.
Figure 11B:
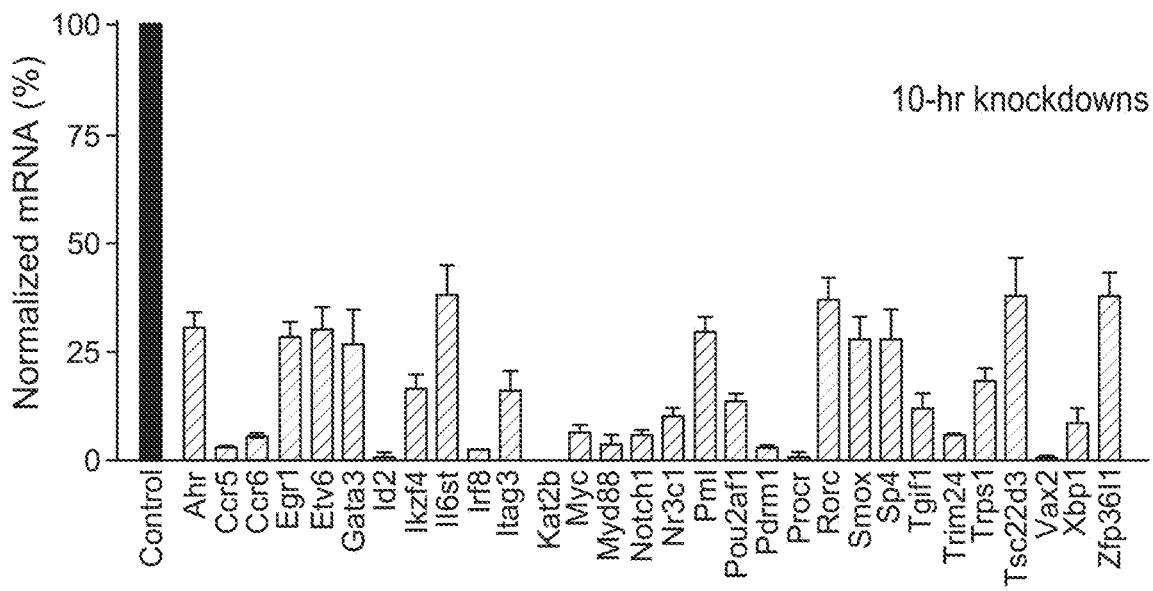
Figure 11C:
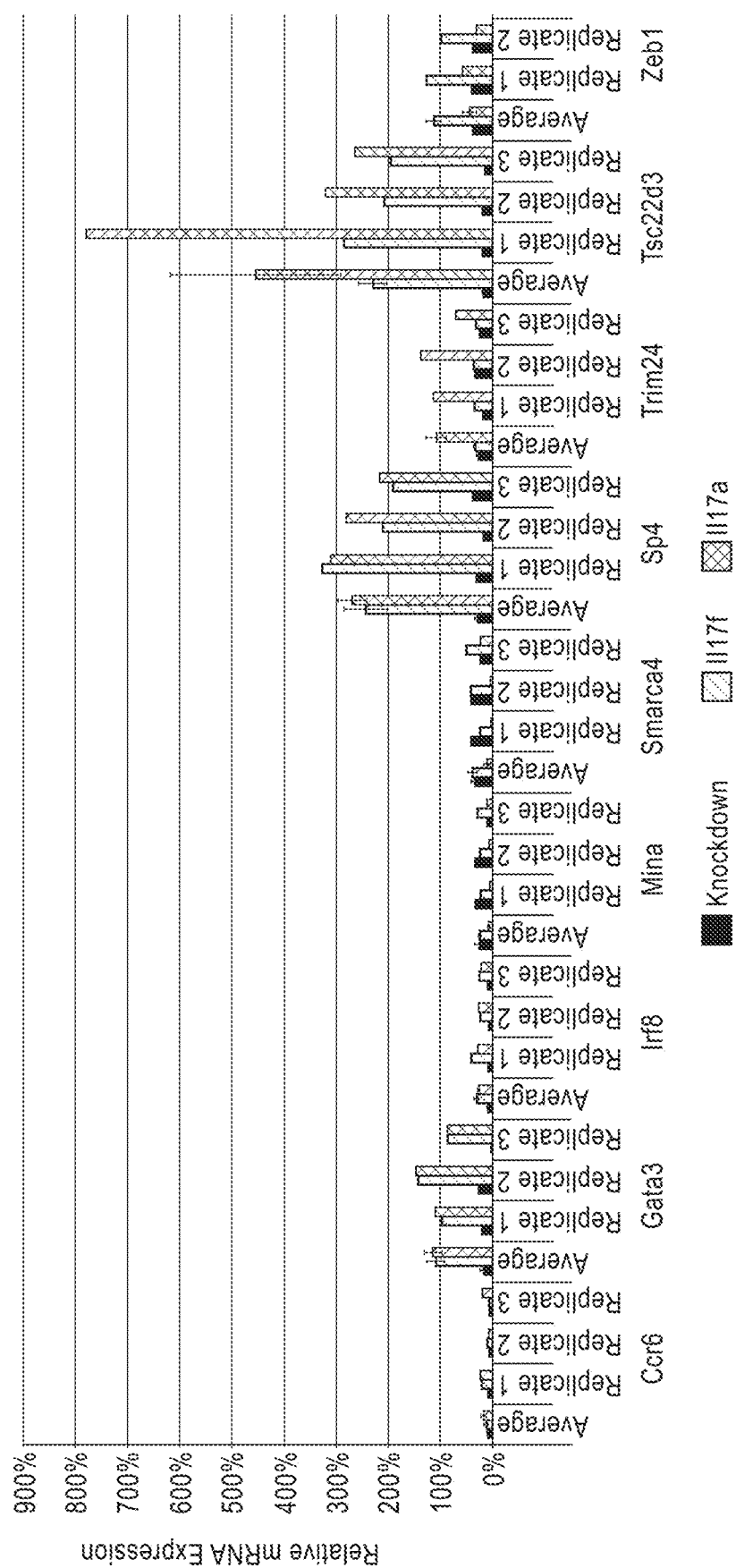

Gene Knockdown Using Silicon Nanowires:

4×4 mm silicon nanowire (NW) substrates were prepared and coated with 3 µL of a 50 µM pool of four siGENOME siRNAs (Dharmacon) in 96 well tissue culture plates, as previously described (Shalek, A. K. et al. Vertical silicon nanowires as a universal platform for delivering biomolecules into living cells. Proceedings of the National Academy of Sciences of the United States of America 107, 1870-1875, doi:10.1073/pnas.0909350107 (2010)). Briefly, 150,000 naïve T cells were seeded on siRNA-laced NWs in 10 µL of complete media and placed in a cell culture incubator (37° C., 5% $CO_2$) to settle for 45 minutes before full media addition. These samples were left undisturbed for 24 hours to allow target transcript knockdown. Afterward, siRNA-transfected T cells were activated with aCd3/Cd28 dynabeads (Invitrogen), according to the manufacturer's recommendations, under Th17 polarization conditions (TGF-β1 & IL-6, as above). 10 or 48 hr post-activation, culture media was removed from each well and samples were gently washed with 100 µL of PBS before being lysed in 20 µL of buffer TCL (Qiagen) supplemented with 2-mercaptoethanol (1:100 by volume). After mRNA was harvested in Turbocapture plates (Qiagen) and converted to cDNA using Sensiscript RT enzyme (Qiagen), qRT-PCR was used to validate both knockdown levels and phenotypic changes relative to 8-12 non-targeting siRNA control samples, as previously described (Chevrier, N. et al. Systematic discovery of TLR signaling components delineates viral-sensing circuits. Cell 147, 853-867, doi:10.1016/j.cell.2011.10.022 (2011)). A 60% reduction in target mRNA was used as the knockdown threshold. In each knockdown experiment, each individual siRNA pool was run in quadruplicate; each siRNA was tested in at least three separate experiments (FIG. 11).

mRNA Measurements in Perturbation Assays:

the nCounter system, presented in full in Geiss et al. (Geiss, G. K. et al. Direct multiplexed measurement of gene expression with color-coded probe pairs. SI. Nature Biotechnology 26, 317-325, doi:10.1038/nbt1385 (2008)), was used to measure a custom CodeSet constructed to detect a total of 293 genes, selected as described above. The Fluidigm BioMark HD system was also used to measure a smaller set of 96 genes. Finally, RNA-Seq was used to follow up and validate 12 of the perturbations.

A custom CodeSet constructed to detect a total of 293 genes, selected as described above, including 18 control genes whose expression remain unaffected during the time course was used. Given the scarcity of input mRNA derived from each NW knockdown, a Nanostring-CodeSet specific, 14 cycle Specific Target Amplification (STA) protocol was performed according to the manufacturer's recommendations by adding 5 µL of TaqMan PreAmp Master Mix (Invitrogen) and 1 µL of pooled mixed primers (500 nM each, see Table S6.1 for primer sequences) to 5 µL of cDNA from a validated knockdown. After amplification, 5 µL of the amplified cDNA product was melted at 95° C. for 2 minutes, snap cooled on ice, and then hybridized with the CodeSet at 65° C. for 16 hours. Finally, the hybridized samples were loaded into the nCounter prep station and product counts were quantified using the nCounter Digital Analyzer following the manufacturer's instructions. Samples that were too concentrated after amplification were diluted and rerun. Serial dilutions (1:1, 1:4, 1:16, & 1:64, pre-STA) of whole spleen and Th17 polarized cDNAs were used to both control for the effects of different amounts of starting input material and check for biases in sample amplification.

Nanostring nCounter Data Analysis:

For each sample, the count values were divided by the sum of counts that were assigned to a set of control genes that showed no change (in time or between treatments) in the microarray data (18 genes altogether). For each condition, a change fold ratio was computed, comparing to at least three different control samples treated with non-targeting (NT) siRNAs. The results of all pairwise comparisons (i.e. A×B pairs for A repeats of the condition and B control (NT) samples) were then pooled together: a substantial fold change (above a threshold value t) in the same direction (up/down regulation) in more than half of the pairwise comparisons was required. The threshold t was determined as max {d1, d2}, where d1 is the mean+std in the absolute log fold change between all pairs of matching NT samples (i.e., form the same batch and the same time point; d1=1.66), and where d2 is the mean+1.645 times the standard deviation in the absolute log fold change shown by the 18 control genes (determined separately for every comparison by taking all the 18×A×B values; corresponding to p=0.05, under assumption of normality). All pairwise comparisons in which both NT and knockdown samples had low counts before normalization (<100) were ignored.

Figure 10A:
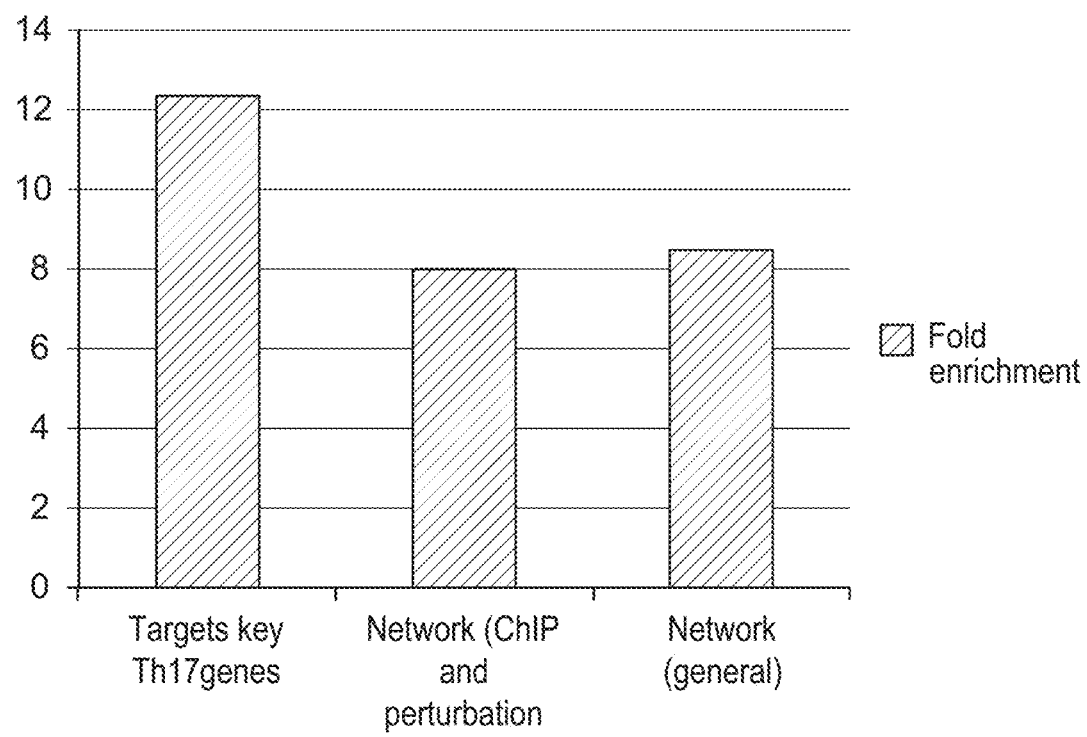
FIGS. 10A, 10B).
Figure 10B:
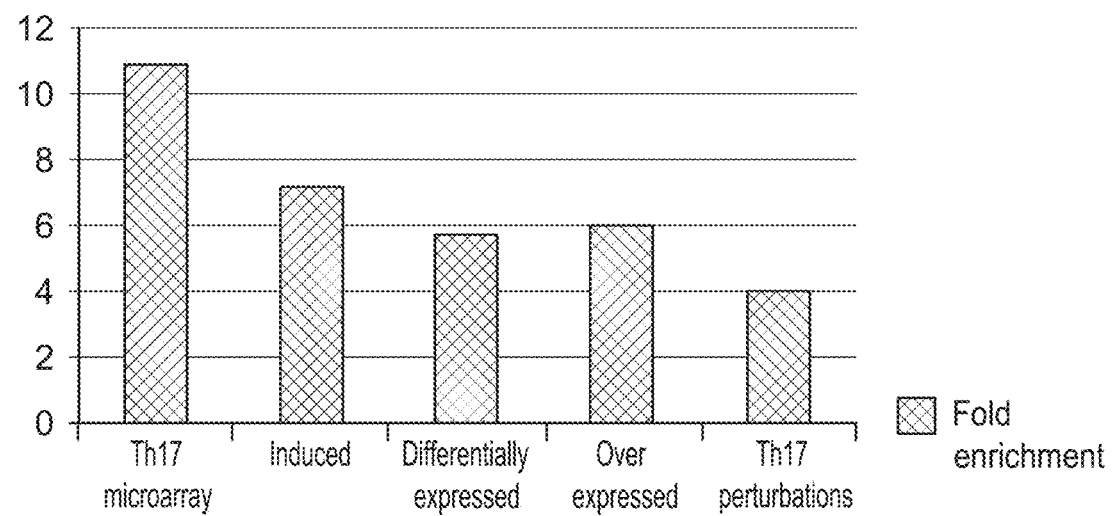

A permutation test was used to evaluate the overlap between the predicted network model (FIG. 2) and the knockdown effects measured in the Nanostring nCounter (FIG. 4, FIG. 10). Two indices were computed for every TF for which predicted target were available: (i) specificity—the percentage of predicted targets that are affected by the respective knockdown (considering only genes measured by nCounter), and (ii) sensitivity—the percentage of genes affected by a given TF knockdown that are also its predicted targets in the model. To avoid circularity, target genes predicted in the original network based on knockout alone were excluded from this analysis. The resulting values (on average, 13.5% and 24.8%, respectively) were combined into an F-score (the harmonic mean of specificity and sensitivity). The calculation of F-score was then repeated in 500 randomized datasets, where the target gene labels in the knockdown result matrix were shuffled. The reported empirical p-value is:

$P=(1+\text{\# randomized datasets with equal of better } F\text{-score})/(1+\text{\# randomized datasets})$ mRNA Measurements on the Fluidigm BioMark HD:

cDNA from validated knockdowns was prepared for quantification on the Fluidigm BioMark HD. Briefly, 5 µL of TaqMan PreAmp Master Mix (Invitrogen), 1 µL of pooled mixed primers (500 nM each, see Table S6.1 for primers), and 1.5 µL of water were added to 2.5 µL of knockdown validated cDNA and 14 cycles of STA were performed according to the manufacturer's recommendations. After the STA, an Exonuclease I digestion (New England Biosystems) was performed to remove unincorporated primers by adding 0.8 µL Exonuclease I, 0.4 µL Exonuclease I Reaction Buffer and 2.8 µL water to each sample, followed by vortexing, centrifuging and heating the sample to 37° C. for 30 minutes. After a 15 minute 80° C. heat inactivation, the amplified sample was diluted 1:5 in Buffer TE. Amplified validated knockdowns and whole spleen and Th17 serial dilution controls (1:1, 1:4, 1:16, & 1:64, pre-STA) were then analyzed using EvaGreen and 96×96 gene expression chips (Fluidigm BioMark HD) (Dalerba, P. et al. Single-cell dissection of transcriptional heterogeneity in human colon tumors. Nat Biotechnol 29, 1120-1127, doi:10.1038/nbt.2038 (2011)).

Fluidigm Data Analysis:

For each sample, the Ct values were subtracted from the geometric mean of the Ct values assigned to a set of four housekeeping genes. For each condition, a fold change ratio was computed, comparing to at least three different control samples treated with non-targeting (NT) siRNAs. The results of all pairwise comparisons (i.e. A×B pairs for A repeats of the condition and B control (NT) samples) were then pooled together: a substantial difference between the normalized Ct values (above a threshold value) in the same direction (up/down regulation) in more than half of the pairwise comparisons was required. The threshold t was determined as max {log 2(1.5), d1(b), d2}, where d1(b) is the mean+std in the delta between all pairs of matching NT samples (i.e., from the same batch and the same time point), over all genes in expression quantile b ($1<=b<=10$). d2 is the mean+1.645 times the standard deviation in the deltas shown by 10 control genes (the 4 housekeeping genes plus 6 control genes from the Nanostring signature); d2 is determined separately for each comparison by taking all the 10×A×B values; corresponding to p=0.05, under assumption of normality). All pairwise comparisons in which both NT and knockdown samples had low counts before normalization (Ct<21 (taking into account the amplification, this cutoff corresponds to a conventional Ct cutoff of 35)) were ignored.

mRNA Measurements Using RNA-Seq:

Validated single stranded cDNAs from the NW-mediated knockdowns were converted to double stranded DNA using the NEBNext mRNA Second Strand Synthesis Module (New England BioLabs) according to the manufacturer's recommendations. The samples were then cleaned using 0.9×SPRI beads (Beckman Coulter). Libraries were prepared using the Nextera XT DNA Sample Prep Kit (Illumina), quantified, pooled, and then sequenced on the HiSeq 2500 (Illumina) to an average depth 20M reads.

RNA-Seq Data Analysis:

a Bowtie index based on the UCSC known Gene transcriptome (Fujita, P. A. et al. The UCSC Genome Browser database: update 2011. Nucleic Acids Res. 39, D876-882, doi:10.1093/nar/gkq963 (2011)) was created, and paired-end reads were aligned directly to this index using Bowtie (Langmead, B., Trapnell, C., Pop, M. & Salzberg, S. L. Ultrafast and memory-efficient alignment of short DNA sequences to the human genome. Genome Biol 10, R25, doi:10.1186/gb-2009-10-3-r25 (2009)). Next, RSEM v1.11 (Li, B. & Dewey, C. N. RSEM: accurate transcript quantification from RNA-Seq data with or without a reference genome. BMC Bioinformatics 12, 323, doi:10.1186/1471-2105-12-323 (2011)) was ran with default parameters on these alignments to estimate expression levels. RSEM's gene level expression estimates (tau) were multiplied by 1,000,000 to obtain transcript per million (TPM) estimates for each gene. Quantile normalization was used to further normalize the TPM values within each batch of samples. For each condition, a fold change ratio was computed, comparing to at least two different control samples treated with nontargeting (NT) siRNAs. The results of all pairwise comparisons (i.e. A×B pairs for A repeats of the condition and B control (NT) samples) were then pooled together: a significant difference between the TPM values in the same direction (up/down regulation) in more than half of the pairwise comparisons was required. The significance cutoff t was determined as max {log 2(1.5), d1(b)}, where d1(b) is the mean+1.645*std in the log fold ratio between all pairs of matching NT samples (i.e., from the same batch and the same time point), over all genes in expression quantile b (1<=b<=20). All pairwise comparisons in which both NT and knockdown samples had low counts (TPM<10) were ignored. To avoid spurious fold levels due to low expression values a small constant, set to the value of the 1st quantile (out of 10) of all TPM values in the respective batch, was add to the expression values.

Figure 4A:
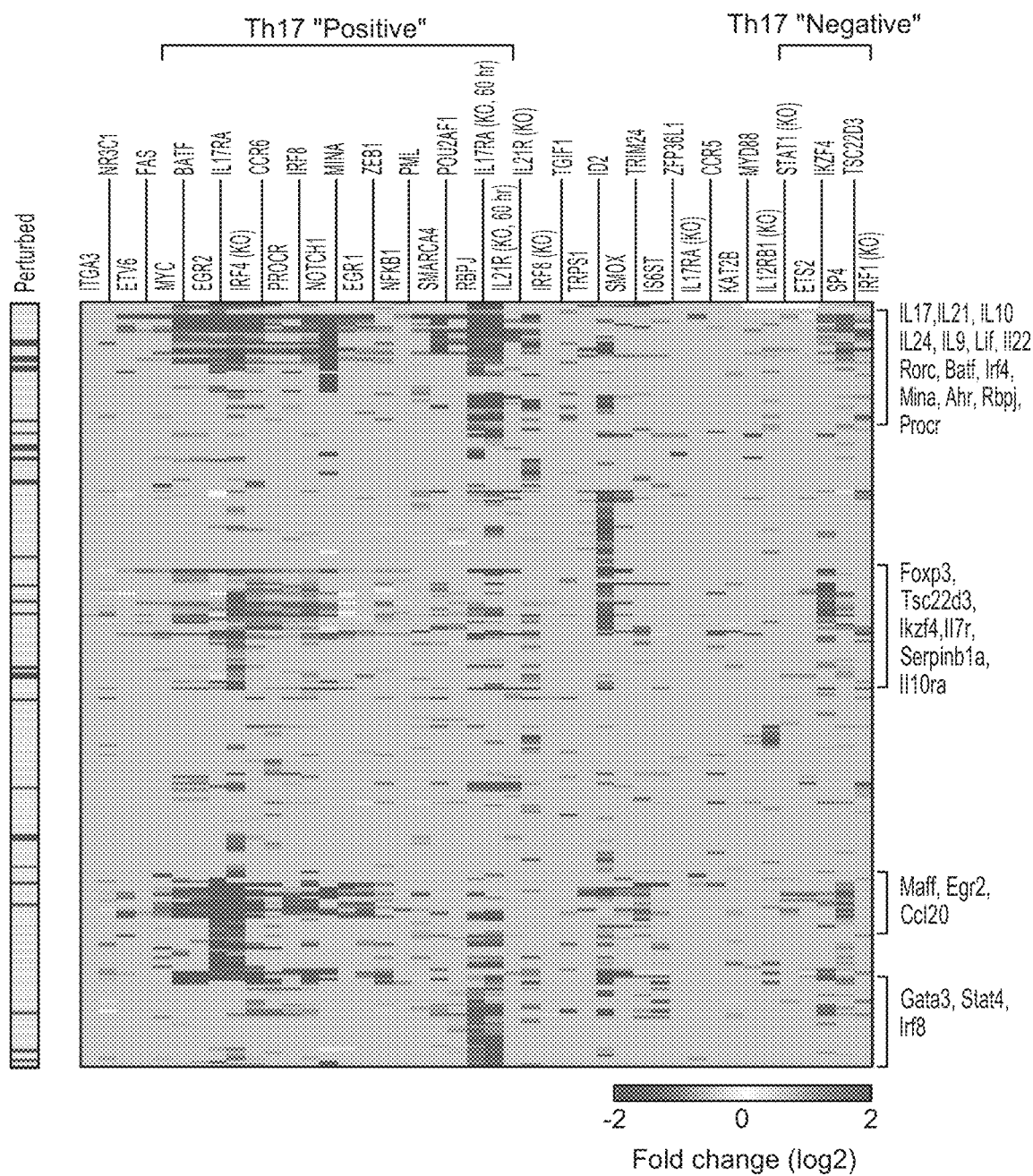
FIGS. 4A, 4B, 4C and 4D are a series of graphs and illustrations depicting coupled and mutually-antagonistic modules in the Th17 network. A color version of these figures can be found in Yosef et al., "Dynamic regulatory network controlling Th17 cell differentiation, Nature, vol. 496: 461-468 (2013)/doi: 10.1038/nature11981.
Figure 4B:
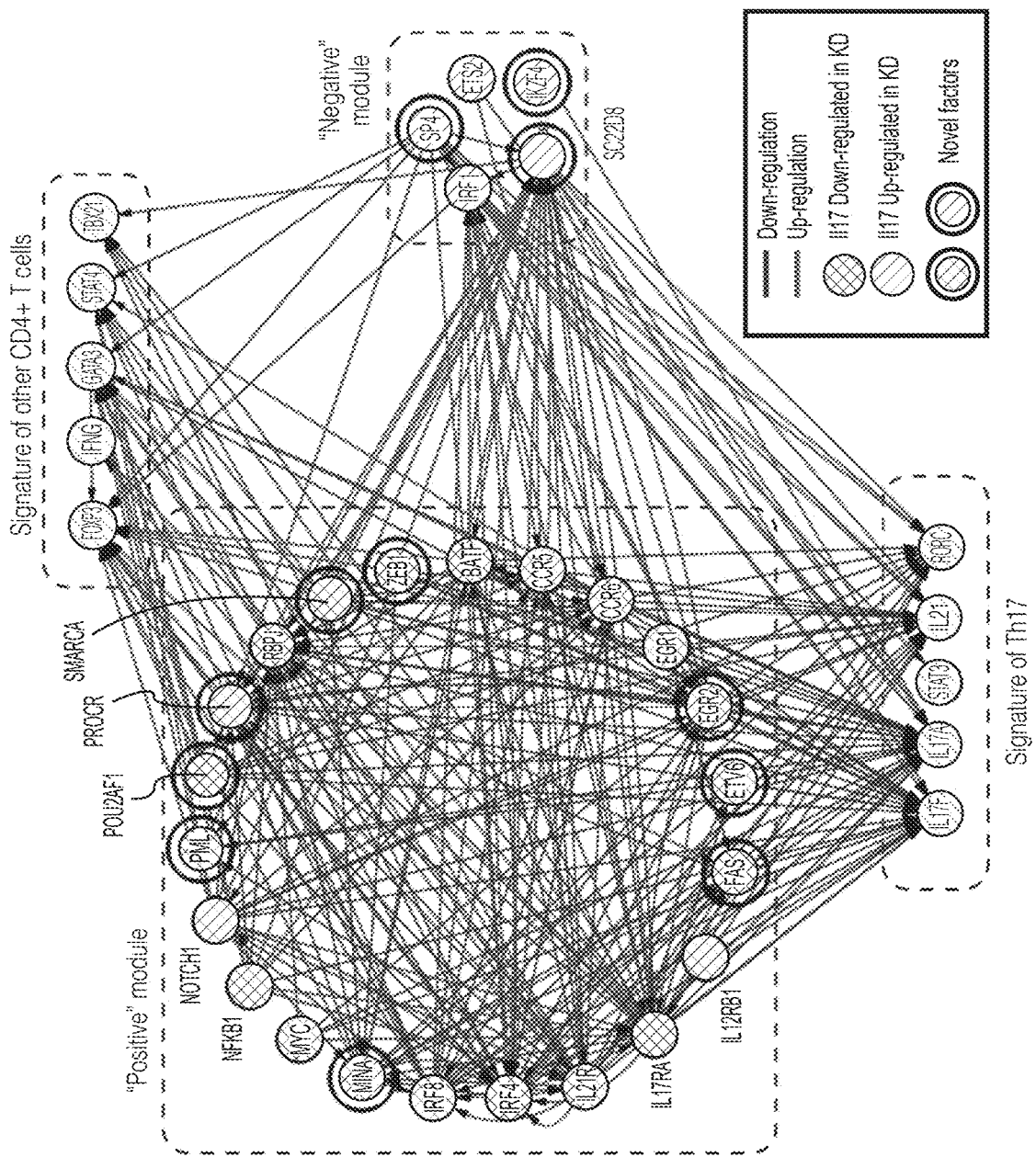
Figure 4C:
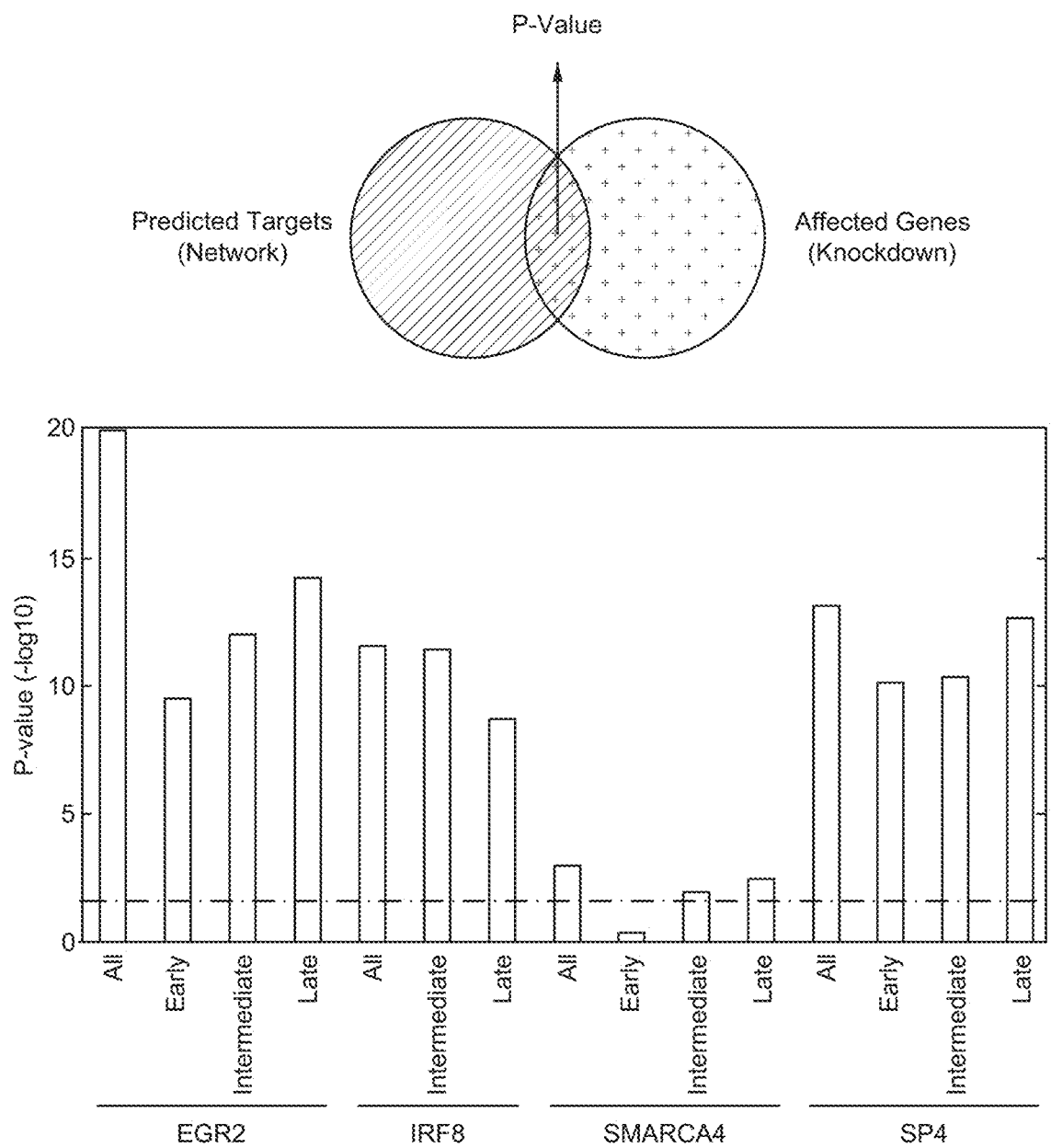
Figure 4D:
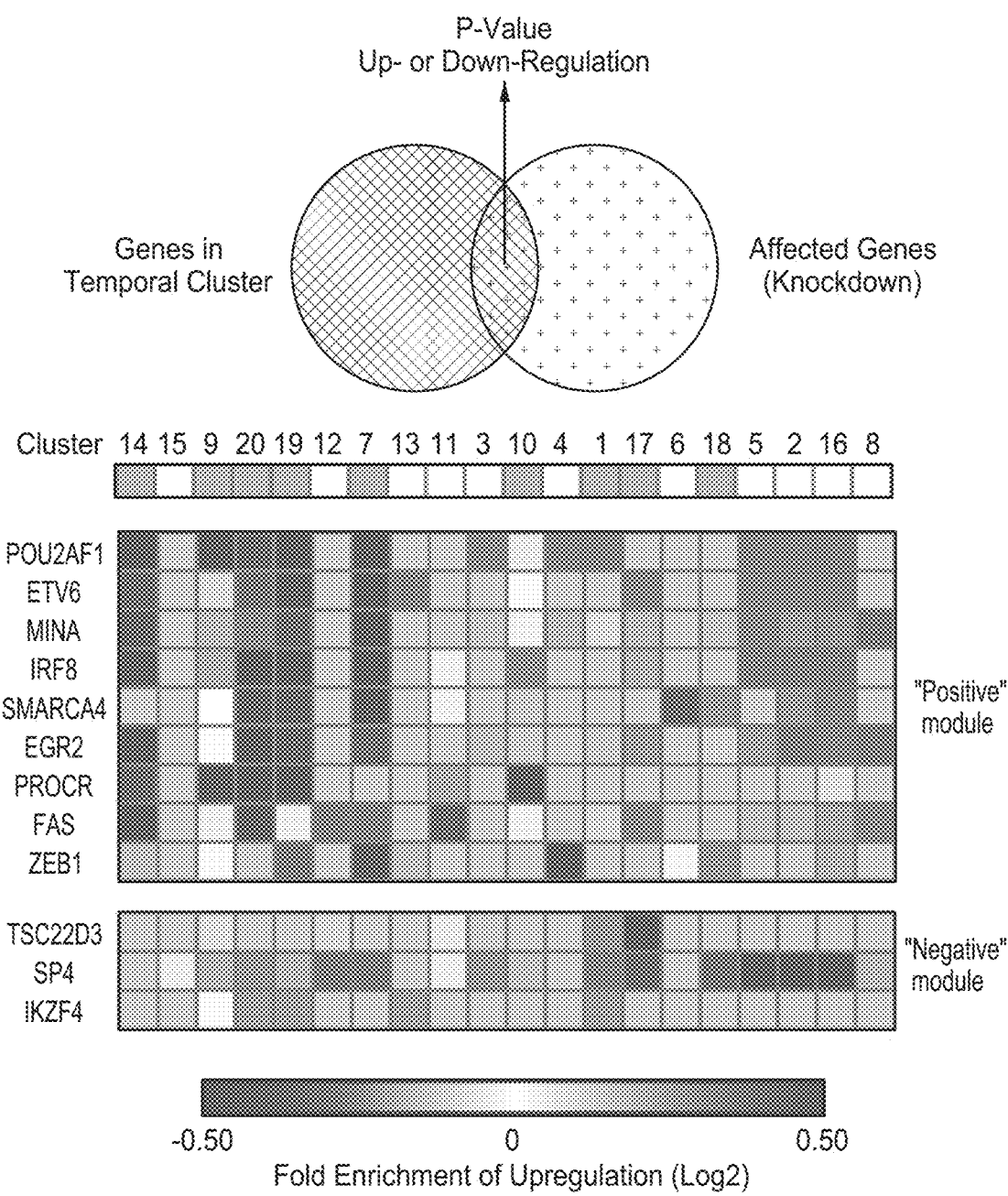

A hypergeometric test was used to evaluate the overlap between the predicted network model (FIG. 2) and the knockdown effects measured by RNA-seq (FIG. 4d). As background, all of the genes that appeared in the microarray data (and hence 20 have the potential to be included in the network) were used. As an additional test, the Wilcoxon-Mann-Whitney rank-sum test was used, comparing the absolute log fold-changes of genes in the annotated set to the entire set of genes (using the same background as before). The rank-sum test does not require setting a significance threshold; instead, it considers the fold change values of all the genes. The p-values produced by the rank-sum test were lower (i.e., more significant) than in the hypergeometric test, and therefore, in FIG. 4c, only the more stringent (hypergeometric) p-values were reported.

Profiling Tsc22d3 DNA Binding Using ChIP-Seq:

ChIP-seq for Tsc22d3 was performed as previously described (Ram, O. et al. Combinatorial Patterning of Chromatin Regulators Uncovered by Genome-wide Location Analysis in Human Cells. Cell 147, 1628-1639 (2011)) using an antibody from Abcam. The analysis of this data was performed as previously described (Ram, O. et al. Combinatorial Patterning of Chromatin Regulators Uncovered by Genome-wide Location Analysis in Human Cells. Cell 147, 1628-1639 (2011)) and is detailed in the Methods described herein.

Analysis of Tsc22d3 ChIP-Seq Data:

ChIP-seq reads were aligned to the NCBI Build 37 (UCSC mm9) of the mouse genome using Bowtie (Langmead, B., Trapnell, C., Pop, M. & Salzberg, S. L. in Genome Biol Vol. 10 R25 (2009)). Enriched binding regions (peaks) were detected using MACS (Zhang, Y. et al. in Genome Biol Vol. 9 R137 (2008)) with a pvalue cutoff of $10^{-8}$. A peak was associated with a gene if it falls in proximity to its 5' end (10 kb upstream and 1 kb downstream from transcription start site) or within the gene's body. The RefSeq transcript annotations for gene's coordinates were used.

The overlap of ChIP-seq peaks with annotated genomic regions was assessed. It was determined that a region A overlap with a peak B if A is within a distance of 50 bp from B's summit (as determined by MACS). The regions used included: (i) regulatory features annotations from the Ensemble database (Flicek, P. et al. Ensembl 2011. Nucleic Acids Res. 39, D800-806, doi:10.1093/nar/gkq1064 (2011)); (ii) regulatory 21 features found by the Oregano algorithm (Smith, R. L. et al. Polymorphisms in the IL-12beta and IL-23R genes are associated with psoriasis of early onset in a UK cohort. J Invest Dermatol 128, 1325-1327, doi:5701140 [pii] 10.1038/sj.jid.5701140 (2008)); (iii) conserved regions annotated by the multiz30way algorithm (here regions with multiz30way score>0.7 were considered); (iv) repeat regions annotated by RepeatMasker; (v) putative promoter regions—taking 10 kb upstream and 1 kb downstream of transcripts annotated in RefSeq (Pruitt, K. D., Tatusova, T. & Maglott, D. R. NCBI reference sequences (RefSeq): a curated non-redundant sequence database of genomes, transcripts and proteins. Nucleic Acids Res. 35, D61-65, doi:10.1093/nar/gk1842 (2007)); (vi) gene body annotations in RefSeq; (vii) 3' proximal regions (taking 1 kb upstream and 5 kb downstream to 3' end); (viii) regions enriched in histone marks H3K4me3 and H3K27me3 in Th17 cells (Wei, G. et al. in Immunity Vol. 30 155-167 (2009)); (ix) regions enriched in binding of Stat3 and Stat5 (Yang, X. P. et al. Opposing regulation of the locus encoding IL-17 through direct, reciprocal actions of STAT3 and STAT5. Nat. Immunol. 12, 247-254, doi:10.1038/ni.1995 (2011)), Irf4 and Batf (Glasmacher, E. et al. A Genomic Regulatory Element That Directs Assembly and Function of Immune-Specific AP-1-IRF Complexes. Science, doi: 10.1126/science.1228309 (2012)), and RORγt (Xiao et al unpublished) in Th17 cells, and Foxp3 in iTreg (Xiao et al., unpublished).

For each set of peaks "x" and each set of genomic regions "y", a binomial pvalue was used to assess their overlap in the genome as described in Mclean, C. Y. et al. in Nature biotechnology Vol. 28 nbt.1630-1639 (2010). The number of hits is defined as the number of x peaks that overlap with y. The background probability in sets (i)-(vii) is set to the overall length of the region (in bp) divided by the overall length of the genome. The background probability in sets (viii)-(ix) is set to the overall length of the region divided by the overall length of annotated genomic regions: this includes annotated regulatory regions (as defined in sets i, and ii), regions annotated as proximal to genes (using the definitions from set v-vii), carry a histone mark in Th17 cells (using the definition from set viii), or bound by transcription regulators in Th17 cells (using the definitions from set ix).

For the transcription regulators (set ix), an additional "gene-level" test was also included: here the overlap between the set of bound genes using a hypergeometric p-value was evaluated. A similar test was used to evaluate the overlap between the bound genes and genes that are differentially expressed in Tsc22d3 knockdown.

The analysis was repeated with a second peak-calling software (Scripture) (Guttman, M. et al. in Nature biotechnology Vol. 28 503-510 (2010); Garber, M. et al. A High-Throughput Chromatin Immunoprecipitation Approach Reveals Principles of Dynamic Gene Regulation in Mammals. Molecular cell, doi:10.1016/j.molcel.2012.07.030 (2012)), and obtained consistent results in all the above tests. Specifically, similar levels of overlap with the Th17 factors tested, both in terms of co-occupied binding sites and in terms of common target genes, was seen.

Estimating Statistical Significance of Monochromatic Interactions Between Modules:

The functional network in FIG. 4b consists of two modules: positive and negative. Two indices were computed: (1) within-module index: the percentage of positive edges between members of the same module (i.e., down-regulation in knockdown/knockout); and, (2) between-module index: the percentage of negative edges between members of the same module that are negative. The network was shuffled 1,000 times, while maintaining the nodes' out degrees (i.e., number of outgoing edges) and edges' signs (positive/negative), and re-computed the two indices. The reported p-values were computed using a t-test.

Using Literature Microarray Data for Deriving a Th17 Signature and for Identifying Genes Responsive to Th17-Related Perturbations:

To define the Th17 signatures genes, the gene expression data from Wei et al., in Immunity, vol. 30 155-167 (2009)

was downloaded and analyzed, and the data was preprocessed using the RMA algorithm, followed by quantile normalization using the default parameters in the ExpressionFileCreator module of the 23 GenePattern suite (Reich, M. et al. GenePattern 2.0. Nat. Genet. 38, 500-501, doi: 10.1038/ng0506-500 (2006)). This data includes replicate microarray measurements from Th17, Th1, Th2, iTreg, nTreg, and Naïve CD4+ T cells. For each gene, it was evaluated whether it is over-expressed in Th17 cells compared to all other cell subsets using a one-sided t-test. All cases that had a p-value<0.05 were retained. As an additional filtering step, it was required that the expression level of a gene in Th17 cells be at least 1.25 fold higher than its expression in all other cell subsets. To avoid spurious fold levels due to low expression values, a small constant (c=50) was added to the expression values.

To define genes responsive to published Th17-related perturbations, gene expression data from several sources that provided transcriptional profiles of Th17 cells under various conditions (listed above) were downloaded and analyzed. These datasets were preprocessed as above. To find genes that were differentially expressed in a given condition (compared to their respective control), the fold change between the expression levels of each probeset in the case and control conditions was computed. To avoid spurious fold levels due to low expression values, a small constant as above was added to the expression values. Only cases where more than 50% of all of the possible case-control comparisons were above a cutoff of 1.5 fold change were reported. As an additional filter, when duplicates are available, a Z-score was computed as above and only cases with a corresponding p-value<0.05 were reported.

Genes:

The abbreviations set forth below in Table 11 are used herein to identify the genes used throughout the disclosure, including but not limited to those shown in Tables 1-9 of the specification.

TABLE 11

Gene Abbreviations, Entrez ID Numbers and Brief Description

| Symbol | Entrez ID | Description |
| --- | --- | --- |
| AAK1 | 22848 | AP2 associated kinase 1 |
| ABCG2 | 9429 | ATP-binding cassette, sub-family G (WHITE), member 2 |
| ACP5 | 54 | acid phosphatase 5, tartrate resistant |
| ACVR1B | 91 | activin A receptor, type 1B |
| ACVR2A | 92 | activin receptor IIA |
| ADAM10 | 102 | a disintegrin and metallopeptidase domain 10 |
| ADAM17 | 6868 | a disintegrin and metallopeptidase domain 17 |
| ADRBK1 | 156 | adrenergic receptor kinase, beta 1 |
| AES | 166 | amino-terminal enhancer of split |
| AHR | 196 | aryl-hydrocarbon receptor |
| AIM1 | 202 | absent in melanoma 1 |
| AKT1 | 207 | thymoma viral proto-oncogene 1 |
| ALPK2 | 115701 | alpha-kinase 2 |
| ANKHD1 | 54882 | ankyrin repeat and KH domain containing 1 |
| ANP32A | 8125 | acidic (leucine-rich) nuclear phosphoprotein 32 family, member A |
| ANXA4 | 307 | annexin A4 |
| AQP3 | 360 | aquaporin 3 |
| ARHGEF3 | 50650 | Rho guanine nucleotide exchange factor (GEF) 3 |
| ARID3A | 1820 | AT rich interactive domain 3A (BRIGHT-like) |
| ARID5A | 10865 | AT rich interactive domain 5A (MRF1-like) |
| ARL5A | 26225 | ADP-ribosylation factor-like 5A |
| ARMCX2 | 9823 | armadillo repeat containing, X-linked 2 |
| ARNTL | 406 | aryl hydrocarbon receptor nuclear translocator-like |
| ASXL1 | 171023 | additional sex combs like 1 (*Drosophila*) |
| ATF2 | 1386 | activating transcription factor 2 |
| ATF3 | 467 | activating transcription factor 3 |
| ATF4 | 468 | activating transcription factor 4 |
| AURKB | 9212 | aurora kinase B |
| AXL | 558 | AXL receptor tyrosine kinase |
| B4GALT1 | 2683 | UDP-Gal: betaGlcNAc beta 1,4-galactosyltransferase, polypeptide 1 |
| BATF | 10538 | basic leucine zipper transcription factor, ATF-like |
| BATF3 | 55509 | basic leucine zipper transcription factor, ATF-like 3 |
| BAZ2B | 29994 | bromodomain adjacent to zinc finger domain, 2B |
| BCL11B | 64919 | B-cell leukemia/lymphoma 11B |
| BCL2L11 | 10018 | BCL2-like 11 (apoptosis facilitator) |
| BCL3 | 602 | B-cell leukemia/lymphoma 3 |
| BCL6 | 604 | B-cell leukemia/lymphoma 6 |
| BHLH40 | 8553 | Basic Helix-Loop-Helix Family, Member E40 |
| BLOC1S1 | 2647 | biogenesis of lysosome-related organelles complex-1, subunit 1 |
| BMP2K | 55589 | BMP2 inducible kinase |
| BMPR1A | 657 | bone morphogenetic protein receptor, type 1A |
| BPGM | 669 | 2,3-bisphosphoglycerate mutase |
| BSG | 682 | basigin |
| BTG1 | 694 | B-cell translocation gene 1, anti-proliferative |
| BTG2 | 7832 | B-cell translocation gene 2, anti-proliferative |
| BUB1 | 699 | budding uninhibited by benzimidazoles 1 homolog (*S. cerevisiae*) |
| C14ORF83 | 161145 | RIKEN cDNA 6330442E10 gene |
| C16ORF80 | 29105 | gene trap locus 3 |

TABLE 11-continued

Gene Abbreviations, Entrez ID Numbers and Brief Description

| Symbol | Entrez ID | Description |
|---|---|---|
| C21ORF66 | 94104 | RIKEN cDNA 1810007M14 gene |
| CAMK4 | 814 | calcium/calmodulin-dependent protein kinase IV |
| CARM1 | 10498 | coactivator-associated arginine methyltransferase 1 |
| CASP1 | 834 | caspase 1 |
| CASP3 | 836 | caspase 3 |
| CASP4 | 837 | caspase 4, apoptosis-related cysteine peptidase |
| CASP6 | 839 | caspase 6 |
| CASP8AP2 | 9994 | caspase 8 associated protein 2 |
| CBFB | 865 | core binding factor beta |
| CBX4 | 8535 | chromobox homolog 4 (*Drosophila* Pc class) |
| CCL1 | 6346 | chemokine (C-C motif) ligand 1 |
| CCL20 | 6364 | chemokine (C-C motif) ligand 20 |
| CCL4 | 6351 | chemokine (C-C motif) ligand 4 |
| CCND2 | 894 | cyclin D2 |
| CCR4 | 1233 | chemokine (C-C motif) receptor 4 |
| CCR5 | 1234 | chemokine (C-C motif) receptor 5 |
| CCR6 | 1235 | chemokine (C-C motif) receptor 6 |
| CCR8 | 1237 | chemokine (C-C motif) receptor 8 |
| CCRN4L | 25819 | CCR4 carbon catabolite repression 4-like (*S. cerevisiae*) |
| CD14 | 929 | CD14 antigen |
| CD2 | 914 | CD2 antigen |
| CD200 | 4345 | CD200 antigen |
| CD226 | 10666 | CD226 antigen |
| CD24 | 934 | CD24a antigen |
| CD247 | 919 | CD247 antigen |
| CD27 | 939 | CD27 antigen |
| CD274 | 29126 | CD274 antigen |
| CD28 | 940 | CD28 antigen |
| CD3D | 915 | CD3 antigen, delta polypeptide |
| CD3G | 917 | CD3 antigen, gamma polypeptide |
| CD4 | 920 | CD4 antigen |
| CD40LG | 959 | CD40 ligand |
| CD44 | 960 | CD44 antigen |
| CD53 | 963 | CD53 antigen |
| CD5L | 922 | CD5 antigen-like |
| CD63 | 967 | CD63 antigen |
| CD68 | 968 | CD68 antigen |
| CD70 | 970 | CD70 antigen |
| CD74 | 972 | CD74 antigen (invariant polypeptide of major histocompatibility complex, cl |
| CD80 | 941 | CD80 antigen |
| CD83 | 9308 | CD83 antigen |
| CD84 | 8832 | CD84 antigen |
| CD86 | 942 | CD86 antigen |
| CD9 | 928 | CD9 antigen |
| CD96 | 10225 | CD96 antigen |
| CDC25B | 994 | cell division cycle 25 homolog B (*S. pombe*) |
| CDC42BPA | 8476 | CDC42 binding protein kinase alpha |
| CDC5L | 988 | cell division cycle 5-like (*S. pombe*) |
| CDK5 | 1020 | cyclin-dependent kinase 5 |
| CDK6 | 1021 | cyclin-dependent kinase 6 |
| CDKN3 | 1033 | cyclin-dependent kinase inhibitor 3 |
| CDYL | 9425 | chromodomain protein, Y chromosome-like |
| CEBPB | 1051 | CCAAT/enhancer binding protein (C/EBP), beta |
| CENPT | 80152 | centromere protein T |
| CHD7 | 55636 | chromodomain helicase DNA binding protein 7 |
| CHMP1B | 57132 | chromatin modifying protein 1B |
| CHMP2A | 27243 | charged multivesicular body protein 2A |
| CHRAC1 | 54108 | chromatin accessibility complex 1 |
| CIC | 23152 | capicua homolog (*Drosophila*) |
| CITED2 | 10370 | Cbp/p300-interacting transactivator, with Glu/Asp-rich carboxy-terminal dom |
| CLCF1 | 23529 | cardiotrophin-like cytokine factor 1 |
| CLK1 | 1195 | CDC-like kinase 1 |
| CLK3 | 1198 | CDC-like kinase 3 |
| CMTM6 | 54918 | CKLF-like MARVEL transmembrane domain containing 6 |
| CNOT2 | 4848 | CCR4-NOT transcription complex, subunit 2 |
| CREB1 | 1385 | cAMP responsive element binding protein 1 |
| CREB3L2 | 64764 | cAMP responsive element binding protein 3-like 2 |
| CREG1 | 8804 | cellular repressor of E1A-stimulated genes 1 |
| CREM | 1390 | cAMP responsive element modulator |
| CSDA | 8531 | cold shock domain protein A |
| CSF1R | 1436 | colony stimulating factor 1 receptor |
| CSF2 | 1437 | colony stimulating factor 2 (granulocyte-macrophage) |
| CTLA4 | 1493 | cytotoxic T-lymphocyte-associated protein 4 |

TABLE 11-continued

Gene Abbreviations, Entrez ID Numbers and Brief Description

| Symbol | Entrez ID | Description |
|---|---|---|
| CTSD | 1509 | cathepsin D |
| CTSW | 1521 | cathepsin W |
| CXCL10 | 3627 | chemokine (C-X-C motif) ligand 10 |
| CXCR3 | 2833 | chemokine (C-X-C motif) receptor 3 |
| CXCR4 | 7852 | chemokine (C-X-C motif) receptor 4 |
| CXCR5 | 643 | chemochine (C-X-C motif) receptor 5 |
| DAPP1 | 27071 | dual adaptor for phosphotyrosine and 3-phosphoinositides 1 |
| DAXX | 1616 | Fas death domain-associated protein |
| DCK | 1633 | deoxycytidine kinase |
| DCLK1 | 9201 | doublecortin-like kinase 1 |
| DDIT3 | 1649 | DNA-damage inducible transcript 3 |
| DDR1 | 780 | discoidin domain receptor family, member 1 |
| DGKA | 1606 | diacylglycerol kinase, alpha |
| DGUOK | 1716 | deoxyguanosine kinase |
| DNAJC2 | 27000 | DnaJ (Hsp40) homolog, subfamily C, member 2 |
| DNTT | 1791 | deoxynucleotidyltransferase, terminal |
| DPP4 | 1803 | dipeptidylpeptidase 4 |
| DUSP1 | 1843 | dual specificity phosphatase 1 |
| DUSP10 | 11221 | dual specificity phosphatase 10 |
| DUSP14 | 11072 | dual specificity phosphatase 14 |
| DUSP16 | 80824 | dual specificity phosphatase 16 |
| DUSP2 | 1844 | dual specificity phosphatase 2 |
| DUSP22 | 56940 | dual specificity phosphatase 22 |
| DUSP6 | 1848 | dual specificity phosphatase 6 |
| E2F1 | 1869 | E2F transcription factor 1 |
| E2F4 | 1874 | E2F transcription factor 4 |
| E2F8 | 79733 | E2F transcription factor 8 |
| ECE2 | 9718 | endothelin converting enzyme 2 |
| EGR1 | 1958 | early growth response 1 |
| EGR2 | 1959 | early growth response 2 |
| EIF2AK2 | 5610 | eukaryotic translation initiation factor 2-alpha kinase 2 |
| ELK3 | 2004 | ELK3, member of ETS oncogene family |
| ELL2 | 22936 | elongation factor RNA polymerase II 2 |
| EMP1 | 2012 | epithelial membrane protein 1 |
| ENTPD1 | 953 | ectonucleoside triphosphate diphosphohydrolase 1 |
| ERCC5 | 2073 | excision repair cross-complementing rodent repair deficiency, complementati |
| ERRFI1 | 54206 | ERBB receptor feedback inhibitor 1 |
| ETS1 | 2113 | E26 avian leukemia oncogene 1, 5' domain |
| ETS2 | 2114 | E26 avian leukemia oncogene 2, 3' domain |
| ETV6 | 2120 | ets variant gene 6 (TEL oncogene) |
| EZH1 | 2145 | enhancer of zeste homolog 1 (Drosophila) |
| FAS | 355 | Fas (TNF receptor superfamily member 6) |
| FASLG | 356 | Fas ligand (TNF superfamily, member 6) |
| FCER1G | 2207 | Fc receptor, IgE, high affinity I, gamma polypeptide |
| FCGR2B | 2213 | Fc receptor, IgG, low affinity IIb |
| FES | 2242 | feline sarcoma oncogene |
| FLI1 | 2313 | Friend leukemia integration 1 |
| FLNA | 2316 | filamin, alpha |
| FOSL2 | 2355 | fos-like antigen 2 |
| FOXJ2 | 55810 | forkhead box J2 |
| FOXM1 | 2305 | forkhead box M1 |
| FOXN3 | 1112 | forkhead box N3 |
| FOXO1 | 2308 | forkhead box O1 |
| FOXP1 | 27086 | forkhead box P1 |
| FOXP3 | 50943 | forkhead box P3 |
| FRMD4B | 23150 | FERM domain containing 4B |
| FUS | 2521 | fusion, derived from t(12; 16) malignant liposarcoma (human) |
| FZD7 | 8324 | frizzled homolog 7 (Drosophila) |
| GAP43 | 2596 | growth associated protein 43 |
| GATA3 | 2625 | GATA binding protein 3 |
| GATAD1 | 57798 | GATA zinc finger domain containing 1 |
| GATAD2B | 57459 | GATA zinc finger domain containing 2B |
| GEM | 2669 | GTP binding protein (gene overexpressed in skeletal muscle) |
| GFI1 | 2672 | growth factor independent 1 |
| GJA1 | 2697 | gap junction protein, alpha 1 |
| GK | 2710 | glycerol kinase |
| GLIPR1 | 11010 | GLI pathogenesis-related 1 (glioma) |
| GMFB | 2764 | glia maturation factor, beta |
| GMFG | 9535 | glia maturation factor, gamma |
| GRN | 2896 | granulin |
| GUSB | 2990 | glucuronidase, beta |
| HCLS1 | 3059 | hematopoietic cell specific Lyn substrate 1 |

TABLE 11-continued

Gene Abbreviations, Entrez ID Numbers and Brief Description

| Symbol | Entrez ID | Description |
| --- | --- | --- |
| HDAC8 | 55869 | histone deacetylase 8 |
| HIF1A | 3091 | hypoxia inducible factor 1, alpha subunit |
| HINT3 | 135114 | histidine triad nucleotide binding protein 3 |
| HIP1R | 9026 | huntingtin interacting protein 1 related |
| HIPK1 | 204851 | homeodomain interacting protein kinase 1 |
| HIPK2 | 28996 | homeodomain interacting protein kinase 2 |
| HK1 | 3098 | hexokinase 1 |
| HK2 | 3099 | hexokinase 2 |
| HLA-A | 3105 | major histocompatibility complex, class I, A |
| HLA-DQA1 | 3117 | histocompatibility 2, class II antigen A, alpha |
| HMGA1 | 3159 | high mobility group AT-hook 1 |
| HMGB2 | 3148 | high mobility group box 2 |
| HMGN1 | 3150 | high mobility group nucleosomal binding domain 1 |
| ICOS | 29851 | inducible T-cell co-stimulator |
| ID1 | 3397 | inhibitor of DNA binding 1 |
| ID2 | 3398 | inhibitor of DNA binding 2 |
| ID3 | 3399 | inhibitor of DNA binding 3 |
| IER3 | 8870 | immediate early response 3 |
| IFI35 | 3430 | interferon-induced protein 35 |
| IFIH1 | 64135 | interferon induced with helicase C domain 1 |
| IFIT1 | 3434 | interferon-induced protein with tetratricopeptide repeats 1 |
| IFITM2 | 10581 | interferon induced transmembrane protein 2 |
| IFNG | 3458 | interferon gamma |
| IFNGR1 | 3459 | interferon gamma receptor 1 |
| IFNGR2 | 3460 | interferon gamma receptor 2 |
| IKZF1 | 10320 | IKAROS family zinc finger 1 |
| IKZF3 | 22806 | IKAROS family zinc finger 3 |
| IKZF4 | 64375 | IKAROS family zinc finger 4 |
| IL10 | 3586 | interleukin 10 |
| IL10RA | 3587 | interleukin 10 receptor, alpha |
| IL12RB1 | 3594 | interleukin 12 receptor, beta 1 |
| IL12RB2 | 3595 | interleukin 12 receptor, beta 2 |
| IL15RA | 3601 | interleukin 15 receptor, alpha chain |
| IL17A | 3605 | interleukin 17A |
| IL17F | 112744 | interleukin 17F |
| IL17RA | 23765 | interleukin 17 receptor A |
| IL18R1 | 8809 | interleukin 18 receptor 1 |
| IL1R1 | 3554 | interleukin 1 receptor, type I |
| IL1RN | 3557 | interleukin 1 receptor antagonist |
| IL2 | 3558 | interleukin 2 |
| IL21 | 59067 | interleukin 21 |
| IL21R | 50615 | interleukin 21 receptor |
| IL22 | 50616 | interleukin 22 |
| IL23R | 149233 | interleukin 23 receptor |
| IL24 | 11009 | interleukin 24 |
| IL27RA | 9466 | interleukin 27 receptor, alpha |
| IL2RA | 3559 | interleukin 2 receptor, alpha chain |
| IL2RB | 3560 | interleukin 2 receptor, beta chain |
| IL2RG | 3561 | interleukin 2 receptor, gamma chain |
| IL3 | 3562 | interleukin 3 |
| IL4 | 3565 | interleukin 4 |
| IL4R | 3566 | interleukin 4 receptor, alpha |
| IL6ST | 3572 | interleukin 6 signal transducer |
| IL7R | 3575 | interleukin 7 receptor |
| IL9 | 3578 | interleukin 9 |
| INHBA | 3624 | inhibin beta-A |
| INPP1 | 3628 | inositol polyphosphate-1-phosphatase |
| IRAK1BP1 | 134728 | interleukin-1 receptor-associated kinase 1 binding protein 1 |
| IRF1 | 3659 | interferon regulatory factor 1 |
| IRF2 | 3660 | interferon regulatory factor 2 |
| IRF3 | 3661 | interferon regulatory factor 3 |
| IRF4 | 3662 | interferon regulatory factor 4 |
| IRF7 | 3665 | interferon regulatory factor 7 |
| IRF8 | 3394 | interferon regulatory factor 8 |
| IRF9 | 10379 | interferon regulatory factor 9 |
| ISG20 | 3669 | interferon-stimulated protein |
| ITGA3 | 3675 | integrin alpha 3 |
| ITGAL | 3683 | integrin alpha L |
| ITGAV | 3685 | integrin alpha V |
| ITGB1 | 3688 | integrin beta 1 (fibronectin receptor beta) |
| ITK | 3702 | IL2-inducible T-cell kinase |
| JAK2 | 3717 | Janus kinase 2 |
| JAK3 | 3718 | Janus kinase 3 |
| JARID2 | 3720 | jumonji, AT rich interactive domain 2 |

TABLE 11-continued

Gene Abbreviations, Entrez ID Numbers and Brief Description

| Symbol | Entrez ID | Description |
|---|---|---|
| JMJD1C | 221037 | jumonji domain containing 1C |
| JUN | 3725 | Jun oncogene |
| JUNB | 3726 | Jun-B oncogene |
| KAT2B | 8850 | K(lysine) acetyltransferase 2B |
| KATNA1 | 11104 | katanin p60 (ATPase-containing) subunit A1 |
| KDM6B | 23135 | lysine (K)-specific demethylase 6B |
| KLF10 | 7071 | Kruppel-like factor 10 |
| KLF13 | 51621 | Kruppel-like factor 13 |
| KLF6 | 1316 | Kruppel-like factor 6 |
| KLF7 | 8609 | Kruppel-like factor 7 (ubiquitous) |
| KLF9 | 687 | Kruppel-like factor 9 |
| KLRD1 | 3824 | killer cell lectin-like receptor, subfamily D, member 1 |
| LAD1 | 3898 | ladinin |
| LAMP2 | 3920 | lysosomal-associated membrane protein 2 |
| LASS4 | 79603 | LAG1 homolog, ceramide synthase 4 |
| LASS6 | 253782 | LAG1 homolog, ceramide synthase 6 |
| LEF1 | 51176 | lymphoid enhancer binding factor 1 |
| LGALS3BP | 3959 | lectin, galactoside-binding, soluble, 3 binding protein |
| LGTN | 1939 | ligatin |
| LIF | 3976 | leukemia inhibitory factor |
| LILRB1, LILRB2, LILRB3, LILRB4, LILRB5 | 10859, 10288, 11025, 11006, 10990 | leukocyte immunoglobulin-like receptor, subfamily B (with TM and ITIM domains), members 1–5 |
| LIMK2 | 3985 | LIM motif-containing protein kinase 2 |
| LITAF | 9516 | LPS-induced TN factor |
| LMNB1 | 4001 | lamin B1 |
| LRRFIP1 | 9208 | leucine rich repeat (in FLII) interacting protein 1 |
| LSP1 | 4046 | lymphocyte specific 1 |
| LTA | 4049 | lymphotoxin A |
| MAF | 4094 | avian musculoaponeurotic fibrosarcoma (v-maf) AS42 oncogene homolog |
| MAFF | 23764 | v-maf musculoaponeurotic fibrosarcoma oncogene family, protein F (avian) |
| MAFG | 4097 | v-maf musculoaponeurotic fibrosarcoma oncogene family, protein G (avian) |
| MAML2 | 84441 | mastermind like 2 (*Drosophila*) |
| MAP3K5 | 4217 | mitogen-activated protein kinase kinase kinase 5 |
| MAP3K8 | 1326 | mitogen-activated protein kinase kinase kinase 8 |
| MAP4K2 | 5871 | mitogen-activated protein kinase kinase kinase kinase 2 |
| MAP4K3 | 8491 | mitogen-activated protein kinase kinase kinase kinase 3 |
| MAPKAPK2 | 9261 | MAP kinase-activated protein kinase 2 |
| MATR3 | 9782 | matrin 3 |
| MAX | 4149 | Max protein |
| MAZ | 4150 | MYC-associated zinc finger protein (purine-binding transcription factor) |
| MBNL1 | 4154 | muscleblind-like 1 (*Drosophila*) |
| MBNL3 | 55796 | muscleblind-like 3 (*Drosophila*) |
| MDM4 | 4194 | transformed mouse 3T3 cell double minute 4 |
| MEN1 | 4221 | multiple endocrine neoplasia 1 |
| MFHAS1 | 9258 | malignant fibrous histiocytoma amplified sequence 1 |
| MGLL | 11343 | monoglyceride lipase |
| MIER1 | 57708 | mesoderm induction early response 1 homolog (*Xenopus laevis* |
| MINA | 84864 | myc induced nuclear antigen |
| MKNK2 | 2872 | MAP kinase-interacting serine/threonine kinase 2 |
| MORF4L1 | 10933 | mortality factor 4 like 1 |
| MORF4L2 | 9643 | mortality factor 4 like 2 |
| MS4A6A | 64231 | membrane-spanning 4-domains, subfamily A, member 6B |
| MST4 | 51765 | serine/threonine protein kinase MST4 |
| MT1A | 4489 | metallothionein 1 |
| MT2A | 4502 | metallothionein 2 |
| MTA3 | 57504 | metastasis associated 3 |
| MXD3 | 83463 | Max dimerization protein 3 |
| MXI1 | 4601 | Max interacting protein 1 |
| MYC | 4609 | myelocytomatosis oncogene |
| MYD88 | 4615 | myeloid differentiation primary response gene 88 |
| MYST4 | 23522 | MYST histone acetyltransferase monocytic leukemia 4 |
| NAGK | 55577 | N-acetylglucosamine kinase |
| NAMPT | 10135 | nicotinamide phosphoribosyltransferase |
| NASP | 4678 | nuclear autoantigenic sperm protein (histone-binding) |
| NCF1C | 654817 | neutrophil cytosolic factor 1 |
| NCOA1 | 8648 | nuclear receptor coactivator 1 |
| NCOA3 | 8202 | nuclear receptor coactivator 3 |
| NEK4 | 6787 | NIMA (never in mitosis gene a)-related expressed kinase 4 |
| NEK6 | 10783 | NIMA (never in mitosis gene a)-related expressed kinase 6 |

TABLE 11-continued

Gene Abbreviations, Entrez ID Numbers and Brief Description

| Symbol | Entrez ID | Description |
| --- | --- | --- |
| NFATC1 | 4772 | nuclear factor of activated T-cells, cytoplasmic, calcineurin-dependent 1 |
| NFATC2 | 4773 | nuclear factor of activated T-cells, cytoplasmic, calcineurin-dependent 2 |
| NFE2L2 | 4780 | nuclear factor, erythroid derived 2, like 2 |
| NFIL3 | 4783 | nuclear factor, interleukin 3, regulated |
| NFKB1 | 4790 | nuclear factor of kappa light polypeptide gene enhancer in B-cells 1, p105 |
| NFKBIA | 4792 | nuclear factor of kappa light polypeptide gene enhancer in B-cells inhibito |
| NFKBIB | 4793 | nuclear factor of kappa light polypeptide gene enhancer in B-cells inhibito |
| NFKBIE | 4794 | nuclear factor of kappa light polypeptide gene enhancer in B-cells inhibito |
| NFKBIZ | 64332 | nuclear factor of kappa light polypeptide gene enhancer in B-cells inhibito |
| NFYC | 4802 | nuclear transcription factor-Y gamma |
| NKG7 | 4818 | natural killer cell group 7 sequence |
| NMI | 9111 | N-myc (and STAT) interactor |
| NOC4L | 79050 | nucleolar complex associated 4 homolog (*S. cerevisiae*) |
| NOTCH1 | 4851 | Notch gene homolog 1 (*Drosophila*) |
| NOTCH2 | 4853 | Notch gene homolog 2 (*Drosophila*) |
| NR3C1 | 2908 | nuclear receptor subfamily 3, group C, member 1 |
| NR4A2 | 4929 | nuclear receptor subfamily 4, group A, member 2 |
| NR4A3 | 8013 | nuclear receptor subfamily 4, group A, member 3 |
| NUDT4 | 11163 | nudix (nucleoside diphosphate linked moiety X)-typemotif 4 |
| OAS2 | 4939 | 2'-5' oligoadenylate synthetase 2 |
| PACSIN1 | 29993 | protein kinase C and casein kinase substrate in neurons 1 |
| PAXBP1 | 94104 | PAX3 and PAX7 binding protein 1 |
| PCTK1 | 5127 | PCTAIRE-motif protein kinase 1 |
| PDCD1 | 5133 | programmed cell death 1 |
| PDCD1LG2 | 80380 | programmed cell death 1 ligand 2 |
| PDK3 | 5165 | pyruvate dehydrogenase kinase, isoenzyme 3 |
| PDPK1 | 5170 | 3-phosphoinositide dependent protein kinase-1 |
| PDXK | 8566 | pyridoxal (pyridoxine, vitamin B6) kinase |
| PECI | 10455 | peroxisomal delta3, delta2-enoyl-Coenzyme A isomerase |
| PELI2 | 57161 | pellino 2 |
| PGK1 | 5230 | phosphoglycerate kinase 1 |
| PHACTR2 | 9749 | phosphatase and actin regulator 2 |
| PHF13 | 148479 | PHD finger protein 13 |
| PHF21A | 51317 | PHD finger protein 21A |
| PHF6 | 84295 | PHD finger protein 6 |
| PHLDA1 | 22822 | pleckstrin homology-like domain, family A, member 1 |
| PHLPP1 | 23239 | PH domain and leucine rich repeat protein phosphatase 1 |
| PI4KA | 5297 | phosphatidylinositol 4-kinase, catalytic, alpha polypeptide |
| PIM1 | 5292 | proviral integration site 1 |
| PIM2 | 11040 | proviral integration site 2 |
| PIP4K2A | 5305 | phosphatidylinositol-5-phosphate 4-kinase, type II, alpha |
| PKM2 | 5315 | pyruvate kinase, muscle |
| PLAC8 | 51316 | placenta-specific 8 |
| PLAGL1 | 5325 | pleiomorphic adenoma gene-like 1 |
| PLAUR | 5329 | plasminogen activator, urokinase receptor |
| PLEK | 5341 | pleckstrin |
| PLEKHF2 | 79666 | pleckstrin homology domain containing, family F (with FYVE domain) member 2 |
| PLK2 | 10769 | polo-like kinase 2 (*Drosophila*) |
| PMEPA1 | 56937 | prostate transmembrane protein, androgen induced 1 |
| PML | 5371 | promyelocytic leukemia |
| PNKP | 11284 | polynucleotide kinase 3'-phosphatase |
| POU2AF1 | 5450 | POU domain, class 2, associating factor 1 |
| POU2F2 | 5452 | POU domain, class 2, transcription factor 2 |
| PPME1 | 51400 | protein phosphatase methylesterase 1 |
| PPP2R5A | 5525 | protein phosphatase 2, regulatory subunit B (B56), alpha isoform |
| PPP3CA | 5530 | protein phosphatase 3, catalytic subunit, alpha isoform |
| PRC1 | 9055 | protein regulator of cytokinesis 1 |
| PRDM1 | 639 | PR domain containing 1, with ZNF domain |
| PRF1 | 5551 | perforin 1 (pore forming protein) |
| PRICKLE1 | 144165 | prickle like 1 (*Drosophila*) |
| PRKCA | 5578 | protein kinase C, alpha |
| PRKCD | 5580 | protein kinase C, delta |
| PRKCH | 5583 | protein kinase C, eta |
| PRKCQ | 5588 | protein kinase C, theta |

TABLE 11-continued

Gene Abbreviations, Entrez ID Numbers and Brief Description

| Symbol | Entrez ID | Description |
|---|---|---|
| PRKD3 | 23683 | protein kinase D3 |
| PRNP | 5621 | prion protein |
| PROCR | 10544 | protein C receptor, endothelial |
| PRPF4B | 8899 | PRP4 pre-mRNA processing factor 4 homolog B (yeast) |
| PRPS1 | 5631 | phosphoribosyl pyrophosphate synthetase 1 |
| PSMB9 | 5698 | proteasome (prosome, macropain) subunit, beta type 9 (large multifunctional |
| PSTPIP1 | 9051 | proline-serine-threonine phosphatase-interactingprotein 1 |
| PTEN | 5728 | phosphatase and tensin homolog |
| PTK2B | 2185 | PTK2 protein tyrosine kinase 2 beta |
| PTP4A1 | 7803 | protein tyrosine phosphatase 4a1 |
| PTPLA | 9200 | protein tyrosine phosphatase-like (proline instead of catalytic arginine), |
| PTPN1 | 5770 | protein tyrosine phosphatase, non-receptor type 1 |
| PTPN18 | 26469 | protein tyrosine phosphatase, non-receptor type 18 |
| PTPN6 | 5777 | protein tyrosine phosphatase, non-receptor type 6 |
| PTPRC | 5788 | protein tyrosine phosphatase, receptor type, C |
| PTPRCAP | 5790 | protein tyrosine phosphatase, receptor type, C polypeptide-associated prote |
| PTPRE | 5791 | protein tyrosine phosphatase, receptor type, E |
| PTPRF | 5792 | protein tyrosine phosphatase, receptor type, F |
| PTPRJ | 5795 | protein tyrosine phosphatase, receptor type, J |
| PTPRS | 5802 | protein tyrosine phosphatase, receptor type, S |
| PVR | 5817 | poliovirus receptor |
| PYCR1 | 5831 | pyrroline-5-carboxylate reductase 1 |
| RAB33A | 9363 | RAB33A, member of RAS oncogene family |
| RAD51AP1 | 10635 | RAD51 associated protein 1 |
| RARA | 5914 | retinoic acid receptor, alpha |
| RASGRP1 | 10125 | RAS guanyl releasing protein 1 |
| RBPJ | 3516 | recombination signal binding protein for immunoglobulin kappa J region |
| REL | 5966 | reticuloendotheliosis oncogene |
| RELA | 5970 | v-rel reticuloendotheliosis viral oncogene homolog A (avian) |
| RFK | 55312 | riboflavin kinase |
| RIPK1 | 8737 | receptor (TNFRSF)-interacting serine-threonine kinase 1 |
| RIPK2 | 8767 | receptor (TNFRSF)-interacting serine-threonine kinase 2 |
| RIPK3 | 11035 | receptor-interacting serine-threonine kinase 3 |
| RNASEL | 6041 | ribonuclease L (2',5'-oligoisoadenylate synthetase-dependent) |
| RNF11 | 26994 | ring finger protein 11 |
| RNF5 | 6048 | ring finger protein 5 |
| RORA | 6095 | RAR-related orphan receptor alpha |
| RORC | 6097 | RAR-related orphan receptor gamma |
| RPP14 | 11102 | ribonuclease P 14 subunit (human) |
| RPS6KB1 | 6198 | ribosomal protein S6 kinase, polypeptide 1 |
| RUNX1 | 861 | runt related transcription factor 1 |
| RUNX2 | 860 | runt related transcription factor 2 |
| RUNX3 | 864 | runt related transcription factor 3 |
| RXRA | 6256 | retinoid X receptor alpha |
| SAP18 | 10284 | Sin3-associated polypeptide 18 |
| SAP30 | 8819 | sin3 associated polypeptide |
| SATB1 | 6304 | special AT-rich sequence binding protein 1 |
| SEMA4D | 10507 | sema domain, immunoglobulin domain (Ig), transmembrane domain (TM) and shor |
| SEMA7A | 8482 | sema domain, immunoglobulin domain (Ig), and GPI membrane anchor, (semaphor |
| SERPINB1 | 1992 | serine (or cysteine) peptidase inhibitor, clade B, member 1a |
| SERPINE2 | 5270 | serine (or cysteine) peptidase inhibitor, clade E, member 2 |
| SERTAD1 | 29950 | SERTA domain containing 1 |
| SGK1 | 6446 | serum/glucocorticoid regulated kinase 1 |
| SH2D1A | 4068 | SH2 domain protein 1A |
| SIK1 | 150094 | salt-inducible kinase 1 |
| SIRT2 | 22933 | sirtuin 2 (silent mating type information regulation 2, homolog) 2 (S. cere |
| SKAP2 | 8935 | src family associated phosphoprotein 2 |
| SKI | 6497 | ski sarcoma viral oncogene homolog (avian) |
| SKIL | 6498 | SKI-like |
| SLAMF7 | 57823 | SLAM family member 7 |
| SLC2A1 | 6513 | solute carrier family 2 (facilitated glucose transporter), member 1 |
| SLC3A2 | 6520 | solute carrier family 3 (activators of dibasic and neutral amino acid trans |
| SLK | 9748 | STE20-like kinase (yeast) |

TABLE 11-continued

Gene Abbreviations, Entrez ID Numbers and Brief Description

| Symbol | Entrez ID | Description |
|---|---|---|
| SMAD2 | 4087 | MAD homolog 2 (*Drosophila*) |
| SMAD3 | 4088 | MAD homolog 3 (*Drosophila*) |
| SMAD4 | 4089 | MAD homolog 4 (*Drosophila*) |
| SMAD7 | 4092 | MAD homolog 7 (*Drosophila*) |
| SMARCA4 | 6597 | SWI/SNF related, matrix associated, actin dependent regulator of chromatin, |
| SMOX | 54498 | spermine oxidase |
| SOCS3 | 9021 | suppressor of cytokine signaling 3 |
| SP1 | 6667 | trans-acting transcription factor 1 |
| SP100 | 6672 | nuclear antigen Sp100 |
| SP4 | 6671 | trans-acting transcription factor 4 |
| SPHK1 | 8877 | sphingosine kinase 1 |
| SPOP | 8405 | speckle-type POZ protein |
| SPP1 | 6696 | secreted phosphoprotein 1 |
| SPRY1 | 10252 | sprouty homolog 1 (*Drosophila*) |
| SRPK2 | 6733 | serine/arginine-rich protein specific kinase 2 |
| SS18 | 6760 | synovial sarcoma translocation, Chromosome 18 |
| STARD10 | 10809 | START domain containing 10 |
| STAT1 | 6772 | signal transducer and activator of transcription 1 |
| STAT2 | 6773 | signal transducer and activator of transcription 2 |
| STAT3 | 6774 | signal transducer and activator of transcription 3 |
| STAT4 | 6775 | signal transducer and activator of transcription 4 |
| STAT5A | 6776 | signal transducer and activator of transcription 5A |
| STAT5B | 6777 | signal transducer and activator of transcription 5B |
| STAT6 | 6778 | signal transducer and activator of transcription 6 |
| STK17B | 9262 | serine/threonine kinase 17b (apoptosis-inducing) |
| STK19 | 8859 | serine/threonine kinase 19 |
| STK38 | 11329 | serine/threonine kinase 38 |
| STK38L | 23012 | serine/threonine kinase 38 like |
| STK39 | 27347 | serine/threonine kinase 39, STE20/SPS1 homolog (yeast) |
| STK4 | 6789 | serine/threonine kinase 4 |
| SULT2B1 | 6820 | sulfotransferase family, cytosolic, 2B, member 1 |
| SUZ12 | 23512 | suppressor of zeste 12 homolog (*Drosophila*) |
| TAF1B | 9014 | TATA box binding protein (Tbp)-associated factor, RNA polymerase I, B |
| TAL2 | 6887 | T-cell acute lymphocytic leukemia 2 |
| TAP1 | 6890 | transporter 1, ATP-binding cassette, sub-family B (MDR/TAP) |
| TBPL1 | 9519 | TATA box binding protein-like 1 |
| TBX21 | 30009 | T-box 21 |
| TCERG1 | 10915 | transcription elongation regulator 1 (CA150) |
| TEC | 7006 | cytoplasmic tyrosine kinase, Dscr28C related (*Drosophila*) |
| TFDP1 | 7027 | transcription factor Dp 1 |
| TFEB | 7942 | transcription factor EB |
| TGFB1 | 7040 | transforming growth factor, beta 1 |
| TGFB3 | 7043 | transforming growth factor, beta 3 |
| TGFBR1 | 7046 | transforming growth factor, beta receptor I |
| TGFBR3 | 7049 | transforming growth factor, beta receptor III |
| TGIF1 | 7050 | TGFB-induced factor homeobox 1 |
| TGM2 | 7052 | transglutaminase 2, C polypeptide |
| THRAP3 | 9967 | thyroid hormone receptor associated protein 3 |
| TIMP2 | 7077 | tissue inhibitor of metalloproteinase 2 |
| TK1 | 7083 | thymidine kinase 1 |
| TK2 | 7084 | thymidine kinase 2, mitochondrial |
| TLE1 | 7088 | transducin-like enhancer of split 1, homolog of *Drosophila* E(spl) |
| TLR1 | 7096 | toll-like receptor 1 |
| TMEM126A | 84233 | transmembrane protein 126A |
| TNFRSF12A | 51330 | tumor necrosis factor receptor superfamily, member 12a |
| TNFRSF13B | 23495 | tumor necrosis factor receptor superfamily, member 13b |
| TNFRSF1B | 7133 | tumor necrosis factor receptor superfamily, member 1b |
| TNFRSF25 | 8718 | tumor necrosis factor receptor superfamily, member 25 |
| TNFRSF4 | 7293 | tumor necrosis factor receptor superfamily, member 4 |
| TNFRSF9 | 3604 | tumor necrosis factor receptor superfamily, member 9 |
| TNFSF11 | 8600 | tumor necrosis factor (ligand) superfamily, member 11 |
| TNFSF8 | 944 | tumor necrosis factor (ligand) superfamily, member 8 |
| TNFSF9 | 8744 | tumor necrosis factor (ligand) superfamily, member 9 |
| TNK2 | 10188 | tyrosine kinase, non-receptor, 2 |
| TOX4 | 9878 | TOX high mobility group box family member 4 |
| TP53 | 7157 | transformation related protein 53 |
| TRAF3 | 7187 | Tnf receptor-associated factor 3 |
| TRAT1 | 50852 | T cell receptor associated transmembrane adaptor 1 |
| TRIM24 | 8805 | tripartite motif-containing 24 |
| TRIM25 | 7706 | tripartite motif-containing 25 |

TABLE 11-continued

Gene Abbreviations, Entrez ID Numbers and Brief Description

| Symbol | Entrez ID | Description |
|---|---|---|
| TRIM28 | 10155 | tripartite motif-containing 28 |
| TRIM5 | 85363 | tripartite motif containing 5 |
| TRIP12 | 9320 | thyroid hormone receptor interactor 12 |
| TRPS1 | 7227 | trichorhinophalangeal syndrome I (human) |
| TRRAP | 8295 | transformation/transcription domain-associated protein |
| TSC22D3 | 1831 | TSC22 domain family, member 3 |
| TSC22D4 | 81628 | TSC22 domain family, member 4 |
| TWF1 | 5756 | twinfilin, actin-binding protein, homolog 1 (*Drosophila*) |
| TXK | 7294 | TXK tyrosine kinase |
| UBE2B | 7320 | ubiquitin-conjugating enzyme E2B, RAD6 homology (*S. cerevisiae*) |
| UBIAD1 | 29914 | UbiA prenyltransferase domain containing 1 |
| ULK2 | 9706 | Unc-51 like kinase 2 (*C. elegans*) |
| VAV1 | 7409 | vav 1 oncogene |
| VAV3 | 10451 | vav 3 oncogene |
| VAX2 | 25806 | ventral anterior homeobox containing gene 2 |
| VRK1 | 7443 | vaccinia related kinase 1 |
| VRK2 | 7444 | vaccinia related kinase 2 |
| WDHD1 | 11169 | WD repeat and HMG-box DNA binding protein 1 |
| WHSC1L1 | 54904 | Wolf-Hirschhorn syndrome candidate 1-like 1 (human) |
| WNK1 | 65125 | WNK lysine deficient protein kinase 1 |
| XAB2 | 56949 | XPA binding protein 2 |
| XBP1 | 7494 | X-box binding protein 1 |
| XRCC5 | 7520 | X-ray repair complementing defective repair in Chinese hamster cells 5 |
| YBX1 | 4904 | Y box protein 1 |
| ZAK | 51776 | RIKEN cDNA B230120H23 gene |
| ZAP70 | 7535 | zeta-chain (TCR) associated protein kinase |
| ZBTB32 | 27033 | zinc finger and BTB domain containing 32 |
| ZEB1 | 6935 | zinc finger E-box binding homeobox 1 |
| ZEB2 | 9839 | zinc finger E-box binding homeobox 2 |
| ZFP161 | 7541 | zinc finger protein 161 |
| ZFP36L1 | 677 | zinc finger protein 36, C3H type-like 1 |
| ZFP36L2 | 678 | zinc finger protein 36, C3H type-like 2 |
| ZFP62 | 92379 | zinc finger protein 62 |
| ZNF238 | 10472 | zinc finger protein 238 |
| ZNF281 | 23528 | zinc finger protein 281 |
| ZNF326 | 284695 | zinc finger protein 326 |
| ZNF703 | 80139 | zinc finger protein 703 |
| ZNRF1 | 84937 | zinc and ring finger 1 |
| ZNRF2 | 223082 | zinc and ring finger 2 |

Primers for Nanostring STA and qRT-PCR/Fluidigm and siRNA Sequences:

Table S6.1 presents the sequences for each forward and reverse primer used in the Fluidigm/qRT-PCR experiments and Nanostring nCounter gene expression profiling. Table S6.2 presents the sequences for RNAi used for knockdown analysis.

TABLE S6.1

Primer Sequences

| Assay | Gene Name | SEQ ID NO: | Forward Sequence | SEQ ID NO: | Reverse Sequence |
|---|---|---|---|---|---|
| Nanostring STA | 1700097 N02Rik | 1 | GGC CAG AGC TTG ACC ATC | 2 | AGC AAG CCA GCC AAA CAG |
| Nanostring STA | Aim1 | 3 | AGC CAA TTT TGA AGG GCA | 4 | GGA AGC CCT GCA TTT CCT |
| Nanostring STA | Arnt1 | 5 | TAT AAC CCC TGG GCC CTC | 6 | GTT GCA GCC CTC GTT GTC |
| Nanostring STA | Bcl6 | 7 | GTC GGG ACA TCT TGA CGG | 8 | GGA GGA TGC AAA ACC CCT |
| Nanostring STA | Ccl20 | 9 | GCA TGG GTA CTG CTG GCT | 10 | TGA GGA GGT TCA CAG CCC |
| Nanostring STA | Cd24a | 11 | GGA CGC GTG AAA GGT TTG | 12 | TGC ACT ATG GCC TTA TCG G |

TABLE S6.1-continued

Primer Sequences

| Assay | Gene Name | SEQ ID NO: | Forward Sequence | SEQ ID NO: | Reverse Sequence |
|---|---|---|---|---|---|
| Nanostring STA | Cd80 | 13 | TGC CTA AGC TCC ATT GGC | 14 | ACG GCA AGG CAG CAA TAG |
| Nanostring STA | Csnk1a1 | 15 | GGG TAT GGC GCG TCA CTG | 16 | CCA CGG CAG ACT GGT TCT |
| Nanostring STA | Ddr1 | 17 | ATG CAC ACT CTG GGA GCC | 18 | CCA AGG ACC TGC AAA GAG G |
| Nanostring STA | Emp1 | 19 | AGC TGC CAT ACC ACT GGC | 20 | AGG CAC ATG GGA TCT GGA |
| Nanostring STA | Flna | 21 | CTT CAC TGC ATT CGC CCT | 22 | CAC AGG ACA ACG GAA GCA |
| Nanostring STA | Gata3 | 23 | CAC CGC CAT GGG TTA GAG | 24 | TGG GAT CCG GAT TCA GTG |
| Nanostring STA | 2900064 A13Rik | 25 | AAG GAA AAA TGC GAG CAA GA | 26 | TCT CCC GTC TCA TGT CAG G |
| Nanostring STA | Anxa4 | 27 | ATG GGG GAC AGA CGA GGT | 28 | TGC CTA AGC CCT TCA TGG |
| Nanostring STA | Atf4 | 29 | GAT GAT GGC TTG GCC AGT | 30 | TGG CCA ATT GGG TTC ACT |
| Nanostring STA | Bmpr1a | 31 | CAT TTG GGA AAT GGC TCG | 32 | ATG GGC CCA ACA TTC TGA |
| Nanostring STA | Ccl4 | 33 | AAG CTC TGC GTG TCT GCC | 34 | ACC ACA GCT GGC TTG GAG |
| Nanostring STA | Cd274 | 35 | CGT GGA TCC AGC CAC TTC | 36 | ATC ATT CGC TGT GGC GTT |
| Nanostring STA | Cd86 | 37 | ATC TGC CGT GCC CAT TTA | 38 | ACG AGC CCA TGT CCT TGA |
| Nanostring STA | Ctla2b | 39 | GGC TCA ACA GCA GGA AGC | 40 | TTA ATT TGA AGA CAT CAT GGC A |
| Nanostring STA | Dntt | 41 | CCC AGA AGC CAC AGA GGA | 42 | TTC CAG CCC TTT CCT TCC |
| Nanostring STA | Ercc5 | 43 | GTG CCA TTT GAC ACA GCG | 44 | CTG GCC TAC CCT CCA CCT |
| Nanostring STA | Foxm1 | 45 | CAAGCCAGGCTG GAA GAA | 46 | TGG GTC GTT TCT GCT GTG |
| Nanostring STA | Gem | 47 | GAC ACG CTT CGG GTT CAC | 48 | CAA CTG TGA TGA GGC CAG C |
| Nanostring STA | 6330442 E10Rik | 49 | CCC AGC ATT AAG GCT CCA | 50 | AGG AGC AAC AGG GGA CCT |
| Nanostring STA | Api5 | 51 | CAG CTT TGA ACA CAG GGT CTT | 52 | AGC TGA CTG AAA TTC CTC CCT |
| Nanostring STA | B4galt1 | 53 | TCA CAG TGG ACA TCG GGA | 54 | CAC TCA CCC TGG GCA TCT |
| Nanostring STA | Cand1 | 55 | CTA CTG CAG GGA GGA GCG | 56 | GGG TCC CTC TTT AGG GCA |
| Nanostring STA | Ccr4 | 57 | GTC CGT GCA GTT TGG CTT | 58 | GGT TTG GGA CAG GCT TTT |
| Nanostring STA | Cd28 | 59 | CCT TTG CAG TGA GTT GGG A | 60 | CGT TTT GAA AAT CTG CAG AGA A |
| Nanostring STA | Cd9 | 61 | GCG GGA AAC ACT CAA AGC | 62 | TGC TGA AGA TCA TGC CGA |
| Nanostring STA | Ctsw | 63 | GCC ACT GGA GCT GAA GGA | 64 | TGA CCT CTC CTG CCC GTA |
| Nanostring STA | Dpp4 | 65 | CCC TGC TCC TGC ATC TGT | 66 | AAA TCT TCC GAC CCA GCC |
| Nanostring STA | Errfi1 | 67 | TCC TGC TTT TCC CAT CCA | 68 | CCA GCA ACA CAA GAC CAG C |
| Nanostring STA | Foxo1 | 69 | TCC ACT CTG GGC AAG AGG | 70 | GGC AGC AGA GGG TGG ATA |
| Nanostring STA | Gfi1 | 71 | ATG TCT TCC CTG CCT CCC | 72 | AAG CCC AAA GCA CAG ACG |
| Nanostring STA | Abcg2 | 73 | GGA ACA TCG GCC TTC AAA | 74 | CAT TCC AGC GGC ATC ATA |
| Nanostring STA | Aqp3 | 75 | CGG CAC AGC TGG AAT CTT | 76 | GGT TGA CGG CAT AGC CAG |
| Nanostring STA | Batf | 77 | CTA CCC AGA GGC CCA GTG | 78 | AAC TAT CCA CCC CCT GCC |

TABLE S6.1-continued

Primer Sequences

| Assay | Gene Name | SEQ ID NO: | Forward Sequence | SEQ ID NO: | Reverse Sequence |
|---|---|---|---|---|---|
| Nanostring STA | Casp1 | 79 | TCC TGA GGG CAA AGA GGA | 80 | GAT TTG GCT TGC CTG GG |
| Nanostring STA | Ccr5 | 81 | AAC TGA ATG GGG AGG TTG G | 82 | TTA CAG CCG CCT TTC AGG |
| Nanostring STA | Cd4 | 83 | CCA GCC CTG GAT CTC CTT | 84 | GCC ACT TTC ATC ACC ACC A |
| Nanostring STA | Cebpb | 85 | TGC ACC GAG GGG ACA C | 86 | AAC CCC GCA GGA ACA TCT |
| Nanostring STA | Cxcl10 | 87 | TGC CGT CAT TTT CTG CCT | 88 | CGT GGC AAT GAT CTC AAC A |
| Nanostring STA | Egr2 | 89 | AGG ACC TTG ATG GAG CCC | 90 | CTG GCA TCC AGG GTC AAC |
| Nanostring STA | Etv6 | 91 | CAT GAG GGA GGA TGC TGG | 92 | AAA TCC CTG CTA TCA AAA ATC C |
| Nanostring STA | Foxp1 | 93 | GCT CTC TGT CTC CAA GGG C | 94 | ACT CAC AAC CCA GAC CGC |
| Nanostring STA | Gja1 | 95 | GGC CTG ATG ACC TGG AGA | 96 | TCC CTA CTT TTG CCG CCT |
| Nanostring STA | Acly | 97 | GAG GGC TGG GAC CAT TG | 98 | GCA GCT GCC CAG AAT CTT |
| Nanostring STA | Arhgef3 | 99 | GCA GCA GGC TGT TTC TTA CC | 100 | TTC CTC CCC ACT CAT CCA |
| Nanostring STA | BC021614 | 101 | AAG GAG GGC AAG GAC CAG | 102 | GAG CTT GGG TCG GGA TTT |
| Nanostring STA | Casp3 | 103 | GGA GAT GGC TTG CCA GAA | 104 | ACT CGA ATT CCG TTG CCA |
| Nanostring STA | Ccr6 | 105 | GCC AGA TCC ATG ACT GAC G | 106 | TTT GGT TGC CTG GAC GAT |
| Nanostring STA | Cd44 | 107 | CAG GGA ACA TCC ACC AGC | 108 | TAG CAT CAC CCT TTG GGG |
| Nanostring STA | Chd7 | 109 | CAT TGT CAG TGG GCG TCA | 110 | GAA TCA CAG GCT CGC CC |
| Nanostring STA | Cxcr3 | 111 | CCA GAT CTA CCG CAG GGA | 112 | CAT GAC CAG AAG GGG CAG |
| Nanostring STA | Eif3e | 113 | GTC AAC CAG GGA TGG CAG | 114 | CAG TTT TCC CCA GAG CGA |
| Nanostring STA | Fas | 115 | GCT GTG GAT CTG GGC TGT | 116 | CCC CCA TTC ATT TTG CAG |
| Nanostring STA | Foxp3 | 117 | TGG AAA CAC CCA GCC ACT | 118 | GGC AAG ACT CCT GGG GAT |
| Nanostring STA | Glipr1 | 119 | TGG ATG GCT TCG TCT GTG | 120 | TGC AGC TGT GGG TTG TGT |
| Nanostring STA | Acvr1b | 121 | GTG CCG ACA TCT ATG CCC | 122 | GCA CTC CCG CAT CAT CTT |
| Nanostring STA | Arid5a | 123 | GGC CTC GGG TCT TTC ACT | 124 | CTA GGC AGC TGG GCT CAC |
| Nanostring STA | Bcl11b | 125 | GGA GGG GTG GCT TTC AA | 126 | AAG ATT CTC GGG GTC CCA |
| Nanostring STA | Casp4 | 127 | GGA ACA GCT GGG CAA AGA | 128 | GCC TGG TCA CAC ACT GAA |
| Nanostring STA | Ccr8 | 129 | GTG GGT GTT TGG GAC TGC | 130 | ATC AAG GGG ATG GTG GCT |
| Nanostring STA | Cd51 | 131 | TGG GGG TAC CAC GAC TGT | 132 | GGG CGT GTA GCC TTG AGA |
| Nanostring STA | Clcf1 | 133 | AAT CCT CCT CGA CTG GGG | 134 | TGA CAC CTG CAA TGC TGC |
| Nanostring STA | Cxcr4 | 135 | CCG ATA GCC TGT GGA TGG | 136 | GTC GAT GCT GAT CCC CAC |
| Nanostring STA | Eif3h | 137 | AGC CTT CGC CAT GTC AAC | 138 | CGC CTT CAG CGA GAG AGA |
| Nanostring STA | Fasl | 139 | GCA AAT AGC CAA CCC CAG | 140 | GTT GCA AGA CTG ACC CCG |
| Nanostring STA | Frmd4b | 141 | GGA GTC CCA GTC CCA CCT | 142 | TGG ACC TTC TTC TCC CCC |
| Nanostring STA | Golga3 | 143 | TCC AAC CAG GTG GAG CAC | 144 | TCA TCT CAG AGT CCA GCC G |

TABLE S6.1-continued

Primer Sequences

| Assay | Gene Name | SEQ ID NO: | Forward Sequence | SEQ ID NO: | Reverse Sequence |
|---|---|---|---|---|---|
| Nanostring STA | Acvr2a | 145 | ATG GCA AAC TTG GAC CCC | 146 | CAA GAT CTG TGC AGG GCA |
| Nanostring STA | Arl5a | 147 | CGG ATT TGA GCG CTT CTG | 148 | ACT CAC TGG TGG GTG GGA |
| Nanostring STA | Bcl2l11 | 149 | TGG CAA GCC CTC TCA CTT | 150 | AAA CAC ACA CAA CCA CGC A |
| Nanostring STA | Casp6 | 151 | TGC TCA AAA TTC ACG AGG TG | 152 | CAC GGG TAC GTC ATG CTG |
| Nanostring STA | Cd2 | 153 | CAC CCT GGT CGC AGA GTT | 154 | GGT TGT GTT GGG GCA TTC |
| Nanostring STA | Cd70 | 155 | CTG GCT GTG GGC ATC TG | 156 | GGA GTT GTG GTC AAG GGC |
| Nanostring STA | Cmtm6 | 157 | TGC TGG TGT AGG CGT CTT T | 158 | TCT CAG CAA TCA CAG TGC AA |
| Nanostring STA | Cxcr5 | 159 | TGG CCT TAA TGT GCC TGT C | 160 | TGC TGG CTT GCC CTT TAC |
| Nanostring STA | Eif3m | 161 | TGG CTT GTT ACA TGA GCA AAA | 162 | CCG ATG TGT GCT GTG ACT G |
| Nanostring STA | Fipl11 | 163 | GGA TAG GAA TGG GAG TGG AA | 164 | CCA ACG CTT GAA CTG GCT |
| Nanostring STA | Fzd7 | 165 | TTC CCT GCA ATA GAA GTC TGG | 166 | TGA AGT AAT CTG TCC TCC CGA |
| Nanostring STA | Grn | 167 | CCG GCC TAC TCA TCC TGA | 168 | AAC TTT ATT GGA GCA ACA CAC G |
| Nanostring STA | Ahr | 169 | GTT GTG ATG CCA AAG GGC | 170 | CAA GCG TGC ATT GGA CTG |
| Nanostring STA | Armcx2 | 171 | TCC AAT CTT GCC ACC ACC | 172 | TTC CAG CAC TTT GGG AGC |
| Nanostring STA | Bcl3 | 173 | CCA GGT TTT GCA CCA AGG | 174 | CCT CCC AGA CCC CTC TGT |
| Nanostring STA | Ccl1 | 175 | CAC TGA TGT GCC TGC TGC | 176 | TGA GGC GCA GCT TTC TCT |
| Nanostring STA | Cd247 | 177 | TAC CAT CCC AGG GAA GCA | 178 | GCA GGT TGG CAG CAG TCT |
| Nanostring STA | Cd74 | 179 | GCT TCC GAA ATC TGC CAA | 180 | CGC CAT CCA TGG AGT TCT |
| Nanostring STA | Csf2 | 181 | GGC CAT CAA AGA AGC CCT | 182 | GCT GTC ATG TTC AAG GCG |
| Nanostring STA | Daxx | 183 | GTT GAC CCC GCA CTG TCT | 184 | ATT CCG AGG AGG CTT TGG |
| Nanostring STA | Elk3 | 185 | CCT GTG GAC CCA GAT GCT | 186 | GAC GGA GTT CAG CTC CCA |
| Nanostring STA | Fli1 | 187 | GAT TCT GAG AAA GGA GTA CGC A | 188 | GCC AGT GTT CCA GTT GCC |
| Nanostring STA | Gap43 | 189 | GCG AGA GAG CGA GTG AGC | 190 | CCA CGG AAG CTA GCC TGA |
| Nanostring STA | Gusb | 191 | ATG GAG CAG ACG CAA TCC | 192 | AAA GGC CGA AGT TTT GGG |
| Nanostring STA | H2-Q10 | 193 | GTG GGC ATC TGT GGT GGT | 194 | TGG AGC GGG AGC ATA GTC |
| Nanostring STA | Ifi35 | 195 | CAG AGT CCC ACT GGA CCG | 196 | AGG CAC AAC TGT CAG GGC |
| Nanostring STA | Il12rb2 | 197 | GCA GCC AAC TCA AAA GGC | 198 | GTG ATG CTC CCT GGT TGG |
| Nanostring STA | Il22 | 199 | TCA GAC AGG TTC CAG CCC | 200 | TCT TCT CGC TCA GAC GCA |
| Nanostring STA | Il4ra | 201 | CCT TCA GCC CCA GTG GTA | 202 | AGC TCA GCC TGG GTT CCT |
| Nanostring STA | Irf8 | 203 | AAG GGA CAC TTC CCG GAG | 204 | TTT CCT GCA GTT CCC CAG |
| Nanostring STA | Katna1 | 205 | CGG TGC GGG AAC TAT CC | 206 | CAT TTG GTC AAG AAC TCC CTG |
| Nanostring STA | Lad1 | 207 | GAA GGA GCT GTC AGG CCA | 208 | GCA TCC AGG GAT GTG GAC |

TABLE S6.1-continued

Primer Sequences

| Assay | Gene Name | SEQ ID NO: | Forward Sequence | SEQ ID NO: | Reverse Sequence |
|---|---|---|---|---|---|
| Nanostring STA | Ly6c2 | 209 | GTC CTT CCA ATG ACC CCC | 210 | CCT CCA GGG CCA AGA ATA G |
| Nanostring STA | Mina | 211 | GTC TGC CGG AGC ATC AGT | 212 | TAA TGT GGA GGG AGG CCC |
| Nanostring STA | Nampt | 213 | CAA GGA GAT GGC GTG GAT | 214 | TGG GAT CAG CAA CTG GGT |
| Nanostring STA | Nkg7 | 215 | TGG CCC TCT GGT CTC AAC | 216 | TTT CAT ACT CAG CCC GAC G |
| Nanostring STA | Hif1a | 217 | AAG AAC TTT TGG GCC GCT | 218 | GCA CTG TGG CTG GGA GTT |
| Nanostring STA | Ifih1 | 219 | GCT GAA AAC CCA AAA TAC GA | 220 | ACT TCA CTG CTG TGC CCC |
| Nanostring STA | Il17a | 221 | ATC AGG ACG CGC AAA CAT | 222 | GAC GTG GAA CGG TTG AGG |
| Nanostring STA | Il23r | 223 | CAC TGC AAG GCA GCA GG | 224 | CGT TTG GTT TGT TGT TGT TTT G |
| Nanostring STA | Il6st | 225 | TCG GAC GGC AAT TTC ACT | 226 | GTT GCT GGA GAT GCT GGG |
| Nanostring STA | Irf9 | 227 | ACT GAT CGT CGC GTC TCC | 228 | TTG GTC TGT CTT CCA AGT GCT |
| Nanostring STA | Kcmf1 | 229 | CTG ACC ACC CGA TGC AGT | 230 | TCC AGG TAA CGC TGC ACA |
| Nanostring STA | Lamp2 | 231 | GGC TGC AGC TGA ACA TCA | 232 | AAG CTG AGC CAT TAG CCA AA |
| Nanostring STA | Maf | 233 | AGG CAG GAG GAT GGC TTC | 234 | TCA TGG GGT GGA GGA AC |
| Nanostring STA | Mkln1 | 235 | GGT TTG CCC ATC AAC TCG | 236 | GGA TCC ATT TGG GCC TTT |
| Nanostring STA | Ncf1 | 237 | GCA AAG GAC AGG ACT GGG | 238 | TTT GAC ACC CTC CCC AAA |
| Nanostring STA | Notch1 | 239 | GCA GGC AAA TGC CTC AAC | 240 | GTG GCC ATT GTG CAG ACA |
| Nanostring STA | Hip1r | 241 | CTC GAG CAG CTG GGA CC | 242 | CCA GCA GGG ACC CTC TTT |
| Nanostring STA | Ifit1 | 243 | TCA TTC GCT ATG CAG CCA | 244 | GGC CTG TTG TGC CAA TTC |
| Nanostring STA | Il17f | 245 | AAG AAC CCC AAA GCA GGG | 246 | CAG CGA TCT CTG AGG GGA |
| Nanostring STA | Il24 | 247 | TCT CCA CTC TGG CCA ACA | 248 | CTG CAT CCA GGT CAG GAG A |
| Nanostring STA | Il7r | 249 | TGG CCT ACT CTC CCC GAT | 250 | CGA GCG GTT TGC ACT GT |
| Nanostring STA | Isg20 | 251 | CTG TGG AAG ATG CCA GGG | 252 | GTG GTT GGT GGC AGT GGT |
| Nanostring STA | Khdrbs1 | 253 | GTT CGT GGA ACC CCA GTG | 254 | TCC CCT TGA CTC TGG CTG |
| Nanostring STA | Lgals3bp | 255 | GGC CAC AGA GCT TCA GGA | 256 | CCA GCT CAC TCT TGG GGA |
| Nanostring STA | Maff | 257 | TCT GAC TCT TGC AGG CCC | 258 | TGG CAC AAT CCA AAG CCT |
| Nanostring STA | Mt1 | 259 | ACT ATG CGT GGG CTG GAG | 260 | GCA GGA GCT GGT GCA AGT |
| Nanostring STA | Ncoa1 | 261 | GCC TCC AGC CCA TCC TAT | 262 | TGA GGG ATT TAT TCG GGG A |
| Nanostring STA | Notch2 | 263 | TAC GAG TGC ACC TGC AA | 264 | GCA GCG TCC TGG AAT GTC |
| Nanostring STA | Hsbp1 | 265 | ATC ACG TGA CCA CAG CCC | 266 | CTC TGA TAC CCT GCC GGA |
| Nanostring STA | Ifng | 267 | TCT GGG CTT CTC CTC CTG | 268 | TCC TTT TGC CAG TTC CTC C |
| Nanostring STA | Il17ra | 269 | GGG GCT GAG CTG CAG ACT | 270 | TGG TGT TCA GCT GCA GGA |
| Nanostring STA | Il27ra | 271 | AAG CTG GCT CTC GAA CTT | 272 | GGG CAG GGA ACC AAA CTT |

TABLE S6.1-continued

Primer Sequences

| Assay | Gene Name | SEQ ID NO: | Forward Sequence | SEQ ID NO: | Reverse Sequence |
|---|---|---|---|---|---|
| Nanostring STA | Il9 | 273 | TGG TGA CAT ACA TCC TTG CC | 274 | TGT GTG GCA TTG GTC AGC |
| Nanostring STA | Itga3 | 275 | GCT TCA CCC AGA ACA CCG | 276 | CCC ATA TGT TGG TGC CGT |
| Nanostring STA | Kif2a | 277 | TGC CGA ATA CAC CAA GCA | 278 | TCC GCC GGT TCT TTA CAA |
| Nanostring STA | Lif | 279 | GGG GCA GGT AGT TGC TCA | 280 | TCG GGA TCA AGG ACA CAG A |
| Nanostring STA | Map3k5 | 281 | CCA TCT TGG AGT GCG AGA A | 282 | GCT CAG TCA GGC CCT TCA |
| Nanostring STA | Mt2 | 283 | TGT GCT GGC CAT ATC CCT | 284 | AGG CAC AGG AGC AGT TGG |
| Nanostring STA | Nfatc2 | 285 | AGC TCC ACG GCT ACA TGG | 286 | CGT TTC GGA GCT TCA GGA |
| Nanostring STA | Nr3c1 | 287 | CAA GTG ATT GCC GCA GTG | 288 | CAT TGG TCA TAG ATG CAG GG |
| Nanostring STA | Icos | 289 | CGG CCG ATC ATA GGA TGT | 290 | TTC CCT GGG AGC TGT CTG |
| Nanostring STA | Ifngr2 | 291 | CGA AAC AAC AGC AAA TGC C | 292 | CGG TGA ACC GTC CTT GTC |
| Nanostring STA | Il1r1 | 293 | ACC CGA GGT CCA GTG GTA | 294 | TCT CAT TCC GAG GGC TCA |
| Nanostring STA | Il2ra | 295 | TGC AAG AGA GGT TTC CGA | 296 | GTT CCC AAG GAG GTG GCT |
| Nanostring STA | Inhba | 297 | AGC AGA AGC ACC CAC AGG | 298 | TCC TGG CAC TGC TCA CAA |
| Nanostring STA | Itgb1 | 299 | TGG AAA ATT CTG CGA GTG TG | 300 | TTG GCC CTT GAA ACT TGG |
| Nanostring STA | Klf10 | 301 | CCC TCC AAA AGG GCC TAA | 302 | GGC AAA AAC AAA GTC CCC A |
| Nanostring STA | Litaf | 303 | AGT GCA CAG AAG GGC TGC | 304 | CCA GCA AAT GGA GAA ATG G |
| Nanostring STA | Max | 305 | AGG ACG CCT GCT CTA CCA | 306 | GCT GCA AAT CTG TCC CCA |
| Nanostring STA | Mta3 | 307 | CGG AGA AGC AGA AGC ACC | 308 | ACT TTG GGC CCA CTC TGA |
| Nanostring STA | Nfe2l2 | 309 | GCC GCT TAG AGG CTC ATC | 310 | TGC TCC AGC TCG ACA ATG |
| Nanostring STA | Nudt4 | 311 | TGG GGT GCC ATC CAG TAT | 312 | ATT CCA CAT GGC TTT GGC |
| Nanostring STA | Id2 | 313 | TCA GCC ATT CA CCA GGA G | 314 | TAA CGT TTT CGC TCC CCA |
| Nanostring STA | Ikzf4 | 315 | GGG GTC TAG CCC AAT TCC | 316 | GCC GGG GAG AGA GGT TAG |
| Nanostring STA | Il1rn | 317 | TGG TAA GCT TTC CTT CTT TCC | 318 | TCA TCA CAT CAG GAA GGG C |
| Nanostring STA | Il2rb | 319 | GCA CCC CAT CCT CAG CTA | 320 | CAA GTC CAG CTC GGT GGT |
| Nanostring STA | Irf1 | 321 | TAA GCA CGG CTG GGA CAT | 322 | CAG CAG AGC TGC CCT TGT |
| Nanostring STA | Jak3 | 323 | CTC CCC AGC GAT TGT CAT | 324 | CAG CCC AAA CCA GTC AGG |
| Nanostring STA | Klf6 | 325 | GAG CGG GAA CTC AGG ACC | 326 | GGG AAA ATG ACC ACT GCG |
| Nanostring STA | Lmnb1 | 327 | TGC CCT AGG GGA CAA AAA | 328 | CAA GCG GGT CTC ATG CTT |
| Nanostring STA | Mbnl3 | 329 | TGG AGC ATG AAT CCA CAC C | 330 | TGA GGG TCC CAT GAG TGG |
| Nanostring STA | Mxi1 | 331 | CTC AGG AGA TGG AGC GGA | 332 | CCT CGT CAC TCC CGA CAC |
| Nanostring STA | Nfil3 | 333 | CAC GGT GGT GAA GGT TCC | 334 | GAA AGG AGG GAG GGA GGA |
| Nanostring STA | Oas2 | 335 | TGC CTG TGC TTG CTC TGA | 336 | GAA GAA GGG CCA GAA GGG |

TABLE S6.1-continued

Primer Sequences

| Assay | Gene Name | SEQ ID NO: | Forward Sequence | SEQ ID NO: | Reverse Sequence |
|---|---|---|---|---|---|
| Nanostring STA | Id3 | 337 | CCG AGG AGC CTC TTA GCC | 338 | GTC TGG ATC GGG AGA TGC |
| Nanostring STA | Il10 | 339 | ACT GCC TTC AGC CAG GTG | 340 | CAG CTT CTC ACC CAG GGA |
| Nanostring STA | Il21 | 341 | CCT GOA GTG GTA TCA TCG C | 342 | TGC GTT GGT TCT GAT TGT G |
| Nanostring STA | Il3 | 343 | CAC ACC ATG CTG CTC CTG | 344 | CTC CTT GGC TTT CCA CGA |
| Nanostring STA | Irf4 | 345 | CAG AGA AAC GCA TTC CTG G | 346 | AGT CCA CCA GCT GGC TTT T |
| Nanostring STA | Jun | 347 | TAT TGG CCG GCA GAC TTT | 348 | GCC TGG CAC TTA CAA GCC |
| Nanostring STA | Klf9 | 349 | AGG GAA GGA AGA CGC CAC | 350 | TGG CCA TGT AAA AGC CAA A |
| Nanostring STA | Lrrfip1 | 351 | GTC TCC AAC GCC CAG CTA | 352 | ATC TCT TCC CTT TGC CGC |
| Nanostring STA | Med24 | 353 | ACT GCT AGG GGT CCT GGG | 354 | TGA GCC ATA GGT CTG GGC |
| Nanostring STA | Myd88 | 355 | GAA GCT GTT TGG CTT CGC | 356 | TCA TTC CTC CCC CAG ACA |
| Nanostring STA | Nfkbie | 357 | TCG AGG CGC TCA CAT ACA | 358 | CGG ACA ACA TCT GGC TGA |
| Nanostring STA | Pcbp2 | 359 | CTC AAC TGA GCG GGC AAT | 360 | AGG GTT GAG GCA CAT GGA |
| Nanostring STA | Ier3 | 361 | CCT TCT CCA GCT CCC TCC | 362 | CCT CTT GGC AAT GTT GGG |
| Nanostring STA | Il10ra | 363 | GTA AAG GCC GGC TCC AGT | 364 | TTT CCA GTG GAG GAT GTG C |
| Nanostring STA | Il21r | 365 | AGG TCT GGC CAC AAC ACC | 366 | GGC CAC AGT CAC GTT CAA |
| Nanostring STA | Il4 | 367 | AGG GCT TCC AAG GTG CTT | 368 | TGC TCT TTA GGC TTT CCA GG |
| Nanostring STA | Irf7 | 369 | GAG GCT GAG GCT GCT GAG | 370 | ATC CTG GGA CAC ACC CCT |
| Nanostring STA | Kat2b | 371 | GGT GCT TTG AGC AGT TGT GA | 372 | GCC CTG CAC AAG CAA AGT |
| Nanostring STA | Klrd1 | 373 | GCC TGG CTA TGG GAG GAT | 374 | CCG TGG ACC TTC CTT GTC |
| Nanostring STA | Lsp1 | 375 | CCT GAG CCC TAG CAC CAA | 376 | GGG CAG CTC TAT GGA GGG |
| Nanostring STA | MgLL | 377 | CGC GCA GTA GTC TGG CTC | 378 | AAG ATG AGG GCC TTG GGT |
| Nanostring STA | Myst4 | 379 | CAA CAA AGG GCA GCA AGC | 380 | TTC AAC ACA AGG GCA GAG G |
| Nanostring STA | Nfkbiz | 381 | TTA GCT GGA TGA GCC CCA | 382 | ATG TTG CTG CTG TGG TGG |
| Nanostring STA | Peli2 | 383 | GCC AGA CGG TAG TGG TGG | 384 | CGT GCT GTG TAT GGC TCG |
| Nanostring STA | Phlda1 | 385 | GAT GAC GGA GGG CAA AGA | 386 | GGG GTT GAG GCT GGA TCT |
| Nanostring STA | Prdm1 | 387 | ACC CTG GCT ATG CAC CTG | 388 | GGG AAG CTG GAT TGA GCA |
| Nanostring STA | Pstpip1 | 389 | GAG AGC GAG GAC CGA GTG | 390 | CCT TCC ACA TCA CAG CCC |
| Nanostring STA | Rela | 391 | TGC GAC AAG GTG CAG AAA | 392 | GAG CTC GCG ATC AGA AGG |
| Nanostring STA | Runx3 | 393 | GCC CCT TCC ACA CAT TTA | 394 | CTC CCC TGC TGC TA CAA |
| Nanostring STA | Sgk1 | 395 | GGC TAG GCA CAA GGC AGA | 396 | AGC GCT CCC TCT GGA GAT |
| Nanostring STA | Smox | 397 | ACA GCC TCG TGT GGT GGT | 398 | GGC CAT GGC TTC CTG CTA |
| Nanostring STA | Stat4 | 399 | GCC TCT ATG GCC TCA CCA | 400 | ACT CCA GGA GTT GGG CCC |
| Nanostring STA | Tbx21 | 401 | TGG GAA GCT GAG AGT CGC | 402 | GCC TTC TGC CTT TCC ACA |

TABLE S6.1-continued

Primer Sequences

| Assay | Gene Name | SEQ ID NO: | Forward Sequence | SEQ ID NO: | Reverse Sequence |
|---|---|---|---|---|---|
| Nanostring STA | Tmed7 | 403 | TGG TTA GCG TAG GGC AGG | 404 | CCC ATG GGG ATA TGC ACT |
| Nanostring STA | Traf3 | 405 | ATC TGT GGG CGC TCT GAC | 406 | GGA CTG TCA AGA TGG GGC |
| Nanostring STA | Vav3 | 407 | TTC TGG CAG GGA CGA AAC | 408 | TTT GGT CCT GTG CCT TAC AA |
| Nanostring STA | Plac8 | 409 | TGC TCC CCA AAA TTC CAA | 410 | AGG AAT GCC GTA TCG GGT |
| Nanostring STA | Prf1 | 411 | ACC AAC CAG GAC TGC TGC | 412 | CCC TGT GGA CAG GAG CAC |
| Nanostring STA | Ptprj | 413 | TCA CCT GGA GCA ATG CAA | 414 | TGG TAC CAT TGG CAT CCG |
| Nanostring STA | Rfk | 415 | TTT CCC TCT TGG TGG CCT | 416 | TCC CTC CCC ACA CCA CTA |
| Nanostring STA | Rxra | 417 | TTG TTG GGC GAC TTT TGC | 418 | TGG AGA GTT GAG GGA CGA A |
| Nanostring STA | Skap2 | 419 | TGG GTG AAC ATT CCT GCC | 420 | AAA CAG CAA CCC TCA CCG |
| Nanostring STA | Socs3 | 421 | TGC AGO AGA GCG GAT TCT | 422 | GAA CTG GCT GCG TGC TTC |
| Nanostring STA | Stat5a | 423 | CCT CCG CTA GAA GCT CCC | 424 | GCT CTT ACA CGA GAG GCC C |
| Nanostring STA | Tgfb1 | 425 | CGC CTG AGT GGC TGT CTT | 426 | ATG TCA TGG ATG GTG CCC |
| Nanostring STA | Tmem126a | 427 | CTG CTT GAA TAT GGA TCA GCA | 428 | CCA ACT AGT GCA CCC CGT |
| Nanostring STA | Trat1 | 429 | CAA TGG ATG CCA ACG TTT C | 430 | CCT TGC CAG TCC CTG TGT |
| Nanostring STA | Vax2 | 431 | GGC CCC CGT GGA CTA TAG | 432 | CAC ACA CAC ACG CAC ACG |
| Nanostring STA | Plagl1 | 433 | TTG AGA CTG TAT CCC CCA GC | 434 | GCA GGG TCT TCA AAG GTC AG |
| Nanostring STA | Prickle1 | 435 | TGG GTT TCC ACT TGC AGT T | 436 | GCC TTT ATT AAA CAC CTC CCT G |
| Nanostring STA | Pycr1 | 437 | CCC TGG GTG TGT GCA GTC | 438 | AAG GGG TTG AAA GGG GTG |
| Nanostring STA | Rngtt | 439 | CCC AAA AGA CTG CAT CGG | 440 | TCC ACA GGG TAA GGC TGA A |
| Nanostring STA | Sav1 | 441 | CGA CCC CCA ATG TAA GGA | 442 | TAG CCC ACC CTG ATG GAA |
| Nanostring STA | Ski | 443 | GGT CCC CTG CAG TGT CTG | 444 | CTT CCG TTT TCG TGG CTG |
| Nanostring STA | Spp1 | 445 | CCA TGA CCA CAT GGA CGA | 446 | CCA AGC TAT CAC CTC GGC |
| Nanostring STA | Stat5b | 447 | ACT CAG CGC CCA CTT CAG | 448 | GCT CTG CAA AGG CGT TGT |
| Nanostring STA | Tgfb3 | 449 | GCC AAA GTC CCC TGG AAT | 450 | AAG GAA GGC AGG AGG AGG |
| Nanostring STA | Tnfrsf12a | 451 | GGG AGC CTT CCA AGG TGT | 452 | GGC ATT ATA GCC CCT CCG |
| Nanostring STA | Trim24 | 453 | CGG TGG TCC TTC GCC | 454 | TGC AGA GCC ATT CAA CAC A |
| Nanostring STA | Xbp1 | 455 | GGA CCT CAT CAG CCA AGC | 456 | GCA GGT TTG AGA TGC CCA |
| Nanostring STA | Plekhf2 | 457 | CGG CAA TAT TGT TAT CCA GAA | 458 | GGG CGT CTT CCC ACT TTT |
| Nanostring STA | Prkca | 459 | TGC TGT CCC AGG GAT GAT | 460 | CAA ATA GCC CAG GAT ACC CA |
| Nanostring STA | Rab33a | 461 | GCT GGC TTG GCA TCC TT | 462 | TTG ATC TTC TCG CCC TCG |
| Nanostring STA | Rora | 463 | GAT GTG GCA GCT GTG TGC | 464 | TTG AAG ACA TCG GGG CTC |
| Nanostring STA | Sema4d | 465 | TTC TTG GGC AGT GAA CCC | 466 | TCG CGG GAT CAT CAA CTT |

TABLE S6.1-continued

Primer Sequences

| Assay | Gene Name | SEQ ID NO: | Forward Sequence | SEQ ID NO: | Reverse Sequence |
|---|---|---|---|---|---|
| Nanostring STA | Slamf7 | 467 | CTC CAT GAA GCT CAG CCA A | 468 | TTG ATT ACG CAG GTG CCA |
| Nanostring STA | Spry1 | 469 | AGG ACT TCC CTT CAC GCC | 470 | AGC CAG GAT TCA ACT TTG TGA |
| Nanostring STA | Stat6 | 471 | TGC TTT TGC CAG TGT GAC C | 472 | ACG CCC AGG GAG TTT ACA |
| Nanostring STA | Tgfbr1 | 473 | TGA TGT CAG CTC TGG GCA | 474 | TCT GCA GCG AGA ACC AAA |
| Nanostring STA | Tnfrsf13b | 475 | GGA AGG CAC CAG GGA TCT | 476 | CTC GTC GCA AGC CTC TGT |
| Nanostring STA | Trim25 | 477 | TCT GCC TTG TGC CTG ACA | 478 | ACG GGT GCA TCA GCC TAA |
| Nanostring STA | Xrcc5 | 479 | AGG GGA CCT GGA CTC TGG | 480 | GAC AAG TTG GGG CCA ATG |
| Nanostring STA | Pmepa1 | 481 | GTG ACC GCT TGA TGG GG | 482 | GCT GTG TCG GCT GAT GAA |
| Nanostring STA | Prkd3 | 483 | CCT GGC CTC TCA GTT CCA | 484 | AGA GGC CTT TCA GCA GGC |
| Nanostring STA | Rad51ap1 | 485 | AGC AGC CAA GTG CGG TAG | 486 | TGC CAC AAG GAG AGG TCC |
| Nanostring STA | Rorc | 487 | CCT CTG ACC CGT CTC CCT | 488 | GCT TCC AGA AGC CAG GGT |
| Nanostring STA | Sema7a | 489 | ATG AAA GGC TAT GCC CCC | 490 | GTG CAC AAT GGT GGC CTT |
| Nanostring STA | Slc2a1 | 491 | GAC CCT GCA CCT CAT TGG | 492 | GAA GCC AGC CAC AGC AAT |
| Nanostring STA | Stard10 | 493 | AGG ACC CAG GAG AGT CGG | 494 | ATC TCC ACA GCC TGC ACC |
| Nanostring STA | Sufu | 495 | ATG GGG AGT CCT TCT GCC | 496 | TAG GCC CTG CAT CAG CTC |
| Nanostring STA | Tgfbr3 | 497 | TCT GGG ATT TGC CAT CCA | 498 | GTG CAG GAA GAG CAG GGA |
| Nanostring STA | Tnfrsf25 | 499 | CGA GCC ATG TGG GAA AAG | 500 | GAG GCT GAG AGA TGG GCA |
| Nanostring STA | Trps1 | 501 | TTG TAA CGC ACT TTG AGA TCC | 502 | CGT GCC TTT TTG GTA GCC |
| Nanostring STA | Zeb1 | 503 | AAG CGC TGT GTC CCT TTG | 504 | GTG AGA TGC CCC ACT GCT |
| Nanostring STA | Pml | 505 | AAT TTG GGT CCT CTC GGC | 506 | GCT CGA GAT GCC AGT GCT |
| Nanostring STA | Prnp | 507 | CCT CCC ACC TGG GAT AGC | 508 | CCG TCA CAG GAG GAC CAA |
| Nanostring STA | Rasgrp1 | 509 | CAA GCA TGC AAA GTC TGA GC | 510 | CGT TAT GAG CGG GGT TTG |
| Nanostring STA | Rpp14 | 511 | GCA GCA GTG GTC TCG TCA | 512 | TGT CAC CAA CAG GGG CTT |
| Nanostring STA | Serpinb1a | 513 | CAA GGT GCT GGA GAT GCC | 514 | GCG GCC CAG GTT AGA GTT |
| Nanostring STA | Slc6a6 | 515 | GGT GCG TTC CTC ATA CCG | 516 | AGG CCA GGA TGA CGA TGT |
| Nanostring STA | Stat1 | 517 | GAG GTA GAG GCC TGG GGA | 518 | TTT AAG CTC TGC CGC CTC |
| Nanostring STA | Sult2b1 | 519 | CGA TGT CGT GGT CTC CCT | 520 | GTC CTC CTG CAG CTC CTC |
| Nanostring STA | Tgif1 | 521 | GGA CCC ACT CCA AAC CCT | 522 | CGG CAA TCA GGA CCG TAT |
| Nanostring STA | Tnfsf11 | 523 | AAC AAG CCT TTC AGG GGG | 524 | AGA GAT CTT GGC CCA GCC |
| Nanostring STA | Tsc22d3 | 525 | TGC CAG TGT GCT CCA GAA | 526 | CTG TGC ACA AAG CCA TGC |
| Nanostring STA | Zfp161 | 527 | CGC CAA GAT TTC CGT GA | 528 | TCC CCG ATT TCT TCC ACA |
| Nanostring STA | Pou2af1 | 529 | GCC CAC TGG CCT TCA TTT | 530 | TGG GAT ATC AAA GAA ACT GTC A |
| Nanostring STA | Procr | 533 | GCC AAA ACG TCA CCA TCC | 532 | ACG GCC ACA TCG AAG AAG |

TABLE S6.1-continued

Primer Sequences

| Assay | Gene Name | SEQ ID NO: | Forward Sequence | SEQ ID NO: | Reverse Sequence |
|---|---|---|---|---|---|
| Nanostring STA | Rbpj | 533 | TCC CTT AAA ACA GGA GCC A | 534 | CTT CCC CTT GAC AAG CCA |
| Nanostring STA | Runx1 | 535 | GCC TGA GAA AAC GGT AGG G | 536 | CAT GTG CCT GAT GGA TTT TT |
| Nanostring STA | Serpine2 | 537 | TGA GCC ATC AAA GGC AAA | 538 | GCT TGT TCA CCT GGC CC |
| Nanostring STA | Smad3 | 539 | ACG TGC CCC TGT CTG AAG | 540 | GAG TGG TGG GAC AGG GC |
| Nanostring STA | Stat2 | 541 | GCA ACC AGG AAC GCA GAC | 542 | TCT TCG GCA AGA ACC TGG |
| Nanostring STA | Tal2 | 543 | GGT GGA GGC AGC AGA GTG | 544 | CAT CCT CAT CTG GCA GGC |
| Nanostring STA | Tgm2 | 545 | GAG TCT CAG TGC GAG CCA | 546 | ATG TCC TCC CGG TCA TCA |
| Nanostring STA | Tnfsf8 | 547 | ACG CCC CCA GAG AAG AGT | 548 | CTG GGT CAG GGG AAG GAG |
| Nanostring STA | Ube3a | 549 | TCG CAT GTA CAG TGA AAG AAG A | 550 | CTT TGG AAA CGC CTC CCT |
| Nanostring STA | Zfp238 | 551 | GCC TTG ATT GAC ATG GGG | 552 | AAG AAA AAG GGA AAA ACA ACC A |
| Nanostring STA | Prc1 | 553 | TCC CAA CCC TGT GCT CAT | 554 | CAG TGT GGG CAG AAC TGG |
| Nanostring STA | Psmb9 | 555 | TGG TTA TGT GGA CGC AGC | 556 | GGA AGG GAC TTC TGG GGA |
| Nanostring STA | Re1 | 557 | GCC CCT CTG GGA TCA ACT | 558 | GGG GTG AGT CAC TGG TGG |
| Nanostring STA | Runx2 | 559 | AAA TCC TCC CCA AGT GGC | 560 | TGC AGA GTT CAG GGA GGG |
| Nanostring STA | Sertad1 | 561 | CTG GGT GCC TTG GAC TTG | 562 | CGC CTC ATC CAA CTC TGG |
| Nanostring STA | Smarca4 | 563 | TAC CGT GCC TCA GGG AAA | 564 | CCC CGG TCT TCT GCT TTT |
| Nanostring STA | Stat3 | 565 | TTC AGC GAG AGC AGC AAA | 556 | AAA TGC CTC CTC CTT GGG |
| Nanostring STA | Tap1 | 567 | TCT CTC TTG CCT TGG GGA | 568 | GGC CCG AAA CAC CTC TCT |
| Nanostring STA | Timp2 | 569 | GCT GGA CGT TGG AGG AAA | 570 | CTC ATC CGG GGA GGA GAT |
| Nanostring STA | Tnfsf9 | 571 | GTT CCC CAC ATT GGC TGC | 572 | AGC CCG GGA CTG TCT ACC |
| Nanostring STA | Ubiad1 | 573 | TAC AGA GCG CTT GTC CCC | 574 | GCC ACC ATG CCA TGT TTT |
| Nanostring STA | Zfp281 | 575 | CCA GAC GTA GTT GGG CAG A | 576 | TGC TGC TGG CAG TTG GTA |
| Nanostring STA | Zfp410 | 577 | CTG AAA GAG CCT CAC GGC | 578 | CCA TCA TGC ACT CTG GGA |
| Fluidigm & QPCR | B2M | 579 | TTC TGG TGC TTG TCT CAC TGA | 580 | CAG TAT GTT CGG CTT CCC ATT C |
| Fluidigm & QPCR | Aim1 | 581 | GAC GAC TCC TTT CAG ACC AAG T | 582 | AAA TTT TCT CCA TCA TAA GCA ACC |
| Fluidigm & QPCR | Cd44 | 583 | GCA TCG CGG TCA ATA GTA GG | 584 | CAC CGT TGA TCA CCA GCT T |
| Fluidigm & QPCR | Ifngr2 | 585 | TCC TGT CAC GAA ACA ACA GC | 586 | ACG AAA TCA GGA TGA CTT GC |
| Fluidigm & QPCR | Il6st | 587 | TCC CAT GGG CAG GAA TAT AG | 588 | CCA TTG GCT TCA GAA AGA GG |
| Fluidigm & QPCR | Klf7 | 589 | AAG TGT AAC CAC TGC GAC AGG | 590 | TCT TCA TAT GGA GCG CAA GA |
| Fluidigm & QPCR | Mt2 | 591 | CAT GGA CCC CAA CTG CTC | 592 | AGC AGG AGC AGC AGC TTT |
| Fluidigm & QPCR | Nudt4 | 593 | CTG CTG TGA GGG AAG TGT ATG A | 594 | CGA GCA GTC TGC CTA GCT TT |

TABLE S6.1-continued

Primer Sequences

| Assay | Gene Name | SEQ ID NO: | Forward Sequence | SEQ ID NO: | Reverse Sequence |
|---|---|---|---|---|---|
| Fluidigm & QPCR | Pstpip1 | 595 | AGC CCT CCT GTG GTG TGA TA | 596 | TGG TCT TGG GAC TTC CAT GT |
| Fluidigm & QPCR | Rxra | 597 | GCT TCG GGA CTG GTA GCC | 598 | GCG GCT TGA TAT CCT CAG TG |
| Fluidigm & QPCR | Sod1 | 599 | CCA GTG CAG GAC CTC ATT TT | 600 | GGT CTC CAA CAT GCC TCT CT |
| Fluidigm & QPCR | Tgfb1 | 601 | TGG AGC AAC ATG TGG AAC TC | 602 | CAG CAG CCG GTT ACC AAG |
| Fluidigm & QPCR | GAPDH | 603 | GGC AAA TTC AAC GGC ACA GT | 604 | AGA TGG TGA TGG GCT TCC C |
| Fluidigm & QPCR | Atf4 | 605 | ATG ATG GCT TGG CCA GTG | 606 | CCA TTT TCT CCA ACA TCC AAT C |
| Fluidigm & QPCR | Cmtm6 | 607 | GAT ACT GGA AAA GTC AAG TCA TCG | 608 | AAT GGG TGG AGA CAA AAA TGA |
| Fluidigm & QPCR | Il10 | 609 | CAG AGC CAC ATG CTC CTA GA | 610 | GTC CAG CTG GTC CTT TGT TT |
| Fluidigm & QPCR | Il7r | 611 | CGA AAC TCC AGA ACC CAA GA | 612 | AAT GGT GAC ACT TGG CAA GAC |
| Fluidigm & QPCR | Lamp2 | 613 | TGC AGA ATG GGA GAT GAA TTT | 614 | GGC ACT ATT CCG GTC ATC C |
| Fluidigm & QPCR | Myc | 615 | CCT AGT GCT GCA TGA GGA GA | 616 | TCT TCC TCA TCT TCT TGC TCT TC |
| Fluidigm & QPCR | Pcbp2 | 617 | CAG CAT TAG CCT GGC TCA GTA | 618 | ATG GAT GGG TCT GCT CTG TT |
| Fluidigm & QPCR | Rasgrp1 | 619 | GTT CAT CCA TGT GGC TCA GA | 620 | TCA CAG CCA TCA GCG TGT |
| Fluidigm & QPCR | Satb1 | 621 | ATG GCG TTG CTG TCT CTA GG | 622 | CTT CCC AAC CTG GAT GAG C |
| Fluidigm & QPCR | Stat1 | 623 | GCA GCA CAA CAT ACG GAA AA | 624 | TCT GTA CGG GAT CTT CTT GGA |
| Fluidigm & QPCR | Tgif1 | 625 | CTC AGA GCA AGA GAA AGC ACT G | 626 | CGT TGA TGA ACC AGT TAG AGA CC |
| Fluidigm & QPCR | HMBS | 627 | TCC CTG AAG GAT GTG CCT AC | 628 | AAG GGT TTT CCC GTT TGC |
| Fluidigm & QPCR | B4galt1 | 629 | GCC ATC AAT GGA TTC CCT AA | 630 | CAT TTG GAC GTG ATA TAG ACA TGC |
| Fluidigm & QPCR | Foxo1 | 631 | CTT CAA GGA TAA GGG CGA CA | 632 | GAC AGA TTG TGG CGA ATT GA |
| Fluidigm & QPCR | Il16 | 633 | CCA CAG AAG GAG AGT CAA GGA | 634 | GTG TTT TCC TGG GGA TGC T |
| Fluidigm & QPCR | Irf1 | 635 | GAG CTG GGC CAT TCA CAC | 636 | TCC ATG TCT TGG GAT CTG G |
| Fluidigm & QPCR | Lmnb1 | 637 | GGG AAG TTT ATT CGC TTG AAG A | 638 | ATC TCC CAG CCT CCC ATT |
| Fluidigm & QPCR | Myd88 | 639 | TGG CCT TGT TAG ACC GTG A | 640 | AAG TAT TTC TGG CAG TCC TCC TC |
| Fluidigm & QPCR | Pmepa1 | 641 | GCT CTT TGT TCC CCA GCA T | 642 | CTA CCA CGA TGA CCA CGA TTT |
| Fluidigm & QPCR | Rkpj | 643 | AGT CTT ACG GAA ATG AAA AAC GA | 644 | CCA ACC ACT GCC CAT AAG AT |

TABLE S6.1-continued

Primer Sequences

| Assay | Gene Name | SEQ ID NO: | Forward Sequence | SEQ ID NO: | Reverse Sequence |
|---|---|---|---|---|---|
| Fluidigm & QPCR | Sema4d | 645 | GAC CCT GGT AAC ACC ACA GG | 646 | TCA CGA CGT CAT GCC AAG |
| Fluidigm & QPCR | Stat3 | 647 | GGA AAT AAC GGT GAA GGT GCT | 648 | CAT GTC AAA CGT GAG CGA CT |
| Fluidigm & QPCR | Timp2 | 649 | CGT TTT GCA ATG CAG ACG TA | 650 | GGA ATC CAC CTC CTT CTC G |
| Fluidigm & QPCR | HPRT | 651 | TCC TCC TCA GAC CGC TTT T | 652 | CCT GGT TCA TCA TCG CTA ATC |
| Fluidigm & QPCR | Cand1 | 653 | GAA CTT CCG CCA GCT TCC | 654 | CTG GTA AGG CGT CCA GTA ATC T |
| Fluidigm & QPCR | Foxp1 | 655 | CTG CAC ACC TCT CAA TGC AG | 656 | GGA AGC GGT AGT GTA CAG AGG T |
| Fluidigm & QPCR | Il17ra | 657 | TGG GAT CTG TCA TCG TGC T | 658 | ATC ACC ATG TTT CTC TTG ATC G |
| Fluidigm & QPCR | Irf4 | 659 | ACA GCA CCT TAT GGC TCT CTG | 660 | ATG GGG TGG CAT CAT GTA GT |
| Fluidigm & QPCR | LOC100048299 /// Max | 661 | CCA GCA AGA CAT TGA TGA CC | 662 | GAT CTT GCC TTC TCC AGT GC |
| Fluidigm & QPCR | Nampt | 663 | CCT GTT CCA GGC TAT TCT GTT C | 664 | TCA TGG TCT TTC CCC AAG |
| Fluidigm & QPCR | Pml | 665 | AGG AAC CCT CCG AAG ACT ATG | 666 | TTC CTC CTG TAT GGC TTG CT |
| Fluidigm & QPCR | Rel | 667 | TTG CAG AGA TGG ATA CTA TGA AGC | 668 | CAC CGA ATA CCC AAA TTT TGA A |
| Fluidigm & QPCR | Sema7a | 669 | GGA GAG ACC TTC CAT GTG CT | 670 | AAG ACA AGC TAT GGT CCT GG T |
| Fluidigm & QPCR | Stat5a | 671 | AAG ATC AAG CTG GGG CAC TA | 672 | CAT GGG ACA GCG GTC ATA C |
| Fluidigm & QPCR | Trim25 | 673 | CCC TAC GAC CCT AAG TCA AGC | 674 | TGT GGC TGT GCA TGA TAG TG |
| Fluidigm & QPCR | pgk1 | 675 | TAC CTG CTG GCT GGA TGG | 676 | CAC AGC CTC GGC ATA TTT CT |
| Fluidigm & QPCR | Casp6 | 677 | TGA AAT GCT TTA ACG ACC TCA G | 678 | GTG GCT GAA GTC GAC ACC T |
| Fluidigm & QPCR | Hif1a | 679 | GCA CTA GAC AAA GTT CAC CTG AGA | 680 | CGC TAT CCA CAT CAA AGC AA |
| Fluidigm & QPCR | Il21r | 681 | GGA GTG ACC CCG TCA TCT T | 682 | AGG AGC AGC AGC ATG TGA G |
| Fluidigm & QPCR | Irf8 | 683 | GAG CCA GAT CCT CCC TGA CT | 684 | GGC ATA TCC GGT CAC CAG T |
| Fluidigm & QPCR | Lsp1 | 685 | CAA AGC GAG AGA CCA GAG GA | 686 | AAG TGG ACT TTG GCT TGG TG |
| Fluidigm & QPCR | Nfatc2 | 687 | GAT CGT AGG CAA CAC CAA GG | 688 | CTT CAG GAT GCC TGC ACA |
| Fluidigm & QPCR | Pou2af1 | 689 | CAT GCT CFG GCA AAA ATC C | 690 | ACT CGA ACA CCC TGG TAT GG |
| Fluidigm & QPCR | Rela | 691 | CCC AGA CCG CAG TAT CCA T | 692 | GCT CCA GGT CTC GCT TCT T |

TABLE S6.1-continued

Primer Sequences

| Assay | Gene Name | SEQ ID NO: | Forward Sequence | SEQ ID NO: | Reverse Sequence |
|---|---|---|---|---|---|
| Fluidigm & QPCR | Skap2 | 693 | GTG CTC CCG ACA AAC GTA TC | 694 | CCC ATT CCT CAG CAT CTT TG |
| Fluidigm & QPCR | Stat5b | 695 | CGA GCT GGT CTT TCA AGT CA | 696 | CTG GCT GCC GTG AAC AAT |
| Fluidigm & QPCR | Xbp1 | 697 | TGA CGA GGT TCC AGA GGT G | 698 | TGC AGA GGT GCA CAT AGT CTG |
| Fluidigm & QPCR | PPIA | 699 | ACG CCA CTG TCG CTT TTC | 700 | GCA AAC AGC TCG AAG GAG AC |
| Fluidigm & QPCR | Cd2 | 701 | TGG GAT GAC TAG GCT GGA GA | 702 | AGT GGA TCA TGG GCT TTG AG |
| Fluidigm & QPCR | Icos | 703 | CGG CAG TCA ACA CAA ACA A | 704 | TCA GGG GAA CTA GTC CAT GC |
| Fluidigm & QPCR | Il24 | 705 | AGA ACC AGC CAC CTT CAC AC | 706 | GTG TTG AAG AAA GGG CCA GT |
| Fluidigm & QPCR | Khdrbs1 | 707 | CTC GAC CCG TCC TTC ACT C | 708 | TTG ACT CTC CCT TCT GAA TCT TCT |
| Fluidigm & QPCR | Lta | 709 | TCC CTC AGA AGC ACT TGA CC | 710 | GAG TTC TGC TTG CTG GGG TA |
| Fluidigm & QPCR | Nfatc3 | 711 | GGG GCA GTG AAA GCC TCT | 712 | GCT TTT CAC TAT AGC CCA GGA G |
| Fluidigm & QPCR | Prf1 | 713 | AAT ATC AAT AAC GAC TGG CGT GT | 714 | CAT GTT TGC CTC TGG CCT A |
| Fluidigm & QPCR | Rora | 715 | TTA CGT GTG AAG GCT GCA AG | 716 | GGA GTA GGT GGC ATT GCT CT |
| Fluidigm & QPCR | Ski | 717 | GAG AAA GAG ACG TCC CCA CA | 718 | TCA AAG CTC TTG TAG GAG TAG AAG C |
| Fluidigm & QPCR | Stat6 | 719 | TCT CCA CGA GCT TCA CAT TG | 720 | GAC CAC CAA GGG CAG AGA C |
| Fluidigm & QPCR | Xrcc5 | 721 | GAA GAT CAC ATC AGC ATC TCC A | 722 | CAG GAT TCA CAC TTC CAA CCT |
| Fluidigm & QPCR | RPL13A | 723 | ATC CCT CCA CCC TAT GAC AA | 724 | GCC CCA GGT AAG CAA ACT T |
| Fluidigm & QPCR | Cd24a | 725 | ATC CCT CCA CCC TAT GAC AA | 726 | GCC CCA GGT AAG CAA ACT T |
| Fluidigm & QPCR | Id2 | 727 | GAC AGA ACC AGG CGT CCA | 728 | AGC TCA GAA GGG AAT TCA GAT G |
| Fluidigm & QPCR | Il2ra | 729 | TGT GCT CAC AAT GGA GTA TAA GG | 730 | CTC AGG AGG AGG ATG CTG AT |
| Fluidigm & QPCR | Klf10 | 731 | AGC CAA CCA TGC TCA ACT TC | 732 | GGC TTT TCA GAA ATT AGT TCC ATT |
| Fluidigm & QPCR | Maf | 733 | TTC CTC TCC CGA ATT TTT CA | 734 | CCA CGG AGC ATT TAA CAA GG |
| Fluidigm & QPCR | Nfe2l2 | 735 | CAT GAT GGA CTT GGA GTT GC | 736 | CCT CCA AAG GAT GTC AAT CAA |
| Fluidigm & QPCR | Prkca | 737 | ACA GAC TTC AAC TTC CTC ATG GT | 738 | CTG TCA GCA GCA TC ACC TT |
| Fluidigm & QPCR | Runx1 | 739 | CTC CGT GCT ACC CAC TCA CT | 740 | ATG ACG TGA CCA GA GTG C |
| Fluidigm & QPCR | Slc2a1 | 741 | ATG GAT CCC AGC AGC AAG | 742 | CCA GTG TTA TAG CCG AAC TGC |

TABLE S6.1-continued

Primer Sequences

| Assay | Gene Name | SEQ ID NO: | Forward Sequence | SEQ ID NO: | Reverse Sequence |
|---|---|---|---|---|---|
| Fluidigm & QPCR | Sufu | 743 | TGT TGG AGG ACT TAG AAG ATC TAA CC | 744 | AGG CCA GCT GTA CTC TTT GG |
| Fluidigm & QPCR | Zeb1 | 745 | GCC AGC AGT CAT GAT GAA AA | 746 | TAT CAC AAT ACG GGC AGG TG |
| Fluidigm & QPCR | Ywhaz | 747 | AAC AGC TTT CGA TGA AGC CAT | 748 | TGG GTA TCC GAT GTC CAC AAT |
| Fluidigm & QPCR | Cd4 | 749 | ACA CAC CTG TGC AAG AAG CA | 750 | GCT CTT GTT GGT TGG GAA TC |
| Fluidigm & QPCR | Ifi35 | 751 | TGA GAG CCA TGT CTG TGA CC | 752 | CTC CTG CAG CCT CAT CTT G |
| Fluidigm & QPCR | Il4ra | 753 | GAG TGG AGT CCT AGC ATC ACG | 754 | CAG TGG AAG GCG CTG TAT C |
| Fluidigm & QPCR | Klf6 | 755 | TCC CAC TTG AAA GCA CAT CA | 756 | ACT TCT TGC AAA ACG CCA CT |
| Fluidigm & QPCR | Mina | 757 | GAA TCT GAG GAC CGG ATC G | 758 | TGG GAA AGT ACA ACA AAT CTC CA |
| Fluidigm & QPCR | Notch1 | 759 | CTG GAC CCC ATG GAC ATC | 760 | AGG ATG ACT GCA CAC ATT GC |
| Fluidigm & QPCR | Prkd3 | 761 | TGG CTA CCA GTA TCT CCG TGT | 762 | TGG TAA ACG CTG CTG ATG TC |
| Fluidigm & QPCR | Runx3 | 763 | TTC AAC GAC CTT CGA TTC GT | 764 | TTG GTG AAC ACG GTG ATT GT |
| Fluidigm & QPCR | Smarca4 | 765 | AGA GAA GCA GTG GCT CAA GG | 766 | ATT TCT TCT GCC GGA CCT C |
| Fluidigm & QPCR | Tap1 | 767 | TTC CCT CAG GGC TAT GAC AC | 768 | CTG TCG CTG ACC TCC TGA C |
| Fluidigm & QPCR | Zfp36l1 | 769 | TTC ACG ACA CAC CAG ATC CT | 770 | TGA GCA TCT TGT TAC CCT TGC |
| Fluidigm & QPCR | B2M | 771 | TTC TGG TGC TTG TCT CAC TGA | 772 | CAG TAT GTT CGG CTT CCC ATT C |
| Fluidigm & QPCR | 1700697 N02Rik | 773 | CCA GAG CTT GAC CAT CAT CAG | 774 | TCC TTT ACA AAT CAT ACA GGA CTG G |
| Fluidigm & QPCR | Armcx2 | 775 | CCC TTC ACC CTG GTC CTT | 776 | CTT CCT CGA ATT AGG CCA GA |
| Fluidigm & QPCR | Ccr4 | 777 | CTC AGG ATC ACT TTC AGA AGA GC | 778 | GGC ATT CAT CTT TGG AAT CG |
| Fluidigm & QPCR | Cebpb | 779 | TGA TGC AAT CCG GAT CAA | 780 | CAC GTG TGT TGC GTC AGT C |
| Fluidigm & QPCR | Emp1 | 781 | AAG AGA GGA CCA GAC CAG CA | 782 | CTT TTT GGT GAC TTC TGA GTA GAG AAT |
| Fluidigm & QPCR | Ier3 | 783 | CAG CCG AAG GGT GCT CTA C | 784 | AAA TCT GGC AGA AGA TGA TGG |
| Fluidigm & QPCR | Itga3 | 785 | AGG GGG AGA CCA GAG TTC C | 786 | GCC ATT GGA GCA GGT CAA |
| Fluidigm & QPCR | Lrrfip1 | 787 | AGT CTC AGC GGC AAT ACG AG | 788 | GCA AAC TGG AAC TGC AGG AT |
| Fluidigm & QPCR | Nfkbiz | 789 | CAG CTG GGG AAG TCA TTT TT | 790 | GGC AAC AGC AAT ATG GAG AAA |

TABLE S6.1-continued

Primer Sequences

| Assay | Gene Name | SEQ ID NO: | Forward Sequence | SEQ ID NO: | Reverse Sequence |
|---|---|---|---|---|---|
| Fluidigm & QPCR | Ptprj | 791 | CCA ATG AGA CCT TGA ACA AAA CT | 792 | GTA GGA GGC AGT GCC ATT TG |
| Fluidigm & QPCR | Stat4 | 793 | CGG CAT CTG CTA GCT CAG T | 794 | TGC CAT AGT TTC ATT GTT AGA AGC |
| Fluidigm & QPCR | GAPDH | 795 | GGC AAA TTC AAC GGC ACA GT | 796 | AGA TGG TGA TGG GCT TCC C |
| Fluidigm & QPCR | Acvr1b | 797 | AGA GGG TGG GGA CCA AAC | 798 | TGC TTC ATG TTG ATT GTC TCG |
| Fluidigm & QPCR | Arnt1 | 799 | GCC CCA CCG ACC TAC TCT | 800 | TGT CTG TGT CCA TAC TTT CTT GG |
| Fluidigm & QPCR | Ccr8 | 801 | AGA AGA AAG GCT CGC TCA GA | 802 | GGC TCC ATC GTG TAA TCC AT |
| Fluidigm & QPCR | Chd7 | 803 | GAG GAC GAA GAC CCA GGT G | 804 | CAG TGT ATC GCT TCC TCT TCA C |
| Fluidigm & QPCR | Fas | 805 | TGC AGA CAT GCT GTG GAT CT | 806 | CTT AAC TGT GAG CCA GCA AGC |
| Fluidigm & QPCR | Il17f | 807 | CCC AGG AAG ACA TAC TTA GAA GAA A | 808 | CAA CAG TAG CAA AGA CTT GAC CA |
| Fluidigm & QPCR | Itgb1 | 809 | TGG CAA CAA TGA AGC TAT CG | 810 | ATG TCG GGA CCA GTA GGA CA |
| Fluidigm & QPCR | Map3k5 | 811 | CAA GAA ATT AGG CAC CTG AAG C | 812 | ACA CAG GAA ACC CAG GGA TA |
| Fluidigm & QPCR | Notch2 | 813 | TGC CTG TTT GAC AAC TTT GAG T | 814 | GTG GTC TGC ACA GTA TTT GTC AT |
| Fluidigm & QPCR | Rorc | 815 | ACC TCT TTT CAC GGG AGG A | 816 | TCC CAC ATC TCC CAC ATT G |
| Fluidigm & QPCR | Tgfbr1 | 817 | CAG CTC CTC ATC GTG TTG G | 818 | CAG AGG TGG CAG AAA CAC TG |
| Fluidigm & QPCR | HMBS | 819 | TCC CTG AAG GAT GTG CCT AC | 820 | AAG GGT TTT CCC GTT TGC |
| Fluidigm & QPCR | Aes | 821 | TGC AAG CGC AGT ATC ACA G | 822 | TGA CGT AAT GCC TCT GCA TC |
| Fluidigm & QPCR | Batf | 823 | AGA AAG CCG ACA CCC TTC A | 824 | CGG AGA GCT GCG TTC TGT |
| Fluidigm & QPCR | Cd247 | 825 | CCA GAG ATG GGA GGC AAA C | 826 | AGT GCA TTG TAT ACG CCT TCC |
| Fluidigm & QPCR | Clcf1 | 827 | TAT GAC CTC ACC CGC TAG CT | 828 | GGG CCC CAG GTA GTT CAG |
| Fluidigm & QPCR | Fip1l1 | 829 | CGT TTC CCT ATG GCA ATG TC | 830 | CCC ACT GCT TGG TGG TGT |
| Fluidigm & QPCR | Il1r1 | 831 | TTG ACA TAG TGC TTT GGT ACA GG | 832 | TCG TAT GTC TTT CCA TCT GAA GC |
| Fluidigm & QPCR | Jun | 833 | CCA GAA GAT GGT GTG GTG TTT | 834 | CTG ACC CTC TCC CCT TGC |
| Fluidigm & QPCR | Mbnl3 | 835 | GCC AAG AGT TTG CCA TGT G | 836 | CTT GCA GTT CTC ACG AGT GC |
| Fluidigm & QPCR | Nr3c1 | 837 | TGA CGT GTG GAA GCT GTA AAG T | 838 | CAT TTC TTC CAG CAC AAA GGT |
| Fluidigm & QPCR | Rpp14 | 839 | GGA ACG CGG TTA TTC CAG T | 840 | CAT CTT CCA ACA TGG ACA CCT |

TABLE S6.1-continued

Primer Sequences

| Assay | Gene Name | SEQ ID NO: | Forward Sequence | SEQ ID NO: | Reverse Sequence |
|---|---|---|---|---|---|
| Fluidigm & QPCR | Tmem126a | 841 | TAG CGA AGG TTG CGG TAG AC | 842 | GGT TTA TGA CTT TCC ATC TTG GAC |
| Fluidigm & QPCR | HPRT | 843 | TCC TCC TCA GAC CGC TTT T | 844 | CCT GGT TCA TCA TCG CTA ATC |
| Fluidigm & QPCR | Ahr | 845 | TGC ACA AGG AGT GGA CGA | 846 | AGG AAG CTG GTC TGG GGT AT |
| Fluidigm & QPCR | BC021614 | 847 | CAC ATT CAA GGC TTC CTG TTT | 848 | GTA TTG GAT TGG TAC AGG GTG AG |
| Fluidigm & QPCR | Cd274 | 849 | CCA TCC TGT TGT TCC TCA TTG | 850 | TCC ACA TCT AGC ATT CTC ACT TG |
| Fluidigm & QPCR | Cmtm7 | 851 | TCG CCT CCA TAG TGA TAG CC | 852 | CTC GCT AGG CAG AGG AAG C |
| Fluidigm & QPCR | Flna | 853 | GCA AGT GCA CAG TCA CAG GT | 854 | TTG CCT GCT GCT TTT GTG T |
| Fluidigm & QPCR | Il2 | 855 | GCT GTT GAT GGA CCT ACA GGA | 856 | TTC AAT TCT GTG GCC TGC TT |
| Fluidigm & QPCR | Lad1 | 857 | CTA CAG CAG TTC CCT CAA ACG | 858 | TGT CTT TCC TGG GGC TCA T |
| Fluidigm & QPCR | Mta3 | 859 | CTT TGT CGT GTA TCA TTG GGT ATT | 860 | TTG GTA GCT GGA GTT TGC AG |
| Fluidigm & QPCR | Peci | 861 | AAC GGT GCT GTG TTA CTG AGG | 862 | CAG CTG GGC CAT TTA CTA CC |
| Fluidigm & QPCR | Sap30 | 863 | CGG TGC AGT GTC AGG TTC | 864 | CTC CCG CAA ACA ACA GAG TT |
| Fluidigm & QPCR | Tnfrsf12a | 865 | CCG CCG GAG AGA AAA GTT | 866 | CTG GAT CAG TGC CAC ACC T |
| Fluidigm & QPCR | Pgk1 | 867 | TAG CTG CTG GCT GGA TGG | 868 | CAC AGC TCG GCA TAT TTC T |
| Fluidigm & QPCR | AI451617 /// Trim30 | 869 | CAA CTG CAG AGT TTG GAG GA | 870 | TGT GTC TGC CTG TCC TGA CT |
| Fluidigm & QPCR | Bcl11b | 871 | TCC CAG AGG GAA CTC ATC AC | 872 | CCA GAC CCT CGT CTT CCT C |
| Fluidigm & QPCR | Cd28 | 873 | CTG GCC CTC ATC AGA ACA AT | 874 | GGC GAC TGC TTT ACC AAA ATC |
| Fluidigm & QPCR | Ctla2b | 875 | GCC TCC TCT GTC AGT TGC TC | 876 | AAG CAG AGG ATG AGC AGG AA |
| Fluidigm & QPCR | Foxp3 | 877 | TCA GGA GCC CAC CAG TAC A | 878 | TCT GAA GGC AGA GTC AGG AGA |
| Fluidigm & QPCR | Il21 | 879 | GAC ATT CAT CAT TGA CCT CGT G | 880 | TCA CAG GAA GGG CAT TTA GC |
| Fluidigm & QPCR | Lif | 881 | AAA CGG CCT GCA TCT AAG G | 882 | AGC AGC AGT AAG GGC ACA AT |
| Fluidigm & QPCR | Myst4 | 883 | GCA ACA AAG GGC AGC AAG | 884 | AGA CAT CTT TAG GAA ACC AAG ACC |
| Fluidigm & QPCR | Peli2 | 885 | TAC ACC TTG CGA GAG ACC AG | 886 | GGA CGT GGG TCT CAC TTT CC |
| Fluidigm & QPCR | Sgk1 | 887 | GAT GCC AGC AAC ACC CTA TG | 888 | TTG ATT TGT TCA GAG GAC TT G |

TABLE S6.1-continued

Primer Sequences

| Assay | Gene Name | SEQ ID NO: | Forward Sequence | SEQ ID NO: | Reverse Sequence |
|---|---|---|---|---|---|
| Fluidigm & QPCR | Tnfrsf25 | 889 | CCC TGG CTT ATC CCA GAC T | 890 | AGA TGC CAG AGG AGT TCC AA |
| Fluidigm & QPCR | PPIA | 891 | ACQ CCA CFG TCG CTT TTC | 892 | GCA AAC AGC TCG AAG GAG AC |
| Fluidigm & QPCR | Aqp3 | 893 | CTG GGG ACC CTC ATC CTT | 894 | TGG TGA GGA AGC CAC CAT |
| Fluidigm & QPCR | Bcl3 | 895 | GAA CAA CAG CCT GAA CAT GG | 896 | TCT GAG CGT TCA CGT TGG |
| Fluidigm & QPCR | Cd74 | 897 | GCC CTA GAG AGC CAG AAA GG | 898 | TGG TAC AGG AAG TAA GCA GTG G |
| Fluidigm & QPCR | Ctsw | 899 | GGT TCA ACC GGA GTT ACT GG | 900 | TGG GCA AAG ATG CTC AGA C |
| Fluidigm & QPCR | Gem | 901 | GAC AGC ATG GAC AGC GAC T | 902 | ACG ACC AGG GTA CGC TCA TA |
| Fluidigm & QPCR | Il27ra | 903 | ACT TCC GOT ACA AGG AAT GC | 904 | ACA GGA GTC AGC CCA TCT GT |
| Fluidigm & QPCR | Litaf | 905 | TCC TGT GGC AGT CTG TGT CT | 906 | CTA CGC AGA ACG GGA TGA AG |
| Fluidigm & QPCR | Ncf1 | 907 | GGA CAC CTT CAT TCG CCA TA | 908 | CTG CCA CTT AAC CAG GAA CAT |
| Fluidigm & QPCR | Plekhf2 | 909 | GTC GGC GAC TAG GAG GAC T | 910 | TCC ACC ATC TTT TGC TAA TAA CC |
| Fluidigm & QPCR | Smad3 | 911 | TCA AGA AGA CGG GGC AGT T | 912 | CCG ACC ATC AGT GAC CT |
| Fluidigm & QPCR | Tnfsf8 | 913 | GAG GAT CTC TTC TGT ACC CTG AAA | 914 | TTG TTG AGA TGC TTT GAC ACT TG |
| Fluidigm & QPCR | RPL13A | 915 | ATC OCT CCA CCC TAT GAC AA | 916 | GCC CCA GGT AAG CAA ACT T |
| Fluidigm & QPCR | Arhgef3 | 917 | GTT GOT CCC ATC CTC GTG | 918 | GAT GCT GCA GTA GCT GTC CG |
| Fluidigm & QPCR | Bcl6 | 919 | CTG CAG ATG GAG CAT GTT GT | 920 | GCC ATT TCT GCT TCA CTG G |
| Fluidigm & QPCR | Cd86 | 921 | GAA GCC GAA TCA GCC TAG C | 922 | CAG CGT TAC TAT CCC GCT CT |
| Fluidigm & QPCR | Cxcr4 | 923 | TGC AAC CGA TCA GTG TGA GT | 924 | GGG CAG GAA GAT CCT ATT GA |
| Fluidigm & QPCR | Glipr1 | 925 | TCC CCT AAT GGA GCA AAT TTT A | 926 | TTA TAT GGC CAC GTT GGG TAA |
| Fluidigm & QPCR | Il2rb | 927 | AGC ATG GGG GAG ACC TTC | 928 | GGG GCT GAA GAA GGA CAA G |
| Fluidigm & QPCR | LOC100045833 /// Ly6c1/// Ly6c2 | 929 | TCT TGT GGC CCT ACT GTG TG | 930 | GCA ATG CAG AAT CCA TCA GA |
| Fluidigm & QPCR | Ncoa1 | 931 | TGG CAT GAA CAT GAG GTC AG | 932 | GCC AAC ATC TGA GCA TTC AA |
| Fluidigm & QPCR | Prc1 | 933 | TGG AAA CTT TTC CTA GAG TTT GAG A | 934 | TTT CCC CCT CGG TTT GTA A |
| Fluidigm & QPCR | Smox | 935 | GAT GGT TCG ACA GTT CAC AGG | 936 | GGA ACC CCG GAA GTA TGG |
| Fluidigm & QPCR | Ubiad1 | 937 | GTC TGG CTC CTT TCT CTA CAC AG | 938 | ACT GAT GAG GAT GAC GAG GTC |

TABLE S6.1-continued

Primer Sequences

| Assay | Gene Name | SEQ ID NO: | Forward Sequence | SEQ ID NO: | Reverse Sequence |
|---|---|---|---|---|---|
| Fluidigm & QPCR | Ywhaz | 939 | AAC AGC TTT CGA TGA AGC CAT | 940 | TGG GTA TCC GAT GTC CAC AAT |
| Fluidigm & QPCR | Arid5a | 941 | CAG AGC AGG AGC CAG AGC | 942 | GCC AAG TTC ATC ATA CAC GTT C |
| Fluidigm & QPCR | Casp3 | 943 | GAG GCT GAC TTC CTG TAT GCT T | 944 | AAC CAC GAC CCG TCC TTT |
| Fluidigm & QPCR | Cd9 | 945 | GAT ATT CGC CAT TGA GAT AGC C | 946 | TGG TAG GTG TCC TTG TAA AAC TCC |
| Fluidigm & QPCR | Elk3 | 947 | GAG GGG CTT TGA GAG TGC T | 948 | TGT CCT GTG TGC CTG TCT TG |
| Fluidigm & QPCR | Golga3 | 949 | ACA GAA AGT GGC AGA TGC AG | 950 | TCT CGC TGG AAC AAT GTC AG |
| Fluidigm & QPCR | Irf9 | 951 | TGA GGC CAC CAT TAG AGA GG | 952 | AGC AGC AGC GAG TAG TCT GA |
| Fluidigm & QPCR | LOC100046232 /// Nfil3 | 953 | GGA CCA GGG AGC AGA ACC | 954 | GTC CGG CAC AGG GTA AAT C |
| Fluidigm & QPCR | Nfkbie | 955 | CCT GGA CCT CCA ACT GAA GA | 956 | TCC TCT GCA ATG TGG CAA T |
| Fluidigm & QPCR | Prnp | 957 | TCC AAT TTA GGA GAG CCA AGC | 958 | GCC GAC ATC AGT CCA CAT AG |
| Fluidigm & QPCR | Stat2 | 959 | GGA ACA GCT GGA ACA GTG GT | 960 | GTA GCT GCC GAA GGT GGA |
| Fluidigm & QPCR | Zfp161 | 961 | GGA GTG AGG AAG TTC GGA AA | 962 | TGG ATT CGG AGT CTC CAT |
| Fluidigm & QPCR | B2M | 963 | TTC TGG TGC TTG TCT CAC TGA | 964 | CAG TAT GTT CGG CTT CCC ATT C |
| Fluidigm & QPCR | Abcg2 | 965 | GCC TTG GAG TAC TTT GCA TCA | 966 | AAA TCC GCA GGG TTG TTG TA |
| Fluidigm & QPCR | Ccr5 | 967 | GAG ACA TCC GTT CCC CCT AC | 968 | GTC GGA ACT GAC CCT TGA AA |
| Fluidigm & QPCR | Cxcr3 | 969 | AGO CAG CAC GAG ACC TGA | 970 | GGC ATC TAG CAC TTG ACG TTC |
| Fluidigm & QPCR | Fli1 | 971 | AGA CCA TGG GCA AGA ACA CT | 972 | GCC CCA GGA TCT GAT AAG G |
| Fluidigm & QPCR | Gzmb | 973 | GCT GCT CAC TGT GAA GGA AGT | 974 | TGG GGA ATG CAT TTT ACC AT |
| Fluidigm & QPCR | Il10ra | 975 | GCT CCC ATT CCT CGT CAC | 976 | AAG GCT TGG CAG TTC TGT |
| Fluidigm & QPCR | Il3 | 977 | TAC ATC TGC GAA TGA CTC TGC | 978 | GGC TGA GGT GGT CTA GAG GTT |
| Fluidigm & QPCR | Klrd1 | 979 | GGA TTG GAA TGC ATT ATA GTG AAA A | 980 | TGC TCT GGC CTG ATA ACT GAG |
| Fluidigm & QPCR | Plac8 | 981 | CAG ACC AGC CTG TGT GAT TG | 982 | CCA AGA CAA GTG AAA CAA AAG GT |
| Fluidigm & QPCR | Sertad1 | 983 | TCC CTC TTC GTT CTG ATT GG | 984 | GCT TGC GCT TCA GAC CTT T |
| Fluidigm & QPCR | Tnfsf9 | 985 | CGC CAA GCT ACT GGC TAA AA | 986 | CGT ACC TCA GAC CTT GAG ATA GGT |
| Fluidigm & QPCR | GAPDH | 987 | GGC AAA TTC AAC GGC ACA GT | 988 | AGA TGG TGA TGG GCT TCC C |

TABLE S6.1-continued

Primer Sequences

| Assay | Gene Name | SEQ ID NO: | Forward Sequence | SEQ ID NO: | Reverse Sequence |
|---|---|---|---|---|---|
| Fluidigm & QPCR | Acvr2a | 989 | CCC TCC TGT ACT TGT TCC TAC TCA | 990 | GCA ATG GCT TCA ACC CTA GT |
| Fluidigm & QPCR | Ccr6 | 991 | TTC GCC ACT CTA ATC AGT AGG AC | 992 | TCT GGT GTA GAA AGG GAA GTG G |
| Fluidigm & QPCR | Cxcr5 | 993 | GAA TGA CGA CAG AGG TTC CTG | 994 | GCC CAG GTT GGC TTC TTA T |
| Fluidigm & QPCR | Foxm1 | 995 | ACT TTA AGC ACA TTG CCA AGC | 996 | GGA GAG AAA GGT TGT GAC GAA |
| Fluidigm & QPCR | Hip1r | 997 | AGT GAG CAA GCT GGA CGA C | 998 | GAA GCC AGG TAC TGG GTG TG |
| Fluidigm & QPCR | Il12rb1 | 999 | CGC AGC CGA GTA ATG TAC AAG | 1000 | AAC GGG AAA TCT GCA CCT C |
| Fluidigm & QPCR | Il9 | 1001 | GCC TCT GTT TTG CTC TTC AGT T | 1002 | GCA TTT TGA CGG TGG ATC A |
| Fluidigm & QPCR | LOC100046643 /// Spry1 | 1003 | TAG GTC AGA TCG GGT CAT CC | 1004 | GTG GGG TCC TCT TTC AAG G |
| Fluidigm & QPCR | Prdm1 | 1005 | TGC GGA GAG GCT CCA CTA | 1006 | TGG GTT GCT TTC CGT TTG |
| Fluidigm & QPCR | Socs3 | 1007 | ATT TCG CTT CGG GAC TAG C | 1008 | AAC TTG CTG TGG GTG ACC AT |
| Fluidigm & QPCR | Trim24 | 1009 | ATC CAG CAG CCT TCC ATC T | 1010 | GGC TTA GGG CTG TGA TTC TG |
| Fluidigm & QPCR | HMBS | 1011 | TCC CTG AAG GAT GTG CCT AC | 1012 | AAG GGT TTT CCC GTT TGC |
| Fluidigm & QPCR | Anxa4 | 1013 | TGA TGC TCT TAT GAA GCA GGA C | 1014 | CGT CTG TCC CCA TCT CTT |
| Fluidigm & QPCR | Cd51 | 1015 | GAG GAC ACA TGG ATG AAT GT | 1016 | ACC CTT GTG TAG CAC CTC CA |
| Fluidigm & QPCR | Daxx | 1017 | CAG GCC ACT GGT CTC TCC | 1018 | TCC GTC TTA CAC ACT TCA AGG A |
| Fluidigm & QPCR | Gap43 | 1019 | CGG AGA CTG CAG AAA GCA G | 1020 | GGT TTG GCT TCG TCT ACA GC |
| Fluidigm & QPCR | Id3 | 1021 | GAG GAG CTT TTG CCA CTG AC | 1022 | GCT CAT CCA TGC CCT CAG |
| Fluidigm & QPCR | Il12rb2 | 1023 | TGT GGG GTG GAG ATC TCA GT | 1024 | TCT CCT TCC TGG ACA CAT GA |
| Fluidigm & QPCR | Inhba | 1025 | ATC ATC ACC TTT GCC GAG TC | 1028 | TCA CTG CCT TCC TTG GAA AT |
| Fluidigm & QPCR | Maff | 1027 | GAC AAG CAC GCA CTG AGC | 1026 | CAT TTT CGC AGA AGA TGA CCT |
| Fluidigm & QPCR | Prickle1 | 1029 | ATG GAT TCT TTG GCG TTG TC | 1030 | TGA CGG TCT TGG CTT GCT |
| Fluidigm & QPCR | Spp1 | 1031 | GGA GGA AAC CAG CCA AGG | 1032 | TGC CAG AAT CAG TCA CTT TCA C |
| Fluidigm & QPCR | Trps1 | 1033 | ACT CTG CAA ACA ACA GAA GAC G | 1034 | TCT TTT CCG GAC CAT ATC TGT |
| Fluidigm & QPCR | HPRT | 1035 | TCC TCC TCA GAC CGC TTT T | 1036 | CCT GGT TCA TCA TCG CTA ATC |
| Fluidigm & QPCR | Bcl2l11 | 1037 | GGA GAC GAG TTC AAC GAA ACT T | 1038 | AAC AGT TGT AAG ATA ACC ATT TGA GG |

TABLE S6.1-continued

Primer Sequences

| Assay | Gene Name | SEQ ID NO: | Forward Sequence | SEQ ID NO: | Reverse Sequence |
|---|---|---|---|---|---|
| Fluidigm & QPCR | Cd80 | 1039 | TCG TCT TTC ACA ACT GTC TTC AG | 1040 | TTG CCA GTA GAT TCG GTC TTC |
| Fluidigm & QPCR | Dntt | 1041 | GAG CAG CAG CTC TTG CAT AA | 1042 | GAT GTC GCA GTA CAA AAG CAA C |
| Fluidigm & QPCR | Gata3 | 1043 | TTA TCA AGC CCA AGC GAA G | 1044 | TGG TGG TGG TCT GAC AGT TC |
| Fluidigm & QPCR | Ifih1 | 1045 | CTA TTA ACC GTG TTC AAA ACA TGA A | 1046 | CAC CTG CAA TTC CAA AAT CTT A |
| Fluidigm & QPCR | Il15ra | 1047 | CCA GTG CCA ACA GTA GTG ACA | 1048 | TTG GGA GAG AAA GCT TCT GG |
| Fluidigm & QPCR | Irf7 | 1049 | CTT CAG CAC TTT CTT CCG AGA | 1050 | TGT AGT GTG TGT ACC CTT GC |
| Fluidigm & QPCR | Mgl1 | 1051 | TCG GAA CAA GTC GGA GGT | 1052 | TCA GCA GCT GTA TGC CAA AG |
| Fluidigm & QPCR | Procr | 1053 | AGC GCA AGG AGA ACG TGT | 1054 | GGG TTC AGA GCC CTC CTC |
| Fluidigm & QPCR | Stard10 | 1055 | GAG CTG CGT CAT CAC CTA CC | 1056 | TGC AGG CCT TGT ACA TCT TCT |
| Fluidigm & QPCR | Tsc22d3 | 1057 | GGT GGC CCT AGA CAA CAA GA | 1058 | TCA GCA GCT CA CGA ATC TG |
| Fluidigm & QPCR | Pgk1 | 1059 | TAG CTG CTG GCT GGA TGG | 1060 | CAC AGC CTC GGC ATA TTT CT |
| Fluidigm & QPCR | Casp1 | 1061 | CCC ACT GCT GAT AGG GTG AC | 1062 | GCA TAG GTA CAT AAG AAT GAA CTG GA |
| Fluidigm & QPCR | Cd83 | 1063 | TGG TTC TGA AGG TGA CAG GA | 1064 | CAA CCA GAG AGA AGA GCA ACA C |
| Fluidigm & QPCR | Dpp4 | 1065 | CGG TAT CAT TTA GTA AAG AGG CAA A | 1066 | GTA GAG TGT AGA GGC GCA GAC C |
| Fluidigm & QPCR | Gfi1 | 1067 | TCC GAG TTC GAG GAC TTT TG | 1068 | GAG CGG CAC AGT GAC TTC T |
| Fluidigm & QPCR | Ifit1 | 1069 | TCT AAA CAG GGC CTT GCA G | 1070 | GCA GAG CCC TTT TGA TAA ATG T |
| Fluidigm & QPCR | Il17a | 1071 | CAG GGA GAG CTT CAT CTG TGT | 1072 | GCT GAG CTT TGA GGG ATG AT |
| Fluidigm & QPCR | Isg20 | 1073 | TTG GTG AAG CCA GGC TAG AG | 1074 | CTT CAG GGC ATT GAA GTC GT |
| Fluidigm & QPCR | Mt1 | 1075 | CAC CAG ATC TCG AAA TGG AC | 1076 | AGG AGC AGC AGC TCT TCT TG |
| Fluidigm & QPCR | Psmb9 | 1077 | CGC TCT GCT GAG ATG CTG | 1078 | CTC CAC TGC CAT GAT GGT T |
| Fluidigm & QPCR | Sult2b1 | 1079 | ACT TCC TGT TTA TCA CCT ATG AGG A | 1080 | AAC TCA CAG ATG CGT TGC AC |
| Fluidigm & QPCR | Vav3 | 1081 | TTA CAC GAA GAT GAG TGC AAA TG | 1082 | CAA CAC TGG ATA GGA CTT TAT TCA TC |
| Fluidigm & QPCR | PPIA | 1083 | ACG CCA CTG TCG CTT TTC | 1084 | GCA AAC AGC TCG AAG GAG AC |
| Fluidigm & QPCR | Casp4 | 1085 | TCC AGA CAT TCT TCA GTG TGG A | 1086 | TCT GGT TCC TCC ATT TCC AG |
| Fluidigm & QPCR | Creb3l2 | 1087 | CCA GCC AGC ATC CTC TGT | 1088 | AGC AGG TTC CTG GAT CTC AC |

TABLE S6.1-continued

Primer Sequences

| Assay | Gene Name | SEQ ID NO: | Forward Sequence | SEQ ID NO: | Reverse Sequence |
|---|---|---|---|---|---|
| Fluidigm & QPCR | Egr2 | 1089 | CTA CCC GGT GGA AGA CCT C | 1090 | AAT GTT GAT CAT GCC ATC TCC |
| Fluidigm & QPCR | Gja1 | 1091 | TCC TTT GAC TTC AGC CTC CA | 1092 | CCA TGT CTG GGC ACC TCT |
| Fluidigm & QPCR | Ifitm2 | 1093 | TGG TCT GGT CCC TGT TCA AT | 1094 | CTG GGC TCC AAC CAC ATC |
| Fluidigm & QPCR | Il1rn | 1095 | TGT GCC AAG TCT GGA GAT GA | 1096 | TTC TTT GTT CTT GCT CAG ATC AGT |
| Fluidigm & QPCR | Jak3 | 1097 | TGG AAG ACC CGG ATA GCA | 1098 | GTC TAG CGC TGG GTC CAC |
| Fluidigm & QPCR | Mxi1 | 1099 | CAA AGC CAA AGC ACA CAT CA | 1100 | AGT CGC CGC TTT AAA AAC CT |
| Fluidigm & QPCR | Rad51ap1 | 1101 | AAA GCA AGA GGC CCA ACT G | 1102 | TGC ATT GCT GCT AGA GTT CC |
| Fluidigm & QPCR | Tbx21 | 1103 | TCA ACC AGC ACC AGA CAG AG | 1104 | AAA CAT CCT GTA ATG GCT TGT G |
| Fluidigm & QPCR | Xcl1 | 1105 | GAG ACT TCT CCT CCT GAC TTT CC | 1106 | GGA CTT CAG TCC CCA CAC C |
| Fluidigm & QPCR | RPL13A | 1107 | ATC CCT CCA CCC TAT GAC AA | 1108 | GCC CCA GGT AAG CAA ACT T |
| Fluidigm & QPCR | Ccl20 | 1109 | AAC TGG GTG AAA AGG GCT GT | 1110 | GTC CAA TTC CAT CCC AAA AA |
| Fluidigm & QPCR | Csf2 | 1111 | GCA TGT AGA GGC CAT CAA AGA | 1112 | CGG GTC TGC ACA CAT GTT A |
| Fluidigm & QPCR | Errfi1 | 1113 | TGC TCA GGA GCA CCT AAC AAC | 1114 | TGG AGA TGG ACC ACA CTC TG |
| Fluidigm & QPCR | Gp49a /// Lilrb4 | 1115 | TGC ACT CCT GGT GTC ATT CC | 1116 | TGT GTG TTC TTC ACA GAA GCA TT |
| Fluidigm & QPCR | Ifng | 1117 | ATC TGG AGG AAC TGG CAA AA | 1118 | TTC AAG ACT TCA AAG AGT CTG AGG TA |
| Fluidigm & QPCR | Il22 /// Iltifb | 1119 | TTT CCT GAC CAA ACT CAG CA | 1120 | TCT GGA TGT TCT GGT CGT CA |
| Fluidigm & QPCR | Kat2b | 1121 | GGA GAA ACT CGG CGT GTA CT | 1122 | CAG CCA TTG CAT TTA CAG GA |
| Fluidigm & QPCR | Nkg7 | 1123 | TCT ACC TAG GCT GGG TCT CCT | 1124 | CCG ACG GGT TCT ACA GTG AG |
| Fluidigm & QPCR | Serpinb1a | 1125 | GGA TTT TCT GCA TGC CTC TG | 1126 | GAC AAC AGT TCT GGG ATT TTC C |
| Fluidigm & QPCR | Tgm2 | 1127 | CTC ACG TTC GGT GCT GTG | 1128 | TCC CTC CTC CAC ATT GTC A |
| Fluidigm & QPCR | Zfp238 | 1129 | TGC ATC TGT CTC TCT TAG TCT GCT | 1130 | TCT GGA AAC TCC ATA CTG TCT TCA |
| Fluidigm & QPCR | Ywhaz | 1131 | AAC AGC TTT CGA TGA AGC CAT | 1132 | TGG GTA TCC GAT GTC CAC AAT |
| Fluidigm & QPCR | Ccl4 | 1133 | GCC CTC TCT CTC CTC TTG CT | 1134 | GAG GGT CAG AGC CCA TTG |
| Fluidigm & QPCR | Cxcl10 | 1135 | GCT GCC GTC ATT TTC TGC | 1336 | TCT CAC TGG CCC GTC ATC |
| Fluidigm & QPCR | Etv6 | 1137 | TCC CTT TCG CTG TGA GAC AT | 1138 | GGG CGT GTA GAA TCG TT |

TABLE S6.1-continued

Primer Sequences

| Assay | Gene Name | SEQ ID NO: | Forward Sequence | SEQ ID NO: | Reverse Sequence |
|---|---|---|---|---|---|
| Fluidigm & QPCR | Grn | 1139 | TGG CTA ATG GAA ATT GAG GTG | 1140 | CAT CAG GAC CCA CAT GGT CT |
| Fluidigm & QPCR | Ikzf4 | 1141 | GCA GAC ATG CAC ACA CCA C | 1142 | TGA GAG CTC CCT CTC CAG AT |
| Fluidigm & QPCR | Il23r | 1143 | CCA AGT ATA TTG TGC ATG TGA AGA | 1144 | AGC TTG AGG CAA GAT ATT GTT GT |
| Fluidigm & QPCR | Klf9 | 1145 | CTC CGA AAA GAG GCA CAA GT | 1146 | GCG AGA ACT TTT AA GGC AGT C |
| Fluidigm & QPCR | Phlda1 | 1147 | CGC ACC AGC CTC TTC ACT | 1148 | TTC CGA AGT CCT CAA AAC CTT |
| Fluidigm & QPCR | Serpine2 | 1149 | TTG GGT CAA AAA TGA GAC CAG | 1150 | CCT TGA AAT ACA CTG CAT TAA CGA |
| Fluidigm & QPCR | Tnfrsf13b | 1151 | GAG CTC GGG AGA CCA CAG | 1152 | TGG TCG CTA CTT AGC CTC AAT |
| Fluidigm & QPCR | Zfp281 | 1153 | GGA GAG GAC GGC GTT ATT TT | 1154 | TTT TCA TAC CCC GGA GGA G |

TABLE S6.2

RNAi sequences

| Duplex Catalog Number | Gene Symbol | GENE ID | Gene Accession | SEQ ID NO: | Sequence |
|---|---|---|---|---|---|
| D-040676-01 | Acvr2a | 11480 | NM_007396 | 1155 | CAAAGAAUCUAGUCUAUGA |
| D-040676-02 | Acvr2a | 11480 | NM_007396 | 1156 | UGACAGGACUGAUUGUAUA |
| D-040676-03 | Acvr2a | 11480 | NM_007396 | 1157 | GCAGAAACAUGCAGGAAUG |
| D-040676-04 | Acvr2a | 11480 | NM_007396 | 1158 | GGCAAUAUGUGUAAUGAAA |
| D-044066-01 | Ahr | 11622 | NM_013464 | 1159 | CCAAUGCACGCUUGAUUUA |
| D-044066-02 | Ahr | 11622 | NM_013464 | 1160 | GAAGGAGAGUUCUUGUUAC |
| D-044066-03 | Ahr | 11622 | NM_013464 | 1161 | CCGCAAGAUGUUAUUAAUA |
| D-044066-04 | Ahr | 11622 | NM_013464 | 1162 | CCAGUUCUCUUAUGAGUGC |
| D-054696-01 | Arid5a | 214855 | NM_145996 | 1163 | GGAAGAACGUGUAUGAUGA |
| D-054696-02 | Arid5a | 214855 | NM_145996 | 1164 | GAAGAGGGAUUCGCUCAUG |
| D-054696-03 | Arid5a | 214855 | NM_145996 | 1165 | CCUCUAAACUUCACCGGUA |
| D-054696-04 | Arid5a | 214855 | NM_145996 | 1166 | GGUCAUCCCUGCUUUCCCA |
| D-040483-02 | ARNTL | 11865 | NM_007489 | 1167 | GCAUCGAUAUGAUAGAUAA |
| D-040483-03 | ARNTL | 11865 | NM_007489 | 1168 | CAGUAAAGGUGGAAGAUAA |
| D-040483-04 | ARNTL | 11865 | NM_007489 | 1169 | GAAAUACGGGUGAAAUCUA |
| D-040483-17 | ARNTL | 11865 | NM_007489 | 1170 | UGUCGUAGGAUGUGACCGA |
| D-049093-01 | Batf | 53314 | NM_016767 | 1171 | GAACGCAGCUCUCCGCAAA |
| D-049093-02 | Batf | 53314 | NM_016767 | 1172 | UCAACAGCUCACCGAGGA |
| D-049093-03 | Batf | 53314 | NM_016767 | 1173 | GAGGAAAGUUCAGAGGAGA |
| D-049093-04 | Batf | 53314 | NM_016767 | 1174 | UCAAGUACUUCACAUCAGU |

TABLE S6.2-continued

RNAi sequences

| Duplex Catalog Number | Gene Symbol | GENE ID | Gene Accession | SEQ ID NO: | Sequence |
|---|---|---|---|---|---|
| D-058452-01 | CCR5 | 12774 | NM_009917 | 1175 | GGAGUUAUCUCUCAGUGUU |
| D-058452-02 | CCR5 | 12774 | NM_009917 | 1176 | UGAAGUUUCUACUGGUUUA |
| D-058452-03 | CCR5 | 12774 | NM_009917 | 1177 | CCUAUGACAUCGAUUAUGG |
| D-058452-04 | CCR5 | 12774 | NM_009917 | 1178 | UGAAACAAAUUGCGGCUCA |
| D-062489-01 | CCR6 | 12458 | NM_009835 | 1179 | GCACAUAUGCGGUCAACUU |
| D-062489-02 | CCR6 | 12458 | NM_009835 | 1180 | CCAAUUGCCUACUCCUUAA |
| D-062489-03 | CCR6 | 12458 | NM_009835 | 1181 | GAACGGAUGAUUAUGACAA |
| D-062489-04 | CCR6 | 12458 | NM_009835 | 1182 | UGUAUGAGAAGGAAGAAUA |
| D-040286-04 | EGR1 | 13653 | NM_007913 | 1183 | CGACAGCAGUCCCAUCUAC |
| D-040286-01 | EGR1 | 13653 | NM_007913 | 1184 | UGACAUCGCUCUGAAUAAU |
| D-040286-02 | EGR1 | 13653 | NM_007913 | 1185 | ACUCCACUAUCCACUAUUA |
| D-040286-03 | EGR1 | 13653 | NM_007913 | 1186 | AUGCGUAACUUCAGUCGUA |
| D-040303-01 | Egr2 | 13654 | NM_010118 | 1187 | GAAGGUAUCAUCAAUAUUG |
| D-040303-02 | Egr2 | 13654 | NM_010118 | 1188 | GAUCUCCCGUAUCCGAGUA |
| D-040303-03 | Egr2 | 13654 | NM_010118 | 1189 | UCUCUACCAUCCGUAAUUU |
| D-040303-04 | Egr2 | 13654 | NM_010118 | 1190 | UGACAUGACUGGAGAGAAG |
| D-058294-01 | ELK3 | 13713 | NM_013508 | 1191 | GUAGAGAUCAGCCGGGAGA |
| D-058294-02 | ELK3 | 13713 | NM_013508 | 1192 | GAUCAGGUUUGUGACCAAU |
| D-058294-03 | ELK3 | 13713 | NM_013508 | 1193 | UCUUUAAUGUUGCCAAAUG |
| D-058294-04 | ELK3 | 13713 | NM_013508 | 1194 | UGAGAUACUAUUACGACAA |
| D-050997-21 | Ets1 | 23871 | NM_001038642 | 1195 | GCUUAGAGAUGUAGCGAUG |
| D-050997-22 | Ets1 | 23871 | NM_001038642 | 1196 | CCUGUUACACCUCGGAUUA |
| D-050997-23 | Ets1 | 23871 | NM_001038642 | 1197 | CAGCUACGGUAUCGAGCAU |
| D-050997-24 | Ets1 | 23871 | NM_001038642 | 1198 | UCAAGUAUGAGAACGACUA |
| D-040983-01 | ETS2 | 23872 | NM_011809 | 1199 | GAUCAACAGCAAUACAUUA |
| D-040983-02 | ETS2 | 23872 | NM_011809 | 1200 | UCAAUUUGCUCAACAACAA |
| D-040983-03 | ETS2 | 23872 | NM_011809 | 1201 | UAGAGCAGAUGAUCAAAGA |
| D-040983-04 | ETS2 | 23872 | NM_011809 | 1202 | GAAUGACUUUGGAAUCAAG |
| D-058395-01 | Etv6 | 14011 | NM_007961 | 1203 | GAACAAACAUGACCUAUGA |
| D-058395-02 | Etv6 | 14011 | NM_007961 | 1204 | CAAAGAGGAUUUCCGCUAC |
| D-058395-03 | Etv6 | 14011 | NM_007961 | 1205 | GCAUUAAGCAGGAACGAAU |
| D-058395-04 | Etv6 | 14011 | NM_007961 | 1206 | CGCCACUACUACAAACUAA |
| D-045283-04 | Fas | 14102 | NM_007987 | 1207 | GAGUAAAUACAUCCCGAGA |
| D-045283-03 | Fas | 14102 | NM_007987 | 1208 | GGAGGCGGGUUCAUGAAAC |
| D-045283-02 | Fas | 14102 | NM_007987 | 1209 | CGCAGAACCUUAGAUAAAU |
| D-045283-01 | Fas | 14102 | NM_007987 | 1210 | GUACCAAUCUCAUGGGAAG |
| D-041127-01 | Foxo1 | 56458 | NM_019739 | 1211 | GAAGACACCUUUACAAGUC |

TABLE S6.2-continued

RNAi sequences

| Duplex Catalog Number | Gene Symbol | GENE ID | Gene Accession | SEQ ID NO: | Sequence |
|---|---|---|---|---|---|
| D-041127-02 | Foxo1 | 56458 | NM_019739 | 1212 | GGACAACAACAGUAAAUUU |
| D-041127-03 | Foxo1 | 56458 | NM_019739 | 1213 | GGAGAUACCUUGGAUUUUA |
| D-041127-04 | Foxo1 | 56458 | NM_019739 | 1214 | GAAAUCAGCAAUCCAGAAA |
| D-040670-01 | GATA3 | 14462 | NM_008091 | 1215 | GAAGAUGUCUAGCAAAUCG |
| D-040670-02 | GATA3 | 14462 | NM_008091 | 1216 | CGGAAGAUGUCUAGCAAAU |
| D-040670-03 | GATA3 | 14462 | NM_008091 | 1217 | GUACAUGGAAGCUCAGUAU |
| D-040670-04 | GATA3 | 14462 | NM_008091 | 1218 | AGAAAGAGUGCCUCAAGUA |
| D-060495-01 | Id2 | 15902 | NM_010496 | 1219 | CAUCUGAAUUCCCUUCUGA |
| D-060495-02 | Id2 | 15902 | NM_010496 | 1220 | GAACACGGACAUCAGCAUC |
| D-060495-03 | Id2 | 15902 | NM_010496 | 1221 | GUCGAAUGAUAGCAAAGUA |
| D-060495-04 | Id2 | 15902 | NM_010496 | 1222 | CGGUGAGGUCCGUUAGGAA |
| D-051517-01 | Ikzf4 | 22781 | NM_011772 | 1223 | GAUGGUGCCUGACUCAAUG |
| D-051517-02 | Ikzf4 | 22781 | NM_011772 | 1224 | CGACUGAACGGCCAACUUU |
| D-051517-03 | Ikzf4 | 22781 | NM_011772 | 1225 | GUGAAGGCCUUUAAGUGUG |
| D-051517-04 | Ikzf4 | 22781 | NM_011772 | 1226 | GAACUCACACCUGUCAUCA |
| D-040810-01 | IL17RA | 16172 | NM_008359 | 1227 | GGACAGAUUUGAGGAGGUU |
| D-040810-02 | IL17RA | 16172 | NM_008359 | 1228 | GAAUAGUACUUGUCUGGAU |
| D-040810-03 | IL17RA | 16172 | NM_008359 | 1229 | UCUGGGAGCUCGAGAAGAA |
| D-040810-04 | IL17RA | 16172 | NM_008359 | 1230 | GAGAGCAACUCCAAAAUCA |
| D-040007-04 | IL6ST | 16195 | NM_010560 | 1231 | GUCCAGAGAUUUCACAUUU |
| D-040007-03 | IL6ST | 16195 | NM_010560 | 1232 | AGACUUACCUUGAAACAAA |
| D-040007-02 | IL6ST | 16195 | NM_010560 | 1233 | GAACUUCACUGCCAUUUGU |
| D-040007-01 | IL6ST | 16195 | NM_010560 | 1234 | GCACAGAGCUGACCGUGAA |
| D-057981-04 | IL7R | 16197 | NM_008372 | 1235 | GGAUUAAACCUGUCGUAUG |
| D-057981-03 | IL7R | 16197 | NM_008372 | 1236 | UAAGAUGCCUGGCUAGAAA |
| D-057981-02 | IL7R | 16197 | NM_008372 | 1237 | GCAACCGCUCGCCUGAGA |
| D-057981-01 | IL7R | 16197 | NM_008372 | 1238 | GAAAGUCGUUUAUCGCAAA |
| D-043796-04 | IRF4 | 16364 | NM_013674 | 1239 | CCAUAUCAAUGUCCUGUGA |
| D-043796-03 | IRF4 | 16364 | NM_013674 | 1240 | CGAGUUACCUGAACACGUU |
| D-043796-02 | IRF4 | 16364 | NM_013674 | 1241 | UAUCAGAGCUGCAAGUGUU |
| D-043796-01 | IRF4 | 16364 | NM_013674 | 1242 | GGACACACCUAUGAUGUUA |
| D-040737-01 | Irf8 | 15900 | NM_008320 | 1243 | GGACAUUUCUGAGCCAUAU |
| D-040737-02 | Irf8 | 15900 | NM_008320 | 1244 | GAGCGAAGUUCCUGAGAUG |
| D-040737-03 | Irf8 | 15900 | NM_008320 | 1245 | GCAAGGGCGUGUUCGUGAA |
| D-040737-04 | Irf8 | 15900 | NM_008320 | 1246 | GCAACGCGGUGGUGUGCAA |
| D-042246-04 | ITGA3 | 16400 | NM_013565 | 1247 | GCGAUGACUGGCAGACAUA |
| D-042246-03 | ITGA3 | 16400 | NM_013565 | 1248 | GAGUGGCCCUAUGAAGUUA |

TABLE S6.2-continued

RNAi sequences

| Duplex Catalog Number | Gene Symbol | GENE ID | Gene Accession | SEQ ID NO: | Sequence |
|---|---|---|---|---|---|
| D-042246-02 | ITGA3 | 16400 | NM_013565 | 1249 | GGACAAUGUUCGCGAUAAA |
| D-042246-01 | ITGA3 | 16400 | NM_013565 | 1250 | CCAGACACCUCCAACAUUA |
| D-043776-01 | Jun | 16476 | NM_010591 | 1251 | GAACAGGUGGCACAGCUUA |
| D-043776-02 | Jun | 16476 | NM_010591 | 1252 | GAAACGACCUUCUACGACG |
| D-043776-03 | Jun | 16476 | NM_010591 | 1253 | CCAAGAACGUGACCGACGA |
| D-043776-04 | Jun | 16476 | NM_010591 | 1254 | GCCAAGAACUCGGACCUUC |
| D-041158-04 | JUNB | 16477 | NM_008416 | 1255 | CAACCUGGCGGAUCCCUAU |
| D-041158-03 | JUNB | 16477 | NM_008416 | 1256 | CAACAGCAACGGCGUGAUC |
| D-041158-02 | JUNB | 16477 | NM_008416 | 1257 | UGGAACAGCCUUUCUAUCA |
| D-041158-01 | JUNB | 16477 | NM_008416 | 1258 | ACACCAACCUCAGCAGUUA |
| D-049885-01 | Kat2b | 18519 | NM_020005 | 1259 | GCAGUAACCUCAAAUGAAC |
| D-049885-02 | Kat2b | 18519 | NM_020005 | 1260 | UCACAUAUGCAGAUGAGUA |
| D-049885-03 | Kat2b | 18519 | NM_020005 | 1261 | GAAGAACCAUCCAAAUGCU |
| D-049885-04 | Kat2b | 18519 | NM_020005 | 1262 | AAACAAGCCCAGAUUCGAA |
| D-047145-02 | LRRFIP1 | 16978 | NM_001111312 | 1263 | GAAGGGCUCCCGUAACAUG |
| D-047145-17 | LRRFIP1 | 16978 | NM_001111312 | 1264 | AAAGAGGCCCUGCGGCAAA |
| D-047145-18 | LRRFIP1 | 16978 | NM_001111312 | 1265 | GCUCGAGAGAUCCGGAUGA |
| D-047145-19 | LRRFIP1 | 16978 | NM_001111312 | 1266 | AGACACAGUAAAUGACGUU |
| D-063455-01 | Mina | 67014 | NM_025910 | 1267 | GUNNACAGUUGCCAAGGUU |
| D-063455-02 | Mina | 67014 | NM_025910 | 1268 | GCACCUACCAGAACAAUUC |
| D-063455-03 | Mina | 67014 | NM_025910 | 1269 | GAAAUGGAACGGAGACGAU |
| D-063455-04 | Mina | 67014 | NM_025910 | 1270 | GGUCACCAAUUCGUGUUAA |
| D-040813-01 | MYC | 17869 | NM_010849 | 1271 | GACGAGACCUUCAUCAAGA |
| D-040813-02 | MYC | 17869 | NM_010849 | 1272 | GACAGCAGCUCGCCCAAAU |
| D-040813-03 | MYC | 17869 | NM_010849 | 1273 | GAAUUUCUAUCACCAGCAA |
| D-040813-04 | MYC | 17869 | NM_010849 | 1274 | CUACAGCCCUAUUUCAUCU |
| D-063057-04 | MYD88 | 17874 | NM_010851 | 1275 | GAUGAUCCGGCAACUAGAA |
| D-063057-03 | MYD88 | 17874 | NM_010851 | 1276 | GUUAGACCGUGAGGAUAUA |
| D-063057-02 | MYD88 | 17874 | NM_010851 | 1277 | CGACUGAUUCCUAUUAAAU |
| D-063057-01 | MYD88 | 17874 | NM_010851 | 1278 | GCCUAUCGCUGUUCUUGAA |
| D-041128-01 | NCOA1 | 17977 | NM_010881 | 1279 | GAACAUGAAUCCAAUGAUG |
| D-041128-02 | NCOA1 | 17977 | NM_010881 | 1280 | GAACAUGGGAGGACAGUUU |
| D-041128-03 | NCOA1 | 17977 | NM_010881 | 1281 | UCAAGAAUCUGCUACCAAA |
| D-041128-04 | NCOA1 | 17977 | NM_010881 | 1282 | CCAAGAAGAUGGUGAAGAU |
| D-047764-01 | Nfkb1 | 18033 | NM_008689 | 1283 | GACAUGGGAUUUCAGGAUA |
| D-047764-02 | Nfkb1 | 18033 | NM_008689 | 1284 | GGAUUUCGAUUCCGCUAUG |
| D-047764-03 | Nfkb1 | 18033 | NM_008689 | 1285 | CUACGGAACUGGGCAAAUG |

TABLE S6.2-continued

RNAi sequences

| Duplex Catalog Number | Gene Symbol | GENE ID | Gene Accession | SEQ ID NO: | Sequence |
|---|---|---|---|---|---|
| D-047764-04 | Nfkb1 | 18033 | NM_008689 | 1286 | GGAAACGCCAGAAGCUUAU |
| D-041110-01 | NOTCH1 | 18128 | NM_008714 | 1287 | GAACAACUCCUUCCACUUU |
| D-041110-02 | NOTCH1 | 18128 | NM_008714 | 1288 | GGAAACAACUGCAAGAAUG |
| D-041110-03 | NOTCH1 | 18128 | NM_008714 | 1289 | GAACCACGCUACACAGGAA |
| D-041110-04 | NOTCH1 | 18128 | NM_008714 | 1290 | GAAGGUGUAUACUGUGAAA |
| D-045970-01 | Nr3c1 | 14815 | NM_008173 | 1291 | GAUCGAGCCUGAGGUGUUA |
| D-045970-02 | Nr3c1 | 14815 | NM_008173 | 1292 | UUACAAAGAUUGCAGGUAU |
| D-045970-03 | Nr3G1 | 14815 | NM_008173 | 1293 | GCCAAGAGUUAUUUGAUGA |
| D-045970-04 | Nr3c1 | 14815 | NM_008173 | 1294 | GCAUGUAUGACCAAUGUAA |
| D-048514-04 | PML | 18854 | NM_008884 | 1295 | GCGCAAGUCCAAUAUCUUC |
| D-048514-03 | PML | 18854 | NM_008884 | 1296 | AGUGGUACCUCAAGCAUGA |
| D-048514-02 | PML | 18854 | NM_008884 | 1297 | GCGCAGACAUUGAGAAGCA |
| D-048514-01 | PML | 18854 | NM_008884 | 1298 | CAGCAUAUCUACUCCUUUA |
| D-048879-01 | POU2AF1 | 18985 | NM_011136 | 1299 | GAAGAAAGCGUGGCCAUAC |
| D-048879-02 | POU2AF1 | 18985 | NM_011136 | 1300 | CGGAGUAUGUGUCCCAUGA |
| D-048879-03 | POU2AF1 | 18985 | NM_011136 | 1301 | UCACUAAUGUCACGCCAAG |
| D-048879-04 | POU2AF1 | 18985 | NM_011136 | 1302 | GCAACACGUACGAGCUCAA |
| D-043089-09 | Prdm1 | 12142 | NM_007548 | 1303 | GGAGAGACCCACCUACAUA |
| D-043069-10 | Prdm1 | 12142 | NM_007548 | 1304 | CCAAUACAGUAGUGAGAAA |
| D-043069-11 | Prdm1 | 12142 | NM_007548 | 1305 | GGAAGGACAUCUACCGUUC |
| D-043069-21 | Prdm1 | 12142 | NM_007548 | 1306 | GUACAUACAUAGUGAACGA |
| D-042664-04 | PROCR | 19124 | NM_011171 | 1307 | UAUCUGACCCAGUUCGAAA |
| D-042664-03 | PROCR | 19124 | NM_011171 | 1308 | UAACUCCGAUGGCUCCCAA |
| D-042664-02 | PROCR | 19124 | NM_011171 | 1309 | GUAAGUUUCCGGCCAAAGA |
| D-042664-01 | PROCR | 19124 | NM_011171 | 1310 | CCAAACAGGUCGCUCUUAC |
| D-042742-01 | Rbpj | 19664 | NM_001080928 | 1311 | CCAAACGACUCACUAGGGA |
| D-042742-02 | Rbpj | 19664 | NM_001080928 | 1312 | UCUCAACCCUGUGCGUUUA |
| D-042742-03 | Rbpj | 19664 | NM_001080928 | 1313 | GCAGACGGCAUUACUGGAU |
| D-042742-04 | Rbpj | 19664 | NM_001080928 | 1314 | GUAGAAGCCGAAACAAUGU |
| D-040776-01 | Rela | 19697 | NM_009045 | 1315 | GGAGUACCCUGAAGCUAUA |
| D-040776-02 | Rela | 19697 | NM_009045 | 1316 | GAAGAAGAGUCCUUUCAAU |
| D-040776-03 | Rela | 19697 | NM_009045 | 1317 | UAUGAGACCUUCAAGAGUA |
| D-040776-04 | Rela | 19697 | NM_009045 | 1318 | GAAUCCAGACCAACAAUAA |
| D-042209-01 | Rorc | 19885 | NM_011281 | 1319 | UGAGUAUAGUCCAGAACGA |
| D-042209-02 | Rorc | 19885 | NM_011281 | 1320 | CAAUGGAAGUCGUCCUAGU |
| D-042209-03 | Rorc | 19885 | NM_011281 | 1321 | GAGUGGAACAUCUGCAAUA |
| D-042209-04 | Rorc | 19885 | NM_011281 | 1322 | GCUCAUCAGCUCCAUAUUU |

TABLE S6.2-continued

RNAi sequences

| Duplex Catalog Number | Gene Symbol | GENE ID | Gene Accession | SEQ ID NO: | Sequence |
|---|---|---|---|---|---|
| D-048982-01 | RUNX1 | 12394 | NM_001111022 | 1323 | UGACCACCCUGGCGAGCUA |
| D-048982-02 | RUNX1 | 12394 | NM_001111022 | 1324 | GCAACUCGCCCACCAACAU |
| D-048982-03 | RUNX1 | 12394 | NM_001111022 | 1325 | GAGCUUCACUCUGACCAUC |
| D-048982-04 | RUNX1 | 12394 | NM_001111022 | 1326 | ACAAAUCCGCCACAAGUUG |
| D-045547-01 | Satb1 | 20230 | NM_009122 | 1327 | CAAAGGAUAUGAUGGUUGA |
| D-045547-02 | Satb1 | 20230 | NM_009122 | 1328 | GAAACGAGCCGGAAUCUCA |
| D-045547-03 | Satb1 | 20230 | NM_009122 | 1329 | GAAGGGAGCACAGACGUUA |
| D-045547-04 | Satb1 | 20230 | NM_009122 | 1330 | GCACGCGGAAUUUGUAUUG |
| D-042265-01 | SKI | 20481 | NM_011385 | 1331 | GACCAUCUCUUGUUUCGUG |
| D-042265-02 | SKI | 20481 | NM_011385 | 1332 | GGAAAGAGAUUGAGCGGCU |
| D-042265-03 | SKI | 20481 | NM_011385 | 1333 | GCUGGUUCCUCCAAUAAGA |
| D-042265-04 | SKI | 20481 | NM_011385 | 1334 | UGAAGGAGAAGUUCGACUA |
| D-040687-04 | SMAD4 | 17128 | NM_008540 | 1335 | GAAGGACUGUUGCAGAUAG |
| D-040687-03 | SMAD4 | 17128 | NM_008540 | 1336 | GCAAAGGAGUGCAGUUGGA |
| D-040687-02 | SMAD4 | 17128 | NM_008540 | 1337 | GAAGUAGGACUGCACCAUA |
| D-040687-01 | SMAD4 | 17128 | NM_008540 | 1338 | AAAGAGCAAUUGAGAGUUU |
| D-041135-01 | Smarca4 | 20586 | NM_011417 | 1339 | GGUCAACGGUGUCCUCAAA |
| D-041135-02 | Smarca4 | 20586 | NM_011417 | 1340 | GAUAAUGGCCUACAAGAUG |
| D-041135-03 | Smarca4 | 20586 | NM_011417 | 1341 | GAGCGAAUGCGGAGGCUUA |
| D-041135-04 | Smarca4 | 20586 | NM_011417 | 1342 | CAACGGGCCUUUCCUCAUC |
| D-051590-01 | SMOX | 228608 | NM_145533 | 1343 | GCACAGAGAUGCUUCGACA |
| D-051590-02 | SMOX | 228608 | NM_145533 | 1344 | CCACGGGAAUCCUAUCUAU |
| D-051590-03 | SMOX | 228608 | NM_145533 | 1345 | AGAAUGGCGUGGCCUGCUA |
| D-051590-04 | SMOX | 228608 | NM_145533 | 1346 | UGAGGAAUUCAGCGAUUUA |
| D-043282-01 | Sp4 | 20688 | NM_009239 | 1347 | GGACAACAGCAGAUUAUUA |
| D-043282-02 | Sp4 | 20688 | NM_009239 | 1348 | GACAAUAGGUGCUGUUAGU |
| D-043282-03 | Sp4 | 20688 | NM_009239 | 1349 | AAUUAGACCUGGCGUUUCA |
| D-043282-04 | Sp4 | 20688 | NM_009239 | 1350 | GGAGUUCCAGUAACAAUCA |
| D-061490-01 | Tgif1 | 21815 | NM_009372 | 1351 | GCAAAUAGCACCCAGCAAC |
| D-061490-02 | Tgif1 | 21815 | NM_009372 | 1352 | CAAACGAGCGGCAGAGAUG |
| D-061490-03 | Tgif1 | 21815 | NM_009372 | 1353 | UCAGUGAUCUGCCAUACCA |
| D-061490-04 | Tgif1 | 21815 | NM_009372 | 1354 | GCCAAGAUUUCAGAAGCUA |
| D-047483-04 | TRIM24 | 21848 | NM_145076 | 1355 | AAACUGACCUGUCGAGACU |
| D-047483-03 | TRIM24 | 21848 | NM_145076 | 1356 | CCAAUACGUUCACCUAGUG |
| D-047483-02 | TRIM24 | 21848 | NM_145076 | 1357 | GAUCAGCCUAGCUCAGUUA |
| D-047483-01 | TRIM24 | 21848 | NM_145076 | 1358 | GCAAGCGGCUGAUUACAUA |
| D-065500-01 | TRPS1 | 83925 | NM_032000 | 1359 | GCAAAUGGCGGAUAUGUAU |

TABLE S6.2-continued

RNAi sequences

| Duplex Catalog Number | Gene Symbol | GENE ID | Gene Accession | SEQ ID NO: | Sequence |
|---|---|---|---|---|---|
| D-065500-02 | TRPS1 | 83925 | NM_032000 | 1360 | GCGAGCAGAUUAUUAGAAG |
| D-065500-03 | TRPS1 | 83925 | NM_032000 | 1361 | CUACGGUUCUGGAGUAAAU |
| D-065500-04 | TRPS1 | 83925 | NM_032000 | 1362 | GAAGUUCGAGAGUCAAACA |
| D-055209-02 | Tsc22d3 | 14605 | NM_010286 | 1363 | GUGAGCUGCUUGAGAAGAA |
| D-055209-17 | Tsc22d3 | 14605 | NM_010286 | 1364 | CUGUACGACUCCAGGAUUU |
| D-055209-18 | Tsc22d3 | 14605 | NM_010286 | 1365 | CUAUAUAGCCAUAAUGCGU |
| D-055209-19 | Tsc22d3 | 14605 | NM_010286 | 1366 | CAGUGAGCCUGUCGUGUCA |
| D-060426-04 | UBE2B | 22210 | NM_009458 | 1367 | CAGAAUCGAUGGAGUCCCA |
| D-060426-03 | UBE2B | 22210 | NM_009458 | 1368 | GAUGGUAGCAUAUGUUUAG |
| D-060426-02 | UBE2B | 22210 | NM_009458 | 1369 | GGAAUGCAGUUAUAUUUGG |
| D-060426-01 | U8E2B | 22210 | NM_009458 | 1370 | GAAGAGAGUUUCGGCCAUU |
| D-047149-02 | VAX2 | 24113 | NM_011912 | 1371 | GGACUUGCCUGCUGGCUAC |
| D-047149-03 | VAX2 | 24113 | NM_011912 | 1372 | UGACACAGGUAGCGCGAGU |
| D-047149-04 | VAX2 | 24113 | NM_011912 | 1373 | CUACAGCAGACUAGAACAA |
| D-047149-17 | VAX2 | 24113 | NM_011912 | 1374 | GCACUGAGUUGGCCCGACA |
| D-040825-04 | XBP1 | 22433 | NM_013842 | 1375 | UCUCAAACCUGCUUUCAUC |
| D-040825-03 | XBP1 | 22433 | NM_013842 | 1376 | GAGUCAAACUAACGUGGUA |
| D-040825-02 | XBP1 | 22433 | NM_013842 | 1377 | GGAUCACCCUGAAUUCAUU |
| D-040825-01 | XBP1 | 22433 | NM_013842 | 1378 | UGACAUGUCUUCUCCACUU |
| D-051513-01 | Zeb1 | 21417 | NM_011546 | 1379 | GAACCCAGCUUGAACGUCA |
| D-051513-02 | Zeb1 | 21417 | NM_011546 | 1380 | GAAAGAGCACUUACGGAUU |
| D-051513-03 | Zeb1 | 21417 | NM_011546 | 1381 | GGUUUGGUAUCUCCCAUAA |
| D-051513-04 | Zeb1 | 21417 | NM_011546 | 1382 | GAAGUGUAUUAGCUUGAUG |
| D-058937-01 | ZFP161 | 22666 | NM_009547 | 1383 | CCUCCGCUCUGACAUAUUU |
| D-058937-02 | ZFP161 | 22666 | NM_009547 | 1384 | GAUUCUCGGUAUCCGGUUU |
| D-058937-03 | ZFP161 | 22666 | NM_009547 | 1385 | CCGCCAAGAUUUCCGUGAA |
| D-058937-04 | ZFP161 | 22666 | NM_009547 | 1386 | AAAGACCAUUUGCGUGUCA |
| D-057818-01 | ZFP281 | 226442 | NM_177643 | 1387 | GCACCACCGCGAUGUAUUA |
| D-057818-02 | ZFP281 | 226442 | NM_177643 | 1388 | GAACAACGUACCAGAUUGA |
| D-057818-03 | ZFP281 | 226442 | NM_177643 | 1389 | AAGCAAGGCCCGAUAAGUA |
| D-057818-04 | ZFP281 | 226442 | NM_177643 | 1390 | GAUCAGUACUCUGGCAAAU |
| D-041703-01 | ZFP36L1 | 12192 | NM_007564 | 1391 | UCAAGACGCCUGCCCAUUU |
| D-041703-02 | ZFP36L1 | 12192 | NM_007564 | 1392 | UCAGCAGCCUUAAGGGUGA |
| D-041703-03 | ZFP36L1 | 12192 | NM_007564 | 1393 | GGAGCUGGCGAGCCUCUUU |
| D-041703-04 | ZFP36L1 | 12192 | NM_007564 | 1394 | CGAAUCCCCUCACAUGUUU |

Example 2: A Transcriptional Time Course of Th17 Differentiation

Figure 2A:
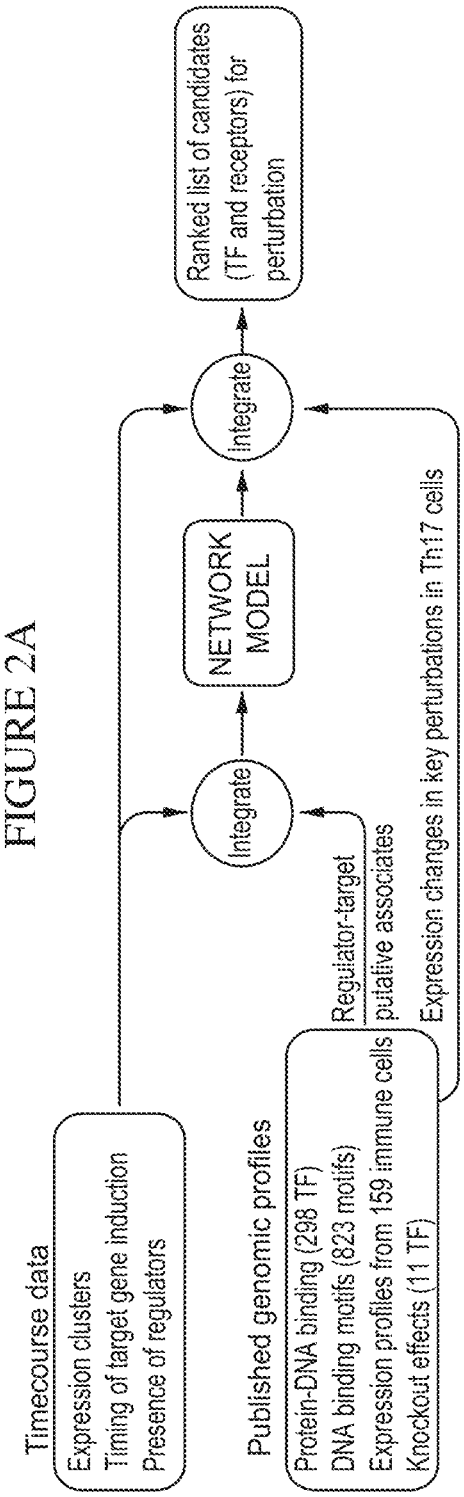
Figure 7:
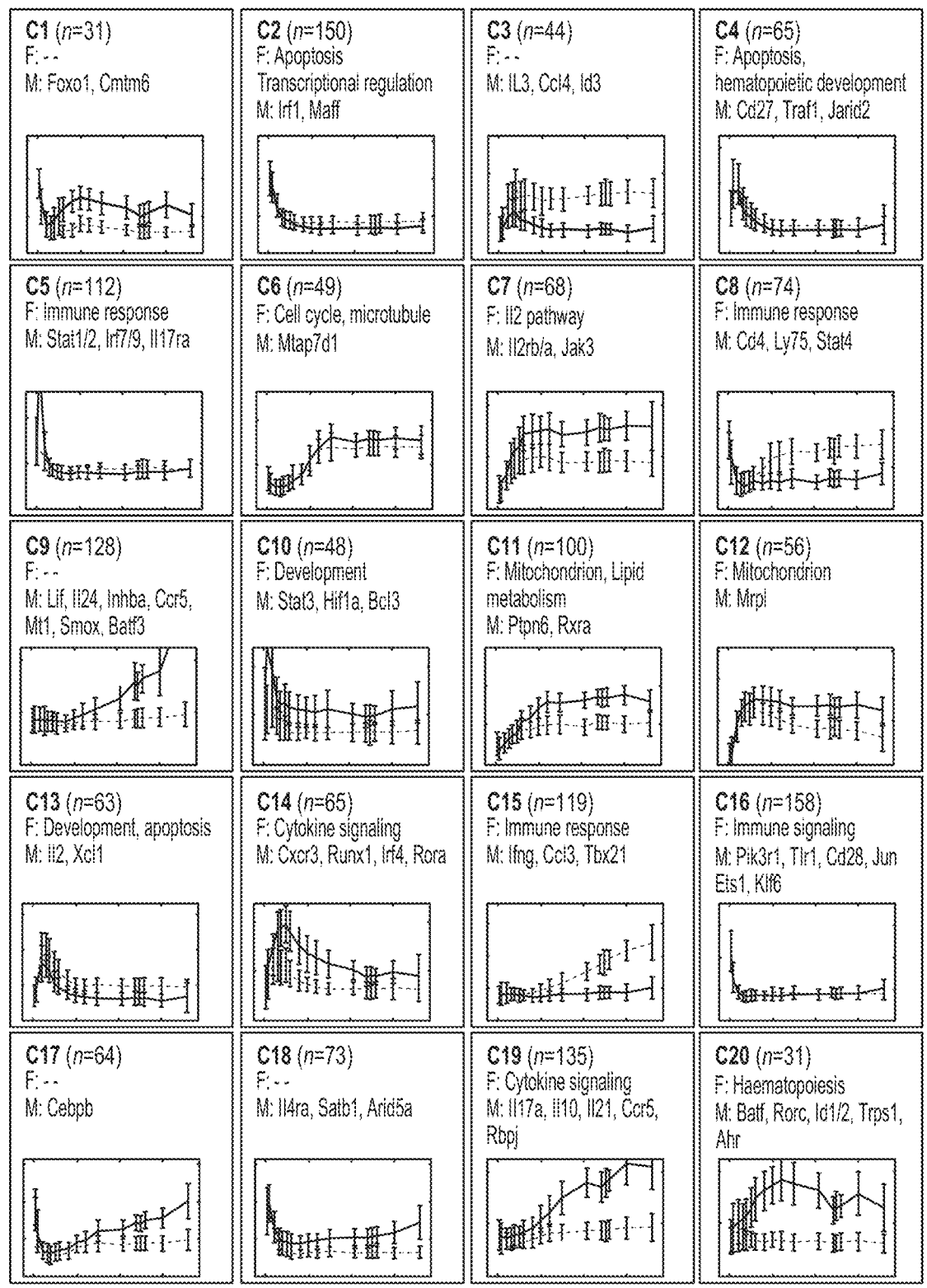
FIG. 7 is a series of graphs depicting clusters of differentially expressed genes in the Th17 time course data. A color version of these figures can be found in Yosef et al., "Dynamic regulatory network controlling Th17 cell differentiation, Nature, vol. 496: 461-468 (2013)/doi: 10.1038/nature11981. For each of the 20 clusters in FIG. 1B shown are the average expression levels (Y axis, ±standard deviation, error bars) at each time point (X axis) under Th17 polarizing (blue) and Th0 (red) conditions. The cluster size ("n"), enriched functional annotations ("F"), and representative member genes ("M") are denoted on top.

The differentiation of naïve CD4+ T-cells into Th17 cells was induced using TGF-β1 and IL-6, and measured transcriptional profiles using microarrays at eighteen time points along a 72 hr time course during the differentiation of naïve CD4+ T-cells into Th17 cells, induced by a combination of the anti-inflammatory cytokine TGF-β1 and the proinflammatory cytokine IL-6 (FIG. 1, FIG. 6A, FIG. 6B and FIG. 6C, see Methods in Example 1). As controls, mRNA profiles were measured for cells that were activated without the addition of differentiating cytokines (Th0). 1,291 genes that were differentially expressed specifically during Th17 differentiation were identified by comparing the Th17 differentiating cells to the control cells (see Methods in Example 1) and partitioned into 20 co-expression clusters (k-means clustering, see Methods in Example 1, FIG. 1b and FIG. 7) that displayed distinct temporal profiles. These clusters were used to characterize the response and reconstruct a regulatory network model, as described below (FIG. 2a).

Three Main Waves of Transcription and Differentiation:

There are three transcriptional phases as the cells transition from a naïve-like state (t=0.5 hr) to Th17 (t=72 hr; FIG. 1c and FIG. 6c): early (up to 4 hr), intermediate (4-20 hr), and late (20-72 hr). Each corresponds, respectively, to a differentiation phase (Korn et al., Annu Rev Immunol 2009): (1) induction, (2) onset of phenotype and amplification, and (3) stabilization and IL-23 signaling.

The early phase is characterized by transient induction (e.g., Cluster C5, FIG. 1b) of immune response pathways (e.g., IL-6 and TGF-β signaling; FIG. 1d). The first transition point (t=4 hr) is marked by a significant increase in the expression level of ROR-γt, which is not detectable at earlier time points. The second transition (t=20 hr) is accompanied by significant changes in cytokine expression, with induction of Th17 signature cytokines (e.g., IL-17) that strengthen the Th17 phenotype and a concomitant decrease in other cytokines (e.g., IFN-γ) that belong to other T cell lineages.

Some early induced genes display sustained expression (e.g., Cluster C10, FIG. 1b); these are enriched for transcription regulators (TRs) also referred to herein as transcription factors (TFs), including the key Th17 factors Stat3, Irf4 and Batf, and the cytokine and receptor molecules IL-21, Lif, and Il2ra.

The transition to the intermediate phase (t=4 hr) is marked by induction of ROR-γt (master TF; FIG. 6d) and another 12 TFs (Cluster C20, FIG. 1b), both known (e.g., Ahr) and novel (e.g., Trps1) to Th17 differentiation. At the 4 hr time point, the expression of ROR-γt, the master TF of Th17 differentiation, significantly increases (FIG. 6d)—marking the beginning of the accumulation of differentiation phenotypes ('intermediate phase')—and remains elevated throughout the rest of the time course. Another 12 factors show a similar pattern (Cluster 8 C20, FIG. 1b). These include Ahr and Rbpj, as well as a number of factors (e.g., Etv6 and Trps1) not described previously as having roles in Th17 differentiation. Overall, the 585 genes that are induced between 4 and 20 hrs are differentially expressed and substantially distinct from the early response genes (FIG. 1b; e.g., clusters C20, C14, and C1).

Figure 8A:
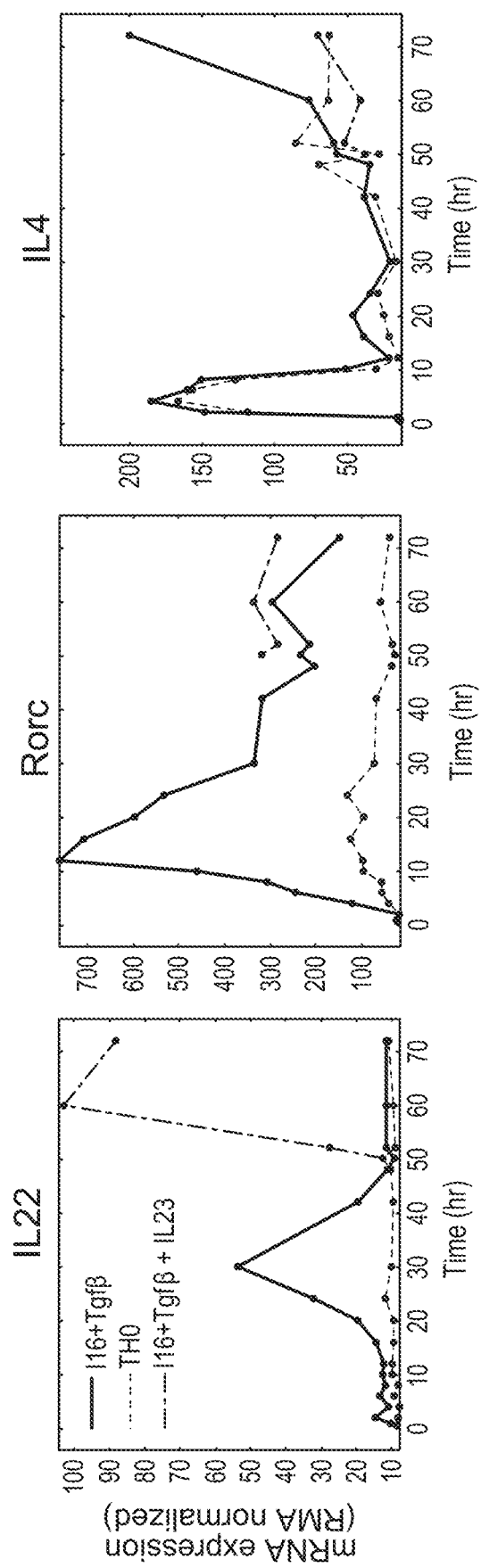
FIGS. 8A and 8B are a series of graphs depicting transcriptional effects of IL-23.
Figure 8B:
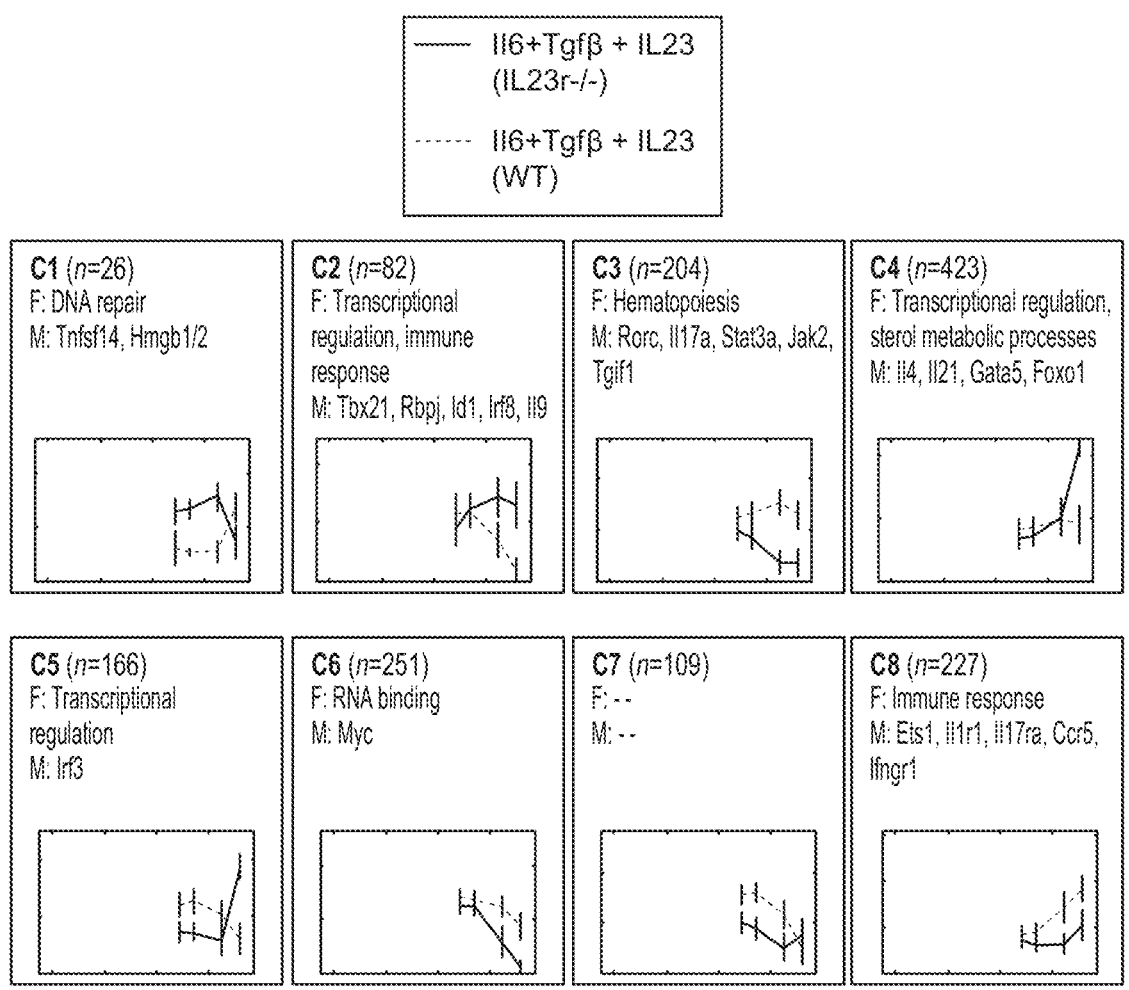

During the transition to the late phase (t=20 hr), mRNAs of Th17 signature cytokines are induced (e.g., IL-17a, IL-9; cluster C19) whereas mRNAs of cytokines that signal other T cell lineages are repressed (e.g., IFN-γ and IL-4). Regulatory cytokines from the IL-10 family are also induced (IL-10, IL-24), possibly as a self-limiting mechanism related to the emergence of 'pathogenic' or 'non-pathogenic' Th17 cells (Lee et al., Induction and Molecular Signature of Pathogenic Th17 Cells, Nature Immunol 13, 991-999; doi: 10.1038/ni.2416). Around 48 hr, the cells induce IL23r (data not shown), which plays an important role in the late phase (FIGS. 8A, 8B).

Between 20 and 42 hrs post activation (i.e., starting 16 hrs after the induction of ROR-γt expression), there is a substantial change compared to Th0 in the expression of 821 genes, including many major cytokines (e.g., cluster C19, FIG. 1b). The expression of Th17-associated inflammatory cytokines, including IL-17a, IL-24, IL-9 and lymphotoxin alpha LTA (Elyaman, W. et al. Notch receptors and Smad3 signaling cooperate in the induction of interleukin-9-producing T cells. Immunity 36, 623-634, doi:10.1016/j.immuni.2012.01.020 (2012)), is strongly induced (FIG. 1d), whereas other cytokines and chemokines are repressed or remain at their low basal level (Clusters C8 and C15, FIG. 1b and FIG. 7). These include cytokines that characterize other T-helper cell types, such as IL-2 (Th17 differentiation inhibitor), IL-4 (Th2), and IFN-γ (Th1), and others (Csf1, Tnfsf9/4 and Ccl3). Finally, regulatory cytokines from the IL-10 family are also induced (IL-10, IL-24), possibly as a self-limiting mechanism. Thus, the 20 hr time point might be crucial for the emergence of the proposed 'pathogenic' versus 'nonpathogenic'/regulatory Th17 cells (Lee et al., Nature Immunol 2012).

Most expression changes in the 1,055 genes differentially expressed in the remainder of the time course (>48 hr) are mild, occur in genes that responded during the 20-42 hr period (FIG. 1, e.g., clusters C18, C19, and C20), and typically continue on the same trajectory (up or down). Among the most strongly late-induced genes is the TF Hif1a, previously shown to enhance Th17 development via interaction with ROR-γt (Dang, E. V. et al. Control of T(H)17/T(reg) balance by hypoxia-inducible factor 1. Cell 146, 772-784, doi:10.1016/j.cell.2011.07.033 (2011)). The genes over-expressed at the latest time point (72 hr) are enriched for apoptotic functions ($p<10^{-6}$), consistent with the limited survival of Th17 cells in primary cultures, and include the Th2 cytokine IL-4 (FIG. 8a), suggesting that under TGF-β1+IL-6 treatment, the cells might have a less stable phenotype.

The peak of induction of IL-23r mRNA expression occurs at 48 hr and, at this time point one begins to see IL-23r protein on the cell surface (data not shown). The late phase response depends in part on IL-23, as observed when comparing temporal transcriptional profiles between cells stimulated with TGF-β1+IL-6 versus TGF-β1+IL-6+IL-23, or between WT and IL-23r−/− cells treated with TGF-β1+ IL-6+IL-23 (FIG. 8). For instance, in IL-23r-deficient Th17 cells, the expression of IL-17ra, IL-1r1, IL-21r, ROR-γt, and Hif1a is decreased, and IL-4 expression is increased. The up-regulated genes in the IL-23r−/− cells are enriched for other CD4+ T cell subsets, suggesting that, in the absence of IL-23 signaling, the cells start to dedifferentiate, thus further supporting the hypothesis that IL-23 may have a role in stabilizing the phenotype of differentiating Th17 cells.

Example 3: Inference of Dynamic Regulatory Interactions

It was hypothesized that each of the clusters (FIG. 1b) encompasses genes that share regulators active in the relevant time points. To predict these regulators, a general network of regulator-target associations from published genomics profiles was assembled (Linhart, C., Halperin, Y.

& Shamir, R. Transcription factor and microRNA motif discovery: the Amadeus platform and a compendium of metazoan target sets. Genome research 18, 1180-1189, doi: 10.1101/gr.076117.108 (2008); Zheng, G. et al. ITFP: an integrated platform of mammalian transcription factors. Bioinformatics 24, 2416-2417, doi:10.1093/bioinformatics/btn439 (2008); Wilson, N. K. et al. Combinatorial transcriptional control in blood stem/progenitor cells: genome-wide analysis of ten major transcriptional regulators. Cell Stem Cell 7, 532-544, doi:10.1016/j.stem.2010.07.016 (2010); Lachmann, A. et al. in Bioinformatics Vol. 26 2438-2444 (2010); Liberzon, A. et al. Molecular signatures database (MSigDB) 3.0. Bioinformatics 27, 1739-1740, doi:10.1093/bioinformatics/btr260 (2011); Jiang, C., Xuan, Z., Zhao, F. & Zhang, M. TRED: a transcriptional regulatory element database, new entries and other development. Nucleic Acids Res 35, D137-140 (2007); Elkon, R., Linhart, C., Sharan, R., Shamir, R. & Shiloh, Y. in Genome Research Vol. 13 773-780 (2003); Heng, T. S. & Painter, M. W. The Immunological Genome Project: networks of gene expression in immune cells. Nat. Immunol. 9, 1091-1094, doi:10.1038/ni1008-1091 (2008)) (FIG. 2a, see Methods in Example 1).

The general network of regulator-target associations from published genomics profiles was assembled as follows: in vivo protein-DNA binding profiles for 298 regulators (Linhart, C., Halperin, Y. & Shamir, R. Transcription factor and microRNA motif discovery: the Amadeus platform and a compendium of metazoan target sets. Genome research 18, 1180-1189, doi:10.1101/gr.076117.108 (2008); Zheng, G. et al. ITFP: an integrated platform of mammalian transcription factors. Bioinformatics 24, 2416-2417, doi:10.1093/bioinformatics/btn439 (2008); Wilson, N. K. et al. Combinatorial transcriptional control in blood stem/progenitor cells: genome-wide analysis of ten major transcriptional regulators. Cell Stem Cell 7, 532-544, doi:10.1016/j.stem.2010.07.016 (2010); Lachmann, A. et al. in Bioinformatics Vol. 26 2438-2444 (2010); Liberzon, A. et al. Molecular signatures database (MSigDB) 3.0. Bioinformatics 27, 1739-1740, doi:10.1093/bioinformatics/btr260 (2011); Jiang, C., Xuan, Z., Zhao, F. & Zhang, M. TRED: a transcriptional regulatory element database, new entries and other development. Nucleic Acids Res 35, D137-140 (2007), 825 DNA cis-regulatory elements scored in each gene's promoter (Elkon, R., Linhart, C., Sharan, R., Shamir, R. & Shiloh, Y. Genome-wide in silico identification of transcriptional regulators controlling the cell cycle in human cells. Genome research 13, 773-780, doi:10.1101/gr.947203 (2003)), transcriptional responses to the knockout of 11 regulatory proteins, and regulatory relations inferred from co-expression patterns across 159 immune cell types (Heng, T. S. & Painter, M. W. The Immunological Genome Project: networks of gene expression in immune cells. Nat. Immunol. 9, 1091-1094, doi:10.1038/ni1008-1091 (2008)) (see Methods in Example 1). While most protein-DNA binding profiles were not measured in Th17 cells, DNA-binding profiles in Th17 cells of a number of key TFs, including Irf4 and Batf (Glasmacher, E. et al. A Genomic Regulatory Element That Directs Assembly and Function of Immune-Specific AP-1-IRF Complexes. Science, doi:10.1126/science.1228309 (2012)), Stat3 and Stat5 (Yang, X. P. et al. Opposing regulation of the locus encoding IL-17 through direct, reciprocal actions of STAT3 and STAT5. Nat. Immunol. 12, 247-254, doi:10.1038/ni.1995 (2011)), and Rorc (Xiao et al., unpublished) has been included.

Figure 2B:
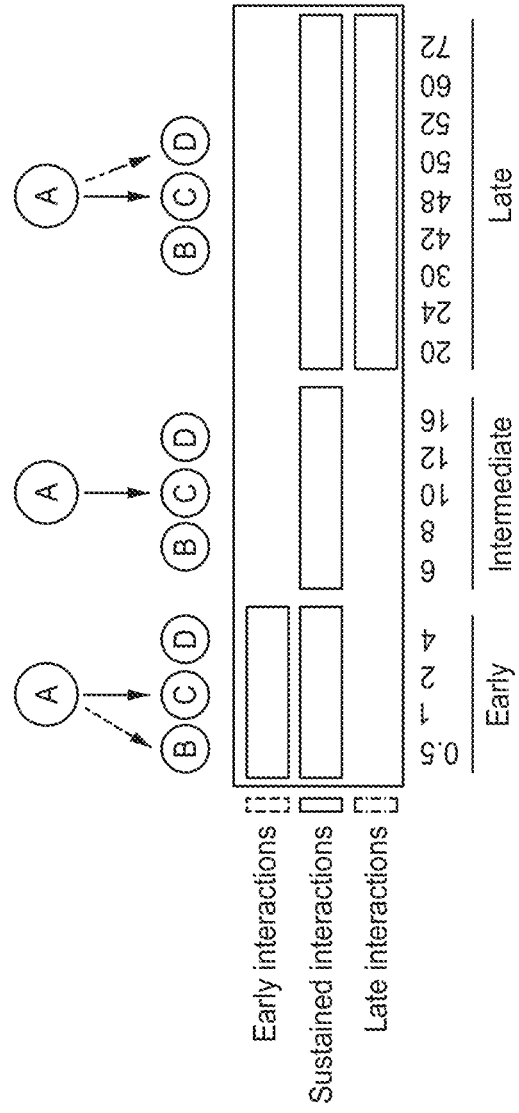
Figure 2C:
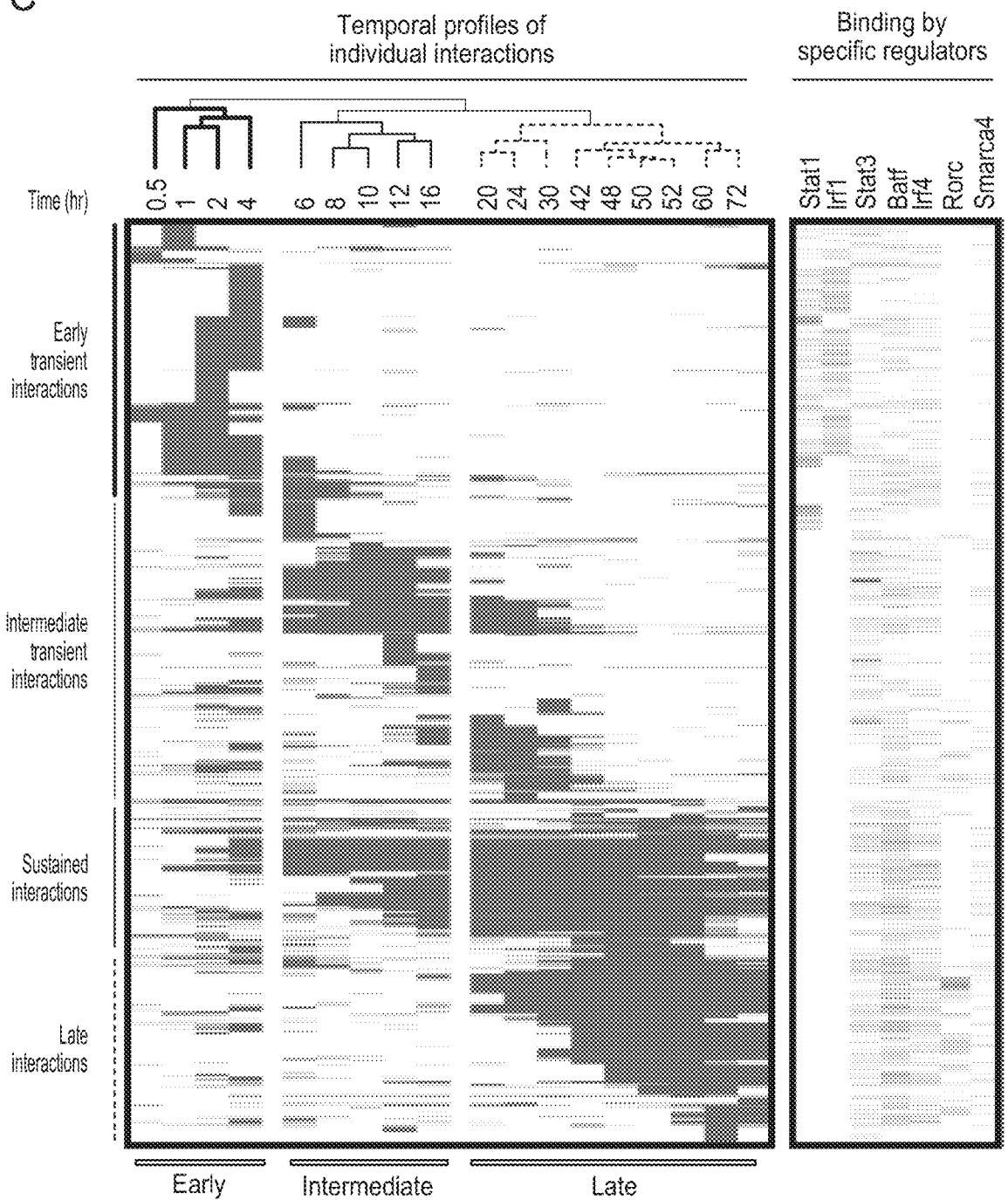
Figure 2D:
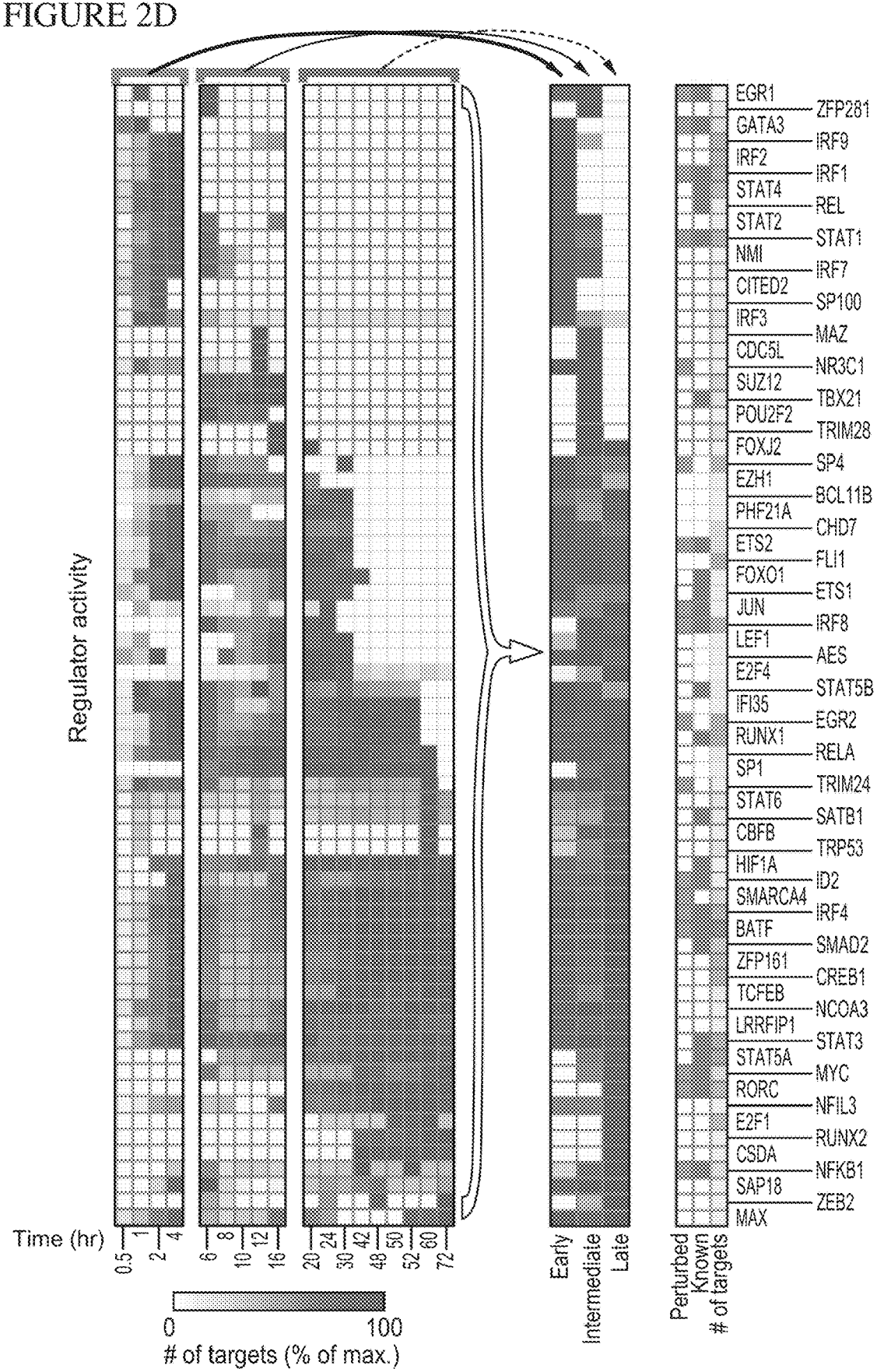

A regulator was then connected to a gene from its set of putative targets only if there was also a significant overlap between the regulator's putative targets and that gene's cluster (see Methods in Example 1). Since different regulators act at different times, the connection between a regulator and its target may be active only within a certain time window. To determine this window, each edge was labeled with a time stamp denoting when both the target gene is regulated (based on its expression profile) and the regulator node is expressed at sufficient levels (based on its mRNA levels and inferred protein levels (Schwanhäusser, B. et al. Global quantification of mammalian gene expression control. Nature 473, 337-342, doi:10.1038/nature10098 (2011)); see Methods in Example 1). For the target gene, the time points in which it is either differentially expressed compared to the Th0 condition or is being induced or repressed compared with preceding time points in the Th17 time course were considered. For the regulator node, only time points where the regulator is sufficiently expressed and not repressed relative to the Th0 condition were included. To this end, the regulator's predicted protein expression level was inferred from its mRNA level using a recently proposed model (Schwanhäusser, B. et al. Global quantification of mammalian gene expression control. Nature 473, 337-342, doi:10.1038/nature10098 (2011)) (see Methods in Example 1). In this way, a network 'snapshot' was derived for each of the 18 time points (FIGS. 2b-d). Overall, 9,159 interactions between 71 regulators and 1,266 genes were inferred in at least one network.

Figure 9A:
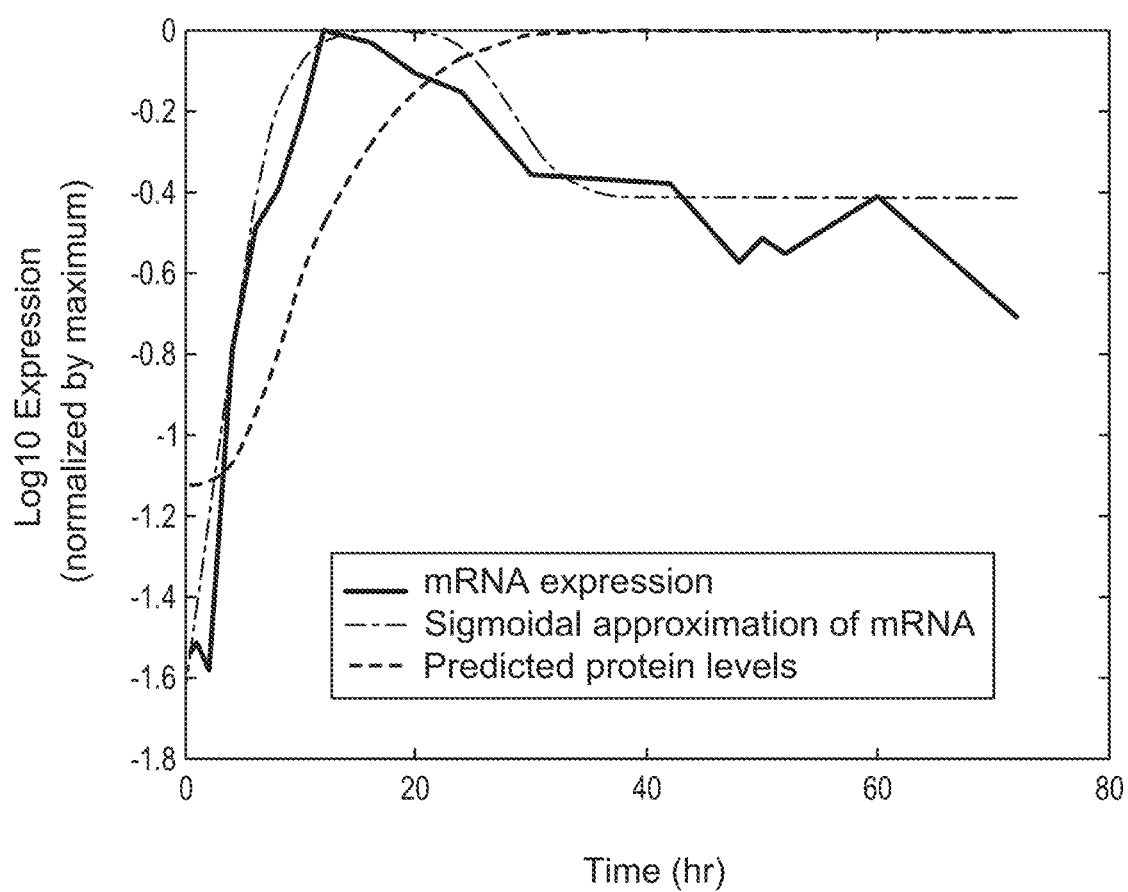

Substantial Regulatory Re-Wiring During Differentiation:

The active factors and interactions change from one network to the next. The vast majority of interactions are active only at some time window (FIG. 2c), even for regulators (e.g., Batf) that participate in all networks. Based on similarity in active interactions, three network classes were identified (FIG. 2c), corresponding to the three differentiation phases (FIG. 2d). All networks in each phase were collapsed into one model, resulting in three consecutive network models (FIGS. 9A, 9B). Among the regulators, 33 are active in all of the networks (e.g. many known master regulators such as Batf1, Irf4, and Stat3), whereas 18 are active in only one (e.g. Stat1 and Irf1 in the early network; ROR-γt in the late network). Indeed, while ROR-γt mRNA levels are induced at −4 h, ROR-γt protein levels increase at approximately 20 h and further rise over time, consistent with the model (FIG. 9).

Figures 1, 2E:
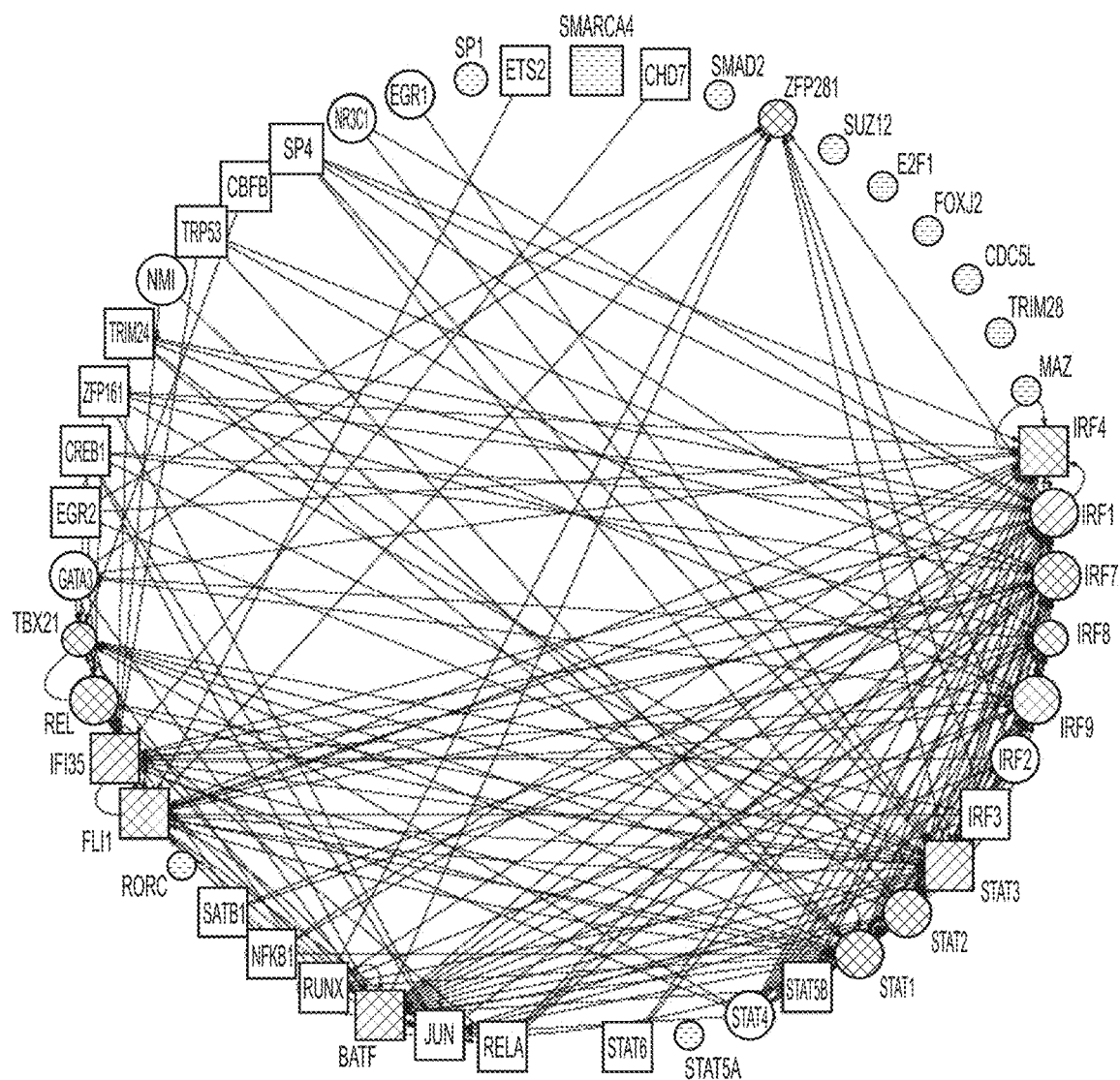
Figures 2, 2E:
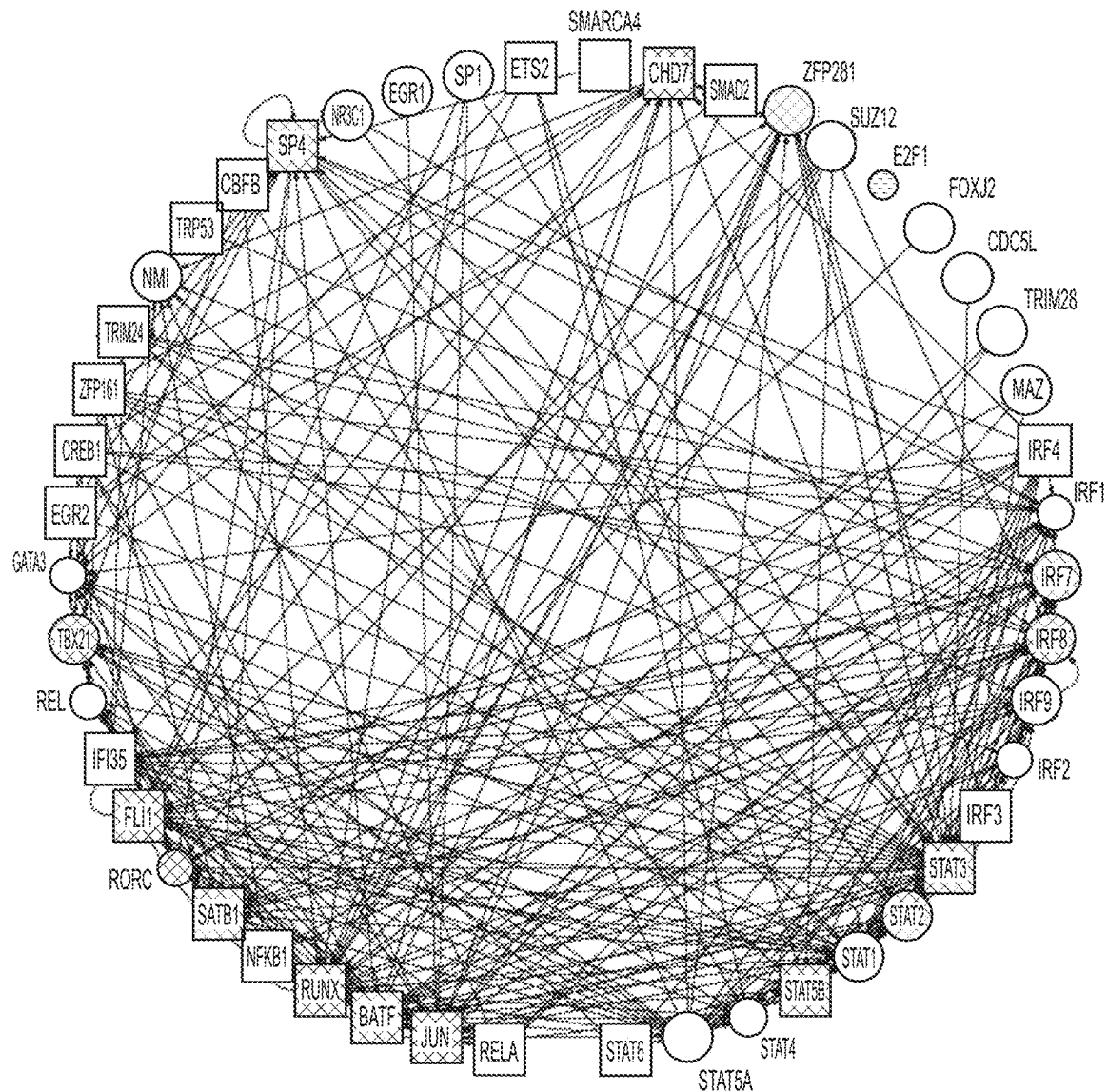
Figures 2, 2E, 3:
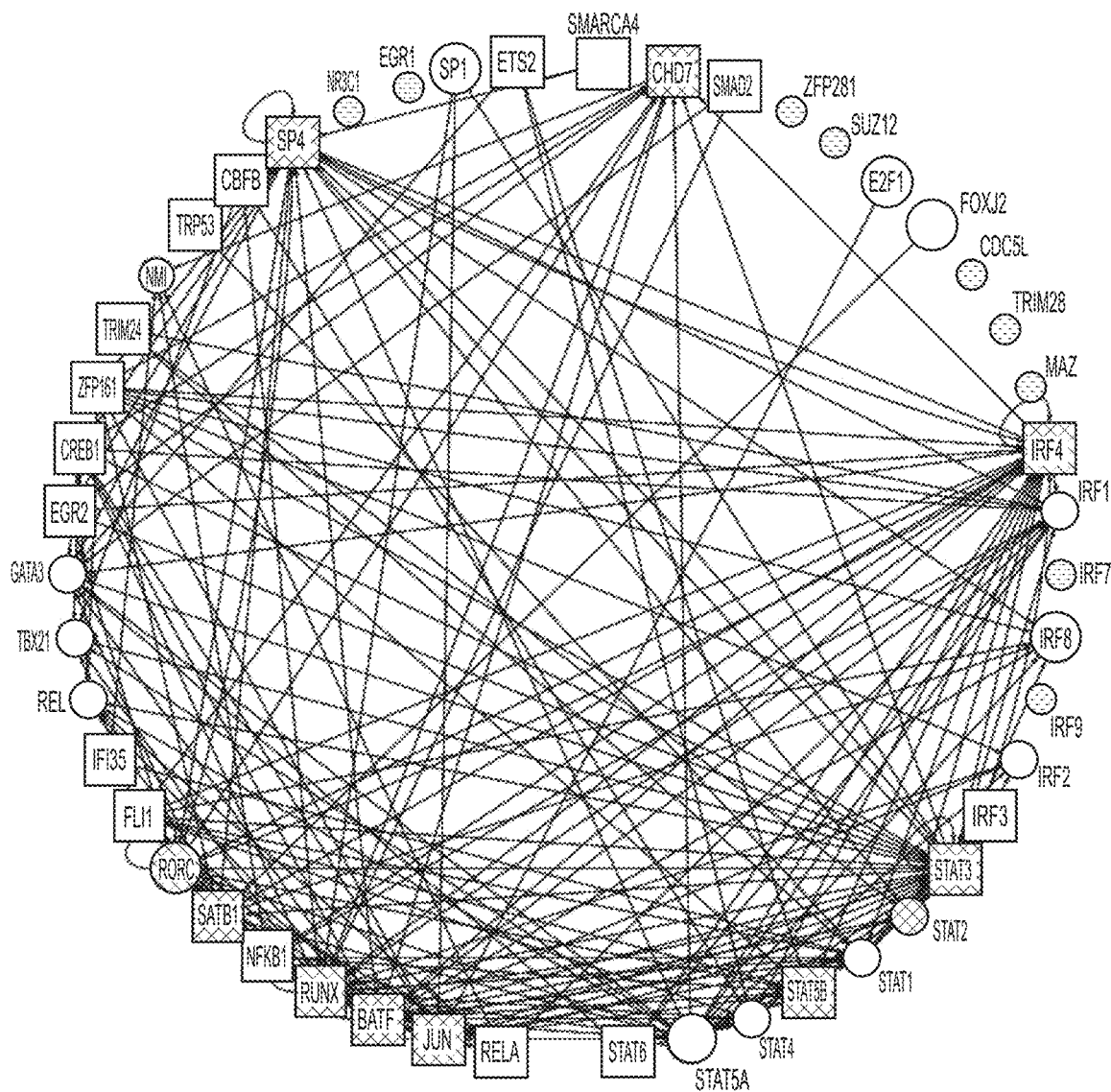

Densely Interconnected Transcriptional Circuits in Each Network:

At the heart of each network is its 'transcriptional circuit', connecting active TFs to target genes that themselves encode TFs. For example, the transcriptional circuit in the early response network connects 48 factors that are predicted to act as regulators to 72 factors whose own transcript is up- or down-regulated during the first four hours (a subset of this model is shown in FIG. 2e). The circuit automatically highlights many TFs that were previously implicated in immune signaling and Th17 differentiation, either as positive or negative regulators, including Stat family members, both negative (Stat1, Stat5) and positive (Stat3), the pioneering factor Batf, TFs targeted by TGF-β signaling (Smad2, Runx1, and Irf7), several TFs targeted by TCR signaling (Rel, Nfkb1, and Jun), and several interferon regulatory factors (Irf4 and Irf1), positioned both as regulators and as target genes that are strongly induced. In addition, 34 regulators that were not previously described to have a role in Th17 differentiation were identified (e.g., Sp4, Egr2, and Smarca4). Overall, the circuit is densely intraconnected (Novershtern et al., Cell 2011), with 16 of the 48 regulators themselves transcriptionally controlled (e.g., Stat1, Irf1, Irf4, Batf). This suggests feedback circuitry, some of which may be auto-regulatory (e.g., for Irf4, Stat3 and Stat1).

As in the early network, there is substantial cross-regulation between the 64 TFs in the intermediate and late transcriptional circuits, which include major Th17 regulators such as ROR-γt, Irf4, Batf, Stat3, and Hif1a (FIG. 2e).

Ranking Novel Regulators for Systematic Perturbation:

In addition to known Th17 regulators, the network includes dozens of novel factors as predicted regulators (FIG. 2d), induced target genes, or both (FIG. 2E). It also contains receptor genes as induced targets, both previously known in Th17 cells (e.g., IL-1R1, IL-17RA) and novel (e.g., Fas, Itga3). This suggests substantial additional complexity compared to current knowledge, but must be systematically tested to validate the role and characterize the function of each candidate.

Figure 3A:
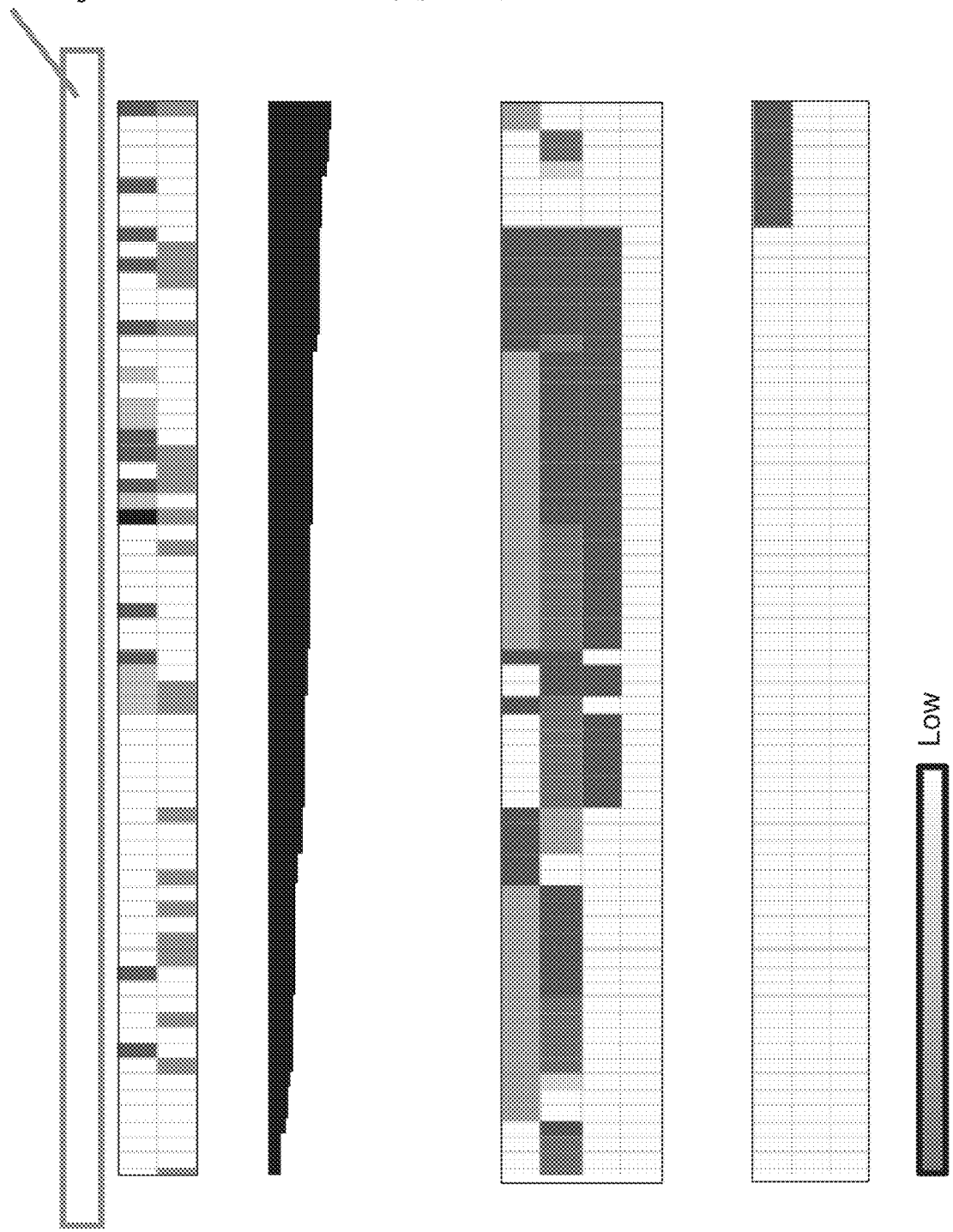
FIGS. 3A, 3B, 3C and 3D are a series of graphs and illustrations depicting knockdown screen in Th17 differentiation using silicon nanowires.

Candidate regulators were ranked for perturbation (FIGS. 2a, 3a, see Methods in Example 1), guided by features that reflect a regulatory role (FIG. 3a, "Network Information") and a role as target (FIG. 3a, "Gene Expression Information").

To this end, a scoring scheme was devised to rank candidate regulators for perturbation (FIG. 2a, FIG. 3a, FIG. 10, Methods), guided by protein activity (participation as a regulator node, FIG. 3a, "Network Information") and mRNA level (changes in expression as a target, FIG. 3a, "Gene Expression Information"; Methods). Under each criterion, several features were considered for selecting genes to perturb (see Methods in Example 1). In "Network Information", it was considered whether the gene acts as regulator in the network, the type of experimental support for this predicted role, and whether it is predicted to target key Th17 genes. In "Gene Expression Information", it was considered changes in mRNA levels of the encoding gene in the time course data (preferring induced genes), under IL23R knockout, or in published data of perturbation in Th17 cells (e.g., Batf knockout (Schraml, B. U. et al. in Nature Vol. 460 405-409 (2009)); See Methods for the complete list); and whether a gene is more highly expressed in Th17 cells as compared to other CD4+ subsets, based on genome wide expression profiles (Wei, G. et al. in Immunity Vol. 30 155-167 (2009)).

The genes were computationally ordered to emphasize certain features (e.g., a predicted regulator of key Th17 genes) over others (e.g., differential expression in the time course data). A similar scheme was used to rank receptor proteins (see Methods in Example 1). Supporting their quality, the top-ranked factors are enriched ($p<10^{-3}$) for manually curated Th17 regulators (FIG. 10), and correlate well (Spearman r>0.86) with a ranking learned by a supervised method (see Methods in Example 1). 65 genes were chosen for perturbation: 52 regulators and 13 receptors. These included most of the top 44 regulators and top 9 receptors (excluding a few well-known Th17 genes and/or those for which knockout data already existed), as well as additional representative lower ranking factors.

Example 4: Nanowire-Based Perturbation of Primary T Cells

Figure 3B:
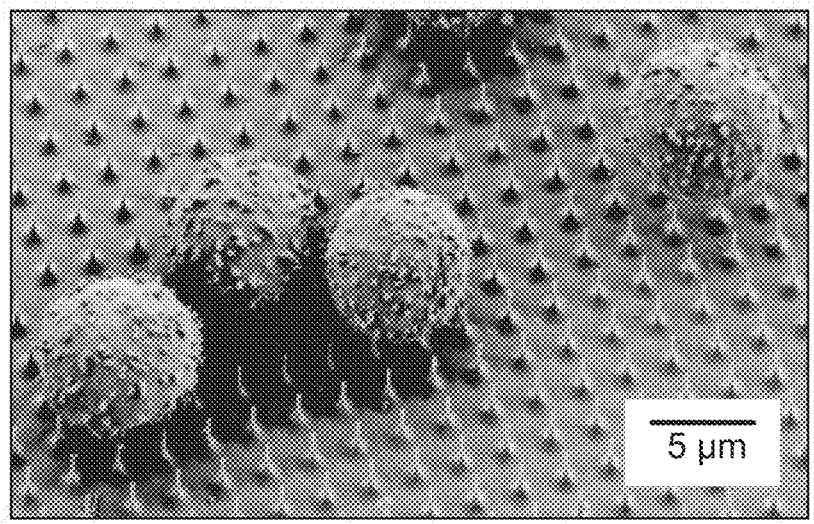

While testing the response of naïve CD4+ T cells from knock-out mice deleted for key factors is a powerful strategy, it is limited by the availability of mouse strains or the ability to generate new ones. In unstimulated primary mouse T cells, viral- or transfection-based siRNA delivery has been nearly impossible because it either alters differentiation or cell viability (Dardalhon, V. et al. Lentivirus-mediated gene transfer in primary T cells is enhanced by a central DNA flap. Gene therapy 8, 190-198 (2001); McManus, M. et al. Small interfering RNA-mediated gene silencing in T lymphocytes. The Journal of Immunology 169, 5754 (2002)). a new delivery technology based on silicon nanowires (NWs) (Shalek et al., Proc Natl Acad Sci U.S.A. 2010; Shalek, A. K. et al. Nanowire-Mediated Delivery Enables Functional Interrogation of Primary Immune Cells: Application to the Analysis of Chronic Lymphocytic Leukemia. Nano Lett. 12, 6498-6504, doi:10.1021/nl3042917 (2012)) was, therefore, used, which was optimized to effectively (>95%) deliver siRNA into naïve T cells without activating them (FIGS. 3b and c) (Shalek et al., Nano Lett 2012).

Figure 3C:
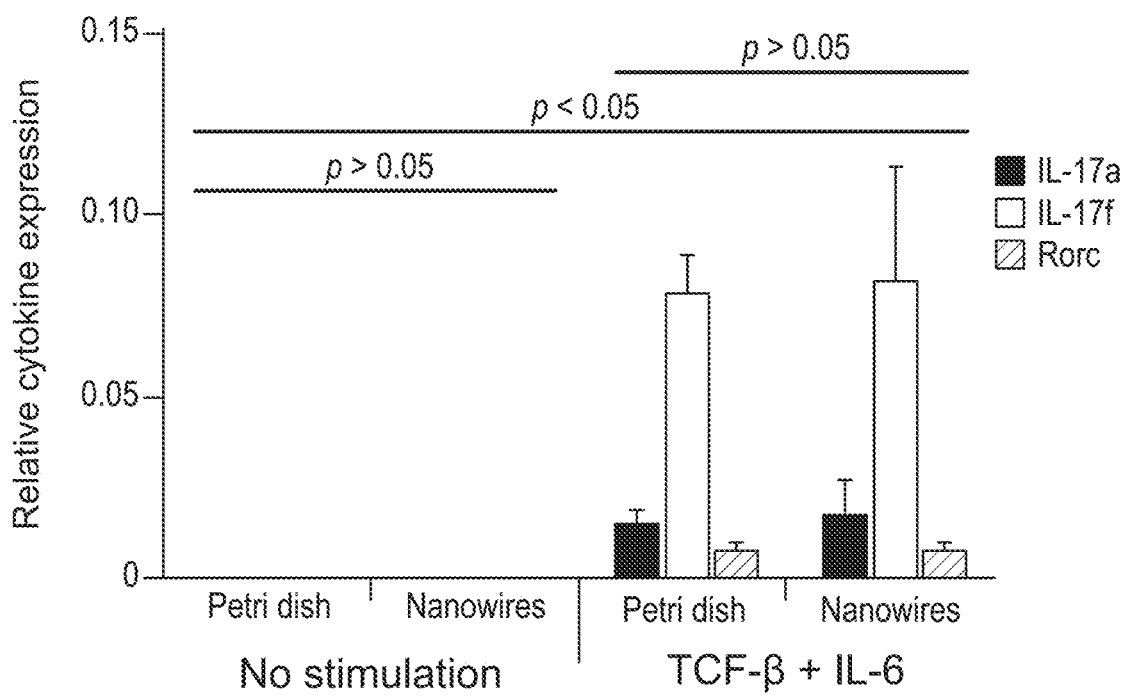

Recently, it was demonstrated that NWs are able to effectively penetrate the membranes of mammalian cells and deliver a broad range of exogenous molecules in a minimally invasive, non-activating fashion (Shalek et al., Proc. Natl. Acad. Sci. U.S.A. 2010; Shalek, et al., Nano Lett. 2012). In particular, the NW-T cell interface (FIG. 3b) was optimized to effectively (>95%) deliver siRNAs into naïve murine T cells. This delivery neither activates nor induces differentiation of naïve T cells and does not affect their response to conventional TCR stimulation with anti-CD3/CD28 (FIG. 3c) (Shalek, et al., Nano Lett. 2012)). Importantly, NW-delivered siRNAs yielded substantial target transcript knockdowns, prior to and even up to 48 h after anti-CD3/CD28 activation, despite rapid cellular proliferation (FIG. 3d).

Figure 3D:
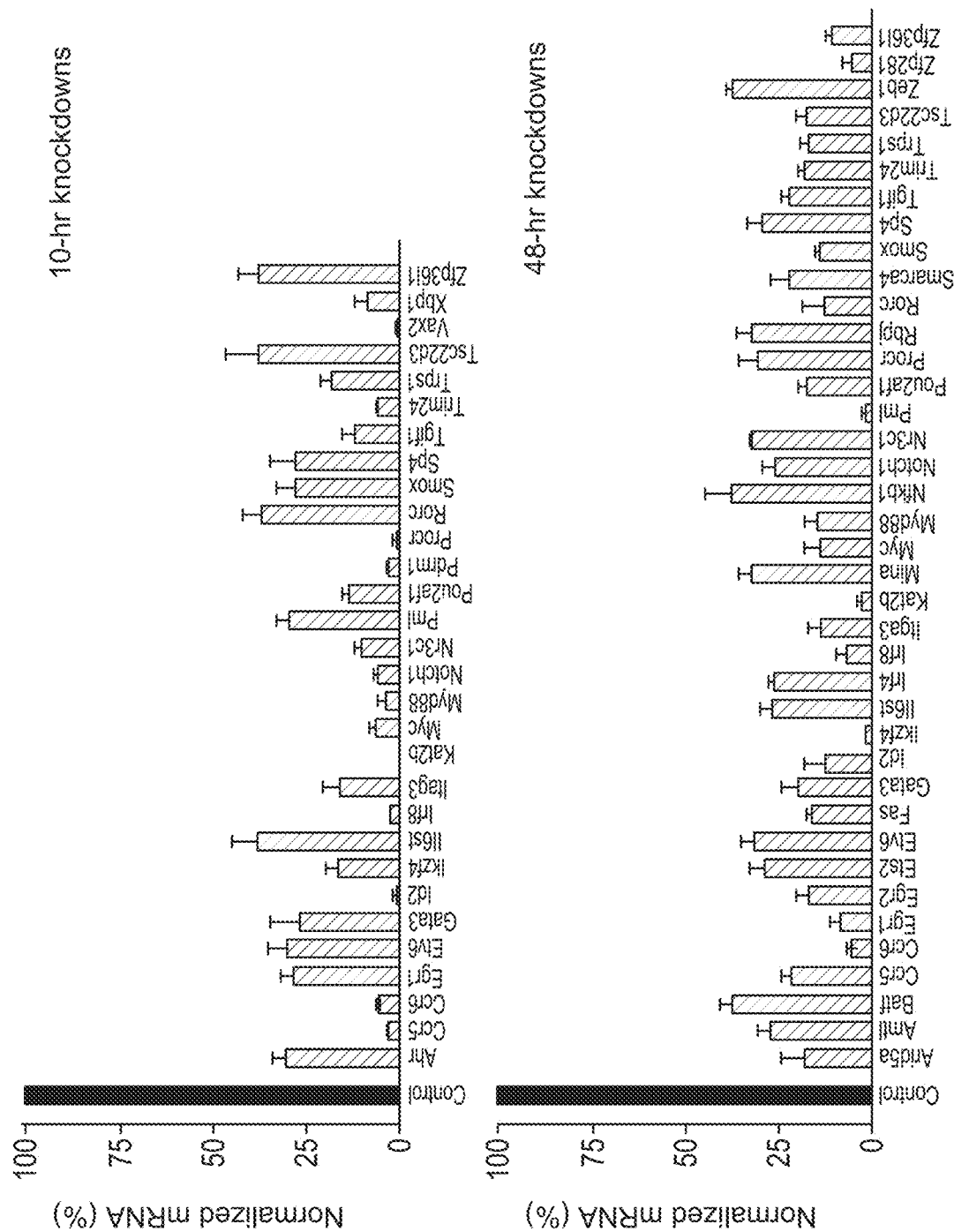

It was then attempted to perturb 60 genes with NW-mediated siRNA delivery and efficient knockdown (<60% transcript remaining at 48 hr post activation) was achieved for 34 genes (FIG. 3d and FIG. 11, Table S6.2). Knockout mice were obtained for seven other genes, two of which (Irf8 and Il17ra) were also in the knockdown set. Altogether, 39 of the 65 selected genes were successfully perturbed—29 regulators and 10 receptors—including 21 genes not previously associated with Th17 differentiation.

Nanowire-Based Screen Validates 39 Regulators in the Th17 Network:

the effects of the perturbation on gene expression were profiled at two time points. 28 of the perturbations were profiled at 10 hr after the beginning of differentiation, soon after the induction of ROR-γt (FIG. 6), and all of the perturbations were profiled at 48 hr, when the Th17 phenotype becomes more established (FIG. 1b). Two of the perturbations (Il17ra and Il21r knockouts) were also profiled at 60 hr.

In particular, the effects of perturbations at 48 hr post-activation on the expression of 275 signature genes were measured using the Nanostring nCounter system (Il17ra and Il21r knockouts were also measured at 60 hr).

Figure 12A:
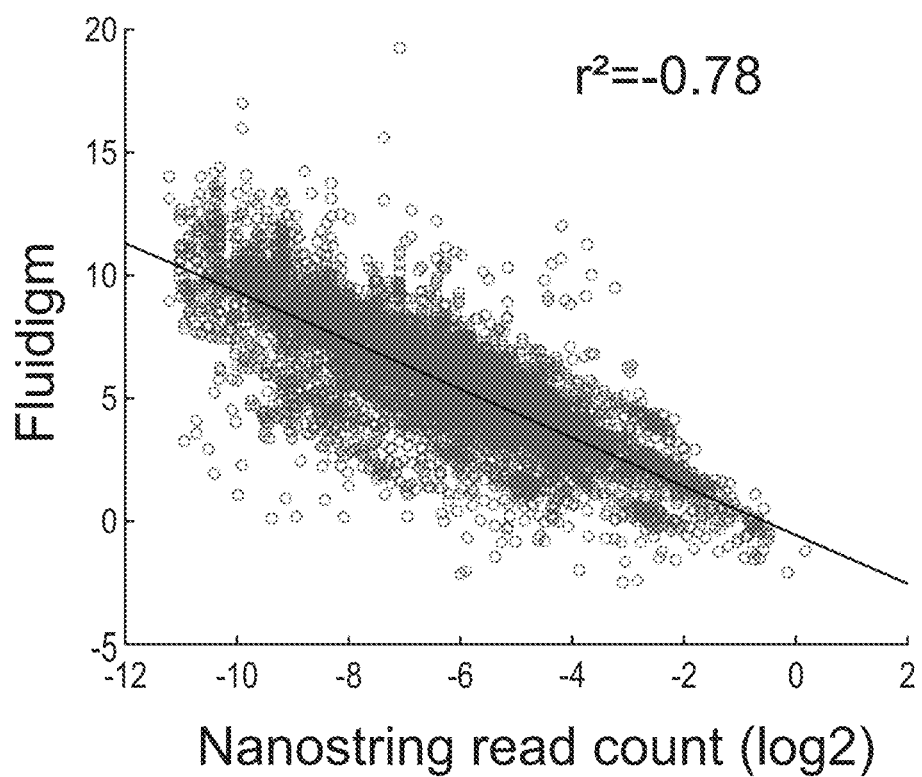
FIGS. 12A and 12B are a series of graphs depicting cross-validation of the Nanostring expression profiles for each nanowire-delivered knockdown using Fluidigm 96×96 gene expression chips.
Figure 12B:
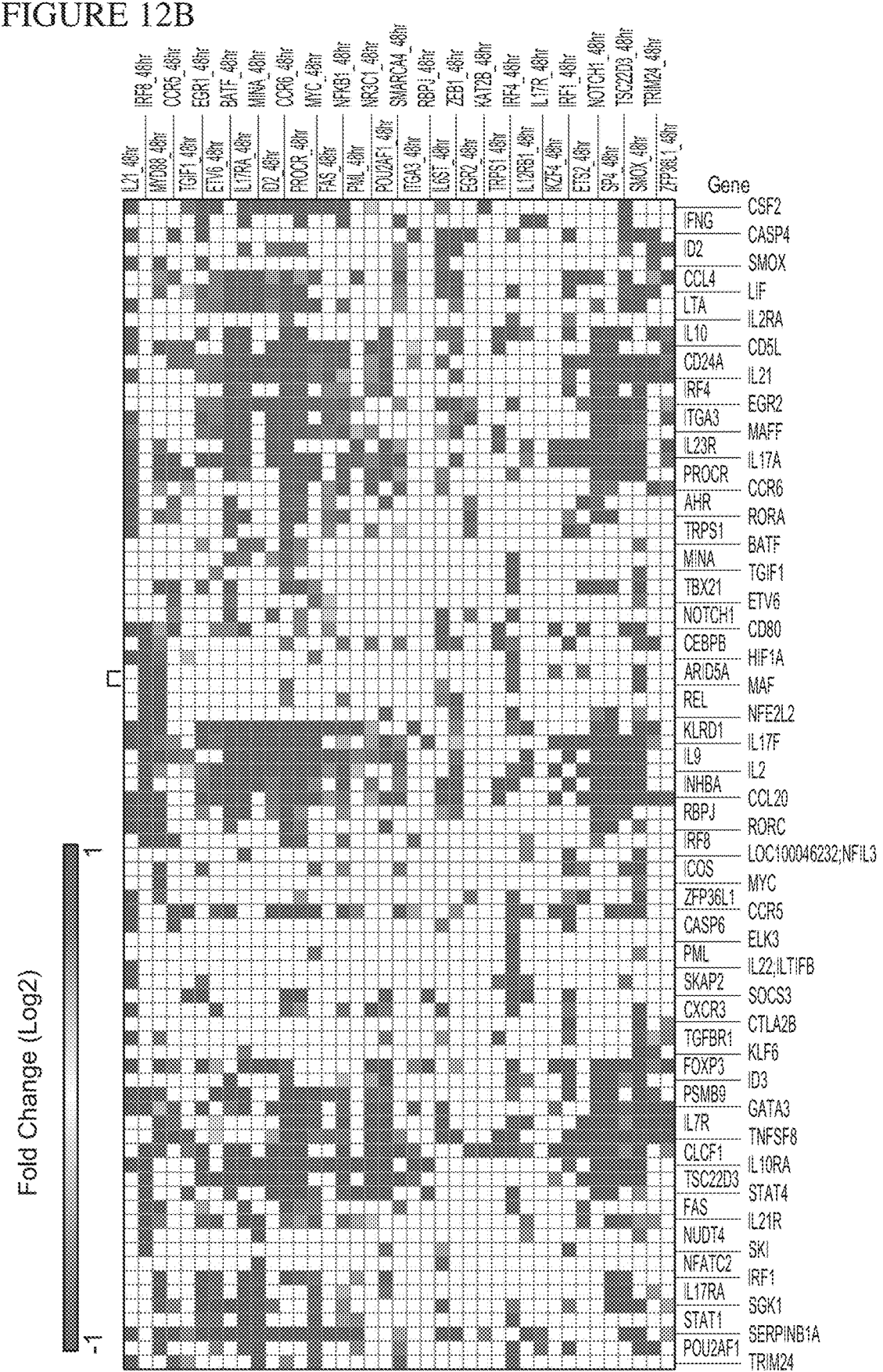

The signature genes were computationally chosen to cover as many aspects of the differentiation process as possible (see Methods in Example 1): they include most differentially expressed cytokines, TFs, and cell surface molecules, as well as representatives from each cluster (FIG. 1B), enriched function, and predicted targets in each network. For validation, a signature of 85 genes was profiled using the Fluidigm BioMark system, obtaining highly reproducible results (FIG. 12).

The signature genes for expression analysis were computationally chosen to cover as many aspects of the differentiation process as possible (see Methods in Example 1). They include the majority of the differentially expressed cytokines, TFs, and cell surface genes, as well as representative genes from each expression cluster (FIG. 1B), enriched biological function, and predicted targets of the regulators in each network. Importantly, since the signature includes most of the genes encoding the perturbed regulators, the connections between them (FIG. 4A, 'perturbed'), including feedback and feed-forward loops, could be determined.

The statistical significance of a perturbation's effect on a signature gene was scored by comparing to non-targeting siRNAs and to 18 control genes that were not differentially expressed (see Methods in Example 1, FIGS. 4a, all non-grey entries are significant). Perturbation of 26 of the tested regulators had a significant effect on the expression of at least 25 signature genes at the 48 hr time point (10% of signature genes that had any response). On average, a perturbation affected 40 genes, and 80% of the signature genes were affected by at least one regulator. Supporting the original network model (FIG. 2), there is a significant overlap between the genes affected by a regulator's knockdown and its predicted targets ($p \leq 0.01$, permutation test; see Methods in Example 1).

Figure 13:
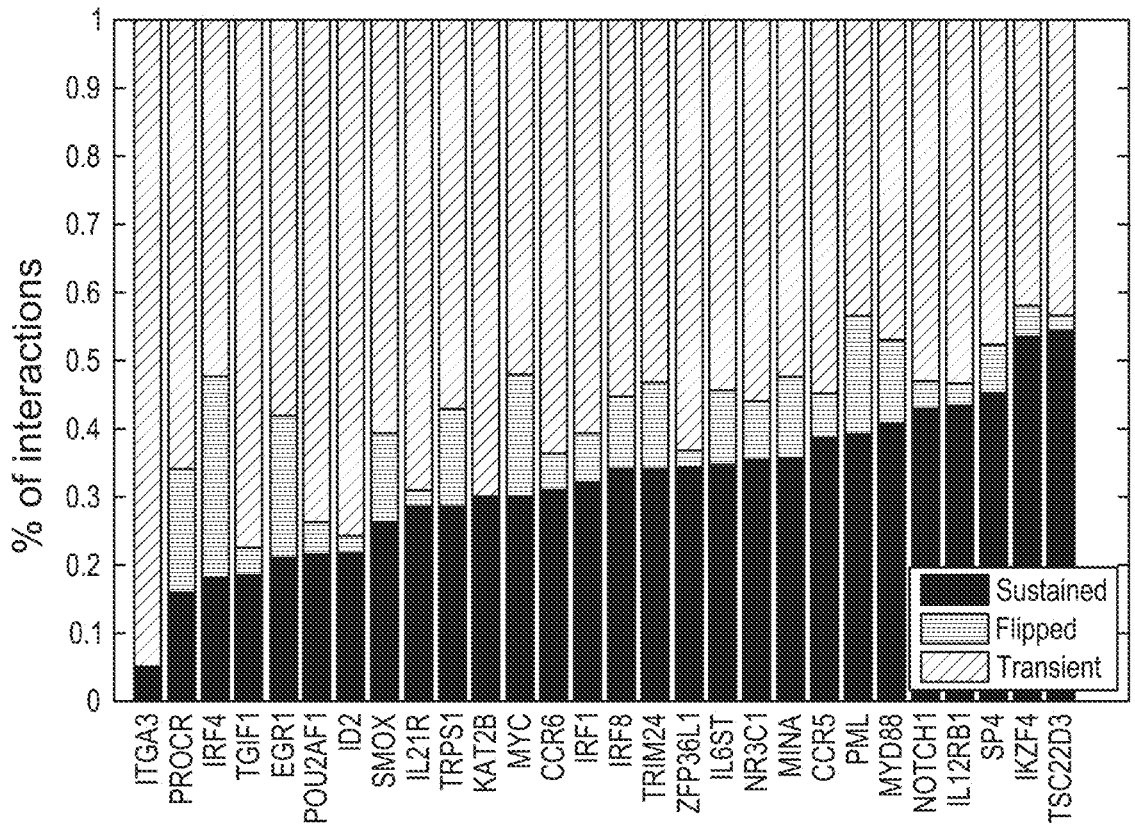
FIG. 13 is a graph depicting rewiring of the Th17 "functional" network between 10 hr to 48 hr post stimulation. For each regulator that was profiled at 10 hr and 48 hr, the percentage of "edges" (i.e., gene A is affected by perturbation of gene B) that either appear in the two time points with the same activation/repression logic (Sustained); appear only in one time point (Transient); or appear in both networks but with a different activation/repression logic (Flipped) were calculated. In the sustained edges, the perturbation effect (fold change) has to be significant in at least one of the time point (see Methods in Example 1), and consistent (in terms of activation/repression) in the other time point (using a more permissive cutoff of 1.25 fold).

To study the network's dynamics, the effect of 28 of the perturbations at 10 hr (shortly after the induction of ROR-γt) was measured using the Fluidigm Biomark system. It was found that 30% of the functional interactions are present with the same activation/repression logic at both 10 hr and 48 hr, whereas the rest are present only in one time point (FIG. 13). This is consistent with the extent of rewiring in the original model (FIG. 2b).

Whenever possible, the function of each regulator was classified as either positive or negative for Th17 differentiation. Specifically, at the 48 hr time point, perturbation of 22 of the regulators significantly attenuated IL-17A or IL-17F expression ('Th17 positive regulators', FIG. 4b, blue) and perturbation of another five, significantly increased IL-17 levels ('Th17 negative regulators', FIG. 4b, red). 12 of these strongly positive or negative regulators were not previously associated with Th17 cells (FIG. 4b, light grey halos around blue and red nodes). A color version of these figures can be found in Yosef et al., "Dynamic regulatory network controlling Th17 cell differentiation, Nature, vol. 496: 461-468 (2013)/doi: 10.1038/nature11981. Next, the role of these strong positive and negative regulators in the development of the Th17 phenotype was focused on.

Figure 14:
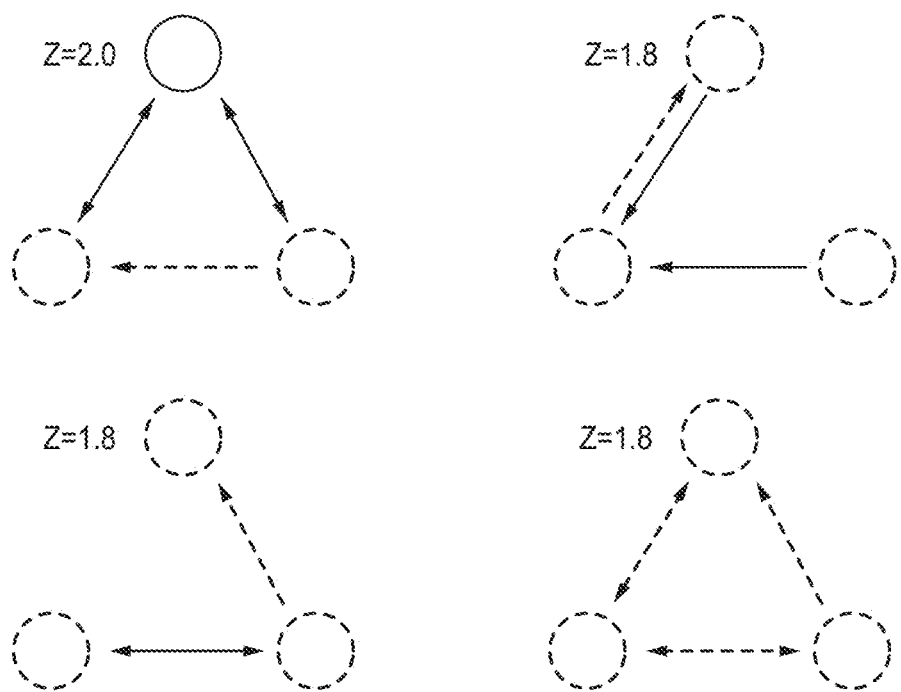
FIG. 14 is an illustration depicting "chromatic" network motifs. A color version of these figures can be found in Yosef et al., "Dynamic regulatory network controlling Th17 cell differentiation, Nature, vol. 496: 461-468 (2013)/doi: 10.1038/nature11981. A 'chromatic' network motif analysis was used to find recurring sub networks with the same topology and the same node and edge colors. Shown are the four significantly enriched motifs (p<0.05). Red nodes: positive regulators; blue nodes: negative regulator; red edges from A to B: knockdown of A downregulates B; blue edge: knockdown of A upregulates B. Motifs were found using the FANMOD software (Wernicke, S. & Rasche, F. FANMOD: a tool for fast network motif detection. Bioinformatics 22, 1152-1153, doi:10.1093/bioinformatics/bt1038 (2006)).

Two Coupled Antagonistic Circuits in the Th17 Network:

Characterizing each regulator by its effect on Th17 signature genes (e.g. IL17A, IL17F, FIG. 4b, grey nodes, bottom), it was found that at 48 hr the network is organized into two antagonistic modules: a module of 22 'Th17 positive factors' (FIG. 4b, blue nodes: 9 novel) whose perturbation decreased the expression of Th17 signature genes (FIG. 4b, grey nodes, bottom), and a module of 5 'Th17 negative factors' (FIG. 4b, red nodes: 3 novel) whose perturbation did the opposite. A color version of these figures can be found in Yosef et al., "Dynamic regulatory network controlling Th17 cell differentiation, Nature, vol. 496: 461-468 (2013)/doi: 10.1038/nature11981. Each of the modules is tightly intra-connected through positive, self-reinforcing interactions between its members (70% of the intra-module edges), whereas most (88%) inter-module interactions are negative. This organization, which is statistically significant (empirical p-value<$10^{-3}$; see Methods in Example 1, FIG. 14), is reminiscent to that observed previously in genetic circuits in yeast (Segré, D., Deluna, A., Church, G. M. & Kishony, R. Modular epistasis in yeast metabolism. Nat. Genet. 37, 77-83, doi:10.1038/ng1489 (2005); Peleg, T., Yosef, N., Ruppin, E. & Sharan, R. Network-free inference of knockout effects in yeast. PLoS Comput Biol 6, e1000635, doi:10.1371/journal.pcbi.1000635 (2010)). At 10 hrs, the same regulators do not yield this clear pattern (p>0.5), suggesting that at that point, the network is still malleable.

The two antagonistic modules may play a key role in maintaining the balance between Th17 and other T cell subsets and in self-limiting the pro-inflammatory status of Th17 cells. Indeed, perturbing Th17 positive factors also induces signature genes of other T cell subsets (e.g., Gata3, FIG. 4b, grey nodes, top), whereas perturbing Th17 negative factors suppresses them (e.g., Foxp3, Gata3, Stat4, and Tbx21).

Example 5: Validation and Characterization of Novel Factors

The studies presented herein focused on the role of 12 of the positive or negative factors (including 11 of the 12 novel factors that have not been associated with Th17 cells; FIG. 4b, light grey halos). RNA-Seq was used after perturbing each factor to test whether its predicted targets (FIG. 2) were affected by perturbation (FIG. 4c, Venn diagram, top). Highly significant overlaps ($p \leq 10^{-5}$) for three of the factors (Egr2, Irf8, and Sp4) that exist in both datasets were found, and a border-line significant overlap for the fourth (Smarca4) was found, validating the quality of the edges in the network.

Figure 15A:
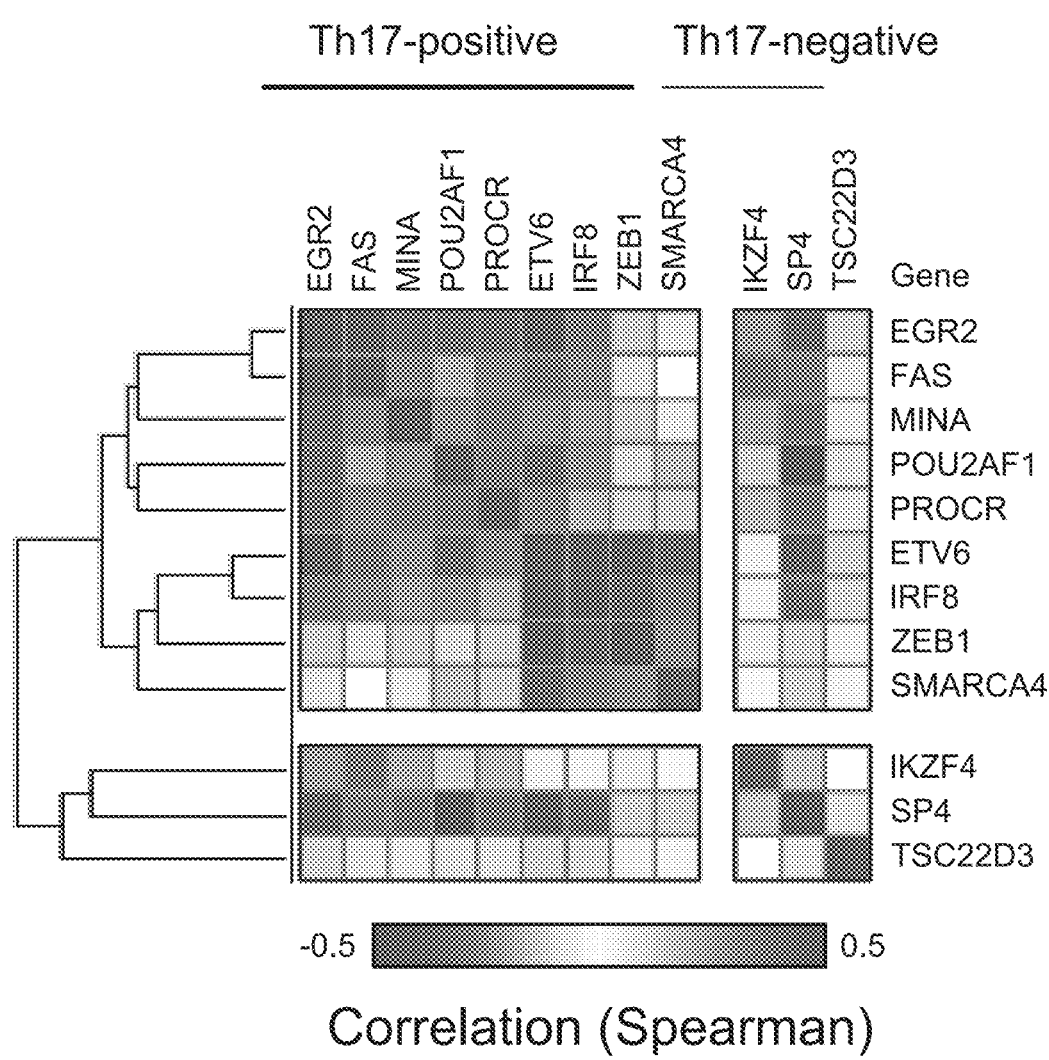
FIGS. 15A, 15B, and 15C are a series of graphs depicting RNA-seq analysis of nanowire-delivered knockdowns. A color version of these figures can be found in Yosef et al., "Dynamic regulatory network controlling Th17 cell differentiation, Nature, vol. 496: 461-468 (2013)/doi: 10.1038/nature11981.

Next, the designation of each of the 12 factors as 'Th17 positive' or 'Th17 negative' was assessed by comparing the set of genes that respond to that factor's knockdown (in RNA-Seq) to each of the 20 clusters (FIG. 1b). Consistent with the original definitions, knockdown of a 'Th17 positive' regulator down-regulated genes in otherwise induced clusters, and up-regulated genes in otherwise repressed or un-induced clusters (and vice versa for 'Th17 negative' regulators; FIG. 4d and FIGS. 15a,b). The genes affected by either positive or negative regulators also significantly overlap with those bound by key CD4+ transcription regulators (e.g., Foxp3 (Marson, A. et al. Foxp3 occupancy and regulation of key target genes during T cell stimulation. Nature 445, 931-935, doi:10.1038/nature05478 (2007); Zheng, Y. et al. Genome-wide analysis of Foxp3 target genes in developing and mature regulatory T cells. Nature 445, 936-940, doi:10.1038/nature05563 (2007)), Batf, Irf4, and ROR-γt (Glasmacher, E. et al. A Genomic Regulatory Element That Directs Assembly and Function of Immune-Specific AP-1-IRF Complexes. Science (New York, N.Y.), doi:10.1126/science.1228309 (2012); Ciofani, M. et al. A Validated Regulatory Network for Th17 Cell Specification. Cell, doi: 10.1016/j.cell.2012.09.016 (2012)), Xiao et al., unpublished data). For instance, genes that are down-regulated following knockdown of the 'Th17-positive' regulator Mina are highly enriched ($p \leq 10^{-6}$) in the late induced clusters (e.g., C19, C20). Conversely, genes in the same late induced clusters become even more up-regulated following knockdown of the 'Th17 negative' regulator Sp4.

Figure 5A:
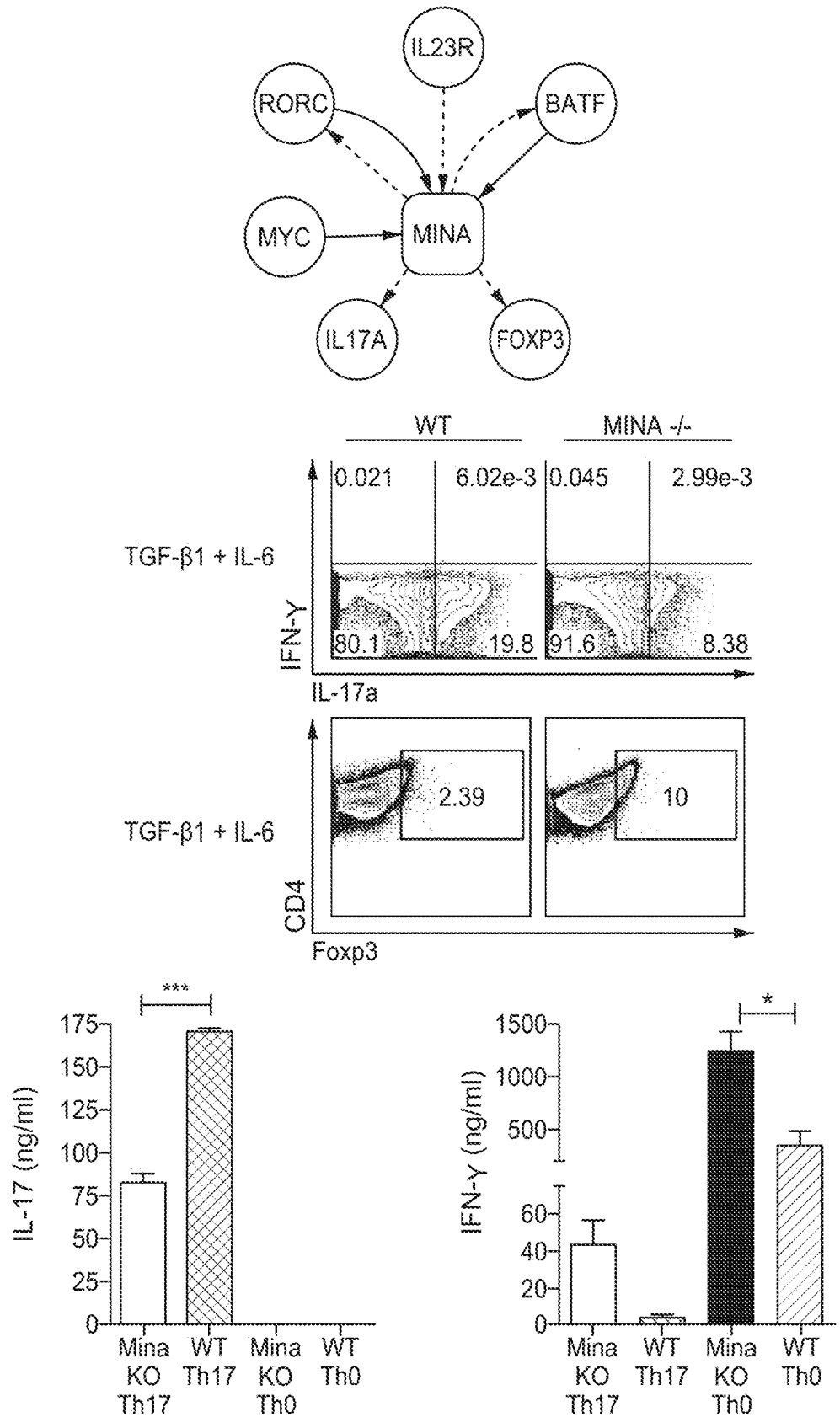
Figure 15B:
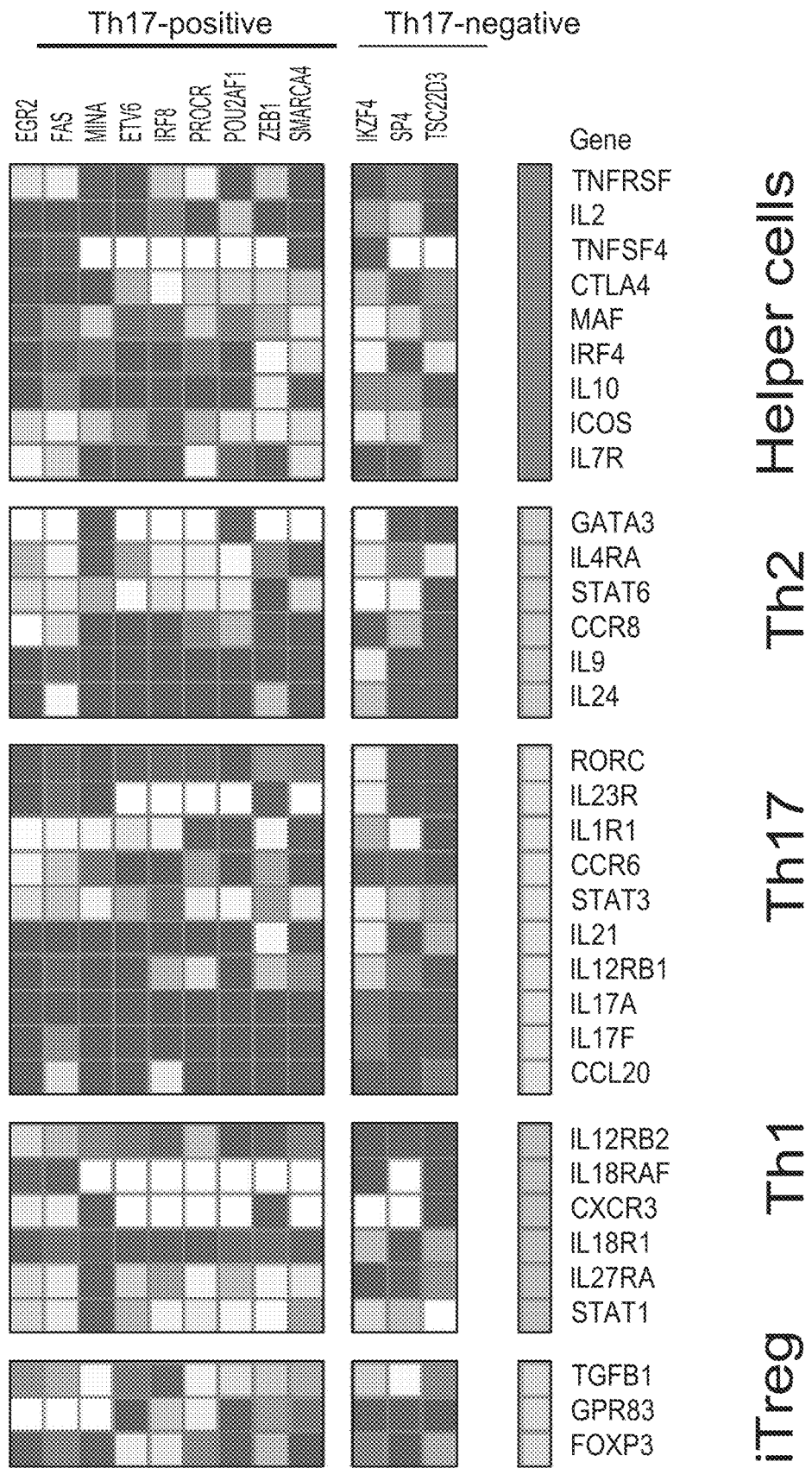
Figure 15C:
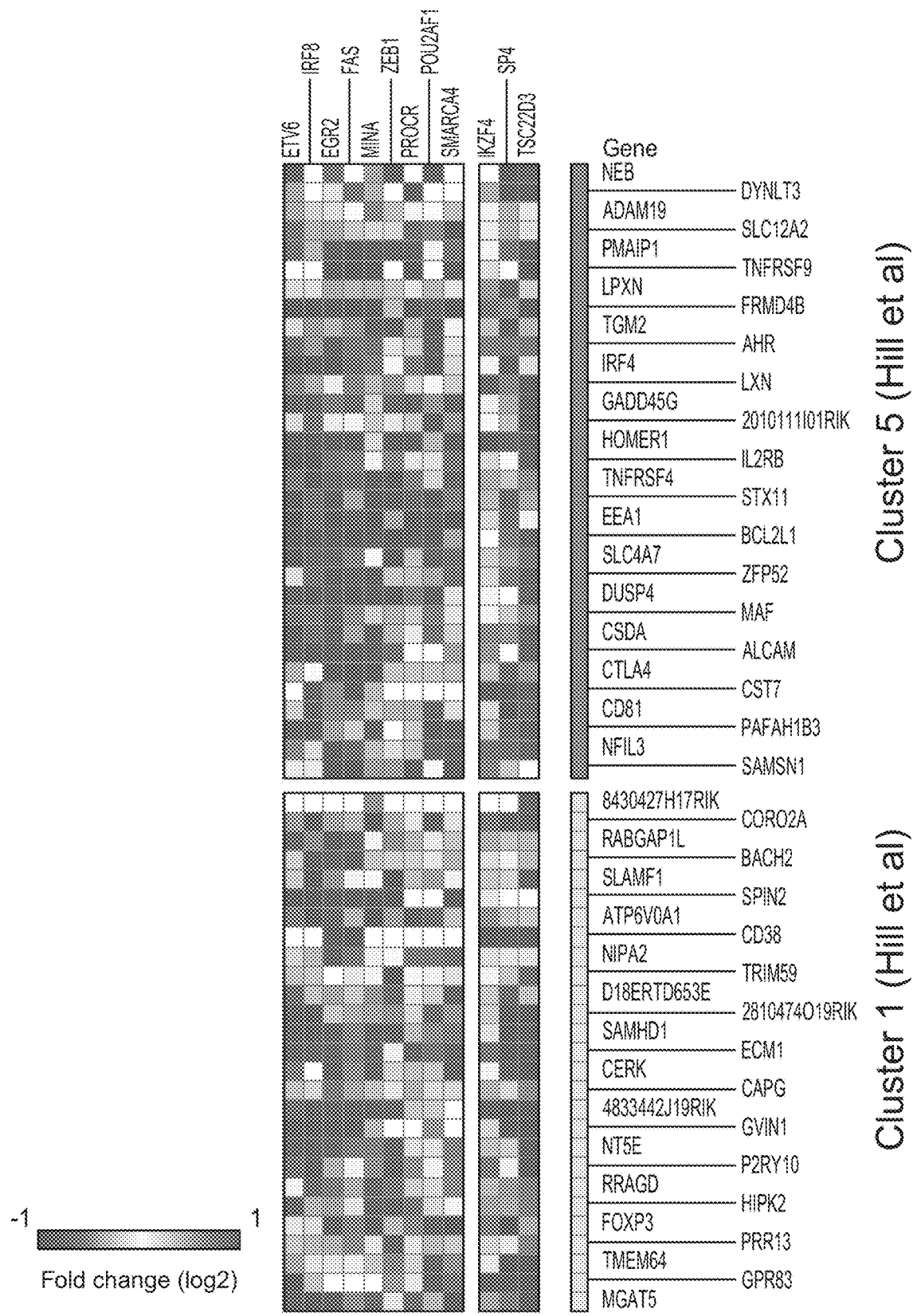

Mina Promotes the Th17 Program and Inhibits the Foxp3 Program:

Knockdown of Mina, a chromatin regulator from the Jumonji C (JmjC) family, represses the expression of signature Th17 cytokines and TFs (e.g. ROR-γt, Batf, Irf4) and of late-induced genes (clusters C9, C19; $p \leq 10^{-5}$), while increasing the expression of Foxp3, the master TF of Treg cells. Mina is strongly induced during Th17 differentiation (cluster C7), is down-regulated in IL23r−/− Th17 cells, and is a predicted target of Batf (Glasmacher, E. et al. A Genomic Regulatory Element That Directs Assembly and Function of Immune-Specific AP-1-IRF Complexes. Science, doi: 10.1126/science.1228309 (2012)), ROR-γt (Glasmacher et al., Science 2012), and Myc in the model (FIG. 5a). Mina was shown to suppress Th2 bias by interacting with the TF NFAT and repressing the IL-4 promoter (Okamoto, M. et al. Mina, an I14 repressor, controls T helper type 2 bias. Nat. Immunol. 10, 872-879, doi:10.1038/ni.1747 (2009)). However, in the cells, Mina knockdown did not induce Th2 genes, suggesting an alternative mode of action via positive feedback loops between Mina, Batf and ROR-γt (FIG. 5a, left). Consistent with this model, Mina expression is reduced in Th17 cells from ROR-γt-knockout mice, and the Mina promoter was found to be bound by ROR-γt by ChIP-Seq (data not shown). Finally, the genes induced by Mina knockdown significantly overlap with those bound by Foxp3 in Treg cells (Marson et al., Nature 2007; Zheng et al., Nature 2007) ($P<10^{-25}$) and with a cluster previously linked to Foxp3 activity in Treg cells (Hill, J. A. et al. Foxp3 transcription-factor-dependent and -independent regulation of the regulatory T cell transcriptional signature. Immunity 27, 786-800, doi:S1074-7613(07)00492-X [pii]10.1016/j.immuni.2007.09.010 (2007)) (FIG. 15c). When comparing to previously defined transcriptional signatures of Treg cells (compared to conventional T cells, (Hill, J. A. et al. Foxp3 transcription-factor-dependent and -independent regulation of the regulatory T cell transcriptional signature. Immunity 27, 786-800, doi:10.1016/j.immuni.2007.09.010 (2007))), genes that are induced in the Mina knockdown are enriched in a cluster tightly linked to functional activity of FoxP3. Conversely, genes down-regulated in the Mina knockdown are more directly responsive to TCR and IL-2 and less responsive to Foxp3 in Treg cells (FIG. 15c).

Figure 16A:
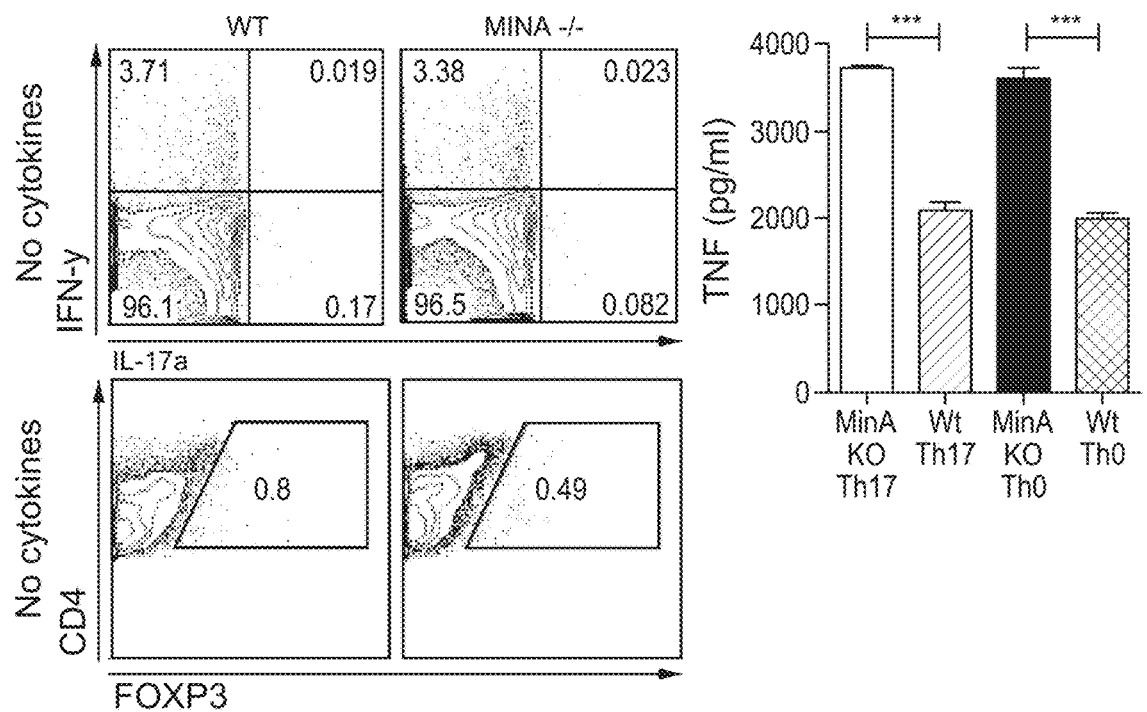

To further analyze the role of Mina, IL-17a and Foxp3 expression was measured following differentiation of naïve T cells from Mina−/− mice. Mina−/− cells had decreased IL-17a and increased Foxp3 compared to wild-type (WT) cells, as detected by intracellular staining (FIG. 5a). Cytokine analysis of the corresponding supernatants confirmed a decrease in IL-17a production and an increase in IFN-γ (FIG. 5a) and TNF-α (FIG. 16a). Under Th17 differentiation conditions, loss of Mina resulted in a decrease in IL-17 expression and increase in FoxP3, as detected by intracellular staining (FIG. 5a). Cytokine analysis of the supernatants from these differentiating cultures confirmed a decrease in IL-17 production with a commensurate increase in IFNγ (FIG. 5a) and TNFα (FIG. 16a).

The reciprocal relationship between Tregs/Th17 cells has been well described (Korn, T. et al. IL-21 initiates an alternative pathway to induce proinflammatory T(H)17 cells. Nature 448, 484-487, doi:10.1038/nature05970 (2007)), and it was assumed that this is achieved by direct binding of the ROR-γt/Foxp3 TFs. However, the analysis suggests a critical role for the regulator Mina in mediating this process. This suggests a model where Mina, induced by ROR-γt and Batf, promotes transcription of ROR-γt, while suppressing induction of Foxp3, thus affecting the reciprocal Tregs/Th17 balance (Korn, et al., Nature 2007)) by favoring rapid Th17 differentiation.

Figure 5B:
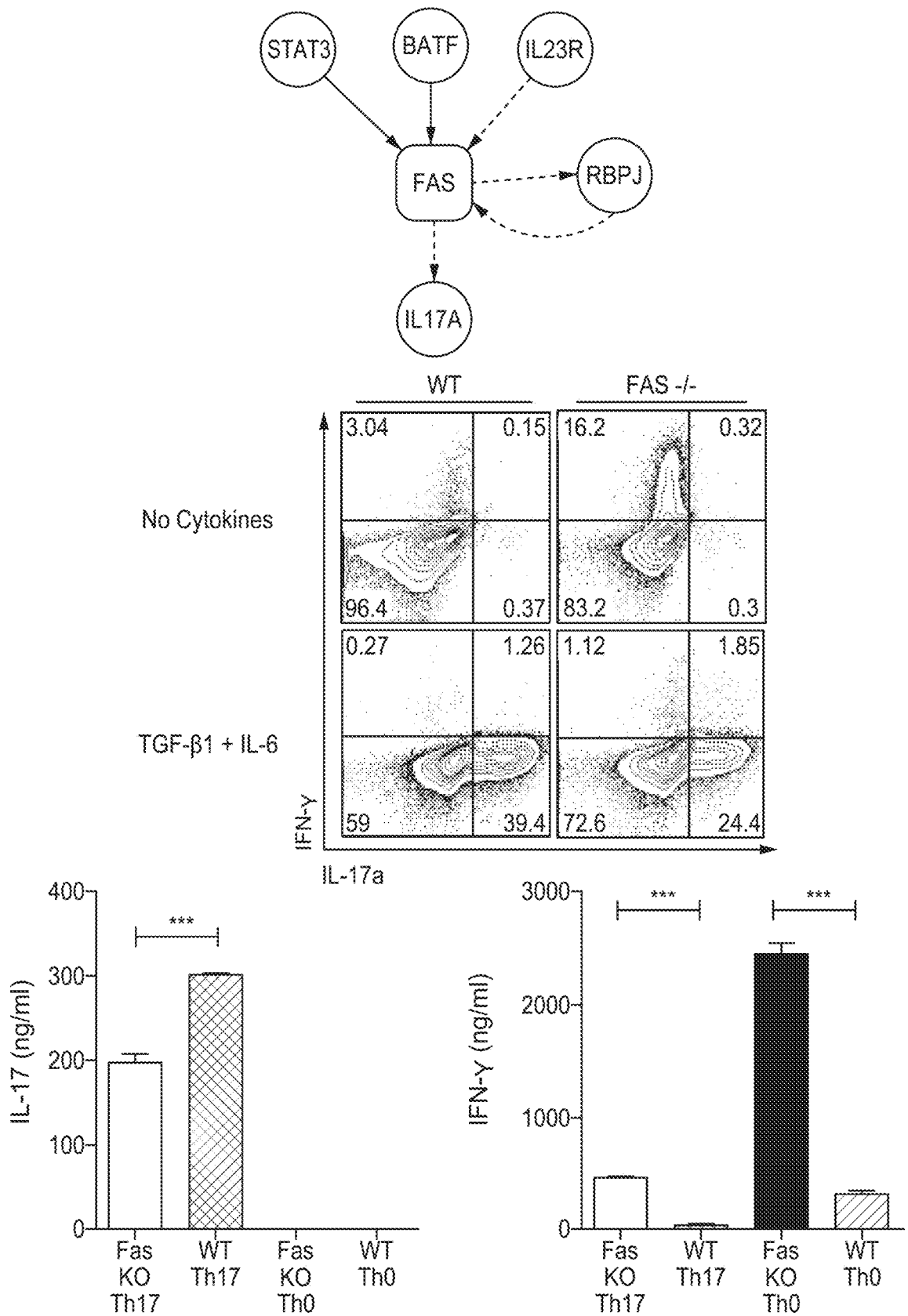

Fas Promotes the Th17 Program and Suppresses IFN-γ Expression:

Fas, the TNF receptor superfamily member 6, is another Th17 positive regulator (FIG. 5b). Fas is induced early, and is a target of Stat3 and Batf in the model. Fas knockdown represses the expression of key Th17 genes (e.g., IL-17a, IL-17f, Hif1a, Irf4, and Rbpj) and of the induced cluster C14, and promotes the expression of Th1-related genes, including IFN-γ receptor 1 and Klrd1 (Cd94; by RNA-Seq, FIG. 4, FIG. 5b, and FIG. 15). Fas and Fas-ligand deficient mice are resistant to the induction of autoimmune encephalomyelitis (EAE) (Waldner, H., Sobel, R. A., Howard, E. & Kuchroo, V. K. Fas- and FasL-deficient mice are resistant to induction of autoimmune encephalomyelitis. J Immunol 159, 3100-3103 (1997)), but have no defect in IFN-γ or Th1 responses. The mechanism underlying this phenomenon was never studied.

To explore this, T cells from Fas−/− mice (FIG. 5b, FIG. 16c) were differentiated. Consistent with the knockdown analysis, expression of IL-17a was strongly repressed and IFN-γ production was strongly increased under both Th17 and Th0 polarizing conditions (FIG. 5b). These results suggest that besides being a death receptor, Fas may play an important role in controlling the Th1/Th17 balance, and Fas−/− mice may be resistant to EAE due to lack of Th17 cells.

Figure 5C:
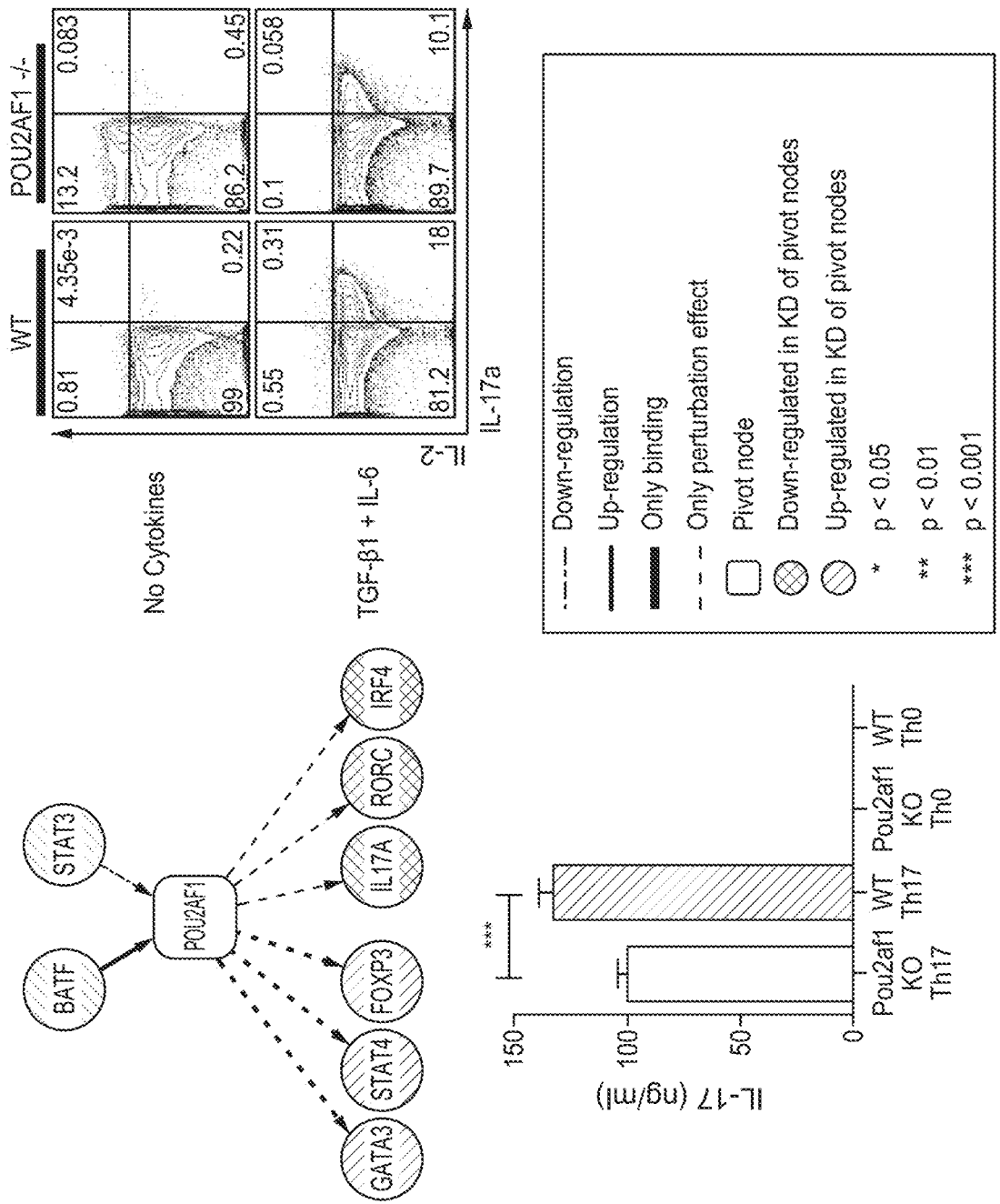
Figure 16B:
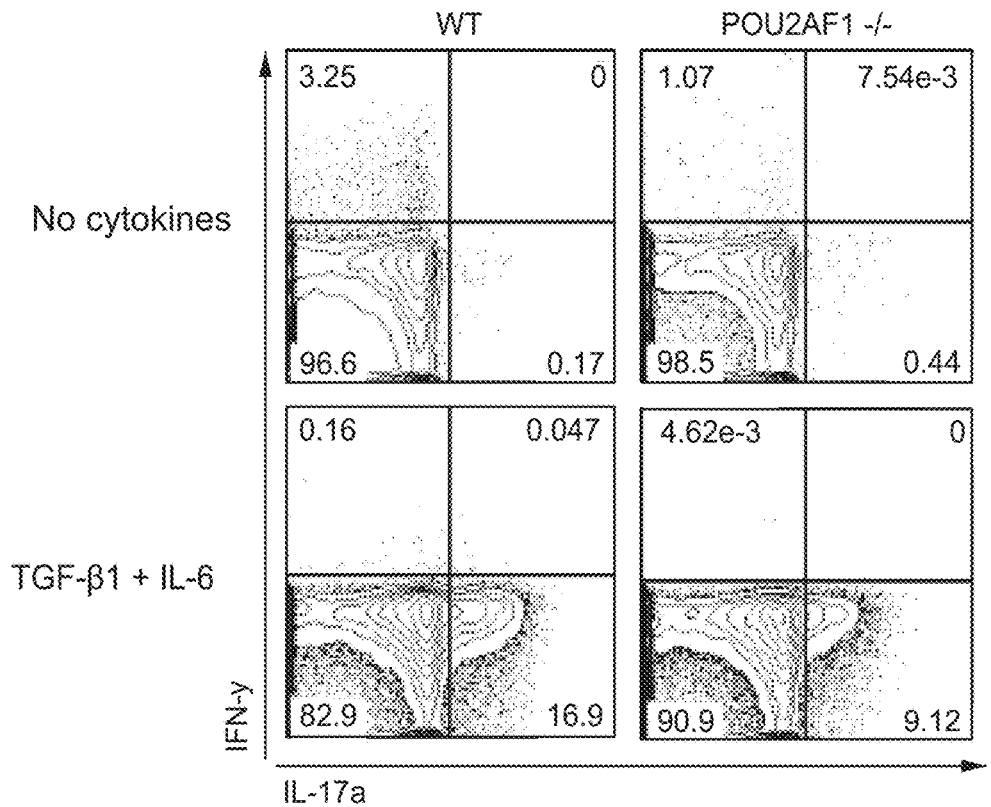
Figure 16D:
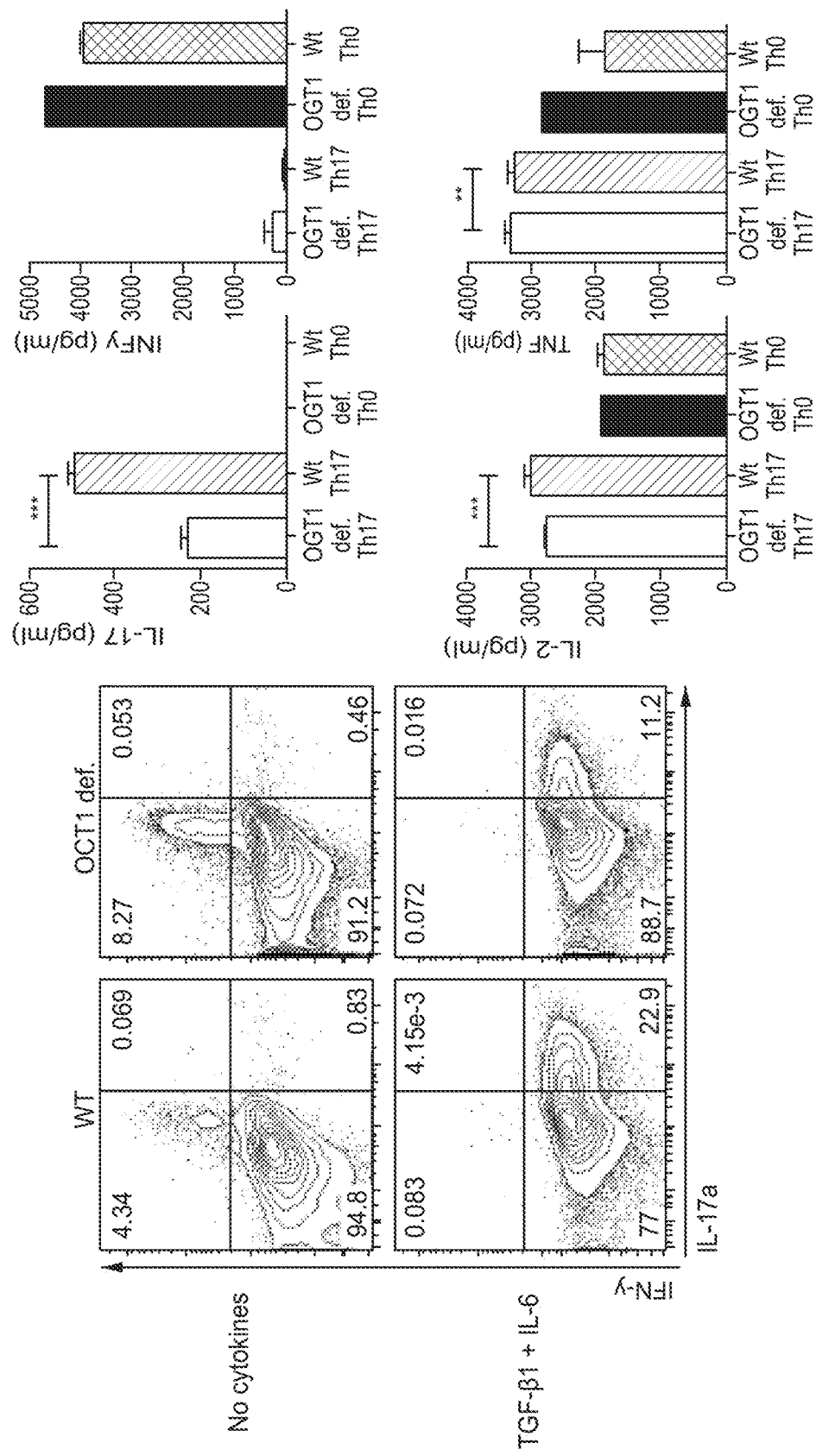

Pou2af1 Promotes the Th17 Program and Suppresses IL-2 Expression:

Knockdown of Pou2af1 (OBF1) strongly decreases the expression of Th17 signature genes (FIG. 5c) and of intermediate- and late-induced genes (clusters C19 and C20, $p<10^{-7}$), while increasing the expression of regulators of other CD4+ subsets (e.g., Foxp3, Stat4, Gata3) and of genes in non-induced clusters (clusters C2 and C16 $p<10^{-9}$). Pou2af1's role in T cell differentiation has not been explored (Teitell, M. A. OCA-B regulation of B-cell development and function. Trends Immunol 24, 546-553 (2003)). To investigate its effects, T cells from Pou2af1−/− mice were differentiated (FIG. 5c, FIG. 16b). Compared to WT cells, IL-17a production was strongly repressed. Interestingly, IL-2 production was strongly increased in Pou2af1−/− T cells under non-polarizing (Th0) conditions. Thus, Pou2af1 may promote Th17 differentiation by blocking production of IL-2, a known endogenous repressor of Th17 cells (Laurence, A. et al. Interleukin-2 signaling via STAT5 constrains T helper 17 cell generation. Immunity 26, 371-381, doi:S1074-7613(07) 00176-8 [pii]10.1016/j.immuni.2007.02.009 (2007)). Pou2af1 acts as a transcriptional co-activator of the TFs OCT1 or OCT2 (Teitell, Trends Immunol 2003). IL-17a production was also strongly repressed in Oct1-deficient cells (FIG. 16d), suggesting that Pou2af1 may exert some of its effects through this co-factor.

TSC22d3 May Limit Th17 Differentiation and Pro-Inflammatory Function:

Knockdown of the TSC22 domain family protein 3 (Tsc22d3) increases the expression of Th17 cytokines (IL-17a, IL-21) and TFs (ROR-γt, Rbpj, Batf), and reduces Foxp3 expression. Previous studies in macrophages have shown that Tsc22d3 expression is stimulated by glucocorticoids and IL-10, and it plays a key role in their anti-inflammatory and immunosuppressive effects (Choi, S.-J. et al. Tsc-22 enhances TGF-beta signaling by associating with Smad4 and induces erythroid cell differentiation. Mol. Cell. Biochem. 271, 23-28 (2005)). Tsc22d3 knockdown in Th17 cells increased the expression of IL-10 and other key genes that enhance its production (FIG. 5d). Although IL-10 production has been shown (Korn et al., Nature 2007; Peters, A., Lee, Y. & Kuchroo, V. K. The many faces of Th17 cells. Curr. Opin. Immunol. 23, 702-706, doi:10.1016/j.coi.2011.08.007 (2011); Chaudhry, A. et al. Interleukin-10 signaling in regulatory T cells is required for suppression of Th17 cell-mediated inflammation. Immunity 34, 566-578, doi:10.1016/j.immuni.2011.03.018 (2011)) to render Th17 cells less pathogenic in autoimmunity, co-production of IL-10 and IL-17a may be the indicated response for clearing certain infections like *Staphylococcus aureus* at mucosal sites (Zielinski, C. E. et al. Pathogen-induced human TH17 cells produce IFN-γ or IL-10 and are regulated by IL-1β. Nature 484, 514-518, doi:10.1038/nature10957 (2012)). This suggests a model where Tsc22d3 is part of a negative feedback loop for the induction of a Th17 cell subtype that coproduce IL-17 and IL-10 and limits their pro-inflammatory capacity. Tsc22d3 is induced in other cells in response to the steroid Dexamethasone (Jing, Y. et al. A mechanistic study on the effect of dexamethasone in moderating cell death in Chinese Hamster Ovary cell cultures. Biotechnol Prog 28, 490-496, doi:10.1002/btpr.747 (2012)), which represses Th17 differentiation and ROR-γt expression (Hu, S. M., Luo, Y. L., Lai, W. Y. & Chen, P. F. [Effects of dexamethasone on intracellular expression of Th17 cytokine interleukin 17 in asthmatic mice]. Nan Fang Yi Ke Da Xue Xue Bao 29, 1185-1188 (2009)). Thus, Tsc22d3 may mediate this effect of steroids.

To further characterize Tsc22d3's role, ChIP-Seq was used to measure its DNA-binding profile in Th17 cells and RNA-Seq following its knockdown to measure its functional effects. There is a significant overlap between Tsc22d3's functional and physical targets ($P<0.01$, e.g., IL-21, Irf4; see Methods in Example 1). For example, Tsc22d3 binds in proximity to IL-21 and Irf4, which also become up regulated in the Tsc22d3 knockdown. Furthermore, the Tsc22d3 binding sites significantly overlap those of major Th17 factors, including Batf, Stat3, Irf4, and ROR-γt (>5 fold enrichment; FIG. 5d, and see Methods in Example 1). This suggests a model where Tsc22d3 exerts its Th17-negative function as a transcriptional repressor that competes with Th17 positive regulators over binding sites, analogous to previous findings in CD4+ regulation (Ciofani et al., Cell 2012; Yang, X. P. et al. Opposing regulation of the locus encoding IL-17 through direct, reciprocal actions of STAT3 and STAT5. Nat. Immunol. 12, 247-254, doi:10.1038/ni.1995 (2011)).

Example 6. Protein C Receptor (PROCR) Regulates Pathogenic Phenotype of Th17 Cells Th17 cells, a recently identified T cell subset, have been implicated in driving inflammatory autoimmune responses as well as mediating protective responses against certain extracellular pathogens. Based on factors such as molecular signature, Th17 cells are classified as pathogenic or non-pathogenic. (See e.g., Lee et al., "Induction and molecular signature of pathogenic Th17 cells," Nature Immunology, vol. 13(10): 991-999 and online methods).

It should be noted that the terms "pathogenic" or "non-pathogenic" as used herein are not to be construed as implying that one Th17 cell phenotype is more desirable than the other. As will be described herein, there are instances in which inhibiting the induction of pathogenic Th17 cells or modulating the Th17 phenotype towards the non-pathogenic Th17 phenotype or towards another T cell phenotype is desirable. Likewise, there are instances where inhibiting the induction of non-pathogenic Th17 cells or modulating the Th17 phenotype towards the pathogenic Th17 phenotype or towards another T cell phenotype is desirable. For example, pathogenic Th17 cells are believed to be involved in immune responses such as autoimmunity and/or inflammation. Thus, inhibition of pathogenic Th17 cell differentiation or otherwise decreasing the balance of Th17 T cells towards non-pathogenic Th17 cells or towards another T cell phenotype is desirable in therapeutic strategies for treating or otherwise ameliorating a symptom of an immune-related disorder such as an autoimmune disease or an inflammatory disorder. In another example, depending on the infection, non-pathogenic or pathogenic Th17 cells are believed to be desirable in building a protective immune response in infectious diseases and other pathogen-based disorders. Thus, inhibition of non-pathogenic Th17 cell differentiation or otherwise decreasing the balance of Th17 T cells towards pathogenic Th17 cells or towards another T cell phenotype or vice versa is desirable in therapeutic strategies for treating or otherwise ameliorating a symptom of an immune-related disorder such as infectious disease.

Th17 cells are considered to be pathogenic when they exhibit a distinct pathogenic signature where one or more of the following genes or products of these genes is upregulated in TGF-β3-induced Th17 cells as compared to TGF-β1-induced Th17 cells: Cxcl3, Il22, Il3, Ccl4, Gzmb, Lrmp, Ccl5, Casp1, Csf2, Ccl3, Tbx21, Icos, Il7r, Stat4, Lgals3 or Lag3. Th17 cells are considered to be non-pathogenic when they exhibit a distinct non-pathogenic signature where one or more of the following genes or products of these genes is down-regulated in TGF-β3-induced Th17 cells as compared to TGF-β1-induced Th17 cells: Il6st, Il1rn, Ikzf3, Maf Ahr, 119 or 1110.

A temporal microarray analysis of developing Th17 cells was performed to identify cell surface molecules, which are differentially expressed in Th17 cells and regulate the development of Th17 cells. PROCR was identified as a receptor that is differentially expressed in Th17 cells and found its expression to be regulated by Th17-specific transcription regulators.

Protein C receptor (PROCR; also called EPCR or CD201) is primarily expressed on endothelial cells, $CD8^+$ dendritic cells and was also reported to be expressed to lower levels on other hematopoietic and stromal cells. It binds to activated protein C as well as factor VII/VIIa and factor Xa and was shown to have diverse biological functions, including anticoagulant, cytoprotective, anti-apoptotic and anti-inflammatory activity. However, prior to these studies, the function of PROCR in T cells had not been explored.

The biological function of PROCR and its ligand activated protein C in Th17 cells was analyzed, and it was found that it decreased the expression of some of the genes identified as a part of the pathogenic signature of Th17 cells. Furthermore, PROCR expression in Th17 cells reduced the pathogenicity of Th17 cells and ameliorated disease in a mouse model for human multiple sclerosis.

These results imply that PROCR functions as a regulatory gene for the pathogenicity of Th17 cells through the binding of its ligand(s). It is therefore conceivable that the regulation of this pathway might be exploited for therapeutic approaches to inflammatory and autoimmune diseases.

These studies are the first to describe the Th17-specific expression of PROCR and its role in reducing autoimmune Th17 pathogenicity. Thus, activation of PROCR through antibodies or other agonists are useful as a therapeutic strategy in an immune response such as inflammatory autoimmune disorders. In addition, blocking of PROCR through antibodies or other inhibitors could be exploited to augment protective Th17 responses against certain infectious agents and pathogens.

Figure 30A:
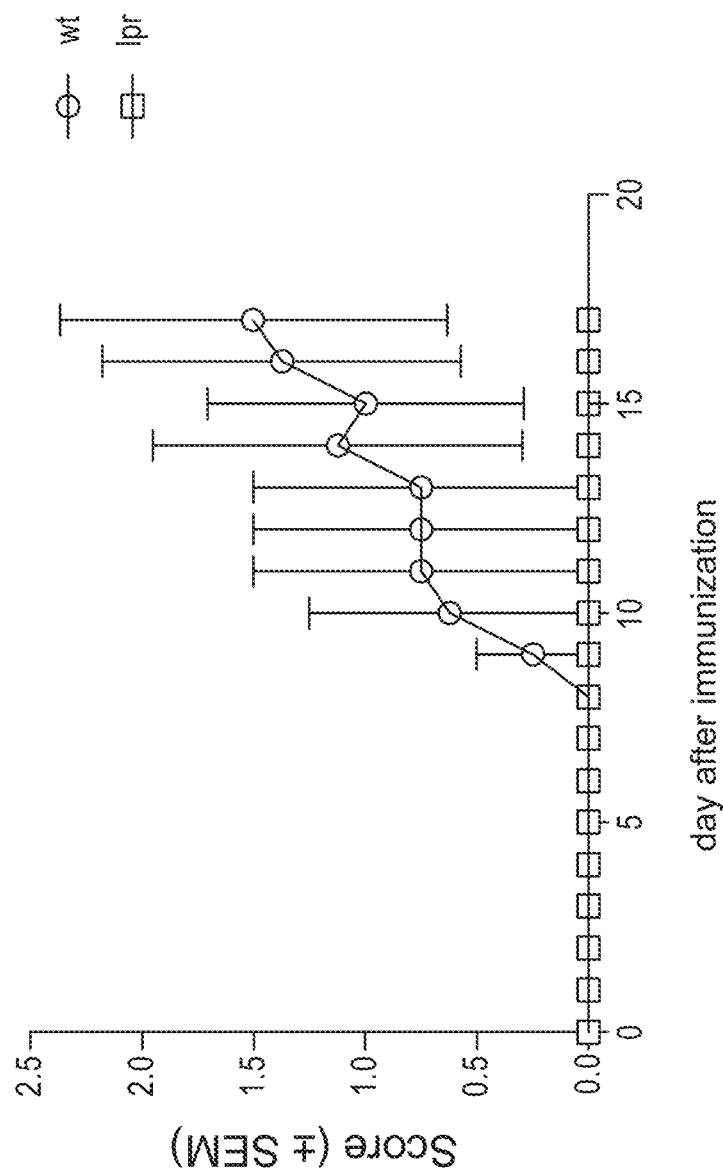
FIGS. 30A and 30B are a series of graphs depicting that FAS-deficient mice are resistant to EAE. Wild type (WT) or FAS-deficient (LPR) mice were immunized with 100 µg MOG$_{35-55}$ in CFA s.c. and received pertussis toxin i.v. to induce EAE.
Figure 30B:
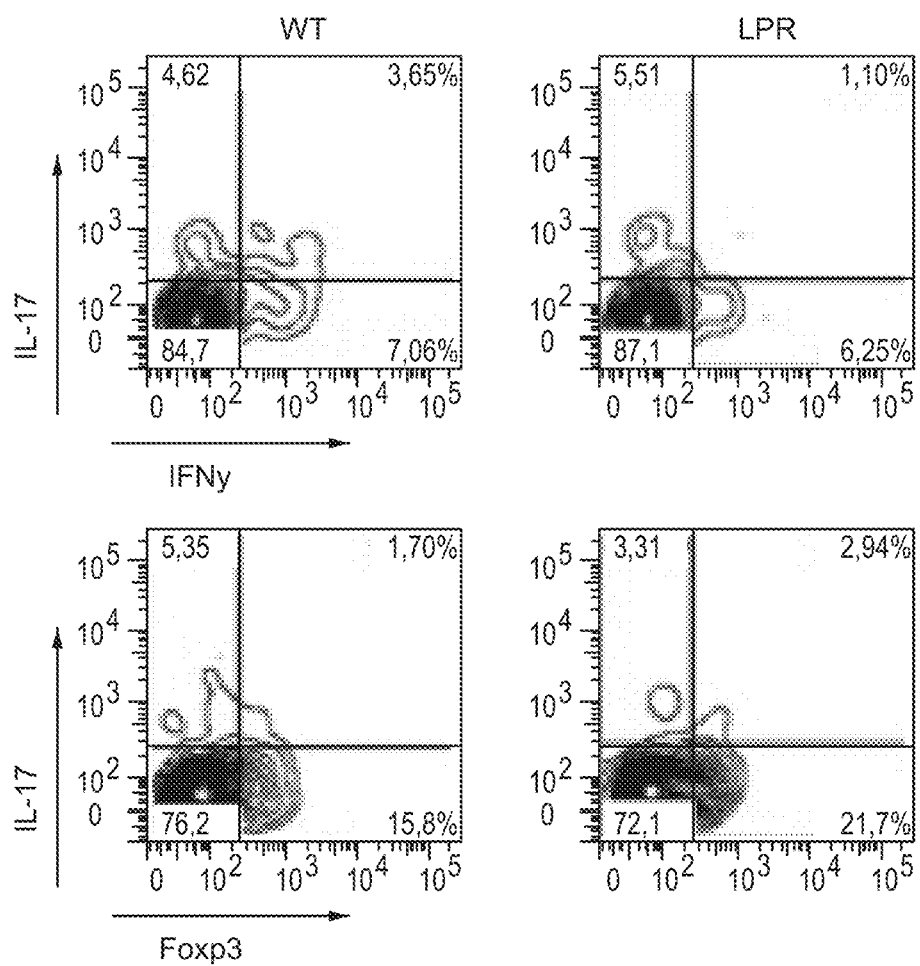
Figure 31A:
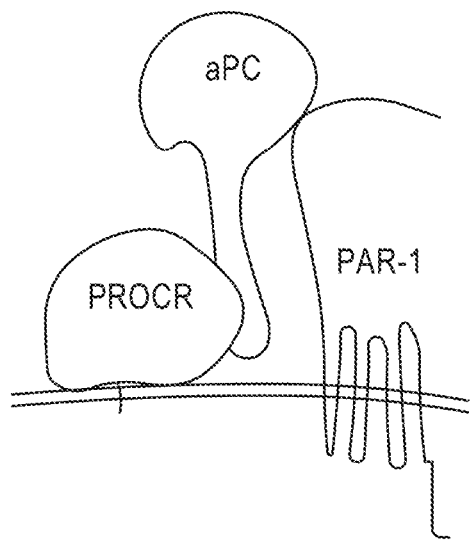
FIGS. 31A, 31B, 31C and 31D are a series of graphs and illustrations depicting that PROCR is expressed on Th17 cells.
Figure 31B:
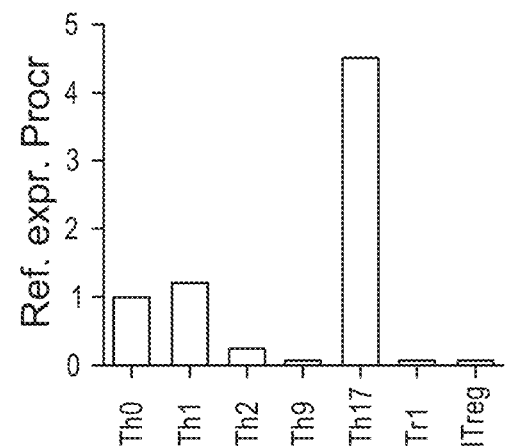
Figure 31C:
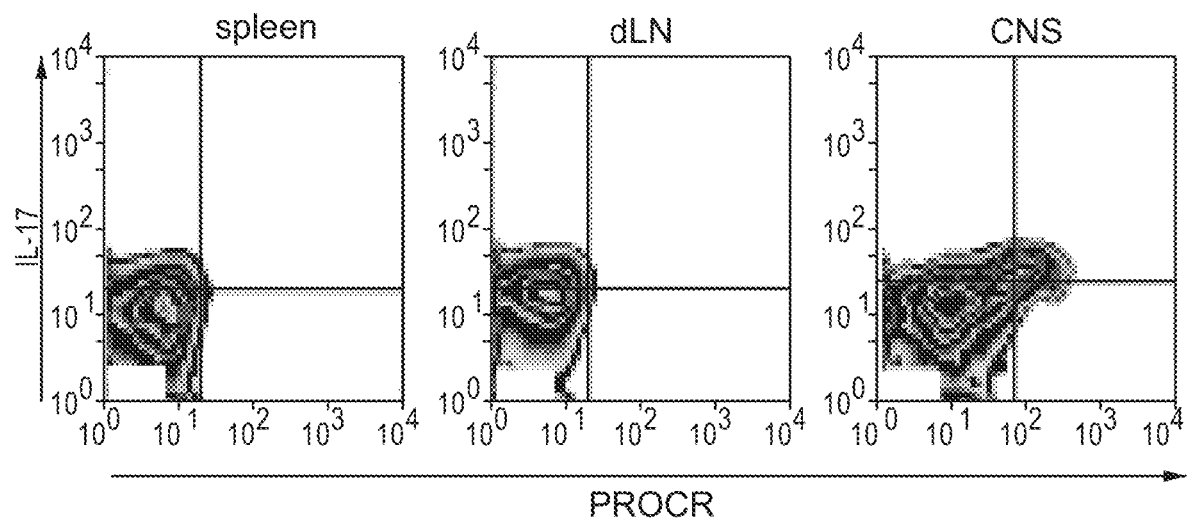
Figure 31D:
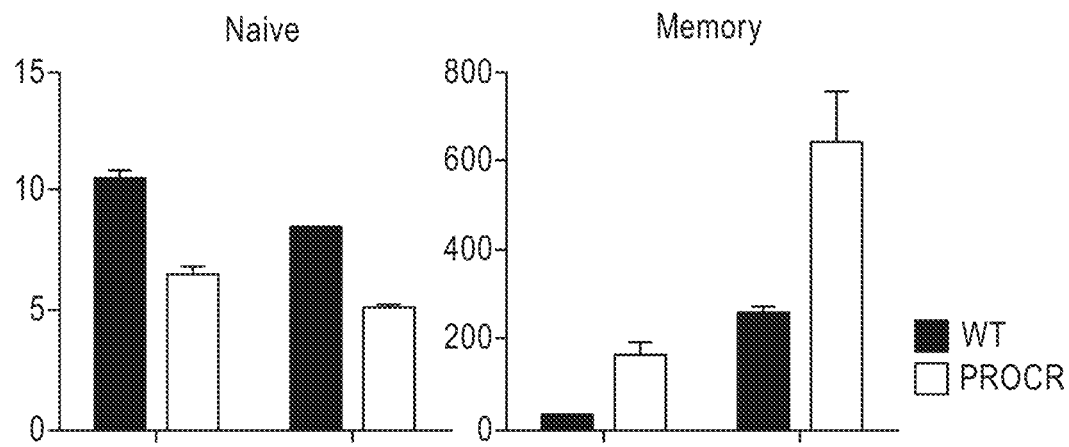

PROCR is Expressed in Th17 Cells:

The membrane receptor PROCR (Protein C receptor; also called EPCR or CD201) is present on epithelial cells, monocytes, macrophages, neutrophils, eosinophils, and natural killer cells but its expression had not previously been reported on T cells (Griffin J H, Zlokovic B V, Mosnier L O. 2012. Protein C anticoagulant and cytoprotective pathways. Int J Hematol 95: 333-45). However, the detailed transcriptomic analysis of Th17 cells described herein has identified PROCR as an important node for Th17 cell differentiation (Yosef N, Shalek A K, Gaublomme J T, Jin H, Lee Y, Awasthi A, Wu C, Karwacz K, Xiao S, Jorgolli M, Gennert D, Satija R, Shakya A, Lu D Y, Trombetta J J, Pillai M R, Ratcliffe P J, Coleman M L, Bix M, Tantin D, Park H, Kuchroo V K, Regev A. 2013. Dynamic regulatory network controlling TH17 cell differentiation. Nature 496: 461-8). PROCR shares structural homologies with the CD1/MHC molecules and binds activated protein C (aPC) as well as blood coagulation factor VII and the Vγ4Vδ5 TCR of γδ T cells. Due to its short cytoplasmic tail PROCR does not signal directly, but rather signals by associating with the G-protein-coupled receptor PAR1 (FIG. 30a; (Griffin et al, Int J Hematol 95: 333-45 (2012))). To analyze PROCR expression on Th subsets, CD4+ T cells were differentiated in vitro under polarizing conditions and determined PROCR expression. As indicated by the network analysis of Th17 cells, high levels of PROCR could be detected in cells differentiated under Th17 conditions (FIG. 31b). To study expression of PROCR on Th17 cells during an immune response, mice were immunized with MOG/CFA to induce EAE. PROCR was not expressed on T cells in spleen and lymph nodes. In contrast, it could be detected on Th17 cells infiltrating the CNS (FIG. 31c). These data indicate that PROCR is expressed on Th17 cells in vitro and in vivo, where it is largely restricted to T cells infiltrating the target organ. To investigate the functions of PROCR in Th17 cells, studies were designed to test how loss of PROCR would affect IL-17 production using T cells from a PROCR hypomorphic mutant (PROCRd/d). PROCR deficiency causes early embryonic lethality (embryonic day 10.5) (Gu J M, Crawley J T, Ferrell G, Zhang F, Li W, Esmon N L, Esmon C T. 2002. Disruption of the endothelial cell protein C receptor gene in mice causes placental thrombosis and early embryonic lethality. J Biol Chem 277: 43335-43), whereas hypomorphic expression of PROCR, which retain only small amounts (<10% of wild-type) of PROCR, is sufficient to completely abolish lethality and mice develop normally under steady state conditions (Castellino F J, Liang Z, Volkir S P, Haalboom E, Martin J A, Sandoval-Cooper M J, Rosen E D. 2002. Mice with a severe deficiency of the endothelial protein C receptor gene develop, survive, and reproduce normally, and do not present with enhanced arterial thrombosis after challenge. Thromb Haemost 88: 462-72). When challenged in a model for septic shock, PROCRd/d mice show compromised survival compared to WT mice (Iwaki T, Cruz D T, Martin J A, Castellino F J. 2005. A cardioprotective role for the endothelial protein C receptor in lipopolysaccharide-induced endotoxemia in the mouse. Blood 105: 2364-71). Naïve CD4+ PROCRd/d T cells differentiated under Th17 conditions produced less IL-17 compared to WT naïve CD4+ T cells (FIG. 31d). Effector memory PROCRd/d T cells cultured with IL-23 produced more IL-17 than WT memory T cells. Therefore PROCR, similar to PD-1, promotes generation of Th17 cells from naïve CD4 T cells, but inhibits the function of Th17 effector T cells.

Figure 34:
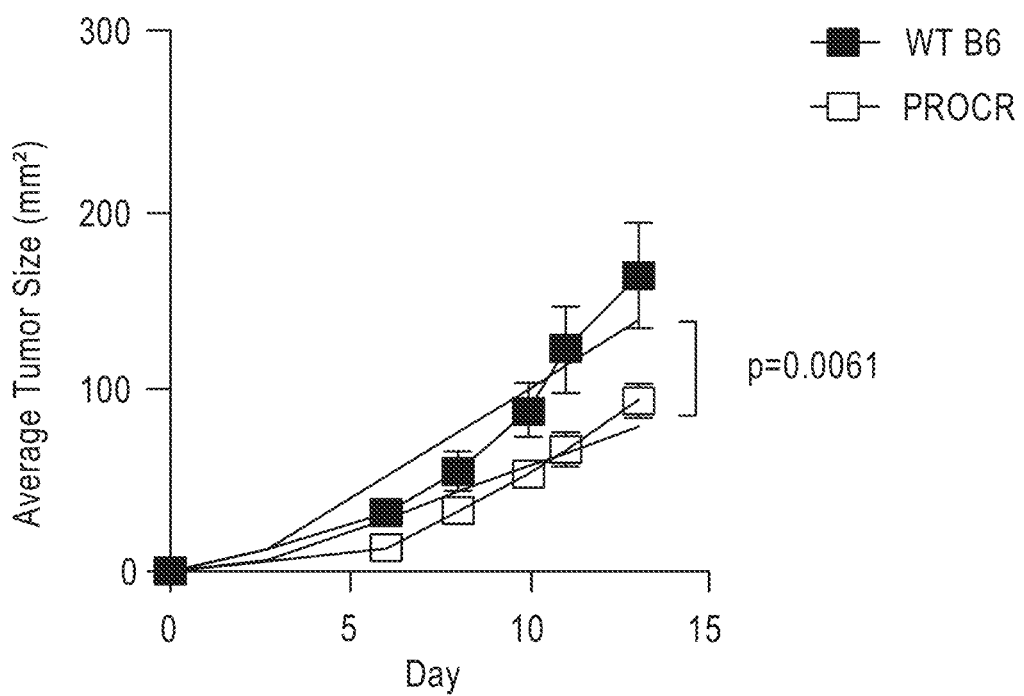
FIG. 34 is a graph depicting B16 tumor inoculation of PROCR mutant mice. 7 week old wild type or PROCR mutant (EPCR delta) C57BL/6 mice were inoculated with $5 \times 10^5$ B16F10 melanoma cells.

Knockdown Analysis of PROCR in Tumor Model:

FIG. 34 is a graph depicting B16 tumor inoculation of PROCR mutant mice. 7 week old wild type or PROCR mutant (EPCR delta) C57BL/6 mice were inoculated with 5×10$^5$ B16F10 melanoma cells. As shown in FIG. 34, inhibition of PROCR slowed tumor growth. Thus, inhibition of PROCR is useful for impeding tumor growth and in other therapeutic applications for treatment of cancer.

PD-1 and PROCR Affect Th17 Pathogenicity:

Th17 cells are very heterogeneous and the pathogenicity of Th17 subsets differs depending on the cytokine environment during their differentiation (Zielinski C E, Mele F, Aschenbrenner D, Jarrossay D, Ronchi F, Gattorno M, Monticelli S, Lanzavecchia A, Sallusto F. 2012. Pathogen-induced human TH17 cells produce IFN-gamma or IL-10 and are regulated by IL-1beta. Nature 484: 514-8; Lee Y, Awasthi A, Yosef N, Quintana F J, Peters A, Xiao S, Kleinewietfeld M, Kunder S, Sobel R A, Regev A, Kuchroo V. 2012. Induction and molecular signature of pathogenic Th17 cells. Nat Immunol In press; and Ghoreschi K, Laurence A, Yang X P, Tato C M, McGeachy M J, Konkel J E, Ramos H L, Wei L, Davidson T S, Bouladoux N, Grainger J R, Chen Q, Kanno Y, Watford W T, Sun H W, Eberl G, Shevach E M, Belkaid Y, Cua D J, Chen W, O'Shea J J. 2010. Generation of pathogenic T(H)17 cells in the absence of TGF-beta signalling. Nature 467: 967-71). In addition to the cytokine milieu, several costimulatory pathways have been implicated in regulating differentiation and function of T helper subsets, including Th17 cells. CTLA-4-B7 interactions inhibit Th17 differentiation (Ying H, Yang L, Qiao G, Li Z, Zhang L, Yin F, Xie D, Zhang J. 2010. Cutting edge: CTLA-4—B7 interaction suppresses Th17 cell differentiation. J Immunol 185: 1375-8). Furthermore, the work described herein revealed that ICOS plays a critical role in the maintenance of Th17 cells (Bauquet A T, Jin H, Paterson A M, Mitsdoerffer M, Ho I C, Sharpe A H, Kuchroo V K. 2009. The costimulatory molecule ICOS regulates the expression of c-Maf and IL-21 in the development of follicular T helper cells and TH-17 cells. Nat Immunol 10: 167-75).

Figure 32A:
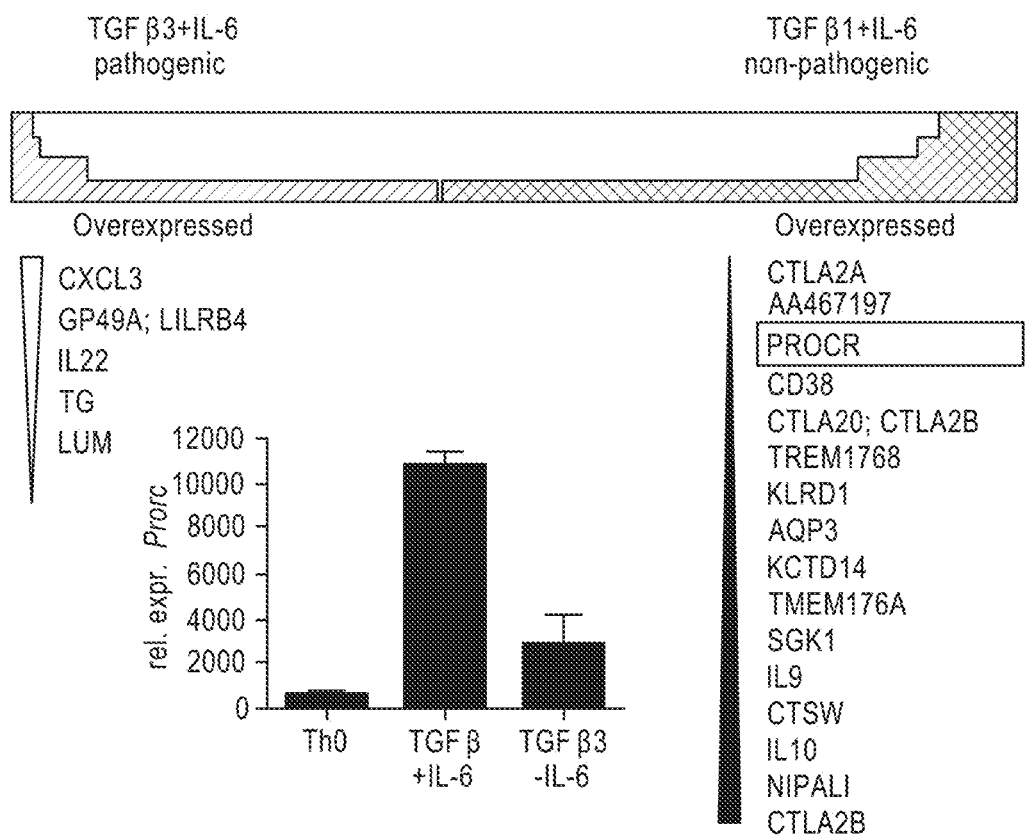
FIGS. 32A, 32B, 32C and 32D are a series of graphs depicting how PROCR and PD-1 expression affects Th17 pathogenicity.
Figure 32B:
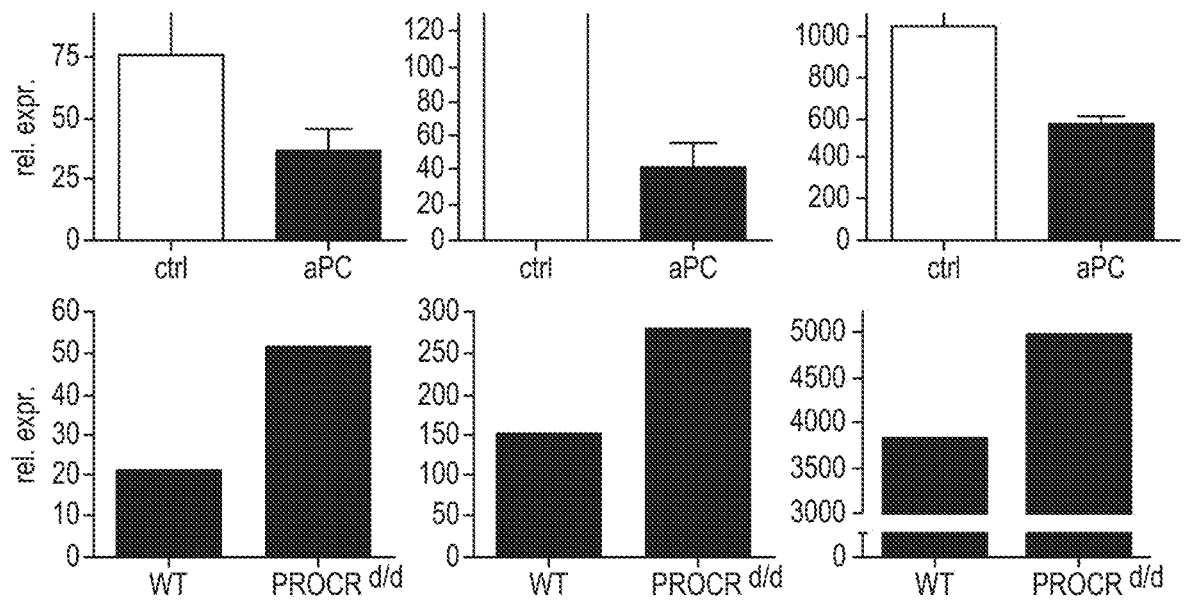
Figure 32C:
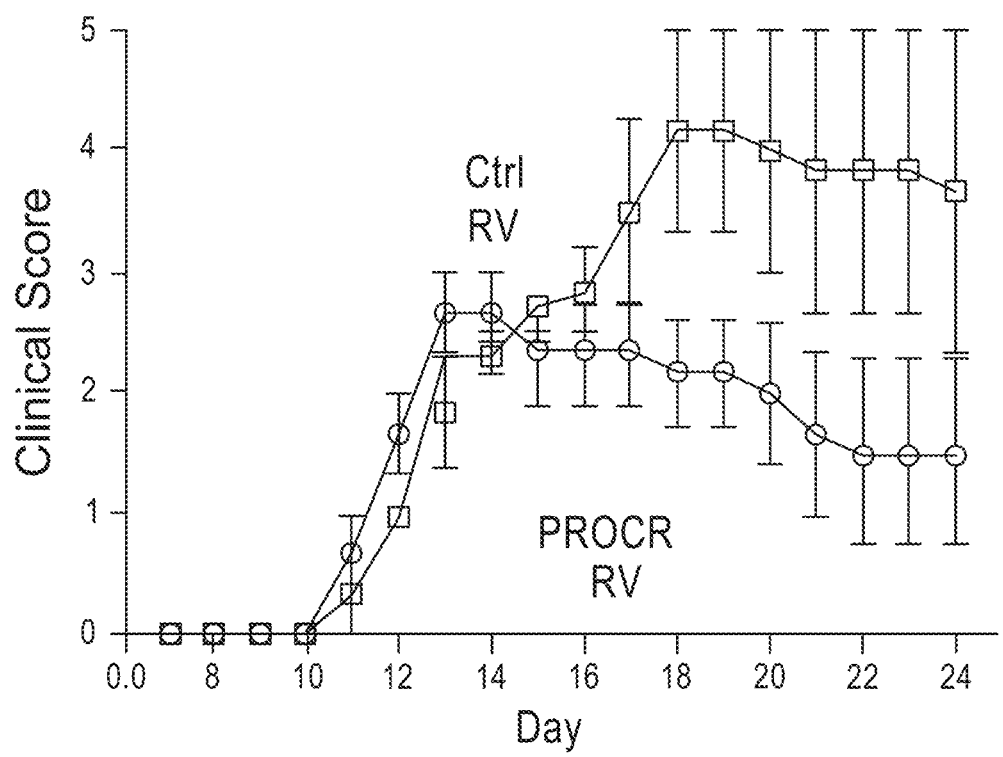
Figure 32D:
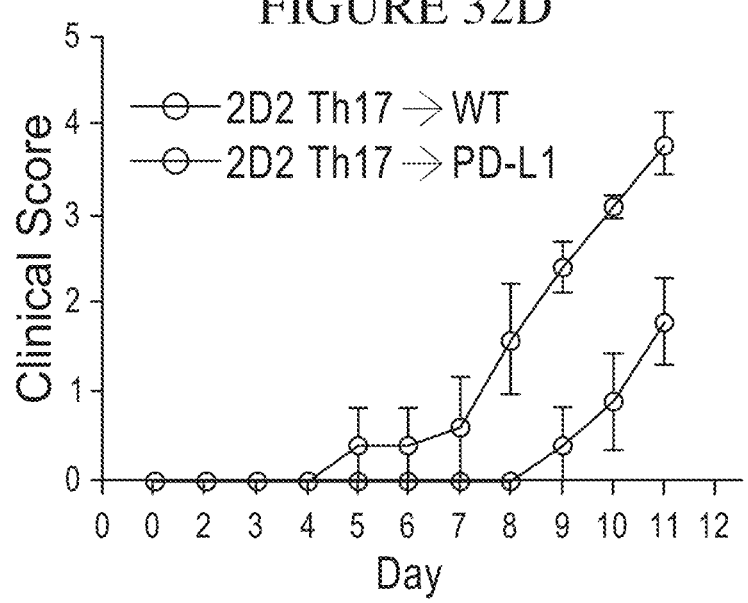

Based on the detailed genomic analysis of pathogenic vs. non-pathogenic Th17 cells herein, it has been determined that the molecular signatures that define pathogenic vs. non-pathogenic effector Th17 cells in autoimmune disease (Lee Y, Awasthi A, Yosef N, Quintana F J, Peters A, Xiao S, Kleinewietfeld M, Kunder S, Sobel R A, Regev A, Kuchroo V. 2012. Induction and molecular signature of pathogenic Th17 cells. Nat Immunol In press). Interestingly, PROCR is part of the signature for non-pathogenic Th17 cells and its expression is highly increased in non-pathogenic subsets (FIG. 32a). Furthermore, PROCR seems to play a functional role in regulating Th17 pathogenicity as engagement of PROCR by its ligand aPC induces some non-pathogenic signature genes, while Th17 cells from PROCRd/d mice show decreased expression of these genes (FIG. 32b). To study whether PROCR could also affect pathogenicity of Th17 cells in an in vivo model of autoimmunity, an adoptive transfer model for EAE was used. To induce disease, MOG-specific 2D2 TCR transgenic T cells were differentiated under Th17 conditions and then transferred into naïve recipients. As shown in FIG. 32c, forced overexpression of PROCR on Th17 cells ameliorated disease, confirming that PROCR drives conversion of pathogenic towards non-pathogenic Th17 cells. In addition, it was found that PD-1: PD-L1 interactions limit the pathogenicity of effector Th17 cells in vivo. When MOG35-55-specific (2D2) Th17 effector cells were transferred into WT vs. PD-L1−/− mice, PD-L1−/− recipients rapidly developed signs of EAE (as early as day 5 post transfer), and EAE severity was markedly increased with most experiments needed to be terminated due to rapid onset of morbidity in PD-L1−/− recipients (FIG. 32d). The number of CNS-infiltrating cells was significantly increased in PD-L1−/− recipients with a greater percentage of 2D2+IL-17+ in PD-L1−/− recipients compared to WT mice. Therefore both PD-1 and PROCR seem to control pathogenicity of effector Th17 cells.

Figure 33A:
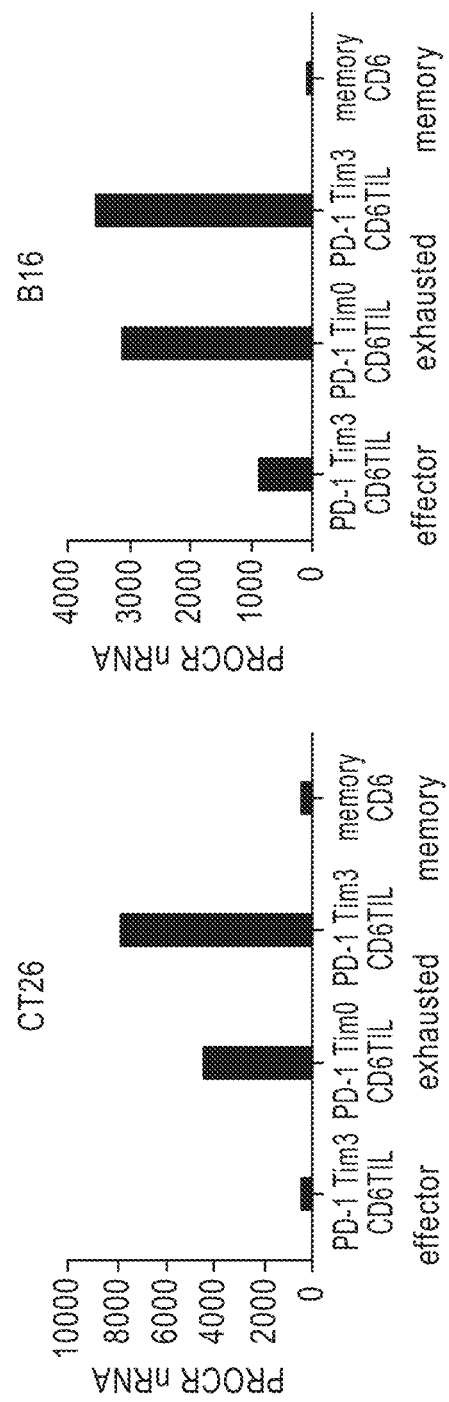
FIGS. 33A and 33B are a series of graphs depicting that PROCR expression is enriched in exhausted T cells.
Figure 33B:
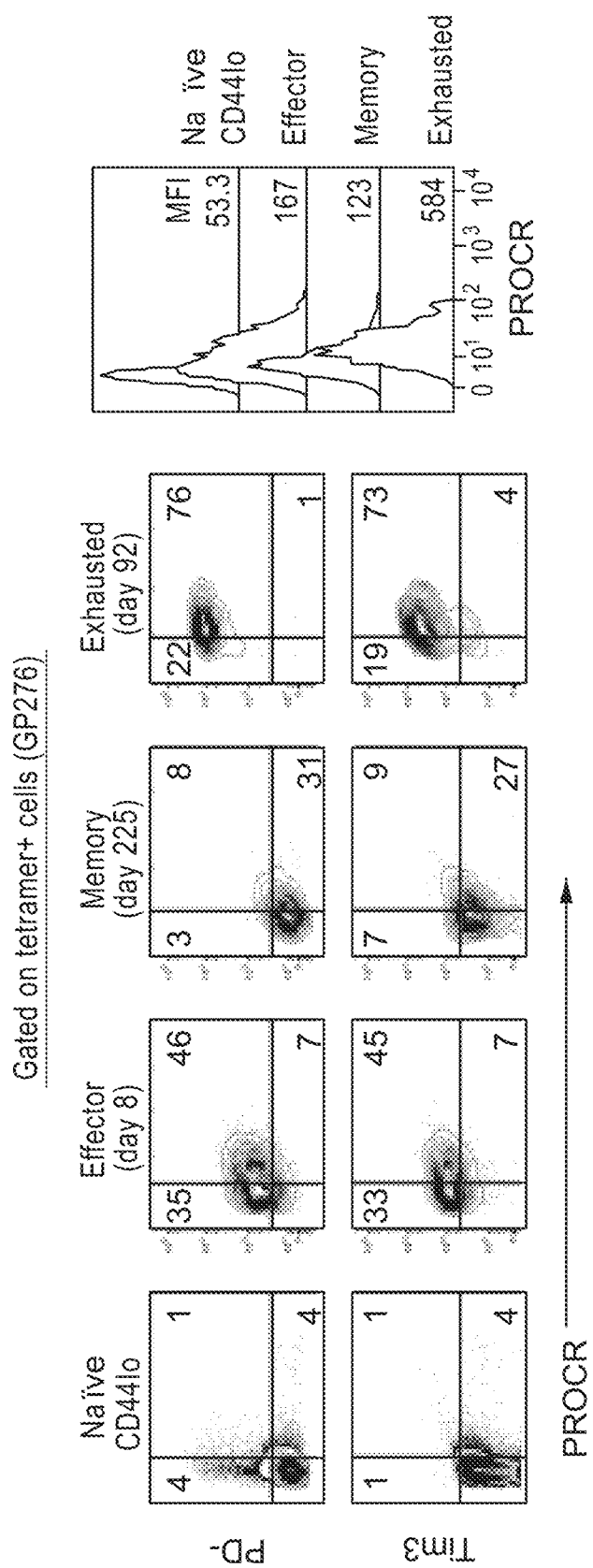

Several co-inhibitory molecules have been implicated in T cell dysfunction during antigen persistence. PD-1 and Tim-3, in particular, have wide implications in cancer and chronic viral infections such as HIV, HCV in human and LCMV in mice. Autoreactive T cell responses in mice and human are characterized with reduced expression of inhibitory molecules. The ability to induce T cell dysfunction in autoimmune settings could be clinically beneficial. MS patients that respond to Copaxone treatment show significantly elevated levels of expression of PROCR and PD-L1. It has been previously demonstrated that increasing Tim-3 expression and promoting T cell exhaustion provides the ability to limit encephalitogenecity of T cells and reduce EAE severity (Rangachari M, Zhu C, Sakuishi K, Xiao S, Karman J, Chen A, Angin M, Wakeham A, Greenfield E A, Sobel R A, Okada H, McKinnon P J, Mak T W, Addo M M, Anderson A C, Kuchroo V K. 2012. Bat3 promotes T cell responses and autoimmunity by repressing Tim-3-mediated cell death and exhaustion. Nat Med 18: 1394-400). Studies were, therefore, designed to determine whether the novel inhibitory molecule PROCR, which is selectively enriched in Th17 cells, could also play a role in T cell exhaustion. It was found that PROCR is expressed in exhausted tumor infiltrating lymphocytes that express both PD-1 and Tim-3 (FIG. 33a). Consistent with this observation, it was found that PROCR was most enriched in antigen-specific exhausted CD8 T cells (FIG. 33b) during chronic LCMV infection. While T cell exhaustion is detrimental in chronic viral infection and tumor immunity, induction of exhaustion may play a beneficial role in controlling potentially pathogenic effector cells that cause autoimmune diseases. Regulating the expression and/or function of PD-1 and PROCR might provide the avenues to accomplish this task in controlling autoimmunity.

Example 7. Fas in Th Cell Differentiation

Fas, also known as FasR, CD95, APO-1, TNFRSF6, is a member of the TNF receptor superfamily. Binding of FasL leads to FAS trimers that bind FADD (death domains), which activates caspase-8 and leads to apoptosis. Fas also exhibits apoptosis independent effects such as interaction with Akt, STAT3, and NF-κB in liver cells and interaction with NF-κB and MAPK pathways in cancer cells.

Lpr mice are dominant negative for Fas (transposon intron 1), creating a functional knockout (KO). These mice exhibit lymphoproliferative disease (lpr); age dependent>25-fold size increase of LN, Spleen; expansion of Thy1+B220+ CD4-CD8-TCRa/b+ T cells. These mice produce spontaneous anti-dsDNA Ab, systemic autoimmunity, which makes them a model of systemic lupus erythematosus (SLE), but these mice are resistant to experimental autoimmune encephalomyelitis (EAE). Gld mice are dominant negative for FasL.

Fas flox mice that are CD4Cre-/CD19Cre-/CD4Cre-CD19Cre-/LckCre-Fasflox exhibit no lymphoproliferation and no expansion of Thy1+B220+CD4-CD8-TCRa/b+ T cells. These mice do exhibit progressive lymphopenia, inflammatory lung fibrosis, and wasting syndrome. Fas flox mice that are MxCre+poly(IC)-Fasflox exhibit an lpr phenotype. Fas flox mice that are MOGCre-Fasflox are resistant to EAE. Fas flox mice that are LysMCre-Fasflox exhibit lymphoproliferation and glomerulonephritis.

Although Fas (CD95) has been identified as a receptor mediating apoptosis, the data herein clearly show that Fas is important for Th17 differentiation and development of EAE. The data herein demonstrates that Fas-deficient mice have a defect in Th17 cell differentiation and preferentially differentiate into Th1 and Treg cells. The expansion of Treg cells and inhibition of Th17 cells in Fas-deficient mice might be responsible for disease resistance in EAE.

Fas-deficient cells are impaired in their ability to differentiate into Th17 cells, and they produce significantly lower levels of IL-17 when cultured in vitro under Th17 conditions (IL-1β+IL-6+IL-23). Furthermore, they display reduced levels of IL-23R, which is crucial for Th17 cells as IL-23 is required for Th17 stability and pathogenicity. In contrast, Fas inhibits IFN-γ production and Th1 differentiation, as cells derived from Fas-deficient mice secrete significantly higher levels of IFN-γ. Similarly, Fas-deficient cells more readily differentiate into Foxp3+ Tregs and secrete higher levels of the Treg effector cytokine IL-10. It therefore seems as if Fas suppresses the differentiation into Tregs and IFN-γ-producing Th1 cells while promoting Th17 differentiation. In inflammatory autoimmune disorders, such as EAE, Fas therefore seems to promote disease progression by shifting the balance in T helper cells away from the protective Tregs and from IFN-γ-producing Th1 cells towards pathogenic Th17 cells.

The invention having now been described by way of written description and example, those of skill in the art will recognize that the invention can be practiced in a variety of embodiments and that the description and examples above are for purposes of illustration and not limitation of the claims.

The invention is further described by the following numbered paragraphs:

1. A method of modulating T cell balance, the method comprising contacting a T cell or a population of T cells with a T cell modulating agent in an amount sufficient to modify differentiation, maintenance and/or function of the T cell or population of T cells by altering balance between Th17 cells, regulatory T cells (Tregs) and other T cell subsets as compared to differentiation, maintenance and/or function of the T cell or population of T cells in the absence of the T cell modulating agent.

2. The method of paragraph 1, wherein the T cell modulating agent is an agent that modulates the expression, activity and/or function of one or more target genes or one or more products of one or more target genes selected from those listed in Tables 3-9.

3. The method of paragraph 2, wherein a desired gene or combination of target genes is selected and identified as a positive regulator of Th17 differentiation, maintenance and/or function or a negative regulator of Th17 differentiation, maintenance and/or function.

4. The method of paragraph 3, wherein the gene or combination of target genes is a positive regulator of Th17 differentiation, maintenance and/or function, and wherein the T cell modulating agent is an antagonist in an amount sufficient to shift differentiation, maintenance and/or function away from the Th17 phenotype.

5. The method of paragraph 3, wherein the target gene or combination of target genes is a positive regulator of Th17 differentiation, maintenance and/or function, and wherein the T cell modulating agent is an agonist in an amount sufficient to shift differentiation, maintenance and/or function toward the Th17 phenotype.

6. The method of paragraph 3, wherein the target gene or combination of target genes is a negative regulator of Th17 differentiation, maintenance and/or function, and wherein the T cell modulating agent is an antagonist in an amount sufficient to shift differentiation, maintenance and/or function toward the Th17 phenotype.

7. The method of paragraph 3, wherein the target gene or combination of target genes is a negative regulator of Th17 differentiation, maintenance and/or function, and wherein the T cell modulating agent is an agonist in an amount sufficient to shift differentiation away from the Th17 phenotype and/or maintenance.

8. The method of paragraph 3, wherein the positive regulator of Th17 differentiation, maintenance and/or function is selected from MINA, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, ITGA3 and combinations thereof.

9. The method of paragraph 3, wherein the positive regulator of Th17 differentiation, maintenance and/or function is selected from MINA, PML, POU2AF1, PROCR, SMARCA4, ZEB1, EGR2, CCR6, FAS and combinations thereof.

10. The method of paragraph 3, wherein the negative regulator of Th17 differentiation, maintenance and/or function is selected from SP4, ETS2, IKZF4, TSC22D3, IRF1 and combinations thereof.

11. The method of paragraph 3, wherein the negative regulator of Th17 differentiation, maintenance and/or function is selected from SP4, IKZF4, TSC22D3 and combinations thereof.

12. The method of paragraph 1, wherein the T cell modulating agent alters the balance between Th17 cells and other T cell subtypes.

13. The method of paragraph 12, wherein the other T cell subtype is regulatory T cell (Treg).

14. The method of paragraph 1, wherein the T cell modulating agent is a soluble Fas polypeptide or a polypeptide derived from FAS in an amount sufficient to induce T cell differentiation toward Th17 cells or an agonist that enhances or increases the expression, activity and/or function of FAS in Th17 cells in an amount sufficient to induce T cell differentiation toward Th17 cells.

15. The method of paragraph 1, wherein the T cell modulating agent is an antagonist that inhibits the expression, activity and/or function of FAS in an amount sufficient to induce differentiation toward regulatory T cells (Tregs), Th1 cells, or a combination of Tregs and Th1 cells.

16. The method of paragraph 1, wherein the T cell modulating agent alters the balance between pathogenic Th17 cells and non-pathogenic Th17 cells.

17. The method of paragraph 16, wherein the T cell modulating agent is a soluble Protein C Receptor (PROCR) polypeptide or a polypeptide derived from PROCR in an amount sufficient to switch Th17 cells from a pathogenic to non-pathogenic signature or an agonist that enhances or increases the expression, activity and/or function of PROCR in Th17 cells in an amount sufficient to switch Th17 cells from a pathogenic to non-pathogenic signature.

18. The method of paragraph 16, wherein the T cell modulating agent is an antagonist of PROCR in Th17 cells in an amount sufficient to switch Th17 cells from a non-pathogenic to a pathogenic signature.

19. The method according to any one of paragraphs 1 to 18, wherein the T cell modulating agent is an antibody, a soluble polypeptide, a polypeptide agent, a peptide agent, a nucleic acid agent, a nucleic acid ligand, or a small molecule agent.

20. The method according to any one of paragraphs 1 to 19, wherein the T cell modulating agent is one or more agents selected from those listed in Table 10.

21. The method according to any one of paragraphs 1 to 20, wherein the T cells are naïve T cells, partially differentiated T cells, differentiated T cells, a combination of naïve T cells and partially differentiated T cells, a combination of naïve T cells and differentiated T cells, a combination of partially differentiated T cells and differentiated T cells, or a combination of naïve T cells, partially differentiated T cells and differentiated T cells.

22. A method of inhibiting tumor growth in a subject in need thereof, the method comprising administering to said subject a therapeutically effective amount of an inhibitor of Protein C Receptor (PROCR).

23. The method of paragraph 22, wherein the inhibitor of PROCR is an antibody, a soluble polypeptide, a polypeptide agent, a peptide agent, a nucleic acid agent, a nucleic acid ligand, or a small molecule agent.

24. The method of paragraph 22, wherein the inhibitor of PROCR is one or more agents selected from the group consisting of lipopolysaccharide; cisplatin; fibrinogen; 1,10-phenanthroline; 5-N-ethylcarboxamido adenosine; cystathionine; hirudin; phospholipid; Drotrecogin alfa; VEGF; Phosphatidylethanolamine; serine; gamma-carboxyglutamic acid; calcium; warfarin; endotoxin; curcumin; lipid; and nitric oxide.

25. A method of inhibiting Th17 differentiation in a cell population and/or increasing expression, activity and/or function of one or more non-Th17-associated cytokines or non-Th17-associated transcription regulators selected from FOXP3, interferon gamma (IFN-γ), GATA3, STAT4, BCL6 and TBX21, comprising contacting a T cell with an agent that inhibits expression, activity and/or function of MINA, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, ITGA3 or combinations thereof.

26. The method of paragraph 25, wherein the agent inhibits expression, activity and/or function of at least one of MINA, PML, POU2AF1, PROCR, SMARCA4, ZEB1, EGR2, CCR6, FAS or combinations thereof.

27. The method of paragraph 25 or paragraph 26, wherein the agent is an antibody, a soluble polypeptide, a polypeptide antagonist, a peptide antagonist, a nucleic acid antagonist, a nucleic acid ligand, or a small molecule antagonist.

28. A method of inhibiting Th17 differentiation in a cell population and/or increasing expression, activity and/or function of one or more non-Th17-associated cytokines or non-Th17-associated transcription factor selected from FOXP3, interferon gamma (IFN-γ), GATA3, STAT4 and TBX21, comprising contacting a T cell with an agent that enhances expression, activity and/or function of SP4, ETS2, IKZF4, TSC22D3, IRF1 or combinations thereof.

29. The method of paragraph 28, wherein the agent enhances expression, activity and/or function of at least one of SP4, IKZF4, TSC22D3 or combinations thereof.

30. The method of paragraph 28 or paragraph 29, wherein the agent is an antibody, a soluble polypeptide, a polypeptide agonist, a peptide agonist, a nucleic acid agonist, a nucleic acid ligand, or a small molecule agonist.

31. A method of enhancing Th17 differentiation in a cell population increasing expression, activity and/or function of one or more Th17-associated cytokines or one or more Th17-associated transcription regulators selected from interleukin 17F (IL-17F), interleukin 17A (IL-17A), STAT3, interleukin 21 (IL-21) and RAR-related orphan receptor C (RORC), and/or decreasing expression, activity and/or function of one or more non-Th17-associated cytokines or non-Th17-associated transcription regulators selected from FOXP3, interferon gamma (IFN-γ), GATA3, STAT4 and TBX21, comprising contacting a T cell with an agent that inhibits expression, activity and/or function of SP4, ETS2, IKZF4, TSC22D3, IRF1 or combinations thereof.

32. The method of paragraph 31, wherein the agent inhibits expression, activity and/or function of at least one of SP4, IKZF4 or TSC22D3.

33. The method of paragraph 31 or paragraph 32, wherein the agent is an antibody, a soluble polypeptide, a polypeptide antagonist, a peptide antagonist, a nucleic acid antagonist, a nucleic acid ligand, or a small molecule antagonist.

34. A method of enhancing Th17 differentiation in a cell population, increasing expression, activity and/or function of one or more Th17-associated cytokines or one or more Th17-associated transcription regulators selected from interleukin 17F (IL-17F), interleukin 17A (IL-17A), STAT3, interleukin 21 (IL-21) and RAR-related orphan receptor C (RORC), and/or decreasing expression, activity and/or function of one or more non-Th17-associated cytokines or non-Th17-associated transcription regulators selected from FOXP3, interferon gamma (IFN-γ), GATA3, STAT4 and TBX21, comprising contacting a T cell with an agent that enhances expression, activity and/or function of MINA, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, ITGA3 or combinations thereof.

35. The method of paragraph 34, wherein the agent enhances expression, activity and/or function of at least one of MINA, PML, POU2AF1, PROCR, SMARCA4, ZEB1, EGR2, CCR6 or FAS.

36. The method of paragraph 34 or paragraph 35, wherein the agent is an antibody, a soluble polypeptide, a polypeptide agonist, a peptide agonist, a nucleic acid agonist, a nucleic acid ligand, or a small molecule agonist.

37. The method of paragraph 27, wherein the agent is one or more agents selected from those listed in Table 10.

38. The method of paragraph 30, wherein the agent is one or more agents selected from those listed in Table 10.

39. The method of paragraph 33, wherein the agent is one or more agents selected from those listed in Table 10.

40. The method of paragraph 36, wherein the agent is one or more agents selected from those listed in Table 10.

41. The method of paragraph 27, wherein the agent is an antibody.

42. The method of paragraph 30, wherein the agent is an antibody.

43. The method of paragraph 33, wherein the agent is an antibody.

44. The method of paragraph 36, wherein the agent is an antibody.

45. The method of paragraph 41, wherein the antibody is a monoclonal antibody.

46. The method of paragraph 42, wherein the antibody is a monoclonal antibody.

47. The method of paragraph 43, wherein the antibody is a monoclonal antibody.

48. The method of paragraph 44, wherein the antibody is a monoclonal antibody.

49. The method of paragraph 41, wherein the antibody is a chimeric, humanized or fully human monoclonal antibody.

50. The method of paragraph 42, wherein the antibody is a chimeric, humanized or fully human monoclonal antibody.

51. The method of paragraph 43, wherein the antibody is a chimeric, humanized or fully human monoclonal antibody.

52. The method of paragraph 44, wherein the antibody is a chimeric, humanized or fully human monoclonal antibody.

53. The method of paragraph 25, wherein the T cell is a naïve T cell, a combination of naïve T cells and partially differentiated T cells, a combination of naïve T cells and differentiated T cells, or a combination of naïve T cells, partially differentiated T cells and differentiated T cells.

54. The method of paragraph 28, wherein the T cell is a naïve T cell, a combination of naïve T cells and partially differentiated T cells, a combination of naïve T cells and differentiated T cells, or a combination of naïve T cells, partially differentiated T cells and differentiated T cells.

55. The method of paragraph 31, wherein the T cell is a naïve T cell, a combination of naïve T cells and partially differentiated T cells, a combination of naïve T cells and differentiated T cells, or a combination of naïve T cells, partially differentiated T cells and differentiated T cells.

56. The method of paragraph 34, wherein the T cell is a naïve T cell, a combination of naïve T cells and partially differentiated T cells, a combination of naïve T cells and differentiated T cells, or a combination of naïve T cells, partially differentiated T cells and differentiated T cells.

57. The method of paragraph 25, wherein the T cell is a partially differentiated T cell, a differentiated T cell, or a combination of partially differentiated T cells and differentiated T cells.

58. The method of paragraph 28, wherein the T cell is a partially differentiated T cell, a differentiated T cell, or a combination of partially differentiated T cells and differentiated T cells.

59. The method of paragraph 31, wherein the T cell is a partially differentiated T cell, a differentiated T cell, or a combination of partially differentiated T cells and differentiated T cells.

60. The method of paragraph 34, wherein the T cell is a partially differentiated T cell, a differentiated T cell, or a combination of partially differentiated T cells and differentiated T cells.

61. The method of paragraph 25 or paragraph 28, wherein the T cell is a Th17 T cell, and wherein the agent is administered in an amount that is sufficient to modulate the phenotype of the Th17 T cell to produce a CD4+ T cell phenotype other than a Th17 T cell phenotype.

62. The method of paragraph 31 or paragraph 34, wherein the T cell is a CD4+ T cell other than a Th17 T cell, and wherein the agent is administered in an amount that is sufficient to modulate the phenotype of the non-Th17 T cell to produce a Th17 T cell phenotype.

63. A method of identifying a signature gene, a gene signature or other genetic element associated with Th17 differentiation, maintenance and/or function comprising:
    a) contacting a T cell with an inhibitor of Th17 differentiation or an agent that enhances Th17 differentiation; and
    b) identifying a signature gene, a gene signature or other genetic element whose expression is modulated by step (a).

64. The method of paragraph 63, further comprising
    c) perturbing expression of the signature gene, gene signature or genetic element identified in step (b) in a T cell that has been contact with an inhibitor of Th17 differentiation or an agent that enhances Th17 differentiation; and
    d) identifying a target gene whose expression is modulated by step (c).

65. The method of paragraph 63 or paragraph 64, wherein the inhibitor of Th17 differentiation is an agent that inhibits the expression, activity and/or function of a target gene or one or more products of one or more target genes selected from those listed in Tables 3-9.

66. The method of paragraph 63 or paragraph 64, wherein the inhibitor of Th17 differentiation is an agent that inhibits the expression, activity and/or function of MINA, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, ITGA3 or combinations thereof.

67. The method of paragraph 66, wherein the agent inhibits expression, activity and/or function of at least one of MINA, PML, POU2AF1, PROCR, SMARCA4, ZEB1, EGR2, CCR6 or FAS.

68. The method of paragraph 66, wherein the agent is an antibody, a soluble polypeptide, a polypeptide antagonist, a peptide antagonist, a nucleic acid antagonist, a nucleic acid ligand, or a small molecule antagonist.

69. The method of paragraph 67, wherein the agent is an antibody, a soluble polypeptide, a polypeptide antagonist, a peptide antagonist, a nucleic acid antagonist, a nucleic acid ligand, or a small molecule antagonist.

70. The method of paragraph 66, wherein the agent is one or more agents selected from those listed in Table 10.

71. The method of paragraph 67, wherein the agent is one or more agents selected from those listed in Table 10.

72. The method of paragraph 63 or paragraph 64, wherein the inhibitor of Th17 differentiation is an agent that enhances expression, activity and/or function of SP4, ETS2, IKZF4, TSC22D3, IRF1 or combinations thereof.

73. The method of paragraph 72, wherein the agent enhances expression, activity and/or function of at least one of SP4, IKZF4, TSC22D3 or combinations thereof.

74. The method of paragraph 72, wherein the agent is an antibody, a soluble polypeptide, a polypeptide agonist, a peptide agonist, a nucleic acid agonist, a nucleic acid ligand, or a small molecule agonist.

75. The method of paragraph 73, wherein the agent is an antibody, a soluble polypeptide, a polypeptide agonist, a peptide agonist, a nucleic acid agonist, a nucleic acid ligand, or a small molecule agonist.

76. The method of paragraph 72, wherein the agent is one or more agents selected from those listed in Table 10.

77. The method of paragraph 73, wherein the agent is one or more agents selected from those listed in Table 10.

78. A method of modulating induction of Th17 differentiation comprising contacting a T cell with an agent that modulates expression, activity and/or function of one or more target genes or one or more products of one or more target genes selected from IRF1, IRF8, IRF9, STAT2, STAT3, IRF7, STAT1, ZFP281, IFI35, REL, TBX21, FLI1, BATF, IRF4, AES, AHR, ARID5A, BCL11B, BCL3, CBFB, CBX4, CHD7, CITED2, CREB1, E2F4, EGR1, EGR2, ELL2, ETS1, ETS2, ETV6, EZH1, FOXO1, GATA3, GATAD2B, HIF1A, ID2, IKZF4, IRF2, IRF3, JMJD1C, JUN, LEF1, LRRFIP1, MAX, NCOA3, NFE2L2, NFIL3, NFKB1, NMI, NOTCH1, NR3C1, PHF21A, PML, PRDM1, RELA, RUNX1, SAP18, SATB1, SMAD2, SMARCA4, SP100, SP4, STAT4, STATSB, STAT6, TFEB, TP53, TRIM24, ZFP161, and any combination thereof.

79. A method of modulating onset of Th17 phenotype and amplification of Th17 T cells comprising contacting a T cell with an agent that modulates expression, activity and/or function of one or more target genes or one or more products of one or more target genes selected from IRF8, STAT2, STAT3, IRF7, JUN, STATSB, ZPF2981, CHD7, TBX21, FLI1, SATB1, RUNX1, BATF, RORC, SP4, AES, AHR, ARID3A, ARID5A, ARNTL, ASXL1, BATF, BCL11B, BCL3, BCL6, CBFB, CBX4, CDC5L, CEBPB, CREB1, CREB3L2, CREM, E2F4, E2F8, EGR1, EGR2, ELK3, ELL2, ETS1, ETS2, ETV6, EZH1, FOSL2, FOXJ2, FOXO1, FUS, HIF1A, HMGB2, ID1, ID2, IFI35, IKZF4, IRF3, IRF4, IRF9, JUNB, KAT2B, KLF10, KLF6, KLF9, LEF1, LRRFIP1, MAFF, MAX, MAZ, MINA, MTA3, MYC, MYST4, NCOA1, NCOA3, NFE2L2, NFIL3, NFKB1, NMI, NOTCH1, NR3C1, PHF21A, PML, POU2AF1, POU2F2, PRDM1, RARA, RBPJ, RELA, RORA, SAP18, SKI, SKIL, SMAD2, SMAD7, SMARCA4, SMOX, SP1, SS18, STAT1, STAT5A, STAT6, SUZ12, TFEB, TLE1, TP53, TRIM24, TRIM28, TRPS1, VAV1, ZEB1, ZEB2, ZFP161, ZFP62, ZNF238, ZNF281, ZNF703, and any combination thereof.

80. A method of modulating stabilization of Th17 cells and/or modulating Th17-associated interleukin 23 (IL-23) signaling comprising contacting a T cell with an agent that modulates expression, activity and/or function of one or more target genes or one or more products of one or more target genes selected from STAT2, STAT3, JUN, STATSB, CHD7, SATB1, RUNX1, BATF, RORC, SP4, IRF4, AES, AHR, ARID3A, ARID5A, ARNTL, ASXL1, ATF3, ATF4, BATF3, BCL11B, BCL3, BCL6, C210RF66, CBFB, CBX4, CDC5L, CDYL, CEBPB, CHMP1B, CIC, CITED2, CREB1, CREB3L2, CREM, CSDA, DDIT3, E2F1, E2F4, E2F8, EGR1, EGR2, ELK3, ELL2, ETS1, ETS2, EZH1, FLI1, FOSL2, FOXJ2, FOXO1, FUS, GATA3, GATAD2B, HCLS1, HIF1A, ID1, ID2, IFI35, IKZF4, IRF3, IRF7, IRF8, IRF9, JARID2, JMJD1C, JUNB, KAT2B, KLF10, KLF6, KLF7, KLF9, LASS4, LEF1, LRRFIP1, MAFF, MAX, MEN1, MINA, MTA3, MXI1, MYC, MYST4, NCOA1, NCOA3, NFE2L2, NFIL3, NFKB1, NMI, NOTCH1, NR3C1, PHF13, PHF21A, PML, POU2AF1, POU2F2, PRDM1, RARA, RBPJ, REL, RELA, RNF11, RORA, RUNX2, SAP18, SAP30, SERTAD1, SIRT2, SKI, SKIL, SMAD2, SMAD4, SMAD7, SMARCA4, SMOX, SP1, SP100, SS18, STAT1, STAT4, STAT5A, STAT6, SUZ12, TBX21, TFEB, TGIF1, TLE1, TP53, TRIM24, TRPS1, TSC22D3, UBE2B, VAV1, VAX2, XBP1, ZEB1, ZEB2, ZFP161, ZFP36L1, ZFP36L2, ZNF238, ZNF281, ZNF703, ZNRF1, ZNRF2, and any combination thereof.

81. A method of modulating one or more of target genes associated with the early stage of Th17 differentiation, maintenance and/or function, wherein the target gene is selected from:

(a) one or more of the target genes listed in Table 5 as being associated with the early stage of Th17 differentiation, maintenance and/or function selected from the group consisting of AES, AHR, ARID5A, BATF, BCL11B, BCL3, CBFB, CBX4, CHD7, CITED2, CREB1, E2F4, EGR1, EGR2, ELL2, ETS1, ETS2, ETV6, EZH1, FLI1, FOXO1, GATA3, GATAD2B, HIF1A, ID2, IFI35, IKZF4, IRF1, IRF2, IRF3, IRF4, IRF7, IRF9, JMJD1C, JUN, LEF1, LRRFIP1, MAX, NCOA3, NFE2L2, NFIL3, NFKB1, NMI, NOTCH1, NR3C1, PHF21A, PML, PRDM1, REL, RELA, RUNX1, SAP18, SATB1, SMAD2, SMARCA4, SP100, SP4, STAT1, STAT2, STAT3, STAT4, STATSB, STAT6, TFEB, TP53, TRIM24, ZFP161, and any combination thereof;

(b) one or more of the target genes listed in Table 6 as being associated with the early stage of Th17 differentiation, maintenance and/or function selected from the group consisting of FAS, CCR5, IL6ST, IL17RA, IL2RA, MYD88, CXCR5, PVR, IL15RA, IL12RB1, and any combination thereof;

(c) one or more of the target genes listed in Table 7 as being associated with the early stage of Th17 differentiation, maintenance and/or function selected from the group consisting of EIF2AK2, DUSP22, HK2, RIPK1, RNASEL, TEC, MAP3K8, SGK1, PRKCQ, DUSP16, BMP2K, PIM2, and any combination thereof;

(d) one or more of the target genes listed in Table 8 as being associated with the early stage of Th17 differentiation, maintenance and/or function selected from the group consisting of HK2, CDKN1A, DUT, DUSP1, NADK, LIMK2, DUSP11, TAOK3, PRPS1, PPP2R4, MKNK2, SGK1, BPGM, TEC, MAPK6, PTP4A2, PRPF4B, ACP1, CCRN4L, and any combination thereof; and (e) one or more of the target genes listed in Table 9 as being associated with the early stage of Th17 differentiation, maintenance and/or function selected from the group consisting of CD200, CD40LG, CD24, CCND2, ADAM17, BSG, ITGAL, FAS, GPR65, SIGMAR1, CAP1, PLAUR, SRPRB, TRPV2, IL2RA, KDELR2, TNFRSF9, and any combination thereof.

82. A method of modulating one or more of target genes associated with the intermediate stage of Th17 differentiation, maintenance and/or function, wherein the target gene is selected from:

(a) one or more of the target genes listed in Table 5 as being associated with the intermediate stage of Th17 differentiation, maintenance and/or function selected from the group consisting of AES, AHR, ARID3A, ARID5A, ARNTL, ASXL1, BATF, BCL11B, BCL3, BCL6, CBFB, CBX4, CDC5L, CEBPB, CHD7, CREB1, CREB3L2, CREM, E2F4, E2F8, EGR1, EGR2, ELK3, ELL2, ETS1, ETS2, ETV6, EZH1, FLI1, FOSL2, FOXJ2, FOXO1, FUS, HIF1A, HMGB2, ID1, ID2, IFI35, IKZF4, IRF3, IRF4, IRF7, IRF8, IRF9, JUN, JUNB, KAT2B, KLF10, KLF6, KLF9, LEF1, LRRFIP1, MAFF, MAX, MAZ, MINA, MTA3, MYC, MYST4, NCOA1, NCOA3, NFE2L2, NFIL3, NFKB1, NMI, NOTCH1, NR3C1, PHF21A, PML, POU2AF1, POU2F2, PRDM1, RARA, RBPJ, RELA, RORA, RUNX1, SAP18, SATB1, SKI, SKIL, SMAD2, SMAD7, SMARCA4, SMOX, SP1, SP4, SS18, STAT1, STAT2, STAT3, STAT5A, STAT5B, STAT6, SUZ12, TBX21, TFEB, TLE1, TP53, TRIM24, TRIM28, TRPS1, VAV1, ZEB1, ZEB2, ZFP161, ZFP62, ZNF238, ZNF281, ZNF703, and any combination thereof;

(b) one or more of the target genes listed in Table 6 as being associated with the intermediate stage of Th17 differentiation, maintenance and/or function selected from the group consisting of IL7R, ITGA3, IL1R1, CCR5, CCR6, ACVR2A, IL6ST, IL17RA, CCR8, DDR1, PROCR, IL2RA, IL12RB2, MYD88, PTPRJ, TNFRSF13B, CXCR3, IL1RN, CXCR5, CCR4, IL4R, IL2RB, TNFRSF12A, CXCR4, KLRD1, IRAK1BP1, PVR, IL12RB1, IL18R1, TRAF3, and any combination thereof;

(c) one or more of the target genes listed in Table 7 as being associated with the intermediate stage of Th17 differentiation, maintenance and/or function selected from the group consisting of PSTPIP1, PTPN1, ACP5, TXK, RIPK3, PTPRF, NEK4, PPME1, PHACTR2, HK2, GMFG, DAPP1, TEC, GMFB, PIM1, NEK6, ACVR2A, FES, CDK6, ZAK, DUSP14, SGK1, JAK3, ULK2, PTPRJ, SPHK1, TNK2, PCTK1, MAP4K3, TGFBR1, HK1, DDR1, BMP2K, DUSP10, ALPK2, and any combination thereof;

(d) one or more of the target genes listed in Table 8 as being associated with the intermediate stage of Th17 differentiation, maintenance and/or function selected from the group consisting of HK2, ZAP70, NEK6, DUSP14, SH2D1A, ITK, DUT, PPP1R11, DUSP1, PMVK, TK1, TAOK3, GMFG, PRPS1, SGK1, TXK, WNK1, DUSP19, TEC, RPS6KA1, PKM2, PRPF4B, ADRBK1, CKB, ULK2, PLK1, PPP2R5A, PLK2, and any combination thereof; and (e) one or more of the target genes listed in Table 9 as being associated with the intermediate stage of Th17 differentiation, maintenance and/or function selected from the group consisting of CTLA4, CD200, CD24, CD6L, CD9, IL2RB, CD53, CD74, CAST, CCR6, IL2RG, ITGAV, FAS, IL4R, PROCR, GPR65, TNFRSF18, RORA, IL1RN, RORC, CYSLTR1, PNRC2, LOC390243, ADAM10, TNFSF9, CD96, CD82, SLAMF7, CD27, PGRMC1, TRPV2, ADRBK1, TRAF6, IL2RA, THY1, IL12RB2, TNFRSF9, and any combination thereof.

83. A method of modulating one or more of target genes associated with the late stage of Th17 differentiation, maintenance and/or function, wherein the target gene is selected from:

(a) one or more of the target genes listed in Table 5 as being associated with the late stage of Th17 differentiation, maintenance and/or function selected from the group consisting of AES, AHR, ARID3A, ARID5A, ARNTL, ASXL1, ATF3, ATF4, BATF, BATF3, BCL11B, BCL3, BCL6, C21ORF66, CBFB, CBX4, CDC5L, CDYL, CEBPB, CHD7, CHMP1B, CIC, CITED2, CREB1, CREB3L2, CREM, CSDA, DDIT3, E2F1, E2F4, E2F8, EGR1, EGR2, ELK3, ELL2, ETS1, ETS2, EZH1, FLI1, FOSL2, FOXJ2, FOXO1, FUS, GATA3, GATAD2B, HCLS1, HIF1A, ID1, ID2, IFI35, IKZF4, IRF3, IRF4, IRF7, IRF8, IRF9, JARID2, JMJD1C, JUN, JUNB, KAT2B, KLF10, KLF6, KLF7, KLF9, LASS4, LEF1, LRRFIP1, MAFF, MAX, MEN1, MINA, MTA3, MXI1, MYC, MYST4, NCOA1, NCOA3, NFE2L2, NFIL3, NFKB1, NMI, NOTCH1, NR3C1, PHF13, PHF21A, PML, POU2AF1, POU2F2, PRDM1, RARA, RBPJ, REL, RELA, RNF11, RORA, RORC, RUNX1, RUNX2, SAP18, SAP30, SATB1, SERTAD1, SIRT2, SKI, SKIL, SMAD2, SMAD4, SMAD7, SMARCA4, SMOX, SP1, SP100, SP4, SS18, STAT1, STAT3, STAT4, STAT5A, STAT5B, STAT6, SUZ12, TBX21, TFEB, TGIF1, TLE1, TP53, TRIM24, TRPS1, TSC22D3, UBE2B, VAV1, VAX2, XBP1, ZEB1, ZEB2, ZFP161, ZFP36L1, ZFP36L2, ZNF238, ZNF281, ZNF703, ZNRF1, ZNRF2, and any combination thereof;

(b) one or more of the target genes listed in Table 6 as being associated with the late stage of Th17 differentiation, maintenance and/or function selected from the group consisting of IL7R, ITGA3, IL1R1, FAS, CCR5, CCR6, ACVR2A, IL6ST, IL17RA, DDR1, PROCR, IL2RA, IL12RB2, MYD88, BMPR1A, PTPRJ, TNFRSF13B, CXCR3, IL1RN, CXCR5, CCR4, IL4R, IL2RB, TNFRSF12A, CXCR4, KLRD1, IRAK1BP1, PVR, IL15RA, TLR1, ACVR1B, IL12RB1, IL18R1, TRAF3, IFNGR1, PLAUR, IL21R, IL23R, and any combination thereof;

(c) one or more of the target genes listed in Table 7 as being associated with the late stage of Th17 differentiation, maintenance and/or function selected from the group consisting of PTPLA, PSTPIP1, TK1, PTEN, BPGM, DCK, PTPRS, PTPN18, MKNK2, PTPN1, PTPRE, SH2D1A, PLK2, DUSP6, CDC25B, SLK, MAP3K5, BMPR1A, ACP5, TXK, RIPK3, PPP3CA, PTPRF, PACSIN1, NEK4, PIP4K2A, PPME1, SRPK2, DUSP2, PHACTR2, DCLK1, PPP2R5A, RIPK1, GK, RNASEL, GMFG, STK4, HINT3, DAPP1, TEC, GMFB, PTPN6, RIPK2, PIM1, NEK6, ACVR2A, AURKB, FES, ACVR1B, CDK6, ZAK, VRK2, MAP3K8, DUSP14, SGK1, PRKCQ, JAK3, ULK2, HIPK2, PTPRJ, INPP1, TNK2, PCTK1, DUSP1, NUDT4, TGFBR1, PTP4A1, HK1, DUSP16, ANP32A, DDR1, ITK, WNK1, NAGK, STK38, BMP2K, BUB1, AAK1, SIK1, DUSP10, PRKCA, PIM2, STK17B, TK2, STK39, ALPK2, MST4, PHLPP1, and any combination thereof;

(d) is one or more of the target genes listed in Table 8 as being associated with the late stage of Th17 differentiation, maintenance and/or function selected from the group consisting of ZAP70, PFKP, NEK6, DUSP14, SH2D1A, INPP5B, ITK, PFKL, PGK1, CDKN1A, DUT, PPP1R11, DUSP1, PMVK, PTPN22, PSPH, TK1, PGAM1, LIMK2, CLK1, DUSP11, TAOK3, RIOK2, GMFG, UCKL1, PRPS1, PPP2R4, MKNK2, DGKA, SGK1, TXK, WNK1, DUSP19, CHP, BPGM, PIP5K1A, TEC, MAP2K1, MAPK6, RPS6KA1, PTP4A2, PKM2, PRPF4B, ADRBK1, CKB, ACP1, ULK2, CCRN4L, PRKCH, PLK1, PPP2R5A, PLK2, and any combination thereof;

(e) one or more of the target genes listed in Table 9 as being associated with the late stage of Th17 differentiation, maintenance and/or function selected from the group consisting of CTLA4, TNFRSF4, CD44, PDCD1, CD200, CD247, CD24, CD6L, CCND2, CD9, IL2RB, CD53, CD74, ADAM17, BSG, CAST, CCR6, IL2RG, CD81, CD6, CD48, ITGAV, TFRC, ICAM2, ATP1B3, FAS, IL4R, CCR7, CD52, PROCR, GPR65, TNFRSF18, FCRL1, RORA, IL1RN, RORC, P2RX4, SSR2, PTPN22, SIGMAR1, CYSLTR1, LOC390243, ADAM10, TNFSF9, CD96, CAP1, CD82, SLAMF7, PLAUR, CD27, SIVA1, PGRMC1, SRPRB, TRPV2, NR1H2, ADRBK1, GABARAPL1, TRAF6, IL2RA, THY1, KDELR2, IL12RB2, TNFRSF9, SCARB1, IFNGR1, and any combination thereof.

84. A method of diagnosing an immune response in a subject, comprising detecting a level of expression, activity and/or function of one or more signature genes or one or more products of one or more signature genes selected from those listed in Table 1 and those listed in Table 2 and comparing the detected level to a control of level of signature gene or gene product expression, activity and/or function, wherein a difference in the detected level and the control level indicates that the presence of an immune response in the subject.

85. The method of paragraph 84, wherein the immune response is an autoimmune response.

86. The method of paragraph 84, wherein the immune response is an inflammatory response.

87. A method of monitoring an immune response in a subject, comprising detecting a first level of expression, activity and/or function of one or more signature genes or one or more products of one or more signature genes selected from those listed in Table 1 or Table 2 at a first time point, detecting a second level of expression, activity and/or function of the one or more signature genes or one or more products of one or more signature genes selected from those listed in Table 1 or Table 2 at a second time point, and comparing the first detected level of expression, activity and/or function with the second detected level of expression, activity and/or function, wherein a change in the first and second detected levels indicates a change in the immune response in the subject.

88. The method of paragraph 87, wherein the immune response is an autoimmune response.

89. The method of paragraph 87, wherein the immune response is an inflammatory response.

90. A method of monitoring an immune response in a subject, comprising isolating a population of T cells from the subject at a first time point, determining a first ratio of T cell subtypes within the T cell population at the first time point, isolating a population of T cells from the subject at a second time point, determining a second ratio of T cell subtypes within the T cell population at the second time point, and comparing the first and second ratio of T cell subtypes, wherein a change in the first and second detected ratios indicates a change in the immune response in the subject.

91. The method of paragraph 90, wherein the first ratio and the second ratio comprise a comparison of the level of Th17 cells to non-Th17 cells in the first and second T cell populations.

92. The method of paragraph 90, wherein the non-Th17 cell is a regulatory T cell (Treg).

93. The method of paragraph 90, wherein the first ratio and the second ratio comprise a comparison of the level of pathogenic Th17 cells to non-pathogenic Th17 cells in the first and second T cell populations.

94. The method of paragraph 90, wherein the immune response is an autoimmune response.

95. The method of paragraph 90, wherein the immune response is an inflammatory response.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for increasing a non-pathogenic phenotype and/or decreasing a pathogenic phenotype in a Th17 cell or a population of Th-17 cells comprising:
   delivering to a Th-17 cell, or a population of Th-17 cells, a vector comprising a nucleotide sequence encoding PROCR and configured to express PROCR, thereby increasing a non-pathogenic Th17 phenotype and/or decreasing a pathogenic phenotype in the Th17 cell or population of Th17 cells.

2. The method of claim 1, wherein the Th17 cell or population of Th17 cells comprise a pathogenic Th17 cell or pathogenic population of Th17 cells.

3. The method of claim 1, wherein the vector is delivered in vitro.

4. The method of claim 1, wherein the vector is a retroviral vector.

* * * * *

UNITED STATES PATENT AND TRADEMARK OFFICE
CERTIFICATE OF CORRECTION

PATENT NO. : 10,822,587 B2  
APPLICATION NO. : 14/837702  
DATED : November 3, 2020  
INVENTOR(S) : Aviv Regev et al.

Page 1 of 5

It is certified that error appears in the above-identified patent and that said Letters Patent is hereby corrected as shown below:

In the Drawings

Figures 1, 1B, 2:
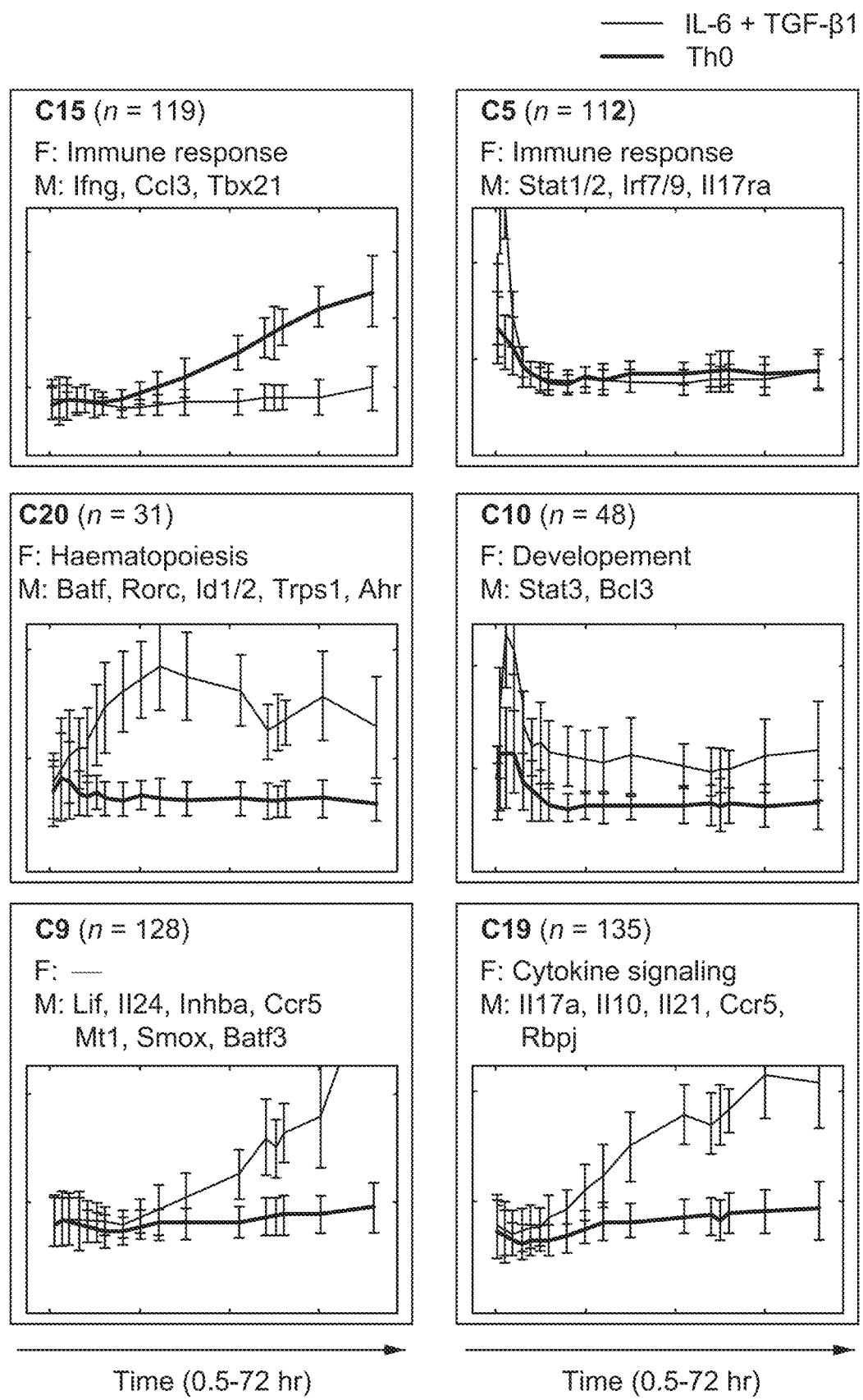
Figure 1C:
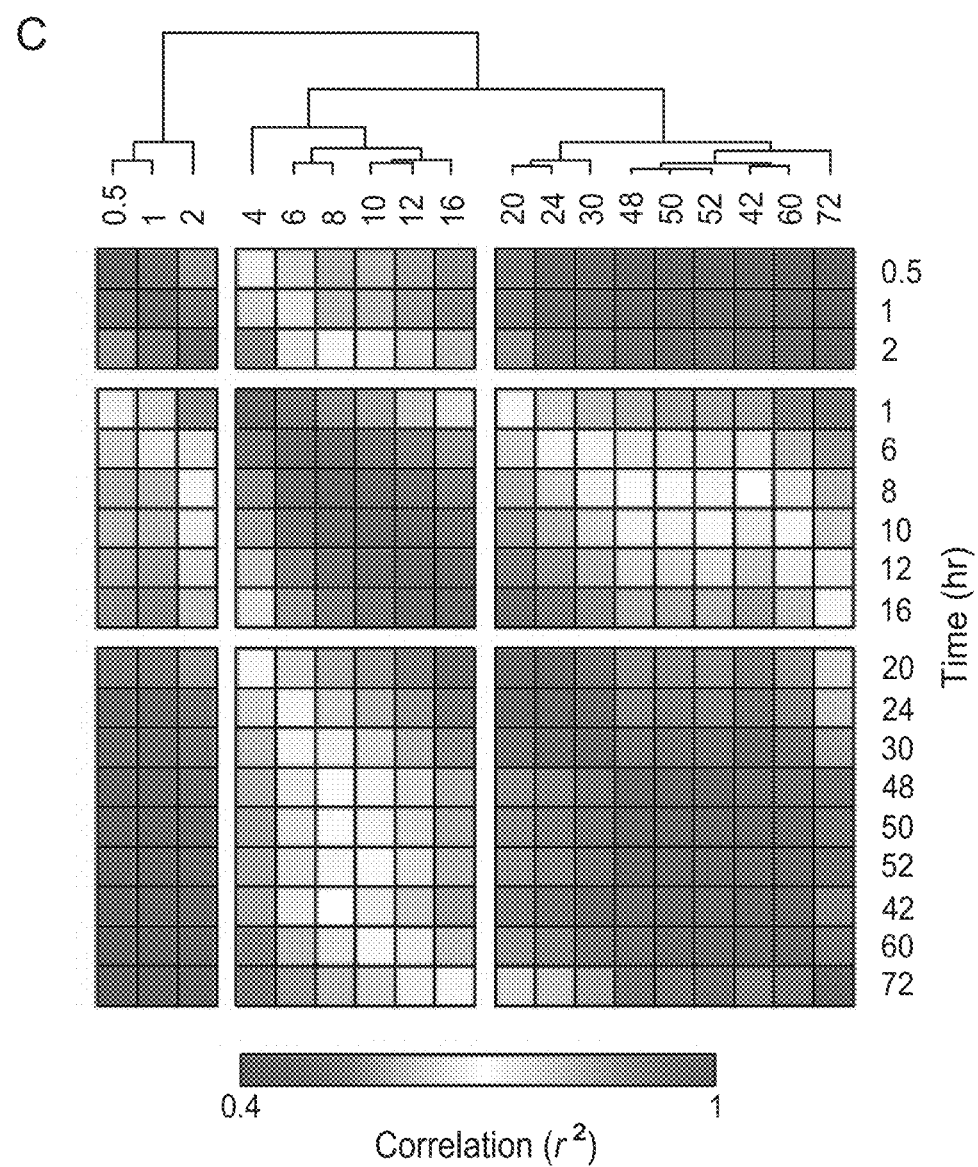
Figure 1D:
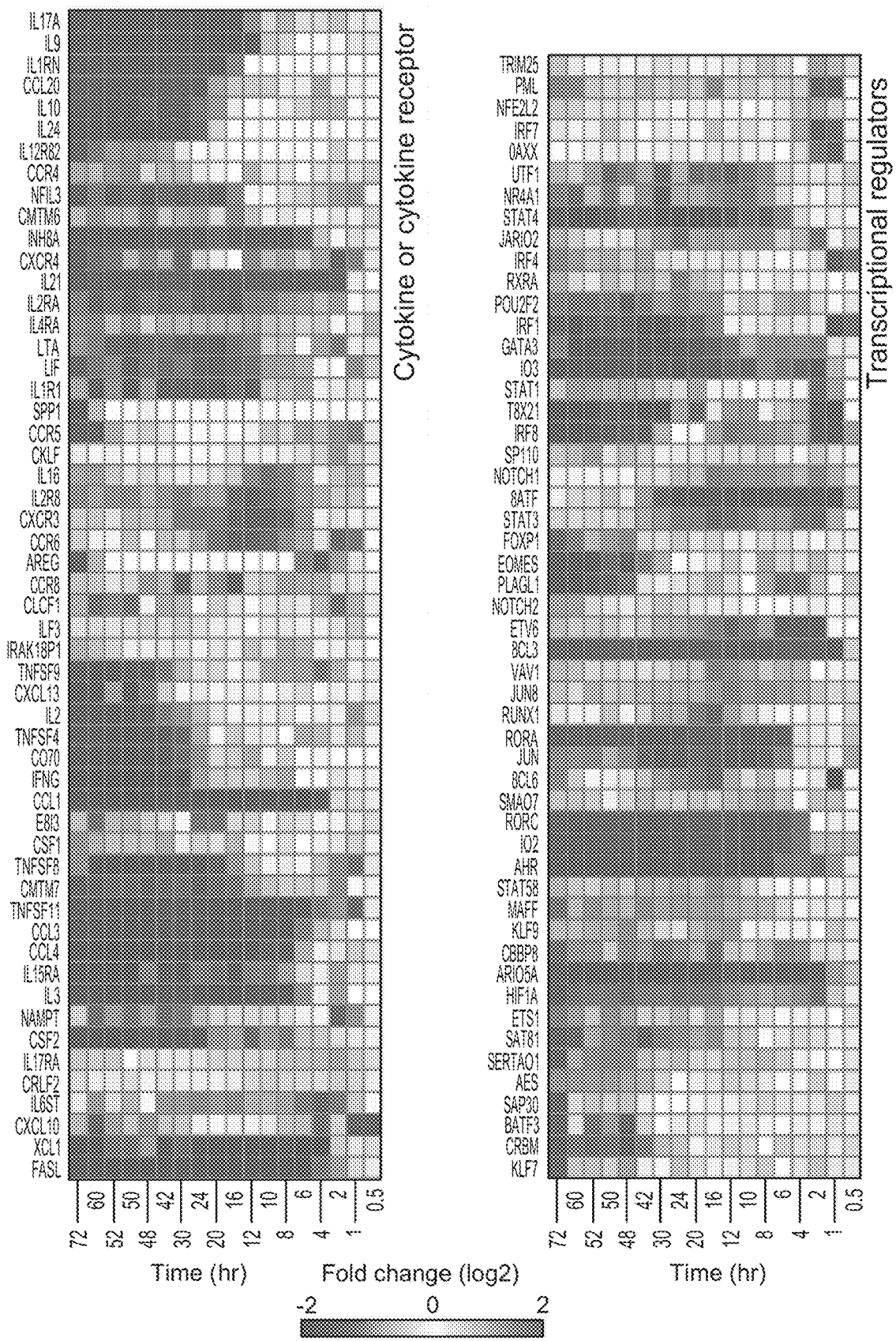

Sheet 3 of 77, in Figure 1B-2, Line 5, delete "Developement" and insert -- Development --.

Figure 26A:
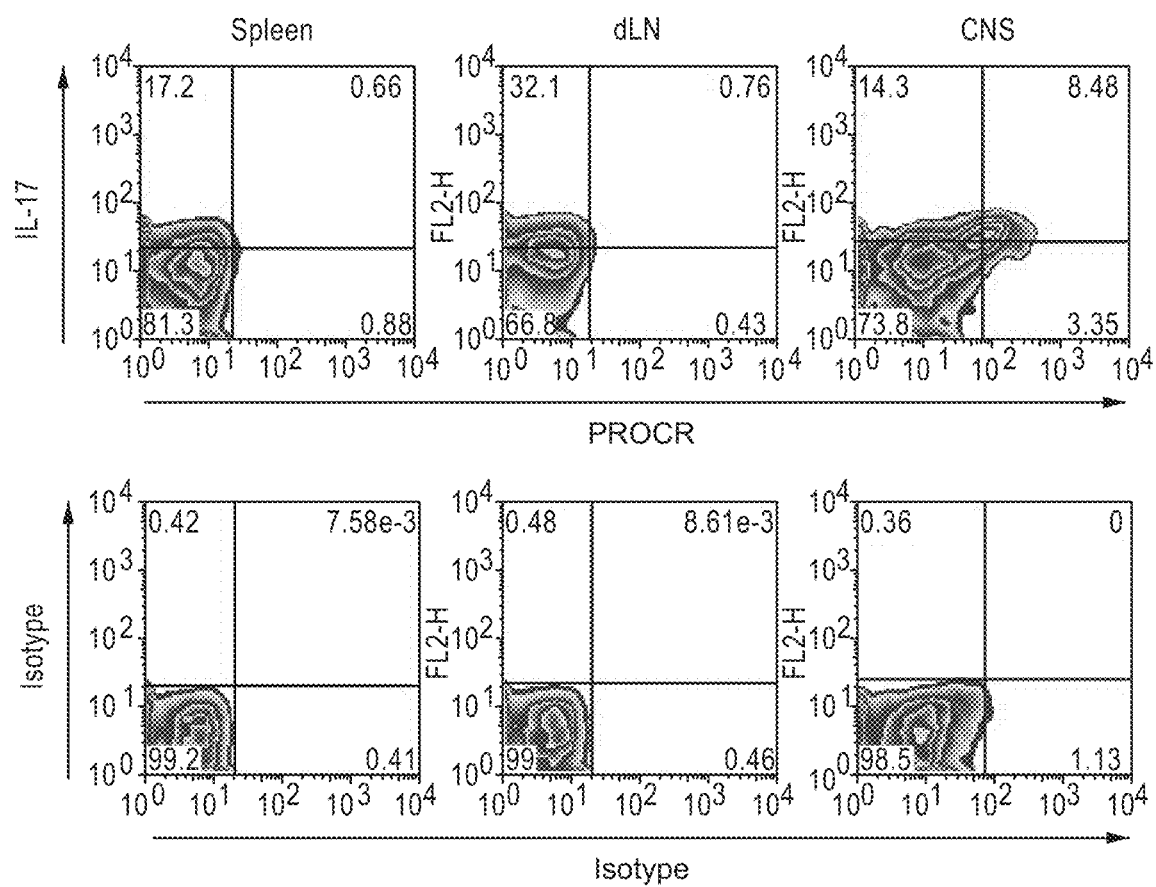
FIGS. 26A, 26B, 26C, and 26D are a series of graphs and illustrations depicting that PROCR deficiency exacerbates EAE severity.
Figure 26B:
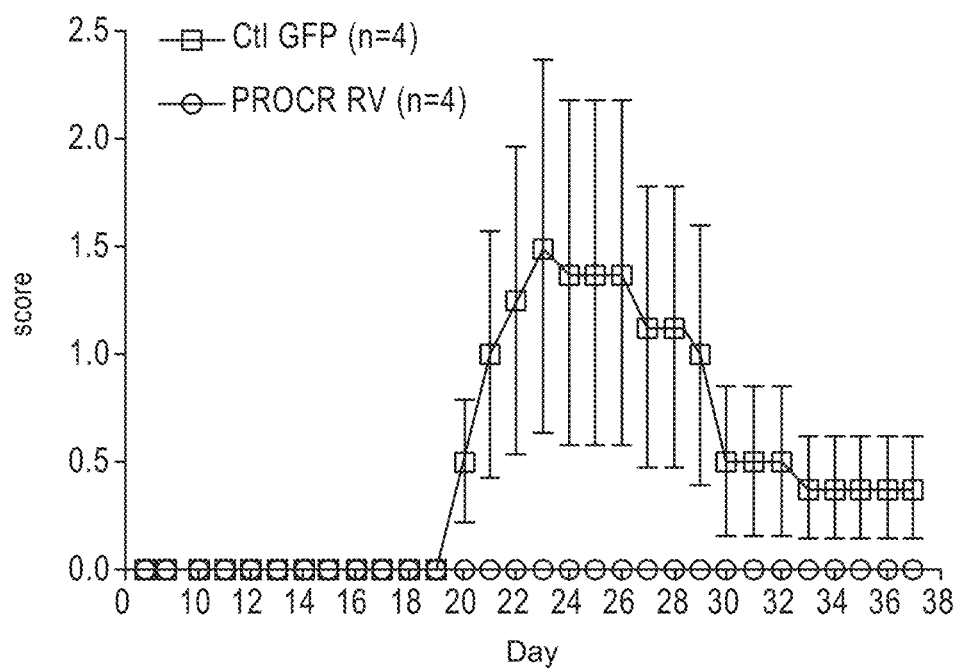
Figure 26C:
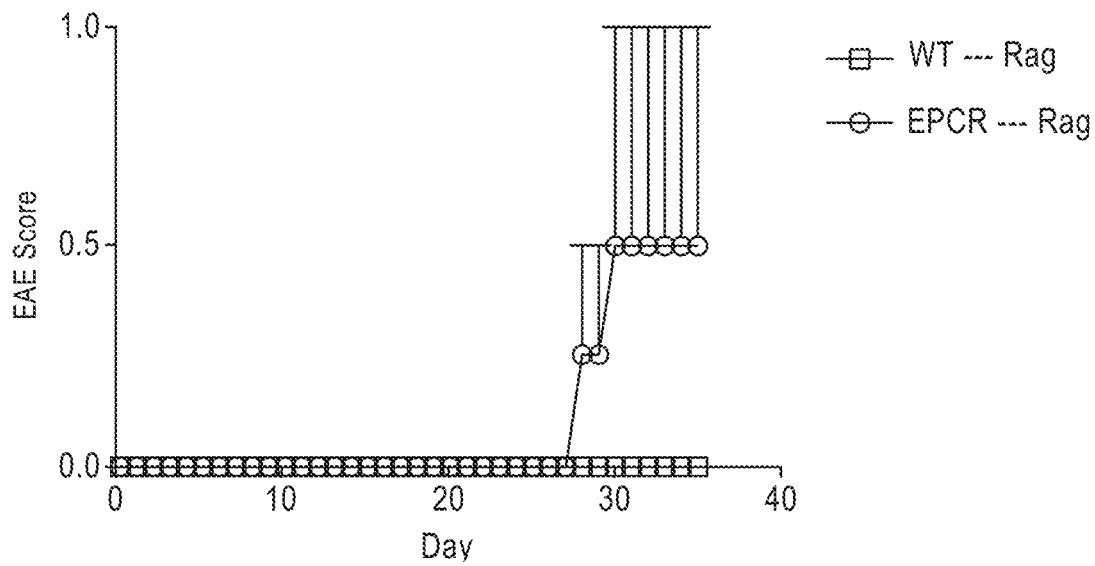
Figure 26D:
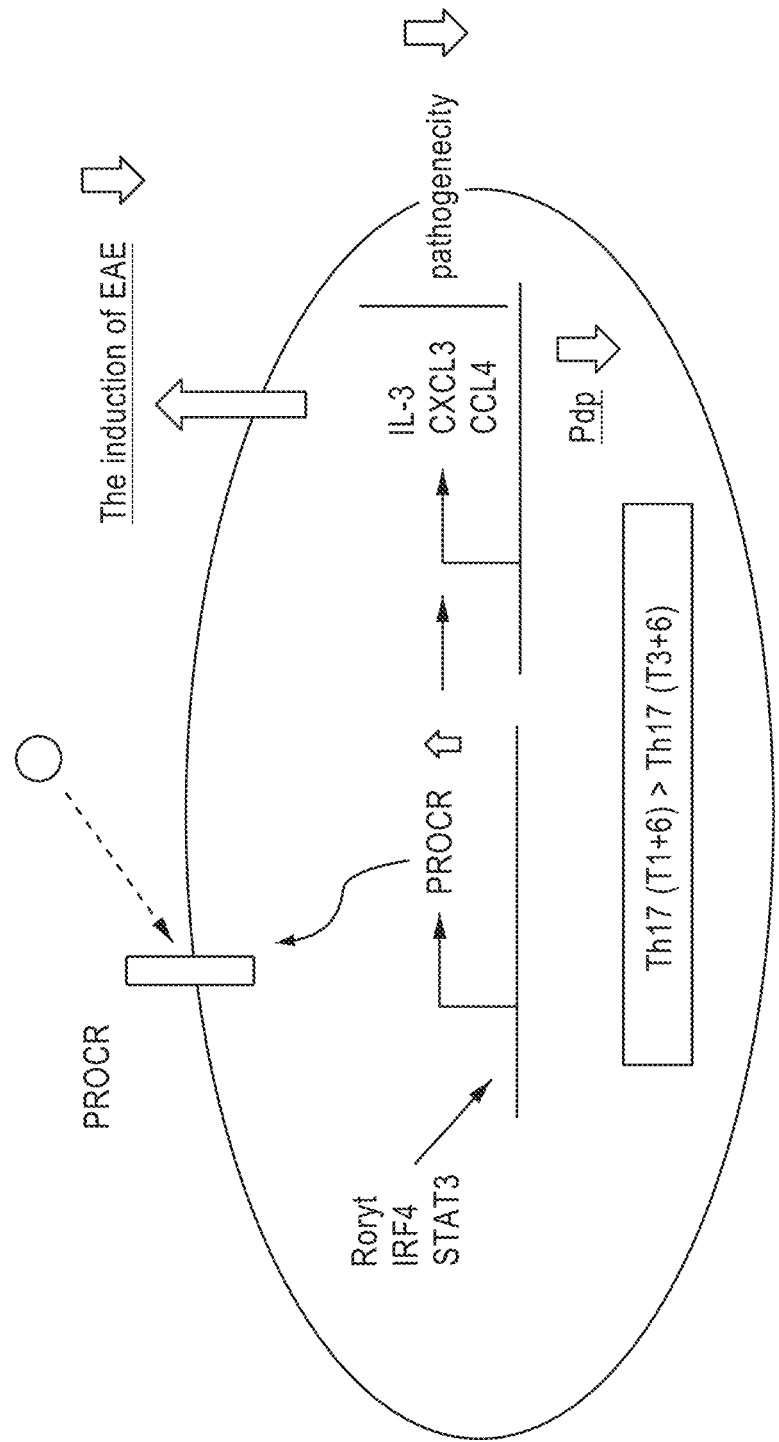
Figure 27A:
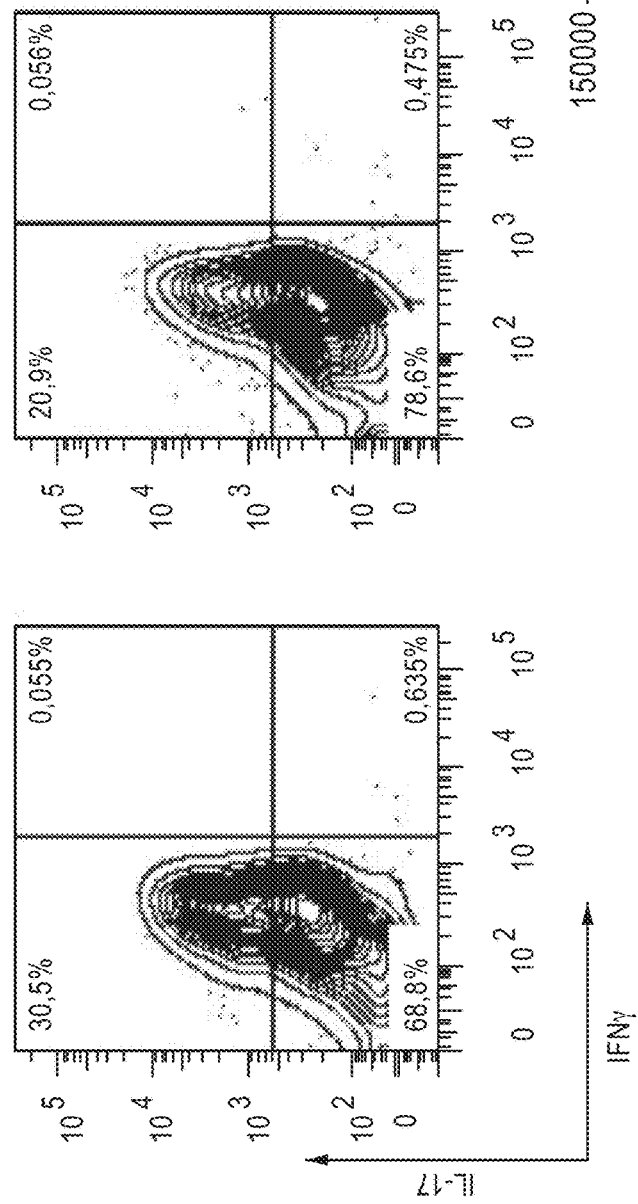
Figure 27B:
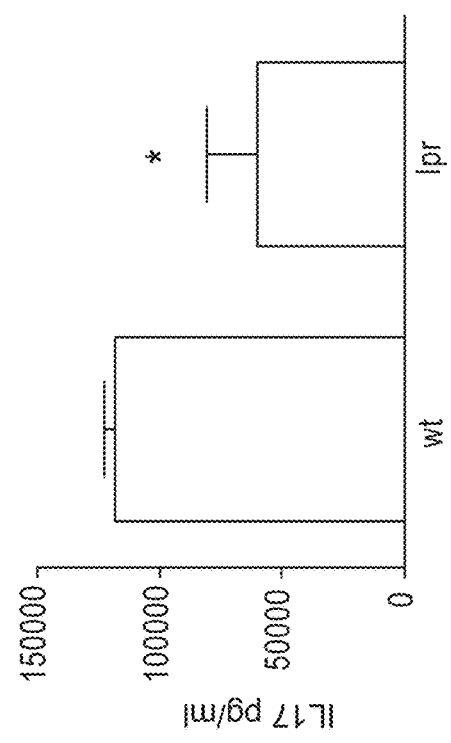
Figure 28B:
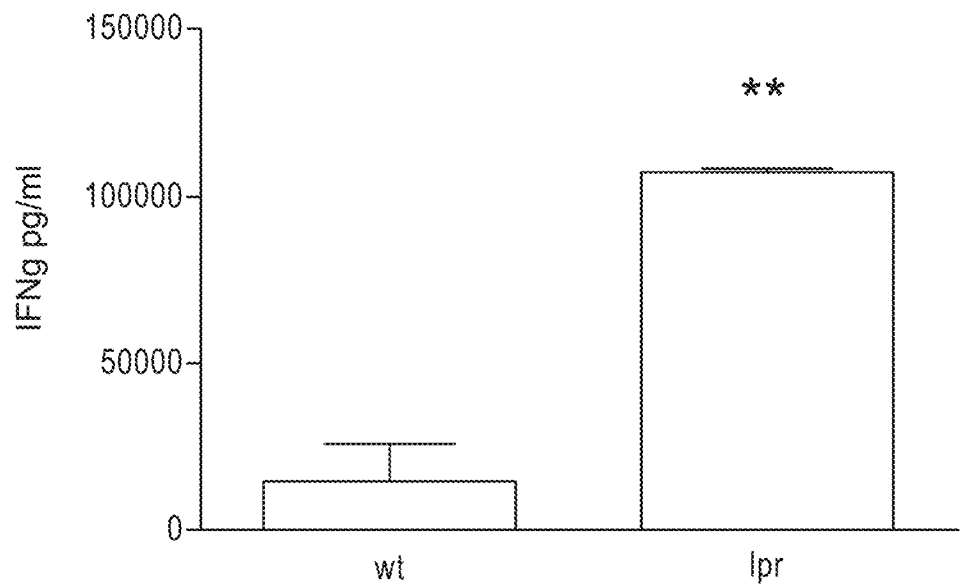
Figure 28C:
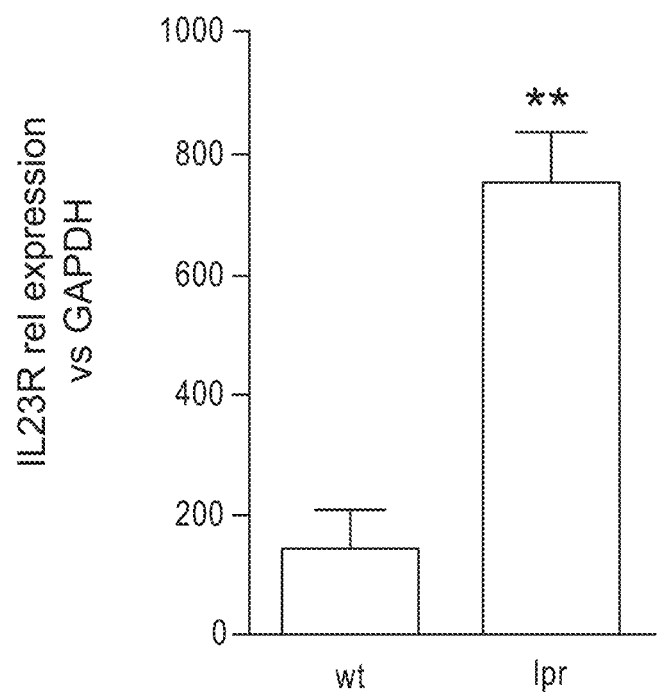
Figure 29A:
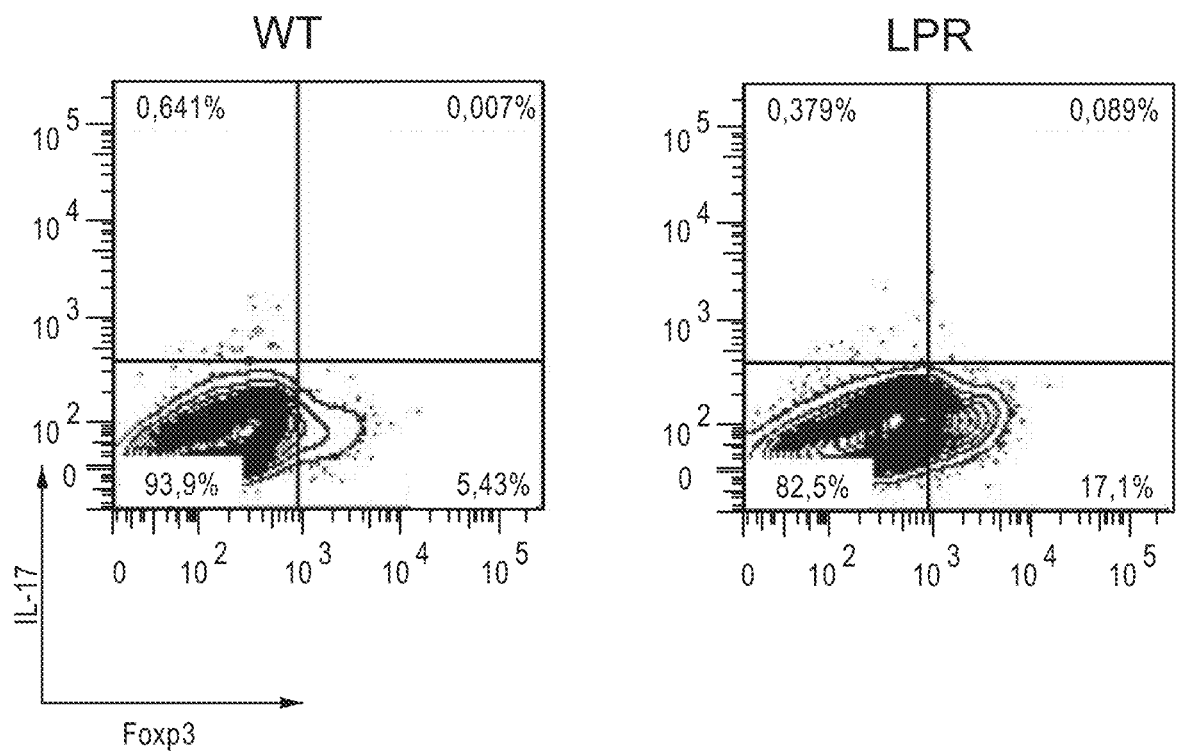
FIGS. 29A and 29B are a series of graphs depicting that FAS inhibits Treg differentiation. Naïve CD4+ T cells from wild type (WT) or FAS-deficient (LPR) mice were differentiated into Tregs by anti-CD3/anti-CD28 stimulation in the presence of TGF-β. On day 4, cells were (FIG. 29A) stimulated with PMA and Ionomycin for 4 hr, stained intracellularly for IL-17 and Foxp3 and analyzed by flow cytometry and (FIG. 29B) IL-10 production was assessed by ELISA.
Figure 29B:
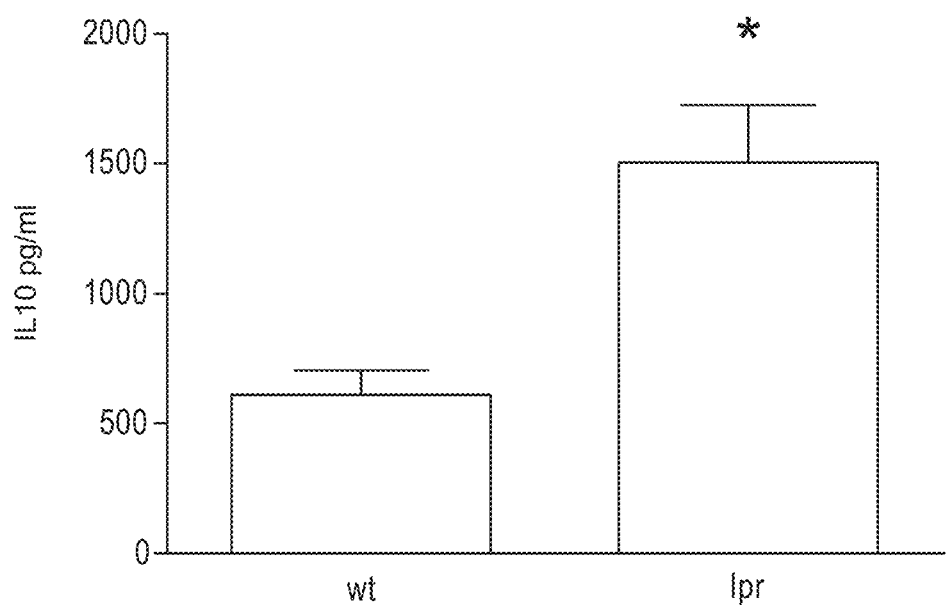

Sheet 65 of 77, in Figure 26D, Line 4, delete "pathogenecity" and insert -- pathogenicity --.

In the Specification

In Column 1, Line 16, delete "("appin" and insert -- ("appln --.

In Column 1, Line 17, delete "appin" and insert -- appln --.

In Column 4, Line 52, delete "STATSB," and insert -- STAT5B, --.

In Column 4, Line 57, delete "STATSB," and insert -- STAT5B, --.

In Column 5, Line 7, delete "STATSB," and insert -- STAT5B, --.

In Column 5, Line 15, delete "STATSB," and insert -- STAT5B, --.

In Column 5, Line 36, delete "STATSB," and insert -- STAT5B, --.

In Column 5, Line 52, delete "CCR5," and insert -- CCR8, --.

In Column 7, Line 4, delete "CD6L," and insert -- CD5L, --.

In Column 7, Line 15, delete "CD6L," and insert -- CD5L, --.

In Column 14, Line 59, delete "STATSB," and insert -- STAT5B, --.

Signed and Sealed this  
Second Day of February, 2021

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 10,822,587 B2

In Column 14, Line 67, delete "STATSB," and insert -- STAT5B, --.

In Column 15, Line 18, delete "STATSB," and insert -- STAT5B, --.

In Column 15, Line 28, delete "STATSB," and insert -- STAT5B, --.

In Column 15, Line 50, delete "STATSB," and insert -- STAT5B, --.

In Column 15, Line 66, delete "CCR5," and insert -- CCR8, --.

In Column 17, Line 23, delete "CD6L," and insert -- CD5L, --.

In Column 17, Line 33, delete "CD6L," and insert -- CD5L, --.

In Column 21, Line 20, delete "STATSB," and insert -- STAT5B, --.

In Column 35, Line 10, in TABLE 1-continued, delete "YAX2" and insert -- VAX2 --.

In Columns 39-40, Line 13, in TABLE 5-continued, delete "CE6PB" and insert -- CEBPB --.

In Columns 43-44, Line 61, in TABLE 6-continued, delete "AMP32A" and insert -- ANP32A --.

In Columns 55-56, Line 22, in TABLE 10, delete "dapta," and insert -- DAPTA, --.

In Columns 57-58, Line 19, in TABLE 10-continued, delete "5fluorouracil, indomethacin," and insert -- indomethacin, --.

In Columns 57-58, Line 26, in TABLE 10-continued, delete "1-nmma," and insert -- l-nmma, --.

In Columns 57-58, Line 61, in TABLE 10-continued, delete "chloropromazine," and insert -- chlorpromazine, --.

In Columns 59-60, Line 39, in TABLE 10-continued, delete "5fluorouracil, phosphatidylcholine," and insert -- phosphatidylcholine, --.

In Columns 59-60, Line 45, in TABLE 10-continued, delete "doxombicin," and insert -- doxorubicin, --.

In Columns 59-60, Line 46, in TABLE 10-continued, delete "adpribose," and insert -- ADP-ribose, --.

In Columns 59-60, Line 56, in TABLE 10-continued, delete "7-ethyl-10-hydroxy-camptomecin," and insert -- 7-ethyl-10-hydroxy-camptothecin, --.

In Columns 59-60, Line 65, in TABLE 10-continued, delete "ornthine," and insert -- ornithine, --.

In Columns 61-62, Line 50, in TABLE 10-continued, delete "doxombicin," and insert -- doxorubicin, --.

In Column 66, Line 21, delete "Irf4$^{-/-}$," and insert -- Irf4$^{fl/fl}$, --.

In Column 67, Line 25, delete ""Onestep" and insert -- "One-step --.

In Column 71, Line 25, delete "(0" and insert -- (f) --.

In Column 71, Line 60, delete "0" and insert -- (f) --.

In Columns 81-82, Line 9, in TABLE 11-continued, delete "chemochine" and insert -- chemokine --.

In Columns 87-88, Line 29, in TABLE 11-continued, delete "X)-typemotif 4" and insert -- X)-type motif 4 --.

In Columns 89-90, Line 29, in TABLE 11-continued, delete "phosphatase-interactingprotein" and insert -- phosphatase-interacting protein --.

In Columns 95-96, Line 40, in TABLE S6.1-continued, delete "ACT" and insert -- AGT --.

In Columns 97-98, Line 35, in TABLE S6.1-continued, delete "ACT" and insert -- AGT --.

In Columns 97-98, Line 36, in TABLE S6.1-continued, delete "Bcll1b" and insert -- Bcl11b --.

In Columns 99-100, Line 6, in TABLE S6.1-continued, delete "ACT" and insert -- AGT --.

In Columns 99-100, Line 17, in TABLE S6.1-continued, delete "TOG" and insert -- TGG --.

In Columns 99-100, Line 19, in TABLE S6.1-continued, delete "Fipl11" and insert -- Fip1l1 --.

In Columns 99-100, Line 19, in TABLE S6.1-continued, delete "TAG" and insert -- TAC --.

In Columns 101-102, Line 32, in TABLE S6.1-continued, delete "ACT" and insert -- AGT --.

In Columns 101-102, Line 44, in TABLE S6.1-continued, delete "ACT" and insert -- AGT --.

In Columns 103-104, Line 15, in TABLE S6.1-continued, delete "TAG" and insert -- TAC --.

In Columns 105-106, Line 7, in TABLE S6.1-continued, delete "GOA" and insert -- GGA --.

In Columns 107-108, Line 16, in TABLE S6.1-continued, delete "AGO" and insert -- AGG --.

In Columns 107-108, Line 24, in TABLE S6.1-continued, delete "TAG" and insert -- TAC --.

In Columns 107-108, Line 25, in TABLE S6.1-continued, delete "Plag11" and insert -- Plagl1 --.

CERTIFICATE OF CORRECTION (continued)
U.S. Pat. No. 10,822,587 B2

In Columns 107-108, Line 27, in TABLE S6.1-continued, delete "ACT" and insert -- AGT --.

In Columns 109-110, Line 27, in TABLE S6.1-continued, delete "ACT" and insert -- AGT --.

In Columns 109-110, Line 32, in TABLE S6.1-continued, delete "TOG" and insert -- TGG --.

In Columns 109-110, Line 36, in TABLE S6.1-continued, delete "CTC" and insert -- CTG --.

In Columns 109-110, Line 43, in TABLE S6.1-continued, delete "533" and insert -- 531 --.

In Columns 111-112, Line 13, in TABLE S6.1-continued, delete "GAG" and insert -- CAG --.

In Columns 117-118, Lines 37-38, in TABLE S6.1-continued, delete "ATC CCT CCA CCC TAT GAC AA" and insert -- CTG GGG TTG CTG CTT CTG --.

In Columns 117-118, Lines 37-38, in TABLE S6.1-continued, delete "GCC CCA GGT AAG CAA ACT T" and insert -- AGA TGT TTG GTT GCA GTA AAT CTG --.

In Columns 121-122, Line 41, in TABLE S6.1-continued, delete "TAG" and insert -- TAC --.

In Columns 123-124, Line 32, in TABLE S6.1-continued, delete "TAG" and insert -- TAC --.

In Columns 123-124, Line 51, in TABLE S6.1-continued, delete "TCA" and insert -- TGA --.

In Columns 125-126, Line 7, in TABLE S6.1-continued, delete "ACQ CCA CFG" and insert -- ACG CCA CTG --.

In Columns 125-126, Line 17, in TABLE S6.1-continued, delete "ACT TCC GOT" and insert -- AGT TCC GGT --.

In Columns 125-126, Line 29, in TABLE S6.1-continued, delete "OCT" and insert -- CCT --.

In Columns 125-126, Line 31, in TABLE S6.1-continued, delete "GOT" and insert -- GGT --.

In Columns 125-126, Line 36, in TABLE S6.1-continued, delete "TGC" and insert -- TGG --.

In Columns 125-126, Line 48, in TABLE S6.1-continued, delete "GGT" and insert -- GCT --.

In Columns 127-128, Line 35, in TABLE S6.1-continued, delete "AGO" and insert -- AGG --.

In Columns 129-130, Line 32, in TABLE S6.1-continued, delete "ACT" and insert -- AGT --.

In Columns 129-130, Line 40, in TABLE S6.1-continued, delete "1028" and insert -- 1026 --.

In Columns 129-130, Line 42, in TABLE S6.1-continued, delete "1026" and insert -- 1028 --.

CERTIFICATE OF CORRECTION (continued)
U.S. Pat. No. 10,822,587 B2

In Columns 131-132, Line 24, in TABLE S6.1-continued, delete "TAG" and insert -- TAC --.

In Columns 131-132, Line 29, in TABLE S6.1-continued, delete "GGC" and insert -- GGG --.

In Columns 133-134, Line 49, in TABLE S6.1-continued, delete "1336" and insert -- 1136 --.

In Columns 137-138, Line 30, in TABLE S6.2-continued, delete "UCAAUUUGCUCAACAACAA" and insert -- UGAAUUUGCUCAACAACAA --.

In Columns 139-140, Line 5, in TABLE S6.2-continued, delete "NM_0i9739" and insert -- NM_09739 --.

In Columns 141-142, Line 23, in TABLE S6.2-continued, delete "GUNNACAGUUGCCAAGGUU" and insert -- GUAAACAGUUGCCAAGGUU --.

In Columns 141-142, Line 30, in TABLE S6.2-continued, delete "CUACAGCCCUAUUUCAUCU" and insert -- GUACAGCCCUAUUUCAUCU --.

In Columns 143-144, Line 8, in TABLE S6.2-continued, delete "GAACCACGCUACACAGGAA" and insert -- GAACCAGGCUACACAGGAA --.

In Columns 143-144, Line 12, in TABLE S6.2-continued, delete "Nr3G1" and insert -- Nr3c1 --.

In Columns 143-144, Line 22, in TABLE S6.2-continued, delete "D-043089-09" and insert -- D-043069-09 --.

In Columns 147-148, Line 15, in TABLE S6.2-continued, delete "U8E2B" and insert -- UBE2B --.

In Column 163, Line 13, delete "encephalitogenecity" and insert -- encephalitogenicity --.

In Column 169, Line 54, delete "STATSB," and insert -- STAT5B, --.

In Column 169, Line 61, delete "STATSB," and insert -- STAT5B, --.

In Column 170, Line 16, delete "STATSB," and insert -- STAT5B, --.

In Column 170, Line 53, delete "STATSB," and insert -- STAT5B, --.

In Column 171, Line 35, delete "STATSB," and insert -- STAT5B, --.

In Column 172, Line 1, delete "CD6L," and insert -- CD5L, --.

In Column 172, Line 32, delete "STATSB," and insert -- STAT5B, --.

In Column 173, Line 14, delete "CD6L," and insert -- CD5L, --.